(12) United States Patent
Leban et al.

(10) Patent No.: US 7,247,736 B2
(45) Date of Patent: *Jul. 24, 2007

(54) METHOD OF IDENTIFYING INHIBITORS OF DHODH

(75) Inventors: Johann Leban, Germering (DE); Bernd Kramer, Aachen (DE); Roland Baumgartner, München (DE); Katharina Aulinger-Fuchs, Neuried (DE); Stefan Tasler, Gilching (DE)

(73) Assignee: 4SC AG, Martinsried (DE)

( * ) Notice: Subject to any disclaimer, the term of this patent is extended or adjusted under 35 U.S.C. 154(b) by 76 days.

This patent is subject to a terminal disclaimer.

(21) Appl. No.: 10/736,739

(22) Filed: Nov. 10, 2004

(65) Prior Publication Data

US 2007/0027193 A1    Feb. 1, 2007

Related U.S. Application Data

(60) Provisional application No. 60/526,992, filed on Dec. 5, 2003, provisional application No. 60/435,258, filed on Dec. 23, 2002, provisional application No. 60/435,285, filed on Dec. 23, 2002.

(51) Int. Cl.
*C07D 333/10* (2006.01)
*C07C 235/84* (2006.01)

(52) U.S. Cl. .......................... 549/71; 549/72; 549/83; 564/163; 562/603; 562/604.6; 562/622

(58) Field of Classification Search ................ 562/503, 562/504, 622; 514/563; 549/71, 72, 83; 564/163
See application file for complete search history.

(56) References Cited

U.S. PATENT DOCUMENTS

| 3,465,001 | A | 9/1969 | Bolhoffer et al. |
| 4,126,691 | A | 11/1978 | Carney et al. |
| 4,661,630 | A | 4/1987 | Harigaya et al. |
| 5,262,537 | A | 11/1993 | Huang et al. |
| 5,886,033 | A | 3/1999 | Schwab et al. |
| 2003/0203951 | A1 | 10/2003 | Leban et al. |

FOREIGN PATENT DOCUMENTS

| EP | 0 097 056 | 12/1983 |
| EP | 0 440 503 | 8/1991 |
| GB | 2 158 440 | 11/1985 |
| WO | WO 98/57937 | 12/1998 |
| WO | WO 99/65867 | 12/1999 |
| WO | WO 01/21160 | 3/2001 |
| WO | WO 01/24785 | 4/2001 |
| WO | WO 02/38153 | 5/2002 |
| WO | WO 02/100851 | 12/2002 |
| WO | WO 03/006424 | 1/2003 |
| WO | WO 03/006425 | 1/2003 |
| WO | WO 03/006443 | 1/2003 |

OTHER PUBLICATIONS

E. Kita, et al., Polish Journal of Chemistry, vol. 53, No. 6, pp. 1211-1219, "Protolytic Equilibriums of 4-Pyridoxyl-4, 5, 6, 7-Tetrahydropyrido-[3, 4-C] Imidazole and Its Derivatives", 1979 (submitting Chemical Abstract only, AN 1979: 592609).

J. E. McLean, et al., Biochemistry, vol. 40, No. 7, pp. 2194-2200, "Multiple Inhibitor Analysis of the Brequinar and Leflunomide Binding Sites on Human Dihydroorotate Dehydrogenase", 2001.

S. Ren, et al., Pharmaceutical Research, vol. 15, No. 2, pp. 286-295, "Dehydroorotate Dehydrogenase Inhibitors: Quantitative Structure-Activity Relationship Analysis", 1998.

J. P. Davis, et al., Biochemistry, vol. 35, No. 4, pp. 1270-1273, "The Immunosuppressive Metabolite of Leflunomide is a Potent Inhibitor of Human Dihydroorotate Dehydrogenase", 1996.

S. Greene, et al., Biochemical Pharmacology, vol. 50, No. 6, pp. 861-867, "Inhibition of Dihydroorotate Dehydrogenase by the Immunosuppressive Agent Leflunomide", 1995.

S-F. Chen, et al., Cancer Research, vol. 52, pp. 3521-3527, "Inhibition of Dihydroorotate Dehydrogenase Activity by Brequinar Sodium", Jul. 1, 1992.

S. Liu, et al., Structure, vol. 8, No. 1, pp. 25-33, "Structures of Human Dihydroorotate Dehydrogenase in Complex With Antiproliferative Agents", 2000.

K. Appelt, et al., Journal of Medicinal Chemistry, vol. 34, No. 7, pp. 1925-1934, "Design of Enzyme Inhibitors Using Iterative Protein Crystallographic Analysis", Jul. 1991.

U.S. Appl. No. 10/736,711, filed Dec. 17, 2003, Leban, et al.
U.S. Appl. No. 10/736,742, filed Dec. 17, 2003, Leban, et al.
U.S. Appl. No. 10/736,739, filed Dec. 17, 2003, Leban, et al.

F. Thorstensson, et al., Journal of Medicinal Chemistry, vol. 46, No. 7, XP-002274167, pp. 1165-1179, "Synthesis of Novel Thrombin Inhibitors. Use of Ring-Closing Metathesis Reactions for Synthesis of P2 Cyclopentene- and Cyclohexenedicarboxylic Acid Derivatives", 2003.

(Continued)

*Primary Examiner*—Kamal A. Saeed
*Assistant Examiner*—Yong Chu
(74) *Attorney, Agent, or Firm*—Womble, Carlyle, Sandridge & Rice, PLLC

(57) ABSTRACT

The present invention provides a compound capable of binding to the ubiquinone binding site of DHODH which contains a non-aromatic ring system as a core structure, a group capable of interacting with structural elements of subsite 2 or 3 of the ubiquinone binding site of DHODH and a group capable of interacting hydrophobically with structural elements of subsite 1 of the ubiquinone binding site of DHODH. Furthermore, the present invention provides a compound capable of binding to the ubiquinone binding site of DHODH which contains an aromatic ring system as a core structure, a group capable of interacting with residues His 56 and/or Tyr 356 of subsite 3 of the ubiquinone binding site of DHODH and a group capable of interacting hydrophobically with structural elements of subsite 1 of the ubiquinone binding site of DHODH.

10 Claims, 2 Drawing Sheets

OTHER PUBLICATIONS

Figure 1:
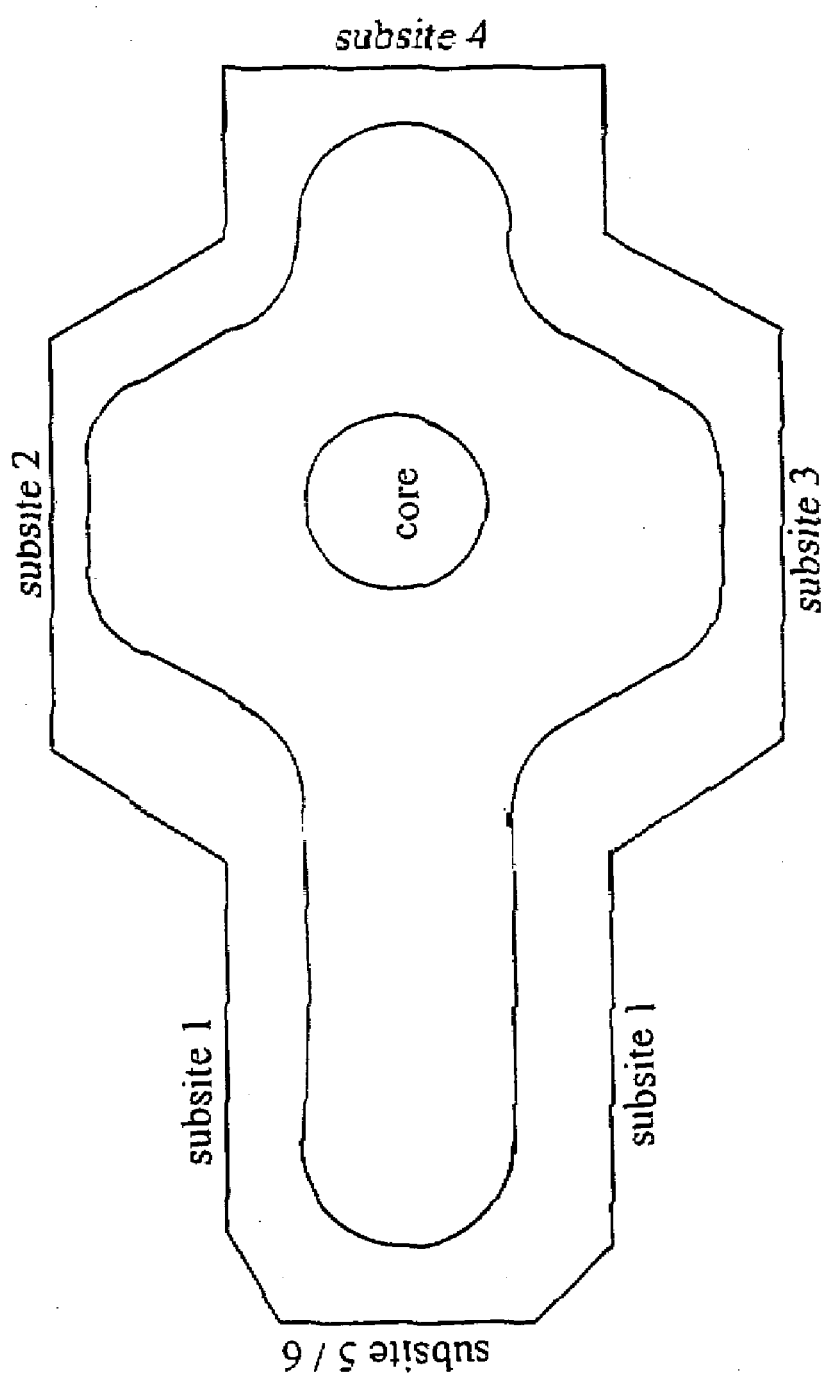

S.-F. Chen, et al., Biochemical Pharmacology, vol. 40, No. 4, XP-000900094, pp. 709-714, "Structure-Activity Relationship of Quinoline Carboxylic Acids. A New Class of Inhibitors of Dihydroorotate Dehydrogenase", 1990.

J. V. De Julian-Ortiz, et al., Journal of Medicinal Chemistry, vol. 42, XP-002199074, pp. 3308-3314, "Virtual Combinatorial Syntheses and Computational Screening of New Potential Anti-Herpes Compounds", 1999.

Takeda Chemical Industries, et al., Chemical Abstracts+Indexes, vol. 94, No. 25, XP-002199076, 1 page, "Tetrahydrophthalamide Derivatives", Jun. 22, 1981.

Matsui, et al., Chemical Abstracts+Indexes, vol. 84, No. 5, XP-002199075, 1 page, "N-Substituted-Δ¹-Cyclopentene-1, 2-Dicarboxylic Acid Monoamides as Herbicides", Feb. 2, 1976.

E. Campaigne, et al., J. Med. Chem., vol. 12, No. 2, XP-002278920, pp. 339-342, "Synthesis of Some Ureidodihydrofurans and Related Pyrimidones as Potential Antimalarials", 1969.

T. Trnovec, et al., Die Pharmazie, vol. 40, No. 6, XP-002275746, pp. 410-411, "Pharmacokinietics of Ethimizol in Man", Jun. 1985.

W. Küster, et al., Berichte Der Deutschen Chemischen Gesellschaft, vol. 57, No. 3, XP-002275747, pp. 409-413, "Über Die Bildung Von Pyrrol-Derivaten Aus Amined Von Beta-Diketonsäure-Estern.", Mar. 12, 1924.

N. Yasuda, Journal of Heterocyclic Chemistry, vol. 22, XP-002275748, pp. 413-416, "Synthesis of Novel Imidazole-4, 5-Dicarboxylic Acid Derivatives", 1985.

A. J. Carpenter, et al., Journal of Organic Chemistry, vol. 50, No. 22, XP-002275749, pp. 4362-4368, "The Scope and Limitations of Carboxamide-Induced β-Directed Metalation of 2-Substituted Furan, Thiophene, and 1-Methylpyrrole Derivatives. Application of the Method to Syntheses of 2, 3-Disubtituted Thiophenes and Furans", Nov. 1, 1985.

U.S. Appl. No. 10/736,739, filed Dec. 17, 2003, Leban et al.

METHOD OF IDENTIFYING INHIBITORS OF DHODH

The present invention relates to a polypeptide which comprises the ligand binding domain of human dihydroorotate dehydrogenase (DHODH), the crystalline forms of this polypeptide complexed with new antiproliferative agents and the use of these crystalline forms to determine the three dimensional structure of the ubiquinone binding site of DHODH complexed with the ligands. The invention also refers to the use of the three dimensional structure of the ubiquinone binding site of DHODH in methods of designing and/or identifying potential inhibitors of dihydroorotate dehydrogenase (DHODH), for example, compounds which are inhibitors of the ubiquinone binding site, for example, compounds which inhibit the binding of a native substrate to the ubiquinone binding site of DHODH.

Inhibitors of DHODH, an enzyme of the pyrimidine biosynthesis, and pharmaceutical compositions containing them, are useful, for example, for the treatment of rheumatoid arthritis (RA). Its treatment with usual medications as for example non-steroid anti-inflammatory agents is not satisfactory. In view of the increasing ageing of the population, especially in the developed Western countries or in Japan, the development of new medications for the treatment of RA is urgently required.

The DHODH inhibiting leflunomide (ARAVA) [EP 780128, WO 97/34600] is the first medicament of this class of compounds (leflunomides) for the treatment of RA. Leflunomide has immunomodulatorial as well as anti-inflammatorial properties [EP 217206, DE 2524929].

In the body, DHODH catalyzes the synthesis of pyrimidines, which are necessary for cell growth. An inhibition of DHODH inhibits the growth of (pathologically) fast proliferating cells, whereas cells which grow at normal speed may obtain their required pyrimidine bases from the normal metabolic cycle. The most important types of cells for the immune response, the lymphocytes, use exclusively the synthesis of pyrimidines for their growth and react particularly sensitively to DHODH inhibition. Substances that inhibit the growth of lymphocytes are important medicaments for the treatment of auto-immune diseases.

WO 99/45926 is a further reference that discloses compounds which act as inhibitors of DHODH. A further object of the present invention is to provide alternative effective agents which can be used for the treatment of diseases which require the inhibition of DHODH.

In Structure, 2000, Vol. 8, No. 1, pages 25-33, the structure of human DHODH in complex with the antiproliferative agents brequinar and leflunomide are described.

In Structure, 2000, Vol. 8, No. 1, pages 1227-1238, crystal structures of DHODH B and its product complex are determined. In Pharmaceutical Reasearch, 1998, Vol. 15, No. 2, pages 286-295, and in Biochemical Pharmacology, 1990, Vol. 40, No. 4, pages 709-714, the structure-activity relationship of leflunomide and quinoline carboxylic acid analogues is analyzed.

In the Journal of Medicinal Chemistry, 1999, Vol. 42, pages 3308-3314, virtual combinatorial syntheses and computational screening of new potential anti-Herpes compounds are described. In Table 3 on page 3313 experimental results regarding $IC_{50}$ and cytotoxicity are presented for 2-(2,3-difluorophenylcarbamoyl)-1-cyclopentene-1-carboxylic acid, 2-(2,6-difluorophenylcarbamoyl)-1-cyclopentene-1-carboxylic acid and 2-(2,3,4-trifluorophenyl-carbamoyl)-1-cyclopentene-1-carboxylic acid.

SUMMARY OF THE INVENTION

In one embodiment, the present invention relates to a polypeptide comprising the ligand binding domain of human dihydroorotate dehydrogenase (DHODH), crystalline forms of this polypeptide complexed with a ligand, and the three dimensional structure of the polypeptide, including the three dimensional structure of the ubiquinone binding site of DHODH.

In another embodiment, the present invention provides a method of determining the three dimensional structure of a crystalline polypeptide comprising the ubiquinone binding site of DHODH complexed with the ligands. The method comprises the steps of (1) obtaining a crystal of the polypeptide comprising the ubiquinone binding site of DHODH complexed with a ligand; (2) obtaining x-ray diffraction data for said crystal; and (3) solving the crystal structure of said crystal by using said x-ray diffraction data and the atomic coordinates for the DHODH complex with the ligand.

The invention further relates to a method of identifying a compound which is a potential inhibitor of DHODH. The method comprises the steps of (1) obtaining a crystal of the polypeptide comprising the ubiquinone binding site of DHODH complexed with a ligand; (2) obtaining the atomic coordinates of the polypeptide in said crystal; (3) using said atomic coordinates to define the ubiquinone binding site of DHODH complexed with a ligand; and (4) identifying a compound which fits the ubiquinone binding site. The method can further include the steps of obtaining or synthesizing the compound to inhibit at least one biological activity of DHODH, such as enzymatic activity.

In another embodiment, the method of identifying a potential inhibitor of DHODH comprises the step of determining the ability of one or more functional groups and/or moieties of the compound, when present in, or bound to, the ubiquinone binding site of DHODH; to interact with one or more subsites of the ubiquinone binding site of DHODH. Generally, the ubiquinone binding site of DHODH is defined by the atomic coordinates of a polypeptide comprising the ubiquinone binding site of DHODH. If the compound is able to interact with a preselected number or set of subsites, or has a calculated interaction energy with a desired or preselected range, the compound is identified as a potential inhibitor of DHODH.

BRIEF DESCRIPTION OF THE INVENTION

FIG. 1 schematically depicts the spatial arrangement of the subsites of DHODH.

Figure 2:
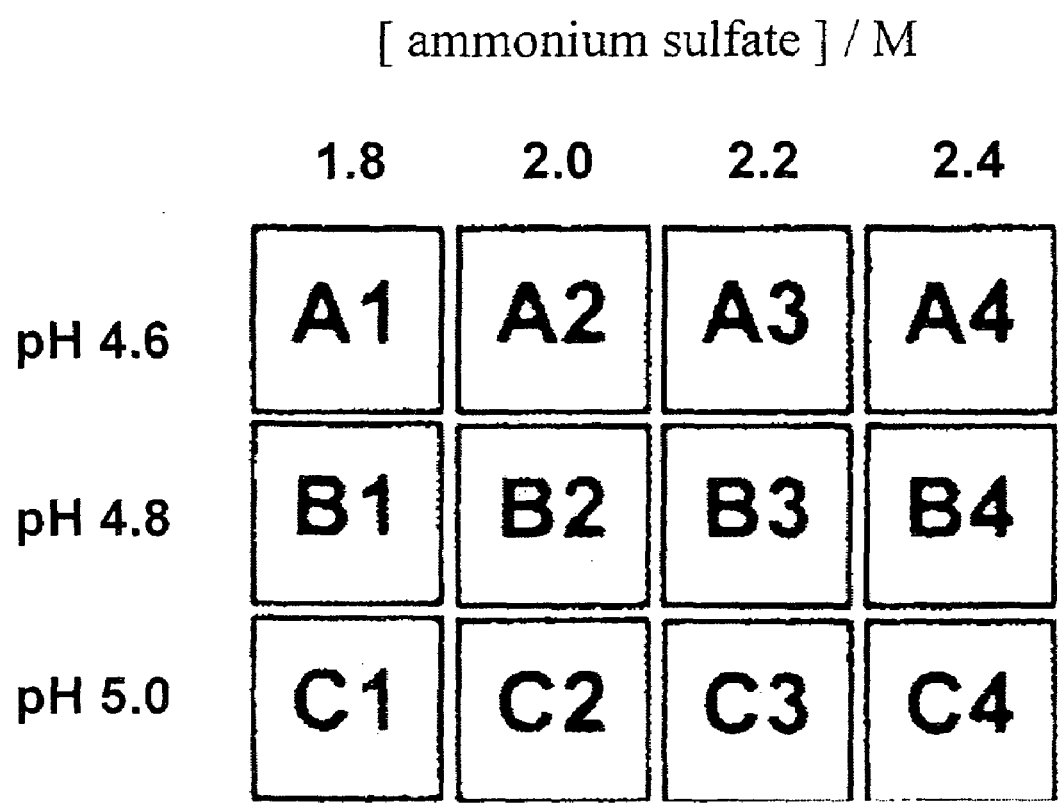

FIG. 2 shows the minimal grid screen used for crystallization trails.

DETAILED DESCRIPTION OF THE INVENTION

The human DHODH enzyme is composed of two domains, namely a large C-terminal domain (Met78 to C-terminus) and a small N-terminal domain (Met30 to Leu68), connected by an extended loop. The large C-terminal domain can be described best as an α/β-barrel fold with a central barrel of eight parallel β strands surrounded by eight α helices. The redox site, formed by the substrate binding site and the site of the cofactor flavine mononucleotide (FMN), is located on this large C-terminal domain. The small N-terminal domain, on the other hand, consists of two α helices, α1 and α2, connected by a short loop. This small N-terminal domain contains the binding site for the cofactor ubiquinone. The helices α1 and α2 span a slot of about 10×20 Å in the so-called hydrophobic patch, with the short α1-α2 loop at the narrow end of that slot. The slot forms the entrance to a tunnel that ends at the FMN cavity nearby the α1-α2 loop. This tunnel is narrowing towards the proximal redox site and ends with several charged or polar sidechains (Gln47, His56, Tyr356, Thr360 and Arg136). It is evident that ubiquinone which can easily diffuse into the mitochondrial inner membrane uses this tunnel to approach the FMN cofactor for a redox reaction.

The structural knowledge mentioned above can be used to design potential inhibitors of the human DHODH activity targeting the tunnel mentioned above and competing with ubiquinone for the ubiquinone binding site. Potential inhibitors were co-crystallized with human DHODH (Met30 to Arg396) and the three dimensional structures were solved by protein X-ray crystallography techniques, ten of the solved structures being three dimensional structures of human DHODH (Met30 to Arg396) in complex with compounds 1, 2, 3, 4, 5, 6, 7, 8, 9, and 10. These crystal structures were solved at atomic resolution and the binding modes of the ten compounds were analyzed. The structural formulars of the co-crystallized compounds are given below.

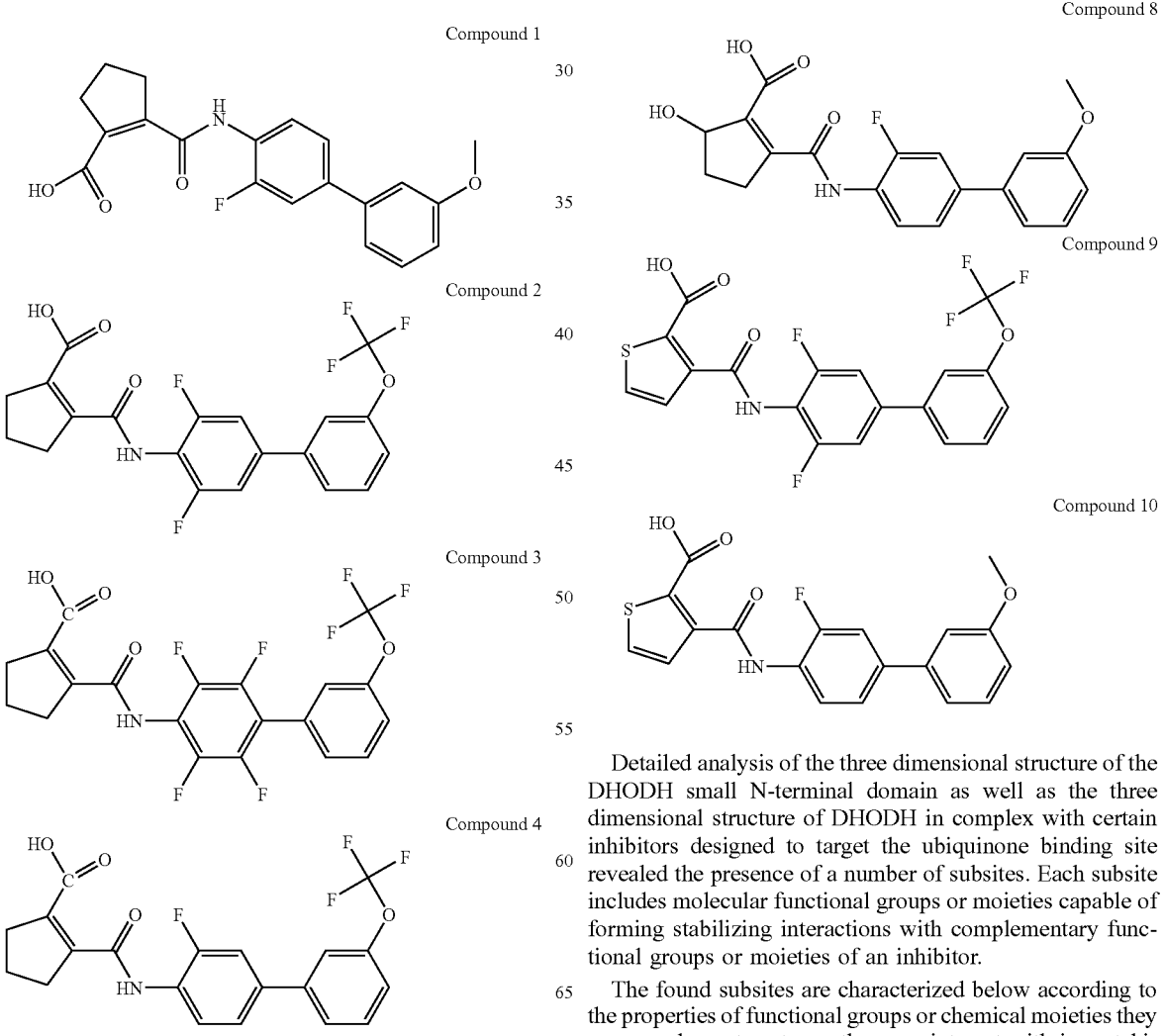

Detailed analysis of the three dimensional structure of the DHODH small N-terminal domain as well as the three dimensional structure of DHODH in complex with certain inhibitors designed to target the ubiquinone binding site revealed the presence of a number of subsites. Each subsite includes molecular functional groups or moieties capable of forming stabilizing interactions with complementary functional groups or moieties of an inhibitor.

The found subsites are characterized below according to the properties of functional groups or chemical moieties they are complementary to, or they can interact with in a stabilizing way, for example, groups or moieties capable of hydrogen bond formation or groups or moieties with hydrophobic (=lipophilic) character. A hydrogen bond is formed between a hydrogen atom covalently bond to an electronegative element (proton donor or hydrogen bond donor) and a lonely electron pair of a second electronegative atom (proton acceptor or hydrogen bond acceptor). Hydrogen bonds typically occur when the hydrogen bond donor and the hydrogen bond acceptor are separated by about 2.5 Å and 3.5 Å. Stabilizing hydrophobic or lipophilic interactions occur if two groups or moieties with hydrophobic/lipophilic character, for example, aliphatic chains or aromatic systems, are separated by distances close to their van der Waals radii.

The method of identifying a potential inhibitor of DHODH comprises the step of determining the ability of one or more functional groups and/or moieties of the compound, when present in the ubiquinone binding site, to interact with one or more subsites of the ubiquinone binding site. Preferably, the ubiquinone binding site is defined by the atomic coordinates of a polypeptide comprising the ubiquinone binding site of DHODH. If the compound is able to interact with a preselected number or set of subsites, the compound is identified as a potential inhibitor of DHODH.

A functional group or moiety of the compound is said to "interact" with a subsite of the ubiquinone binding site if it participates in an energetically favourable, or stabilizing, interaction with one or more complementary moieties within the subsite.

Two chemical moieties are "complementary" if they are capable, when suitably positioned, of participating in an attractive, or stabilizing, interaction, such as an electrostatic or an van der Waals interaction. Typically, the attractive interaction is an ion-ion, a salt bridge, ion-dipole, dipole-dipole, hydrogen bond, pi-pi or hydrophobic interaction. An extreme case of attractive interaction is the formation of a covalent bond by a chemical reaction between the test compound and the enzyme. For example, a negatively charged moiety and a positively charged moiety are complementary because, if suitably positioned, they can form a salt bridge. Likewise, a hydrogen bond donor and a hydrogen bond acceptor are complementary if suitably positioned.

Preferably, the groups capable of hydrogen bond formation ("HB") are selected from halogen, such as fluorine, chlorine, bromine and iodine, $NO_2$, haloalkyl, haloalkyloxy, CN, hydroxyl, amino, hydroxylamine, hydroxamic acid, carbonyl, carbonic acid, sulfonamide, amide, sulfone, sulfonic acid, alkylthio, alkoxy, ester, hydroxyalkylamino group, and other groups including a heteroatom having at least one lone pair of electrons, such as groups containing trivalent phosphorous, di- and tetravalent sulfur, oxygen and nitrogen atoms;

Preferably, hydrophobic groups ("H") are selected from groups, such as linear, branched or cyclic alkyl groups; linear, branched or cyclic alkenyl groups; linear, branched or cyclic alkynyl groups; aryl groups, such as mono- and polycyclic aromatic hydrocarbyl groups and mono- and polycyclic heteroaryl groups;

Preferably, negatively charged groups ("N") are selected from groups, such as carboxylate, sulfonamide, sulfamate, boronate, vanadate, sulfonate, sulfinate and phosphonate groups. A given chemical moiety can contain one or more of these groups.

In the following a detailed description of identified subsites is provided. Residue numbering and atom labeling is identical to the numbering and labeling in Tables 29, 30, and 31.

Subsite 1: Hydrophobic pocket; interacting chemical moieties: H;
Residues involved: Leu 42; Met 43; Leu 46; Ala 55; Ala 59; Phe 98; Met 111; Leu 359; Pro 364;
Non-hydrogen atoms which interact with H: Leu 42 CB, CG, CD1, CD2; Met 43 SD, CE; Leu 46 CB, CG, CD1, CD2; Ala 55 CB; Ala 59 CA, CB; Phe 98 CG, CD1, CD2, CE1, CE2; Met 111 SD, CE; Leu 359 CA, CB, CG, CD1, CD2; Pro 364 CB, CD, CG;
Preferably for the hydrophobic interacting with subsite 1, the group is selected from aryl groups, such as an aromatic group having five to fifteen carbon atoms, which can optionally be substituted by one or more substituents R'. More preferably the aryl group is a phenyl group, such as —$CH_2Ph$, —$C_2H_4Ph$, —CH=CH-Ph, —C≡C-Ph, -o-$C_6H_4$—R', -m-$C_6H_4$—R', —p—$C_6H_4$—R', -o-$CH_2$—$C_6H_4$—R', -m-$CH_2$—$C_6H_4$—R', -p-$CH_2$—$C_6H_4$—R'; or a biphenyl group, in which the phenyl rings can optionally be substituted by one or more substituents R', such biphenyl groups are —$C_6H_4$—$C_6H_5$; —$C_6H_4$—$C_6H_4$—R'; —$C_6H_3$—R'—$C_6H_5$; —$C_6H_3$—R'—$C_6H_4$—R'; —$C_6H_3$—R'—$C_6H_4$—R'; —$C_6H_4$—O—$C_6H_5$; —$C_6H_3$—R'—O—$C_6H_4$—R'; —$C_6H_4$—O—$C_6H_4$—R'; —$C_6H_3$—R'—O—$C_6H_5$; —$C_6H_4$—O—$CH_2$—$C_6H_5$; —$C_6H_3$—R'—O—$CH_2$—$C_6H_4$—R'; —$C_6H_4$—O—$CH_2$—$C_6H_4$—R'; —$C_6H_3$—R'—O—$CH_2$—$C_6H_5$;
R' is independently H, —$CO_2$R", —CONHR", —CR"O, —$SO_2$NR", —NR"—CO-haloalkyl, —$NO_2$, —NR"—$SO_2$-haloalkyl, —NR"—$SO_2$-alkyl, —$SO_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;
R" is independently hydrogen, haloalkyl, hydroxyalkyl, alkyl, cycloalkyl, aryl, heteroaryl or aminoalkyl;
R' is preferably F, Cl, Br, I, $CF_3$, $OCF_3$, or $OCH_3$;
Subsite 2: First anion binding site; interacting with HB, N, HB and N, HB and HB, or N and N;
Residues involved: Gln 47; Arg 136; one conserved water molecule
Non-hydrogen atoms which interact with HB and N: Glu 47 OE1, NE2; Arg 136 NE, NH1, NH2; conserved water molecule OH2.
preferably for one or two hydrogen bond formations with subsite 2 the group is selected from halogen, such as fluorine, chlorine, bromine and iodine, $NO_2$, haloalkyl, haloalkyloxy, CN, hydroxyl, amino, hydroxylamine, hydroxamic acids, carbonyl, carbonic acid, sulfonamide, amide, sulfone, sulfonic acid, alkylthio, alkoxy, such as methoxy, ester, hydroxyalkylamino, carboxylate, tetrazole, sulfonamide, sulfamate, boronate, vanadate, sulfonate, sulfinate and phosphonate group, more preferably from a carboxylate, sulfonamide, sulfamate, sulfonate, carbonyl or carbonic acid group.
Subsite 3: Second anion binding site; interacting with HB, N, HB and N, HB and HB, or N and N;
Residues involved: His 56; Tyr 356; Tyr 147 (interacting via a conserved water molecule);
Non-hydrogen atoms which interact with HB and N: His 56 N, ND1; Tyr 356 OH; Tyr 147 OH (interacting via a conserved water molecule);
preferably for one or two hydrogen bond formations with subsite 2 the group is selected from halogen, such as fluorine, chlorine, bromine and iodine, $NO_2$, haloalkyl, haloalkyloxy, CN, hydroxyl, amino, hydroxylamine, hydroxamic acids, carbonyl, carbonic acid, sulfonamide, amide, sulfone, sulfonic acid, alkylthio, alkoxy, such as methoxy, ester, hydroxyalkylamino, carboxylate, tetrazole, sulfonamide, sulfamate, boronate, vanadate, sulfonate, sulfinate and phosphonate group, more preferably from a carboxylate, sulfonamide, sulfamate, sulfonate, carbonyl or carbonic acid group.

Subsite 4: Remote hydrophobic pocket; interacting chemical moieties: H;

Residues involved: Pro 52; Val 134; Arg 136; Val 143; Thr 360; FMN;

Non-hydrogen atoms which interact with H: Pro 52 CB, CG, CD; Val 134 CB, CG1, CG2; Val 143 CB, CG1, CG2; Thr 360 CG2; FMN C7M, C8M;

Preferably for the hydrophobic interacting with subsite 4, the group is selected from such as linear, branched or cyclic $C_1$-$C_6$-alkyl groups; such as methyl, ethyl, propyl, butyl, tert. butyl, linear, branched or cyclic $C_1$-$C_6$-alkenyl groups; linear, branched or cyclic $C_1$-$C_6$-alkynyl groups; aryl groups, such as mono- and bi aromatic hydrocarbyl groups, such as —$CH_2$Ph, —$C_2H_4$Ph, —CH=CH-Ph, —C≡C-Ph, -o-$C_6H_4$—R', -m-$C_6H_4$—R, —p—$C_6H_4$—R, -o-$CH_2$—$C_6H_4$—R, -m-$CH_2$—$C_6H_4$—R, -p-$CH_2$—$C_6H_4$—R and mono- and bicyclic heteroaryl groups, such as thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, indolyl, indolinyl, tetrazolyl, benzo-[b]-furanyl, benzo[b]thiophenyl, benzimidazolyl, benzothiazolyl, quinazolinyl, quinoxazolinyl, or preferably isoxazol-3-yl, isoxazol-4-yl, isoxazol-5-yl, quinolinyl, tetrahydroquinolinyl, isoquinolinyl, tetrahydroisoquinolinyl; all this groups can optionally be substituted by one or more substituents R, such as H, amino, alkoxy, OH, SH, alkylthio, hydroxyalkyl, haloalkyl, haloalkyloxy hydroxyalkylamino, halogen; R is preferably F, Cl, Br, I, $CF_3$, $OCF_3$, or $OCH_3$;

Core: chemical moiety connecting the different moieties interacting with Subsite 1, Subsite 2, Subsite 3, and Subsite 4;

Preferably, the core is selected from cyclic alkyl groups; cyclic alkenyl groups; cyclic alkynyl groups; aryl groups, such as mono- and polycyclic aromatic hydrocarbyl groups and mono- and polycyclic heteroaryl groups; more preferably it is selected from mono-, or bicyclic aromatic or non-aromatic ring systems, most preferably from 5-membered mono-, or bicyclic aromatic or non-aromatic ring systems, such as trans-cyclopentan-1,2-diyl, trans-cyclohexan-1,2-diyl, cis-cyclopentan-1,2-diyl, cis-cyclohexan-1,2-diyl, 1-cyclopenten-1,2-diyl, 2-cyclopenten-1,2-diyl, 3-cyclopenten-1,2-diyl, 4-cyclopenten-1,2-diyl, 5-cyclopenten-1,2-diyl, 1-cyclopenten-1,3-diyl, 1-cyclopenten-1,4-diyl, 1-cyclohexen-1,2-diyl, 1-cyclohepten-1,2-diyl or 1-cycloocten-1,2-diyl, 2,5-dihydrothiophene-3,4-diyl, 2,5-dihydro-furan-3,4-diyl, 2,5-dihydro-1H-pyrrole-3,4-diyl, 2,5-dihydro-1-methyl-pyrrole-3,4-diyl, 2,5-dihydro-1-ethyl-pyrrole-3,4-diyl, 2,5-dihydro-1-acetyl-pyrrole-3,4-diyl, 2,5-dihydro-1-methylsulfonyl-pyrrole-3,4-diyl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, indolyl, indolinyl, tetrazolyl, benzo-[b]-furanyl, benzo[b]thiophenyl, benzimidazolyl, benzothiazolyl, quinazolinyl, quinoxazolinyl, or preferably quinolinyl, tetrahydroquinolinyl, isoquinolinyl, tetrahydroisoquinolinyl or from a group comprising of:

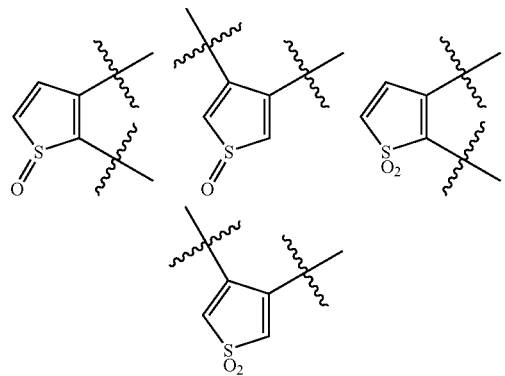

Bridge: chemical moiety connecting the core with Subsite 1;

Preferably, the bridge is selected from —NH; —O; —CO—NH; —NH—CO; —NH—CO—NH; alkyl; —O—$CH_2$; —$CH_2$—O; —O—$CH_2$—$CH_2$; —$CH_2$—$CH_2$—O; —NH—$CH_2$; —$CH_2$—NH; —NH—$CH_2$—$CH_2$; —$CH_2$—$CH_2$—NH; —$CH_2$—CO—NH; —$CH_2$—NH—CO;

Subsite 5: Solvent anchor; interacting chemical moieties: HB

Residues involved: Met 30; Tyr 38; Leu 67;

Non-hydrogen atoms which interact with HB: Met 30 O, SD, CE; Tyr 38 OH, CE2, CD2; Leu 67 O;

preferably for the hydrogen bond formation with subsite 5, the group is selected from F, Cl, Br, I, $CF_3$, $OCF_3$, or $OCH_3$ Subsite 6: Solvent anchor; interacting chemical moieties: H;

Residues involved: Leu 68;

Non-hydrogen atoms which interact with H: Leu 68 CB, CG, CD1, CD2;

Preferably for the hydrophobic interacting with subsite 6, the group is selected from such as linear, branched or cyclic $C_1$-$C_6$-alkyl groups; such as methyl, ethyl, propyl, butyl, tert. butyl, linear, branched or cyclic $C_1$-$C_6$-alkenyl groups; linear, branched or cyclic $C_1$-$C_6$-alkynyl groups; aryl groups, such as mono- and bi aromatic hydrocarbyl groups, such as —$CH_2$Ph, —$C_2H_4$Ph, —CH=CH-Ph, —C≡C-Ph, -o-$C_6H_4$—R', -m-$C_6H_4$—R, -p-$C_6H_4$—R, -o-$CH_2$—$C_6H_4$—R, -m-$CH_2$—$C_6H_4$—R, -p-$CH_2$—$C_6H_4$—R and mono- and bicyclic heteroaryl groups.

An alkyl group, if not stated otherwise, denotes a linear or branched $C_1$-$C_6$-alkyl, preferably a linear or branched chain of one to five carbon atoms, a linear or branched $C_1$-$C_6$-alkenyl or a linear or branched $C_{1-6}$-alkinyl group, which can optionally be substituted by one or more substituents R', preferably by halogen;

the $C_1$-$C_6$-alkyl, $C_1$-$C_6$-alkenyl and $C_{1-6}$-alkinyl residue may be selected from the group comprising —$CH_3$, —$C_2H_5$, —CH=$CH_2$, —C≡CH, —$C_3H_7$, —CH($CH_3$)$_2$, —$CH_2$—CH=$CH_2$, —C($CH_3$)=$CH_2$, —CH=CH—

$CH_3$, $-C\equiv C-CH_3$, $-CH_2-C\equiv CH$, $-C_4H_9$, $-CH_2-CH(CH_3)_2$, $-CH(CH_3)-C_2H_5$, $-C(CH_3)_3$, $-C_5H_{11}$, $-C_6H_{13}$, $-C(R')_3$, $-C_2(R')_5$, $-CH_2-C(R')_3$, $-C_3(R')_7$, $-C_2H_4-C(R')_3$, $-C_2H_4-CH=CH_2$, $-CH=CH-C_2H_5$, $-CH=C(CH_3)_2$, $-CH_2-CH=CH-CH_3$, $-CH=CH-CH=CH_2$, $-C_2H_4-C\equiv CH$, $-C\equiv C_2H_5$, $-CH_2-C\equiv C-CH_3$, $-C\equiv C-CH=CH_2$, $-CH=CH-C\equiv CH$, $-C\equiv C-C\equiv CH$, $-C_2H_4-CH(CH_3)_2$, $-CH(CH_3)-C_3H_7$, $-CH_2-CH(CH_3)-C_2H_5$, $-CH(CH_3)-CH(CH_3)_2$, $-C(CH_3)_2-C_2H_5$, $-CH_2-C(CH_3)_3$, $-C_3H_6-CH=CH_2$, $-CH=CH-C_3H_7$, $-C_2H_4-CH=CH-CH_3$, $-CH_2-CH=CH-C_2H_5$, $-CH_2-CH=CH-CH=CH_2$, $-CH=CH-CH=CH-CH_3$, $-CH=CH-CH_2-CH=CH_2$, $-C(CH_3)=CH-CH=CH_2$, $-CH=C(CH_3)CH=CH_2$, $-CH=CH-C(CH_3)=CH_2$, $-CH_2-CH=C(CH_3)_2$, $C(CH_3)=C(CH_3)_2$, $-C_3H_6-C\equiv CH$, $-C\equiv C-C_3H_7$, $-C_2H_4-C\equiv CH_3$, $-CH_2-C\equiv C-C_2H_5$, $-CH_2-C\equiv C-CH=CH_2$, $-CH_2-CH=CH-C\equiv CH$, $-CH_2-C\equiv C-C\equiv CH$, $-C\equiv C-CH=CH-CH_3$, $-CH=CH-C\equiv C-CH_3$, $-C\equiv C-C\equiv C-CH_3$, $-C\equiv C-CH_2-CH=CH_2$, $-CH=CH-CH_2-C\equiv CH$, $-C\equiv C-CH_2-CH=CH_2$, $-C(CH_3)=CH-CH=CH_2$, $-CH=C(CH_3)CH=CH_2$, $-CH=CH-C(CH_3)=CH_2$, $-C(CH_3)=CH-C\equiv CH$, $-CH=C(CH_3)-C\equiv CH$, $-C\equiv C-C(CH_3)=CH_2$, $-C_3H_6-CH(CH_3)_2$, $-C_2H_4-CH(CH_3)-C_2H_5$, $-CH(CH_3)-C_4H_9$, $-CH_2-CH(CH_3)-C_3H_7$, $-CH(CH_3)-CH_2-CH(CH_3)_2$, $-CH(CH_3)-CH(CH_3)-C_2H_5$, $-CH_2-CH(CH_3)-CH(CH_3)_2$, $-CH_2-C(CH_3)_2-C_2H_5$, $-C(CH_3)_2-C_3H_7$, $-C(CH_3)_2-CH(CH_3)_2$, $-C_2H_4-C(CH_3)_3$, $-CH(CH_3)-C(CH_3)_3$, $-C_4H_8-CH=CH_2$, $-CH=CH-C_4H_9$, $-C_3H_6-CH=CH-CH_3$, $-CH_2-CH=CH-C_3H_7$, $-C_2H_4-CH=CH-C_2H_5$, $CH_2-C(CH_3)=C(CH_3)_2$, $-C_2H_4-CH=C(CH_3)_2$, $-C_4H_8-C\equiv CH$, $-C\equiv C-C_4H_9$, $-C_3H_6-C\equiv C-CH_3$, $-CH_2-C\equiv C-C_3H_7$, $-C_2H_4-C\equiv C-C_2H_5$;

R' is independently H, $-CO_2R''$, $-CONHR''$, $-CR''O$, $-SO_2NR''$, $-NR''-CO$-haloalkyl, $-NO_2$, $-NR''-SO_2$-haloalkyl, $-NR''-SO_2$-alkyl, $-SO_2$-alkyl, $-NR''-CO$-alkyl, $-CN$, alkyl, cycloalkyl, aminoalkyl, alkylamino, alkoxy, $-OH$, $-SH$, alkylthio, hydroxyalkyl, hydroxyalkylamino, halogen, haloalkyl, haloalkyloxy, aryl, arylalkyl or heteroaryl;

R" is independently hydrogen, haloalkyl, hydroxyalkyl, alkyl, cycloalkyl, aryl, heteroaryl or aminoalkyl;

a cycloalkyl group denotes a non-aromatic ring system containing four to eight carbon atoms, preferably four to eight carbon atoms, wherein one or more of the carbon atoms in the ring can be substituted by a group X, X being as defined above; the $C_4$-$C_8$-cycloalkyl residue may be selected from the group comprising -cyclo-$C_4H_7$, -cyclo-$C_5H_9$, -cyclo-$C_6H_{11}$, -cyclo-$C_7H_{13}$, -cyclo-$C_8H_{15}$;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above.

an haloalkyl group denotes an alkyl group which is substituted by one to five halogen atoms, the alkyl group being as defined above; the haloalkyl group is preferably a $-C(R^{10})_3$, $-CR^{10}(R^{10'})_2$, $-CR^{10}(R^{10'})R^{10''}$, $-C_2(R^{10})_5$, $-CH_2-C(R^{10})_3$, $-CH_2-CR^{10}(R^{10'})_2$, $-CH_2-CR^{10}(R^{10'})R^{10''}$, $-C_3(R^{10})_7$ or $-C_2H_4-C(R^{10})_3$, wherein $R^{10}$, $R^{10'}$, $R^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a $-OC(R^{10})_3$, $-OCR^{10}(R^{10'})_2$, $-OCR^{10}(R^{10'})R^{10''}$, $-OC_2(R^{10})_5$, $-OCH_2-C(R^{10})_3$, $-OCH_2-CR^{10}(R^{10'})_2$, $-OCH_2-CR^{10}(R^{10'})R^{10''}$, $-OC_3(R^{10})_7$ or $-OC_2H_4-C(R^{10})_3$, wherein $R^{10}$, $R^{10'}$, $R^{10''}$ represent F, Cl, Br or I, preferably F;

a hydroxyalkylamino group denotes an (HO-alkyl)$_2$-N— group or HO-alkyl-NH— group, the alkyl group being as defined above;

an alkylamino group denotes an HN-alkyl or N-dialkyl group, the alkyl group being as defined above;

a halogen group is chlorine, bromine, fluorine or iodine, fluorine being preferred;

an aryl group preferably denotes an aromatic group having five to fifteen carbon atoms, which can optionally be substituted by one or more substituents R', where R' is as defined above; the aryl group is preferably a phenyl group, $-CH_2Ph$, $-C_2H_4Ph$, $-CH=CH-Ph$, $-C\equiv C-Ph$, -o-$C_6H_4$—R', -m-$C_6H_4$—R', -p-$C_6H_4$—R', -o-$CH_2$—$C_6H_4$—R', -m-$CH_2$—$C_6H_4$—R', -p-$CH_2$—$C_6H_4$—R';

a heteroaryl group denotes a 5- or 6-membered heterocyclic group which contains at least one heteroatom like O, N, S. This heterocyclic group can be fused to another ring. For example, this group can be selected from a thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, indolyl, indolinyl, benzo-[b]-furanyl, benzo[b]thiophenyl, benzimidazolyl, benzothiazolyl, quinazolinyl, quinoxazolinyl, or preferably quinolinyl, tetrahydroquinolinyl, isoquinolinyl, tetrahydroisoquinolinyl group. This heterocyclic group can optionally be substituted by one or more substituents R', where R' is as defined above. In another embodiment, the present invention provides DHODH inhibitors, and methods of use thereof, which are capable of binding to the ubiquinone binding site of DHODH, for example, compounds wich are identified as inhibitors of DHODH or which are designed by the methods described above to inhibit DHODH. For example, the invention includes compounds which interact with one or more, preferably two or more, and more preferably, three or more of DHODH subsites 1 to 6.

Preferably an inhibitor of DHODH should have a core-unit and interact with subsite 1, 2, 3 and 5 or an inhibitor of DHODH should have a core-unit and interact with subsite 1, 2 and 5, or an inhibitor of DHODH should have a core-unit and interact with subsite 1, 3 and 5.

More preferably an inhibitor of DHODH should have a core-unit and interact with subsite 1, 2 and 3, or an inhibitor of DHODH should have a core-unit and interact with subsite 1 and 3. In FIG. 1, the spatial arrangement of the subsites is depicted schematically.

The three dimensional structure published by Shenpig et al. shows human DHODH(Met30-Arg396) in complex with brequinar and the leflunomide metabolite A771726, respectively. The main interaction in the binding of brequinar to DHODH is the formation of a salt bridge between the carboxy group of brequinar and the sidechain of Arg136. In particular, the salt bridge is formed between the carboxylic group and the atoms NE, NH1 or NH2. More precisely, the above mentioned subsite 2, the first anion binding site, is addressed in this kind of interaction. In the following, this type of interactioned will be termed "brequinar-like binding mode".

Analysis of the three dimensional structures of human DHODH in complex with ligands presented here clearly shows a new binding mode for inhibitors containing a carboxylic acid group. This binding mode differs from the brequinar-like binding mode in interacting not with subsite 2 but with subsite 3, termed the second anion binding site. In particular this is true for inhibitor compounds 1, 4, 5, 7 and 8 as can be seen from Table 29. This so far unobserved binding mode will be termed "non-brequinar-like" binding mode in the following.

The "non-brequinar-like" binding mode is characterized by a number of hydrogen bonds formed between the ligand and protein residues belonging to subsite 3. In particular this residues are His 56, Tyr 356 and Tyr 147. Non-hydrogen atoms involved in the formation of hydrogen bonds are N and ND1 of His 56, the oxygen of the hydroxyl group of Tyr 356 and the oxygen of the hydroxyl group of Tyr 147. The latter interaction involves a conserved water molecule bridging the space between the carboxyl function of the ligand molecule and the hydroxyl group of the tyrosine residue 147.

Similar findings can be seen in the three dimensional structure of human DHODH in complex with the compounds 2, 6 and 10. As can be seen clearly from the electron density map, the compounds 2, 6 and 10 are able to utilize both anion binding sites (subsite 2 and 3) by adopting two alternative conformations. Therefore, both a brequinar-like and a non-brequinar-like binding mode can be utilized. In the brequinar-like binding mode the carboxy group of compounds 2, 6 and 10 forms hydrogen bonds to the sidechains of residues Gln 47 and Arg 136. In the non-brequinar-like binding mode the five membered ring of compounds 2, 6 and 10 containing the carboxy group is rotated by almost 180 degrees and forms hydrogen bonds to residues His 56 and Tyr 356. Non-hydrogen atoms involved in the formation of hydrogen bonds are N and ND1 of His 56 and the oxygen of the hydroxyl group of Tyr 356.

The compounds 2, 3 and 4 are particularly interesting for a structure-activity-relationship (SAR) analysis. These molecules differ only in the degree of ring substitution (see structures above). Clearly, one can observe a correlation between the number of fluorinated positions at the aromatic ring in the middle of the molecules and the corresponding $IC_{50}$ values. The higher the number of ring substituents the lower the $IC_{50}$. Interestingly compound 2 and compound 3 display both the brequinar-like and non-brequinar-like binding mode in the crystal structure (see table 27). It is quite reasonable to speculate whether the ring substituents exhibit a steering effect on the five membered ring and by such facilitate the formation of the more favourable brequinar-like binding mode. Therefore, the presence of both binding modes might explain the increased affinity of this compounds.

TABLE 27

Relation of inhibitor binding mode and degree of ring substitutions. Structures of the compounds are shown above.

| Compound | Brequinar-like | Non-Brequinar-like |
| --- | --- | --- |
| 3 | X | X |
| 2 | X | X |
| 4 |   | X |

A similar structure-activity-relationship can be deduced from the crystal structures of humann DHODH in complex with compounds 9 and 10. These compounds carry a sulfur atom at an ortho position with respect to the carboxylic group in the five membered ring. Compound 10 is single substituted with fluorine at the biaryl ring system, whereas compound 9 bears two substituents. Interestingly, compound 9 exhibits a pure brequinar-like binding mode whereas compound 10 shows both alternatives. Additionally, the sulfur atom in the ortho position on the five membered ring can favourably interact with the protein's subsite 4 (remote hydrophobic pocket). The activity data correlate to a very high degree with the presence of a particular binding mode (Table 28). Obviously, not only the degree of ring subsitution but also ring planarity might contribute to the formation of a particular binding mode.

TABLE 28

Relation of inhibitor binding mode and degree of ring substitutions. Structures of the compounds are shown above.

| Compound | Brequinar-like | Non-Brequinar-like |
| --- | --- | --- |
| 9 | X |   |
| 10 | X | X |

From the discussion above several possibilities for further synthesis of compounds emerge. First, one could try to stabilize the Brequinar-like conformation by a more elaborate variation of substitution patterns at the aromatic ring system. A second way to improve on the affinity might comprise the addition of a second functional group, which is able to form hydrogen bonds or salt bridges to the five membered ring opposite to the position of the carboxy group. Thus the molecule should be able to address both anion subsites and utilize brequinar-like as well as non-brequinar-like binding modes at the same time. This is highly supported by the evidence of structural data. Mobility at the site of Gln47 and Arg136 indicates that the protein should be able to exhibit sufficient conformational flexibility to adopt ligand molecules displaying more demanding sterical requirements.

Another interesting finding is that the DHODH binding pocket is able to selectively discriminate between enantiomeres. Compounds 5 and 6 were synthesized as a racemic mixtures caused by the presence of a stereo centre at the five membered ring (see above). The racemic mixtures were used for crystallization experiments. In both cases the refined structures unequivocally showed the inhibitor bound in its R-form. It is not possible to fit the S-enantiomer into the electron density.

The invention further provides a method of designing a compound which is a potential inhibitor of DHODH. The method includes the steps of (1) identifying one or more functional groups capable of interacting with one or more subsites of the ubiquinone binding site of DHODH; and (2)

identifying a scaffold which presents the functional group or functional groups identified in step 1 in a suitable orientation for interacting with one or more subsites of the ubiquinone binding site of DHODH. The compound which results from attachment of the identified functional groups or moieties to the identified scaffold is a potential inhibitor of DHODH. The DHODH ubiquinone binding site is, generally, defined by the atomic coordinates of a polypeptide comprising the DHODH ubiquinone binding site.

The present invention also provides several advantages. For example, the invention provides a new three dimensional structure of a crystalline polypeptide comprising the ubiquinone binding site of DHODH complexed with the ligands. This structure enables the rational development of inhibitors of DHODH by permitting the design and/or identification of molecular structures having features which facilitate binding to the ubiquinone binding site of DHODH. The methods of use of this structure disclosed herein, thus, permit more rapid discovery of compounds which are potentially useful for the treatment of conditions which are mediated, at least in part, by DHODH activity.

The polypeptide preferably comprises the ubiquinone binding site of a mammalian DHODH. More preferably the polypeptide comprises the ubiquinone binding site of human DHODH. In a preferred embodiment, the polypeptide is a polypeptide of the present invention, as described above.

The polypeptide can be crystallized using methods known in the art, such as the methods described in Structure, 2000, Vol. 8, No. 1, pages 25-33, to afford polypeptide crystals which are suitable for x-ray diffraction studies. A crystalline polypeptide/ligand complex can be produced by co-crystallizing the polypeptide with a solution including the ligand.

The atomic coordinates of the polypeptide and the ligand can be determined, for example, by x-ray crystallography using methods known in the art. The data obtained from the crystallography can be used to generate atomic coordinates, for example, of the polypeptide and ligand, if present. As is known in the art, solution and refinement of the x-ray crystal structure can result in the determination of coordinates for some or all of the non-hydrogen atoms.

The atomic coordinates of the polypeptide can be used, as is known in the art, to generate a three-dimensional structure of the ubiquinone binding site of DHODH. This structure can then be used to assess the ability of any given compound, preferably using computer-based methods, to fit into the ubiquinone binding site.

The atomic coordinates of the polypeptide/ligand complex can be used, as is known in the art, to generate a three-dimensional structure of the ligand in its binding conformation. This structure can then be used to assess the ability of any given compound, preferably using computer-based methods, to exhibit a similar spatial orientation and electrostatic and/or van der Waals interactions as the ligand and therefore, to fit into the addressed binding site.

A compound fits into the ubiquinone binding site if it is of suitable size and shape to physically reside in the ubiquinone binding site, that is if it has a shape which is complementary to the ubiquinone binding site and can reside in the ubiquinone binding site without significant unfavorable sterical or van der Waals interactions. Preferably, the compound includes one or more functional groups and/or moieties which interact with one or more subsites within the ubiquinone binding site. Computational methods for evaluating the ability of a compound to fit into the ubiquinone binding site, as defined by the atomic coordinates of the polypeptide, are known in the art, and representative examples are provided below.

In another embodiment, the method of identifying a potential inhibitor of DHODH comprises the step of determining the ability of one or more functional groups and/or moieties of the compound, when present in the DHODH ubiquinone binding site, to interact with one or more subsites of the DHODH ubiquinone binding site. Preferably, the DHODH ubiquinone binding site is defined by the atomic coordinates of a polypeptide comprising the DHODH ubiquinone binding site. If the compound is able to interact with a preselected number of subsites, the compound is identified as a potential inhibitor of DHODH.

In yet another embodiment, the method of identifying a potential inhibitor of DHODH comprises the steps of (1) identifying the size and shape of the ligand co-crystallized in the polypeptide/ligand complex and/or identifying functional groups or moieties of the ligand which are capable to form stabilizing interactions with the polypeptide, and (2) by comparison with these, identifying one or more functional groups and/or moieties of any given compound which have similar size and shape as the cocrystallized ligand and/or are capable to form one or more interactions to the polypeptide in a similar manner as the co-crystallized ligand. If a compound exhibits one or more of these features, the compound is identified as a potential inhibitor of DHODH.

A functional group or moiety of the compound is said to "interact" with a subsite of the DHODH ubiquinone binding site if it participates in an energetically favourable, or stabilizing, interaction with one or more complementary moieties within the subsite, as defined above.

A functional group or moiety of the compound is said to interact in a "similar" manner as the co-crystallized ligand if one or more, preferably two or more of its functional groups or moieties capable of forming the attractive interactions mentioned above can be superimposed on those functional groups or moieties of the co-crystallized ligand capable of forming the attractive interactions. The superposition can be performed based on the identity of atoms, and/or the identity or similarity of functional groups, and/or the similarity of molecular shape and/or the identity or similarity of interaction possibilities. For example, an —OH group of a compound and an —NH group of the cocrystallized ligand may interact in the same way, namely as hydrogen bond donors, with a hydrogen bond acceptor atom suitably positioned in the enzyme. Therefore, the —OH group and the —NH group are said to have similar interaction properties, and a molecule containing an —OH group may be superimposed onto a molecule carrying an —NH group at the corresponding position.

Typically, the assessment of interactions between (1) the test compound and the DHODH ubiquinone binding site and (2) the superposition of a test compound and the co-crystallized ligand employ computer-based computational methods, such as those known in the art, in which, for the first case, possible interactions of a compound with the protein, as defined by atomic coordinates, are evaluated with respect to interaction strength by calculating the interaction energy upon binding the compound to the protein. For the second case, the superposition of a test compound and the cocrystallized ligand is performed according to the identity of atoms, and/or the identity or similarity of functional groups, and/or the similarity of molecular shape and/or the identity or similarity of interaction possibilities in a process termed alignment. Matching atoms/functional groups/shape/interaction possibilities are evaluated and summarized to an alignment score enabling the ranking of the tested molecules.

Compounds which have calculated interaction energies within a preselected range or which otherwise, in the opinion of the computational chemist employing the method, have the greatest potential as DHODH inhibitors, can then be provided, for example, from a compound library or via synthesis, and assayed for the ability to inhibit DHODH. The interaction energy for a given compound generally depends upon the ability of the compound to interact with one or more subsites within the protein catalytic domain.

In one embodiment, the atomic coordinates used in the method are the atomic coordinates set forth in Tables 29, 30, and 31. It is to be understood that the coordinates set forth in Tables 29, 30, and 31 can be transformed, for example, into a different coordinate system, in ways known to those of skill in the art without substantially changing the three dimensional structure represented thereby.

In certain cases a moiety of the compound can interact with a subsite via two or more individual interactions. A moiety of the compound and a subsite can interact if they have complementary properties and are positioned in sufficient proximity and in a suitable orientation for a stabilizing interaction to occur. The possible range of distances for the moiety of the compound and the subsite depends upon the distance dependence of the interaction, as known in the art. For example, a hydrogen bond typically occurs when a hydrogen bond donor atom, which bears a hydrogen atom, and a hydrogen bond acceptor atom are separated by about 2.5 Å and about 3.5 Å. Hydrogen bonds are well known in the art. Generally, the overall interaction, or binding, between the compound and the ubiquinone binding site will depend upon the number and strength of these individual interactions.

The ability of a test compound to interact with one or more subsites of the ubiquinone binding site can be determined by computationally evaluating interactions between functional groups, or moieties, of the test compound and one or more amino acid side chains and/or backbone atoms in the ubiquinone binding site. Typically, a compound which is capable of participating in stabilizing interactions with a preselected number of subsites, preferably without simultaneously participating in significant destabilizing interactions, is identified as a potential inhibitor of DHODH. Such a compound will interact with one or more subsites, preferably with two or more subsites and, more preferably, with three or more subsites.

The invention further provides methods of designing a compound which is a potential inhibitor of DHODH.

The first method includes the steps of (1) identifying one or more functional groups capable of interacting with one or more subsites of the DHODH ubiquinone binding site; and (2) identifying a scaffold which presents the functional group or functional groups identified in step 1 in a suitable orientation for interacting with one or more subsites of the DHODH ubiquinone binding site. The compound which results from attachment of the identified functional groups or moieties to the identified scaffold is a potential inhibitor of DHODH. The DHODH ubiquinone binding site is, generally, defined by the atomic coordinates of a polypeptide comprising the DHODH ubiquinone binding site, for example, the atomic coordinates set forth in Tables 29, 30, and 31.

The second method comprises the steps of (1) identifying one or more functional groups or moieties capable of interacting in a similar way as one or more functional groups or moieties of the co-crystallized ligand, and (2) identifying a scaffold which presents the functional group or functional groups identified in step 1 in a suitable orientation for interacting in a similar way as one or more functional groups or moieties of the co-crystallized ligand. The compound which results from attachment of the identified functional groups or moieties to the identified scaffold is a potential inhibitor of DHODH. The co-crystallized ligand is, generally, defined by the atomic coordinates of a ligand complexed in the polypeptide comprising the DHODH ubiquinone binding site, for example, the atomic coordinates set forth in Tables 29, 30, and 31.

Suitable methods, as known in the art, can be used to identify chemical moieties, fragments or functional groups which are capable of interacting favorably with a particular subsite or sets of subsites. These methods include, but are not limited to: interactive molecular graphics; molecular mechanics; conformational analysis; energy evaluation; docking; database searching; virtual high-throughput screening (U.S. Pat. No. 422,303, DE 10009479, EP 1094415, U.S. Pat. Nos. 693,731, 885,893, 885,517); structural alignment; functional group alignment; interaction-point alignment; pharmacophore modeling; de novo design; property estimation and descriptor-based database searching. These methods can also be employed to assemble chemical moieties, fragments or functional groups into a single inhibitor molecule. These same methods can also be used to determine whether a given chemical moiety, fragment or functional group is able to interact favorably with a particular subsite or sets of subsites.

In one embodiment, the design of potential DHODH inhibitors begins from the general perspective of three-dimensional shape and electrostatic complementarity for the ubiquinone binding site, and subsequently, interactive molecular modeling techniques can be applied by one skilled in the art to visually inspect the quality of the fit of a candidate molecule into the binding site. Suitable visualization programs include SYBYL (Tripos Inc., St. Louis, Mo.), MOLOC (Gerber Molecular Design, Basel), RASMOL (Sayle et al. Trends Biochem. Sci. 20:374-376 (1995)) and MOE (Chemical Computing Group Inc., Montreal).

A further embodiment of the present invention utilizes a database searching program which is capable of scanning a database of small molecules of known three-dimensional structure for candidates which fit into the target protein site. Suitable software programs include 4SCan® (U.S. Pat. No. 422,303, DE 10009479, EP 1094415, U.S. Pat. Nos. 693, 731, 885,893, 885,517), FLEXX (Rarey et al., J. Mol. Biol. 261:470-489 (1996)), and UNITY (Tripos Inc., St. Louis, Mo.). Especially 4SCan® was developed to scan/screen large virtual databases up to several millions of small molecules in a reasonable time-frame.

A further embodiment of the present invention utilizes a database searching program which is capable of scanning a database of small molecules of known three-dimensional structure for candidates which align properly with the co-crystallized ligand, both in shape and interaction properties. Suitable software programs include 4SCan® (U.S. Pat. No. 422,303, DE 10009479, EP 1094415, U.S. Pat. Nos. 693, 731, 885,893, 885,517) and FLEXS (Lemmen et al., J. Med. Chem 41:4502-4520 (1998)). Especially 4SCan® is capable of aligning large virtual databases up to several millions of small molecules in a reasonable time-frame.

It is not expected that the molecules found in the search will necessarily be leads themselves, since a complete evaluation of all interactions will necessarily be made during the initial search. Rather, it is anticipated that such candidates might act as the framework for further design, providing molecular skeletons to which appropriate atomic replacements can be made. Of course, the chemical complementarity of these molecules can be evaluated, but it is expected that the scaffold, functional groups, linkers and/or monomers may be changed to maximize the electrostatic, hydrogen bonding, and hydrophobic interactions with the enzyme.

Goodford (Goodford J. Med. Chem. 28:849-857 (1985)) has produced a computer program, GRID, which seeks to determine regions of high affinity for different chemical groups (termed probes) on the molecular surface of the binding site. GRID hence provides a tool for suggesting modifications to known ligands that might enhance binding.

Consequently, virtual combinatorial libraries covering numerous variations of the addressed scaffold, functional groups, linkers and/or monomers can be build up using suitable software programs including LEGION (Tripos Inc., St. Louis, Mo.) or ACCORD FOR EXCEL (Accelrys Inc., San Diego, Calif.), followed by scanning or virtual screening or docking of these libraries using suitable software mentioned above.

A range of factors, including electrostatic interactions, hydrogen bonding, hydrophobic interactions, desolvation effects, conformational strain, ligand flexibility and cooperative motions of ligand and enzyme, all influence the binding effect and should be taken into account in attempts to design bioactive inhibitors.

Yet another embodiment of a computer-assisted molecular design method for identifying inhibitors of DHODH comprises searching for fragments which fit into a binding region subsite and link to a pre-defined scaffold. The scaffold itself may be identified in such a manner. A representative program suitable for the searching of such functional groups and monomers include LUDI (Boehm, J. Comp. Aid. Mol. Des. 6:61-78 (1992)) and MCSS (Miranker et al., Proteins 11: 314-328 (1991)).

Yet another embodiment of a computer-assisted molecular design method for identifying inhibitors of DHODH comprises the de novo synthesis of potential inhibitors by algorithmic connection of small molecular fragments that will exhibit the desired structural and electrostatic complementarity with the active site of the enzyme. The methodology employs a large template set of small molecules which are iteratively pierced together in a model of the DHODH ubiquinone binding site. Programs suitable for this task include GROW (Moon et al. Proteins 11:314-328 (1991)) and SPROUT (Gillet et al. J. Comp. Aid. Mol. Des. 7:127 (1993)).

In yet another embodiment, the suitability of inhibitor candidates can be determined using an empirical scoring function, which can rank the binding affinities for a set of inhibitors. For examples of such a method see Muegge et al. and references therein (Muegge et al., J. Med. Chem. 42:791-804 (1999)) and ScoreDock (Tao et al. J. Comp. Aid. Mol. Des. 15: 429-446 (2001)).

Other modeling techniques can be used in accordance with this invention, for example, those described by Stahl (Stahl, in: Virtual Screening for Bioactive Molecules, Wiley-VCH, Weinheim, 2000, pp. 229-264), Cohen et al. (J. Med. Chem. 33:883-894 (1990)); Navia et al. (Current Opinions in Structural Biology 2 :202-210 (1992)); Baldwin et al. (J. Med. Chem. 32:2510-2513 (1989)); Appelt et al. (J. Med. Chem. 34:1925-1934 (1991)); Ealick et al. (Proc. Nat. Acad. Sci. USA 88:11540-11544 (1991));

A compound which is identified by one of the foregoing methods as a potential inhibitor of DHODH can then be obtained, for example, by synthesis or from a compound library, and assessed for the ability to inhibit DHODH in vitro. Such an in vitro assay can be performed as is known in the art, for example, by contacting DHODH in solution with the test compound in the presence of the substrate and cofactor of DHODH and ubiquinone. The rate of substrate transformation can be determined in the presence of the test compound and compared with the rate in the absence of the test compound. Suitable assays for DHODH biological activity are described below, the teachings of each of which are hereby incorporated by reference herein in their entity.

An inhibitor identified or designed by a method of the present invention can be a competitive inhibitor, an uncompetitive inhibitor or a noncompetitive inhibitor with respect to ubiquinone.

A screen of thousands of compounds using 4Scan® as described above was performed. Hits were ranked according to consensus score.

In table 25 the structures of the highest ranking compounds of the combinatorial library are shown. The consensus score of each molecule is calculated by the summation of the two predicted 4SCan® activity scores for the two different structures of the ubiquinone binding site.

The compounds of the present invention can be used for a variety of human and animal diseases, preferably human diseases, where inhibition of the pyrimidine metabolism is beneficial. Such diseases are:

fibrosis, uveitis, rhinitis, asthma or arthropathy, in particular, arthrosis all forms of rheumatism acute immunological events and disorders such as sepsis, septic shock, endotoxic shock, Gram-negative sepsis, toxic shock syndrome, acute respiratory distress syndrome, stroke, reperfusion injury, CNS injury, serious forms of allergy, graft versus host and host versus graft reactions, alzheimer's disease or pyresis, restenosis, chronic pulmonary inflammatory disease, silicosis, pulmonary sarcosis, bone resorption disease. These immunological events also include a desired modulation and suppression of the immune system;

all types of autoimmune diseases, in particular rheumatoid arthritis, rheumatoid spondylitis, osteoarthritis, gouty arthritis, multiple sclerosis, insulin dependent diabetes mellitus and non-insulin dependent diabetes mellitus, and lupus erythematoidis, ulcerative colitis, Morbus Crohn, inflammatory bowel disease, as well as other chronic inflammations, chronic diarrhea;

dermatological disorders such as psoriasis progressive retinal atrophy all kinds of infections including opportunistic infections.

The compounds according to the invention and medicaments prepared therewith are generally useful for the treatment of cell proliferation disorders, for the treatment or prophylaxis, immunological diseases and conditions (as for instance inflammatory diseases, neuroimmunological diseases, autoimmune diseases or other).

The compounds of the present invention are also useful for the development of immunomodulatory and anti-inflammatory medicaments or, more generally, for the treatment of diseases where the inhibition of the pyrimidine biosynthesis is beneficial.

The compounds of the present invention are also useful for the treatment of diseases which are caused by malignant cell proliferation, such as all forms of hematological and solid cancer. Therefore the compounds according to the invention and medicaments prepared therewith are generally useful for regulating cell activation, cell proliferation, cell survival, cell differentiation, cell cycle, cell maturation and cell death or to induce systemic changes in metabolism such as changes in sugar, lipid or protein metabolism. They can also be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

These diseases and conditions include but are not limited to cancer as hematological (e.g. leukemia, lymphoma, myeloma) or solid tumors (for example breast, prostate, liver, bladder, lung, esophageal, stomach, colorectal, genitourinary, gastrointestinal, skin, pancreatic, brain, uterine, colon, head and neck, ovarian, melanoma, astrocytoma, small cell lung cancer, glioma, basal and squameous cell carcinoma, sarcomas as Kaposi's sarcoma and osteosarcoma), treatment of disorders involving T-cells such as aplastic anemia and DiGeorge syndrome, Graves' disease.

Leflunomide was previously found to inhibit HCMV replication in cell culture. Ocular herpes is the most common cause of infectious blindness in the developed world. There are about 50,000 cases per year in the US alone, of which 90% are recurrences of initial infections. Recurrences are treated with antivirals and corticosteroids. Cytomegalovirus, another herpes virus, is a common cause of retinal damage and blindness in patients with aids. The compounds of the present invention can be used alone or in combination with other antiviral compounds such as ganciclovir and foscarnet to treat such diseases.

The compounds of the present invention can further be used for diseases that are caused by protozoal infestations in humans and animals. Such veterinary and human pathogenic protozoas are preferably intracellular active parasites of the phylum Apicomplexa or Sarcomastigophora, especially *Trypanosoma*, Plasmodia, *Leishmania, Babesia* and Theileria, Cryptosporidia, Sacrocystida, Amoebia, Coccidia and Trichomonadia. These active substances or corresponding drugs are especially suitable for the treatment of Malaria tropica, caused by *Plasmodium falciparum*, Malaria tertiana, caused by *Plasmodium vivax* or *Plasmodium ovale* and for the treatment of Malaria quartana, caused by *Plasmodium malariae*. They are also suitable for the treatment of Toxoplasmosis, caused by *Toxoplasma gondii*, Coccidiosis, caused for instance by *Isospora belli*, intestinal Sarcosporidiosis, caused by *Sarcocystis suihominis*, dysentery caused by *Entamoeba histolytica*, Cryptosporidiosis, caused by *Cryptosporidium parvum*, Chargas' disease, caused by *Trypanosoma cruzi*, sleeping sickness, caused by *Trypanosoma brucei rhodesiense* or *gambiense*, the cutaneous and visceral as well as other forms of Leishmaniosis. They are also suitable for the treatment of animals infected by veterinary pathogenic protozoa, like *Theileria parva*, the pathogen causing bovine East coast fever, *Trypanosoma congolense congolense* or *Trypanosoma vivax vivax, Trypanosoma brucei brucei*, pathogens causing Nagana cattle disease in Africa, *Trypanosoma brucei evansi* causing Surra, *Babesia bigemina*, the pathogen causing Texas fever in cattle and buffalos, *Babesia bovis*, the pathogen causing european bovine Babesiosis as well as Babesiosis in dogs, cats and sheep, *Sarcocystis ovicanis* and *ovifelis* pathogens causing Sarcocystiosis in sheep, cattle and pigs, Cryptosporidia, pathogens causing Cryptosporidioses in cattle and birds, Eimeria and *Isospora* species, pathogens causing Coccidiosis in rabbits, cattle, sheep, goats, pigs and birds, especially in chickens and turkeys. The use of the compounds of the present invention is preferred in particular for the treatment of Coccidiosis or Malaria infections, or for the preparation of a drug or feed stuff for the treatment of these diseases. This treatment can be prophylactic or curative. In the treatment of malaria, the compounds of the present invention may be combined with other anti-malaria agents.

The compounds of the present invention can further be used for viral infections or other infections caused for instance by *Pneumocystis carinii*.

EXAMPLES

1. X-Ray Structure Determination

Expression and Purification

The cDNA encoding for an N-terminally truncated human DHODH(Met30-Arg396) was amplified by the polymerase chain reaction (PCR) from a human liver cDNA bank (Invitrogen, Groningen). The following primers were used to amplify the DHODH gene form the cDNA bank:

```
DHODH-V:
5'-GGA ATT CCA TAT GGC CAC GGG AGA        (SEQ ID NO:1)
TGA GCG-3'

DHODH-R:
5'-GCG CGG ATC CTC ACC TCC GAT GAT        (SEQ ID NO:2)
CTG C-3'
```

The underlined sequence regions encode for the cutting sites of the restriction enzymes NdeI (DHODH-V) and BamHI (DHODH-R), respectively. The primers are designed such that subcloning using the NdeI and BamHI restriction sites into a pET-19b vector is possible. The amplified DNA bands were purified and isolated from an agarose gel (QIAquick PCR purification kit). The band showed the expected length of 1.2 kb. The isolated PCR fragment was subcloned into a TOPO vector (Invitrogen, Groningen) according to the protocol outlined in the TOPT TA Cloning Kit. The TOPO vector including the ligated PCR fragment was digested with the restriction enzymes NdeI and BamHI (New England Biolabs Inc.) to produce sticky ends. Finally, the fragment was cloned into the NdeI/BamHI sites of a pET-19b vector (Novagen, Madison, Wis.). This vector produced the human DHODH(Met30-Arg396) as an N-terminal ten histidine fusion protein (his10-hDHODH (Met30-Arg396)). The vector was transformed into chemical competent *E. coli* BL21(DE3)Gold cells (Stratagene, LaJolla, Calif.). Cells were stored as glycerol stocks at −80° C. until further use.

100 ml LB-medium in 250 ml flasks containing 100 µL freshly prepared ampicilline were inoculated with BL21 (DE3)Gold cells hosting the pET-19b/hDHODH(Met30-Arg396) construct. Cells were grown overnight at 25° C. and constantly vortexed with 150 rpm.

For the expression cultures four 2 L flasks each were filled with 800 mL rich medium (LB) containing 800 µL ampicilline. The flasks were inoculated with 40 mL of overnight culture and were grown to an optical density O.D.$_{600}$ of 0.6-0.8 at 25° C. The cells were induced with 80 µL of a 1 M isopropyl-β-D-thiogalactoside (IPTG) stock solution and grown for another 20 h at 25° C.

The cells were harvested by centrifugation for 15 min in a JA-10 Beckmann rotor at 5000 rpm at 4° C. The cell pellet was stored until further use at −20° C.

The pellets of 4×800 mL expression were thawed on ice and resuspended in 100 mL lysisbuffer containing 50 mM HEPES at pH 7.7, 300 mM NaCl, 10% glycerol, 10% bugbuster (Novagen, 10×), two tablets of protease-inhibitor mix (Complete Tabletes EDTA-free, Roche) and 1% triton X-100. The cell suspension was incubated under gentle rocking for 20 min at room temperature.

Cell lysis was performed via ultra sonification using a Branson sonotrode. The chosen parameters for sonification were the following:

| | |
|---|---|
| amplitude: | 60% |
| duration: | 3 × 3 min |
| maximal allowed temperature: | 37° C. |
| pulse duration: | 0.5 sec |
| duty cycle: | 0.1 sec |

The resulting suspension was centrifuged in a JA-25.50 rotor (Beckmann) at 25.000 rpm for 1 hour at 4° C.

The supernatant was loaded onto a Ni-NTA-column (resin was from Quiagen, column adapter from Pharmacia). The column had a bed volume of 3 mL and was equilibrated with 5 column volumes (CV) of starting buffer (50 mM HEPES pH 7.7; 300 mM NaCl; 10% glycerol and 10 mM imidazole). The sample was loaded with a flow rate of 1 mL/min at 4° C. using a BioRad Econopump. Then the column was mounted on a BioRad BioLogic-LP chromatography system and washed with 5-10 CVs of 50 mM HEPES pH 7.7, 300 mM NaCl, 10% glycerol, 10 mM imidazole and 10 mM N,N-dimethylundecylamin-N-oxide (C11DAO) at a rate of 1 mL/min. Another more stringent washing step was performed by applying step gradients consisting of the above washing buffer containing 20 mM and 50 mM imidazole, respectively. At this point, pure DHODH was eluted with 50 mM HEPES pH 7.7, 300 mM NaCl, 10% glycerol, 200 mM imidazole and 10 mM N,N-dimethylundecylamin-N-oxide. Elution was carried out with a flow rate of 0.5 mL/min and the eluate was collected in 4 mL fractions. Fractions containing hDHODH(Met30-Arg396) are characterized by a bright yellow colour and showed full activity in an in vitro assay (as described above/below).

Fractions containing hDHODH were combined (approx. 10 mL) and dialysed against 3 L of buffer containing 50 mM HEPES pH 7.7, 400 mM NaCl, 30% glycerol, 1 mM EDTA and 10 mM N,N-dimethylundecylamin-N-oxide overnight at 4° C. The dialysed protein sample was concentrated to a final concentration of 20 mg/mL using an Ultrafree 4/YM-30 device from Millipore. During the concentrating procedure the temperature was kept at 4° C. The protein concentration was determined spectrometrically. The His-tag was not removed for further studies.

Finally, aliquots of 50 µL were flash frozen in liquid nitrogen and stored at −80° C. until further use.

Crystallization and Data Collection

Human his10-hDHODH(Met30-Arg396) was co-crystallized with compound 1 and compound 2 at 20° C. using the hanging-drop vapour diffusion method. Drops were formed by mixing equal amounts of 20 mg/ml protein in 50 mM HEPES pH 7.7, 400 mM NaCl, 30% glycerol, 1 mM EDTA and 10 mM N,N-dimethylundecylamin-N-oxide (C11DAO) with a precipitant solution of 0.1 M acetate pH 4.6-5.0, 40 mM C11DAO, 20.8 mM N,N-dimethyldecylamine-N-oxide (DDAO), 2 mM dihydroorotate (DHO), 1.8-2.4 M ammonium sulfate, 1 mM compound 1 or 2. The hanging drops were incubated against 0.5 mL reservoir of 0.1 M acetate pH 4.8, 2.4-2.6 M ammonium sulfate and 30% glycerol. The crystallization conditions were screened by variation of pH versus ammonium sulfate concentration using a small grid screen (see FIG. 2):

The same procedure was applied to obtain single crystals of DHODH(Met30-Arg396) in complex with compounds 3, 4, 5, 6, 7, 8, 9 and 10. Compounds 5 and 6 were synthesized as racemic mixtures due to the presence of a stereo center at the five membered ring. The racemic mixtures were used for crystallization experiments.

Crystals usually appeared as small cubes within three days. They usually reached a full size of 0.2×0.2×0.2 mm within three to four weeks. The protein crystallized in the space group $P3_221$. Crystals were harvested with pre-mounted loops of size 0.5 mm (Hampton Research) and were flash frozen directly in the cryo stream of the measurement device.

Data were collected at the beamline BW6 at the DESY Hamburg on a MAR-CCD camera. A total of 120 frames (0.5° each) were collected from a human DHODH(Met30-Arg396) crystal co-crystallized with compound 1. For the crystal cocrystallized with compound 2 a total of 85 frames (1° each) was recorded. The crystals were maintained at a temperature of 100 K during data collection. The indexing and integration of the reflection intensities were performed with the program MOSFLM (Collaborative Computational Project, Number 4 (1994). Acta Cryst. D50, 760-763.). Data were scaled and merged with SCALA and reduced to structure factor amplitudes with TRUNCATE, both from the CCP4 program suite (Collaborative Computational Project, Number 4 (1994). Acta Cryst. D50, 760-763.). At this stage 5% and 10% (the "test set") of unique reflections were flagged for cross validation to calculate the free R-factor ($R_{free}$) during the refinement process later on for compound 1 and compound 2, respectively. The remaining 95% and 90% of the reflections constituted the "working set" for calculation of the R-factor (R), respectively. The statistics of data collection are shown in table 1 and table 2.

TABLE 1

Crystal & Data collection statistics for compound 1

A. Crystal data

| | |
|---|---|
| Spacegroup | $P3_221$ |
| Cell dimensions (Å) | a = 90.69 b = 90.69 c = 123.22 |
| Molecules/asymmetric unit | 1 |
| Matthews' constant ($V_m$)(Å³/Da) | 4.1 |
| Maximum resolution (Å) | 2.35 |

B. Data Collection

| | |
|---|---|
| X-Ray source | DESY BW6 |
| Wavelength (Å) | 1.05 |
| Total/unique reflections | 91431/24977 |
| Completeness (%) | 98.2 (99.0) |
| I/sigma | 23.9 (6.5) |
| $R_{merge}$ (%) | 5.7 (20.2) |

TABLE 2

Crystal & Data collection statistics for compound 2

A. Crystal data

| | |
|---|---|
| Spacegroup | $P3_221$ |
| Cell dimensions (Å) | a = 90.65 b = 90.65 c = 123.07 |
| Molecules/asymmetric unit | 1 |
| Matthews' constant ($V_m$)(Å³/Da) | 4.1 |
| Maximum resolution (Å) | 2.4 |

TABLE 2-continued

Crystal & Data collection statistics for compound 2

B. Data Collection

| | |
|---|---|
| X-Ray source | DESY BW6 |
| Wavelength (Å) | 1.05 |
| Total/unique reflections | 101935/22253 |
| Completeness (%) | 95.8 (97.1) |
| I/sigma | 14.6 (3.8) |
| $R_{merge}$ (%) | 9.1 (38.1) |

Datasets for the crystals of human DHODH(Met30-Arg396) co-crystallized with compounds 3, 4, 6, 7, 8, 9 and 10 were also collected at the beamline BW6 at the DESY Hamburg on a MAR-CCD camera. Co-crystals with compound 5 were recorded at an in house generator using CuKα radiation and a MAR-dtb image plate.

A total of 55 frames, 65 frames, 96 frames, 62 frames, 120 frames, 60 frames, 100 frames and 100 frames (1° each) were collected from human DHODH(Met30-Arg396) crystals co-crystallized with compound 3, 4, 5, 6, 7, 8, 9 and 10 respectively. The crystals were maintained at a temperature of 100 K during data collection. The indexing and integration of the reflection intensities were performed with the program MOSFLM (Collaborative Computational Project, Number 4 (1994). Acta Cryst. D50, 760-763.). Data were scaled and merged with SCALA and reduced to structure factor amplitudes with TRUNCATE, both from the CCP4 program suite (Collaborative Computational Project, Number 4 (1994). Acta Cryst. D50, 760-763.). At this stage 5% or 10% (the "test set") of unique reflections were flagged for cross validation to calculate the free R-factor ($R_{free}$) during the refinement process. The remaining 95% or 90% of the reflections constituted the "working set" for calculation of the R-factor (R), respectively. The statistics of data collection are shown in tables 5 to 12, respectively.

TABLE 5

Crystal & Data collection statistics for compound 3

A. Crystal data

| | |
|---|---|
| Spacegroup | $P3_221$ |
| Cell dimensions (Å) | a = 90.43 b = 90.43 c = 123.00 |
| Molecules/asymmetric unit | 1 |
| Matthews' constant ($V_m$)(Å³/Da) | 4.1 |
| Maximum resolution (Å) | 1.95 |

B. Data Collection

| | |
|---|---|
| X-Ray source | DESY BW6 |
| Wavelength (Å) | 1.05 |
| Total/unique reflections | 142628/42908 |
| Completeness (%) | 99.8/99.9 |
| I/sigma | 12.6/3.4 |
| $R_{merge}$ (%) | 8.2/38.3 |

TABLE 6

Crystal & Data collection statistics for compound 4

A. Crystal data

| | |
|---|---|
| Spacegroup | $P3_221$ |
| Cell dimensions (Å) | a = 90.65 b = 90.65 c = 123.21 |
| Molecules/asymmetric unit | 1 |
| Matthews' constant ($V_m$)(Å³/Da) | 4.1 |
| Maximum resolution (Å) | 2.15 |

TABLE 6-continued

Crystal & Data collection statistics for compound 4

B. Data Collection

| | |
|---|---|
| X-Ray source | DESY BW6 |
| Wavelength (Å) | 1.05 |
| Total/unique reflections | 124056/32175 |
| Completeness (%) | 99.2/99.0 |
| I/sigma | 14.7/5.7 |
| $R_{merge}$ (%) | 7.1/24.8 |

TABLE 7

Crystal & Data collection statistics for compound 5

A. Crystal data

| | |
|---|---|
| Spacegroup | $P3_221$ |
| Cell dimensions (Å) | a = 90.30 b = 90.30 c = 123.09 |
| Molecules/asymmetric unit | 1 |
| Matthews' constant ($V_m$)(Å³/Da) | 4.1 |
| Maximum resolution (Å) | 2.2 |

B. Data Collection

| | |
|---|---|
| X-Ray source | CuKα |
| Wavelength (Å) | 1.54 |
| Total/unique reflections | 171127/30057 |
| Completeness (%) | 99.9 (99.9) |
| I/sigma | 4.0/1.9 |
| $R_{merge}$ (%) | 15.4/43.5 |

TABLE 8

Crystal & Data collection statistics for compound 6

A. Crystal data

| | |
|---|---|
| Spacegroup | $P3_221$ |
| Cell dimensions (Å) | a = 90.44 b = 90.44 c = 123.20 |
| Molecules/asymmetric unit | 1 |
| Matthews' constant ($V_m$)(Å³/Da) | 4.1 |
| Maximum resolution (Å) | 1.9 |

B. Data Collection

| | |
|---|---|
| X-Ray source | DESY BW 6 |
| Wavelength (Å) | 1.05 |
| Total/unique reflections | 173775/46257 |
| Completeness (%) | 99.4/99.9 |
| I/sigma | 13.8/2.8 |
| $R_{merge}$ (%) | 8.5/46.0 |

TABLE 9

Crystal & Data collection statistics for compound 7

A. Crystal data

| | |
|---|---|
| Spacegroup | $P3_221$ |
| Cell dimensions (Å) | a = 90.74 b = 90.74 c = 122.88 |
| Molecules/asymmetric unit | 1 |
| Matthews' constant ($V_m$)(Å³/Da) | 4.1 |
| Maximum resolution (Å) | 1.9 |

B. Data Collection

| | |
|---|---|
| X-Ray source | DESY BW 6 |
| Wavelength (Å) | 1.05 |
| Total/unique reflections | 341319/46198 |
| Completeness (%) | 98.6/99.7 |
| I/sigma | 23.5/5.1 |
| $R_{merge}$ (%) | 8.2/21.8 |

TABLE 10

Crystal & Data collection statistics for compound 8

A. Crystal data

| | |
|---|---|
| Spacegroup | P3$_2$21 |
| Cell dimensions (Å) | a = 90.56 b = 90.56 |
| | c = 123.06 |
| Molecules/asymmetric unit | 1 |
| Matthews' constant (V$_m$)(Å$^3$/Da) | 4.1 |
| Maximum resolution (Å) | 1.8 |

B. Data Collection

| | |
|---|---|
| X-Ray source | DESY BW 6 |
| Wavelength (Å) | 1.05 |
| Total/unique reflections | 190208/53993 |
| Completeness (%) | 98.8/96.7 |
| I/sigma | 16.7/2.9 |
| R$_{merge}$ (%) | 6.3/38.3 |

TABLE 11

Crystal & Data collection statistics for compound 9

A. Crystal data

| | |
|---|---|
| Spacegroup | P3$_2$21 |
| Cell dimensions (Å) | a = 90.29 b = 90.29 |
| | c = 122.69 |
| Molecules/asymmetric unit | 1 |
| Matthews' constant (V$_m$)(Å$^3$/Da) | 4.1 |
| Maximum resolution (Å) | 2.0 |

B. Data Collection

| | |
|---|---|
| X-Ray source | DESY BW 6 |
| Wavelength (Å) | 1.05 |
| Total/unique reflections | 103711/39080 |
| Completeness (%) | 98.6/99.0 |
| I/sigma | 14.1/3.9 |
| R$_{merge}$ (%) | 6.5/24.8 |

TABLE 12

Crystal & Data collection statistics for compound 10

A. Crystal data

| | |
|---|---|
| Spacegroup | P3$_2$21 |
| Cell dimensions (Å) | a = 90.75 b = 90.75 |
| | c = 122.71 |
| Molecules/asymmetric unit | 1 |
| Matthews' constant (V$_m$)(Å$^3$/Da) | 4.1 |
| Maximum resolution (Å) | 1.8 |

B. Data Collection

| | |
|---|---|
| X-Ray source | DESY BW 6 |
| Wavelength (Å) | 1.05 |
| Total/unique reflections | 326425/54728 |
| Completeness (%) | 99.9/100 |
| I/sigma | 27.5/6.0 |
| R$_{merge}$ (%) | 6.0/30.6 |

Structure Determination and Refinement of DHODH/Compound 1 Complex

The structure for the human DHODH(Met30-Arg396) in complex with compound 1 was solved using the method of molecular replacement (MR). The free accessible pdb entry 1D3G.pdb was used as a search model. The ligands brequinar and DDQ as well as all of the water molecules were removed prior to the MR search. The search model included the polypeptide chain of hDHODH(Met30-Arg396), one molecule of orotate, one molecule of the cofactor flavinmononucleotide (FMN) and one acetate molecule which was present under the crystallization conditions. A standard rotational and translational molecular replacement search at 3.5 Å was performed using the program molrep (Collaborative Computational Project, Number 4 (1994). Acta Cryst. D50, 760-763.). Solutions for both the rotational and translational search were well above the next ranking solutions. The MR resulted in an R-factor of 35.6% and a correlation coefficient of 69.4% for compound 1 complex.

In a first round of refinement the MR model was subjected to rigid body refinement and a slow cooling simulated annealing protocol using a maximum likelihood target to remove model bias (Accelrys Inc. CNX program suite, CNX2002). Additionally, an individual b-factor refinement was carried out using standard CNX protocols. Finally, SIGMAA weighted 2Fo-Fc and Fo-Fc electron density maps were calculated and displayed together with the protein model in the program 0 (DatOno A B; Jones, T. A., Zou, J. Y., Cowan, S. W. & Kjelgaard, M. (1991). Acta Cryst. A47, 110-119.). The resulting experimental electron density was so excellent that the conformation of compound 1 could be interpreted unambiguously.

A pdb file for compound 1 was created using the program MOE (Chemical Computing Group Inc., MOE 2002.02). After energy minimization the compound was built into the electron density manually. Topology and parameter files for compound 1 were created using the program Xplo2d (Uppsala Software Factory; Kleywegt, G. M. (1997) J. Mol. Biol. 273, 371-376). After an additional round of model building and water picking using CNX another complete round of refinement was performed. The final model included the DHODH(Met30-Arg396) protein, the cofactor flavinmononucleotide (FMN), one orotate molecule (ORO), one acetate molecule (ACT), two sulfate ions (SO4), one molecule of compound 1 (INH) and 153 water molecules (TIP) (see Table 29). The model is well refined and has very good geometry. The refinement process which included data from 12.0-2.35 Å resulted in an R-factor of 18.5% and a free R-factor of 21.7%. With the exception of glycine residues, 92.4% (278) of the residues are located in the most favoured region of the ramachandran plot and 7.6% (22) cluster in the additional allowed regions. Table 13 summarizes the refinement statistics for the inhibitor compound 1 in complex with human DHODH. Values in parentheses give the R-factor and R$_{free}$-factors, respectively, for the last resolution bin ranging from 2.50 to 2.35.

The N-terminal His tag could not be detected in the electron density map.

TABLE 13

Refinement Statistics for DHODH/compound 1 complex

| | |
|---|---|
| R-factor (%) | 18.5 (19.6) |
| R$_{free}$ | 21.7 (24.2) |
| RMS deviation from ideal values | |
| bond length (Å) | 0.006 |
| Bond angle (°) | 1.2 |
| Dihedral angles (°) | 21.4 |
| Improper angles (°) | 0.83 |

Structure Determination and Refinement of DHODH/Compound 2 Complex

The structure for the human DHODH(Met30-Arg396) in complex with compound 2 was solved using the method of molecular replacement (MR). The free accessible pdb entry 1D3G.pdb was used as a search model. The ligands brequinar and DDQ as well as all of the water molecules were removed prior to the MR search. The search model included the polypeptide chain of hDHODH(Met30-Arg396), one molecule of orotate, one molecule of the cofactor flavin-mononucleotide (FMN) and one acetate molecule which was present under the crystallization conditions. A standard rotational and translational molecular replacement search at 3.5 Å was performed using the program molrep (Collaborative Computational Project, Number 4 (1994). Acta Cryst. D50, 760-763.). Solutions for both the rotational and translational search were well above the next ranking solutions. The MR resulted in an R-factor of 33.8% and a correlation coefficient of 68.2% for the DHODH/compound 2 complex.

In a first round of refinement the MR model was subjected to rigid body refinement and a slow cooling simulated annealing protocol using a maximum likelihood target to remove model bias (Accelrys Inc. CNX program suite, CNX2002). Additionally, an individual b-factor refinement was carried out using standard CNX-protocols. Finally a SIGMAA weighted 2Fo-Fc and Fo-Fc electron density maps were calculated and displayed together with the protein model in the program O (DatOno A B; Jones, T. A., Zou, J. Y., Cowan, S. W. & Kjelgaard, M. (1991). Acta Cryst. A47, 110-119.). The resulting experimental electron density was so excellent that the conformation of the inhibitor compound 2 could be interpreted unambiguously. The electron density around the five-membered ring carrying the carboxy group clearly showed the presence of two alternative conformations of compound 2. In one conformation (conformation A) the carboxy group interacts with residues Gln 47 and Arg 136, whereas in the second conformation (conformation B) the interaction involves residues His 56 and Tyr 356 (see above). For each conformation a separate DHODH/compound 2 complex was subjected to refinement.

Pdb files for the compound 2 in conformation A and B were created using the program MOE (Chemical Computing Group Inc., MOE 2002.02). Both compounds were energy minimized and built into the electron density manually. Topology and parameter files for compound 2 were created using the program Xplo2d (Uppsala Software Factory; Kleywegt, G. M. (1997) J. Mol. Biol., 273, 371-376). After an additional round of model building and water picking using CNX, another complete round of refinement was performed. The final model included the human DHODH(Met30-Arg396) protein, the cofactor flavinmononucleotide (FMN), one orotate molecule (ORO), one acetate molecule (ACT), four sulfate ions (SO4), one molecule of compound 2 (INH) either in conformation A or conformation B and 250 water molecules (TIP) (see Tables 30 and 31). The models are well refined and show very good geometry. The refinement process which included data from 12.0-2.4 Å resulted in an R-factor of 17.5% and a free R-factor of 21.1% for conformation A complex and an R-factor of 17.6% and a free R-factor of 21.6% for conformation B complex, respectively. With the exception of glycine residues, 91.7% (276) of the residues are located in the most favoured region of the ramachandran plot and 8.3% (24) cluster in the additional allowed regions. Table 14 summarizes the refinement statistics for compound 2 in complex with human DHODH. Values in parentheses give the R-factor and $R_{free}$-factors, respectively, for the last resolution bin ranging from 2.55 to 2.40.

TABLE 14

Refinement Statistics for DHODH/compound 2 complex

| | Conformation A | Conformation B |
|---|---|---|
| R-factor (%) | 17.5 (19.6) | 17.6 (19.4) |
| $R_{free}$ | 21.1 (23.6) | 21.6 (23.2) |
| RMS deviation from ideal values | | |
| bond length (Å) | 0.005 | 0.005 |
| Bond angle (°) | 1.2 | 1.2 |
| Dihedral angles (°) | 21.3 | 21.3 |
| Improper angles (°) | 0.81 | 0.81 |

Structure Determination and Refinement of DHODH/Compound 3 Complex

The structure for the human DHODH(Met30-Arg396) in complex with compound 3 was solved using the method of molecular replacement (MR). The free accessible pdb entry 1D3G.pdb was used as a search model. The ligands brequinar and DDQ as well as all of the water molecules were removed prior to the MR search. The search model included the polypeptide chain of hDHODH(Met30-Arg396), one molecule of orotate, one molecule of the cofactor flavin-mononucleotide (FMN) and one acetate molecule which was present under the crystallization conditions. A standard rotational and translational molecular replacement search at 3.0 Å was performed using the program molrep (Collaborative Computational Project, Number 4 (1994). Acta Cryst. D50, 760-763.). Solutions for both the rotational and translational search were well above the next ranking solutions. The MR resulted in an R-factor of 33.9% and a correlation coefficient of 72.5 for the DHODH/compound 3 complex.

In a first round of refinement the MR model was subjected to rigid body refinement and a slow cooling simulated annealing protocol using a maximum likelihood target to remove model bias (Accelrys Inc. CNX program suite, CNX2002). Additionally, an individual b-factor refinement was carried out using standard CNX-protocols. Finally SIGMAA weighted 2Fo-Fc and Fo-Fc electron density maps were calculated and displayed together with the protein model in the program O (DatOno A B; Jones, T. A., Zou, J. Y., Cowan, S. W. & Kjelgaard, M. (1991). Acta Cryst. A47, 110-119.). The resulting experimental electron density was so excellent that the conformation of the inhibitor compound 3 could be interpreted unambiguously. The electron density around the five-membered ring carrying the carboxy group clearly showed the presence of two alternative conformations of compound 3. In one conformation (conformation A) the carboxy group interacts with residues Gln 47 and Arg 136, whereas in the second conformation (conformation B) the interaction involves residues His 56 and Tyr 356 (see above). For each conformation a separate DHODH/compound 3 complex was subjected to refinement.

The pdb files for the compound 3 in conformation A and B were created using the program MOE (Chemical Computing Group Inc., MOE 2002.02). Both compounds were energy minimized and built into the electron density manually. Topology and parameter files for compound 3 were created using the program Xplo2d (Uppsala Software Factory; Kleywegt, G. M. (1997) J. Mol. Biol., 273, 371-376). After an additional round of model building and water picking using CNX, another complete round of refinement was performed. The final model included the human DHODH(Met30-Arg396) protein, the cofactor flavinmononucleotide (FMN), one orotate molecule (ORO), two acetate molecules (ACT), two sulfate ions (SO4), one molecule of compound 3 (INH) either in conformation A or conformation B and 263 water molecules (WAT). Residues which are missing the coordinate file due to very poor electron density are listed in the header of the pdb files.

The models are well refined and show very good geometry. The refinement process which included data from 19.9-1.95 Å resulted in an R-factor of 18.5% and a free R-factor of 20.3% for the complex in conformation A and an R-factor of 18.5% and a free R-factor of 20.3% for the complex in conformation B, respectively. The almost identical R-factors indicate that non of the conformers A and B represent a preferred conformation. Except for non-glycine and non-proline residues 91.6% are located in the most favoured region of the ramachandran plot and 8% cluster in the additional allowed regions. There are no residues in the disallowed region. Table 15 summarizes the refinement statistics for compound 3 in complex with human DHODH. Values in parentheses give the R-factor and $R_{free}$-factors, respectively, for the last resolution bin ranging from 2.07 to 1.95.

TABLE 15

Refinement Statistics for DHODH/compound 3 complex

|  | conformation A | conformation B |
| --- | --- | --- |
| R-factor (%) | 18.5 (20.6) | 18.5 (20.6) |
| $R_{free}$ | 20.3 (23.5) | 20.2 (23.6) |
| RMS deviation from ideal values |  |  |
| bond length (Å) | 0.005 | 0.005 |
| Bond angle (°) | 1.2 | 1.2 |
| Dihedral angles (°) | 21.2 | 21.2 |
| Improper angles (°) | 0.81 | 0.81 |

Structure Determination and Refinement of DHODH/Compound 4 Complex

The structure for the human DHODH(Met30-Arg396) in complex with compound 4 was solved using the method of molecular replacement (MR). The free accessible pdb entry 1D3G.pdb was used as a search model. The ligands brequinar and DDQ as well as all of the water molecules were removed prior to the MR search. The search model included the polypeptide chain of hDHODH(Met30-Arg396), one molecule of orotate, one molecule of the cofactor flavin-mononucleotide (FMN) and one acetate molecule which was present under the crystallization conditions. A standard rotational and translational molecular replacement search at 3.0 Å was performed using the program molrep (Collaborative Computational Project, Number 4 (1994). Acta Cryst. D50, 760-763.). Solutions for both the rotational and translational search were well above the next ranking solutions. The MR resulted in an R-factor of 34.6% and a correlation coefficient of 71.1 for the DHODH/compound 4 complex.

In a first round of refinement the MR model was subjected to rigid body refinement and a slow cooling simulated annealing protocol using a maximum likelihood target to remove model bias (Accelrys Inc. CNX program suite, CNX2002). Additionally, an individual b-factor refinement was carried out using standard CNX-protocols. Finally SIGMAA weighted 2Fo-Fc and Fo-Fc electron density maps were calculated and displayed together with the protein model in the program O (DatOno A B; Jones, T. A., Zou, J. Y., Cowan, S. W. & Kjelgaard, M. (1991). Acta Cryst. A47, 110-119.). The resulting experimental electron density was so excellent that the conformation of the inhibitor compound 4 could be interpreted unambiguously. The electron density around the five-membered ring carrying the carboxy group clearly showed the carboxy group in contact with residues His 56 and Tyr 356 in non-brequinar-like conformation.

A pdb file for compound 4 was created using the program MOE (Chemical Computing Group Inc., MOE 2002.02). After energy minimization the compound was built into the electron density manually. Topology and parameter files for compound 4 were created using the program Xplo2d (Uppsala Software Factory; Kleywegt, G. M. (1997) J. Mol. Biol. 273, 371-376). After an additional round of model building and water picking using CNX another complete round of refinement was performed. The final model included the DHODH(Met30-Arg396) protein, the cofactor flavinmononucleotide (FMN), one orotate molecule (ORO), one acetate molecule (ACT), one sulfate ion (SO4), one molecule of compound 4 (INH) and 192 water molecules (TIP).

The model is well refined and shows very good stereochemical geometry. The refinement process which included data from 19.9-2.15 Å resulted in an R-factor of 20.1% and a free R-factor of 22.1%. Except for non-glycine and non-proline residues 91.6% of the residues are located in the most favoured region of the ramachandran plot and 8% and 0.3% cluster in the additional allowed or generously allowed regions, respectively. There are no residues in the disallowed region. Table 16 summarizes the refinement statistics for compound 4 in complex with human DHODH. Values in parentheses give the R-factor and $R_{free}$-factors, respectively, for the last resolution bin ranging from 2.28 to 2.15.

TABLE 16

Refinement Statistics for DHODH/compound 4 complex

| R-factor (%) | 20.1 (19.1) |
| --- | --- |
| $R_{free}$ | 22.1 (20.9) |
| RMS deviation from ideal values |  |
| bond length (Å) | 0.005 |
| Bond angle (°) | 1.2 |
| Dihedral angles (°) | 21.5 |
| Improper angles (°) | 0.80 |

Structure Determination and Refinement of DHODH/Compound 5 Complex

The structure for the human DHODH(Met30-Arg396) in complex with compound 5 was solved using the method of molecular replacement (MR). The free accessible pdb entry 1D3G.pdb was used as a search model. The ligands brequinar and DDQ as well as all of the water molecules were removed prior to the MR search. The search model included the polypeptide chain of hDHODH(Met30-Arg396), one molecule of orotate, one molecule of the cofactor flavin-mononucleotide (FMN) and one acetate molecule which was present under the crystallization conditions. A standard rotational and translational molecular replacement search at 3.0 Å was performed using the program molrep (Collaborative Computational Project, Number 4 (1994). Acta Cryst. D50, 760-763.). Solutions for both the rotational and translational search were well above the next ranking solutions. The MR resulted in an R-factor of 33.8% and a correlation coefficient of 71.5 for the DHODH/compound 5 complex.

In a first round of refinement the MR model was subjected to rigid body refinement and a slow cooling simulated annealing protocol using a maximum likelihood target to remove model bias (Accelrys Inc. CNX program suite, CNX2002). Additionally, an individual b-factor refinement was carried out using standard CNX-protocols. Finally SIGMAA weighted 2Fo-Fc and Fo-Fc electron density maps were calculated and displayed together with the protein model in the program O (DatOno A B; Jones, T. A., Zou, J. Y., Cowan, S. W. & Kjelgaard, M. (1991). Acta Cryst. A47, 110-119.). The resulting experimental electron density was so excellent that the conformation of the inhibitor compound 5 could be interpreted unambiguously. The electron density around the five-membered ring carrying the carboxy group clearly showed the carboxy group in contact with residues His 56 and Tyr 356 in non-brequinar-like conformation. Interestingly the protein's active site discriminates between the S- and R-enantiomere. Inspection of the corresponding electron density unequivocally shows the presences of the R-enantiomere only.

A pdb file for compound 5 was created using the program MOE (Chemical Computing Group Inc., MOE 2002.02). After energy minimization the compound was built into the electron density manually. Topology and parameter files for compound 5 were created using the program Xplo2d (Uppsala Software Factory; Kleywegt, G. M. (1997) J. Mol. Biol. 273, 371-376). After an additional round of model building and water picking using CNX another complete round of refinement was performed. The final model included the DHODH(Met30-Arg396) protein, the cofactor flavinmononucleotide (FMN), one orotate molecule (ORO), one acetate molecule (ACT), two sulfate ions (SO4), one molecule of compound 5 (INH) and 287 water molecules (TIP).

The model is well refined and shows very good stereochemical geometry. The refinement process which included data from 25.5-2.2 Å resulted in an R-factor of 18.3% and a free R-factor of 20.9%. Except for non-glycine and non-proline residues 92.6% of the residues are located in the most favoured region of the ramachandran plot and 7% and 0.3% cluster in the additional allowed or generously allowed regions, respectively. There are no residues in the disallowed region. Table 17 summarizes the refinement statistics for compound 5 in complex with human DHODH. Values in parentheses give the R-factor and $R_{free}$-factors, respectively, for the last resolution bin ranging from 2.34 to 2.2.

TABLE 17

Refinement Statistics for DHODH/compound 5 complex

| R-factor (%) | 18.3 (19.4) |
| $R_{free}$ | 20.9 (22.0) |
| RMS deviation from ideal values | |
| bond length (Å) | 0.005 |
| Bond angle (°) | 1.2 |
| Dihedral angles (°) | 21.3 |
| Improper angles (°) | 0.83 |

Structure Determination and Refinement of DHODH/Compound 6 Complex

The structure for the human DHODH(Met30-Arg396) in complex with compound 6 was solved using the method of molecular replacement (MR). The free accessible pdb entry 1D3G.pdb was used as a search model. The ligands brequinar and DDQ as well as all of the water molecules were removed prior to the MR search. The search model included the polypeptide chain of hDHODH(Met30-Arg396), one molecule of orotate, one molecule of the cofactor flavin-mononucleotide (FMN) and one acetate molecule which was present under the crystallization conditions. A standard rotational and translational molecular replacement search at 3.0 Å was performed using the program molrep (Collaborative Computational Project, Number 4 (1994). Acta Cryst. D50, 760-763.). Solutions for both the rotational and translational search were well above the next ranking solutions. The MR resulted in an R-factor of 32.7% and a correlation coefficient of 74.5 for the DHODH/compound 6 complex.

In a first round of refinement the MR model was subjected to rigid body refinement and a slow cooling simulated annealing protocol using a maximum likelihood target to remove model bias (Accelrys Inc. CNX program suite, CNX2002). Additionally, an individual b-factor refinement was carried out using standard CNX-protocols. Finally SIGMAA weighted 2Fo-Fc and Fo-Fc electron density maps were calculated and displayed together with the protein model in the program O (DatOno A B; Jones, T. A., Zou, J. Y., Cowan, S. W. & Kjelgaard, M. (1991). Acta Cryst. A47, 110-119.). The resulting experimental electron density was so excellent that the conformation of the inhibitor compound 6 could be interpreted unambiguously. The electron density around the five-membered ring carrying the carboxy group clearly showed that the inhibitor molecule adopts both the brequinar and non-brequinar binding mode. The carboxy group is in contact with both anion binding sites. Interestingly the protein's active site discriminates between the S- and R-enantiomere. Inspection of the corresponding electron density unequivocally shows the presences of the R-enantiomere only.

A pdb file for compound 6 was created using the program MOE (Chemical Computing Group Inc., MOE 2002.02). After energy minimization the compound was built into the electron density manually. Topology and parameter files for compound 6 were created using the program Xplo2d (Uppsala Software Factory; Kleywegt, G. M. (1997) J. Mol. Biol. 273, 371-376). After an additional round of model building and water picking using CNX another complete round of refinement was performed. The final model included the DHODH(Met30-Arg396) protein, the cofactor flavinmononucleotide (FMN), one orotate molecule (ORO), one acetate molecule (ACT), one sulfate ion (SO4), one molecule of compound 6 (INH) and 312 water molecules (TIP).

The models are well refined and show very good geometry. The refinement process which included data from 19.3-1.9 Å resulted in an R-factor of 18.5% and a free R-factor of 20.8% for the complex in conformation A and an R-factor of 18.5% and a free R-factor of 20.7% for the complex in conformation B, respectively. The almost identical R-factors indicate that non of the conformers A and B represent a preferred conformation. Except for non-glycine and non-proline residues 92.6% are located in the most favoured region of the ramachandran plot and 7.4% cluster in the additional allowed regions. There are no residues in the disallowed region. Table 18 summarizes the refinement statistics for compound 6 in complex with human DHODH. Values in parentheses give the R-factor and $R_{free}$-factors, respectively, for the last resolution bin ranging from 2.02 to 1.9.

TABLE 18

Refinement Statistics for DHODH/compound 6 complex

| | conformation A | conformation B |
|---|---|---|
| R-factor (%) | 18.5 (21.1) | 18.5 (21.2) |
| $R_{free}$ | 20.8 (21.5) | 20.7 (21.6) |
| RMS deviation from ideal values | | |
| bond length (Å) | 0.005 | 0.005 |
| Bond angle (°) | 1.2 | 1.2 |
| Dihedral angles (°) | 21.3 | 21.3 |
| Improper angles (°) | 0.79 | 0.79 |

Structure Determination and Refinement of DHODH/Compound 7 Complex

The structure for the human DHODH(Met30-Arg396) in complex with compound 7 was solved using the method of molecular replacement (MR). The free accessible pdb entry 1D3G.pdb was used as a search model. The ligands brequinar and DDQ as well as all of the water molecules were removed prior to the MR search. The search model included the polypeptide chain of hDHODH(Met30-Arg396), one molecule of orotate, one molecule of the cofactor flavin-mononucleotide (FMN) and one acetate molecule which was present under the crystallization conditions. A standard rotational and translational molecular replacement search at 3.0 Å was performed using the program molrep (Collaborative Computational Project, Number 4 (1994). Acta Cryst. D50, 760-763.). Solutions for both the rotational and translational search were well above the next ranking solutions. The MR resulted in an R-factor of 32.7% and a correlation coefficient of 73.9 for the DHODH/compound 7 complex.

In a first round of refinement the MR model was subjected to rigid body refinement and a slow cooling simulated annealing protocol using a maximum likelihood target to remove model bias (Accelrys Inc. CNX program suite, CNX2002). Additionally, an individual b-factor refinement was carried out using standard CNX-protocols. Finally SIGMAA weighted 2Fo-Fc and Fo-Fc electron density maps were calculated and displayed together with the protein model in the program O (DatOno A B; Jones, T. A., Zou, J. Y., Cowan, S. W. & Kjelgaard, M. (1991). Acta Cryst. A47, 110-119.). The resulting experimental electron density was so excellent that the conformation of the inhibitor compound 7 could be interpreted unambiguously. The electron density around the five-membered ring carrying the carboxy group clearly showed the carboxy group in contact with residues His 56 and Tyr 356 in non-brequinar-like conformation addressing subsite 3. In compound 7 a hydroxy group at 3-position at the five membered ring was introduced creating a stereo center at this position. The racemic mixture was used for crystallization experiments. Analysis of the electron density reveals the presence of both enantiomeres. Interestingly only the R-enantiomere is able to form additional contacts to the side chains of residues Gln47 and Arg136 and to a conserved water molecule. As is clearly shown from experimental data compound 7 is able to form interactions with both subsite 2 and subsite 3 at the same time. This feature clearly discriminates this compound class from, for example, compounds 2, 6 and 10 which can address both binding sites utilizing alternative conformations but not at the same time.

A pdb file for compound 7 was created using the program MOE (Chemical Computing Group Inc., MOE 2002.02). After energy minimization the compound was built into the electron density manually. Topology and parameter files for compound 7 were created using the program Xplo2d (Uppsala Software Factory; Kleywegt, G. M. (1997) J. Mol. Biol. 273, 371-376). After an additional round of model building and water picking using CNX another complete round of refinement was performed. The final model included the DHODH(Met30-Arg396) protein, the cofactor flavinmononucleotide (FMN), one orotate molecule (ORO), one acetate molecule (ACT), two sulfate ions (SO4), one molecule of compound 7 (INH) and 229 water molecules (TIP).

The model is well refined and shows very good stereochemical geometry. The refinement process which included data from 17.0-2.0 Å resulted in an R-factor of 17.5% and a free R-factor of 20.4% for the R-form and S-form. Except for non-glycine and non-proline residues 92.3% of the residues are located in the most favoured region of the ramachandran plot and 7.7% cluster in the additional allowed regions. There are no residues in the disallowed region. Table 19 summarizes the refinement statistics for compound 7 in complex with human DHODH. Values in parentheses give the R-factor and $R_{free}$-factors, respectively, for the last resolution bin ranging from 2.13 to 2.0.

TABLE 19

Refinement Statistics for DHODH/compound 7 complex

|  | R-form | S-form |
| --- | --- | --- |
| R-factor (%) | 17.5 (17.3) | 17.5 (17.3) |
| $R_{free}$ | 20.4 (21.4) | 20.4 (21.4) |
| RMS deviation from ideal values |  |  |
| bond length (Å) | 0.005 | 0.008 |
| Bond angle (°) | 1.2 | 1.2 |
| Dihedral angles (°) | 21.2 | 21.2 |
| Improper angles (°) | 0.82 | 0.81 |

Structure Determination and Refinement of DHODH/Compound 8 Complex

The structure for the human DHODH(Met30-Arg396) in complex with compound 8 was solved using the method of molecular replacement (MR). The free accessible pdb entry 1D3G.pdb was used as a search model. The ligands brequinar and DDQ as well as all of the water molecules were removed prior to the MR search. The search model included the polypeptide chain of hDHODH(Met30-Arg396), one molecule of orotate, one molecule of the cofactor flavin-mononucleotide (FMN) and one acetate molecule which was present under the crystallization conditions. A standard rotational and translational molecular replacement search at 3.0 Å was performed using the program molrep (Collaborative Computational Project, Number 4 (1994). Acta Cryst. D50, 760-763.). Solutions for both the rotational and translational search were well above the next ranking solutions. The MR resulted in an R-factor of 33.3% and a correlation coefficient of 73.9 for the DHODH/compound 8 complex.

In a first round of refinement the MR model was subjected to rigid body refinement and a slow cooling simulated annealing protocol using a maximum likelihood target to remove model bias (Accelrys Inc. CNX program suite, CNX2002). Additionally, an individual b-factor refinement was carried out using standard CNX-protocols. Finally SIGMAA weighted 2Fo-Fc and Fo-Fc electron density maps were calculated and displayed together with the protein model in the program O (DatOno A B; Jones, T. A., Zou, J. Y., Cowan, S. W. & Kjelgaard, M. (1991). Acta Cryst. A47, 110-119.). The resulting experimental electron density was so excellent that the conformation of the inhibitor compound 8 could be interpreted unambiguously. The electron density around the five-membered ring carrying the carboxy group clearly showed the carboxy group in contact with residues His 56 and Tyr 356 in non-brequinar-like conformation addressing subsite 3. In compound 8 a hydroxy group at 5-position at the five membered ring was introduced creating a stereo center at this position. The racemic mixture was used for crystallization experiments. Analysis of the electron density reveals that both enantiomeres fit into the electron density. The R-enantiomere appears to be positioned in a more favourable position to form interactions with subsite 3 whereas in the S-enantiomere the hydroxy group protrudes into the direction of subsite 4 (remote hydrophobic pocket) in a less favourable manner.

A pdb file for compound 8 was created using the program MOE (Chemical Computing Group Inc., MOE 2002.02). After energy minimization the compound was built into the electron density manually. Topology and parameter files for compound 8 were created using the program Xplo2d (Uppsala Software Factory; Kleywegt, G. M. (1997) J. Mol. Biol. 273, 371-376). After an additional round of model building and water picking using CNX another complete round of refinement was performed. The final model included the DHODH(Met30-Arg396) protein, the cofactor flavinmononucleotide (FMN), one orotate molecule (ORO), one acetate molecule (ACT), five sulfate ions (SO4), one molecule of compound 8 (INH) and 218 water molecules (TIP).

The model is well refined and shows very good stereochemical geometry. The refinement process which included data from 19.0-1.8 Å resulted in an R-factor of 18.2% and a free R-factor of 19.6% for the R-form and S-form (statistics are given only for R-form). Except for non-glycine and non-proline residues 91.6% of the residues are located in the most favoured region of the ramachandran plot and 8.4% cluster in the additional allowed regions. There are no residues in the disallowed region. Table 20 summarizes the refinement statistics for compound 8 in complex with human DHODH. Values in parentheses give the R-factor and $R_{free}$-factors, respectively, for the last resolution bin ranging from 1.91 to 1.8.

TABLE 20

| Refinement Statistics for DHODH/compound 8 complex | |
|---|---|
| R-factor (%) | 18.2 (22.1) |
| $R_{free}$ | 19.6 (24.6) |
| RMS deviation from ideal values | |
| bond length (Å) | 0.005 |
| Bond angle (°) | 1.2 |
| Dihedral angles (°) | 21.2 |
| Improper angles (°) | 0.83 |

Structure Determination and Refinement of DHODH/Compound 9 Complex

The structure for the human DHODH(Met30-Arg396) in complex with compound 9 was solved using the method of molecular replacement (MR). The free accessible pdb entry 1D3G.pdb was used as a search model. The ligands brequinar and DDQ as well as all of the water molecules were removed prior to the MR search. The search model included the polypeptide chain of hDHODH(Met30-Arg396), one molecule of orotate, one molecule of the cofactor flavinmononucleotide (FMN) and one acetate molecule which was present under the crystallization conditions. A standard rotational and translational molecular replacement search at 3.0 Å was performed using the program molrep (Collaborative Computational Project, Number 4 (1994). Acta Cryst. D50, 760-763.). Solutions for both the rotational and translational search were well above the next ranking solutions. The MR resulted in an R-factor of 32.8% and a correlation coefficient of 73.6 for the DHODH/compound 9 complex.

In a first round of refinement the MR model was subjected to rigid body refinement and a slow cooling simulated annealing protocol using a maximum likelihood target to remove model bias (Accelrys Inc. CNX program suite, CNX2002). Additionally, an individual b-factor refinement was carried out using standard CNX-protocols. Finally SIGMAA weighted 2Fo-Fc and Fo-Fc electron density maps were calculated and displayed together with the protein model in the program O (DatOno A B; Jones, T. A., Zou, J. Y., Cowan, S. W. & Kjelgaard, M. (1991). Acta Cryst. A47, 110-119.). The resulting experimental electron density was so excellent that the conformation of the inhibitor compound 9 could be interpreted unambiguously. The electron density around the five-membered ring carrying the carboxy group clearly showed the carboxy group in contact with residues Gln 47 and Arg 136 and a conserved water molecule in a unique brequinar-like conformation addressing subsite 2 only. In this conformation the sulfur atom of the five membered ring comes into close contact to Val 134 and Val 143 which form in part subsite 4 (remote hydrophobic pocket).

A pdb file for compound 9 was created using the program MOE (Chemical Computing Group Inc., MOE 2002.02). After energy minimization the compound was built into the electron density manually. Topology and parameter files for compound 9 were created using the program Xplo2d (Uppsala Software Factory; Kleywegt, G. M. (1997) J. Mol. Biol. 273, 371-376). After an additional round of model building and water picking using CNX another complete round of refinement was performed. The final model included the DHODH(Met30-Arg396) protein, the cofactor flavinmononucleotide (FMN), one orotate molecule (ORO), one acetate molecule (ACT), five sulfate ions (SO4), one molecule of compound 9 (INH) and 291 water molecules (TIP).

The model is well refined and shows very good stereochemical geometry. The refinement process which included data from 17.2-2.0 Å resulted in an R-factor of 18.1% and a free R-factor of 20.0%. Except for non-glycine and non-proline residues 92.1% of the residues are located in the most favoured region of the ramachandran plot and 7.9% cluster in the additional allowed regions. There are no residues in the disallowed region. Table 21 summarizes the refinement statistics for compound 9 in complex with human DHODH. Values in parentheses give the R-factor and $R_{free}$-factors, respectively, for the last resolution bin ranging from 2.13 to 2.0.

TABLE 21

| Refinement Statistics for DHODH/compound 9 complex | |
|---|---|
| R-factor (%) | 18.1 (19.7) |
| $R_{free}$ | 20.0 (22.0) |
| RMS deviation from ideal values | |
| bond length (Å) | 0.005 |
| Bond angle (°) | 1.2 |
| Dihedral angles (°) | 21.2 |
| Improper angles (°) | 0.80 |

Structure Determination and Refinement of DHODH/Compound 10 Complex

The structure for the human DHODH(Met30-Arg396) in complex with compound 10 was solved using the method of molecular replacement (MR). The free accessible pdb entry 1D3G.pdb was used as a search model. The ligands brequinar and DDQ as well as all of the water molecules were removed prior to the MR search. The search model included the polypeptide chain of hDHODH(Met30-Arg396), one molecule of orotate, one molecule of the cofactor flavinmononucleotide (FMN) and one acetate molecule which was present under the crystallization conditions. A standard rotational and translational molecular replacement search at 3.0 Å was performed using the program molrep (Collaborative Computational Project, Number 4 (1994). Acta Cryst. D50, 760-763.). Solutions for both the rotational and translational search were well above the next ranking solutions.

The MR resulted in an R-factor of 32.8% and a correlation coefficient of 74.1 for the DHODH/compound 10 complex.

In a first round of refinement the MR model was subjected to rigid body refinement and a slow cooling simulated annealing protocol using a maximum likelihood target to remove model bias (Accelrys Inc. CNX program suite, CNX2002). Additionally, an individual b-factor refinement was carried out using standard CNX-protocols. Finally SIGMAA weighted 2Fo-Fc and Fo-Fc electron density maps were calculated and displayed together with the protein model in the program O (DatOno A B; Jones, T. A., Zou, J. Y., Cowan, S. W. & Kjelgaard, M. (1991). Acta Cryst. A47, 110-119.). The resulting experimental electron density was so excellent that the conformation of the inhibitor compound 10 could be interpreted unambiguously. The electron density around the five-membered ring carrying the carboxy group clearly showed the presence of two alternative conformations of compound 10. In one conformation (conformation A) the carboxy group interacts with residues Gln 47 and Arg 136, whereas in the second conformation (conformation B) the interaction involves residues His 56 and Tyr 356 (see above). For each conformation a separate DHODH/compound 10 complex was subjected to refinement.

The pdb files for the compound 10 in conformation A and B were created using the program MOE (Chemical Computing Group Inc., MOE 2002.02). Both compounds were energy minimized and built into the electron density manually. Topology and parameter files for compound 10 were created using the program Xplo2d (Uppsala Software Factory; Kleywegt, G. M. (1997) J. Mol. Biol., 273, 371-376). After an additional round of model building and water picking using CNX, another complete round of refinement was performed. The final model included the human DHODH(Met30-Arg396) protein, the cofactor flavinmononucleotide (FMN), one orotate molecule (ORO), two acetate molecules (ACT), four sulfate ions (SO4), one molecule of compound 10 (INH) either in conformation A or conformation B and 226 water molecules (TIP). Residues which are missing the coordinate file due to very poor electron density are listed in the header of the pdb files.

The models are well refined and show very good geometry. The refinement process which included data from 19.5-1.8 Å resulted in an R-factor of 19.5% and a free R-factor of 20.5% for the complex in conformation A and for the complex in conformation B, respectively. The identical R-factors indicate that non of the conformers A and B represent a preferred conformation. Except for non-glycine and non-proline residues 91.6% are located in the most favoured region of the ramachandran plot and 8.4% cluster in the additional allowed regions. There are no residues in the disallowed region. Table 22 summarizes the refinement statistics for compound 10 in complex with human DHODH. Values in parentheses give the R-factor and $R_{free}$-factors, respectively, for the last resolution bin ranging from 1.91 to 1.8.

TABLE 22

Refinement Statistics for DHODH/compound 10 complex

|  | conformation A & B |
|---|---|
| R-factor (%) | 19.5 (20.5) |
| $R_{free}$ | 20.5 (22.7) |
| RMS deviation from ideal values | |
| bond length (Å) | 0.005 |
| Bond angle (°) | 1.2 |

TABLE 22-continued

Refinement Statistics for DHODH/compound 10 complex

|  | conformation A & B |
|---|---|
| Dihedral angles (°) | 21.9 |
| Improper angles (°) | 0.82 |

While this invention has been particularly shown and described with references to preferred embodiments thereof, it will be understood by those skilled in the art that various changes in form and details may be made therein without departing from the scope of the invention encompassed by the appended claims.

The following compounds are preferred: 3-(Biphenyl-4-ylcarbamoyl)-thiophene-2-carboxylic acid; 3-(2'-Ethoxy-3,5-difluoro-biphenyl-4-ylcarbamoyl)-thiophene-2-carboxylic acid; 3-(3'-Ethoxy-3,5-difluoro-biphenyl-4-yl-carbamoyl)-thiophene-2-carboxylic acid; 3-(3,5-Difluoro-2',4'-dimethoxy-biphenyl-4-yl-carbamoyl)-thiophene-2-carboxylic acid; 3-(2,3,5,6-Tetrafluoro-2'-methoxy-biphenyl-4-yl-carbamoyl)-thiophene-2-carboxylic acid; 3-(2'-Chloro-3,5-difluoro-biphenyl-4-ylcarbamoyl)-thiophene-2-carboxylic acid; 3-(3,5,2'-Trifluoro-biphenyl-4-ylcarbamoyl)-thiophene-2-carboxylic acid; 3-(2-Chloro-2'-methoxy-biphenyl-4-ylcarbamoyl)-thiophene-2-carboxylic acid; 3-(2,3,5,6-Tetrafluoro-3'-trifluoromethoxy-biphenyl-4-ylcarbamoyl)-thiophene-2-carboxylic acid; 3-(3-Fluoro-3'-methoxy-biphenyl-4-ylcarbamoyl)-thiophene-2-carboxylic acid; 3-(3,5-Difluoro-3'-trifluoromethoxy-biphenyl-4-ylcarbamoyl)-thiophene-2-carboxylic acid; 3-(Biphenyl-4-ylcarbamoyl)-furan-2-carboxylic acid; 4-(Biphenyl-4-ylcarbamoyl)-thiophene-3-carboxylic acid; 4-(2-Chloro-2'-methoxy-biphenyl-4-ylcarbamoyl)-thiophene-3-carboxylic acid; 4-(3,5,2'-Trifluoro-biphenyl-4-ylcarbamoyl)-thiophene-3-carboxylic acid; 4-(3'-Ethoxy-3,5-difluoro-biphenyl-4-ylcarbamoyl)-thiophene-3-carboxylic acid; 4-(2'-Ethoxy-3,5-difluoro-biphenyl-4-ylcarbamoyl)-thiophene-3-carboxylic acid; 4-(3,5-Difluoro-3'-trifluoromethoxy-biphenyl-4-ylcarbamoyl)-thiophene-3-carboxylic acid; 4-(3-Fluoro-3'-methoxy-biphenyl-4-ylcarbamoyl)-thiophene-3-carboxylic acid; 4-(Biphenyl-4-ylcarbamoyl)-furan-3-carboxylic acid; 2-(Biphenyl-4-ylcarbamoyl)-thiophene-3-carboxylic acid; 2-(Biphenyl-4-ylcarbamoyl)-furan-3-carboxylic acid; 3-(3-Fluoro-3'-methoxy-biphenyl-4-yl-carbamoyl)-cyclopent-1-ene-1,2-dicarboxylic acid; 2-(3-Fluoro-3'-methoxy-biphenyl-4-ylcarbamoyl)-cyclopent-1-ene-1,3-dicarboxylic acid; 2-(3-Fluoro-3'-methoxy-biphenyl-4-ylcarbamoyl)-cyclopent-1-enecarboxylic acid methyl ester; Cyclopent-1-ene-1,2-dicarboxylic acid 1-[(3-fluoro-3'-methoxy-biphenyl-4-yl)-amide]2-hydroxyamide; 3-Hydroxy-2-(2,3,5,6-tetrafluoro-3'-trifluoromethoxy-biphenyl-4-ylcarbamoyl)-cyclopent-1-enecarboxylic acid; 5-Hydroxy-2-(2,3,5,6-tetrafluoro-3'-trifluoromethoxy-biphenyl-4-ylcarbamoyl)-cyclopent-1-enecarboxylic acid; 2-(3'-Ethoxy-3,5-difluoro-biphenyl-4-ylcarbamoyl)-3-hydroxy-cyclopent-1-enecarboxylic acid; 2-(3'-Ethoxy-3,5-difluoro-biphenyl-4-ylcarbamoyl)-5-hydroxy-cyclo-pent-1-enecarboxylic acid; 2-(1',3'di-methoxy-3,5-difluoro-biphenyl-4-ylcarbamoyl)-3-hydroxy-cyclopent-1-enecarboxylic acid; 2-(1',3'di-methoxy-3,5-difluoro-biphenyl-4-yl-carbamoyl)-5-hydroxy-cyclopent-1-enecarboxylic acid; 3-Hydroxy-2-(3,5,2'-trifluoro-biphenyl-4-ylcarbamoyl)-cyclopent-1-enecarboxylic acid; 5-Hydroxy-2-(3,5,2'-trifluoro-biphenyl-4-ylcarbamoyl)-cyclopent-1-enecarboxylic acid; 2-(2-Chloro-2'-methoxy-biphenyl-4-ylcarbamoyl)-3-hydroxycyclopent-1-enecarboxylic acid; 2-(2-Chloro-2'-methoxy-biphenyl-4-ylcarbamoyl)-5-hydroxy-cyclopent-1-enecarboxylic acid; 2-(2'-Chloro-3,5-difluoro-biphenyl-4-ylcarbamoyl)-3-hydroxy-cyclopent-1-enecarboxylic acid; 2-(2'-Chloro-3,5-difluoro-biphenyl-4-ylcarbamoyl)-5-hydroxy-cyclopent-1-enecarboxylic acid; 2-(3-Fluoro-3'-methoxy-biphenyl-4-ylcarbamoyl)-3-hydroxy-cyclopent-1-enecarboxylic acid; 2-(3-Fluoro-3'-methoxy-biphenyl-4-ylcarbamoyl)-5-hydroxy-cyclopent-1-enecarboxylic acid; trans 2-(3-Fluoro-3'-methoxy-biphenyl-4-ylcarbamoyl)-cyclopentane carboxylic acid; cis-2-(3-Fluoro-3'-methoxy-biphenyl-4-ylcarbamoyl)-cyclopentane carboxylic acid; 2-(2'-Chloro-3,5-difluoro-biphenyl-4-ylcarbamoyl)-cyclopentane carboxylic acid; 2-(3,5-Difluoro-2',4'-dimethoxy-biphenyl-4-ylcarbamoyl)-cyclopentane carboxylic acid; 2-(3'-Ethoxy-3,5-difluoro-biphenyl-4-ylcarbamoyl)-cyclopentane carboxylic acid; 2-(2'-Ethoxy-3,5-difluoro-biphenyl-4-ylcarbamoyl)-cyclopentane carboxylic acid; 2-(Biphenyl-4-ylcarbamoyl)-cyclopentane carboxylic acid; 2-(2,3,5,6-Tetrafluoro-3'-trifluoro-methoxy-biphenyl-4-ylcarbamoyl)-cyclopentane carboxylic acid; 2-(3,5-Difluoro-3'-trifluoro-methoxy-biphenyl-4-yl-carbamoyl)-cyclopentane carboxylic acid

TABLE 25

| Structure | Consensus Score |
|---|---|
| 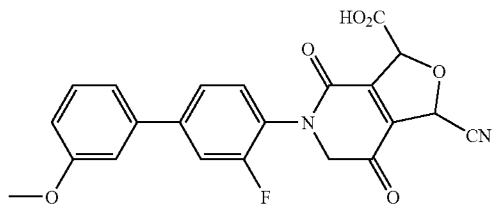 | −63.04 |
| 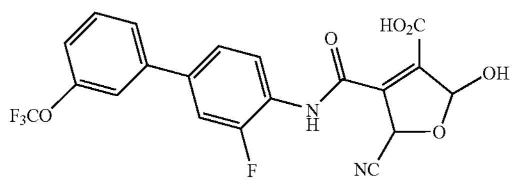 | −61.85 |
| 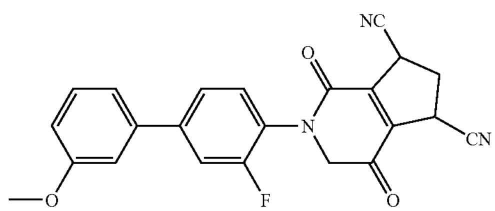 | −60.26 |
| 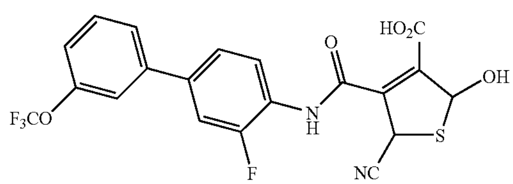 | −59.46 |
| 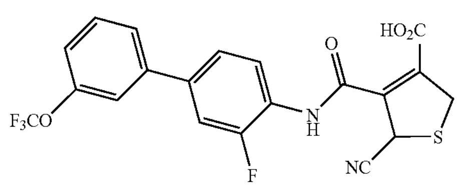 | −58.50 |
| 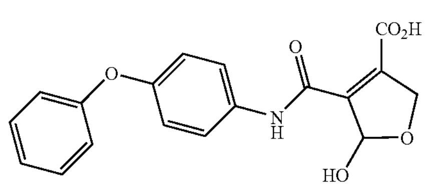 | −58.21 |

TABLE 25-continued

| Structure | Consensus Score |
|---|---|
| 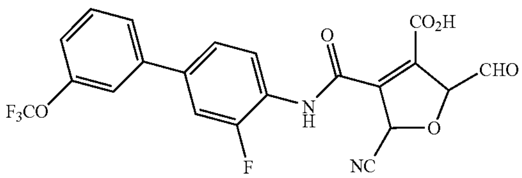 | −58.13 |
| 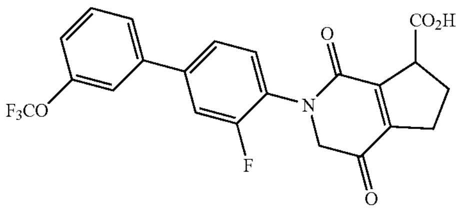 | −58.12 |
| 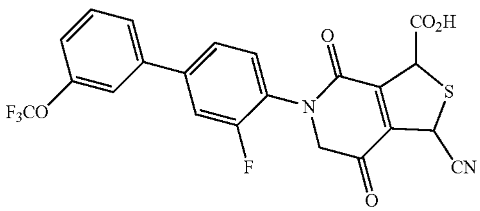 | −58.05 |
| 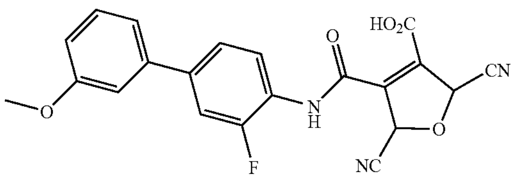 | −57.99 |
| 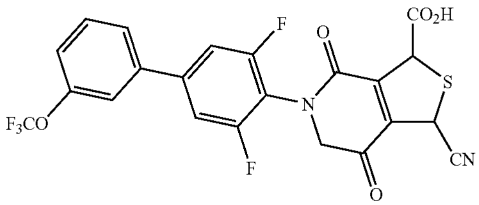 | −57.66 |
| 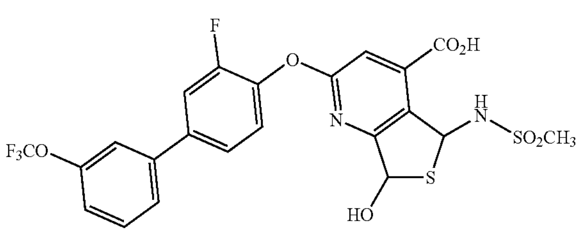 | −57.60 |
| 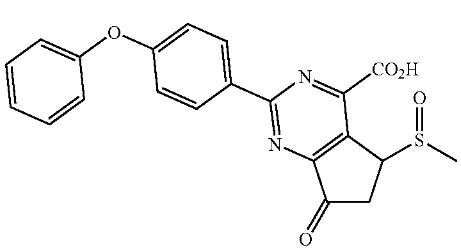 | −57.56 |

TABLE 25-continued
| Structure | Consensus Score |
|---|---|
| 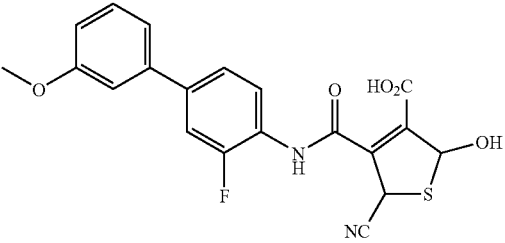 | −57.55 |
| 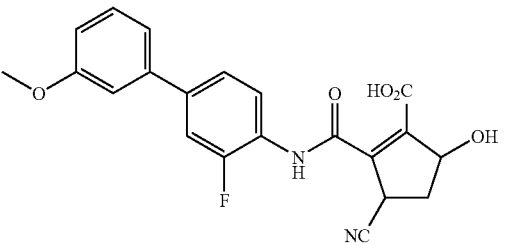 | −57.51 |
| 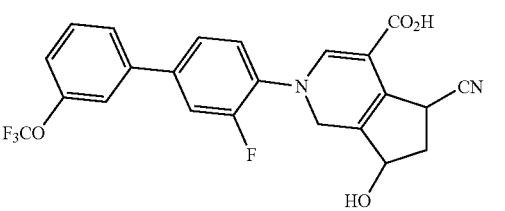 | −56.85 |
| 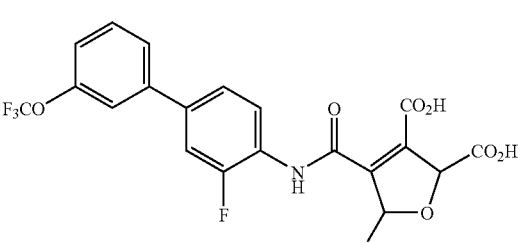 | −56.85 |
| 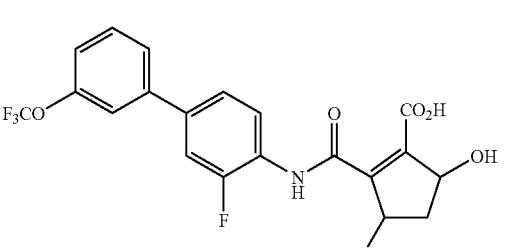 | −56.72 |
| 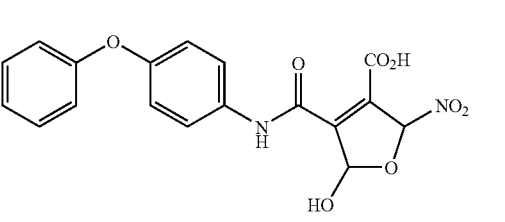 | −56.71 |

TABLE 25-continued

| Structure | Consensus Score |
|---|---|
| 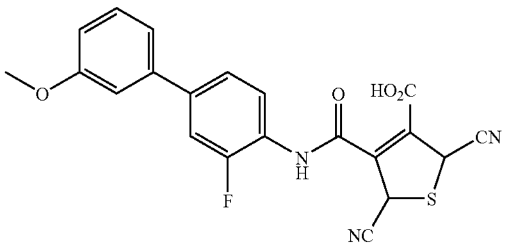 | −56.31 |
| 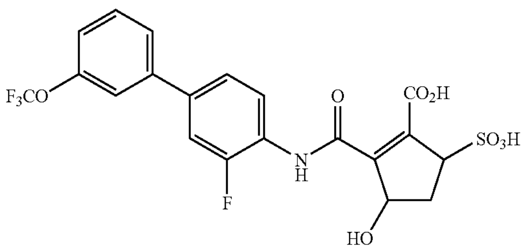 | −57.18 |
| 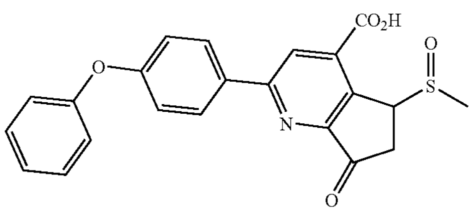 | −57.14 |
| 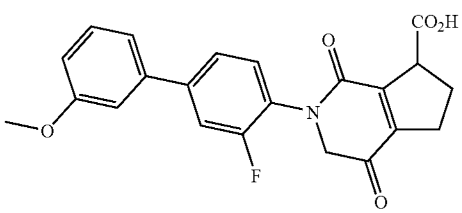 | −57.00 |
| 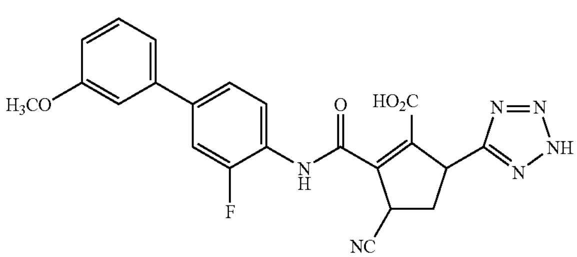 | −56.93 |
| 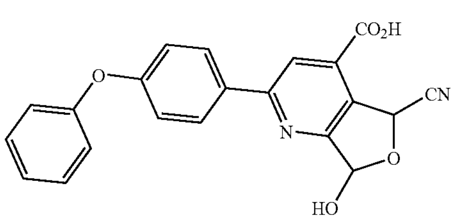 | −56.25 |

TABLE 25-continued

| Structure | Consensus Score |
|---|---|
| (structure) | −55.96 |
| (structure) | −55.93 |
| (structure) | −55.89 |
| (structure) | −55.67 |
| (structure) | −55.64 |
| (structure) | −55.58 |
| (structure) | −55.52 |

TABLE 25-continued
| Structure | Consensus Score |
|---|---|
| 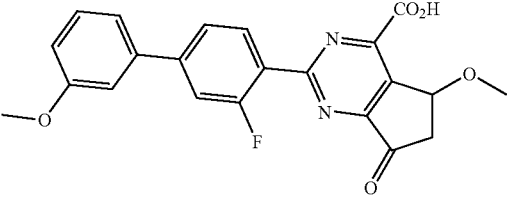 | −55.51 |
| 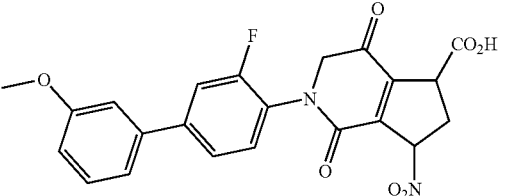 | −55.29 |
| 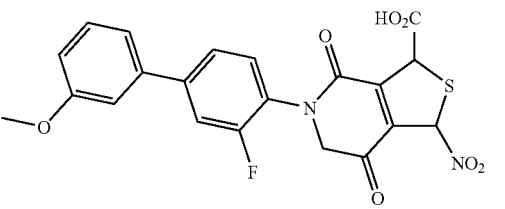 | −55.14 |
| 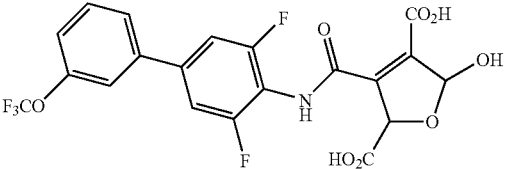 | −55.10 |
| 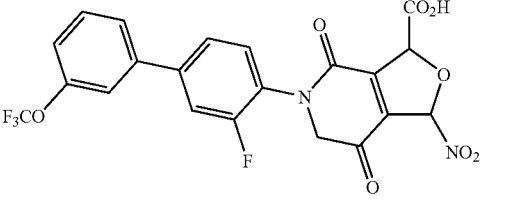 | −54.92 |
| 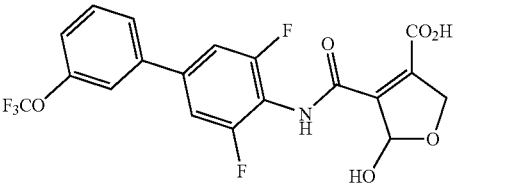 | −54.72 |
| 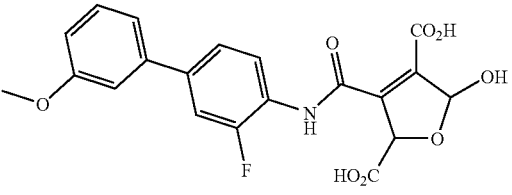 | −54.51 |

TABLE 25-continued

| Structure | Consensus Score |
|---|---|
| 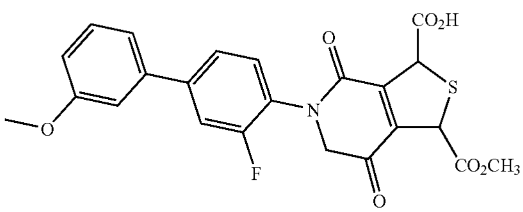 | −54.49 |
| | −54.47 |
| | −54.47 |
| 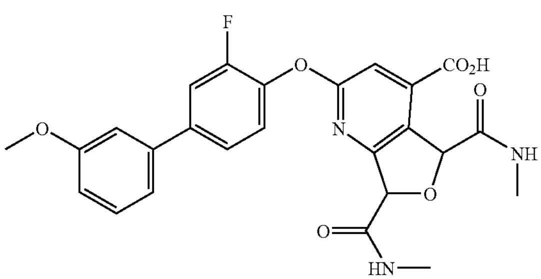 | −54.38 |
| | −54.35 |
| | −54.35 |

TABLE 25-continued
| Structure | Consensus Score |
|---|---|
| 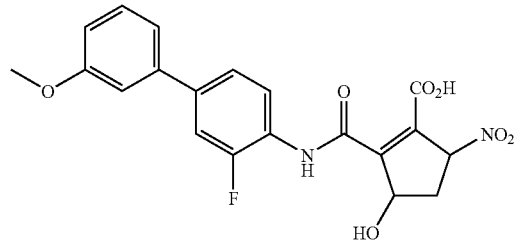 | −54.29 |
| 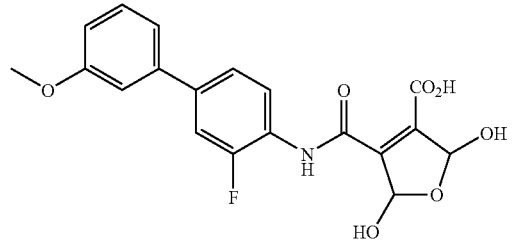 | −54.29 |
| 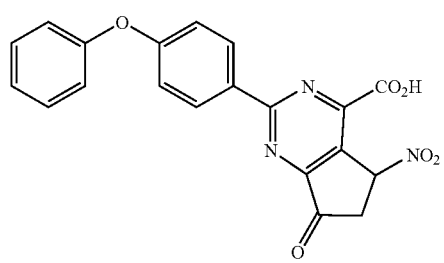 | −54.28 |
| 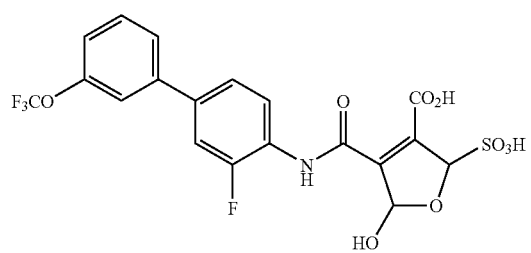 | −54.16 |
| 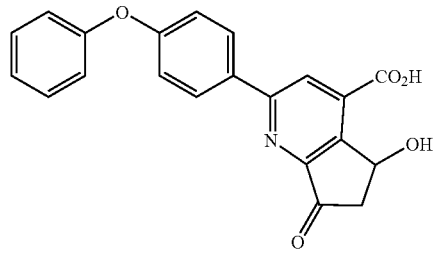 | −54.10 |
| 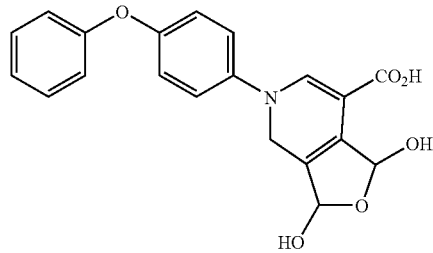 | −54.10 |

TABLE 25-continued
| Structure | Consensus Score |
|---|---|
| 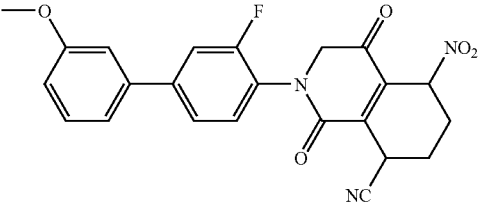 | −54.07 |
| 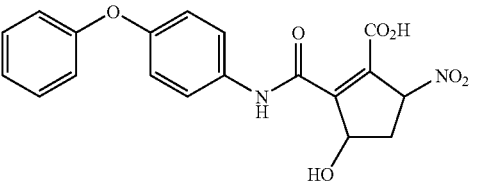 | −54.05 |
| 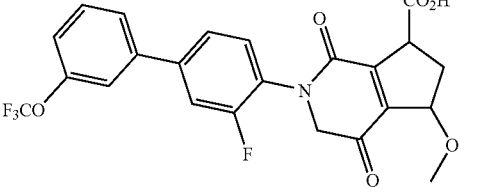 | −54.04 |
| 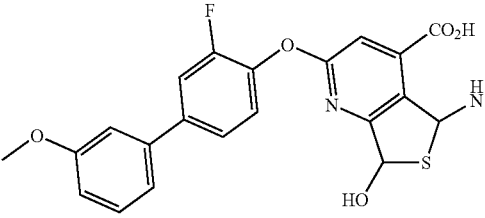 | −53.92 |
| 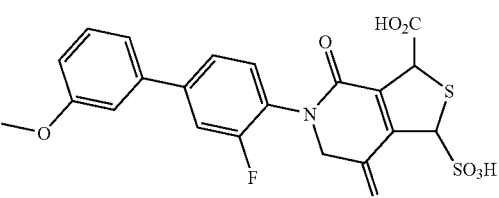 | −53.92 |
| 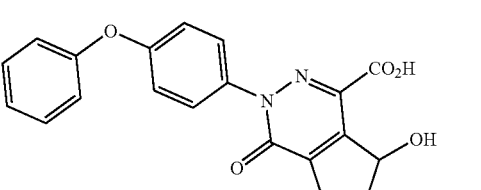 | −53.79 |
| 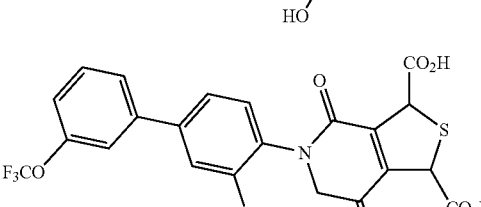 | −53.75 |

TABLE 25-continued

| Structure | Consensus Score |
|---|---|
| (structure) | −53.73 |
| (structure) | −53.70 |
| (structure) | −53.56 |
| (structure) | −53.54 |
| (structure) | −53.21 |
| (structure) | −53.20 |
| (structure) | −53.18 |

TABLE 25-continued
| Structure | Consensus Score |
|---|---|
| 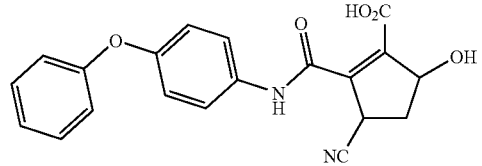 | −53.15 |
| 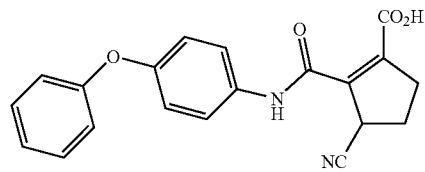 | −53.15 |
| 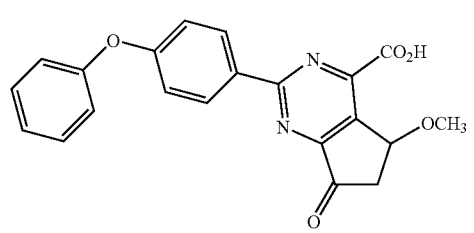 | −53.08 |
| 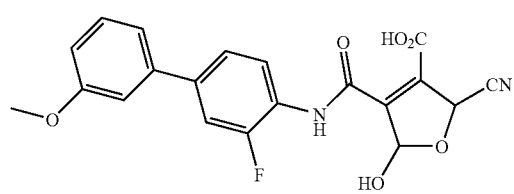 | −53.01 |
| 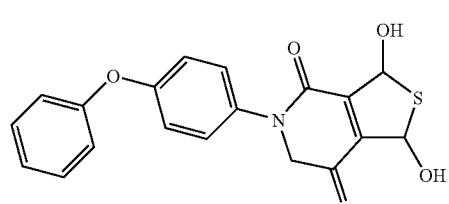 | −53.01 |
| 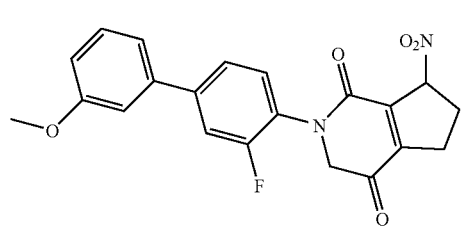 | −53.00 |
| 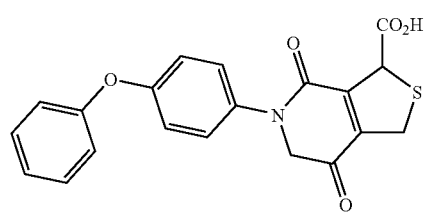 | −52.99 |

TABLE 25-continued

| Structure | Consensus Score |
|---|---|
| 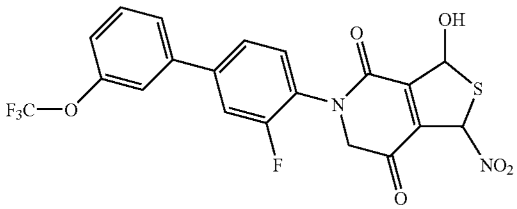 | −52.89 |
| 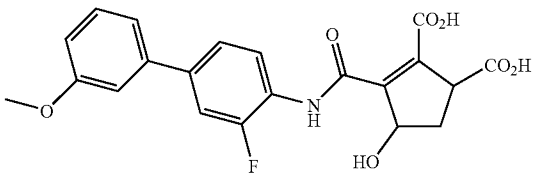 | −52.74 |
| 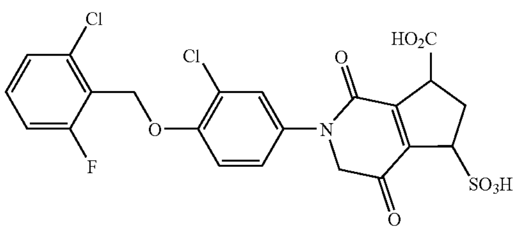 | −52.73 |
| 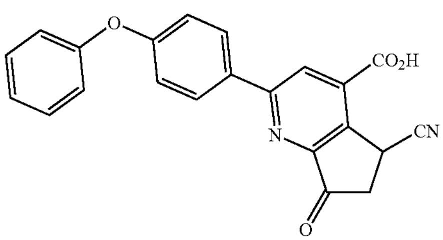 | −52.69 |
| 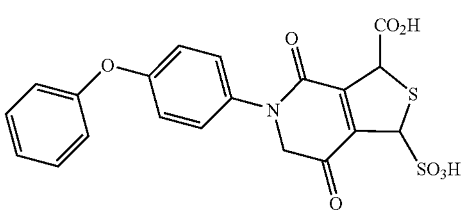 | −52.65 |
| 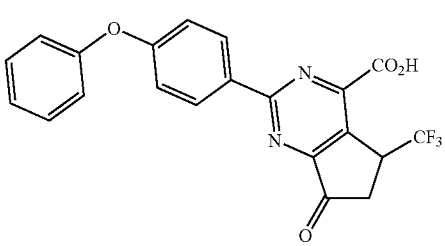 | −52.60 |
| 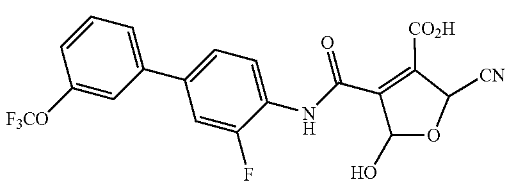 | −52.58 |

TABLE 25-continued

| Structure | Consensus Score |
|---|---|
| 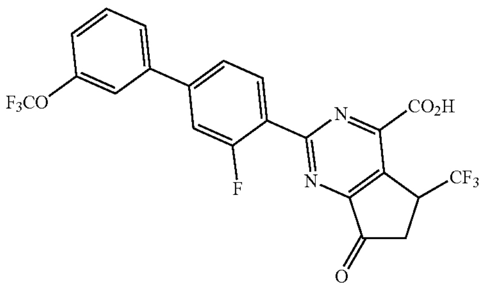 | −52.57 |
| 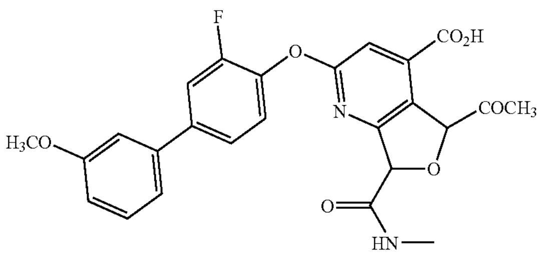 | −52.51 |
| 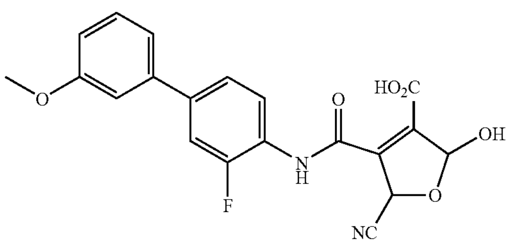 | −52.49 |
| 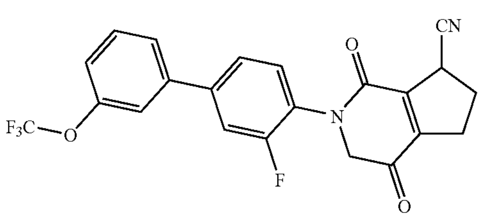 | −52.33 |
| 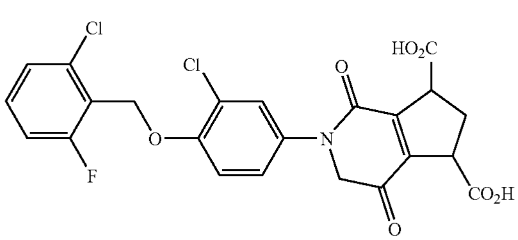 | −52.30 |
| 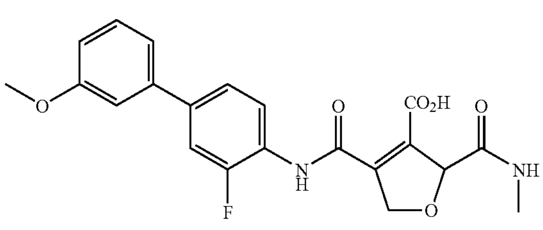 | −52.12 |

TABLE 25-continued
| Structure | Consensus Score |
|---|---|
| 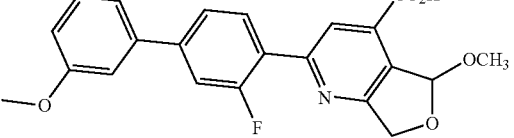 | −52.08 |
| 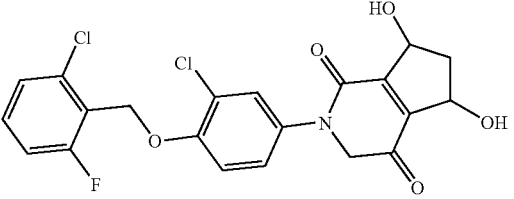 | −52.04 |
| 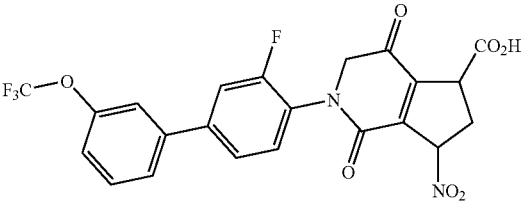 | −51.98 |
| 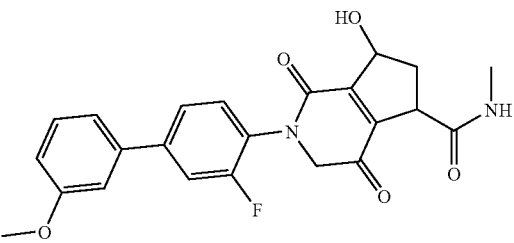 | −51.91 |
| 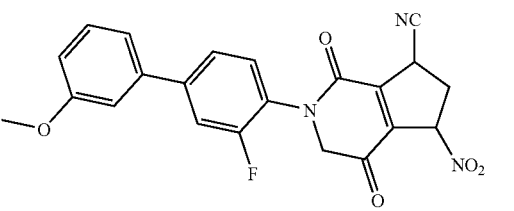 | −51.86 |
| 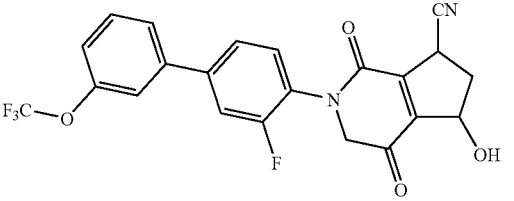 | −51.76 |
| 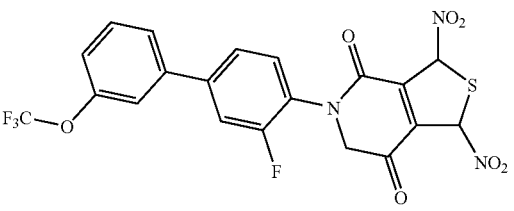 | −51.76 |

TABLE 25-continued
| Structure | Consensus Score |
|---|---|
| 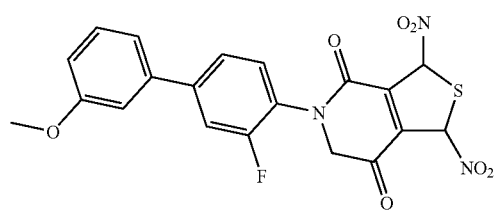 | −51.74 |
| 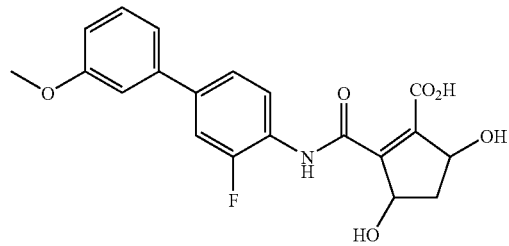 | −51.66 |
| 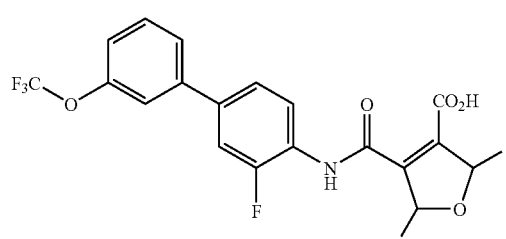 | −51.65 |
| 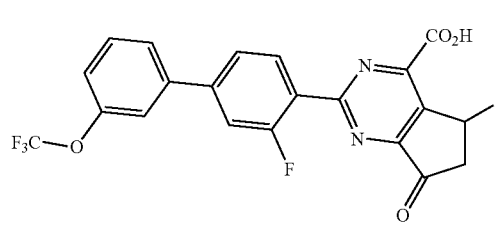 | −51.55 |
| 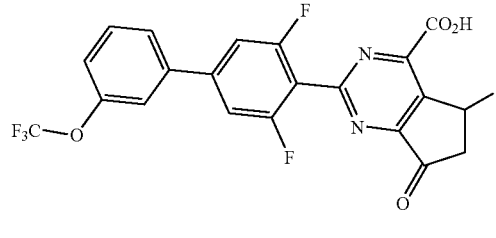 | −51.54 |
| 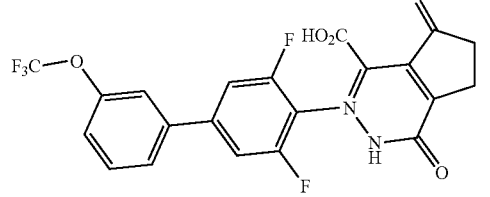 | −51.45 |

TABLE 25-continued

| Structure | Consensus Score |
|---|---|
| 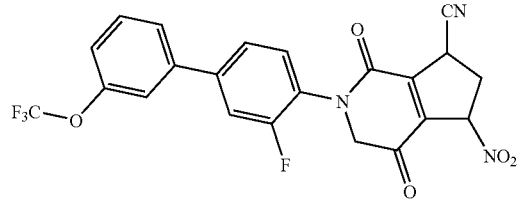 | −51.40 |
| 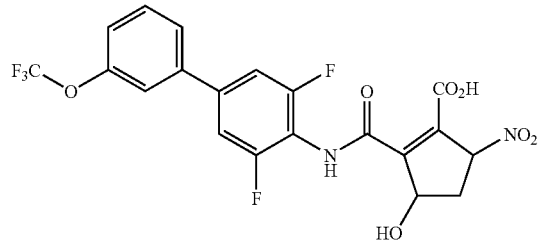 | −51.37 |

TABLE 29

| | | | | | | | | | | | |
|---|---|---|---|---|---|---|---|---|---|---|---|
| CRYST1 | | 90.651 | 90.651 | 123.072 | 90.00 | 90.00 | 120.00 | P | 32 2 1 | | 12 |
| ORIGX1 | | 1.000000 | | 0.000000 | | 0.000000 | | 0.00000 | | | |
| ORIGX2 | | 0.000000 | | 1.000000 | | 0.000000 | | 0.00000 | | | |
| ORIGX3 | | 0.000000 | | 0.000000 | | 1.000000 | | 0.00000 | | | |
| SCALE1 | | 0.011031 | | 0.006369 | | 0.000000 | | 0.00000 | | | |
| SCALE2 | | 0.000000 | | 0.012738 | | 0.000000 | | 0.00000 | | | |
| SCALE3 | | 0.000000 | | 0.000000 | | 0.008125 | | 0.00000 | | | |
| ATOM | 2779 | N1 | FMN | 398 | 41.764 | 36.130 | 8.647 | 1.00 | 13.22 | | |
| ATOM | 2780 | C2 | FMN | 398 | 42.155 | 35.485 | 9.782 | 1.00 | 16.74 | | |
| ATOM | 2781 | O2 | FMN | 398 | 41.551 | 35.587 | 10.834 | 1.00 | 15.99 | | |
| ATOM | 2782 | N3 | FMN | 398 | 43.334 | 34.654 | 9.723 | 1.00 | 15.64 | | |
| ATOM | 2783 | C4 | FMN | 398 | 44.085 | 34.461 | 8.625 | 1.00 | 15.45 | | |
| ATOM | 2784 | O4 | FMN | 398 | 45.083 | 33.724 | 8.672 | 1.00 | 15.51 | | |
| ATOM | 2785 | C4A | FMN | 398 | 43.662 | 35.157 | 7.396 | 1.00 | 14.11 | | |
| ATOM | 2786 | N5 | FMN | 398 | 44.352 | 35.025 | 6.251 | 1.00 | 13.88 | | |
| ATOM | 2787 | C5A | FMN | 398 | 43.933 | 35.705 | 5.122 | 1.00 | 11.84 | | |
| ATOM | 2788 | C6 | FMN | 398 | 44.672 | 35.590 | 3.867 | 1.00 | 10.31 | | |
| ATOM | 2789 | C7 | FMN | 398 | 44.292 | 36.270 | 2.717 | 1.00 | 11.40 | | |
| ATOM | 2790 | C7M | FMN | 398 | 45.109 | 36.125 | 1.414 | 1.00 | 9.20 | | |
| ATOM | 2791 | C8 | FMN | 398 | 43.119 | 37.130 | 2.739 | 1.00 | 11.94 | | |
| ATOM | 2792 | C8M | FMN | 398 | 42.649 | 37.914 | 1.520 | 1.00 | 13.94 | | |
| ATOM | 2793 | C9 | FMN | 398 | 42.397 | 37.245 | 3.923 | 1.00 | 11.56 | | |
| ATOM | 2794 | C9A | FMN | 398 | 42.767 | 36.561 | 5.119 | 1.00 | 13.59 | | |
| ATOM | 2795 | N10 | FMN | 398 | 42.048 | 36.664 | 6.371 | 1.00 | 13.81 | | |
| ATOM | 2796 | C10 | FMN | 398 | 42.448 | 36.000 | 7.512 | 1.00 | 14.45 | | |
| ATOM | 2797 | C1* | FMN | 398 | 40.845 | 37.508 | 6.453 | 1.00 | 12.64 | | |
| ATOM | 2798 | C2* | FMN | 398 | 41.112 | 39.002 | 6.630 | 1.00 | 13.30 | | |
| ATOM | 2799 | O2* | FMN | 398 | 41.776 | 39.190 | 7.920 | 1.00 | 13.46 | | |
| ATOM | 2800 | C3* | FMN | 398 | 39.786 | 39.812 | 6.672 | 1.00 | 12.09 | | |
| ATOM | 2801 | O3* | FMN | 398 | 38.927 | 39.299 | 7.749 | 1.00 | 12.88 | | |
| ATOM | 2802 | C4* | FMN | 398 | 38.953 | 39.699 | 5.366 | 1.00 | 12.40 | | |
| ATOM | 2803 | O4* | FMN | 398 | 39.803 | 39.461 | 4.214 | 1.00 | 11.71 | | |
| ATOM | 2804 | C5* | FMN | 398 | 38.115 | 40.952 | 5.105 | 1.00 | 9.96 | | |
| ATOM | 2805 | O5* | FMN | 398 | 38.918 | 42.129 | 4.957 | 1.00 | 13.77 | | |
| ATOM | 2806 | P | FMN | 398 | 39.368 | 42.735 | 3.536 | 1.00 | 12.98 | | |
| ATOM | 2807 | O1P | FMN | 398 | 40.420 | 41.816 | 2.954 | 1.00 | 14.29 | | |
| ATOM | 2808 | O2P | FMN | 398 | 39.893 | 44.111 | 3.861 | 1.00 | 12.03 | | |
| ATOM | 2809 | O3P | FMN | 398 | 38.119 | 42.812 | 2.647 | 1.00 | 13.57 | | |
| ATOM | 2810 | N1 | ORO | 399 | 41.668 | 32.377 | 4.927 | 1.00 | 16.79 | | |
| ATOM | 2811 | C2 | ORO | 399 | 40.653 | 33.293 | 5.236 | 1.00 | 16.19 | | |
| ATOM | 2812 | O2 | ORO | 399 | 40.042 | 33.934 | 4.385 | 1.00 | 20.26 | | |
| ATOM | 2813 | N3 | ORO | 399 | 40.353 | 33.457 | 6.587 | 1.00 | 14.42 | | |
| ATOM | 2814 | C4 | ORO | 399 | 40.966 | 32.794 | 7.654 | 1.00 | 14.86 | | |
| ATOM | 2815 | O4 | ORO | 399 | 40.645 | 32.999 | 8.803 | 1.00 | 14.43 | | |
| ATOM | 2816 | C5 | ORO | 399 | 42.023 | 31.842 | 7.276 | 1.00 | 14.27 | | |
| ATOM | 2817 | C6 | ORO | 399 | 42.317 | 31.682 | 5.968 | 1.00 | 16.76 | | |
| ATOM | 2818 | C7 | ORO | 399 | 43.403 | 30.705 | 5.524 | 1.00 | 17.77 | | |
| ATOM | 2819 | O71 | ORO | 399 | 44.513 | 30.665 | 6.039 | 1.00 | 19.80 | | |

TABLE 29-continued

| ATOM | 2820 | O72 | ORO | 399 | 42.936 | 29.994 | 4.595 | 1.00 | 18.75 |
|---|---|---|---|---|---|---|---|---|---|
| ATOM | 2821 | S | SO4 | 400 | 56.428 | 40.104 | 34.632 | 1.00 | 33.94 |
| ATOM | 2822 | O1 | SO4 | 400 | 56.122 | 41.420 | 35.218 | 1.00 | 34.17 |
| ATOM | 2823 | O2 | SO4 | 400 | 55.206 | 39.280 | 34.611 | 1.00 | 35.21 |
| ATOM | 2824 | O3 | SO4 | 400 | 56.931 | 40.290 | 33.260 | 1.00 | 35.14 |
| ATOM | 2825 | O4 | SO4 | 400 | 57.461 | 39.431 | 35.440 | 1.00 | 35.91 |
| ATOM | 2826 | C | ACT | 401 | 24.612 | 49.259 | 4.963 | 1.00 | 34.33 |
| ATOM | 2827 | O | ACT | 401 | 23.428 | 49.625 | 4.658 | 1.00 | 33.50 |
| ATOM | 2828 | OXT | ACT | 401 | 24.926 | 48.987 | 6.156 | 1.00 | 35.35 |
| ATOM | 2829 | CH3 | ACT | 401 | 24.980 | 48.156 | 3.942 | 1.00 | 30.98 |
| ATOM | 2830 | S | SO4 | 402 | 56.699 | 36.609 | 28.290 | 1.00 | 39.30 |
| ATOM | 2831 | O1 | SO4 | 402 | 55.391 | 37.270 | 28.281 | 1.00 | 48.45 |
| ATOM | 2832 | O2 | SO4 | 402 | 56.512 | 35.164 | 28.489 | 1.00 | 46.40 |
| ATOM | 2833 | O3 | SO4 | 402 | 57.362 | 36.850 | 26.997 | 1.00 | 48.09 |
| ATOM | 2834 | O4 | SO4 | 402 | 57.515 | 37.166 | 29.380 | 1.00 | 46.88 |
| ATOM | 2835 | S | SO4 | 403 | 48.271 | 43.913 | 28.816 | 1.00 | 92.32 |
| ATOM | 2836 | O1 | SO4 | 403 | 49.281 | 42.998 | 28.253 | 1.00 | 91.75 |
| ATOM | 2837 | O2 | SO4 | 403 | 47.936 | 43.487 | 30.189 | 1.00 | 91.47 |
| ATOM | 2838 | O3 | SO4 | 403 | 48.811 | 45.286 | 28.848 | 1.00 | 91.52 |
| ATOM | 2839 | O4 | SO4 | 403 | 47.056 | 43.882 | 27.977 | 1.00 | 91.67 |
| ATOM | 2840 | S | SO4 | 404 | 32.887 | 23.014 | 6.481 | 1.00 | 79.75 |
| ATOM | 2841 | O1 | SO4 | 404 | 32.953 | 24.098 | 7.479 | 1.00 | 80.39 |
| ATOM | 2842 | O2 | SO4 | 404 | 32.083 | 23.456 | 5.326 | 1.00 | 79.78 |
| ATOM | 2843 | O3 | SO4 | 404 | 34.249 | 22.673 | 6.029 | 1.00 | 79.79 |
| ATOM | 2844 | O4 | SO4 | 404 | 32.257 | 21.829 | 7.091 | 1.00 | 79.81 |
| ATOM | 2845 | OH2 | TIP | 2 | 35.590 | 55.465 | −5.472 | 1.00 | 26.63 |
| ATOM | 2846 | OH2 | TIP | 3 | 38.348 | 45.654 | 5.431 | 1.00 | 10.48 |
| ATOM | 2847 | OH2 | TIP | 4 | 26.302 | 32.577 | −2.704 | 1.00 | 19.39 |
| ATOM | 2848 | OH2 | TIP | 5 | 32.739 | 49.699 | 5.057 | 1.00 | 5.11 |
| ATOM | 2849 | OH2 | TIP | 6 | 40.173 | 36.489 | 0.177 | 1.00 | 9.37 |
| ATOM | 2850 | OH2 | TIP | 7 | 28.781 | 46.327 | 21.174 | 1.00 | 10.19 |
| ATOM | 2851 | OH2 | TIP | 8 | 50.103 | 40.154 | 27.008 | 1.00 | 11.09 |
| ATOM | 2852 | OH2 | TIP | 9 | 52.699 | 35.114 | 39.857 | 1.00 | 14.19 |
| ATOM | 2853 | OH2 | TIP | 10 | 32.651 | 48.949 | 19.281 | 1.00 | 9.20 |
| ATOM | 2854 | OH2 | TIP | 11 | 31.681 | 31.390 | 6.490 | 1.00 | 17.24 |
| ATOM | 2855 | OH2 | TIP | 12 | 54.417 | 36.438 | 7.903 | 1.00 | 15.61 |
| ATOM | 2856 | OH2 | TIP | 13 | 48.745 | 30.174 | −4.588 | 1.00 | 19.16 |
| ATOM | 2857 | OH2 | TIP | 14 | 52.941 | 44.773 | 24.555 | 1.00 | 23.37 |
| ATOM | 2858 | OH2 | TIP | 15 | 56.887 | 41.485 | 19.910 | 1.00 | 12.52 |
| ATOM | 2859 | OH2 | TIP | 16 | 24.269 | 48.192 | 0.627 | 1.00 | 11.85 |
| ATOM | 2860 | OH2 | TIP | 17 | 35.611 | 30.647 | −11.558 | 1.00 | 19.10 |
| ATOM | 2861 | OH2 | TIP | 19 | 27.016 | 52.988 | 8.586 | 1.00 | 12.80 |
| ATOM | 2862 | OH2 | TIP | 20 | 33.134 | 44.858 | −12.599 | 1.00 | 21.07 |
| ATOM | 2863 | OH2 | TIP | 21 | 41.811 | 40.231 | 11.637 | 1.00 | 8.18 |
| ATOM | 2864 | OH2 | TIP | 22 | 42.183 | 27.798 | 7.499 | 1.00 | 16.55 |
| ATOM | 2865 | OH2 | TIP | 23 | 55.491 | 43.097 | 24.315 | 1.00 | 20.61 |
| ATOM | 2866 | OH2 | TIP | 24 | 22.596 | 45.819 | 3.212 | 1.00 | 20.68 |
| ATOM | 2867 | OH2 | TIP | 25 | 40.140 | 46.060 | 2.081 | 1.00 | 12.15 |
| ATOM | 2868 | OH2 | TIP | 28 | 52.896 | 40.807 | 35.670 | 1.00 | 26.75 |
| ATOM | 2869 | OH2 | TIP | 29 | 39.349 | 36.839 | −11.592 | 1.00 | 16.06 |
| ATOM | 2870 | OH2 | TIP | 30 | 29.722 | 63.391 | 4.730 | 1.00 | 30.50 |
| ATOM | 2871 | OH2 | TIP | 31 | 31.088 | 52.800 | 1.900 | 1.00 | 16.24 |
| ATOM | 2872 | OH2 | TIP | 33 | 48.477 | 40.642 | 9.325 | 1.00 | 18.06 |
| ATOM | 2873 | OH2 | TIP | 34 | 48.151 | 60.664 | −5.676 | 1.00 | 38.87 |
| ATOM | 2874 | OH2 | TIP | 35 | 33.824 | 25.066 | −2.250 | 1.00 | 26.85 |
| ATOM | 2875 | OH2 | TIP | 36 | 27.559 | 36.164 | −15.409 | 1.00 | 20.80 |
| ATOM | 2876 | OH2 | TIP | 37 | 36.106 | 58.318 | 1.505 | 1.00 | 17.98 |
| ATOM | 2877 | OH2 | TIP | 38 | 18.439 | 32.041 | 12.105 | 1.00 | 33.41 |
| ATOM | 2878 | OH2 | TIP | 39 | 30.083 | 49.589 | 4.400 | 1.00 | 25.73 |
| ATOM | 2879 | OH2 | TIP | 40 | 22.237 | 50.945 | 6.710 | 1.00 | 15.44 |
| ATOM | 2880 | OH2 | TIP | 41 | 25.160 | 53.838 | 20.665 | 1.00 | 38.02 |
| ATOM | 2881 | OH2 | TIP | 42 | 28.378 | 43.059 | 0.383 | 1.00 | 15.63 |
| ATOM | 2882 | OH2 | TIP | 43 | 48.055 | 30.902 | 8.812 | 1.00 | 25.12 |
| ATOM | 2883 | OH2 | TIP | 44 | 37.474 | 35.997 | 32.369 | 1.00 | 32.92 |
| ATOM | 2884 | OH2 | TIP | 45 | 36.065 | 52.338 | −1.345 | 1.00 | 20.39 |
| ATOM | 2885 | OH2 | TIP | 46 | 48.124 | 51.068 | 24.354 | 1.00 | 27.11 |
| ATOM | 2886 | OH2 | TIP | 47 | 31.748 | 42.518 | −7.963 | 1.00 | 13.51 |
| ATOM | 2887 | OH2 | TIP | 48 | 60.117 | 28.753 | 24.514 | 1.00 | 24.03 |
| ATOM | 2888 | OH2 | TIP | 49 | 39.433 | 48.490 | −3.629 | 1.00 | 30.32 |
| ATOM | 2889 | OH2 | TIP | 50 | 48.317 | 58.149 | 0.954 | 1.00 | 30.47 |
| ATOM | 2890 | OH2 | TIP | 51 | 55.691 | 32.327 | 25.490 | 1.00 | 27.61 |
| ATOM | 2891 | OH2 | TIP | 52 | 64.195 | 35.380 | 20.138 | 1.00 | 19.56 |
| ATOM | 2892 | OH2 | TIP | 53 | 58.833 | 49.910 | 15.155 | 1.00 | 27.93 |
| ATOM | 2893 | OH2 | TIP | 54 | 51.798 | 31.467 | 11.336 | 1.00 | 13.39 |
| ATOM | 2894 | OH2 | TIP | 55 | 39.565 | 45.795 | −2.524 | 1.00 | 14.64 |
| ATOM | 2895 | OH2 | TIP | 56 | 24.410 | 28.634 | 17.373 | 1.00 | 22.71 |
| ATOM | 2896 | OH2 | TIP | 57 | 51.724 | 20.261 | 6.842 | 1.00 | 27.61 |
| ATOM | 2897 | OH2 | TIP | 58 | 41.381 | 26.139 | −9.718 | 1.00 | 20.97 |

TABLE 29-continued

| | | | | | | | | | |
|---|---|---|---|---|---|---|---|---|---|
| ATOM | 2898 | OH2 | TIP | 59 | 25.055 | 40.702 | 6.956 | 1.00 | 19.36 |
| ATOM | 2899 | OH2 | TIP | 60 | 23.993 | 41.143 | 9.391 | 1.00 | 25.03 |
| ATOM | 2900 | OH2 | TIP | 61 | 38.010 | 29.506 | −11.416 | 1.00 | 23.41 |
| ATOM | 2901 | OH2 | TIP | 62 | 36.303 | 47.966 | −1.088 | 1.00 | 30.41 |
| ATOM | 2902 | OH2 | TIP | 63 | 38.481 | 26.042 | 1.645 | 1.00 | 31.40 |
| ATOM | 2903 | OH2 | TIP | 64 | 53.281 | 23.398 | 20.183 | 1.00 | 41.21 |
| ATOM | 2904 | OH2 | TIP | 65 | 59.227 | 43.487 | 12.586 | 1.00 | 16.75 |
| ATOM | 2905 | OH2 | TIP | 66 | 19.680 | 42.939 | 12.681 | 1.00 | 37.20 |
| ATOM | 2906 | OH2 | TIP | 67 | 34.545 | 51.641 | 22.341 | 1.00 | 33.42 |
| ATOM | 2907 | OH2 | TIP | 68 | 47.228 | 63.064 | 3.669 | 1.00 | 42.40 |
| ATOM | 2908 | OH2 | TIP | 69 | 45.044 | 42.104 | −5.477 | 1.00 | 28.59 |
| ATOM | 2909 | OH2 | TIP | 70 | 61.334 | 39.614 | 15.105 | 1.00 | 33.49 |
| ATOM | 2910 | OH2 | TIP | 71 | 63.480 | 33.513 | 24.510 | 1.00 | 29.51 |
| ATOM | 2911 | OH2 | TIP | 72 | 56.468 | 35.136 | 4.213 | 1.00 | 43.21 |
| ATOM | 2912 | OH2 | TIP | 73 | 38.377 | 59.761 | 19.196 | 1.00 | 29.60 |
| ATOM | 2913 | OH2 | TIP | 74 | 44.178 | 24.030 | 9.805 | 1.00 | 20.05 |
| ATOM | 2914 | OH2 | TIP | 75 | 59.041 | 44.570 | 9.927 | 1.00 | 18.74 |
| ATOM | 2915 | OH2 | TIP | 76 | 57.140 | 34.369 | 26.067 | 1.00 | 16.87 |
| ATOM | 2916 | OH2 | TIP | 77 | 39.600 | 50.271 | 27.318 | 1.00 | 30.06 |
| ATOM | 2917 | OH2 | TIP | 78 | 18.395 | 33.040 | 20.240 | 1.00 | 39.24 |
| ATOM | 2918 | OH2 | TIP | 80 | 46.253 | 28.328 | 18.697 | 1.00 | 23.12 |
| ATOM | 2919 | OH2 | TIP | 81 | 21.439 | 37.365 | 21.789 | 1.00 | 23.23 |
| ATOM | 2920 | OH2 | TIP | 82 | 20.542 | 32.670 | 21.994 | 1.00 | 27.90 |
| ATOM | 2921 | OH2 | TIP | 83 | 24.655 | 41.169 | −5.254 | 1.00 | 24.02 |
| ATOM | 2922 | OH2 | TIP | 84 | 55.024 | 41.551 | 26.503 | 1.00 | 26.29 |
| ATOM | 2923 | OH2 | TIP | 85 | 38.257 | 32.272 | 33.898 | 1.00 | 23.92 |
| ATOM | 2924 | OH2 | TIP | 86 | 44.348 | 24.278 | −3.540 | 1.00 | 35.59 |
| ATOM | 2925 | OH2 | TIP | 87 | 27.444 | 36.842 | 9.754 | 1.00 | 30.73 |
| ATOM | 2926 | OH2 | TIP | 88 | 31.179 | 49.190 | 21.579 | 1.00 | 26.24 |
| ATOM | 2927 | OH2 | TIP | 89 | 47.770 | 20.871 | 17.535 | 1.00 | 24.51 |
| ATOM | 2928 | OH2 | TIP | 91 | 38.465 | 53.285 | −2.768 | 1.00 | 34.79 |
| ATOM | 2929 | OH2 | TIP | 92 | 46.308 | 60.185 | 17.231 | 1.00 | 28.55 |
| ATOM | 2930 | OH2 | TIP | 93 | 28.701 | 66.849 | 4.531 | 1.00 | 40.45 |
| ATOM | 2931 | OH2 | TIP | 94 | 60.902 | 30.818 | 9.650 | 1.00 | 33.92 |
| ATOM | 2932 | OH2 | TIP | 96 | 19.893 | 46.306 | 21.698 | 1.00 | 30.29 |
| ATOM | 2933 | OH2 | TIP | 97 | 45.510 | 23.104 | 6.071 | 1.00 | 28.35 |
| ATOM | 2934 | OH2 | TIP | 98 | 55.196 | 41.435 | 21.940 | 1.00 | 16.83 |
| ATOM | 2935 | OH2 | TIP | 99 | 47.253 | 53.876 | −3.810 | 1.00 | 23.52 |
| ATOM | 2936 | OH2 | TIP | 100 | 39.089 | 57.043 | −2.142 | 1.00 | 24.05 |
| ATOM | 2937 | OH2 | TIP | 101 | 42.036 | 65.124 | 6.183 | 1.00 | 24.43 |
| ATOM | 2938 | OH2 | TIP | 102 | 50.161 | 38.979 | 37.857 | 1.00 | 34.83 |
| ATOM | 2939 | OH2 | TIP | 103 | 24.826 | 38.099 | 6.266 | 1.00 | 52.04 |
| ATOM | 2940 | OH2 | TIP | 104 | 37.666 | 19.146 | 18.942 | 1.00 | 44.29 |
| ATOM | 2941 | OH2 | TIP | 105 | 34.064 | 23.132 | 21.675 | 1.00 | 37.52 |
| ATOM | 2942 | OH2 | TIP | 106 | 50.935 | 24.631 | 25.846 | 1.00 | 22.54 |
| ATOM | 2943 | OH2 | TIP | 108 | 43.565 | 44.627 | 28.144 | 1.00 | 49.40 |
| ATOM | 2944 | OH2 | TIP | 109 | 31.117 | 28.110 | 31.273 | 1.00 | 32.65 |
| ATOM | 2945 | OH2 | TIP | 110 | 20.805 | 49.008 | 19.699 | 1.00 | 46.79 |
| ATOM | 2946 | OH2 | TIP | 111 | 52.650 | 36.241 | 5.934 | 1.00 | 27.82 |
| ATOM | 2947 | OH2 | TIP | 112 | 58.236 | 26.559 | 10.967 | 1.00 | 36.15 |
| ATOM | 2948 | OH2 | TIP | 113 | 43.031 | 36.731 | 36.240 | 1.00 | 44.91 |
| ATOM | 2949 | OH2 | TIP | 114 | 24.141 | 50.228 | 27.710 | 1.00 | 47.63 |
| ATOM | 2950 | OH2 | TIP | 115 | 30.276 | 30.961 | −7.868 | 1.00 | 31.47 |
| ATOM | 2951 | OH2 | TIP | 116 | 48.292 | 22.098 | 6.628 | 1.00 | 25.84 |
| ATOM | 2952 | OH2 | TIP | 117 | 39.234 | 38.015 | −14.279 | 1.00 | 31.09 |
| ATOM | 2953 | OH2 | TIP | 119 | 46.519 | 32.215 | −8.891 | 1.00 | 39.56 |
| ATOM | 2954 | OH2 | TIP | 121 | 20.107 | 49.247 | 17.242 | 1.00 | 29.89 |
| ATOM | 2955 | OH2 | TIP | 122 | 35.093 | 44.434 | 26.730 | 1.00 | 43.37 |
| ATOM | 2956 | OH2 | TIP | 124 | 49.192 | 64.685 | 7.996 | 1.00 | 51.57 |
| ATOM | 2957 | OH2 | TIP | 125 | 37.926 | 56.308 | 22.575 | 1.00 | 45.89 |
| ATOM | 2958 | OH2 | TIP | 126 | 35.206 | 25.843 | 8.170 | 1.00 | 43.48 |
| ATOM | 2959 | OH2 | TIP | 128 | 53.408 | 48.397 | 27.188 | 1.00 | 32.97 |
| ATOM | 2960 | OH2 | TIP | 130 | 31.779 | 41.307 | 27.403 | 1.00 | 51.72 |
| ATOM | 2961 | OH2 | TIP | 133 | 45.206 | 19.827 | 20.469 | 1.00 | 48.38 |
| ATOM | 2962 | OH2 | TIP | 135 | 62.104 | 49.309 | 13.802 | 1.00 | 52.21 |
| ATOM | 2963 | OH2 | TIP | 136 | 36.380 | 24.415 | 5.240 | 1.00 | 39.20 |
| ATOM | 2964 | OH2 | TIP | 137 | 37.147 | 47.795 | 25.950 | 1.00 | 44.17 |
| ATOM | 2965 | OH2 | TIP | 139 | 33.823 | 32.635 | 6.973 | 1.00 | 21.67 |
| ATOM | 2966 | OH2 | TIP | 140 | 37.744 | 20.754 | 21.527 | 1.00 | 35.36 |
| ATOM | 2967 | OH2 | TIP | 141 | 27.926 | 24.074 | 16.116 | 1.00 | 35.24 |
| ATOM | 2968 | OH2 | TIP | 142 | 28.721 | 24.539 | 25.917 | 1.00 | 43.93 |
| ATOM | 2969 | OH2 | TIP | 143 | 29.978 | 30.667 | 9.311 | 1.00 | 26.87 |
| ATOM | 2970 | OH2 | TIP | 145 | 32.683 | 65.958 | 1.323 | 1.00 | 39.30 |
| ATOM | 2971 | OH2 | TIP | 146 | 43.026 | 23.254 | 7.640 | 1.00 | 42.61 |
| ATOM | 2972 | OH2 | TIP | 149 | 45.148 | 45.063 | 12.836 | 1.00 | 30.97 |
| ATOM | 2973 | OH2 | TIP | 150 | 56.809 | 54.243 | 24.922 | 1.00 | 36.26 |
| ATOM | 2974 | OH2 | TIP | 154 | 28.303 | 35.710 | −8.702 | 1.00 | 36.61 |
| ATOM | 2975 | OH2 | TIP | 157 | 49.266 | 20.617 | 1.054 | 1.00 | 39.92 |
| ATOM | 2976 | OH2 | TIP | 161 | 35.433 | 24.497 | 28.823 | 1.00 | 31.77 |

TABLE 29-continued

| | | | | | | | | | |
|---|---|---|---|---|---|---|---|---|---|
| ATOM | 2977 | OH2 | TIP | 162 | 48.071 | 19.322 | 10.918 | 1.00 | 50.89 |
| ATOM | 2978 | OH2 | TIP | 170 | 52.214 | 41.890 | 26.882 | 1.00 | 29.94 |
| ATOM | 2979 | OH2 | TIP | 171 | 43.481 | 68.261 | 20.226 | 1.00 | 50.24 |
| ATOM | 2980 | OH2 | TIP | 173 | 30.552 | 59.616 | 2.762 | 1.00 | 44.94 |
| ATOM | 2981 | OH2 | TIP | 177 | 49.192 | 23.653 | 29.887 | 1.00 | 45.14 |
| ATOM | 2982 | OH2 | TIP | 179 | 34.894 | 68.176 | 14.392 | 1.00 | 41.94 |
| ATOM | 2983 | OH2 | TIP | 180 | 34.153 | 33.362 | 32.215 | 1.00 | 41.27 |
| ATOM | 2984 | OH2 | TIP | 183 | 23.367 | 59.922 | 15.715 | 1.00 | 40.54 |
| ATOM | 2985 | OH2 | TIP | 184 | 37.180 | 22.990 | −4.060 | 1.00 | 29.83 |
| ATOM | 2986 | OH2 | TIP | 186 | 59.902 | 32.926 | 5.795 | 1.00 | 48.68 |
| ATOM | 2987 | OH2 | TIP | 187 | 38.635 | 46.185 | −0.225 | 1.00 | 14.36 |
| ATOM | 2988 | OH2 | TIP | 188 | 52.924 | 26.976 | 2.822 | 1.00 | 20.37 |
| ATOM | 2989 | OH2 | TIP | 189 | 56.875 | 26.651 | 15.240 | 1.00 | 18.86 |
| ATOM | 2990 | OH2 | TIP | 190 | 55.306 | 25.358 | 16.983 | 1.00 | 13.37 |
| ATOM | 2991 | OH2 | TIP | 191 | 51.595 | 53.593 | 12.466 | 1.00 | 17.70 |
| ATOM | 2992 | OH2 | TIP | 192 | 27.679 | 24.004 | 18.956 | 1.00 | 35.95 |
| ATOM | 2993 | OH2 | TIP | 193 | 28.677 | 32.820 | −8.974 | 1.00 | 32.62 |
| ATOM | 2994 | OH2 | TIP | 194 | 20.577 | 38.735 | 10.813 | 1.00 | 31.02 |
| ATOM | 2995 | OH2 | TIP | 195 | 24.128 | 43.401 | 2.958 | 1.00 | 26.14 |
| ATOM | 2996 | OH2 | TIP | 196 | 21.872 | 27.301 | 26.191 | 1.00 | 44.90 |
| ATOM | 2997 | OH2 | TIP | 197 | 63.765 | 33.808 | 21.998 | 1.00 | 36.70 |
| ATOM | 2998 | OH2 | TIP | 198 | 32.846 | 49.810 | 23.746 | 1.00 | 37.36 |
| ATOM | 2999 | OH2 | TIP | 199 | 58.905 | 40.769 | 13.020 | 1.00 | 30.69 |
| ATOM | 3000 | OH2 | TIP | 200 | 22.377 | 49.968 | 21.592 | 1.00 | 39.90 |
| ATOM | 3001 | OH2 | TIP | 201 | 49.605 | 32.015 | −6.500 | 1.00 | 33.85 |
| ATOM | 3002 | OH2 | TIP | 202 | 19.520 | 32.689 | 24.514 | 1.00 | 40.34 |
| ATOM | 3003 | OH2 | TIP | 203 | 18.186 | 43.942 | 25.261 | 1.00 | 37.04 |
| ATOM | 3004 | OH2 | TIP | 204 | 31.924 | 23.419 | 9.913 | 1.00 | 41.07 |
| ATOM | 3005 | OH2 | TIP | 205 | 59.551 | 39.040 | 29.664 | 1.00 | 48.01 |
| ATOM | 3006 | OH2 | TIP | 206 | 24.747 | 35.005 | −2.252 | 1.00 | 38.50 |
| ATOM | 3007 | OH2 | TIP | 207 | 51.726 | 24.271 | 23.364 | 1.00 | 45.92 |
| ATOM | 3008 | OH2 | TIP | 208 | 41.227 | 63.077 | 0.564 | 1.00 | 52.88 |
| ATOM | 3009 | OH2 | TIP | 209 | 45.043 | 24.853 | −7.064 | 1.00 | 63.99 |
| ATOM | 3010 | OH2 | TIP | 210 | 60.297 | 33.503 | 0.872 | 1.00 | 44.71 |
| ATOM | 3011 | OH2 | TIP | 211 | 55.354 | 57.898 | −5.181 | 1.00 | 67.46 |
| ATOM | 3012 | OH2 | TIP | 212 | 26.342 | 34.721 | 3.607 | 1.00 | 43.97 |
| ATOM | 3013 | OH2 | TIP | 213 | 57.229 | 58.636 | 2.147 | 1.00 | 56.52 |
| ATOM | 3014 | OH2 | TIP | 214 | 48.952 | 19.413 | 7.794 | 1.00 | 36.39 |
| ATOM | 3015 | OH2 | TIP | 215 | 18.698 | 34.346 | 22.436 | 1.00 | 40.47 |
| ATOM | 3016 | OH2 | TIP | 216 | 50.056 | 55.688 | 3.654 | 1.00 | 41.15 |
| ATOM | 3017 | OH2 | TIP | 217 | 23.808 | 39.359 | −3.697 | 1.00 | 38.56 |
| ATOM | 3018 | OH2 | TIP | 219 | 30.490 | 25.063 | 28.451 | 1.00 | 52.43 |
| ATOM | 3019 | OH2 | TIP | 220 | 26.031 | 30.526 | 16.823 | 1.00 | 35.58 |
| ATOM | 3020 | OH2 | TIP | 222 | 54.897 | 58.072 | 2.961 | 1.00 | 48.36 |
| ATOM | 3021 | OH2 | TIP | 223 | 59.398 | 53.141 | −2.805 | 1.00 | 58.38 |
| ATOM | 3022 | OH2 | TIP | 224 | 51.436 | 23.394 | 27.949 | 1.00 | 42.69 |
| ATOM | 3023 | OH2 | TIP | 225 | 37.497 | 39.534 | 29.612 | 1.00 | 29.55 |
| ATOM | 3024 | OH2 | TIP | 226 | 20.525 | 42.018 | 22.609 | 1.00 | 59.58 |
| ATOM | 3025 | OH2 | TIP | 227 | 38.073 | 51.947 | −4.969 | 1.00 | 45.26 |
| ATOM | 3026 | OH2 | TIP | 228 | 52.416 | 32.620 | 0.869 | 1.00 | 58.50 |
| ATOM | 3027 | OH2 | TIP | 229 | 58.152 | 50.912 | 12.884 | 1.00 | 32.92 |
| ATOM | 3028 | OH2 | TIP | 230 | 56.059 | 24.385 | 3.859 | 1.00 | 54.19 |
| ATOM | 3029 | OH2 | TIP | 231 | 51.657 | 20.142 | 23.177 | 1.00 | 49.92 |
| ATOM | 3030 | OH2 | TIP | 232 | 48.247 | 18.532 | 16.124 | 1.00 | 47.86 |
| ATOM | 3031 | OH2 | TIP | 233 | 49.710 | 20.786 | 19.715 | 1.00 | 37.69 |
| ATOM | 3032 | OH2 | TIP | 234 | 61.171 | 40.499 | 27.294 | 1.00 | 41.21 |
| ATOM | 3033 | OH2 | TIP | 235 | 60.229 | 28.450 | 9.873 | 1.00 | 39.53 |
| ATOM | 3034 | OH2 | TIP | 236 | 39.482 | 20.654 | 25.665 | 1.00 | 40.24 |
| ATOM | 3035 | OH2 | TIP | 237 | 21.898 | 39.040 | 23.981 | 1.00 | 49.44 |
| ATOM | 3036 | OH2 | TIP | 238 | 41.482 | 40.544 | −15.377 | 1.00 | 41.34 |
| ATOM | 3037 | OH2 | TIP | 239 | 53.795 | 60.848 | 4.850 | 1.00 | 53.61 |
| ATOM | 3038 | OH2 | TIP | 240 | 34.935 | 52.929 | −3.681 | 1.00 | 35.26 |
| ATOM | 3039 | OH2 | TIP | 241 | 55.320 | 34.524 | −10.024 | 1.00 | 38.15 |
| ATOM | 3040 | OH2 | TIP | 243 | 26.335 | 37.508 | −0.149 | 1.00 | 39.86 |
| ATOM | 3041 | OH2 | TIP | 244 | 50.998 | 60.568 | 3.880 | 1.00 | 65.48 |
| ATOM | 3042 | OH2 | TIP | 246 | 30.232 | 56.037 | 21.276 | 1.00 | 50.32 |
| ATOM | 3043 | OH2 | TIP | 247 | 25.549 | 38.311 | 8.586 | 1.00 | 39.52 |
| ATOM | 3044 | OH2 | TIP | 248 | 56.414 | 42.750 | 28.581 | 1.00 | 44.10 |
| ATOM | 3045 | OH2 | TIP | 249 | 50.755 | 57.649 | 7.886 | 1.00 | 35.64 |
| ATOM | 3046 | OH2 | TIP | 250 | 41.230 | 43.187 | 29.095 | 1.00 | 43.86 |
| ATOM | 3047 | OH2 | TIP | 251 | 44.998 | 22.901 | 28.299 | 1.00 | 53.89 |
| ATOM | 3048 | OH2 | TIP | 252 | 20.352 | 42.557 | 15.132 | 1.00 | 52.49 |
| ATOM | 3049 | OH2 | TIP | 253 | 26.184 | 65.798 | 8.905 | 1.00 | 43.68 |
| ATOM | 3050 | OH2 | TIP | 254 | 45.893 | 38.490 | −11.594 | 1.00 | 51.24 |
| ATOM | 3051 | OH2 | TIP | 255 | 42.710 | 41.577 | 34.594 | 1.00 | 40.69 |
| ATOM | 3052 | OH2 | TIP | 256 | 48.240 | 52.727 | 26.492 | 1.00 | 43.49 |
| ATOM | 3053 | OH2 | TIP | 257 | 39.554 | 58.190 | 23.447 | 1.00 | 49.04 |
| ATOM | 3054 | OH2 | TIP | 258 | 37.575 | 57.178 | 25.056 | 1.00 | 45.47 |
| ATOM | 3055 | OH2 | TIP | 259 | 50.664 | 56.391 | 11.881 | 1.00 | 31.43 |

TABLE 29-continued

| | | | | | | | | | |
|---|---|---|---|---|---|---|---|---|---|
| ATOM | 3056 | OH2 | TIP | 260 | 59.974 | 24.777 | 12.397 | 1.00 | 37.68 |
| ATOM | 3057 | OH2 | TIP | 261 | 23.885 | 35.887 | 6.227 | 1.00 | 46.04 |
| ATOM | 3058 | OH2 | TIP | 262 | 64.702 | 52.392 | 26.765 | 1.00 | 59.22 |
| ATOM | 3059 | OH2 | TIP | 263 | 35.576 | 61.522 | 20.195 | 1.00 | 49.81 |
| ATOM | 3060 | OH2 | TIP | 264 | 43.682 | 65.275 | −7.504 | 1.00 | 43.86 |
| ATOM | 3061 | OH2 | TIP | 266 | 60.870 | 47.912 | 27.467 | 1.00 | 53.93 |
| ATOM | 3062 | OH2 | TIP | 268 | 51.707 | 34.577 | 42.346 | 1.00 | 45.87 |
| ATOM | 3063 | OH2 | TIP | 269 | 29.465 | 40.196 | 30.722 | 1.00 | 38.31 |
| ATOM | 3064 | OH2 | TIP | 270 | 22.879 | 53.243 | 8.461 | 1.00 | 43.09 |
| ATOM | 3065 | OH2 | TIP | 272 | 42.793 | 30.638 | 35.734 | 1.00 | 54.91 |
| ATOM | 3066 | OH2 | TIP | 273 | 39.878 | 24.302 | 0.355 | 1.00 | 42.81 |
| ATOM | 3067 | OH2 | TIP | 274 | 45.874 | 43.477 | 32.353 | 1.00 | 44.64 |
| ATOM | 3068 | OH2 | TIP | 276 | 60.439 | 26.457 | 22.587 | 1.00 | 58.50 |
| ATOM | 3069 | OH2 | TIP | 277 | 33.501 | 19.630 | 7.711 | 1.00 | 40.97 |
| ATOM | 3070 | OH2 | TIP | 278 | 31.136 | 37.255 | 33.009 | 1.00 | 49.32 |
| ATOM | 3071 | OH2 | TIP | 279 | 54.504 | 24.817 | 21.938 | 1.00 | 49.97 |
| ATOM | 3072 | OH2 | TIP | 280 | 47.280 | 60.101 | 19.796 | 1.00 | 43.35 |
| ATOM | 3073 | OH2 | TIP | 282 | 54.430 | 30.932 | 0.309 | 1.00 | 63.58 |
| ATOM | 3074 | OH2 | TIP | 283 | 61.848 | 32.266 | 15.111 | 1.00 | 38.33 |
| ATOM | 3075 | OH2 | TIP | 284 | 24.901 | 34.423 | −6.980 | 1.00 | 40.77 |
| ATOM | 3076 | OH2 | TIP | 285 | 24.740 | 32.154 | 26.786 | 1.00 | 43.19 |
| ATOM | 3077 | OH2 | TIP | 286 | 32.495 | 60.380 | 1.080 | 1.00 | 46.07 |
| ATOM | 3078 | OH2 | TIP | 287 | 55.139 | 56.211 | 24.904 | 1.00 | 43.70 |
| ATOM | 3079 | OH2 | TIP | 288 | 43.595 | 38.488 | 39.052 | 1.00 | 50.51 |
| ATOM | 3080 | OH2 | TIP | 292 | 20.724 | 36.629 | 8.924 | 1.00 | 43.74 |
| ATOM | 3081 | OH2 | TIP | 293 | 46.686 | 64.930 | 9.425 | 1.00 | 50.38 |
| ATOM | 3082 | OH2 | TIP | 294 | 17.201 | 60.221 | 10.522 | 1.00 | 43.72 |
| ATOM | 3083 | OH2 | TIP | 295 | 17.500 | 28.964 | 19.499 | 1.00 | 38.98 |
| ATOM | 3084 | OH2 | TIP | 297 | 36.397 | 31.380 | 32.306 | 1.00 | 41.95 |
| ATOM | 3085 | OH2 | TIP | 300 | 46.747 | 59.180 | −13.611 | 1.00 | 47.00 |
| ATOM | 3086 | OH2 | TIP | 301 | 29.632 | 25.523 | 9.658 | 1.00 | 45.27 |
| ATOM | 3087 | OH2 | TIP | 302 | 50.813 | 58.467 | 0.387 | 1.00 | 40.01 |
| ATOM | 3088 | OH2 | TIP | 303 | 29.510 | 51.948 | 22.195 | 1.00 | 37.26 |
| ATOM | 3089 | OH2 | TIP | 304 | 34.546 | 62.038 | 23.290 | 1.00 | 43.28 |
| ATOM | 3090 | OH2 | TIP | 305 | 28.994 | 20.945 | 23.473 | 1.00 | 43.57 |
| ATOM | 3091 | OH2 | TIP | 306 | 50.928 | 49.942 | 27.992 | 1.00 | 49.74 |
| ATOM | 3092 | OH2 | TIP | 307 | 18.603 | 51.462 | 16.940 | 1.00 | 45.75 |
| ATOM | 3093 | OH2 | TIP | 309 | 42.013 | 36.897 | −13.981 | 1.00 | 47.94 |
| ATOM | 3094 | OH2 | TIP | 310 | 45.087 | 42.847 | −9.324 | 1.00 | 47.04 |
| ATOM | 3095 | C1 | INH | 1 | 55.236 | 47.264 | 0.315 | 0.00 | 19.32 |
| ATOM | 3096 | C2 | INH | 1 | 55.731 | 48.195 | −0.664 | 0.00 | 19.20 |
| ATOM | 3097 | C3 | INH | 1 | 55.258 | 48.140 | −2.050 | 0.00 | 19.12 |
| ATOM | 3098 | C4 | INH | 1 | 54.265 | 47.124 | −2.434 | 0.00 | 19.23 |
| ATOM | 3099 | C5 | INH | 1 | 53.756 | 46.171 | −1.432 | 0.00 | 19.43 |
| ATOM | 3100 | C6 | INH | 1 | 52.787 | 45.139 | −1.726 | 0.00 | 19.40 |
| ATOM | 3101 | C7 | INH | 1 | 54.267 | 46.267 | −0.057 | 0.00 | 19.29 |
| ATOM | 3102 | C8 | INH | 1 | 53.065 | 44.157 | −2.777 | 0.00 | 19.48 |
| ATOM | 3103 | C9 | INH | 1 | 52.120 | 43.114 | −3.081 | 0.00 | 19.61 |
| ATOM | 3104 | F10 | INH | 1 | 52.396 | 42.242 | −4.029 | 0.00 | 19.47 |
| ATOM | 3105 | C11 | INH | 1 | 50.854 | 43.001 | −2.347 | 0.00 | 19.73 |
| ATOM | 3106 | N12 | INH | 1 | 49.946 | 41.963 | −2.657 | 0.00 | 19.81 |
| ATOM | 3107 | C13 | INH | 1 | 50.566 | 43.971 | −1.304 | 0.00 | 19.50 |
| ATOM | 3108 | F14 | INH | 1 | 49.438 | 43.905 | −0.620 | 0.00 | 19.51 |
| ATOM | 3109 | C15 | INH | 1 | 51.512 | 45.029 | −0.990 | 0.00 | 19.42 |
| ATOM | 3110 | C16 | INH | 1 | 49.182 | 41.562 | −3.767 | 0.00 | 20.05 |
| ATOM | 3111 | C17 | INH | 1 | 48.294 | 40.370 | −3.753 | 0.00 | 20.24 |
| ATOM | 3112 | C18 | INH | 1 | 49.255 | 42.235 | −4.804 | 0.00 | 20.11 |
| ATOM | 3113 | C19 | INH | 1 | 47.993 | 39.496 | −2.733 | 0.00 | 20.33 |
| ATOM | 3114 | C20 | INH | 1 | 47.042 | 38.465 | −3.244 | 0.00 | 20.37 |
| ATOM | 3115 | C21 | INH | 1 | 46.405 | 39.116 | −4.465 | 0.00 | 20.37 |
| ATOM | 3116 | C22 | INH | 1 | 47.561 | 39.964 | −4.990 | 0.00 | 20.30 |
| ATOM | 3117 | C23 | INH | 1 | 48.435 | 39.426 | −1.307 | 0.00 | 20.38 |
| ATOM | 3118 | C24 | INH | 1 | 49.215 | 40.225 | −0.791 | 0.00 | 20.42 |
| ATOM | 3119 | C25 | INH | 1 | 47.969 | 38.433 | −0.500 | 0.00 | 20.42 |
| ATOM | 3120 | C26 | INH | 1 | 55.745 | 49.052 | −2.996 | 0.00 | 19.20 |
| ATOM | 3121 | C27 | INH | 1 | 57.043 | 48.675 | −3.568 | 0.00 | 19.22 |
| ATOM | 3122 | F28 | INH | 1 | 57.052 | 47.408 | −3.962 | 0.00 | 18.96 |
| ATOM | 3123 | F29 | INH | 1 | 57.283 | 49.439 | −4.611 | 0.00 | 18.96 |
| ATOM | 3124 | F30 | INH | 1 | 58.012 | 48.867 | −2.686 | 0.00 | 18.96 |
| TER | 1 | | INH | 1 | | | | | |
| ATOM | 1 | CB | MET A | 30 | 59.689 | 55.188 | −5.634 | 1.00 | 78.93 |
| ATOM | 2 | CG | MET A | 30 | 59.846 | 54.459 | −6.959 | 1.00 | 79.24 |
| ATOM | 3 | SD | MET A | 30 | 59.231 | 52.765 | −6.869 | 1.00 | 79.21 |
| ATOM | 4 | CE | MET A | 30 | 60.653 | 51.913 | −6.175 | 1.00 | 79.18 |
| ATOM | 5 | C | MET A | 30 | 58.206 | 55.626 | −3.674 | 1.00 | 77.77 |
| ATOM | 6 | O | MET A | 30 | 57.247 | 55.273 | −2.989 | 1.00 | 77.07 |
| ATOM | 7 | N | MET A | 30 | 57.559 | 56.411 | −5.965 | 1.00 | 78.11 |
| ATOM | 8 | CA | MET A | 30 | 58.237 | 55.344 | −5.173 | 1.00 | 78.21 |
| ATOM | 9 | N | ALA A | 31 | 59.261 | 56.261 | −3.170 | 1.00 | 77.18 |

TABLE 29-continued

| ATOM | 10 | CA | ALA A | 31 | 59.357 | 56.584 | −1.750 | 1.00 | 75.83 |
|---|---|---|---|---|---|---|---|---|---|
| ATOM | 11 | CB | ALA A | 31 | 60.804 | 56.889 | −1.382 | 1.00 | 76.33 |
| ATOM | 12 | C | ALA A | 31 | 58.466 | 57.766 | −1.386 | 1.00 | 74.57 |
| ATOM | 13 | O | ALA A | 31 | 58.120 | 57.955 | −0.220 | 1.00 | 74.68 |
| ATOM | 14 | N | THR A | 32 | 58.098 | 58.559 | −2.388 | 1.00 | 73.02 |
| ATOM | 15 | CA | THR A | 32 | 57.247 | 59.724 | −2.172 | 1.00 | 70.94 |
| ATOM | 16 | CB | THR A | 32 | 57.070 | 60.531 | −3.474 | 1.00 | 71.72 |
| ATOM | 17 | OG1 | THR A | 32 | 58.350 | 60.991 | −3.929 | 1.00 | 71.26 |
| ATOM | 18 | CG2 | THR A | 32 | 56.155 | 61.727 | −3.242 | 1.00 | 71.64 |
| ATOM | 19 | C | THR A | 32 | 55.872 | 59.303 | −1.660 | 1.00 | 68.92 |
| ATOM | 20 | O | THR A | 32 | 55.231 | 60.029 | −0.897 | 1.00 | 69.22 |
| ATOM | 21 | N | GLY A | 33 | 55.423 | 58.127 | −2.086 | 1.00 | 65.85 |
| ATOM | 22 | CA | GLY A | 33 | 54.133 | 57.627 | −1.650 | 1.00 | 61.62 |
| ATOM | 23 | C | GLY A | 33 | 52.950 | 58.306 | −2.308 | 1.00 | 58.54 |
| ATOM | 24 | O | GLY A | 33 | 52.111 | 58.899 | −1.630 | 1.00 | 59.44 |
| ATOM | 25 | N | ASP A | 34 | 52.875 | 58.220 | −3.631 | 1.00 | 53.96 |
| ATOM | 26 | CA | ASP A | 34 | 51.773 | 58.831 | −4.358 | 1.00 | 48.74 |
| ATOM | 27 | CB | ASP A | 34 | 52.285 | 59.470 | −5.648 | 1.00 | 48.47 |
| ATOM | 28 | CG | ASP A | 34 | 51.171 | 60.046 | −6.488 | 1.00 | 48.19 |
| ATOM | 29 | OD1 | ASP A | 34 | 50.675 | 59.329 | −7.383 | 1.00 | 47.90 |
| ATOM | 30 | OD2 | ASP A | 34 | 50.783 | 61.210 | −6.245 | 1.00 | 48.88 |
| ATOM | 31 | C | ASP A | 34 | 50.687 | 57.803 | −4.663 | 1.00 | 45.54 |
| ATOM | 32 | O | ASP A | 34 | 50.947 | 56.760 | −5.266 | 1.00 | 42.96 |
| ATOM | 33 | N | GLU A | 35 | 49.467 | 58.115 | −4.237 | 1.00 | 42.40 |
| ATOM | 34 | CA | GLU A | 35 | 48.319 | 57.236 | −4.420 | 1.00 | 39.88 |
| ATOM | 35 | CB | GLU A | 35 | 47.072 | 57.897 | −3.824 | 1.00 | 39.71 |
| ATOM | 36 | CG | GLU A | 35 | 47.055 | 57.882 | −2.298 | 1.00 | 41.04 |
| ATOM | 37 | CD | GLU A | 35 | 46.065 | 58.866 | −1.695 | 1.00 | 42.39 |
| ATOM | 38 | OE1 | GLU A | 35 | 44.959 | 59.028 | −2.254 | 1.00 | 43.92 |
| ATOM | 39 | OE2 | GLU A | 35 | 46.391 | 59.468 | −0.649 | 1.00 | 40.71 |
| ATOM | 40 | C | GLU A | 35 | 48.058 | 56.800 | −5.859 | 1.00 | 38.11 |
| ATOM | 41 | O | GLU A | 35 | 47.820 | 55.618 | −6.109 | 1.00 | 36.81 |
| ATOM | 42 | N | ARG A | 36 | 48.107 | 57.738 | −6.804 | 1.00 | 36.86 |
| ATOM | 43 | CA | ARG A | 36 | 47.867 | 57.397 | −8.205 | 1.00 | 36.42 |
| ATOM | 44 | CB | ARG A | 36 | 47.761 | 58.650 | −9.077 | 1.00 | 39.87 |
| ATOM | 45 | CG | ARG A | 36 | 46.462 | 59.421 | −8.961 | 1.00 | 44.23 |
| ATOM | 46 | CD | ARG A | 36 | 46.287 | 60.321 | −10.176 | 1.00 | 46.52 |
| ATOM | 47 | NE | ARG A | 36 | 45.492 | 61.506 | −9.878 | 1.00 | 50.65 |
| ATOM | 48 | CZ | ARG A | 36 | 45.852 | 62.445 | −9.008 | 1.00 | 52.47 |
| ATOM | 49 | NH1 | ARG A | 36 | 46.997 | 62.336 | −8.346 | 1.00 | 52.64 |
| ATOM | 50 | NH2 | ARG A | 36 | 45.073 | 63.500 | −8.804 | 1.00 | 53.33 |
| ATOM | 51 | C | ARG A | 36 | 48.950 | 56.509 | −8.791 | 1.00 | 34.75 |
| ATOM | 52 | O | ARG A | 36 | 48.657 | 55.559 | −9.513 | 1.00 | 34.22 |
| ATOM | 53 | N | PHE A | 37 | 50.204 | 56.826 | −8.488 | 1.00 | 33.66 |
| ATOM | 54 | CA | PHE A | 37 | 51.316 | 56.048 | −9.014 | 1.00 | 33.12 |
| ATOM | 55 | CB | PHE A | 37 | 52.653 | 56.602 | −8.521 | 1.00 | 34.20 |
| ATOM | 56 | CG | PHE A | 37 | 53.836 | 55.879 | −9.088 | 1.00 | 36.60 |
| ATOM | 57 | CD1 | PHE A | 37 | 54.115 | 55.945 | −10.444 | 1.00 | 36.51 |
| ATOM | 58 | CD2 | PHE A | 37 | 54.647 | 55.101 | −8.277 | 1.00 | 38.02 |
| ATOM | 59 | CE1 | PHE A | 37 | 55.180 | 55.247 | −10.980 | 1.00 | 38.42 |
| ATOM | 60 | CE2 | PHE A | 37 | 55.714 | 54.398 | −8.808 | 1.00 | 38.15 |
| ATOM | 61 | CZ | PHE A | 37 | 55.980 | 54.471 | −10.161 | 1.00 | 38.74 |
| ATOM | 62 | C | PHE A | 37 | 51.217 | 54.577 | −8.639 | 1.00 | 31.06 |
| ATOM | 63 | O | PHE A | 37 | 51.387 | 53.702 | −9.485 | 1.00 | 30.53 |
| ATOM | 64 | N | TYR A | 38 | 50.949 | 54.304 | −7.368 | 1.00 | 30.51 |
| ATOM | 65 | CA | TYR A | 38 | 50.833 | 52.924 | −6.919 | 1.00 | 31.07 |
| ATOM | 66 | CB | TYR A | 38 | 50.801 | 52.852 | −5.392 | 1.00 | 29.44 |
| ATOM | 67 | CG | TYR A | 38 | 52.169 | 52.881 | −4.759 | 1.00 | 29.09 |
| ATOM | 68 | CD1 | TYR A | 38 | 52.904 | 54.060 | −4.694 | 1.00 | 29.44 |
| ATOM | 69 | CE1 | TYR A | 38 | 54.167 | 54.082 | −4.129 | 1.00 | 28.77 |
| ATOM | 70 | CD2 | TYR A | 38 | 52.738 | 51.721 | −4.242 | 1.00 | 26.55 |
| ATOM | 71 | CE2 | TYR A | 38 | 53.996 | 51.731 | −3.680 | 1.00 | 26.62 |
| ATOM | 72 | CZ | TYR A | 38 | 54.706 | 52.912 | −3.626 | 1.00 | 28.87 |
| ATOM | 73 | OH | TYR A | 38 | 55.963 | 52.921 | −3.078 | 1.00 | 29.87 |
| ATOM | 74 | C | TYR A | 38 | 49.596 | 52.252 | −7.486 | 1.00 | 31.66 |
| ATOM | 75 | O | TYR A | 38 | 49.656 | 51.117 | −7.954 | 1.00 | 30.99 |
| ATOM | 76 | N | ALA A | 39 | 48.476 | 52.965 | −7.454 | 1.00 | 33.37 |
| ATOM | 77 | CA | ALA A | 39 | 47.215 | 52.433 | −7.952 | 1.00 | 35.76 |
| ATOM | 78 | CB | ALA A | 39 | 46.076 | 53.365 | −7.562 | 1.00 | 35.92 |
| ATOM | 79 | C | ALA A | 39 | 47.203 | 52.212 | −9.460 | 1.00 | 37.51 |
| ATOM | 80 | O | ALA A | 39 | 46.769 | 51.161 | −9.939 | 1.00 | 37.40 |
| ATOM | 81 | N | GLU A | 40 | 47.692 | 53.199 | −10.203 | 1.00 | 39.90 |
| ATOM | 82 | CA | GLU A | 40 | 47.697 | 53.129 | −11.660 | 1.00 | 41.43 |
| ATOM | 83 | CB | GLU A | 40 | 47.505 | 54.531 | −12.247 | 1.00 | 43.66 |
| ATOM | 84 | CG | GLU A | 40 | 46.253 | 55.250 | −11.764 | 1.00 | 47.51 |
| ATOM | 85 | CD | GLU A | 40 | 46.103 | 56.633 | −12.372 | 1.00 | 50.59 |
| ATOM | 86 | OE1 | GLU A | 40 | 46.046 | 56.728 | −13.618 | 1.00 | 53.22 |
| ATOM | 87 | OE2 | GLU A | 40 | 46.041 | 57.623 | −11.609 | 1.00 | 51.67 |
| ATOM | 88 | C | GLU A | 40 | 48.920 | 52.493 | −12.311 | 1.00 | 40.64 |

TABLE 29-continued

| ATOM | 89 | O | GLU A | 40 | 48.804 | 51.910 | −13.387 | 1.00 | 41.18 |
|------|----|----|-------|----|--------|--------|---------|------|-------|
| ATOM | 90 | N | HIS A | 41 | 50.085 | 52.585 | −11.678 | 1.00 | 39.76 |
| ATOM | 91 | CA | HIS A | 41 | 51.282 | 52.028 | −12.303 | 1.00 | 38.73 |
| ATOM | 92 | CB | HIS A | 41 | 52.275 | 53.153 | −12.616 | 1.00 | 40.77 |
| ATOM | 93 | CG | HIS A | 41 | 51.702 | 54.239 | −13.470 | 1.00 | 44.26 |
| ATOM | 94 | CD2 | HIS A | 41 | 51.815 | 54.482 | −14.797 | 1.00 | 45.53 |
| ATOM | 95 | ND1 | HIS A | 41 | 50.869 | 55.218 | −12.971 | 1.00 | 46.11 |
| ATOM | 96 | CE1 | HIS A | 41 | 50.494 | 56.018 | −13.954 | 1.00 | 46.63 |
| ATOM | 97 | NE2 | HIS A | 41 | 51.054 | 55.593 | −15.072 | 1.00 | 47.73 |
| ATOM | 98 | C | HIS A | 41 | 52.034 | 50.903 | −11.605 | 1.00 | 35.82 |
| ATOM | 99 | O | HIS A | 41 | 52.166 | 49.809 | −12.153 | 1.00 | 36.05 |
| ATOM | 100 | N | LEU A | 42 | 52.537 | 51.168 | −10.407 | 1.00 | 33.50 |
| ATOM | 101 | CA | LEU A | 42 | 53.317 | 50.166 | −9.688 | 1.00 | 32.13 |
| ATOM | 102 | CB | LEU A | 42 | 53.872 | 50.770 | −8.393 | 1.00 | 30.83 |
| ATOM | 103 | CG | LEU A | 42 | 54.988 | 49.962 | −7.723 | 1.00 | 33.78 |
| ATOM | 104 | CD1 | LEU A | 42 | 55.923 | 50.904 | −6.983 | 1.00 | 32.87 |
| ATOM | 105 | CD2 | LEU A | 42 | 54.391 | 48.919 | −6.784 | 1.00 | 33.61 |
| ATOM | 106 | C | LEU A | 42 | 52.589 | 48.852 | −9.394 | 1.00 | 30.33 |
| ATOM | 107 | O | LEU A | 42 | 52.988 | 47.801 | −9.893 | 1.00 | 31.41 |
| ATOM | 108 | N | MET A | 43 | 51.530 | 48.907 | −8.593 | 1.00 | 28.07 |
| ATOM | 109 | CA | MET A | 43 | 50.781 | 47.701 | −8.243 | 1.00 | 28.07 |
| ATOM | 110 | CB | MET A | 43 | 49.559 | 48.057 | −7.389 | 1.00 | 24.63 |
| ATOM | 111 | CG | MET A | 43 | 49.917 | 48.620 | −6.024 | 1.00 | 24.00 |
| ATOM | 112 | SD | MET A | 43 | 51.097 | 47.580 | −5.115 | 1.00 | 25.98 |
| ATOM | 113 | CE | MET A | 43 | 50.029 | 46.223 | −4.620 | 1.00 | 22.82 |
| ATOM | 114 | C | MET A | 43 | 50.350 | 46.873 | −9.451 | 1.00 | 28.45 |
| ATOM | 115 | O | MET A | 43 | 50.534 | 45.657 | −9.470 | 1.00 | 27.65 |
| ATOM | 116 | N | PRO A | 44 | 49.759 | 47.517 | −10.471 | 1.00 | 30.19 |
| ATOM | 117 | CD | PRO A | 44 | 49.318 | 48.922 | −10.520 | 1.00 | 28.99 |
| ATOM | 118 | CA | PRO A | 44 | 49.320 | 46.795 | −11.670 | 1.00 | 30.48 |
| ATOM | 119 | CB | PRO A | 44 | 48.748 | 47.903 | −12.545 | 1.00 | 30.20 |
| ATOM | 120 | CG | PRO A | 44 | 48.214 | 48.872 | −11.543 | 1.00 | 30.28 |
| ATOM | 121 | C | PRO A | 44 | 50.481 | 46.067 | −12.352 | 1.00 | 32.32 |
| ATOM | 122 | O | PRO A | 44 | 50.348 | 44.916 | −12.767 | 1.00 | 32.75 |
| ATOM | 123 | N | THR A | 45 | 51.616 | 46.750 | −12.468 | 1.00 | 33.19 |
| ATOM | 124 | CA | THR A | 45 | 52.796 | 46.170 | −13.099 | 1.00 | 34.66 |
| ATOM | 125 | CB | THR A | 45 | 53.930 | 47.214 | −13.231 | 1.00 | 35.79 |
| ATOM | 126 | OG1 | THR A | 45 | 53.475 | 48.321 | −14.019 | 1.00 | 33.62 |
| ATOM | 127 | CG2 | THR A | 45 | 55.155 | 46.591 | −13.896 | 1.00 | 35.42 |
| ATOM | 128 | C | THR A | 45 | 53.301 | 45.003 | −12.261 | 1.00 | 36.33 |
| ATOM | 129 | O | THR A | 45 | 53.666 | 43.951 | −12.787 | 1.00 | 36.54 |
| ATOM | 130 | N | LEU A | 46 | 53.317 | 45.201 | −10.949 | 1.00 | 37.72 |
| ATOM | 131 | CA | LEU A | 46 | 53.770 | 44.173 | −10.022 | 1.00 | 38.02 |
| ATOM | 132 | CB | LEU A | 46 | 53.686 | 44.700 | −8.590 | 1.00 | 38.12 |
| ATOM | 133 | CG | LEU A | 46 | 54.340 | 43.856 | −7.500 | 1.00 | 39.50 |
| ATOM | 134 | CD1 | LEU A | 46 | 55.808 | 43.642 | −7.839 | 1.00 | 41.34 |
| ATOM | 135 | CD2 | LEU A | 46 | 54.202 | 44.562 | −6.161 | 1.00 | 38.74 |
| ATOM | 136 | C | LEU A | 46 | 52.912 | 42.920 | −10.164 | 1.00 | 38.63 |
| ATOM | 137 | O | LEU A | 46 | 53.430 | 41.806 | −10.244 | 1.00 | 38.89 |
| ATOM | 138 | N | GLN A | 47 | 51.596 | 43.108 | −10.203 | 1.00 | 38.81 |
| ATOM | 139 | CA | GLN A | 47 | 50.669 | 41.990 | −10.329 | 1.00 | 40.49 |
| ATOM | 140 | CB | GLN A | 47 | 49.254 | 42.446 | −9.957 | 1.00 | 40.67 |
| ATOM | 141 | CG | GLN A | 47 | 49.138 | 42.901 | −8.503 | 1.00 | 42.61 |
| ATOM | 142 | CD | GLN A | 47 | 47.756 | 43.414 | −8.147 | 1.00 | 44.18 |
| ATOM | 143 | OE1 | GLN A | 47 | 47.259 | 44.366 | −8.750 | 1.00 | 46.67 |
| ATOM | 144 | NE2 | GLN A | 47 | 47.127 | 42.787 | −7.159 | 1.00 | 43.17 |
| ATOM | 145 | C | GLN A | 47 | 50.688 | 41.377 | −11.729 | 1.00 | 39.96 |
| ATOM | 146 | O | GLN A | 47 | 50.273 | 40.234 | −11.923 | 1.00 | 39.12 |
| ATOM | 147 | N | GLY A | 48 | 51.182 | 42.137 | −12.701 | 1.00 | 40.79 |
| ATOM | 148 | CA | GLY A | 48 | 51.260 | 41.634 | −14.061 | 1.00 | 39.68 |
| ATOM | 149 | C | GLY A | 48 | 52.515 | 40.806 | −14.283 | 1.00 | 39.30 |
| ATOM | 150 | O | GLY A | 48 | 52.687 | 40.200 | −15.339 | 1.00 | 40.84 |
| ATOM | 151 | N | LEU A | 49 | 53.391 | 40.772 | −13.283 | 1.00 | 37.80 |
| ATOM | 152 | CA | LEU A | 49 | 54.636 | 40.017 | −13.377 | 1.00 | 37.34 |
| ATOM | 153 | CB | LEU A | 49 | 55.836 | 40.947 | −13.175 | 1.00 | 38.41 |
| ATOM | 154 | CG | LEU A | 49 | 56.089 | 42.039 | −14.217 | 1.00 | 38.40 |
| ATOM | 155 | CD1 | LEU A | 49 | 57.229 | 42.929 | −13.751 | 1.00 | 38.36 |
| ATOM | 156 | CD2 | LEU A | 49 | 56.414 | 41.402 | −15.558 | 1.00 | 38.65 |
| ATOM | 157 | C | LEU A | 49 | 54.717 | 38.886 | −12.359 | 1.00 | 36.86 |
| ATOM | 158 | O | LEU A | 49 | 55.440 | 37.913 | −12.564 | 1.00 | 36.92 |
| ATOM | 159 | N | LEU A | 50 | 53.978 | 39.016 | −11.263 | 1.00 | 36.23 |
| ATOM | 160 | CA | LEU A | 50 | 53.992 | 38.009 | −10.207 | 1.00 | 35.06 |
| ATOM | 161 | CB | LEU A | 50 | 54.594 | 38.605 | −8.929 | 1.00 | 35.63 |
| ATOM | 162 | CG | LEU A | 50 | 56.039 | 39.102 | −8.996 | 1.00 | 36.84 |
| ATOM | 163 | CD1 | LEU A | 50 | 56.382 | 39.831 | −7.707 | 1.00 | 36.77 |
| ATOM | 164 | CD2 | LEU A | 50 | 56.982 | 37.925 | −9.220 | 1.00 | 36.09 |
| ATOM | 165 | C | LEU A | 50 | 52.608 | 37.460 | −9.886 | 1.00 | 34.37 |
| ATOM | 166 | O | LEU A | 50 | 51.627 | 38.206 | −9.843 | 1.00 | 34.32 |
| ATOM | 167 | N | ASP A | 51 | 52.530 | 36.152 | −9.655 | 1.00 | 33.01 |

TABLE 29-continued

| | | | | | | | | | |
|---|---|---|---|---|---|---|---|---|---|
| ATOM | 168 | CA | ASP A | 51 | 51.258 | 35.534 | −9.309 | 1.00 | 33.05 |
| ATOM | 169 | CB | ASP A | 51 | 51.365 | 34.008 | −9.370 | 1.00 | 34.40 |
| ATOM | 170 | CG | ASP A | 51 | 52.309 | 33.450 | −8.331 | 1.00 | 37.10 |
| ATOM | 171 | OD1 | ASP A | 51 | 53.510 | 33.791 | −8.377 | 1.00 | 39.23 |
| ATOM | 172 | OD2 | ASP A | 51 | 51.850 | 32.670 | −7.469 | 1.00 | 38.47 |
| ATOM | 173 | C | ASP A | 51 | 50.917 | 35.999 | −7.890 | 1.00 | 30.99 |
| ATOM | 174 | O | ASP A | 51 | 51.801 | 36.411 | −7.135 | 1.00 | 30.97 |
| ATOM | 175 | N | PRO A | 52 | 49.633 | 35.935 | −7.510 | 1.00 | 28.90 |
| ATOM | 176 | CD | PRO A | 52 | 48.538 | 35.321 | −8.280 | 1.00 | 27.63 |
| ATOM | 177 | CA | PRO A | 52 | 49.161 | 36.357 | −6.185 | 1.00 | 27.61 |
| ATOM | 178 | CB | PRO A | 52 | 47.781 | 35.715 | −6.097 | 1.00 | 28.92 |
| ATOM | 179 | CG | PRO A | 52 | 47.313 | 35.772 | −7.514 | 1.00 | 27.88 |
| ATOM | 180 | C | PRO A | 52 | 50.054 | 35.993 | −4.996 | 1.00 | 25.59 |
| ATOM | 181 | O | PRO A | 52 | 50.463 | 36.864 | −4.237 | 1.00 | 25.26 |
| ATOM | 182 | N | GLU A | 53 | 50.363 | 34.713 | −4.836 | 1.00 | 24.82 |
| ATOM | 183 | CA | GLU A | 53 | 51.189 | 34.290 | −3.714 | 1.00 | 25.88 |
| ATOM | 184 | CB | GLU A | 53 | 51.229 | 32.761 | −3.632 | 1.00 | 26.19 |
| ATOM | 185 | CG | GLU A | 53 | 51.892 | 32.254 | −2.366 | 1.00 | 27.45 |
| ATOM | 186 | CD | GLU A | 53 | 51.418 | 30.874 | −1.956 | 1.00 | 28.77 |
| ATOM | 187 | OE1 | GLU A | 53 | 51.973 | 30.337 | −0.977 | 1.00 | 32.06 |
| ATOM | 188 | OE2 | GLU A | 53 | 50.496 | 30.328 | −2.600 | 1.00 | 27.91 |
| ATOM | 189 | C | GLU A | 53 | 52.612 | 34.863 | −3.730 | 1.00 | 25.94 |
| ATOM | 190 | O | GLU A | 53 | 53.103 | 35.326 | −2.698 | 1.00 | 24.19 |
| ATOM | 191 | N | SER A | 54 | 53.273 | 34.835 | −4.887 | 1.00 | 24.50 |
| ATOM | 192 | CA | SER A | 54 | 54.625 | 35.380 | −4.990 | 1.00 | 24.72 |
| ATOM | 193 | CB | SER A | 54 | 55.195 | 35.170 | −6.395 | 1.00 | 26.25 |
| ATOM | 194 | OG | SER A | 54 | 55.432 | 33.797 | −6.656 | 1.00 | 29.09 |
| ATOM | 195 | C | SER A | 54 | 54.610 | 36.871 | −4.676 | 1.00 | 25.01 |
| ATOM | 196 | O | SER A | 54 | 55.537 | 37.395 | −4.059 | 1.00 | 24.88 |
| ATOM | 197 | N | ALA A | 55 | 53.550 | 37.549 | −5.111 | 1.00 | 23.57 |
| ATOM | 198 | CA | ALA A | 55 | 53.404 | 38.977 | −4.876 | 1.00 | 22.63 |
| ATOM | 199 | CB | ALA A | 55 | 52.163 | 39.500 | −5.602 | 1.00 | 21.92 |
| ATOM | 200 | C | ALA A | 55 | 53.285 | 39.221 | −3.371 | 1.00 | 22.63 |
| ATOM | 201 | O | ALA A | 55 | 53.909 | 40.127 | −2.822 | 1.00 | 22.32 |
| ATOM | 202 | N | HIS A | 56 | 52.481 | 38.402 | −2.706 | 1.00 | 22.16 |
| ATOM | 203 | CA | HIS A | 56 | 52.304 | 38.533 | −1.267 | 1.00 | 23.00 |
| ATOM | 204 | CB | HIS A | 56 | 51.295 | 37.507 | −0.757 | 1.00 | 18.21 |
| ATOM | 205 | CG | HIS A | 56 | 51.244 | 37.422 | 0.734 | 1.00 | 18.62 |
| ATOM | 206 | CD2 | HIS A | 56 | 51.508 | 36.398 | 1.580 | 1.00 | 16.96 |
| ATOM | 207 | ND1 | HIS A | 56 | 50.926 | 38.503 | 1.527 | 1.00 | 18.90 |
| ATOM | 208 | CE1 | HIS A | 56 | 50.996 | 38.149 | 2.797 | 1.00 | 19.09 |
| ATOM | 209 | NE2 | HIS A | 56 | 51.349 | 36.878 | 2.857 | 1.00 | 18.86 |
| ATOM | 210 | C | HIS A | 56 | 53.620 | 38.348 | −0.508 | 1.00 | 24.69 |
| ATOM | 211 | O | HIS A | 56 | 53.945 | 39.127 | 0.394 | 1.00 | 24.05 |
| ATOM | 212 | N | ARG A | 57 | 54.368 | 37.310 | −0.873 | 1.00 | 25.73 |
| ATOM | 213 | CA | ARG A | 57 | 55.638 | 37.015 | −0.224 | 1.00 | 28.93 |
| ATOM | 214 | CB | ARG A | 57 | 56.230 | 35.724 | −0.792 | 1.00 | 32.78 |
| ATOM | 215 | CG | ARG A | 57 | 55.243 | 34.565 | −0.760 | 1.00 | 40.35 |
| ATOM | 216 | CD | ARG A | 57 | 55.890 | 33.236 | −1.119 | 1.00 | 45.50 |
| ATOM | 217 | NE | ARG A | 57 | 56.855 | 32.813 | −0.110 | 1.00 | 51.35 |
| ATOM | 218 | CZ | ARG A | 57 | 57.402 | 31.603 | −0.063 | 1.00 | 54.26 |
| ATOM | 219 | NH1 | ARG A | 57 | 57.078 | 30.691 | −0.971 | 1.00 | 54.88 |
| ATOM | 220 | NH2 | ARG A | 57 | 58.270 | 31.303 | 0.896 | 1.00 | 56.37 |
| ATOM | 221 | C | ARG A | 57 | 56.625 | 38.163 | −0.382 | 1.00 | 27.70 |
| ATOM | 222 | O | ARG A | 57 | 57.345 | 38.500 | 0.554 | 1.00 | 28.64 |
| ATOM | 223 | N | LEU A | 58 | 56.653 | 38.763 | −1.567 | 1.00 | 26.64 |
| ATOM | 224 | CA | LEU A | 58 | 57.543 | 39.887 | −1.828 | 1.00 | 26.14 |
| ATOM | 225 | CB | LEU A | 58 | 57.484 | 40.268 | −3.310 | 1.00 | 29.02 |
| ATOM | 226 | CG | LEU A | 58 | 58.480 | 41.323 | −3.798 | 1.00 | 31.41 |
| ATOM | 227 | CD1 | LEU A | 58 | 59.896 | 40.765 | −3.693 | 1.00 | 32.43 |
| ATOM | 228 | CD2 | LEU A | 58 | 58.167 | 41.709 | −5.237 | 1.00 | 32.16 |
| ATOM | 229 | C | LEU A | 58 | 57.086 | 41.070 | −0.971 | 1.00 | 25.90 |
| ATOM | 230 | O | LEU A | 58 | 57.903 | 41.836 | −0.454 | 1.00 | 24.40 |
| ATOM | 231 | N | ALA A | 59 | 55.769 | 41.205 | −0.832 | 1.00 | 24.36 |
| ATOM | 232 | CA | ALA A | 59 | 55.166 | 42.275 | −0.042 | 1.00 | 23.05 |
| ATOM | 233 | CB | ALA A | 59 | 53.641 | 42.159 | −0.074 | 1.00 | 20.54 |
| ATOM | 234 | C | ALA A | 59 | 55.651 | 42.188 | 1.391 | 1.00 | 20.64 |
| ATOM | 235 | O | ALA A | 59 | 56.037 | 43.190 | 1.992 | 1.00 | 21.25 |
| ATOM | 236 | N | VAL A | 60 | 55.612 | 40.982 | 1.941 | 1.00 | 20.09 |
| ATOM | 237 | CA | VAL A | 60 | 56.056 | 40.766 | 3.308 | 1.00 | 19.99 |
| ATOM | 238 | CB | VAL A | 60 | 55.817 | 39.300 | 3.741 | 1.00 | 18.43 |
| ATOM | 239 | CG1 | VAL A | 60 | 56.407 | 39.054 | 5.129 | 1.00 | 17.76 |
| ATOM | 240 | CG2 | VAL A | 60 | 54.324 | 39.003 | 3.742 | 1.00 | 14.72 |
| ATOM | 241 | C | VAL A | 60 | 57.541 | 41.111 | 3.425 | 1.00 | 21.05 |
| ATOM | 242 | O | VAL A | 60 | 57.951 | 41.785 | 4.365 | 1.00 | 21.13 |
| ATOM | 243 | N | ARG A | 61 | 58.340 | 40.664 | 2.459 | 1.00 | 23.89 |
| ATOM | 244 | CA | ARG A | 61 | 59.776 | 40.944 | 2.471 | 1.00 | 27.66 |
| ATOM | 245 | CB | ARG A | 61 | 60.469 | 40.352 | 1.239 | 1.00 | 29.95 |
| ATOM | 246 | CG | ARG A | 61 | 60.426 | 38.838 | 1.122 | 1.00 | 38.36 |

TABLE 29-continued

| | | | | | | | | | |
|---|---|---|---|---|---|---|---|---|---|
| ATOM | 247 | CD | ARG A | 61 | 61.548 | 38.355 | 0.196 | 1.00 | 44.69 |
| ATOM | 248 | NE | ARG A | 61 | 61.477 | 36.926 | −0.101 | 1.00 | 50.18 |
| ATOM | 249 | CZ | ARG A | 61 | 60.671 | 36.388 | −1.014 | 1.00 | 51.97 |
| ATOM | 250 | NH1 | ARG A | 61 | 59.863 | 37.159 | −1.729 | 1.00 | 51.92 |
| ATOM | 251 | NH2 | ARG A | 61 | 60.674 | 35.076 | −1.212 | 1.00 | 53.20 |
| ATOM | 252 | C | ARG A | 61 | 60.065 | 42.443 | 2.510 | 1.00 | 27.16 |
| ATOM | 253 | O | ARG A | 61 | 60.778 | 42.925 | 3.392 | 1.00 | 25.78 |
| ATOM | 254 | N | PHE A | 62 | 59.514 | 43.175 | 1.546 | 1.00 | 26.45 |
| ATOM | 255 | CA | PHE A | 62 | 59.737 | 44.611 | 1.470 | 1.00 | 28.86 |
| ATOM | 256 | CB | PHE A | 62 | 59.039 | 45.194 | −0.239 | 1.00 | 31.67 |
| ATOM | 257 | CG | PHE A | 62 | 59.842 | 45.074 | −1.024 | 1.00 | 35.37 |
| ATOM | 258 | CD1 | PHE A | 62 | 60.354 | 43.852 | −1.424 | 1.00 | 36.62 |
| ATOM | 259 | CD2 | PHE A | 62 | 60.081 | 46.186 | −1.816 | 1.00 | 38.91 |
| ATOM | 260 | CE1 | PHE A | 62 | 61.089 | 43.739 | −2.591 | 1.00 | 38.37 |
| ATOM | 261 | CE2 | PHE A | 62 | 60.816 | 46.079 | −2.986 | 1.00 | 40.05 |
| ATOM | 262 | CZ | PHE A | 62 | 61.320 | 44.853 | −3.373 | 1.00 | 39.06 |
| ATOM | 263 | C | PHE A | 62 | 59.277 | 45.345 | 2.717 | 1.00 | 28.84 |
| ATOM | 264 | O | PHE A | 62 | 59.950 | 46.265 | 3.184 | 1.00 | 28.63 |
| ATOM | 265 | N | THR A | 63 | 58.131 | 44.941 | 3.252 | 1.00 | 28.32 |
| ATOM | 266 | CA | THR A | 63 | 57.598 | 45.576 | 4.446 | 1.00 | 27.37 |
| ATOM | 267 | CB | THR A | 63 | 56.196 | 45.023 | 4.798 | 1.00 | 26.41 |
| ATOM | 268 | OG1 | THR A | 63 | 55.298 | 45.267 | 3.709 | 1.00 | 24.23 |
| ATOM | 269 | CG2 | THR A | 63 | 55.653 | 45.700 | 6.044 | 1.00 | 25.26 |
| ATOM | 270 | C | THR A | 63 | 58.537 | 45.351 | 5.626 | 1.00 | 28.52 |
| ATOM | 271 | O | THR A | 63 | 58.851 | 46.284 | 6.369 | 1.00 | 27.19 |
| ATOM | 272 | N | SER A | 64 | 58.991 | 44.112 | 5.793 | 1.00 | 28.48 |
| ATOM | 273 | CA | SER A | 64 | 59.890 | 43.790 | 6.895 | 1.00 | 30.95 |
| ATOM | 274 | CB | SER A | 64 | 60.206 | 42.291 | 6.909 | 1.00 | 30.12 |
| ATOM | 275 | OG | SER A | 64 | 60.986 | 41.918 | 5.787 | 1.00 | 34.09 |
| ATOM | 276 | C | SER A | 64 | 61.186 | 44.592 | 6.791 | 1.00 | 31.50 |
| ATOM | 277 | O | SER A | 64 | 61.789 | 44.940 | 7.803 | 1.00 | 31.30 |
| ATOM | 278 | N | LEU A | 65 | 61.603 | 44.893 | 5.565 | 1.00 | 33.16 |
| ATOM | 279 | CA | LEU A | 65 | 62.830 | 45.654 | 5.343 | 1.00 | 34.16 |
| ATOM | 280 | CB | LEU A | 65 | 63.497 | 45.212 | 4.035 | 1.00 | 33.74 |
| ATOM | 281 | CG | LEU A | 65 | 63.989 | 43.762 | 3.999 | 1.00 | 36.53 |
| ATOM | 282 | CD1 | LEU A | 65 | 64.580 | 43.449 | 2.636 | 1.00 | 34.22 |
| ATOM | 283 | CD2 | LEU A | 65 | 65.026 | 43.543 | 5.098 | 1.00 | 36.82 |
| ATOM | 284 | C | LEU A | 65 | 62.599 | 47.165 | 5.320 | 1.00 | 34.01 |
| ATOM | 285 | O | LEU A | 65 | 63.543 | 47.939 | 5.177 | 1.00 | 34.34 |
| ATOM | 286 | N | GLY A | 66 | 61.345 | 47.582 | 5.457 | 1.00 | 33.51 |
| ATOM | 287 | CA | GLY A | 66 | 61.041 | 49.002 | 5.463 | 1.00 | 34.57 |
| ATOM | 288 | C | GLY A | 66 | 61.063 | 49.698 | 4.110 | 1.00 | 35.92 |
| ATOM | 289 | O | GLY A | 66 | 61.089 | 50.930 | 4.044 | 1.00 | 35.49 |
| ATOM | 290 | N | LEU A | 67 | 61.056 | 48.924 | 3.030 | 1.00 | 36.20 |
| ATOM | 291 | CA | LEU A | 67 | 61.062 | 49.500 | 1.689 | 1.00 | 37.47 |
| ATOM | 292 | CB | LEU A | 67 | 61.477 | 48.439 | 0.665 | 1.00 | 39.14 |
| ATOM | 293 | CG | LEU A | 67 | 62.785 | 47.701 | 0.982 | 1.00 | 41.61 |
| ATOM | 294 | CD1 | LEU A | 67 | 63.070 | 46.664 | −0.092 | 1.00 | 41.43 |
| ATOM | 295 | CD2 | LEU A | 67 | 63.931 | 48.701 | 1.077 | 1.00 | 43.31 |
| ATOM | 296 | C | LEU A | 67 | 59.647 | 49.992 | 1.400 | 1.00 | 36.88 |
| ATOM | 297 | O | LEU A | 67 | 58.908 | 49.377 | 0.635 | 1.00 | 36.23 |
| ATOM | 298 | N | LEU A | 68 | 59.281 | 51.106 | 2.024 | 1.00 | 37.29 |
| ATOM | 299 | CA | LEU A | 68 | 57.947 | 51.677 | 1.881 | 1.00 | 38.19 |
| ATOM | 300 | CB | LEU A | 68 | 57.206 | 51.575 | 3.215 | 1.00 | 38.57 |
| ATOM | 301 | CG | LEU A | 68 | 57.206 | 50.198 | 3.878 | 1.00 | 39.38 |
| ATOM | 302 | CD1 | LEU A | 68 | 56.690 | 50.310 | 5.299 | 1.00 | 39.44 |
| ATOM | 303 | CD2 | LEU A | 68 | 56.356 | 49.244 | 3.059 | 1.00 | 40.05 |
| ATOM | 304 | C | LEU A | 68 | 57.983 | 53.137 | 1.449 | 1.00 | 38.35 |
| ATOM | 305 | O | LEU A | 68 | 58.922 | 53.865 | 1.764 | 1.00 | 38.77 |
| ATOM | 306 | N | PRO A | 69 | 56.945 | 53.583 | 0.726 | 1.00 | 38.45 |
| ATOM | 307 | CD | PRO A | 69 | 55.780 | 52.778 | 0.323 | 1.00 | 37.87 |
| ATOM | 308 | CA | PRO A | 69 | 56.819 | 54.956 | 0.232 | 1.00 | 39.07 |
| ATOM | 309 | CB | PRO A | 69 | 55.580 | 54.885 | −0.657 | 1.00 | 38.36 |
| ATOM | 310 | CG | PRO A | 69 | 54.754 | 53.842 | 0.012 | 1.00 | 38.12 |
| ATOM | 311 | C | PRO A | 69 | 56.666 | 55.976 | 1.358 | 1.00 | 39.55 |
| ATOM | 312 | O | PRO A | 69 | 56.798 | 55.640 | 2.535 | 1.00 | 40.34 |
| ATOM | 313 | N | PHE A | 73 | 51.509 | 61.626 | 6.239 | 1.00 | 57.41 |
| ATOM | 314 | CA | PHE A | 73 | 50.304 | 61.905 | 7.014 | 1.00 | 57.56 |
| ATOM | 315 | CB | PHE A | 73 | 49.146 | 61.013 | 6.554 | 1.00 | 57.94 |
| ATOM | 316 | CG | PHE A | 73 | 47.896 | 61.178 | 7.376 | 1.00 | 57.97 |
| ATOM | 317 | CD1 | PHE A | 73 | 47.046 | 62.252 | 7.167 | 1.00 | 58.09 |
| ATOM | 318 | CD2 | PHE A | 73 | 47.592 | 60.279 | 8.388 | 1.00 | 58.00 |
| ATOM | 319 | CE1 | PHE A | 73 | 45.918 | 62.427 | 7.950 | 1.00 | 57.86 |
| ATOM | 320 | CE2 | PHE A | 73 | 46.465 | 60.451 | 9.175 | 1.00 | 56.97 |
| ATOM | 321 | CZ | PHE A | 73 | 45.628 | 61.525 | 8.956 | 1.00 | 56.70 |
| ATOM | 322 | C | PHE A | 73 | 50.519 | 61.683 | 8.506 | 1.00 | 56.61 |
| ATOM | 323 | O | PHE A | 73 | 50.884 | 60.586 | 8.932 | 1.00 | 56.50 |
| ATOM | 324 | N | GLN A | 74 | 50.289 | 62.727 | 9.295 | 1.00 | 55.80 |
| ATOM | 325 | CA | GLN A | 74 | 50.434 | 62.632 | 10.743 | 1.00 | 54.27 |

TABLE 29-continued

| | | | | | | | | | |
|---|---|---|---|---|---|---|---|---|---|
| ATOM | 326 | CB | GLN A | 74 | 51.067 | 63.902 | 11.316 | 1.00 | 55.72 |
| ATOM | 327 | CG | GLN A | 74 | 52.551 | 64.063 | 11.029 | 1.00 | 58.53 |
| ATOM | 328 | CD | GLN A | 74 | 53.176 | 65.195 | 11.835 | 1.00 | 60.58 |
| ATOM | 329 | OE1 | GLN A | 74 | 52.868 | 66.371 | 11.625 | 1.00 | 60.54 |
| ATOM | 330 | NE2 | GLN A | 74 | 54.050 | 64.839 | 12.770 | 1.00 | 60.75 |
| ATOM | 331 | C | GLN A | 74 | 49.061 | 62.429 | 11.366 | 1.00 | 51.91 |
| ATOM | 332 | O | GLN A | 74 | 48.107 | 63.128 | 11.029 | 1.00 | 51.26 |
| ATOM | 333 | N | ASP A | 75 | 48.965 | 61.464 | 12.271 | 1.00 | 49.71 |
| ATOM | 334 | CA | ASP A | 75 | 47.705 | 61.173 | 12.940 | 1.00 | 47.29 |
| ATOM | 335 | CB | ASP A | 75 | 47.826 | 59.868 | 13.733 | 1.00 | 46.43 |
| ATOM | 336 | CG | ASP A | 75 | 48.173 | 58.681 | 12.853 | 1.00 | 44.45 |
| ATOM | 337 | OD1 | ASP A | 75 | 48.650 | 57.657 | 13.391 | 1.00 | 41.73 |
| ATOM | 338 | OD2 | ASP A | 75 | 47.960 | 58.771 | 11.626 | 1.00 | 44.21 |
| ATOM | 339 | C | ASP A | 75 | 47.359 | 62.319 | 13.884 | 1.00 | 46.48 |
| ATOM | 340 | O | ASP A | 75 | 48.217 | 62.803 | 14.622 | 1.00 | 46.43 |
| ATOM | 341 | N | SER A | 76 | 46.106 | 62.757 | 13.853 | 1.00 | 45.52 |
| ATOM | 342 | CA | SER A | 76 | 45.666 | 63.839 | 14.726 | 1.00 | 43.83 |
| ATOM | 343 | CB | SER A | 76 | 44.732 | 64.791 | 13.976 | 1.00 | 43.83 |
| ATOM | 344 | OG | SER A | 76 | 43.519 | 64.147 | 13.630 | 1.00 | 45.56 |
| ATOM | 345 | C | SER A | 76 | 44.935 | 63.239 | 15.916 | 1.00 | 42.06 |
| ATOM | 346 | O | SER A | 76 | 44.492 | 62.094 | 15.866 | 1.00 | 42.96 |
| ATOM | 347 | N | ASP A | 77 | 44.814 | 64.014 | 16.985 | 1.00 | 40.79 |
| ATOM | 348 | CA | ASP A | 77 | 44.131 | 63.558 | 18.188 | 1.00 | 40.57 |
| ATOM | 349 | CB | ASP A | 77 | 43.969 | 64.725 | 19.167 | 1.00 | 42.86 |
| ATOM | 350 | CG | ASP A | 77 | 45.303 | 65.296 | 19.620 | 1.00 | 46.39 |
| ATOM | 351 | OD1 | ASP A | 77 | 45.301 | 66.339 | 20.307 | 1.00 | 48.20 |
| ATOM | 352 | OD2 | ASP A | 77 | 46.354 | 64.702 | 19.294 | 1.00 | 47.94 |
| ATOM | 353 | C | ASP A | 77 | 42.761 | 62.959 | 17.866 | 1.00 | 38.52 |
| ATOM | 354 | O | ASP A | 77 | 42.285 | 62.070 | 18.568 | 1.00 | 37.86 |
| ATOM | 355 | N | MET A | 78 | 42.137 | 63.451 | 16.799 | 1.00 | 37.07 |
| ATOM | 356 | CA | MET A | 78 | 40.819 | 62.976 | 16.376 | 1.00 | 35.68 |
| ATOM | 357 | CB | MET A | 78 | 40.371 | 63.700 | 15.105 | 1.00 | 36.68 |
| ATOM | 358 | CG | MET A | 78 | 40.022 | 65.154 | 15.279 | 1.00 | 38.98 |
| ATOM | 359 | SD | MET A | 78 | 39.373 | 65.811 | 13.731 | 1.00 | 43.55 |
| ATOM | 360 | CE | MET A | 78 | 37.673 | 65.195 | 13.798 | 1.00 | 40.05 |
| ATOM | 361 | C | MET A | 78 | 40.758 | 61.476 | 16.104 | 1.00 | 33.08 |
| ATOM | 362 | O | MET A | 78 | 39.758 | 60.823 | 16.405 | 1.00 | 32.55 |
| ATOM | 363 | N | LEU A | 79 | 41.823 | 60.937 | 15.521 | 1.00 | 29.66 |
| ATOM | 364 | CA | LEU A | 79 | 41.861 | 59.523 | 15.186 | 1.00 | 28.85 |
| ATOM | 365 | CB | LEU A | 79 | 42.852 | 59.286 | 14.043 | 1.00 | 26.36 |
| ATOM | 366 | CG | LEU A | 79 | 42.531 | 60.008 | 12.728 | 1.00 | 27.00 |
| ATOM | 367 | CD1 | LEU A | 79 | 43.494 | 59.545 | 11.640 | 1.00 | 24.52 |
| ATOM | 368 | CD2 | LEU A | 79 | 41.090 | 59.723 | 12.316 | 1.00 | 23.83 |
| ATOM | 369 | C | LEU A | 79 | 42.197 | 58.611 | 16.359 | 1.00 | 28.62 |
| ATOM | 370 | O | LEU A | 79 | 42.120 | 57.387 | 16.237 | 1.00 | 27.51 |
| ATOM | 371 | N | GLU A | 80 | 42.558 | 59.199 | 17.495 | 1.00 | 27.92 |
| ATOM | 372 | CA | GLU A | 80 | 42.905 | 58.408 | 18.666 | 1.00 | 28.74 |
| ATOM | 373 | CB | GLU A | 80 | 43.609 | 59.272 | 19.717 | 1.00 | 30.72 |
| ATOM | 374 | CG | GLU A | 80 | 43.731 | 58.592 | 21.078 | 1.00 | 36.88 |
| ATOM | 375 | CD | GLU A | 80 | 44.634 | 59.344 | 22.045 | 1.00 | 40.61 |
| ATOM | 376 | OE1 | GLU A | 80 | 44.556 | 59.070 | 23.262 | 1.00 | 40.98 |
| ATOM | 377 | OE2 | GLU A | 80 | 45.427 | 60.199 | 21.591 | 1.00 | 43.20 |
| ATOM | 378 | C | GLU A | 80 | 41.686 | 57.743 | 19.286 | 1.00 | 28.29 |
| ATOM | 379 | O | GLU A | 80 | 40.633 | 58.357 | 19.432 | 1.00 | 29.91 |
| ATOM | 380 | N | VAL A | 81 | 41.841 | 56.478 | 19.649 | 1.00 | 26.82 |
| ATOM | 381 | CA | VAL A | 81 | 40.762 | 55.717 | 20.255 | 1.00 | 27.29 |
| ATOM | 382 | CB | VAL A | 81 | 40.157 | 54.697 | 19.253 | 1.00 | 27.96 |
| ATOM | 383 | CG1 | VAL A | 81 | 38.975 | 53.978 | 19.891 | 1.00 | 26.13 |
| ATOM | 384 | CG2 | VAL A | 81 | 39.736 | 55.401 | 17.976 | 1.00 | 27.50 |
| ATOM | 385 | C | VAL A | 81 | 41.306 | 54.939 | 21.441 | 1.00 | 27.37 |
| ATOM | 386 | O | VAL A | 81 | 42.470 | 54.529 | 21.445 | 1.00 | 27.61 |
| ATOM | 387 | N | ARG A | 82 | 40.468 | 54.738 | 22.450 | 1.00 | 27.98 |
| ATOM | 388 | CA | ARG A | 82 | 40.887 | 53.977 | 23.615 | 1.00 | 29.54 |
| ATOM | 389 | CB | ARG A | 82 | 40.957 | 54.860 | 24.862 | 1.00 | 32.27 |
| ATOM | 390 | CG | ARG A | 82 | 42.033 | 54.387 | 25.823 | 1.00 | 39.97 |
| ATOM | 391 | CD | ARG A | 82 | 41.640 | 54.494 | 27.289 | 1.00 | 45.20 |
| ATOM | 392 | NE | ARG A | 82 | 42.662 | 53.886 | 28.145 | 1.00 | 48.67 |
| ATOM | 393 | CZ | ARG A | 82 | 43.059 | 52.618 | 28.050 | 1.00 | 48.74 |
| ATOM | 394 | NH1 | ARG A | 82 | 42.523 | 51.816 | 27.139 | 1.00 | 49.38 |
| ATOM | 395 | NH2 | ARG A | 82 | 43.999 | 52.153 | 28.859 | 1.00 | 50.09 |
| ATOM | 396 | C | ARG A | 82 | 39.912 | 52.836 | 23.853 | 1.00 | 28.48 |
| ATOM | 397 | O | ARG A | 82 | 38.738 | 53.064 | 24.133 | 1.00 | 29.58 |
| ATOM | 398 | N | VAL A | 83 | 40.408 | 51.609 | 23.729 | 1.00 | 28.50 |
| ATOM | 399 | CA | VAL A | 83 | 39.604 | 50.406 | 23.930 | 1.00 | 28.91 |
| ATOM | 400 | CB | VAL A | 83 | 38.780 | 50.041 | 22.673 | 1.00 | 29.46 |
| ATOM | 401 | CG1 | VAL A | 83 | 37.530 | 50.896 | 22.597 | 1.00 | 31.26 |
| ATOM | 402 | CG2 | VAL A | 83 | 39.633 | 50.220 | 21.423 | 1.00 | 25.10 |
| ATOM | 403 | C | VAL A | 83 | 40.493 | 49.216 | 24.245 | 1.00 | 29.96 |
| ATOM | 404 | O | VAL A | 83 | 41.710 | 49.284 | 24.086 | 1.00 | 29.44 |

TABLE 29-continued

| | | | | | | | | | |
|---|---|---|---|---|---|---|---|---|---|
| ATOM | 405 | N | LEU A | 84 | 39.873 | 48.124 | 24.688 | 1.00 | 31.71 |
| ATOM | 406 | CA | LEU A | 84 | 40.596 | 46.896 | 25.005 | 1.00 | 32.74 |
| ATOM | 407 | CB | LEU A | 84 | 41.132 | 46.263 | 23.712 | 1.00 | 31.47 |
| ATOM | 408 | CG | LEU A | 84 | 40.080 | 46.012 | 22.622 | 1.00 | 31.62 |
| ATOM | 409 | CD1 | LEU A | 84 | 40.753 | 45.558 | 21.343 | 1.00 | 31.18 |
| ATOM | 410 | CD2 | LEU A | 84 | 39.079 | 44.976 | 23.103 | 1.00 | 27.96 |
| ATOM | 411 | C | LEU A | 84 | 41.752 | 47.136 | 25.973 | 1.00 | 33.44 |
| ATOM | 412 | O | LEU A | 84 | 42.748 | 46.413 | 25.946 | 1.00 | 35.00 |
| ATOM | 413 | N | GLY A | 85 | 41.613 | 48.151 | 26.824 | 1.00 | 33.39 |
| ATOM | 414 | CA | GLY A | 85 | 42.654 | 48.466 | 27.790 | 1.00 | 31.80 |
| ATOM | 415 | C | GLY A | 85 | 43.896 | 49.059 | 27.148 | 1.00 | 31.85 |
| ATOM | 416 | O | GLY A | 85 | 44.998 | 48.962 | 27.694 | 1.00 | 30.17 |
| ATOM | 417 | N | HIS A | 86 | 43.718 | 49.683 | 25.988 | 1.00 | 31.24 |
| ATOM | 418 | CA | HIS A | 86 | 44.836 | 50.281 | 25.271 | 1.00 | 31.52 |
| ATOM | 419 | CB | HIS A | 86 | 45.423 | 49.271 | 24.275 | 1.00 | 33.75 |
| ATOM | 420 | CG | HIS A | 86 | 45.969 | 48.034 | 24.915 | 1.00 | 36.55 |
| ATOM | 421 | CD2 | HIS A | 86 | 45.508 | 46.760 | 24.931 | 1.00 | 37.53 |
| ATOM | 422 | ND1 | HIS A | 86 | 47.121 | 48.033 | 25.672 | 1.00 | 37.68 |
| ATOM | 423 | CE1 | HIS A | 86 | 47.346 | 46.814 | 26.128 | 1.00 | 37.36 |
| ATOM | 424 | NE2 | HIS A | 86 | 46.381 | 46.022 | 25.693 | 1.00 | 39.46 |
| ATOM | 425 | C | HIS A | 86 | 44.453 | 51.546 | 24.511 | 1.00 | 30.30 |
| ATOM | 426 | O | HIS A | 86 | 43.280 | 51.835 | 24.280 | 1.00 | 29.95 |
| ATOM | 427 | N | LYS A | 87 | 45.471 | 52.297 | 24.122 | 1.00 | 29.57 |
| ATOM | 428 | CA | LYS A | 87 | 45.272 | 53.512 | 23.357 | 1.00 | 28.75 |
| ATOM | 429 | CB | LYS A | 87 | 46.130 | 54.643 | 23.928 | 1.00 | 31.29 |
| ATOM | 430 | CG | LYS A | 87 | 46.065 | 55.930 | 23.131 | 1.00 | 36.25 |
| ATOM | 431 | CD | LYS A | 87 | 46.998 | 56.986 | 23.704 | 1.00 | 39.73 |
| ATOM | 432 | CB | LYS A | 87 | 48.452 | 56.557 | 23.603 | 1.00 | 41.38 |
| ATOM | 433 | NZ | LYS A | 87 | 49.372 | 57.604 | 24.134 | 1.00 | 43.32 |
| ATOM | 434 | C | LYS A | 87 | 45.710 | 53.199 | 21.931 | 1.00 | 26.30 |
| ATOM | 435 | O | LYS A | 87 | 46.724 | 52.525 | 21.724 | 1.00 | 24.62 |
| ATOM | 436 | N | PHE A | 88 | 44.928 | 53.657 | 20.958 | 1.00 | 22.40 |
| ATOM | 437 | CA | PHE A | 88 | 45.251 | 53.453 | 19.549 | 1.00 | 21.04 |
| ATOM | 438 | CB | PHE A | 88 | 44.151 | 52.648 | 18.845 | 1.00 | 17.91 |
| ATOM | 439 | CG | PHE A | 88 | 43.990 | 51.239 | 19.358 | 1.00 | 16.58 |
| ATOM | 440 | CD1 | PHE A | 88 | 43.489 | 50.995 | 20.628 | 1.00 | 15.22 |
| ATOM | 441 | CD2 | PHE A | 88 | 44.321 | 50.157 | 18.555 | 1.00 | 13.45 |
| ATOM | 442 | CE1 | PHE A | 88 | 43.317 | 49.703 | 21.087 | 1.00 | 15.04 |
| ATOM | 443 | CE2 | PHE A | 88 | 44.153 | 48.866 | 19.007 | 1.00 | 13.65 |
| ATOM | 444 | CZ | PHE A | 88 | 43.650 | 48.636 | 20.275 | 1.00 | 15.42 |
| ATOM | 445 | C | PHE A | 88 | 45.350 | 54.841 | 18.917 | 1.00 | 21.32 |
| ATOM | 446 | O | PHE A | 88 | 44.363 | 55.578 | 18.900 | 1.00 | 21.11 |
| ATOM | 447 | N | ARG A | 89 | 46.524 | 55.203 | 18.399 | 1.00 | 21.70 |
| ATOM | 448 | CA | ARG A | 89 | 46.681 | 56.526 | 17.797 | 1.00 | 23.91 |
| ATOM | 449 | CB | ARG A | 89 | 48.142 | 56.803 | 17.422 | 1.00 | 27.51 |
| ATOM | 450 | CG | ARG A | 89 | 48.735 | 55.905 | 16.369 | 1.00 | 34.45 |
| ATOM | 451 | CD | ARG A | 89 | 50.095 | 56.441 | 15.949 | 1.00 | 39.63 |
| ATOM | 452 | NE | ARG A | 89 | 50.942 | 56.726 | 17.103 | 1.00 | 43.01 |
| ATOM | 453 | CZ | ARG A | 89 | 52.223 | 57.073 | 17.025 | 1.00 | 45.72 |
| ATOM | 454 | NH1 | ARG A | 89 | 52.814 | 57.180 | 15.840 | 1.00 | 45.78 |
| ATOM | 455 | NH2 | ARG A | 89 | 52.915 | 57.309 | 18.133 | 1.00 | 46.24 |
| ATOM | 456 | C | ARG A | 89 | 45.764 | 56.722 | 16.593 | 1.00 | 21.40 |
| ATOM | 457 | O | ARG A | 89 | 45.350 | 57.839 | 16.308 | 1.00 | 20.59 |
| ATOM | 458 | N | ASN A | 90 | 45.467 | 55.643 | 15.877 | 1.00 | 19.60 |
| ATOM | 459 | CA | ASN A | 90 | 44.525 | 55.708 | 14.759 | 1.00 | 19.44 |
| ATOM | 460 | CB | ASN A | 90 | 45.218 | 56.045 | 13.418 | 1.00 | 17.27 |
| ATOM | 461 | CG | ASN A | 90 | 45.918 | 54.870 | 12.782 | 1.00 | 17.47 |
| ATOM | 462 | OD1 | ASN A | 90 | 45.286 | 53.885 | 12.404 | 1.00 | 18.85 |
| ATOM | 463 | ND2 | ASN A | 90 | 47.236 | 54.977 | 12.635 | 1.00 | 17.61 |
| ATOM | 464 | C | ASN A | 90 | 43.814 | 54.357 | 14.762 | 1.00 | 19.17 |
| ATOM | 465 | O | ASN A | 90 | 44.377 | 53.351 | 15.199 | 1.00 | 20.42 |
| ATOM | 466 | N | PRO A | 91 | 42.555 | 54.325 | 14.307 | 1.00 | 17.95 |
| ATOM | 467 | CD | PRO A | 91 | 41.802 | 55.495 | 13.815 | 1.00 | 18.80 |
| ATOM | 468 | CA | PRO A | 91 | 41.721 | 53.123 | 14.259 | 1.00 | 17.08 |
| ATOM | 469 | CB | PRO A | 91 | 40.319 | 53.708 | 14.339 | 1.00 | 17.82 |
| ATOM | 470 | CG | PRO A | 91 | 40.444 | 54.896 | 13.443 | 1.00 | 15.11 |
| ATOM | 471 | C | PRO A | 91 | 41.872 | 52.197 | 13.059 | 1.00 | 17.57 |
| ATOM | 472 | O | PRO A | 91 | 41.071 | 51.277 | 12.889 | 1.00 | 17.10 |
| ATOM | 473 | N | VAL A | 92 | 42.889 | 52.425 | 12.236 | 1.00 | 17.30 |
| ATOM | 474 | CA | VAL A | 92 | 43.086 | 51.607 | 11.040 | 1.00 | 17.64 |
| ATOM | 475 | CB | VAL A | 92 | 43.391 | 52.504 | 9.816 | 1.00 | 17.72 |
| ATOM | 476 | CG1 | VAL A | 92 | 43.497 | 51.666 | 8.555 | 1.00 | 14.42 |
| ATOM | 477 | CG2 | VAL A | 92 | 42.310 | 53.560 | 9.678 | 1.00 | 16.61 |
| ATOM | 478 | C | VAL A | 92 | 44.206 | 50.588 | 11.201 | 1.00 | 18.02 |
| ATOM | 479 | O | VAL A | 92 | 45.377 | 50.948 | 11.280 | 1.00 | 18.29 |
| ATOM | 480 | N | GLY A | 93 | 43.840 | 49.311 | 11.242 | 1.00 | 17.60 |
| ATOM | 481 | CA | GLY A | 93 | 44.839 | 48.274 | 11.394 | 1.00 | 16.36 |
| ATOM | 482 | C | GLY A | 93 | 44.907 | 47.332 | 10.212 | 1.00 | 16.58 |
| ATOM | 483 | O | GLY A | 93 | 44.043 | 47.352 | 9.336 | 1.00 | 17.37 |

TABLE 29-continued

| | | | | | | | | | |
|---|---|---|---|---|---|---|---|---|---|
| ATOM | 484 | N | ILE A | 94 | 45.956 | 46.517 | 10.174 | 1.00 | 16.03 |
| ATOM | 485 | CA | ILE A | 94 | 46.123 | 45.541 | 9.106 | 1.00 | 14.28 |
| ATOM | 486 | CB | ILE A | 94 | 47.621 | 45.319 | 8.772 | 1.00 | 15.21 |
| ATOM | 487 | CG2 | ILE A | 94 | 48.409 | 45.008 | 10.035 | 1.00 | 14.14 |
| ATOM | 488 | CG1 | ILE A | 94 | 47.766 | 44.197 | 7.740 | 1.00 | 15.27 |
| ATOM | 489 | CD1 | ILE A | 94 | 47.288 | 44.580 | 6.347 | 1.00 | 15.14 |
| ATOM | 490 | C | ILE A | 94 | 45.494 | 44.236 | 9.595 | 1.00 | 14.89 |
| ATOM | 491 | O | ILE A | 94 | 45.868 | 43.707 | 10.639 | 1.00 | 14.26 |
| ATOM | 492 | N | ALA A | 95 | 44.521 | 43.729 | 8.847 | 1.00 | 14.41 |
| ATOM | 493 | CA | ALA A | 95 | 43.837 | 42.501 | 9.228 | 1.00 | 14.87 |
| ATOM | 494 | CB | ALA A | 95 | 42.665 | 42.244 | 8.282 | 1.00 | 14.00 |
| ATOM | 495 | C | ALA A | 95 | 44.770 | 41.292 | 9.248 | 1.00 | 14.88 |
| ATOM | 496 | O | ALA A | 95 | 45.877 | 41.338 | 8.715 | 1.00 | 13.34 |
| ATOM | 497 | N | ALA A | 96 | 44.314 | 40.215 | 9.878 | 1.00 | 14.32 |
| ATOM | 498 | CA | ALA A | 96 | 45.092 | 38.989 | 9.952 | 1.00 | 17.35 |
| ATOM | 499 | CB | ALA A | 96 | 44.392 | 37.976 | 10.856 | 1.00 | 16.42 |
| ATOM | 500 | C | ALA A | 96 | 45.240 | 38.419 | 8.546 | 1.00 | 17.48 |
| ATOM | 501 | O | ALA A | 96 | 44.386 | 38.641 | 7.686 | 1.00 | 19.61 |
| ATOM | 502 | N | GLY A | 97 | 46.326 | 37.691 | 8.309 | 1.00 | 18.20 |
| ATOM | 503 | CA | GLY A | 97 | 46.534 | 37.106 | 6.997 | 1.00 | 16.78 |
| ATOM | 504 | C | GLY A | 97 | 47.697 | 37.681 | 6.214 | 1.00 | 15.75 |
| ATOM | 505 | O | GLY A | 97 | 48.411 | 36.937 | 5.551 | 1.00 | 16.02 |
| ATOM | 506 | N | PHE A | 98 | 47.894 | 38.995 | 6.266 | 1.00 | 15.54 |
| ATOM | 507 | CA | PHE A | 98 | 49.006 | 39.586 | 5.533 | 1.00 | 16.58 |
| ATOM | 508 | CB | PHE A | 98 | 48.955 | 41.115 | 5.550 | 1.00 | 16.83 |
| ATOM | 509 | CG | PHE A | 98 | 50.097 | 41.747 | 4.815 | 1.00 | 18.26 |
| ATOM | 510 | CD1 | PHE A | 98 | 50.166 | 41.680 | 3.429 | 1.00 | 19.90 |
| ATOM | 511 | CD2 | PHE A | 98 | 51.139 | 42.346 | 5.505 | 1.00 | 19.00 |
| ATOM | 512 | CE1 | PHE A | 98 | 51.254 | 42.193 | 2.748 | 1.00 | 19.02 |
| ATOM | 513 | CE2 | PHE A | 98 | 52.233 | 42.863 | 4.831 | 1.00 | 18.84 |
| ATOM | 514 | CZ | PHE A | 98 | 52.291 | 42.786 | 3.451 | 1.00 | 20.99 |
| ATOM | 515 | C | PHE A | 98 | 50.315 | 39.127 | 6.164 | 1.00 | 15.86 |
| ATOM | 516 | O | PHE A | 98 | 51.200 | 38.620 | 5.482 | 1.00 | 15.58 |
| ATOM | 517 | N | ASP A | 99 | 50.433 | 39.322 | 7.472 | 1.00 | 16.10 |
| ATOM | 518 | CA | ASP A | 99 | 51.626 | 38.905 | 8.203 | 1.00 | 15.76 |
| ATOM | 519 | CB | ASP A | 99 | 52.158 | 40.070 | 9.040 | 1.00 | 15.13 |
| ATOM | 520 | CG | ASP A | 99 | 53.540 | 39.802 | 9.610 | 1.00 | 18.19 |
| ATOM | 521 | OD1 | ASP A | 99 | 54.167 | 38.794 | 9.224 | 1.00 | 17.29 |
| ATOM | 522 | OD2 | ASP A | 99 | 54.006 | 40.612 | 10.439 | 1.00 | 19.53 |
| ATOM | 523 | C | ASP A | 99 | 51.228 | 37.729 | 9.101 | 1.00 | 16.25 |
| ATOM | 524 | O | ASP A | 99 | 50.995 | 37.894 | 10.300 | 1.00 | 14.46 |
| ATOM | 525 | N | LYS A | 100 | 51.134 | 36.546 | 8.499 | 1.00 | 16.78 |
| ATOM | 526 | CA | LYS A | 100 | 50.750 | 35.335 | 9.215 | 1.00 | 17.78 |
| ATOM | 527 | CB | LYS A | 100 | 50.484 | 34.194 | 8.222 | 1.00 | 19.95 |
| ATOM | 528 | CG | LYS A | 100 | 49.149 | 34.250 | 7.478 | 1.00 | 21.28 |
| ATOM | 529 | CD | LYS A | 100 | 49.084 | 33.139 | 6.426 | 1.00 | 24.43 |
| ATOM | 530 | CB | LYS A | 100 | 47.727 | 33.060 | 5.714 | 1.00 | 25.79 |
| ATOM | 531 | NZ | LYS A | 100 | 46.644 | 32.486 | 6.578 | 1.00 | 23.81 |
| ATOM | 532 | C | LYS A | 100 | 51.767 | 34.849 | 10.247 | 1.00 | 18.87 |
| ATOM | 533 | O | LYS A | 100 | 51.389 | 34.269 | 11.267 | 1.00 | 19.75 |
| ATOM | 534 | N | HIS A | 101 | 53.050 | 35.083 | 9.993 | 1.00 | 18.22 |
| ATOM | 535 | CA | HIS A | 101 | 54.088 | 34.601 | 10.902 | 1.00 | 20.19 |
| ATOM | 536 | CB | HIS A | 101 | 55.109 | 33.779 | 10.106 | 1.00 | 17.78 |
| ATOM | 537 | CG | HIS A | 101 | 54.507 | 33.029 | 8.959 | 1.00 | 18.92 |
| ATOM | 538 | CD2 | HIS A | 101 | 54.760 | 33.081 | 7.629 | 1.00 | 17.74 |
| ATOM | 539 | ND1 | HIS A | 101 | 53.491 | 32.110 | 9.120 | 1.00 | 18.19 |
| ATOM | 540 | CE1 | HIS A | 101 | 53.145 | 31.629 | 7.938 | 1.00 | 17.82 |
| ATOM | 541 | NE2 | HIS A | 101 | 53.899 | 32.202 | 7.017 | 1.00 | 17.25 |
| ATOM | 542 | C | HIS A | 101 | 54.818 | 35.677 | 11.705 | 1.00 | 20.40 |
| ATOM | 543 | O | HIS A | 101 | 55.859 | 35.403 | 12.299 | 1.00 | 22.15 |
| ATOM | 544 | N | GLY A | 102 | 54.277 | 36.892 | 11.718 | 1.00 | 21.38 |
| ATOM | 545 | CA | GLY A | 102 | 54.896 | 37.979 | 12.460 | 1.00 | 21.06 |
| ATOM | 546 | C | GLY A | 102 | 56.275 | 38.379 | 11.969 | 1.00 | 20.98 |
| ATOM | 547 | O | GLY A | 102 | 57.179 | 38.593 | 12.768 | 1.00 | 22.33 |
| ATOM | 548 | N | GLU A | 103 | 56.435 | 38.503 | 10.656 | 1.00 | 22.97 |
| ATOM | 549 | CA | GLU A | 103 | 57.723 | 38.867 | 10.062 | 1.00 | 22.35 |
| ATOM | 550 | CB | GLU A | 103 | 57.952 | 38.059 | 8.787 | 1.00 | 21.09 |
| ATOM | 551 | CG | GLU A | 103 | 58.004 | 36.564 | 8.992 | 1.00 | 24.78 |
| ATOM | 552 | CD | GLU A | 103 | 58.049 | 35.808 | 7.683 | 1.00 | 26.81 |
| ATOM | 553 | OE1 | GLU A | 103 | 57.014 | 35.763 | 6.980 | 1.00 | 26.94 |
| ATOM | 554 | OE2 | GLU A | 103 | 59.125 | 35.266 | 7.353 | 1.00 | 29.11 |
| ATOM | 555 | C | GLU A | 103 | 57.883 | 40.342 | 9.713 | 1.00 | 21.88 |
| ATOM | 556 | O | GLU A | 103 | 58.999 | 40.806 | 9.500 | 1.00 | 22.98 |
| ATOM | 557 | N | ALA A | 104 | 56.784 | 41.084 | 9.651 | 1.00 | 21.38 |
| ATOM | 558 | CA | ALA A | 104 | 56.870 | 42.491 | 9.269 | 1.00 | 20.31 |
| ATOM | 559 | CB | ALA A | 104 | 56.378 | 42.650 | 7.841 | 1.00 | 17.37 |
| ATOM | 560 | C | ALA A | 104 | 56.116 | 43.451 | 10.175 | 1.00 | 19.53 |
| ATOM | 561 | O | ALA A | 104 | 55.704 | 44.523 | 9.738 | 1.00 | 18.99 |
| ATOM | 562 | N | VAL A | 105 | 55.945 | 43.079 | 11.436 | 1.00 | 19.90 |

TABLE 29-continued

| | | | | | | | | | |
|---|---|---|---|---|---|---|---|---|---|
| ATOM | 563 | CA | VAL A | 105 | 55.216 | 43.924 | 12.375 | 1.00 | 19.69 |
| ATOM | 564 | CB | VAL A | 105 | 55.345 | 43.387 | 13.808 | 1.00 | 19.43 |
| ATOM | 565 | CG1 | VAL A | 105 | 54.673 | 44.339 | 14.779 | 1.00 | 17.75 |
| ATOM | 566 | CG2 | VAL A | 105 | 54.725 | 41.997 | 13.892 | 1.00 | 17.02 |
| ATOM | 567 | C | VAL A | 105 | 55.660 | 45.386 | 12.361 | 1.00 | 20.42 |
| ATOM | 568 | O | VAL A | 105 | 54.831 | 46.293 | 12.260 | 1.00 | 21.86 |
| ATOM | 569 | N | ASP A | 106 | 56.965 | 45.615 | 12.454 | 1.00 | 18.26 |
| ATOM | 570 | CA | ASP A | 106 | 57.489 | 46.975 | 12.472 | 1.00 | 19.05 |
| ATOM | 571 | CB | ASP A | 106 | 58.962 | 46.960 | 12.888 | 1.00 | 18.62 |
| ATOM | 572 | CG | ASP A | 106 | 59.144 | 46.470 | 14.308 | 1.00 | 19.89 |
| ATOM | 573 | OD1 | ASP A | 106 | 59.732 | 45.383 | 14.502 | 1.00 | 21.15 |
| ATOM | 574 | OD2 | ASP A | 106 | 58.677 | 47.171 | 15.231 | 1.00 | 19.02 |
| ATOM | 575 | C | ASP A | 106 | 57.315 | 47.721 | 11.158 | 1.00 | 18.20 |
| ATOM | 576 | O | ASP A | 106 | 57.043 | 48.924 | 11.154 | 1.00 | 18.32 |
| ATOM | 577 | N | GLY A | 107 | 57.474 | 47.013 | 10.048 | 1.00 | 15.97 |
| ATOM | 578 | CA | GLY A | 107 | 57.300 | 47.645 | 8.756 | 1.00 | 16.89 |
| ATOM | 579 | C | GLY A | 107 | 55.847 | 48.039 | 8.558 | 1.00 | 18.68 |
| ATOM | 580 | O | GLY A | 107 | 55.542 | 48.944 | 7.781 | 1.00 | 20.07 |
| ATOM | 581 | N | LEU A | 108 | 54.945 | 47.361 | 9.265 | 1.00 | 17.60 |
| ATOM | 582 | CA | LEU A | 108 | 53.519 | 47.655 | 9.163 | 1.00 | 17.75 |
| ATOM | 583 | CB | LEU A | 108 | 52.694 | 46.456 | 9.649 | 1.00 | 18.20 |
| ATOM | 584 | CG | LEU A | 108 | 52.741 | 45.283 | 8.662 | 1.00 | 17.32 |
| ATOM | 585 | CD1 | LEU A | 108 | 52.194 | 44.020 | 9.297 | 1.00 | 15.87 |
| ATOM | 586 | CD2 | LEU A | 108 | 51.954 | 45.655 | 7.415 | 1.00 | 18.07 |
| ATOM | 587 | C | LEU A | 108 | 53.150 | 48.923 | 9.931 | 1.00 | 17.52 |
| ATOM | 588 | O | LEU A | 108 | 52.326 | 49.706 | 9.465 | 1.00 | 17.59 |
| ATOM | 589 | N | TYR A | 109 | 53.747 | 49.132 | 11.103 | 1.00 | 17.99 |
| ATOM | 590 | CA | TYR A | 109 | 53.475 | 50.356 | 11.863 | 1.00 | 19.57 |
| ATOM | 591 | CB | TYR A | 109 | 54.181 | 50.346 | 13.231 | 1.00 | 17.67 |
| ATOM | 592 | CG | TYR A | 109 | 53.572 | 49.412 | 14.257 | 1.00 | 15.68 |
| ATOM | 593 | CD1 | TYR A | 109 | 54.319 | 48.386 | 14.818 | 1.00 | 15.06 |
| ATOM | 594 | CE1 | TYR A | 109 | 53.761 | 47.514 | 15.739 | 1.00 | 16.14 |
| ATOM | 595 | CD2 | TYR A | 109 | 52.244 | 49.546 | 14.649 | 1.00 | 14.34 |
| ATOM | 596 | CE2 | TYR A | 109 | 51.677 | 48.681 | 15.571 | 1.00 | 14.45 |
| ATOM | 597 | CZ | TYR A | 109 | 52.439 | 47.665 | 16.110 | 1.00 | 16.08 |
| ATOM | 598 | OH | TYR A | 109 | 51.877 | 46.785 | 17.006 | 1.00 | 15.83 |
| ATOM | 599 | C | TYR A | 109 | 54.017 | 51.522 | 11.039 | 1.00 | 20.38 |
| ATOM | 600 | O | TYR A | 109 | 53.438 | 52.610 | 11.014 | 1.00 | 20.47 |
| ATOM | 601 | N | LYS A | 110 | 55.138 | 51.285 | 10.365 | 1.00 | 20.32 |
| ATOM | 602 | CA | LYS A | 110 | 55.761 | 52.310 | 9.542 | 1.00 | 22.38 |
| ATOM | 603 | CB | LYS A | 110 | 57.145 | 51.851 | 9.077 | 1.00 | 22.88 |
| ATOM | 604 | CG | LYS A | 110 | 57.824 | 52.849 | 8.162 | 1.00 | 26.65 |
| ATOM | 605 | CD | LYS A | 110 | 59.186 | 52.374 | 7.706 | 1.00 | 30.71 |
| ATOM | 606 | CB | LYS A | 110 | 59.848 | 53.417 | 6.812 | 1.00 | 33.71 |
| ATOM | 607 | NZ | LYS A | 110 | 61.216 | 53.007 | 6.386 | 1.00 | 37.17 |
| ATOM | 608 | C | LYS A | 110 | 54.900 | 52.651 | 8.327 | 1.00 | 22.82 |
| ATOM | 609 | O | LYS A | 110 | 55.035 | 53.729 | 7.742 | 1.00 | 21.86 |
| ATOM | 610 | N | MET A | 111 | 54.020 | 51.726 | 7.953 | 1.00 | 22.62 |
| ATOM | 611 | CA | MET A | 111 | 53.134 | 51.921 | 6.810 | 1.00 | 21.33 |
| ATOM | 612 | CB | MET A | 111 | 52.596 | 50.568 | 6.330 | 1.00 | 22.37 |
| ATOM | 613 | CG | MET A | 111 | 52.116 | 50.555 | 4.883 | 1.00 | 23.26 |
| ATOM | 614 | SD | MET A | 111 | 51.647 | 48.908 | 4.295 | 1.00 | 22.91 |
| ATOM | 615 | CB | MET A | 111 | 53.239 | 48.159 | 4.039 | 1.00 | 22.34 |
| ATOM | 616 | C | MET A | 111 | 51.979 | 52.849 | 7.198 | 1.00 | 21.50 |
| ATOM | 617 | O | MET A | 111 | 51.237 | 53.332 | 6.341 | 1.00 | 21.61 |
| ATOM | 618 | N | GLY A | 112 | 51.829 | 53.095 | 8.497 | 1.00 | 20.35 |
| ATOM | 619 | CA | GLY A | 112 | 50.774 | 53.981 | 8.954 | 1.00 | 18.20 |
| ATOM | 620 | C | GLY A | 112 | 49.652 | 53.346 | 9.754 | 1.00 | 17.70 |
| ATOM | 621 | O | GLY A | 112 | 48.757 | 54.049 | 10.222 | 1.00 | 18.34 |
| ATOM | 622 | N | PHE A | 113 | 49.687 | 52.027 | 9.922 | 1.00 | 15.93 |
| ATOM | 623 | CA | PHE A | 113 | 48.640 | 51.340 | 10.676 | 1.00 | 15.61 |
| ATOM | 624 | CB | PHE A | 113 | 48.761 | 49.824 | 10.503 | 1.00 | 15.10 |
| ATOM | 625 | CG | PHE A | 113 | 48.390 | 49.340 | 9.132 | 1.00 | 15.46 |
| ATOM | 626 | CD1 | PHE A | 113 | 49.361 | 48.889 | 8.254 | 1.00 | 15.32 |
| ATOM | 627 | CD2 | PHE A | 113 | 47.064 | 49.328 | 8.724 | 1.00 | 15.07 |
| ATOM | 628 | CE1 | PHE A | 113 | 49.017 | 48.428 | 6.991 | 1.00 | 17.40 |
| ATOM | 629 | CE2 | PHE A | 113 | 46.710 | 48.870 | 7.464 | 1.00 | 15.20 |
| ATOM | 630 | CZ | PHE A | 113 | 47.687 | 48.418 | 6.596 | 1.00 | 16.29 |
| ATOM | 631 | C | PHE A | 113 | 48.664 | 51.686 | 12.157 | 1.00 | 14.59 |
| ATOM | 632 | O | PHE A | 113 | 49.726 | 51.750 | 12.768 | 1.00 | 15.40 |
| ATOM | 633 | N | GLY A | 114 | 47.482 | 51.908 | 12.726 | 1.00 | 13.85 |
| ATOM | 634 | CA | GLY A | 114 | 47.372 | 52.246 | 14.136 | 1.00 | 13.80 |
| ATOM | 635 | C | GLY A | 114 | 47.582 | 51.040 | 15.032 | 1.00 | 15.27 |
| ATOM | 636 | O | GLY A | 114 | 47.808 | 51.175 | 16.232 | 1.00 | 16.43 |
| ATOM | 637 | N | PHE A | 115 | 47.479 | 49.850 | 14.452 | 1.00 | 15.37 |
| ATOM | 638 | CA | PHE A | 115 | 47.692 | 48.623 | 15.199 | 1.00 | 15.37 |
| ATOM | 639 | CB | PHE A | 115 | 46.548 | 48.373 | 16.197 | 1.00 | 15.72 |
| ATOM | 640 | CG | PHE A | 115 | 45.216 | 48.075 | 15.568 | 1.00 | 14.48 |
| ATOM | 641 | CD1 | PHE A | 115 | 44.723 | 46.781 | 15.547 | 1.00 | 13.96 |

TABLE 29-continued

| ATOM | 642 | CD2 | PHE A | 115 | 44.431 | 49.096 | 15.050 | 1.00 | 14.85 |
|---|---|---|---|---|---|---|---|---|---|
| ATOM | 643 | CE1 | PHE A | 115 | 43.468 | 46.505 | 15.026 | 1.00 | 13.14 |
| ATOM | 644 | CE2 | PHE A | 115 | 43.174 | 48.828 | 14.526 | 1.00 | 14.58 |
| ATOM | 645 | CZ | PHE A | 115 | 42.694 | 47.528 | 14.516 | 1.00 | 14.33 |
| ATOM | 646 | C | PHE A | 115 | 47.865 | 47.457 | 14.240 | 1.00 | 15.74 |
| ATOM | 647 | O | PHE A | 115 | 47.335 | 47.467 | 13.132 | 1.00 | 15.07 |
| ATOM | 648 | N | VAL A | 116 | 48.636 | 46.463 | 14.668 | 1.00 | 16.41 |
| ATOM | 649 | CA | VAL A | 116 | 48.926 | 45.301 | 13.844 | 1.00 | 15.02 |
| ATOM | 650 | CB | VAL A | 116 | 50.460 | 45.168 | 13.617 | 1.00 | 15.50 |
| ATOM | 651 | CG1 | VAL A | 116 | 50.778 | 43.903 | 12.810 | 1.00 | 11.14 |
| ATOM | 652 | CG2 | VAL A | 116 | 50.992 | 46.415 | 12.911 | 1.00 | 13.00 |
| ATOM | 653 | C | VAL A | 116 | 48.422 | 43.998 | 14.450 | 1.00 | 16.38 |
| ATOM | 654 | O | VAL A | 116 | 48.447 | 43.815 | 15.669 | 1.00 | 16.18 |
| ATOM | 655 | N | GLU A | 117 | 47.957 | 43.100 | 13.585 | 1.00 | 16.09 |
| ATOM | 656 | CA | GLU A | 117 | 47.487 | 41.786 | 14.007 | 1.00 | 17.47 |
| ATOM | 657 | CB | GLU A | 117 | 45.975 | 41.659 | 13.838 | 1.00 | 15.90 |
| ATOM | 658 | CG | GLU A | 117 | 45.431 | 40.316 | 14.303 | 1.00 | 16.28 |
| ATOM | 659 | CD | GLU A | 117 | 43.919 | 40.264 | 14.271 | 1.00 | 17.25 |
| ATOM | 660 | OE1 | GLU A | 117 | 43.365 | 39.320 | 13.664 | 1.00 | 15.76 |
| ATOM | 661 | OE2 | GLU A | 117 | 43.291 | 41.171 | 14.856 | 1.00 | 14.09 |
| ATOM | 662 | C | GLU A | 117 | 48.188 | 40.778 | 13.109 | 1.00 | 17.93 |
| ATOM | 663 | O | GLU A | 117 | 48.071 | 40.850 | 11.886 | 1.00 | 19.54 |
| ATOM | 664 | N | ILE A | 118 | 48.921 | 39.840 | 13.697 | 1.00 | 17.75 |
| ATOM | 665 | CA | ILE A | 118 | 49.626 | 38.874 | 12.873 | 1.00 | 20.53 |
| ATOM | 666 | CB | ILE A | 118 | 50.982 | 38.474 | 13.503 | 1.00 | 18.57 |
| ATOM | 667 | CG2 | ILE A | 118 | 51.865 | 39.707 | 13.612 | 1.00 | 20.32 |
| ATOM | 668 | CG1 | ILE A | 118 | 50.790 | 37.870 | 14.887 | 1.00 | 18.39 |
| ATOM | 669 | CD1 | ILE A | 118 | 52.086 | 37.427 | 15.508 | 1.00 | 18.60 |
| ATOM | 670 | C | ILE A | 118 | 48.782 | 37.649 | 12.554 | 1.00 | 21.57 |
| ATOM | 671 | O | ILE A | 118 | 48.186 | 37.040 | 13.441 | 1.00 | 19.31 |
| ATOM | 672 | N | GLY A | 119 | 48.730 | 37.343 | 11.255 | 1.00 | 26.73 |
| ATOM | 673 | CA | GLY A | 119 | 47.954 | 36.242 | 10.701 | 1.00 | 23.17 |
| ATOM | 674 | C | GLY A | 119 | 47.786 | 35.075 | 11.630 | 1.00 | 24.76 |
| ATOM | 675 | O | GLY A | 119 | 48.553 | 34.929 | 12.584 | 1.00 | 25.45 |
| ATOM | 676 | N | SER A | 120 | 46.791 | 34.236 | 11.348 | 1.00 | 22.08 |
| ATOM | 677 | CA | SER A | 120 | 46.528 | 33.078 | 12.191 | 1.00 | 20.62 |
| ATOM | 678 | CB | SER A | 120 | 45.364 | 32.255 | 11.634 | 1.00 | 20.16 |
| ATOM | 679 | OG | SER A | 120 | 44.124 | 32.899 | 11.883 | 1.00 | 19.34 |
| ATOM | 680 | C | SER A | 120 | 47.746 | 32.192 | 12.354 | 1.00 | 19.19 |
| ATOM | 681 | O | SER A | 120 | 48.446 | 31.888 | 11.389 | 1.00 | 19.88 |
| ATOM | 682 | N | VAL A | 121 | 47.990 | 31.786 | 13.593 | 1.00 | 18.69 |
| ATOM | 683 | CA | VAL A | 121 | 49.112 | 30.922 | 13.930 | 1.00 | 15.40 |
| ATOM | 684 | CB | VAL A | 121 | 50.010 | 31.571 | 15.016 | 1.00 | 15.21 |
| ATOM | 685 | CG1 | VAL A | 121 | 51.319 | 30.784 | 15.169 | 1.00 | 9.68 |
| ATOM | 686 | CG2 | VAL A | 121 | 50.281 | 33.032 | 14.663 | 1.00 | 12.28 |
| ATOM | 687 | C | VAL A | 121 | 48.534 | 29.624 | 14.485 | 1.00 | 16.35 |
| ATOM | 688 | O | VAL A | 121 | 47.607 | 29.646 | 15.300 | 1.00 | 15.33 |
| ATOM | 689 | N | THR A | 122 | 49.067 | 28.497 | 14.028 | 1.00 | 15.14 |
| ATOM | 690 | CA | THR A | 122 | 48.617 | 27.194 | 14.495 | 1.00 | 16.81 |
| ATOM | 691 | CB | THR A | 122 | 48.447 | 26.210 | 13.308 | 1.00 | 16.39 |
| ATOM | 692 | OG1 | THR A | 122 | 49.671 | 26.118 | 12.572 | 1.00 | 16.99 |
| ATOM | 693 | CG2 | THR A | 122 | 47.351 | 26.701 | 12.372 | 1.00 | 16.20 |
| ATOM | 694 | C | THR A | 122 | 49.668 | 26.680 | 15.480 | 1.00 | 16.05 |
| ATOM | 695 | O | THR A | 122 | 50.811 | 27.120 | 15.446 | 1.00 | 17.14 |
| ATOM | 696 | N | PRO A | 123 | 49.289 | 25.768 | 16.390 | 1.00 | 17.33 |
| ATOM | 697 | CD | PRO A | 123 | 47.925 | 25.295 | 16.685 | 1.00 | 16.88 |
| ATOM | 698 | CA | PRO A | 123 | 50.249 | 25.234 | 17.369 | 1.00 | 18.81 |
| ATOM | 699 | CB | PRO A | 123 | 49.423 | 24.203 | 18.128 | 1.00 | 17.77 |
| ATOM | 700 | CG | PRO A | 123 | 48.054 | 24.837 | 18.126 | 1.00 | 17.60 |
| ATOM | 701 | C | PRO A | 123 | 51.500 | 24.634 | 16.732 | 1.00 | 20.92 |
| ATOM | 702 | O | PRO A | 123 | 52.625 | 25.008 | 17.074 | 1.00 | 21.41 |
| ATOM | 703 | N | LYS A | 124 | 51.300 | 23.700 | 15.810 | 1.00 | 21.70 |
| ATOM | 704 | CA | LYS A | 124 | 52.413 | 23.074 | 15.113 | 1.00 | 23.21 |
| ATOM | 705 | CB | LYS A | 124 | 52.190 | 21.561 | 14.967 | 1.00 | 26.03 |
| ATOM | 706 | CG | LYS A | 124 | 51.885 | 20.840 | 16.270 | 1.00 | 30.90 |
| ATOM | 707 | CD | LYS A | 124 | 52.954 | 21.122 | 17.314 | 1.00 | 36.86 |
| ATOM | 708 | CE | LYS A | 124 | 52.546 | 20.585 | 18.679 | 1.00 | 41.85 |
| ATOM | 709 | NZ | LYS A | 124 | 53.576 | 20.858 | 19.723 | 1.00 | 43.99 |
| ATOM | 710 | C | LYS A | 124 | 52.482 | 23.701 | 13.732 | 1.00 | 23.17 |
| ATOM | 711 | O | LYS A | 124 | 51.500 | 24.267 | 13.245 | 1.00 | 23.15 |
| ATOM | 712 | N | PRO A | 125 | 53.651 | 23.629 | 13.087 | 1.00 | 21.56 |
| ATOM | 713 | CD | PRO A | 125 | 54.955 | 23.187 | 13.617 | 1.00 | 21.14 |
| ATOM | 714 | CA | PRO A | 125 | 53.785 | 24.204 | 11.748 | 1.00 | 20.21 |
| ATOM | 715 | CB | PRO A | 125 | 55.288 | 24.096 | 11.470 | 1.00 | 20.65 |
| ATOM | 716 | CG | PRO A | 125 | 55.917 | 24.036 | 12.842 | 1.00 | 19.52 |
| ATOM | 717 | C | PRO A | 125 | 52.972 | 23.351 | 10.766 | 1.00 | 19.97 |
| ATOM | 718 | O | PRO A | 125 | 52.731 | 22.172 | 11.016 | 1.00 | 18.81 |
| ATOM | 719 | N | GLN A | 126 | 52.539 | 23.951 | 9.664 | 1.00 | 19.59 |
| ATOM | 720 | CA | GLN A | 126 | 51.802 | 23.224 | 8.634 | 1.00 | 20.28 |

TABLE 29-continued

| ATOM | 721 | CB | GLN A | 126 | 50.354 | 22.921 | 9.064 | 1.00 | 21.32 |
|------|-----|-----|-------|-----|--------|--------|-------|------|-------|
| ATOM | 722 | CG | GLN A | 126 | 49.449 | 24.115 | 9.324 | 1.00 | 20.84 |
| ATOM | 723 | CD | GLN A | 126 | 47.998 | 23.694 | 9.555 | 1.00 | 22.01 |
| ATOM | 724 | OE1 | GLN A | 126 | 47.718 | 22.753 | 10.309 | 1.00 | 19.72 |
| ATOM | 725 | NE2 | GLN A | 126 | 47.070 | 24.398 | 8.914 | 1.00 | 20.71 |
| ATOM | 726 | C | GLN A | 126 | 51.840 | 24.032 | 7.343 | 1.00 | 20.63 |
| ATOM | 727 | O | GLN A | 126 | 51.800 | 25.260 | 7.366 | 1.00 | 20.52 |
| ATOM | 728 | N | GLU A | 127 | 51.932 | 23.332 | 6.220 | 1.00 | 23.02 |
| ATOM | 729 | CA | GLU A | 127 | 52.034 | 23.978 | 4.917 | 1.00 | 26.27 |
| ATOM | 730 | CB | GLU A | 127 | 52.620 | 22.989 | 3.903 | 1.00 | 30.03 |
| ATOM | 731 | CG | GLU A | 127 | 53.967 | 22.418 | 4.329 | 1.00 | 37.96 |
| ATOM | 732 | CD | GLU A | 127 | 54.686 | 21.687 | 3.208 | 1.00 | 43.29 |
| ATOM | 733 | OE1 | GLU A | 127 | 54.069 | 20.799 | 2.577 | 1.00 | 46.06 |
| ATOM | 734 | OE2 | GLU A | 127 | 55.873 | 21.998 | 2.963 | 1.00 | 45.91 |
| ATOM | 735 | C | GLU A | 127 | 50.764 | 24.596 | 4.345 | 1.00 | 24.39 |
| ATOM | 736 | O | GLU A | 127 | 50.839 | 25.493 | 3.508 | 1.00 | 22.88 |
| ATOM | 737 | N | GLY A | 128 | 49.604 | 24.131 | 4.791 | 1.00 | 23.27 |
| ATOM | 738 | CA | GLY A | 128 | 48.365 | 24.667 | 4.263 | 1.00 | 23.54 |
| ATOM | 739 | C | GLY A | 128 | 48.014 | 23.952 | 2.971 | 1.00 | 25.46 |
| ATOM | 740 | O | GLY A | 128 | 48.638 | 22.943 | 2.631 | 1.00 | 24.72 |
| ATOM | 741 | N | ASN A | 129 | 47.021 | 24.462 | 2.246 | 1.00 | 25.50 |
| ATOM | 742 | CA | ASN A | 129 | 46.608 | 23.841 | 0.992 | 1.00 | 25.75 |
| ATOM | 743 | CB | ASN A | 129 | 45.268 | 24.412 | 0.524 | 1.00 | 24.81 |
| ATOM | 744 | CG | ASN A | 129 | 44.126 | 24.050 | 1.447 | 1.00 | 25.93 |
| ATOM | 745 | OD1 | ASN A | 129 | 44.056 | 22.927 | 1.948 | 1.00 | 26.55 |
| ATOM | 746 | ND2 | ASN A | 129 | 43.214 | 24.993 | 1.666 | 1.00 | 21.27 |
| ATOM | 747 | C | ASN A | 129 | 47.642 | 24.024 | −0.113 | 1.00 | 26.24 |
| ATOM | 748 | O | ASN A | 129 | 48.488 | 24.915 | −0.050 | 1.00 | 25.50 |
| ATOM | 749 | N | PRO A | 130 | 47.587 | 23.165 | −1.140 | 1.00 | 26.81 |
| ATOM | 750 | CD | PRO A | 130 | 46.723 | 21.973 | −1.221 | 1.00 | 25.39 |
| ATOM | 751 | CA | PRO A | 130 | 48.515 | 23.226 | −2.274 | 1.00 | 26.99 |
| ATOM | 752 | CB | PRO A | 130 | 48.284 | 21.887 | −2.978 | 1.00 | 26.46 |
| ATOM | 753 | CG | PRO A | 130 | 46.849 | 21.581 | −2.671 | 1.00 | 25.27 |
| ATOM | 754 | C | PRO A | 130 | 48.227 | 24.424 | −3.180 | 1.00 | 28.67 |
| ATOM | 755 | O | PRO A | 130 | 47.087 | 24.880 | −3.263 | 1.00 | 29.58 |
| ATOM | 756 | N | ARG A | 131 | 49.262 | 24.931 | −3.846 | 1.00 | 29.41 |
| ATOM | 757 | CA | ARG A | 131 | 49.124 | 26.075 | −4.746 | 1.00 | 31.07 |
| ATOM | 758 | CB | ARG A | 131 | 50.482 | 26.732 | −4.998 | 1.00 | 32.70 |
| ATOM | 759 | CG | ARG A | 131 | 51.180 | 27.354 | −3.797 | 1.00 | 34.79 |
| ATOM | 760 | CD | ARG A | 131 | 52.260 | 28.298 | −4.315 | 1.00 | 40.39 |
| ATOM | 761 | NE | ARG A | 131 | 53.147 | 28.840 | −3.287 | 1.00 | 45.17 |
| ATOM | 762 | CZ | ARG A | 131 | 54.017 | 29.827 | −3.508 | 1.00 | 45.61 |
| ATOM | 763 | NH1 | ARG A | 131 | 54.107 | 30.376 | −4.714 | 1.00 | 44.09 |
| ATOM | 764 | NH2 | ARG A | 131 | 54.802 | 30.261 | −2.529 | 1.00 | 45.19 |
| ATOM | 765 | C | ARG A | 131 | 48.543 | 25.652 | −6.096 | 1.00 | 32.15 |
| ATOM | 766 | O | ARG A | 131 | 48.760 | 24.530 | −6.548 | 1.00 | 33.75 |
| ATOM | 767 | N | PRO A | 132 | 47.800 | 26.552 | −6.764 | 1.00 | 30.94 |
| ATOM | 768 | CD | PRO A | 132 | 47.331 | 26.344 | −8.145 | 1.00 | 31.60 |
| ATOM | 769 | CA | PRO A | 132 | 47.488 | 27.913 | −6.316 | 1.00 | 28.61 |
| ATOM | 770 | CB | PRO A | 132 | 47.078 | 28.607 | −7.612 | 1.00 | 29.31 |
| ATOM | 771 | CG | PRO A | 132 | 46.386 | 27.513 | −8.350 | 1.00 | 30.17 |
| ATOM | 772 | C | PRO A | 132 | 46.375 | 27.914 | −5.268 | 1.00 | 25.00 |
| ATOM | 773 | O | PRO A | 132 | 45.484 | 27.068 | −5.296 | 1.00 | 23.59 |
| ATOM | 774 | N | ARG A | 133 | 46.431 | 28.869 | −4.347 | 1.00 | 21.85 |
| ATOM | 775 | CA | ARG A | 133 | 45.438 | 28.952 | −3.290 | 1.00 | 19.55 |
| ATOM | 776 | CB | ARG A | 133 | 46.013 | 28.323 | −2.017 | 1.00 | 21.24 |
| ATOM | 777 | CG | ARG A | 133 | 47.422 | 28.794 | −1.688 | 1.00 | 18.90 |
| ATOM | 778 | CD | ARG A | 133 | 48.095 | 27.880 | −0.678 | 1.00 | 16.85 |
| ATOM | 779 | NE | ARG A | 133 | 49.426 | 28.373 | −0.334 | 1.00 | 17.49 |
| ATOM | 780 | CZ | ARG A | 133 | 50.196 | 27.856 | 0.617 | 1.00 | 15.57 |
| ATOM | 781 | NH1 | ARG A | 133 | 51.389 | 28.377 | 0.861 | 1.00 | 13.29 |
| ATOM | 782 | NH2 | ARG A | 133 | 49.775 | 26.818 | 1.323 | 1.00 | 15.73 |
| ATOM | 783 | C | ARG A | 133 | 44.954 | 30.376 | −3.023 | 1.00 | 19.32 |
| ATOM | 784 | O | ARG A | 133 | 44.233 | 30.627 | −2.056 | 1.00 | 19.05 |
| ATOM | 785 | N | VAL A | 134 | 45.357 | 31.307 | −3.882 | 1.00 | 18.51 |
| ATOM | 786 | CA | VAL A | 134 | 44.937 | 32.700 | −3.763 | 1.00 | 18.75 |
| ATOM | 787 | CB | VAL A | 134 | 46.058 | 33.613 | −3.222 | 1.00 | 18.82 |
| ATOM | 788 | CG1 | VAL A | 134 | 45.451 | 34.900 | −2.680 | 1.00 | 15.57 |
| ATOM | 789 | CG2 | VAL A | 134 | 46.848 | 32.896 | −2.162 | 1.00 | 18.29 |
| ATOM | 790 | C | VAL A | 134 | 44.600 | 33.157 | −5.173 | 1.00 | 18.69 |
| ATOM | 791 | O | VAL A | 134 | 45.294 | 32.800 | −6.119 | 1.00 | 20.02 |
| ATOM | 792 | N | PHE A | 135 | 43.542 | 33.944 | −5.320 | 1.00 | 19.00 |
| ATOM | 793 | CA | PHE A | 135 | 43.146 | 34.398 | −6.643 | 1.00 | 17.47 |
| ATOM | 794 | CB | PHE A | 135 | 42.059 | 33.476 | −7.198 | 1.00 | 17.16 |
| ATOM | 795 | CG | PHE A | 135 | 42.387 | 32.011 | −7.067 | 1.00 | 17.50 |
| ATOM | 796 | CD1 | PHE A | 135 | 42.102 | 31.325 | −5.894 | 1.00 | 16.24 |
| ATOM | 797 | CD2 | PHE A | 135 | 43.029 | 31.334 | −8.097 | 1.00 | 18.52 |
| ATOM | 798 | CE1 | PHE A | 135 | 42.453 | 29.988 | −5.749 | 1.00 | 17.65 |
| ATOM | 799 | CE2 | PHE A | 135 | 43.384 | 29.998 | −7.960 | 1.00 | 16.80 |

TABLE 29-continued

| ATOM | 800 | CZ | PHE A | 135 | 43.096 | 29.325 | −6.784 | 1.00 | 16.83 |
|---|---|---|---|---|---|---|---|---|---|
| ATOM | 801 | C | PHE A | 135 | 42.664 | 35.841 | −6.657 | 1.00 | 18.35 |
| ATOM | 802 | O | PHE A | 135 | 41.996 | 36.303 | −5.729 | 1.00 | 17.26 |
| ATOM | 803 | N | ARG A | 136 | 43.026 | 36.554 | −7.717 | 1.00 | 17.14 |
| ATOM | 804 | CA | ARG A | 136 | 42.628 | 37.939 | −7.874 | 1.00 | 17.83 |
| ATOM | 805 | CB | ARG A | 136 | 43.726 | 38.754 | −8.567 | 1.00 | 19.09 |
| ATOM | 806 | CG | ARG A | 136 | 45.089 | 38.802 | −7.892 | 1.00 | 21.68 |
| ATOM | 807 | CD | ARG A | 136 | 45.990 | 39.767 | −8.661 | 1.00 | 23.63 |
| ATOM | 808 | NE | ARG A | 136 | 47.345 | 39.863 | −8.121 | 1.00 | 29.57 |
| ATOM | 809 | CZ | ARG A | 136 | 48.412 | 39.256 | −8.638 | 1.00 | 31.45 |
| ATOM | 810 | NH1 | ARG A | 136 | 49.600 | 39.408 | −8.070 | 1.00 | 31.05 |
| ATOM | 811 | NH2 | ARG A | 136 | 48.297 | 38.504 | −9.726 | 1.00 | 31.93 |
| ATOM | 812 | C | ARG A | 136 | 41.375 | 38.029 | −8.739 | 1.00 | 17.93 |
| ATOM | 813 | O | ARG A | 136 | 41.218 | 37.266 | −9.699 | 1.00 | 17.19 |
| ATOM | 814 | N | LEU A | 137 | 40.488 | 38.953 | −8.377 | 1.00 | 15.76 |
| ATOM | 815 | CA | LEU A | 137 | 39.268 | 39.241 | −9.132 | 1.00 | 14.78 |
| ATOM | 816 | CB | LEU A | 137 | 38.006 | 38.849 | −8.359 | 1.00 | 15.58 |
| ATOM | 817 | CG | LEU A | 137 | 37.574 | 37.378 | −8.285 | 1.00 | 17.50 |
| ATOM | 818 | CD1 | LEU A | 137 | 38.617 | 36.547 | −7.540 | 1.00 | 17.15 |
| ATOM | 819 | CD2 | LEU A | 137 | 36.231 | 37.301 | −7.580 | 1.00 | 12.95 |
| ATOM | 820 | C | LEU A | 137 | 39.324 | 40.759 | −9.273 | 1.00 | 15.42 |
| ATOM | 821 | O | LEU A | 137 | 38.583 | 41.485 | −8.608 | 1.00 | 14.16 |
| ATOM | 822 | N | PRO A | 138 | 40.233 | 41.258 | −10.126 | 1.00 | 15.71 |
| ATOM | 823 | CD | PRO A | 138 | 41.193 | 40.490 | −10.941 | 1.00 | 15.13 |
| ATOM | 824 | CA | PRO A | 138 | 40.389 | 42.701 | −10.338 | 1.00 | 16.47 |
| ATOM | 825 | CB | PRO A | 138 | 41.537 | 42.789 | −11.354 | 1.00 | 15.41 |
| ATOM | 826 | CG | PRO A | 138 | 41.515 | 41.448 | −12.048 | 1.00 | 15.79 |
| ATOM | 827 | C | PRO A | 138 | 39.132 | 43.456 | −10.773 | 1.00 | 16.15 |
| ATOM | 828 | O | PRO A | 138 | 38.948 | 44.611 | −10.399 | 1.00 | 16.79 |
| ATOM | 829 | N | GLU A | 139 | 38.263 | 42.814 | −11.545 | 1.00 | 16.16 |
| ATOM | 830 | CA | GLU A | 139 | 37.037 | 43.479 | −11.981 | 1.00 | 17.26 |
| ATOM | 831 | CB | GLU A | 139 | 36.310 | 42.648 | −13.046 | 1.00 | 18.03 |
| ATOM | 832 | CG | GLU A | 139 | 37.059 | 42.477 | −14.367 | 1.00 | 21.85 |
| ATOM | 833 | CD | GLU A | 139 | 38.073 | 41.340 | −14.348 | 1.00 | 24.50 |
| ATOM | 834 | OE1 | GLU A | 139 | 38.713 | 41.115 | −15.397 | 1.00 | 27.97 |
| ATOM | 835 | OE2 | GLU A | 139 | 38.234 | 40.671 | −13.300 | 1.00 | 23.28 |
| ATOM | 836 | C | GLU A | 139 | 36.083 | 43.714 | −10.807 | 1.00 | 17.84 |
| ATOM | 837 | O | GLU A | 139 | 35.157 | 44.522 | −10.902 | 1.00 | 17.94 |
| ATOM | 838 | N | ASP A | 140 | 36.308 | 43.008 | −9.702 | 1.00 | 14.82 |
| ATOM | 839 | CA | ASP A | 140 | 35.448 | 43.132 | −8.531 | 1.00 | 12.95 |
| ATOM | 840 | CB | ASP A | 140 | 34.943 | 41.749 | −8.100 | 1.00 | 10.76 |
| ATOM | 841 | CG | ASP A | 140 | 34.317 | 40.968 | −9.245 | 1.00 | 13.87 |
| ATOM | 842 | OD1 | ASP A | 140 | 33.260 | 41.395 | −9.756 | 1.00 | 12.48 |
| ATOM | 843 | OD2 | ASP A | 140 | 34.882 | 39.922 | −9.635 | 1.00 | 14.76 |
| ATOM | 844 | C | ASP A | 140 | 36.187 | 43.761 | −7.362 | 1.00 | 13.94 |
| ATOM | 845 | O | ASP A | 140 | 35.609 | 43.956 | −6.287 | 1.00 | 12.55 |
| ATOM | 846 | N | GLN A | 141 | 37.460 | 44.084 | −7.574 | 1.00 | 14.25 |
| ATOM | 847 | CA | GLN A | 141 | 38.279 | 44.639 | −6.508 | 1.00 | 14.42 |
| ATOM | 848 | CB | GLN A | 141 | 37.791 | 46.038 | −6.125 | 1.00 | 15.62 |
| ATOM | 849 | CG | GLN A | 141 | 38.168 | 47.096 | −7.160 | 1.00 | 22.74 |
| ATOM | 850 | CD | GLN A | 141 | 37.666 | 48.493 | −6.819 | 1.00 | 25.08 |
| ATOM | 851 | OE1 | GLN A | 141 | 37.883 | 48.998 | −5.713 | 1.00 | 28.72 |
| ATOM | 852 | NE2 | GLN A | 141 | 37.002 | 49.130 | −7.779 | 1.00 | 25.38 |
| ATOM | 853 | C | GLN A | 141 | 38.157 | 43.669 | −5.336 | 1.00 | 14.40 |
| ATOM | 854 | O | GLN A | 141 | 37.979 | 44.067 | −4.182 | 1.00 | 15.04 |
| ATOM | 855 | N | ALA A | 142 | 38.244 | 42.380 | −5.661 | 1.00 | 13.51 |
| ATOM | 856 | CA | ALA A | 142 | 38.138 | 41.322 | −4.669 | 1.00 | 13.56 |
| ATOM | 857 | CB | ALA A | 142 | 36.775 | 40.644 | −4.780 | 1.00 | 11.87 |
| ATOM | 858 | C | ALA A | 142 | 39.245 | 40.278 | −4.801 | 1.00 | 13.69 |
| ATOM | 859 | O | ALA A | 142 | 39.996 | 40.255 | −5.779 | 1.00 | 12.41 |
| ATOM | 860 | N | VAL A | 143 | 39.328 | 39.414 | −3.795 | 1.00 | 13.04 |
| ATOM | 861 | CA | VAL A | 143 | 40.302 | 38.337 | −3.753 | 1.00 | 11.89 |
| ATOM | 862 | CB | VAL A | 143 | 41.527 | 38.696 | −2.852 | 1.00 | 13.64 |
| ATOM | 863 | CG1 | VAL A | 143 | 42.349 | 37.439 | −2.551 | 1.00 | 9.11 |
| ATOM | 864 | CG2 | VAL A | 143 | 42.410 | 39.735 | −3.541 | 1.00 | 8.79 |
| ATOM | 865 | C | VAL A | 143 | 39.615 | 37.112 | −3.163 | 1.00 | 14.15 |
| ATOM | 866 | O | VAL A | 143 | 38.687 | 37.234 | −2.364 | 1.00 | 16.13 |
| ATOM | 867 | N | ILE A | 144 | 40.052 | 35.933 | −3.585 | 1.00 | 14.22 |
| ATOM | 868 | CA | ILE A | 144 | 39.522 | 34.685 | −3.057 | 1.00 | 13.02 |
| ATOM | 869 | CB | ILE A | 144 | 38.737 | 33.883 | −4.121 | 1.00 | 13.56 |
| ATOM | 870 | CG2 | ILE A | 144 | 38.571 | 32.429 | −3.673 | 1.00 | 10.97 |
| ATOM | 871 | CG1 | ILE A | 144 | 37.362 | 34.519 | −4.339 | 1.00 | 11.41 |
| ATOM | 872 | CD1 | ILE A | 144 | 36.502 | 33.760 | −5.312 | 1.00 | 14.19 |
| ATOM | 873 | C | ILE A | 144 | 40.744 | 33.895 | −2.630 | 1.00 | 13.99 |
| ATOM | 874 | O | ILE A | 144 | 41.722 | 33.807 | −3.378 | 1.00 | 14.68 |
| ATOM | 875 | N | ASN A | 145 | 40.706 | 33.334 | −1.428 | 1.00 | 13.97 |
| ATOM | 876 | CA | ASN A | 145 | 41.846 | 32.571 | −0.942 | 1.00 | 13.60 |
| ATOM | 877 | CB | ASN A | 145 | 42.716 | 33.455 | −0.040 | 1.00 | 13.33 |
| ATOM | 878 | CG | ASN A | 145 | 42.255 | 33.447 | 1.412 | 1.00 | 16.34 |

TABLE 29-continued

| | | | | | | | | | |
|---|---|---|---|---|---|---|---|---|---|
| ATOM | 879 | OD1 | ASN A | 145 | 42.556 | 32.518 | 2.163 | 1.00 | 14.09 |
| ATOM | 880 | ND2 | ASN A | 145 | 41.510 | 34.478 | 1.809 | 1.00 | 15.79 |
| ATOM | 881 | C | ASN A | 145 | 41.426 | 31.328 | −0.170 | 1.00 | 14.55 |
| ATOM | 882 | O | ASN A | 145 | 40.380 | 31.308 | 0.485 | 1.00 | 13.20 |
| ATOM | 883 | N | ARG A | 146 | 42.249 | 30.289 | −0.262 | 1.00 | 14.22 |
| ATOM | 884 | CA | ARG A | 146 | 42.011 | 29.047 | 0.458 | 1.00 | 15.92 |
| ATOM | 885 | CB | ARG A | 146 | 41.327 | 28.007 | −0.440 | 1.00 | 14.93 |
| ATOM | 886 | CG | ARG A | 146 | 41.972 | 27.778 | −1.797 | 1.00 | 14.62 |
| ATOM | 887 | CD | ARG A | 146 | 41.403 | 26.513 | −2.428 | 1.00 | 15.20 |
| ATOM | 888 | NE | ARG A | 146 | 41.958 | 26.231 | −3.751 | 1.00 | 15.82 |
| ATOM | 889 | CZ | ARG A | 146 | 41.423 | 26.632 | −4.903 | 1.00 | 16.69 |
| ATOM | 890 | NH1 | ARG A | 146 | 40.305 | 27.344 | −4.917 | 1.00 | 16.41 |
| ATOM | 891 | NH2 | ARG A | 146 | 42.008 | 26.311 | −6.050 | 1.00 | 18.44 |
| ATOM | 892 | C | ARG A | 146 | 43.352 | 28.519 | 0.965 | 1.00 | 18.18 |
| ATOM | 893 | O | ARG A | 146 | 43.697 | 27.355 | 0.758 | 1.00 | 18.08 |
| ATOM | 894 | N | TYR A | 147 | 44.104 | 29.394 | 1.632 | 1.00 | 18.01 |
| ATOM | 895 | CA | TYR A | 147 | 45.410 | 29.039 | 2.171 | 1.00 | 19.04 |
| ATOM | 896 | CB | TYR A | 147 | 45.993 | 30.199 | 2.979 | 1.00 | 18.66 |
| ATOM | 897 | CG | TYR A | 147 | 46.860 | 31.121 | 2.166 | 1.00 | 18.81 |
| ATOM | 898 | CD1 | TYR A | 147 | 46.405 | 32.371 | 1.774 | 1.00 | 19.25 |
| ATOM | 899 | CE1 | TYR A | 147 | 47.196 | 33.208 | 1.007 | 1.00 | 22.14 |
| ATOM | 900 | CD2 | TYR A | 147 | 48.135 | 30.728 | 1.768 | 1.00 | 20.06 |
| ATOM | 901 | CE2 | TYR A | 147 | 48.933 | 31.555 | 1.000 | 1.00 | 21.49 |
| ATOM | 902 | CZ | TYR A | 147 | 48.458 | 32.793 | 0.624 | 1.00 | 22.84 |
| ATOM | 903 | OH | TYR A | 147 | 49.244 | 33.617 | −0.147 | 1.00 | 28.55 |
| ATOM | 904 | C | TYR A | 147 | 45.381 | 27.795 | 3.042 | 1.00 | 19.59 |
| ATOM | 905 | O | TYR A | 147 | 46.232 | 26.917 | 2.903 | 1.00 | 21.39 |
| ATOM | 906 | N | GLY A | 148 | 44.409 | 27.732 | 3.946 | 1.00 | 19.48 |
| ATOM | 907 | CA | GLY A | 148 | 44.288 | 26.589 | 4.830 | 1.00 | 17.98 |
| ATOM | 908 | C | GLY A | 148 | 45.183 | 26.683 | 6.052 | 1.00 | 19.49 |
| ATOM | 909 | O | GLY A | 148 | 45.692 | 25.671 | 6.534 | 1.00 | 20.15 |
| ATOM | 910 | N | PHE A | 149 | 45.389 | 27.897 | 6.551 | 1.00 | 19.05 |
| ATOM | 911 | CA | PHE A | 149 | 46.218 | 28.097 | 7.738 | 1.00 | 19.22 |
| ATOM | 912 | CB | PHE A | 149 | 45.632 | 27.334 | 8.935 | 1.00 | 18.23 |
| ATOM | 913 | CG | PHE A | 149 | 44.456 | 28.009 | 9.586 | 1.00 | 19.24 |
| ATOM | 914 | CD1 | PHE A | 149 | 43.609 | 27.289 | 10.423 | 1.00 | 20.94 |
| ATOM | 915 | CD2 | PHE A | 149 | 44.203 | 29.354 | 9.386 | 1.00 | 20.56 |
| ATOM | 916 | CE1 | PHE A | 149 | 42.529 | 27.903 | 11.046 | 1.00 | 22.07 |
| ATOM | 917 | CE2 | PHE A | 149 | 43.124 | 29.976 | 10.007 | 1.00 | 21.74 |
| ATOM | 918 | CZ | PHE A | 149 | 42.286 | 29.251 | 10.836 | 1.00 | 21.98 |
| ATOM | 919 | C | PHE A | 149 | 47.678 | 27.673 | 7.569 | 1.00 | 19.04 |
| ATOM | 920 | O | PHE A | 149 | 48.191 | 26.895 | 8.370 | 1.00 | 20.36 |
| ATOM | 921 | N | ASN A | 150 | 48.346 | 28.150 | 6.527 | 1.00 | 17.55 |
| ATOM | 922 | CA | ASN A | 150 | 49.753 | 27.821 | 6.369 | 1.00 | 18.25 |
| ATOM | 923 | CB | ASN A | 150 | 50.277 | 28.309 | 5.013 | 1.00 | 16.65 |
| ATOM | 924 | CG | ASN A | 150 | 49.959 | 29.768 | 4.752 | 1.00 | 18.63 |
| ATOM | 925 | OD1 | ASN A | 150 | 48.805 | 30.191 | 4.846 | 1.00 | 18.40 |
| ATOM | 926 | ND2 | ASN A | 150 | 50.981 | 30.544 | 4.409 | 1.00 | 17.11 |
| ATOM | 927 | C | ASN A | 150 | 50.389 | 28.597 | 7.524 | 1.00 | 19.71 |
| ATOM | 928 | O | ASN A | 150 | 50.140 | 29.793 | 7.676 | 1.00 | 20.26 |
| ATOM | 929 | N | SER A | 151 | 51.188 | 27.925 | 8.346 | 1.00 | 18.09 |
| ATOM | 930 | CA | SER A | 151 | 51.781 | 28.589 | 9.498 | 1.00 | 18.68 |
| ATOM | 931 | CB | SER A | 151 | 50.775 | 28.556 | 10.655 | 1.00 | 17.80 |
| ATOM | 932 | OG | SER A | 151 | 51.372 | 28.931 | 11.883 | 1.00 | 16.50 |
| ATOM | 933 | C | SER A | 151 | 53.117 | 28.017 | 9.974 | 1.00 | 19.15 |
| ATOM | 934 | O | SER A | 151 | 53.339 | 26.802 | 9.931 | 1.00 | 18.28 |
| ATOM | 935 | N | HIS A | 152 | 53.992 | 28.911 | 10.438 | 1.00 | 18.31 |
| ATOM | 936 | CA | HIS A | 152 | 55.307 | 28.532 | 10.956 | 1.00 | 18.93 |
| ATOM | 937 | CB | HIS A | 152 | 56.217 | 29.762 | 11.083 | 1.00 | 18.91 |
| ATOM | 938 | CG | HIS A | 152 | 56.661 | 30.333 | 9.771 | 1.00 | 21.17 |
| ATOM | 939 | CD2 | HIS A | 152 | 56.387 | 29.964 | 8.496 | 1.00 | 21.16 |
| ATOM | 940 | ND1 | HIS A | 152 | 57.499 | 31.424 | 9.681 | 1.00 | 22.49 |
| ATOM | 941 | CE1 | HIS A | 152 | 57.721 | 31.704 | 8.409 | 1.00 | 20.95 |
| ATOM | 942 | NE2 | HIS A | 152 | 57.058 | 30.833 | 7.669 | 1.00 | 22.06 |
| ATOM | 943 | C | HIS A | 152 | 55.165 | 27.877 | 12.329 | 1.00 | 18.38 |
| ATOM | 944 | O | HIS A | 152 | 56.096 | 27.235 | 12.818 | 1.00 | 17.60 |
| ATOM | 945 | N | GLY A | 153 | 54.001 | 28.053 | 12.953 | 1.00 | 17.75 |
| ATOM | 946 | CA | GLY A | 153 | 53.774 | 27.460 | 14.259 | 1.00 | 16.61 |
| ATOM | 947 | C | GLY A | 153 | 54.052 | 28.398 | 15.419 | 1.00 | 15.59 |
| ATOM | 948 | O | GLY A | 153 | 54.717 | 29.419 | 15.262 | 1.00 | 13.71 |
| ATOM | 949 | N | LEU A | 154 | 53.546 | 28.035 | 16.592 | 1.00 | 15.84 |
| ATOM | 950 | CA | LEU A | 154 | 53.713 | 28.837 | 17.799 | 1.00 | 16.70 |
| ATOM | 951 | CB | LEU A | 154 | 52.984 | 28.164 | 18.970 | 1.00 | 13.15 |
| ATOM | 952 | CG | LEU A | 154 | 51.456 | 28.175 | 18.853 | 1.00 | 14.44 |
| ATOM | 953 | CD1 | LEU A | 154 | 50.819 | 27.344 | 19.964 | 1.00 | 9.83 |
| ATOM | 954 | CD2 | LEU A | 154 | 50.969 | 29.622 | 18.911 | 1.00 | 12.21 |
| ATOM | 955 | C | LEU A | 154 | 55.167 | 29.127 | 18.189 | 1.00 | 17.86 |
| ATOM | 956 | O | LEU A | 154 | 55.521 | 30.286 | 18.426 | 1.00 | 18.59 |
| ATOM | 957 | N | SER A | 155 | 56.001 | 28.088 | 18.264 | 1.00 | 17.56 |

TABLE 29-continued

| | | | | | | | | | |
|---|---|---|---|---|---|---|---|---|---|
| ATOM | 958 | CA | SER A | 155 | 57.410 | 28.262 | 18.638 | 1.00 | 19.51 |
| ATOM | 959 | CB | SER A | 155 | 58.181 | 26.944 | 18.510 | 1.00 | 17.58 |
| ATOM | 960 | OG | SER A | 155 | 57.825 | 26.045 | 19.536 | 1.00 | 26.25 |
| ATOM | 961 | C | SER A | 155 | 58.139 | 29.320 | 17.816 | 1.00 | 19.49 |
| ATOM | 962 | O | SER A | 155 | 58.681 | 30.283 | 18.366 | 1.00 | 19.42 |
| ATOM | 963 | N | VAL A | 156 | 58.171 | 29.131 | 16.500 | 1.00 | 17.97 |
| ATOM | 964 | CA | VAL A | 156 | 58.856 | 30.081 | 15.640 | 1.00 | 19.36 |
| ATOM | 965 | CB | VAL A | 156 | 58.746 | 29.679 | 14.152 | 1.00 | 19.76 |
| ATOM | 966 | CG1 | VAL A | 156 | 59.197 | 30.834 | 13.270 | 1.00 | 18.20 |
| ATOM | 967 | CG2 | VAL A | 156 | 59.616 | 28.452 | 13.884 | 1.00 | 15.89 |
| ATOM | 968 | C | VAL A | 156 | 58.346 | 31.509 | 15.821 | 1.00 | 19.10 |
| ATOM | 969 | O | VAL A | 156 | 59.141 | 32.440 | 15.945 | 1.00 | 21.48 |
| ATOM | 970 | N | VAL A | 157 | 57.029 | 31.686 | 15.846 | 1.00 | 17.35 |
| ATOM | 971 | CA | VAL A | 157 | 56.465 | 33.021 | 16.013 | 1.00 | 17.52 |
| ATOM | 972 | CB | VAL A | 157 | 54.927 | 33.012 | 15.806 | 1.00 | 18.44 |
| ATOM | 973 | CG1 | VAL A | 157 | 54.354 | 34.404 | 16.046 | 1.00 | 15.23 |
| ATOM | 974 | CG2 | VAL A | 157 | 54.600 | 32.545 | 14.393 | 1.00 | 16.29 |
| ATOM | 975 | C | VAL A | 157 | 56.792 | 33.557 | 17.404 | 1.00 | 17.04 |
| ATOM | 976 | O | VAL A | 157 | 57.067 | 34.742 | 17.576 | 1.00 | 16.81 |
| ATOM | 977 | N | GLU A | 158 | 56.770 | 32.668 | 18.393 | 1.00 | 18.06 |
| ATOM | 978 | CA | GLU A | 158 | 57.073 | 33.031 | 19.772 | 1.00 | 17.48 |
| ATOM | 979 | CB | GLU A | 158 | 57.027 | 31.784 | 20.657 | 1.00 | 18.28 |
| ATOM | 980 | CG | GLU A | 158 | 57.403 | 32.037 | 22.108 | 1.00 | 20.80 |
| ATOM | 981 | CD | GLU A | 158 | 57.983 | 30.802 | 22.777 | 1.00 | 22.98 |
| ATOM | 982 | OE1 | GLU A | 158 | 57.303 | 29.760 | 22.803 | 1.00 | 27.17 |
| ATOM | 983 | OE2 | GLU A | 158 | 59.123 | 30.871 | 23.276 | 1.00 | 24.43 |
| ATOM | 984 | C | GLU A | 158 | 58.456 | 33.679 | 19.877 | 1.00 | 16.66 |
| ATOM | 985 | O | GLU A | 158 | 58.604 | 34.773 | 20.423 | 1.00 | 15.53 |
| ATOM | 986 | N | HIS A | 159 | 59.467 | 32.999 | 19.350 | 1.00 | 16.18 |
| ATOM | 987 | CA | HIS A | 159 | 60.831 | 33.515 | 19.395 | 1.00 | 18.93 |
| ATOM | 988 | CB | HIS A | 159 | 61.809 | 32.435 | 18.925 | 1.00 | 20.44 |
| ATOM | 989 | CG | HIS A | 159 | 61.858 | 31.248 | 19.833 | 1.00 | 25.76 |
| ATOM | 990 | CD2 | HIS A | 159 | 62.038 | 31.161 | 21.173 | 1.00 | 26.46 |
| ATOM | 991 | ND1 | HIS A | 159 | 61.666 | 29.957 | 19.388 | 1.00 | 29.18 |
| ATOM | 992 | CE1 | HIS A | 159 | 61.723 | 29.127 | 20.414 | 1.00 | 29.23 |
| ATOM | 993 | NE2 | HIS A | 159 | 61.947 | 29.832 | 21.508 | 1.00 | 30.03 |
| ATOM | 994 | C | HIS A | 159 | 60.986 | 34.772 | 18.555 | 1.00 | 17.73 |
| ATOM | 995 | O | HIS A | 159 | 61.760 | 35.664 | 18.892 | 1.00 | 18.91 |
| ATOM | 996 | N | ARG A | 160 | 60.237 | 34.840 | 17.465 | 1.00 | 17.89 |
| ATOM | 997 | CA | ARG A | 160 | 60.281 | 35.990 | 16.574 | 1.00 | 19.60 |
| ATOM | 998 | CB | ARG A | 160 | 59.516 | 35.652 | 15.293 | 1.00 | 20.86 |
| ATOM | 999 | CG | ARG A | 160 | 59.537 | 36.703 | 14.206 | 1.00 | 21.57 |
| ATOM | 1000 | CD | ARG A | 160 | 58.928 | 36.111 | 12.933 | 1.00 | 24.64 |
| ATOM | 1001 | NE | ARG A | 160 | 59.805 | 35.113 | 12.323 | 1.00 | 23.48 |
| ATOM | 1002 | CZ | ARG A | 160 | 59.388 | 34.084 | 11.587 | 1.00 | 24.74 |
| ATOM | 1003 | NH1 | ARG A | 160 | 58.092 | 33.895 | 11.365 | 1.00 | 22.08 |
| ATOM | 1004 | NH2 | ARG A | 160 | 60.273 | 33.250 | 11.056 | 1.00 | 21.93 |
| ATOM | 1005 | C | ARG A | 160 | 59.693 | 37.227 | 17.269 | 1.00 | 20.13 |
| ATOM | 1006 | O | ARG A | 160 | 60.167 | 38.346 | 17.069 | 1.00 | 20.73 |
| ATOM | 1007 | N | LEU A | 161 | 58.669 | 37.030 | 18.093 | 1.00 | 19.56 |
| ATOM | 1008 | CA | LEU A | 161 | 58.073 | 38.154 | 18.812 | 1.00 | 19.51 |
| ATOM | 1009 | CB | LEU A | 161 | 56.632 | 37.833 | 19.226 | 1.00 | 19.35 |
| ATOM | 1010 | CG | LEU A | 161 | 55.606 | 37.704 | 18.092 | 1.00 | 20.03 |
| ATOM | 1011 | CD1 | LEU A | 161 | 54.225 | 37.460 | 18.685 | 1.00 | 18.09 |
| ATOM | 1012 | CD2 | LEU A | 161 | 55.599 | 38.974 | 17.248 | 1.00 | 16.90 |
| ATOM | 1013 | C | LEU A | 161 | 58.911 | 38.497 | 20.048 | 1.00 | 18.36 |
| ATOM | 1014 | O | LEU A | 161 | 58.990 | 39.654 | 20.454 | 1.00 | 17.75 |
| ATOM | 1015 | N | ARG A | 162 | 59.545 | 37.489 | 20.640 | 1.00 | 17.94 |
| ATOM | 1016 | CA | ARG A | 162 | 60.385 | 37.717 | 21.814 | 1.00 | 17.80 |
| ATOM | 1017 | CB | ARG A | 162 | 60.853 | 36.392 | 22.412 | 1.00 | 16.66 |
| ATOM | 1018 | CG | ARG A | 162 | 59.814 | 35.688 | 23.264 | 1.00 | 17.05 |
| ATOM | 1019 | CD | ARG A | 162 | 60.431 | 34.482 | 23.946 | 1.00 | 16.29 |
| ATOM | 1020 | NE | ARG A | 162 | 59.503 | 33.831 | 24.862 | 1.00 | 15.68 |
| ATOM | 1021 | CZ | ARG A | 162 | 59.806 | 32.758 | 25.584 | 1.00 | 16.71 |
| ATOM | 1022 | NH1 | ARG A | 162 | 61.018 | 32.219 | 25.493 | 1.00 | 15.01 |
| ATOM | 1023 | NH2 | ARG A | 162 | 58.900 | 32.220 | 26.391 | 1.00 | 16.25 |
| ATOM | 1024 | C | ARG A | 162 | 61.605 | 38.566 | 21.482 | 1.00 | 17.51 |
| ATOM | 1025 | O | ARG A | 162 | 62.080 | 39.329 | 22.320 | 1.00 | 17.44 |
| ATOM | 1026 | N | ALA A | 163 | 62.106 | 38.431 | 20.258 | 1.00 | 17.07 |
| ATOM | 1027 | CA | ALA A | 163 | 63.275 | 39.188 | 19.825 | 1.00 | 16.71 |
| ATOM | 1028 | CB | ALA A | 163 | 63.727 | 38.711 | 18.450 | 1.00 | 15.44 |
| ATOM | 1029 | C | ALA A | 163 | 62.998 | 40.688 | 19.786 | 1.00 | 16.78 |
| ATOM | 1030 | O | ALA A | 163 | 63.927 | 41.489 | 19.687 | 1.00 | 14.49 |
| ATOM | 1031 | N | ARG A | 164 | 61.723 | 41.062 | 19.867 | 1.00 | 17.00 |
| ATOM | 1032 | CA | ARG A | 164 | 61.334 | 42.468 | 19.834 | 1.00 | 18.86 |
| ATOM | 1033 | CB | ARG A | 164 | 60.782 | 42.836 | 18.451 | 1.00 | 19.13 |
| ATOM | 1034 | CG | ARG A | 164 | 59.511 | 42.079 | 18.068 | 1.00 | 19.61 |
| ATOM | 1035 | CD | ARG A | 164 | 59.029 | 42.462 | 16.674 | 1.00 | 17.87 |
| ATOM | 1036 | NE | ARG A | 164 | 58.541 | 43.837 | 16.610 | 1.00 | 17.41 |

TABLE 29-continued

| | | | | | | | | | |
|---|---|---|---|---|---|---|---|---|---|
| ATOM | 1037 | CZ | ARG A | 164 | 57.361 | 44.237 | 17.074 | 1.00 | 19.05 |
| ATOM | 1038 | NH1 | ARG A | 164 | 56.533 | 43.364 | 17.639 | 1.00 | 17.96 |
| ATOM | 1039 | NH2 | ARG A | 164 | 57.004 | 45.511 | 16.970 | 1.00 | 18.08 |
| ATOM | 1040 | C | ARG A | 164 | 60.278 | 42.776 | 20.882 | 1.00 | 19.19 |
| ATOM | 1041 | O | ARG A | 164 | 59.597 | 43.797 | 20.795 | 1.00 | 19.50 |
| ATOM | 1042 | N | GLN A | 165 | 60.152 | 41.900 | 21.874 | 1.00 | 20.49 |
| ATOM | 1043 | CA | GLN A | 165 | 59.155 | 42.073 | 22.924 | 1.00 | 20.58 |
| ATOM | 1044 | CB | GLN A | 165 | 59.274 | 40.936 | 23.954 | 1.00 | 20.12 |
| ATOM | 1045 | CG | GLN A | 165 | 58.313 | 41.046 | 25.145 | 1.00 | 21.82 |
| ATOM | 1046 | CD | GLN A | 165 | 58.141 | 39.729 | 25.904 | 1.00 | 22.47 |
| ATOM | 1047 | OE1 | GLN A | 165 | 59.064 | 38.921 | 25.994 | 1.00 | 22.27 |
| ATOM | 1048 | NE2 | GLN A | 165 | 56.954 | 39.520 | 26.464 | 1.00 | 21.18 |
| ATOM | 1049 | C | GLN A | 165 | 59.205 | 43.433 | 23.623 | 1.00 | 21.76 |
| ATOM | 1050 | O | GLN A | 165 | 58.161 | 44.037 | 23.888 | 1.00 | 22.56 |
| ATOM | 1051 | N | GLN A | 166 | 60.405 | 43.926 | 23.914 | 1.00 | 21.90 |
| ATOM | 1052 | CA | GLN A | 166 | 60.533 | 45.209 | 24.595 | 1.00 | 22.73 |
| ATOM | 1053 | CB | GLN A | 166 | 61.931 | 45.366 | 25.194 | 1.00 | 25.53 |
| ATOM | 1054 | CG | GLN A | 166 | 62.185 | 44.389 | 26.321 | 1.00 | 27.06 |
| ATOM | 1055 | CD | GLN A | 166 | 61.005 | 44.313 | 27.268 | 1.00 | 28.22 |
| ATOM | 1056 | OE1 | GLN A | 166 | 60.585 | 45.321 | 27.834 | 1.00 | 28.38 |
| ATOM | 1057 | NE2 | GLN A | 166 | 60.456 | 43.116 | 27.437 | 1.00 | 29.05 |
| ATOM | 1058 | C | GLN A | 166 | 60.218 | 46.382 | 23.693 | 1.00 | 22.07 |
| ATOM | 1059 | O | GLN A | 166 | 59.645 | 47.378 | 24.138 | 1.00 | 20.88 |
| ATOM | 1060 | N | LYS A | 167 | 60.597 | 46.271 | 22.425 | 1.00 | 21.93 |
| ATOM | 1061 | CA | LYS A | 167 | 60.307 | 47.334 | 21.478 | 1.00 | 21.45 |
| ATOM | 1062 | CB | LYS A | 167 | 60.884 | 47.006 | 20.101 | 1.00 | 21.05 |
| ATOM | 1063 | CG | LYS A | 167 | 60.402 | 47.954 | 19.027 | 1.00 | 25.54 |
| ATOM | 1064 | CD | LYS A | 167 | 60.905 | 47.574 | 17.648 | 1.00 | 30.01 |
| ATOM | 1065 | CE | LYS A | 167 | 62.375 | 47.894 | 17.486 | 1.00 | 33.62 |
| ATOM | 1066 | NZ | LYS A | 167 | 62.788 | 47.798 | 16.057 | 1.00 | 36.58 |
| ATOM | 1067 | C | LYS A | 167 | 58.787 | 47.467 | 21.379 | 1.00 | 20.51 |
| ATOM | 1068 | O | LYS A | 167 | 58.248 | 48.574 | 21.405 | 1.00 | 20.50 |
| ATOM | 1069 | N | GLN A | 168 | 58.102 | 46.330 | 21.274 | 1.00 | 19.09 |
| ATOM | 1070 | CA | GLN A | 168 | 56.646 | 46.330 | 21.172 | 1.00 | 18.76 |
| ATOM | 1071 | CB | GLN A | 168 | 56.114 | 44.906 | 20.982 | 1.00 | 17.10 |
| ATOM | 1072 | CG | GLN A | 168 | 54.593 | 44.830 | 20.823 | 1.00 | 17.73 |
| ATOM | 1073 | CD | GLN A | 168 | 54.072 | 45.640 | 19.636 | 1.00 | 18.32 |
| ATOM | 1074 | OE1 | GLN A | 168 | 54.439 | 45.390 | 18.483 | 1.00 | 17.02 |
| ATOM | 1075 | NE2 | GLN A | 168 | 53.210 | 46.615 | 19.918 | 1.00 | 16.42 |
| ATOM | 1076 | C | GLN A | 168 | 56.027 | 46.954 | 22.413 | 1.00 | 17.97 |
| ATOM | 1077 | O | GLN A | 168 | 55.049 | 47.689 | 22.315 | 1.00 | 17.66 |
| ATOM | 1078 | N | ALA A | 169 | 56.608 | 46.678 | 23.579 | 1.00 | 17.93 |
| ATOM | 1079 | CA | ALA A | 169 | 56.089 | 47.243 | 24.824 | 1.00 | 18.74 |
| ATOM | 1080 | CB | ALA A | 169 | 56.957 | 46.817 | 26.005 | 1.00 | 18.28 |
| ATOM | 1081 | C | ALA A | 169 | 56.042 | 48.766 | 24.728 | 1.00 | 18.92 |
| ATOM | 1082 | O | ALA A | 169 | 55.083 | 49.394 | 25.177 | 1.00 | 19.50 |
| ATOM | 1083 | N | LYS A | 170 | 57.078 | 49.359 | 24.143 | 1.00 | 19.73 |
| ATOM | 1084 | CA | LYS A | 170 | 57.122 | 50.809 | 23.992 | 1.00 | 22.09 |
| ATOM | 1085 | CB | LYS A | 170 | 58.536 | 51.278 | 23.637 | 1.00 | 23.45 |
| ATOM | 1086 | CG | LYS A | 170 | 59.524 | 51.155 | 24.791 | 1.00 | 28.29 |
| ATOM | 1087 | CD | LYS A | 170 | 60.839 | 51.866 | 24.492 | 1.00 | 30.12 |
| ATOM | 1088 | CE | LYS A | 170 | 61.786 | 51.792 | 25.680 | 1.00 | 30.79 |
| ATOM | 1089 | NZ | LYS A | 170 | 62.112 | 50.377 | 26.041 | 1.00 | 34.64 |
| ATOM | 1090 | C | LYS A | 170 | 56.138 | 51.275 | 22.925 | 1.00 | 20.81 |
| ATOM | 1091 | O | LYS A | 170 | 55.509 | 52.321 | 23.072 | 1.00 | 20.80 |
| ATOM | 1092 | N | LEU A | 171 | 56.010 | 50.499 | 21.852 | 1.00 | 19.17 |
| ATOM | 1093 | CA | LEU A | 171 | 55.082 | 50.839 | 20.778 | 1.00 | 18.67 |
| ATOM | 1094 | CB | LEU A | 171 | 55.199 | 49.823 | 19.639 | 1.00 | 17.59 |
| ATOM | 1095 | CG | LEU A | 171 | 56.489 | 49.947 | 18.823 | 1.00 | 16.99 |
| ATOM | 1096 | CD1 | LEU A | 171 | 56.702 | 48.707 | 17.965 | 1.00 | 12.77 |
| ATOM | 1097 | CD2 | LEU A | 171 | 56.411 | 51.210 | 17.968 | 1.00 | 14.39 |
| ATOM | 1098 | C | LEU A | 171 | 53.651 | 50.867 | 21.315 | 1.00 | 18.05 |
| ATOM | 1099 | O | LEU A | 171 | 52.890 | 51.797 | 21.040 | 1.00 | 15.95 |
| ATOM | 1100 | N | THR A | 172 | 53.295 | 49.845 | 22.088 | 1.00 | 18.35 |
| ATOM | 1101 | CA | THR A | 172 | 51.964 | 49.756 | 22.677 | 1.00 | 19.52 |
| ATOM | 1102 | CB | THR A | 172 | 51.801 | 48.442 | 23.473 | 1.00 | 17.84 |
| ATOM | 1103 | OG1 | THR A | 172 | 51.889 | 47.330 | 22.572 | 1.00 | 16.09 |
| ATOM | 1104 | CG2 | THR A | 172 | 50.456 | 48.409 | 24.186 | 1.00 | 14.72 |
| ATOM | 1105 | C | THR A | 172 | 51.708 | 50.956 | 23.595 | 1.00 | 21.19 |
| ATOM | 1106 | O | THR A | 172 | 50.658 | 51.596 | 23.517 | 1.00 | 19.87 |
| ATOM | 1107 | N | GLU A | 173 | 52.675 | 51.263 | 24.454 | 1.00 | 23.39 |
| ATOM | 1108 | CA | GLU A | 173 | 52.553 | 52.398 | 25.362 | 1.00 | 26.67 |
| ATOM | 1109 | CB | GLU A | 173 | 53.799 | 52.506 | 26.246 | 1.00 | 30.55 |
| ATOM | 1110 | CG | GLU A | 173 | 53.745 | 53.637 | 27.265 | 1.00 | 38.76 |
| ATOM | 1111 | CD | GLU A | 173 | 52.656 | 53.438 | 28.317 | 1.00 | 43.68 |
| ATOM | 1112 | OE1 | GLU A | 173 | 52.394 | 54.389 | 29.089 | 1.00 | 44.95 |
| ATOM | 1113 | OE2 | GLU A | 173 | 52.067 | 52.333 | 28.378 | 1.00 | 45.55 |
| ATOM | 1114 | C | GLU A | 173 | 52.396 | 53.673 | 24.533 | 1.00 | 26.37 |
| ATOM | 1115 | O | GLU A | 173 | 51.811 | 54.657 | 24.982 | 1.00 | 25.62 |

TABLE 29-continued

| ATOM | 1116 | N | ASP A | 174 | 52.918 | 53.637 | 23.313 | 1.00 | 27.07 |
|---|---|---|---|---|---|---|---|---|---|
| ATOM | 1117 | CA | ASP A | 174 | 52.845 | 54.772 | 22.405 | 1.00 | 28.13 |
| ATOM | 1118 | CB | ASP A | 174 | 54.059 | 54.770 | 21.481 | 1.00 | 32.94 |
| ATOM | 1119 | CG | ASP A | 174 | 54.971 | 55.946 | 21.724 | 1.00 | 38.63 |
| ATOM | 1120 | OD1 | ASP A | 174 | 54.537 | 57.094 | 21.468 | 1.00 | 40.07 |
| ATOM | 1121 | OD2 | ASP A | 174 | 56.117 | 55.722 | 22.176 | 1.00 | 40.59 |
| ATOM | 1122 | C | ASP A | 174 | 51.570 | 54.793 | 21.560 | 1.00 | 27.18 |
| ATOM | 1123 | O | ASP A | 174 | 51.445 | 55.610 | 20.649 | 1.00 | 27.16 |
| ATOM | 1124 | N | GLY A | 175 | 50.636 | 53.892 | 21.851 | 1.00 | 24.85 |
| ATOM | 1125 | CA | GLY A | 175 | 49.393 | 53.856 | 21.100 | 1.00 | 24.01 |
| ATOM | 1126 | C | GLY A | 175 | 49.405 | 52.977 | 19.860 | 1.00 | 23.65 |
| ATOM | 1127 | O | GLY A | 175 | 48.579 | 53.159 | 18.965 | 1.00 | 23.96 |
| ATOM | 1128 | N | LEU A | 176 | 50.330 | 52.021 | 19.804 | 1.00 | 22.56 |
| ATOM | 1129 | CA | LEU A | 176 | 50.439 | 51.117 | 18.658 | 1.00 | 20.60 |
| ATOM | 1130 | CB | LEU A | 176 | 51.726 | 51.419 | 17.887 | 1.00 | 19.76 |
| ATOM | 1131 | CG | LEU A | 176 | 51.773 | 52.805 | 17.236 | 1.00 | 20.88 |
| ATOM | 1132 | CD1 | LEU A | 176 | 53.156 | 53.073 | 16.645 | 1.00 | 20.36 |
| ATOM | 1133 | CD2 | LEU A | 176 | 50.698 | 52.885 | 16.155 | 1.00 | 21.58 |
| ATOM | 1134 | C | LEU A | 176 | 50.422 | 49.654 | 19.107 | 1.00 | 19.32 |
| ATOM | 1135 | O | LEU A | 176 | 51.444 | 48.968 | 19.071 | 1.00 | 19.23 |
| ATOM | 1136 | N | PRO A | 177 | 49.241 | 49.160 | 19.520 | 1.00 | 17.22 |
| ATOM | 1137 | CD | PRO A | 177 | 48.007 | 49.957 | 19.601 | 1.00 | 14.81 |
| ATOM | 1138 | CA | PRO A | 177 | 49.000 | 47.795 | 19.998 | 1.00 | 16.26 |
| ATOM | 1139 | CB | PRO A | 177 | 47.534 | 47.831 | 20.437 | 1.00 | 16.17 |
| ATOM | 1140 | CG | PRO A | 177 | 47.281 | 49.277 | 20.721 | 1.00 | 15.79 |
| ATOM | 1141 | C | PRO A | 177 | 49.264 | 46.660 | 19.003 | 1.00 | 15.92 |
| ATOM | 1142 | O | PRO A | 177 | 49.265 | 46.851 | 17.784 | 1.00 | 15.28 |
| ATOM | 1143 | N | LEU A | 178 | 49.467 | 45.470 | 19.557 | 1.00 | 14.24 |
| ATOM | 1144 | CA | LEU A | 178 | 49.728 | 44.268 | 18.779 | 1.00 | 15.03 |
| ATOM | 1145 | CB | LEU A | 178 | 51.130 | 43.738 | 19.087 | 1.00 | 12.96 |
| ATOM | 1146 | CG | LEU A | 178 | 51.516 | 42.404 | 18.444 | 1.00 | 14.74 |
| ATOM | 1147 | CD1 | LEU A | 178 | 51.571 | 42.573 | 16.932 | 1.00 | 14.67 |
| ATOM | 1148 | CD2 | LEU A | 178 | 52.869 | 41.938 | 18.976 | 1.00 | 11.17 |
| ATOM | 1149 | C | LEU A | 178 | 48.702 | 43.190 | 19.116 | 1.00 | 14.20 |
| ATOM | 1150 | O | LEU A | 178 | 48.456 | 42.897 | 20.283 | 1.00 | 15.66 |
| ATOM | 1151 | N | GLY A | 179 | 48.096 | 42.609 | 18.090 | 1.00 | 14.51 |
| ATOM | 1152 | CA | GLY A | 179 | 47.131 | 41.552 | 18.309 | 1.00 | 11.48 |
| ATOM | 1153 | C | GLY A | 179 | 47.674 | 40.287 | 17.677 | 1.00 | 12.92 |
| ATOM | 1154 | O | GLY A | 179 | 48.433 | 40.355 | 16.706 | 1.00 | 11.41 |
| ATOM | 1155 | N | VAL A | 180 | 47.312 | 39.137 | 18.235 | 1.00 | 12.74 |
| ATOM | 1156 | CA | VAL A | 180 | 47.754 | 37.857 | 17.700 | 1.00 | 12.66 |
| ATOM | 1157 | CB | VAL A | 180 | 48.702 | 37.135 | 18.670 | 1.00 | 13.16 |
| ATOM | 1158 | CG1 | VAL A | 180 | 49.025 | 35.746 | 18.135 | 1.00 | 11.92 |
| ATOM | 1159 | CG2 | VAL A | 180 | 49.981 | 37.946 | 18.838 | 1.00 | 14.00 |
| ATOM | 1160 | C | VAL A | 180 | 46.535 | 36.981 | 17.437 | 1.00 | 14.54 |
| ATOM | 1161 | O | VAL A | 180 | 45.723 | 36.733 | 18.334 | 1.00 | 15.05 |
| ATOM | 1162 | N | ASN A | 181 | 46.411 | 36.523 | 16.197 | 1.00 | 14.43 |
| ATOM | 1163 | CA | ASN A | 181 | 45.285 | 35.701 | 15.774 | 1.00 | 16.18 |
| ATOM | 1164 | CB | ASN A | 181 | 44.913 | 36.081 | 14.337 | 1.00 | 16.86 |
| ATOM | 1165 | CG | ASN A | 181 | 43.622 | 35.450 | 13.872 | 1.00 | 18.28 |
| ATOM | 1166 | OD1 | ASN A | 181 | 43.439 | 34.233 | 13.961 | 1.00 | 16.72 |
| ATOM | 1167 | ND2 | ASN A | 181 | 42.717 | 36.278 | 13.353 | 1.00 | 17.72 |
| ATOM | 1168 | C | ASN A | 181 | 45.657 | 34.217 | 15.867 | 1.00 | 16.98 |
| ATOM | 1169 | O | ASN A | 181 | 46.650 | 33.781 | 15.281 | 1.00 | 17.21 |
| ATOM | 1170 | N | LEU A | 182 | 44.843 | 33.452 | 16.593 | 1.00 | 15.71 |
| ATOM | 1171 | CA | LEU A | 182 | 45.079 | 32.029 | 16.804 | 1.00 | 16.75 |
| ATOM | 1172 | CB | LEU A | 182 | 44.890 | 31.691 | 18.283 | 1.00 | 15.56 |
| ATOM | 1173 | CG | LEU A | 182 | 45.709 | 32.502 | 19.285 | 1.00 | 16.48 |
| ATOM | 1174 | CD1 | LEU A | 182 | 45.285 | 32.136 | 20.703 | 1.00 | 14.81 |
| ATOM | 1175 | CD2 | LEU A | 182 | 47.190 | 32.233 | 19.068 | 1.00 | 14.85 |
| ATOM | 1176 | C | LEU A | 182 | 44.187 | 31.105 | 15.980 | 1.00 | 17.41 |
| ATOM | 1177 | O | LEU A | 182 | 42.981 | 31.309 | 15.876 | 1.00 | 18.39 |
| ATOM | 1178 | N | GLY A | 183 | 44.800 | 30.078 | 15.406 | 1.00 | 17.73 |
| ATOM | 1179 | CA | GLY A | 183 | 44.066 | 29.113 | 14.613 | 1.00 | 18.55 |
| ATOM | 1180 | C | GLY A | 183 | 44.348 | 27.733 | 15.176 | 1.00 | 20.03 |
| ATOM | 1181 | O | GLY A | 183 | 44.939 | 27.602 | 16.250 | 1.00 | 18.94 |
| ATOM | 1182 | N | LYS A | 184 | 43.931 | 26.695 | 14.465 | 1.00 | 20.89 |
| ATOM | 1183 | CA | LYS A | 184 | 44.172 | 25.346 | 14.943 | 1.00 | 22.37 |
| ATOM | 1184 | CB | LYS A | 184 | 42.898 | 24.755 | 15.553 | 1.00 | 24.26 |
| ATOM | 1185 | CG | LYS A | 184 | 41.916 | 24.217 | 14.540 | 1.00 | 28.42 |
| ATOM | 1186 | CD | LYS A | 184 | 40.864 | 23.363 | 15.221 | 1.00 | 32.20 |
| ATOM | 1187 | CE | LYS A | 184 | 40.116 | 22.506 | 14.210 | 1.00 | 35.25 |
| ATOM | 1188 | NZ | LYS A | 184 | 41.029 | 21.545 | 13.531 | 1.00 | 35.90 |
| ATOM | 1189 | C | LYS A | 184 | 44.672 | 24.465 | 13.808 | 1.00 | 20.68 |
| ATOM | 1190 | O | LYS A | 184 | 44.369 | 24.700 | 12.644 | 1.00 | 21.35 |
| ATOM | 1191 | N | ASN A | 185 | 45.449 | 23.452 | 14.157 | 1.00 | 21.49 |
| ATOM | 1192 | CA | ASN A | 185 | 45.997 | 22.547 | 13.161 | 1.00 | 22.53 |
| ATOM | 1193 | CB | ASN A | 185 | 47.052 | 21.645 | 13.801 | 1.00 | 20.30 |
| ATOM | 1194 | CG | ASN A | 185 | 48.371 | 22.360 | 14.025 | 1.00 | 20.21 |

TABLE 29-continued

| | | | | | | | | | |
|---|---|---|---|---|---|---|---|---|---|
| ATOM | 1195 | OD1 | ASN A | 185 | 48.812 | 22.536 | 15.161 | 1.00 | 20.64 |
| ATOM | 1196 | ND2 | ASN A | 185 | 49.010 | 22.773 | 12.938 | 1.00 | 19.38 |
| ATOM | 1197 | C | ASN A | 185 | 44.940 | 21.692 | 12.469 | 1.00 | 24.32 |
| ATOM | 1198 | O | ASN A | 185 | 43.929 | 21.307 | 13.063 | 1.00 | 22.56 |
| ATOM | 1199 | N | LYS A | 186 | 45.200 | 21.392 | 11.201 | 1.00 | 27.23 |
| ATOM | 1200 | CA | LYS A | 186 | 44.305 | 20.582 | 10.390 | 1.00 | 30.05 |
| ATOM | 1201 | CB | LYS A | 186 | 44.886 | 20.441 | 8.982 | 1.00 | 30.82 |
| ATOM | 1202 | CG | LYS A | 186 | 44.054 | 19.581 | 8.047 | 1.00 | 33.61 |
| ATOM | 1203 | CD | LYS A | 186 | 44.711 | 19.487 | 6.685 | 1.00 | 35.69 |
| ATOM | 1204 | CE | LYS A | 186 | 43.865 | 18.692 | 5.710 | 1.00 | 37.08 |
| ATOM | 1205 | NZ | LYS A | 186 | 44.525 | 18.604 | 4.374 | 1.00 | 39.36 |
| ATOM | 1206 | C | LYS A | 186 | 44.051 | 19.190 | 10.981 | 1.00 | 31.18 |
| ATOM | 1207 | O | LYS A | 186 | 42.914 | 18.726 | 11.013 | 1.00 | 30.53 |
| ATOM | 1208 | N | THR A | 187 | 45.107 | 18.530 | 11.449 | 1.00 | 33.43 |
| ATOM | 1209 | CA | THR A | 187 | 44.973 | 17.187 | 12.011 | 1.00 | 36.34 |
| ATOM | 1210 | CB | THR A | 187 | 46.204 | 16.314 | 11.685 | 1.00 | 36.53 |
| ATOM | 1211 | OG1 | THR A | 187 | 47.348 | 16.819 | 12.389 | 1.00 | 35.83 |
| ATOM | 1212 | CG2 | THR A | 187 | 46.480 | 16.323 | 10.184 | 1.00 | 35.68 |
| ATOM | 1213 | C | THR A | 187 | 44.776 | 17.175 | 13.524 | 1.00 | 38.23 |
| ATOM | 1214 | O | THR A | 187 | 44.924 | 16.134 | 14.169 | 1.00 | 39.65 |
| ATOM | 1215 | N | SER A | 188 | 44.449 | 18.330 | 14.091 | 1.00 | 38.70 |
| ATOM | 1216 | CA | SER A | 188 | 44.225 | 18.424 | 15.524 | 1.00 | 38.55 |
| ATOM | 1217 | CB | SER A | 188 | 44.078 | 19.886 | 15.940 | 1.00 | 38.64 |
| ATOM | 1218 | OG | SER A | 188 | 43.782 | 19.988 | 17.320 | 1.00 | 40.20 |
| ATOM | 1219 | C | SER A | 188 | 42.964 | 17.654 | 15.904 | 1.00 | 39.15 |
| ATOM | 1220 | O | SER A | 188 | 42.006 | 17.601 | 15.134 | 1.00 | 38.68 |
| ATOM | 1221 | N | VAL A | 189 | 42.971 | 17.061 | 17.094 | 1.00 | 39.48 |
| ATOM | 1222 | CA | VAL A | 189 | 41.829 | 16.296 | 17.583 | 1.00 | 41.01 |
| ATOM | 1223 | CB | VAL A | 189 | 42.284 | 14.984 | 18.260 | 1.00 | 41.97 |
| ATOM | 1224 | CG1 | VAL A | 189 | 41.102 | 14.309 | 18.927 | 1.00 | 42.79 |
| ATOM | 1225 | CG2 | VAL A | 189 | 42.910 | 14.052 | 17.230 | 1.00 | 41.86 |
| ATOM | 1226 | C | VAL A | 189 | 41.015 | 17.101 | 18.595 | 1.00 | 41.66 |
| ATOM | 1227 | O | VAL A | 189 | 39.789 | 16.980 | 18.660 | 1.00 | 43.36 |
| ATOM | 1228 | N | ASP A | 190 | 41.704 | 17.925 | 19.379 | 1.00 | 40.34 |
| ATOM | 1229 | CA | ASP A | 190 | 41.055 | 18.748 | 20.394 | 1.00 | 38.77 |
| ATOM | 1230 | CB | ASP A | 190 | 41.708 | 18.502 | 21.755 | 1.00 | 41.42 |
| ATOM | 1231 | CG | ASP A | 190 | 40.907 | 19.084 | 22.900 | 1.00 | 43.96 |
| ATOM | 1232 | OD1 | ASP A | 190 | 40.362 | 20.197 | 22.746 | 1.00 | 44.17 |
| ATOM | 1233 | OD2 | ASP A | 190 | 40.831 | 18.431 | 23.961 | 1.00 | 48.33 |
| ATOM | 1234 | C | ASP A | 190 | 41.176 | 20.228 | 20.031 | 1.00 | 36.65 |
| ATOM | 1235 | O | ASP A | 190 | 42.153 | 20.886 | 20.396 | 1.00 | 36.03 |
| ATOM | 1236 | N | ALA A | 191 | 40.178 | 20.749 | 19.322 | 1.00 | 33.62 |
| ATOM | 1237 | CA | ALA A | 191 | 40.181 | 22.147 | 18.902 | 1.00 | 30.36 |
| ATOM | 1238 | CB | ALA A | 191 | 38.860 | 22.493 | 18.232 | 1.00 | 30.25 |
| ATOM | 1239 | C | ALA A | 191 | 40.433 | 23.101 | 20.060 | 1.00 | 28.52 |
| ATOM | 1240 | O | ALA A | 191 | 41.192 | 24.058 | 19.930 | 1.00 | 26.66 |
| ATOM | 1241 | N | ALA A | 192 | 39.793 | 22.835 | 21.193 | 1.00 | 26.87 |
| ATOM | 1242 | CA | ALA A | 192 | 39.942 | 23.685 | 22.367 | 1.00 | 25.59 |
| ATOM | 1243 | CB | ALA A | 192 | 39.013 | 23.205 | 23.479 | 1.00 | 23.07 |
| ATOM | 1244 | C | ALA A | 192 | 41.382 | 23.740 | 22.871 | 1.00 | 25.06 |
| ATOM | 1245 | O | ALA A | 192 | 41.863 | 24.804 | 23.248 | 1.00 | 26.91 |
| ATOM | 1246 | N | GLU A | 193 | 42.067 | 22.600 | 22.881 | 1.00 | 24.69 |
| ATOM | 1247 | CA | GLU A | 193 | 43.449 | 22.553 | 23.348 | 1.00 | 25.36 |
| ATOM | 1248 | CB | GLU A | 193 | 43.941 | 21.104 | 23.430 | 1.00 | 28.55 |
| ATOM | 1249 | CG | GLU A | 193 | 45.386 | 20.980 | 23.892 | 1.00 | 33.86 |
| ATOM | 1250 | CD | GLU A | 193 | 45.625 | 21.605 | 25.259 | 1.00 | 38.09 |
| ATOM | 1251 | OE1 | GLU A | 193 | 46.803 | 21.800 | 25.628 | 1.00 | 40.81 |
| ATOM | 1252 | OE2 | GLU A | 193 | 44.637 | 21.895 | 25.969 | 1.00 | 40.22 |
| ATOM | 1253 | C | GLU A | 193 | 44.373 | 23.373 | 22.444 | 1.00 | 23.89 |
| ATOM | 1254 | O | GLU A | 193 | 45.281 | 24.050 | 22.929 | 1.00 | 23.13 |
| ATOM | 1255 | N | ASP A | 194 | 44.137 | 23.309 | 21.136 | 1.00 | 21.11 |
| ATOM | 1256 | CA | ASP A | 194 | 44.925 | 24.071 | 20.171 | 1.00 | 21.43 |
| ATOM | 1257 | CB | ASP A | 194 | 44.373 | 23.875 | 18.755 | 1.00 | 22.24 |
| ATOM | 1258 | CG | ASP A | 194 | 45.043 | 22.736 | 18.017 | 1.00 | 22.08 |
| ATOM | 1259 | OD1 | ASP A | 194 | 45.526 | 21.802 | 18.679 | 1.00 | 25.23 |
| ATOM | 1260 | OD2 | ASP A | 194 | 45.080 | 22.768 | 16.769 | 1.00 | 23.80 |
| ATOM | 1261 | C | ASP A | 194 | 44.910 | 25.561 | 20.520 | 1.00 | 21.42 |
| ATOM | 1262 | O | ASP A | 194 | 45.962 | 26.207 | 20.552 | 1.00 | 22.27 |
| ATOM | 1263 | N | TYR A | 195 | 43.723 | 26.110 | 20.771 | 1.00 | 19.34 |
| ATOM | 1264 | CA | TYR A | 195 | 43.618 | 27.522 | 21.119 | 1.00 | 19.62 |
| ATOM | 1265 | CB | TYR A | 195 | 42.159 | 27.999 | 21.080 | 1.00 | 18.69 |
| ATOM | 1266 | CG | TYR A | 195 | 41.558 | 28.005 | 19.693 | 1.00 | 19.61 |
| ATOM | 1267 | CD1 | TYR A | 195 | 40.769 | 26.953 | 19.250 | 1.00 | 19.06 |
| ATOM | 1268 | CE1 | TYR A | 195 | 40.262 | 26.930 | 17.968 | 1.00 | 19.80 |
| ATOM | 1269 | CD2 | TYR A | 195 | 41.819 | 29.043 | 18.809 | 1.00 | 19.96 |
| ATOM | 1270 | CE2 | TYR A | 195 | 41.316 | 29.030 | 17.520 | 1.00 | 20.62 |
| ATOM | 1271 | CZ | TYR A | 195 | 40.539 | 27.970 | 17.106 | 1.00 | 21.15 |
| ATOM | 1272 | OH | TYR A | 195 | 40.043 | 27.943 | 15.822 | 1.00 | 22.18 |
| ATOM | 1273 | C | TYR A | 195 | 44.199 | 27.762 | 22.504 | 1.00 | 19.30 |

TABLE 29-continued

| ATOM | 1274 | O | TYR A | 195 | 44.812 | 28.799 | 22.755 | 1.00 | 19.17 |
|---|---|---|---|---|---|---|---|---|---|
| ATOM | 1275 | N | ALA A | 196 | 44.006 | 26.800 | 23.401 | 1.00 | 19.01 |
| ATOM | 1276 | CA | ALA A | 196 | 44.530 | 26.918 | 24.756 | 1.00 | 19.63 |
| ATOM | 1277 | CB | ALA A | 196 | 44.143 | 25.697 | 25.578 | 1.00 | 19.27 |
| ATOM | 1278 | C | ALA A | 196 | 46.051 | 27.058 | 24.699 | 1.00 | 19.64 |
| ATOM | 1279 | O | ALA A | 196 | 46.634 | 27.865 | 25.426 | 1.00 | 19.80 |
| ATOM | 1280 | N | GLU A | 197 | 46.685 | 26.274 | 23.828 | 1.00 | 18.51 |
| ATOM | 1281 | CA | GLU A | 197 | 48.136 | 26.320 | 23.667 | 1.00 | 21.13 |
| ATOM | 1282 | CB | GLU A | 197 | 48.615 | 25.222 | 22.708 | 1.00 | 24.77 |
| ATOM | 1283 | CG | GLU A | 197 | 48.308 | 23.810 | 23.169 | 1.00 | 34.07 |
| ATOM | 1284 | CD | GLU A | 197 | 49.001 | 22.761 | 22.321 | 1.00 | 38.95 |
| ATOM | 1285 | OE1 | GLU A | 197 | 48.692 | 21.560 | 22.478 | 1.00 | 40.42 |
| ATOM | 1286 | OE2 | GLU A | 197 | 49.863 | 23.141 | 21.501 | 1.00 | 43.50 |
| ATOM | 1287 | C | GLU A | 197 | 48.564 | 27.679 | 23.125 | 1.00 | 19.10 |
| ATOM | 1288 | O | GLU A | 197 | 49.540 | 28.264 | 23.598 | 1.00 | 17.04 |
| ATOM | 1289 | N | GLY A | 198 | 47.830 | 28.168 | 22.128 | 1.00 | 16.78 |
| ATOM | 1290 | CA | GLY A | 198 | 48.136 | 29.460 | 21.545 | 1.00 | 15.98 |
| ATOM | 1291 | C | GLY A | 198 | 48.061 | 30.564 | 22.582 | 1.00 | 14.72 |
| ATOM | 1292 | O | GLY A | 198 | 48.887 | 31.476 | 22.595 | 1.00 | 14.32 |
| ATOM | 1293 | N | VAL A | 199 | 47.061 | 30.483 | 23.453 | 1.00 | 15.12 |
| ATOM | 1294 | CA | VAL A | 199 | 46.887 | 31.471 | 24.508 | 1.00 | 15.39 |
| ATOM | 1295 | CB | VAL A | 199 | 45.619 | 31.187 | 25.345 | 1.00 | 15.96 |
| ATOM | 1296 | CG1 | VAL A | 199 | 45.617 | 32.059 | 26.599 | 1.00 | 12.02 |
| ATOM | 1297 | CG2 | VAL A | 199 | 44.371 | 31.445 | 24.505 | 1.00 | 15.82 |
| ATOM | 1298 | C | VAL A | 199 | 48.084 | 31.458 | 25.452 | 1.00 | 17.58 |
| ATOM | 1299 | O | VAL A | 199 | 48.561 | 32.511 | 25.876 | 1.00 | 18.81 |
| ATOM | 1300 | N | ARG A | 200 | 48.576 | 30.263 | 25.769 | 1.00 | 16.78 |
| ATOM | 1301 | CA | ARG A | 200 | 49.709 | 30.132 | 26.679 | 1.00 | 19.56 |
| ATOM | 1302 | CB | ARG A | 200 | 49.822 | 28.693 | 27.193 | 1.00 | 21.47 |
| ATOM | 1303 | CG | ARG A | 200 | 48.759 | 28.305 | 28.205 | 1.00 | 24.99 |
| ATOM | 1304 | CD | ARG A | 200 | 49.163 | 27.043 | 28.944 | 1.00 | 26.41 |
| ATOM | 1305 | NE | ARG A | 200 | 49.109 | 25.863 | 28.092 | 1.00 | 28.52 |
| ATOM | 1306 | CZ | ARG A | 200 | 48.004 | 25.167 | 27.861 | 1.00 | 30.32 |
| ATOM | 1307 | NH1 | ARG A | 200 | 46.865 | 25.536 | 28.425 | 1.00 | 31.74 |
| ATOM | 1308 | NH2 | ARG A | 200 | 48.037 | 24.102 | 27.069 | 1.00 | 31.33 |
| ATOM | 1309 | C | ARG A | 200 | 51.052 | 30.549 | 26.098 | 1.00 | 18.41 |
| ATOM | 1310 | O | ARG A | 200 | 51.892 | 31.109 | 26.805 | 1.00 | 18.76 |
| ATOM | 1311 | N | VAL A | 201 | 51.258 | 30.281 | 24.815 | 1.00 | 16.94 |
| ATOM | 1312 | CA | VAL A | 201 | 52.525 | 30.610 | 24.181 | 1.00 | 14.62 |
| ATOM | 1313 | CB | VAL A | 201 | 52.843 | 29.618 | 23.035 | 1.00 | 15.42 |
| ATOM | 1314 | CG1 | VAL A | 201 | 54.164 | 30.004 | 22.367 | 1.00 | 13.35 |
| ATOM | 1315 | CG2 | VAL A | 201 | 52.919 | 28.188 | 23.585 | 1.00 | 8.55 |
| ATOM | 1316 | C | VAL A | 201 | 52.627 | 32.037 | 23.643 | 1.00 | 16.13 |
| ATOM | 1317 | O | VAL A | 201 | 53.659 | 32.691 | 23.816 | 1.00 | 13.21 |
| ATOM | 1318 | N | LEU A | 202 | 51.565 | 32.529 | 23.006 | 1.00 | 15.76 |
| ATOM | 1319 | CA | LEU A | 202 | 51.598 | 33.875 | 22.445 | 1.00 | 14.49 |
| ATOM | 1320 | CB | LEU A | 202 | 51.104 | 33.852 | 20.999 | 1.00 | 15.50 |
| ATOM | 1321 | CG | LEU A | 202 | 51.984 | 33.075 | 20.017 | 1.00 | 16.36 |
| ATOM | 1322 | CD1 | LEU A | 202 | 51.499 | 33.329 | 18.595 | 1.00 | 15.07 |
| ATOM | 1323 | CD2 | LEU A | 202 | 53.439 | 33.511 | 20.170 | 1.00 | 15.62 |
| ATOM | 1324 | C | LEU A | 202 | 50.828 | 34.931 | 23.233 | 1.00 | 15.05 |
| ATOM | 1325 | O | LEU A | 202 | 51.067 | 36.125 | 23.068 | 1.00 | 14.28 |
| ATOM | 1326 | N | GLY A | 203 | 49.906 | 34.498 | 24.086 | 1.00 | 15.24 |
| ATOM | 1327 | CA | GLY A | 203 | 49.143 | 35.444 | 24.878 | 1.00 | 16.41 |
| ATOM | 1328 | C | GLY A | 203 | 50.007 | 36.412 | 25.675 | 1.00 | 16.95 |
| ATOM | 1329 | O | GLY A | 203 | 49.647 | 37.582 | 25.841 | 1.00 | 13.97 |
| ATOM | 1330 | N | PRO A | 204 | 51.155 | 35.953 | 26.195 | 1.00 | 17.99 |
| ATOM | 1331 | CD | PRO A | 204 | 51.561 | 34.543 | 26.328 | 1.00 | 17.43 |
| ATOM | 1332 | CA | PRO A | 204 | 52.045 | 36.824 | 26.976 | 1.00 | 18.92 |
| ATOM | 1333 | CB | PRO A | 204 | 53.032 | 35.835 | 27.605 | 1.00 | 16.96 |
| ATOM | 1334 | CG | PRO A | 204 | 52.254 | 34.545 | 27.658 | 1.00 | 17.45 |
| ATOM | 1335 | C | PRO A | 204 | 52.761 | 37.885 | 26.132 | 1.00 | 19.12 |
| ATOM | 1336 | O | PRO A | 204 | 53.361 | 38.820 | 26.672 | 1.00 | 20.34 |
| ATOM | 1337 | N | LEU A | 205 | 52.693 | 37.740 | 24.812 | 1.00 | 17.62 |
| ATOM | 1338 | CA | LEU A | 205 | 53.355 | 38.676 | 23.901 | 1.00 | 16.92 |
| ATOM | 1339 | CB | LEU A | 205 | 54.234 | 37.896 | 22.918 | 1.00 | 16.82 |
| ATOM | 1340 | CG | LEU A | 205 | 55.406 | 37.112 | 23.519 | 1.00 | 18.96 |
| ATOM | 1341 | CD1 | LEU A | 205 | 55.752 | 35.918 | 22.646 | 1.00 | 16.58 |
| ATOM | 1342 | CD2 | LEU A | 205 | 56.599 | 38.040 | 23.679 | 1.00 | 17.87 |
| ATOM | 1343 | C | LEU A | 205 | 52.388 | 39.558 | 23.110 | 1.00 | 17.18 |
| ATOM | 1344 | O | LEU A | 205 | 52.810 | 40.324 | 22.241 | 1.00 | 16.67 |
| ATOM | 1345 | N | ALA A | 206 | 51.099 | 39.469 | 23.417 | 1.00 | 16.36 |
| ATOM | 1346 | CA | ALA A | 206 | 50.108 | 40.243 | 22.686 | 1.00 | 16.19 |
| ATOM | 1347 | CB | ALA A | 206 | 49.216 | 39.295 | 21.900 | 1.00 | 16.04 |
| ATOM | 1348 | C | ALA A | 206 | 49.245 | 41.166 | 23.532 | 1.00 | 17.13 |
| ATOM | 1349 | O | ALA A | 206 | 48.995 | 40.912 | 24.708 | 1.00 | 18.07 |
| ATOM | 1350 | N | ASP A | 207 | 48.788 | 42.251 | 22.924 | 1.00 | 17.38 |
| ATOM | 1351 | CA | ASP A | 207 | 47.913 | 43.169 | 23.627 | 1.00 | 18.09 |
| ATOM | 1352 | CB | ASP A | 207 | 47.941 | 44.542 | 22.964 | 1.00 | 17.76 |

TABLE 29-continued

| | | | | | | | | | |
|---|---|---|---|---|---|---|---|---|---|
| ATOM | 1353 | CG | ASP A | 207 | 49.253 | 45.267 | 23.216 | 1.00 | 20.83 |
| ATOM | 1354 | OD1 | ASP A | 207 | 49.628 | 45.409 | 24.400 | 1.00 | 22.34 |
| ATOM | 1355 | OD2 | ASP A | 207 | 49.912 | 45.691 | 22.245 | 1.00 | 19.95 |
| ATOM | 1356 | C | ASP A | 207 | 46.519 | 42.547 | 23.600 | 1.00 | 16.94 |
| ATOM | 1357 | O | ASP A | 207 | 45.740 | 42.702 | 24.534 | 1.00 | 16.96 |
| ATOM | 1358 | N | TYR A | 208 | 46.217 | 41.825 | 22.526 | 1.00 | 16.01 |
| ATOM | 1359 | CA | TYR A | 208 | 44.941 | 41.136 | 22.420 | 1.00 | 16.14 |
| ATOM | 1360 | CB | TYR A | 208 | 43.843 | 42.043 | 21.830 | 1.00 | 16.24 |
| ATOM | 1361 | CG | TYR A | 208 | 43.913 | 42.321 | 20.340 | 1.00 | 16.53 |
| ATOM | 1362 | CD1 | TYR A | 208 | 44.391 | 43.540 | 19.861 | 1.00 | 17.20 |
| ATOM | 1363 | CE1 | TYR A | 208 | 44.403 | 43.824 | 18.504 | 1.00 | 16.56 |
| ATOM | 1364 | CD2 | TYR A | 208 | 43.454 | 41.388 | 19.414 | 1.00 | 15.47 |
| ATOM | 1365 | CE2 | TYR A | 208 | 43.465 | 41.659 | 18.055 | 1.00 | 14.96 |
| ATOM | 1366 | CZ | TYR A | 208 | 43.939 | 42.878 | 17.605 | 1.00 | 18.58 |
| ATOM | 1367 | OH | TYR A | 208 | 43.955 | 43.148 | 16.254 | 1.00 | 18.48 |
| ATOM | 1368 | C | TYR A | 208 | 45.102 | 39.879 | 21.579 | 1.00 | 16.18 |
| ATOM | 1369 | O | TYR A | 208 | 45.899 | 39.842 | 20.640 | 1.00 | 15.69 |
| ATOM | 1370 | N | LEU A | 209 | 44.361 | 38.842 | 21.951 | 1.00 | 16.49 |
| ATOM | 1371 | CA | LEU A | 209 | 44.385 | 37.570 | 21.244 | 1.00 | 17.41 |
| ATOM | 1372 | CB | LEU A | 209 | 44.519 | 36.407 | 22.226 | 1.00 | 16.83 |
| ATOM | 1373 | CG | LEU A | 209 | 45.850 | 36.202 | 22.939 | 1.00 | 17.95 |
| ATOM | 1374 | CD1 | LEU A | 209 | 45.708 | 35.059 | 23.936 | 1.00 | 18.86 |
| ATOM | 1375 | CD2 | LEU A | 209 | 46.940 | 35.901 | 21.916 | 1.00 | 16.17 |
| ATOM | 1376 | C | LEU A | 209 | 43.082 | 37.413 | 20.479 | 1.00 | 17.21 |
| ATOM | 1377 | O | LEU A | 209 | 42.036 | 37.885 | 20.919 | 1.00 | 17.18 |
| ATOM | 1378 | N | VAL A | 210 | 43.148 | 36.742 | 19.336 | 1.00 | 18.27 |
| ATOM | 1379 | CA | VAL A | 210 | 41.962 | 36.525 | 18.525 | 1.00 | 17.38 |
| ATOM | 1380 | CB | VAL A | 210 | 42.105 | 37.155 | 17.122 | 1.00 | 17.53 |
| ATOM | 1381 | CG1 | VAL A | 210 | 40.819 | 36.931 | 16.314 | 1.00 | 15.25 |
| ATOM | 1382 | CG2 | VAL A | 210 | 42.424 | 38.633 | 17.242 | 1.00 | 13.97 |
| ATOM | 1383 | C | VAL A | 210 | 41.688 | 35.045 | 18.334 | 1.00 | 18.13 |
| ATOM | 1384 | O | VAL A | 210 | 42.503 | 34.323 | 17.767 | 1.00 | 18.42 |
| ATOM | 1385 | N | VAL A | 211 | 40.545 | 34.589 | 18.826 | 1.00 | 18.92 |
| ATOM | 1386 | CA | VAL A | 211 | 40.168 | 33.198 | 18.638 | 1.00 | 18.84 |
| ATOM | 1387 | CB | VAL A | 211 | 39.141 | 32.732 | 19.691 | 1.00 | 17.39 |
| ATOM | 1388 | CG1 | VAL A | 211 | 38.712 | 31.309 | 19.395 | 1.00 | 14.12 |
| ATOM | 1389 | CG2 | VAL A | 211 | 39.741 | 32.826 | 21.086 | 1.00 | 17.05 |
| ATOM | 1390 | C | VAL A | 211 | 39.514 | 33.164 | 17.256 | 1.00 | 19.52 |
| ATOM | 1391 | O | VAL A | 211 | 38.355 | 33.554 | 17.100 | 1.00 | 18.05 |
| ATOM | 1392 | N | ASN A | 212 | 40.265 | 32.728 | 16.250 | 1.00 | 19.73 |
| ATOM | 1393 | CA | ASN A | 212 | 39.725 | 32.665 | 14.904 | 1.00 | 20.91 |
| ATOM | 1394 | CB | ASN A | 212 | 40.835 | 32.725 | 13.858 | 1.00 | 19.36 |
| ATOM | 1395 | CG | ASN A | 212 | 40.287 | 32.677 | 12.448 | 1.00 | 18.94 |
| ATOM | 1396 | OD1 | ASN A | 212 | 39.074 | 32.682 | 12.253 | 1.00 | 19.73 |
| ATOM | 1397 | ND2 | ASN A | 212 | 41.169 | 32.632 | 11.461 | 1.00 | 18.71 |
| ATOM | 1398 | C | ASN A | 212 | 38.924 | 31.388 | 14.714 | 1.00 | 22.66 |
| ATOM | 1399 | O | ASN A | 212 | 39.479 | 30.291 | 14.606 | 1.00 | 23.56 |
| ATOM | 1400 | N | VAL A | 213 | 37.610 | 31.538 | 14.660 | 1.00 | 21.24 |
| ATOM | 1401 | CA | VAL A | 213 | 36.744 | 30.387 | 14.499 | 1.00 | 22.82 |
| ATOM | 1402 | CB | VAL A | 213 | 35.893 | 30.196 | 15.768 | 1.00 | 23.98 |
| ATOM | 1403 | CG1 | VAL A | 213 | 34.778 | 31.242 | 15.822 | 1.00 | 23.80 |
| ATOM | 1404 | CG2 | VAL A | 213 | 35.343 | 28.811 | 15.800 | 1.00 | 27.23 |
| ATOM | 1405 | C | VAL A | 213 | 35.838 | 30.579 | 13.282 | 1.00 | 21.82 |
| ATOM | 1406 | O | VAL A | 213 | 34.813 | 29.904 | 13.134 | 1.00 | 21.63 |
| ATOM | 1407 | N | SER A | 214 | 36.243 | 31.492 | 12.402 | 1.00 | 21.12 |
| ATOM | 1408 | CA | SER A | 214 | 35.468 | 31.811 | 11.211 | 1.00 | 19.76 |
| ATOM | 1409 | CB | SER A | 214 | 35.010 | 33.270 | 11.273 | 1.00 | 19.69 |
| ATOM | 1410 | OG | SER A | 214 | 36.100 | 34.142 | 11.527 | 1.00 | 15.15 |
| ATOM | 1411 | C | SER A | 214 | 36.181 | 31.556 | 9.887 | 1.00 | 20.87 |
| ATOM | 1412 | O | SER A | 214 | 35.712 | 31.995 | 8.837 | 1.00 | 18.78 |
| ATOM | 1413 | N | SER A | 215 | 37.311 | 30.859 | 9.921 | 1.00 | 22.57 |
| ATOM | 1414 | CA | SER A | 215 | 38.012 | 30.570 | 8.678 | 1.00 | 23.58 |
| ATOM | 1415 | CB | SER A | 215 | 39.388 | 29.976 | 8.951 | 1.00 | 25.79 |
| ATOM | 1416 | OG | SER A | 215 | 40.016 | 29.608 | 7.732 | 1.00 | 25.68 |
| ATOM | 1417 | C | SER A | 215 | 37.187 | 29.571 | 7.874 | 1.00 | 24.56 |
| ATOM | 1418 | O | SER A | 215 | 36.750 | 28.544 | 8.393 | 1.00 | 24.98 |
| ATOM | 1419 | N | PRO A | 216 | 36.955 | 29.866 | 6.591 | 1.00 | 26.27 |
| ATOM | 1420 | CD | PRO A | 216 | 37.219 | 31.148 | 5.908 | 1.00 | 24.27 |
| ATOM | 1421 | CA | PRO A | 216 | 36.174 | 28.969 | 5.737 | 1.00 | 27.15 |
| ATOM | 1422 | CB | PRO A | 216 | 35.594 | 29.921 | 4.703 | 1.00 | 26.46 |
| ATOM | 1423 | CG | PRO A | 216 | 36.739 | 30.875 | 4.492 | 1.00 | 24.79 |
| ATOM | 1424 | C | PRO A | 216 | 37.035 | 27.897 | 5.084 | 1.00 | 28.49 |
| ATOM | 1425 | O | PRO A | 216 | 36.519 | 27.019 | 4.398 | 1.00 | 30.31 |
| ATOM | 1426 | N | ASN A | 217 | 38.345 | 27.966 | 5.308 | 1.00 | 30.00 |
| ATOM | 1427 | CA | ASN A | 217 | 39.270 | 27.026 | 4.686 | 1.00 | 31.48 |
| ATOM | 1428 | CB | ASN A | 217 | 40.438 | 27.803 | 4.080 | 1.00 | 31.24 |
| ATOM | 1429 | CG | ASN A | 217 | 39.969 | 28.926 | 3.176 | 1.00 | 32.97 |
| ATOM | 1430 | OD1 | ASN A | 217 | 39.213 | 28.699 | 2.230 | 1.00 | 33.41 |
| ATOM | 1431 | ND2 | ASN A | 217 | 40.410 | 30.147 | 3.465 | 1.00 | 32.16 |

TABLE 29-continued

| | | | | | | | | | |
|---|---|---|---|---|---|---|---|---|---|
| ATOM | 1432 | C | ASN A | 217 | 39.792 | 25.889 | 5.554 | 1.00 | 32.38 |
| ATOM | 1433 | O | ASN A | 217 | 40.776 | 25.234 | 5.204 | 1.00 | 31.80 |
| ATOM | 1434 | N | THR A | 218 | 39.135 | 25.658 | 6.685 | 1.00 | 33.60 |
| ATOM | 1435 | CA | THR A | 218 | 39.507 | 24.567 | 7.581 | 1.00 | 34.67 |
| ATOM | 1436 | CB | THR A | 218 | 40.182 | 25.079 | 8.875 | 1.00 | 35.71 |
| ATOM | 1437 | OG1 | THR A | 218 | 41.502 | 25.553 | 8.574 | 1.00 | 34.15 |
| ATOM | 1438 | CG2 | THR A | 218 | 40.276 | 23.961 | 9.902 | 1.00 | 34.11 |
| ATOM | 1439 | C | THR A | 218 | 38.231 | 23.809 | 7.933 | 1.00 | 35.34 |
| ATOM | 1440 | O | THR A | 218 | 37.313 | 24.365 | 8.539 | 1.00 | 35.59 |
| ATOM | 1441 | N | ALA A | 219 | 38.182 | 22.541 | 7.531 | 1.00 | 35.68 |
| ATOM | 1442 | CA | ALA A | 219 | 37.027 | 21.677 | 7.761 | 1.00 | 35.27 |
| ATOM | 1443 | CB | ALA A | 219 | 37.366 | 20.243 | 7.356 | 1.00 | 33.44 |
| ATOM | 1444 | C | ALA A | 219 | 36.482 | 21.693 | 9.185 | 1.00 | 35.21 |
| ATOM | 1445 | O | ALA A | 219 | 37.205 | 21.424 | 10.145 | 1.00 | 35.80 |
| ATOM | 1446 | N | GLY A | 220 | 35.196 | 22.013 | 9.304 | 1.00 | 35.33 |
| ATOM | 1447 | CA | GLY A | 220 | 34.533 | 22.038 | 10.598 | 1.00 | 35.53 |
| ATOM | 1448 | C | GLY A | 220 | 34.909 | 23.125 | 11.589 | 1.00 | 35.22 |
| ATOM | 1449 | O | SLY A | 220 | 34.434 | 23.102 | 12.723 | 1.00 | 35.56 |
| ATOM | 1450 | N | LEU A | 221 | 35.743 | 24.079 | 11.183 | 1.00 | 34.69 |
| ATOM | 1451 | CA | LEU A | 221 | 36.157 | 25.148 | 12.088 | 1.00 | 34.37 |
| ATOM | 1452 | CB | LEU A | 221 | 37.303 | 25.961 | 11.478 | 1.00 | 34.53 |
| ATOM | 1453 | CG | LEU A | 221 | 37.918 | 26.976 | 12.450 | 1.00 | 34.35 |
| ATOM | 1454 | CD1 | LEU A | 221 | 38.857 | 26.238 | 13.396 | 1.00 | 35.01 |
| ATOM | 1455 | CD2 | LEU A | 221 | 38.671 | 28.060 | 11.695 | 1.00 | 33.25 |
| ATOM | 1456 | C | LEU A | 221 | 35.012 | 26.095 | 12.443 | 1.00 | 34.00 |
| ATOM | 1457 | O | LEU A | 221 | 34.831 | 26.462 | 13.605 | 1.00 | 34.07 |
| ATOM | 1458 | N | ARG A | 222 | 34.240 | 26.491 | 11.438 | 1.00 | 34.48 |
| ATOM | 1459 | CA | ARG A | 222 | 33.124 | 27.404 | 11.650 | 1.00 | 34.48 |
| ATOM | 1460 | CB | ARG A | 222 | 32.544 | 27.837 | 10.304 | 1.00 | 34.91 |
| ATOM | 1461 | CG | ARG A | 222 | 33.445 | 28.786 | 9.525 | 1.00 | 35.80 |
| ATOM | 1462 | CD | ARG A | 222 | 32.870 | 29.056 | 8.148 | 1.00 | 38.02 |
| ATOM | 1463 | NE | ARG A | 222 | 32.938 | 27.873 | 7.293 | 1.00 | 38.82 |
| ATOM | 1464 | CZ | ARG A | 222 | 32.210 | 27.700 | 6.195 | 1.00 | 39.23 |
| ATOM | 1465 | NH1 | ARG A | 222 | 31.349 | 28.635 | 5.812 | 1.00 | 37.27 |
| ATOM | 1466 | NH2 | ARG A | 222 | 32.348 | 26.593 | 5.476 | 1.00 | 38.53 |
| ATOM | 1467 | C | ARG A | 222 | 32.018 | 26.836 | 12.536 | 1.00 | 34.30 |
| ATOM | 1468 | O | ARG A | 222 | 31.224 | 27.592 | 13.100 | 1.00 | 33.00 |
| ATOM | 1469 | N | SER A | 223 | 31.963 | 25.514 | 12.665 | 1.00 | 34.10 |
| ATOM | 1470 | CA | SER A | 223 | 30.940 | 24.892 | 13.498 | 1.00 | 33.94 |
| ATOM | 1471 | CB | SER A | 223 | 30.930 | 23.371 | 13.311 | 1.00 | 32.71 |
| ATOM | 1472 | OG | SER A | 223 | 32.106 | 22.778 | 13.831 | 1.00 | 36.35 |
| ATOM | 1473 | C | SER A | 223 | 31.212 | 25.236 | 14.959 | 1.00 | 33.63 |
| ATOM | 1474 | O | SER A | 223 | 30.335 | 25.103 | 15.814 | 1.00 | 32.92 |
| ATOM | 1475 | N | LEU A | 224 | 32.433 | 25.683 | 15.240 | 1.00 | 33.63 |
| ATOM | 1476 | CA | LEU A | 224 | 32.806 | 26.062 | 16.598 | 1.00 | 34.04 |
| ATOM | 1477 | CB | LEU A | 224 | 34.328 | 26.196 | 16.721 | 1.00 | 33.19 |
| ATOM | 1478 | CG | LEU A | 224 | 35.192 | 24.950 | 16.506 | 1.00 | 34.59 |
| ATOM | 1479 | CD1 | LEU A | 224 | 36.664 | 25.336 | 16.506 | 1.00 | 31.62 |
| ATOM | 1480 | CD2 | LEU A | 224 | 34.900 | 23.932 | 17.599 | 1.00 | 31.62 |
| ATOM | 1481 | C | LEU A | 224 | 32.135 | 27.384 | 16.974 | 1.00 | 33.88 |
| ATOM | 1482 | O | LEU A | 224 | 32.244 | 27.845 | 18.110 | 1.00 | 33.46 |
| ATOM | 1483 | N | GLN A | 225 | 31.452 | 27.997 | 16.011 | 1.00 | 34.56 |
| ATOM | 1484 | CA | GLN A | 225 | 30.751 | 29.251 | 16.270 | 1.00 | 35.35 |
| ATOM | 1485 | CB | GLN A | 225 | 30.539 | 30.046 | 14.970 | 1.00 | 34.80 |
| ATOM | 1486 | CG | GLN A | 225 | 31.825 | 30.373 | 14.212 | 1.00 | 35.04 |
| ATOM | 1487 | CD | GLN A | 225 | 31.583 | 31.194 | 12.951 | 1.00 | 34.62 |
| ATOM | 1488 | OE1 | GLN A | 225 | 31.541 | 32.428 | 12.991 | 1.00 | 32.02 |
| ATOM | 1489 | NE2 | GLN A | 225 | 31.410 | 30.508 | 11.824 | 1.00 | 32.11 |
| ATOM | 1490 | C | GLN A | 225 | 29.402 | 28.920 | 16.910 | 1.00 | 34.70 |
| ATOM | 1491 | O | GLN A | 225 | 28.696 | 29.809 | 17.386 | 1.00 | 34.24 |
| ATOM | 1492 | N | GLY A | 226 | 29.055 | 27.634 | 16.917 | 1.00 | 34.70 |
| ATOM | 1493 | CA | GLY A | 226 | 27.802 | 27.198 | 17.516 | 1.00 | 34.95 |
| ATOM | 1494 | C | GLY A | 226 | 27.786 | 27.497 | 19.005 | 1.00 | 35.26 |
| ATOM | 1495 | O | GLY A | 226 | 28.831 | 27.463 | 19.654 | 1.00 | 36.21 |
| ATOM | 1496 | N | LYS A | 227 | 26.604 | 27.772 | 19.549 | 1.00 | 34.42 |
| ATOM | 1497 | CA | LYS A | 227 | 26.453 | 28.116 | 20.964 | 1.00 | 34.17 |
| ATOM | 1498 | CB | LYS A | 227 | 24.968 | 28.234 | 21.321 | 1.00 | 32.71 |
| ATOM | 1499 | CG | LYS A | 227 | 24.712 | 28.922 | 22.658 | 1.00 | 32.69 |
| ATOM | 1500 | CD | LYS A | 227 | 23.236 | 29.227 | 22.852 | 1.00 | 32.86 |
| ATOM | 1501 | CE | LYS A | 227 | 22.974 | 29.932 | 24.175 | 1.00 | 34.60 |
| ATOM | 1502 | NZ | LYS A | 227 | 23.622 | 31.274 | 24.244 | 1.00 | 37.35 |
| ATOM | 1503 | C | LYS A | 227 | 27.142 | 27.193 | 21.968 | 1.00 | 34.30 |
| ATOM | 1504 | O | LYS A | 227 | 27.965 | 27.648 | 22.764 | 1.00 | 33.44 |
| ATOM | 1505 | N | ALA A | 228 | 26.807 | 25.906 | 21.942 | 1.00 | 34.25 |
| ATOM | 1506 | CA | ALA A | 228 | 27.403 | 24.950 | 22.877 | 1.00 | 35.39 |
| ATOM | 1507 | CB | ALA A | 228 | 26.742 | 23.585 | 22.722 | 1.00 | 33.05 |
| ATOM | 1508 | C | ALA A | 228 | 28.912 | 24.822 | 22.681 | 1.00 | 35.36 |
| ATOM | 1509 | O | ALA A | 228 | 29.685 | 24.947 | 23.629 | 1.00 | 34.05 |
| ATOM | 1510 | N | GLU A | 229 | 29.322 | 24.566 | 21.443 | 1.00 | 36.97 |

TABLE 29-continued

| | | | | | | | | | |
|---|---|---|---|---|---|---|---|---|---|
| ATOM | 1511 | CA | GLU A | 229 | 30.733 | 24.424 | 21.108 | 1.00 | 38.17 |
| ATOM | 1512 | CB | GLU A | 229 | 30.885 | 24.141 | 19.608 | 1.00 | 42.08 |
| ATOM | 1513 | CG | GLU A | 229 | 31.463 | 22.771 | 19.271 | 1.00 | 48.40 |
| ATOM | 1514 | CD | GLU A | 229 | 31.399 | 22.459 | 17.782 | 1.00 | 51.77 |
| ATOM | 1515 | OE1 | GLU A | 229 | 30.279 | 22.273 | 17.258 | 1.00 | 54.82 |
| ATOM | 1516 | OE2 | GLU A | 229 | 32.467 | 22.402 | 17.133 | 1.00 | 53.10 |
| ATOM | 1517 | C | GLU A | 229 | 31.506 | 25.691 | 21.470 | 1.00 | 35.95 |
| ATOM | 1518 | O | GLU A | 229 | 32.587 | 25.627 | 22.052 | 1.00 | 36.51 |
| ATOM | 1519 | N | LEU A | 230 | 30.935 | 26.842 | 21.133 | 1.00 | 33.64 |
| ATOM | 1520 | CA | LEU A | 230 | 31.573 | 28.123 | 21.399 | 1.00 | 30.71 |
| ATOM | 1521 | CB | LEU A | 230 | 30.768 | 29.265 | 20.763 | 1.00 | 28.43 |
| ATOM | 1522 | CG | LEU A | 230 | 31.388 | 30.665 | 20.836 | 1.00 | 26.75 |
| ATOM | 1523 | CD1 | LEU A | 230 | 32.723 | 30.679 | 20.096 | 1.00 | 24.08 |
| ATOM | 1524 | CD2 | LEU A | 230 | 30.438 | 31.680 | 20.223 | 1.00 | 26.42 |
| ATOM | 1525 | C | LEU A | 230 | 31.751 | 28.401 | 22.884 | 1.00 | 29.09 |
| ATOM | 1526 | O | LEU A | 230 | 32.787 | 28.918 | 23.300 | 1.00 | 28.84 |
| ATOM | 1527 | N | ARG A | 231 | 30.745 | 28.065 | 23.684 | 1.00 | 28.50 |
| ATOM | 1528 | CA | ARG A | 231 | 30.820 | 28.312 | 25.118 | 1.00 | 28.34 |
| ATOM | 1529 | CB | ARG A | 231 | 29.473 | 28.016 | 25.787 | 1.00 | 29.52 |
| ATOM | 1530 | CG | ARG A | 231 | 29.427 | 28.407 | 27.260 | 1.00 | 32.29 |
| ATOM | 1531 | CD | ARG A | 231 | 28.148 | 27.937 | 27.936 | 1.00 | 36.19 |
| ATOM | 1532 | NE | ARG A | 231 | 26.969 | 28.685 | 27.506 | 1.00 | 38.72 |
| ATOM | 1533 | CZ | ARG A | 231 | 25.885 | 28.128 | 26.974 | 1.00 | 39.27 |
| ATOM | 1534 | NH1 | ARG A | 231 | 25.833 | 26.815 | 26.799 | 1.00 | 40.30 |
| ATOM | 1535 | NH2 | ARG A | 231 | 24.848 | 28.881 | 26.632 | 1.00 | 38.91 |
| ATOM | 1536 | C | ARG A | 231 | 31.925 | 27.492 | 25.788 | 1.00 | 27.28 |
| ATOM | 1537 | O | ARG A | 231 | 32.681 | 28.015 | 26.601 | 1.00 | 25.62 |
| ATOM | 1538 | N | ARG A | 232 | 32.014 | 26.210 | 25.448 | 1.00 | 27.02 |
| ATOM | 1539 | CA | ARG A | 232 | 33.035 | 25.343 | 26.026 | 1.00 | 28.51 |
| ATOM | 1540 | CB | ARG A | 232 | 32.813 | 23.887 | 25.603 | 1.00 | 31.69 |
| ATOM | 1541 | CG | ARG A | 232 | 33.898 | 22.937 | 26.103 | 1.00 | 37.81 |
| ATOM | 1542 | CD | ARG A | 232 | 33.653 | 21.483 | 25.692 | 1.00 | 42.26 |
| ATOM | 1543 | NE | ARG A | 232 | 32.323 | 21.016 | 26.081 | 1.00 | 46.87 |
| ATOM | 1544 | CZ | ARG A | 232 | 31.239 | 21.131 | 25.318 | 1.00 | 49.45 |
| ATOM | 1545 | NH1 | ARG A | 232 | 31.329 | 21.691 | 24.118 | 1.00 | 49.90 |
| ATOM | 1546 | NH2 | ARG A | 232 | 30.064 | 20.697 | 25.758 | 1.00 | 49.90 |
| ATOM | 1547 | C | ARG A | 232 | 34.421 | 25.793 | 25.584 | 1.00 | 26.98 |
| ATOM | 1548 | O | ARG A | 232 | 35.372 | 25.776 | 26.363 | 1.00 | 26.34 |
| ATOM | 1549 | N | LEU A | 233 | 34.529 | 26.196 | 24.324 | 1.00 | 25.27 |
| ATOM | 1550 | CA | LEU A | 233 | 35.796 | 26.657 | 23.782 | 1.00 | 24.87 |
| ATOM | 1551 | CB | LEU A | 233 | 35.655 | 26.912 | 22.282 | 1.00 | 25.82 |
| ATOM | 1552 | CG | LEU A | 233 | 36.829 | 27.628 | 21.615 | 1.00 | 26.85 |
| ATOM | 1553 | CD1 | LEU A | 233 | 38.077 | 26.783 | 21.734 | 1.00 | 28.70 |
| ATOM | 1554 | CD2 | LEU A | 233 | 36.500 | 27.896 | 20.161 | 1.00 | 28.50 |
| ATOM | 1555 | C | LEU A | 233 | 36.285 | 27.932 | 24.475 | 1.00 | 24.30 |
| ATOM | 1556 | O | LEU A | 233 | 37.423 | 27.995 | 24.943 | 1.00 | 22.17 |
| ATOM | 1557 | N | LEU A | 234 | 35.417 | 28.939 | 24.546 | 1.00 | 22.83 |
| ATOM | 1558 | CA | LEU A | 234 | 35.767 | 30.222 | 25.153 | 1.00 | 22.68 |
| ATOM | 1559 | CB | LEU A | 234 | 34.721 | 31.278 | 24.782 | 1.00 | 23.83 |
| ATOM | 1560 | CG | LEU A | 234 | 34.666 | 31.550 | 23.275 | 1.00 | 26.75 |
| ATOM | 1561 | CD1 | LEU A | 234 | 33.574 | 32.559 | 22.952 | 1.00 | 28.02 |
| ATOM | 1562 | CD2 | LEU A | 234 | 36.025 | 32.053 | 22.815 | 1.00 | 26.81 |
| ATOM | 1563 | C | LEU A | 234 | 35.956 | 30.183 | 26.665 | 1.00 | 21.66 |
| ATOM | 1564 | O | LEU A | 234 | 36.697 | 30.991 | 27.221 | 1.00 | 20.64 |
| ATOM | 1565 | N | THR A | 235 | 35.286 | 29.257 | 27.336 | 1.00 | 21.48 |
| ATOM | 1566 | CA | THR A | 235 | 35.447 | 29.143 | 28.779 | 1.00 | 22.71 |
| ATOM | 1567 | CB | THR A | 235 | 34.468 | 28.115 | 29.378 | 1.00 | 23.15 |
| ATOM | 1568 | OG1 | THR A | 235 | 33.136 | 28.640 | 29.321 | 1.00 | 24.32 |
| ATOM | 1569 | CG2 | THR A | 235 | 34.833 | 27.812 | 30.824 | 1.00 | 20.23 |
| ATOM | 1570 | C | THR A | 235 | 36.882 | 28.701 | 29.075 | 1.00 | 21.92 |
| ATOM | 1571 | O | THR A | 235 | 37.530 | 29.227 | 29.980 | 1.00 | 22.20 |
| ATOM | 1572 | N | LYS A | 236 | 37.371 | 27.743 | 28.293 | 1.00 | 19.41 |
| ATOM | 1573 | CA | LYS A | 236 | 38.724 | 27.233 | 28.456 | 1.00 | 21.47 |
| ATOM | 1574 | CB | LYS A | 236 | 38.906 | 25.956 | 27.634 | 1.00 | 23.11 |
| ATOM | 1575 | CG | LYS A | 236 | 40.249 | 25.277 | 27.855 | 1.00 | 30.29 |
| ATOM | 1576 | CD | LYS A | 236 | 40.274 | 23.875 | 27.258 | 1.00 | 32.54 |
| ATOM | 1577 | CE | LYS A | 236 | 41.569 | 23.162 | 27.600 | 1.00 | 35.14 |
| ATOM | 1578 | NZ | LYS A | 236 | 41.531 | 21.727 | 27.194 | 1.00 | 38.21 |
| ATOM | 1579 | C | LYS A | 236 | 39.766 | 28.276 | 28.043 | 1.00 | 20.48 |
| ATOM | 1580 | O | LYS A | 236 | 40.778 | 28.455 | 28.720 | 1.00 | 19.24 |
| ATOM | 1581 | N | VAL A | 237 | 39.512 | 28.966 | 26.937 | 1.00 | 19.58 |
| ATOM | 1582 | CA | VAL A | 237 | 40.425 | 29.997 | 26.456 | 1.00 | 19.48 |
| ATOM | 1583 | CB | VAL A | 237 | 39.911 | 30.614 | 25.138 | 1.00 | 19.06 |
| ATOM | 1584 | CG1 | VAL A | 237 | 40.647 | 31.918 | 24.836 | 1.00 | 15.24 |
| ATOM | 1585 | CG2 | VAL A | 237 | 40.104 | 29.621 | 24.003 | 1.00 | 17.14 |
| ATOM | 1586 | C | VAL A | 237 | 40.587 | 31.104 | 27.495 | 1.00 | 20.14 |
| ATOM | 1587 | O | VAL A | 237 | 41.708 | 31.499 | 27.826 | 1.00 | 20.24 |
| ATOM | 1588 | N | LEU A | 238 | 39.462 | 31.594 | 28.010 | 1.00 | 20.89 |
| ATOM | 1589 | CA | LEU A | 238 | 39.462 | 32.657 | 29.013 | 1.00 | 21.10 |

TABLE 29-continued

| | | | | | | | | |
|---|---|---|---|---|---|---|---|---|
| ATOM | 1590 | CB | LEU A | 238 | 38.032 | 33.116 | 29.296 | 1.00 | 19.72 |
| ATOM | 1591 | CG | LEU A | 238 | 37.359 | 33.891 | 28.159 | 1.00 | 21.61 |
| ATOM | 1592 | CD1 | LEU A | 238 | 35.889 | 34.122 | 28.486 | 1.00 | 21.43 |
| ATOM | 1593 | CD2 | LEU A | 238 | 38.079 | 35.218 | 27.956 | 1.00 | 21.42 |
| ATOM | 1594 | C | LEU A | 238 | 40.132 | 32.228 | 30.315 | 1.00 | 21.64 |
| ATOM | 1595 | O | LEU A | 238 | 40.772 | 33.041 | 30.989 | 1.00 | 20.34 |
| ATOM | 1596 | N | GLN A | 239 | 39.986 | 30.954 | 30.669 | 1.00 | 21.87 |
| ATOM | 1597 | CA | GLN A | 239 | 40.601 | 30.446 | 31.888 | 1.00 | 22.65 |
| ATOM | 1598 | CB | GLN A | 239 | 40.119 | 29.023 | 32.185 | 1.00 | 24.73 |
| ATOM | 1599 | CG | GLN A | 239 | 40.644 | 28.468 | 33.500 | 1.00 | 29.71 |
| ATOM | 1600 | CD | GLN A | 239 | 40.120 | 27.073 | 33.799 | 1.00 | 36.85 |
| ATOM | 1601 | OE1 | GLN A | 239 | 38.906 | 26.850 | 33.859 | 1.00 | 40.00 |
| ATOM | 1602 | NE2 | GLN A | 239 | 41.033 | 26.126 | 33.991 | 1.00 | 35.90 |
| ATOM | 1603 | C | GLN A | 239 | 42.122 | 30.460 | 31.739 | 1.00 | 20.03 |
| ATOM | 1604 | O | GLN A | 239 | 42.839 | 30.880 | 32.645 | 1.00 | 20.49 |
| ATOM | 1605 | N | GLU A | 240 | 42.611 | 29.996 | 30.596 | 1.00 | 19.71 |
| ATOM | 1606 | CA | GLU A | 240 | 44.049 | 29.985 | 30.344 | 1.00 | 20.04 |
| ATOM | 1607 | CB | GLU A | 240 | 44.346 | 29.343 | 28.989 | 1.00 | 21.58 |
| ATOM | 1608 | CG | GLU A | 240 | 44.001 | 27.864 | 28.918 | 1.00 | 28.50 |
| ATOM | 1609 | CD | GLU A | 240 | 44.957 | 26.990 | 29.720 | 1.00 | 32.28 |
| ATOM | 1610 | OE1 | GLU A | 240 | 44.689 | 25.775 | 29.834 | 1.00 | 36.62 |
| ATOM | 1611 | OE2 | GLU A | 240 | 45.980 | 27.504 | 30.225 | 1.00 | 32.81 |
| ATOM | 1612 | C | GLU A | 240 | 44.566 | 31.424 | 30.358 | 1.00 | 19.32 |
| ATOM | 1613 | O | GLU A | 240 | 45.654 | 31.697 | 30.860 | 1.00 | 20.01 |
| ATOM | 1614 | N | ARG A | 241 | 43.767 | 32.337 | 29.811 | 1.00 | 17.04 |
| ATOM | 1615 | CA | ARG A | 241 | 44.120 | 33.750 | 29.754 | 1.00 | 17.15 |
| ATOM | 1616 | CB | ARG A | 241 | 43.081 | 34.504 | 28.914 | 1.00 | 15.66 |
| ATOM | 1617 | CG | ARG A | 241 | 43.402 | 35.966 | 28.629 | 1.00 | 15.53 |
| ATOM | 1618 | CD | ARG A | 241 | 43.191 | 36.870 | 29.840 | 1.00 | 13.45 |
| ATOM | 1619 | NE | ARG A | 241 | 41.804 | 36.911 | 30.299 | 1.00 | 15.41 |
| ATOM | 1620 | CZ | ARG A | 241 | 40.832 | 37.624 | 29.731 | 1.00 | 16.80 |
| ATOM | 1621 | NH1 | ARG A | 241 | 39.605 | 37.584 | 30.236 | 1.00 | 14.85 |
| ATOM | 1622 | NH2 | ARG A | 241 | 41.077 | 38.384 | 28.669 | 1.00 | 13.90 |
| ATOM | 1623 | C | ARG A | 241 | 44.218 | 34.369 | 31.149 | 1.00 | 18.11 |
| ATOM | 1624 | O | ARG A | 241 | 45.172 | 35.090 | 31.445 | 1.00 | 16.96 |
| ATOM | 1625 | N | ASP A | 242 | 43.234 | 34.093 | 32.004 | 1.00 | 18.89 |
| ATOM | 1626 | CA | ASP A | 242 | 43.233 | 34.643 | 33.358 | 1.00 | 18.99 |
| ATOM | 1627 | CB | ASP A | 242 | 41.902 | 34.352 | 34.071 | 1.00 | 18.23 |
| ATOM | 1628 | CG | ASP A | 242 | 40.708 | 35.016 | 33.391 | 1.00 | 20.88 |
| ATOM | 1629 | OD1 | ASP A | 242 | 40.884 | 36.078 | 32.759 | 1.00 | 20.84 |
| ATOM | 1630 | OD2 | ASP A | 242 | 39.583 | 34.484 | 33.506 | 1.00 | 20.07 |
| ATOM | 1631 | C | ASP A | 242 | 44.393 | 34.097 | 34.196 | 1.00 | 18.74 |
| ATOM | 1632 | O | ASP A | 242 | 44.788 | 34.709 | 35.188 | 1.00 | 18.25 |
| ATOM | 1633 | N | GLY A | 243 | 44.939 | 32.955 | 33.789 | 1.00 | 17.54 |
| ATOM | 1634 | CA | GLY A | 243 | 46.050 | 32.365 | 34.517 | 1.00 | 17.70 |
| ATOM | 1635 | C | GLY A | 243 | 47.396 | 33.010 | 34.212 | 1.00 | 18.91 |
| ATOM | 1636 | O | GLY A | 243 | 48.415 | 32.658 | 34.813 | 1.00 | 18.37 |
| ATOM | 1637 | N | LEU A | 244 | 47.417 | 33.954 | 33.277 | 1.00 | 18.18 |
| ATOM | 1638 | CA | LEU A | 244 | 48.665 | 34.629 | 32.930 | 1.00 | 19.11 |
| ATOM | 1639 | CB | LEU A | 244 | 48.623 | 35.130 | 31.481 | 1.00 | 16.84 |
| ATOM | 1640 | CG | LEU A | 244 | 48.395 | 34.083 | 30.391 | 1.00 | 17.33 |
| ATOM | 1641 | CD1 | LEU A | 244 | 48.265 | 34.771 | 29.046 | 1.00 | 16.03 |
| ATOM | 1642 | CD2 | LEU A | 244 | 49.545 | 33.085 | 30.388 | 1.00 | 18.05 |
| ATOM | 1643 | C | LEU A | 244 | 48.908 | 35.810 | 33.864 | 1.00 | 19.01 |
| ATOM | 1644 | O | LEU A | 244 | 47.964 | 36.402 | 34.387 | 1.00 | 18.42 |
| ATOM | 1645 | N | ARG A | 245 | 50.176 | 36.147 | 34.073 | 1.00 | 19.39 |
| ATOM | 1646 | CA | ARG A | 245 | 50.523 | 37.272 | 34.930 | 1.00 | 20.56 |
| ATOM | 1647 | CB | ARG A | 245 | 52.046 | 37.354 | 35.091 | 1.00 | 19.53 |
| ATOM | 1648 | CG | ARG A | 245 | 52.602 | 36.290 | 36.052 | 1.00 | 19.09 |
| ATOM | 1649 | CD | ARG A | 245 | 54.072 | 35.987 | 35.813 | 1.00 | 18.19 |
| ATOM | 1650 | NE | ARG A | 245 | 54.973 | 37.051 | 36.252 | 1.00 | 19.29 |
| ATOM | 1651 | CZ | ARG A | 245 | 55.412 | 37.201 | 37.499 | 1.00 | 19.63 |
| ATOM | 1652 | NH1 | ARG A | 245 | 56.233 | 38.201 | 37.796 | 1.00 | 15.65 |
| ATOM | 1653 | NH2 | ARG A | 245 | 55.036 | 36.350 | 38.449 | 1.00 | 17.09 |
| ATOM | 1654 | C | ARG A | 245 | 49.951 | 38.569 | 34.353 | 1.00 | 22.53 |
| ATOM | 1655 | O | ARG A | 245 | 49.890 | 38.748 | 33.133 | 1.00 | 21.12 |
| ATOM | 1656 | N | ARG A | 246 | 49.525 | 39.456 | 35.250 | 1.00 | 25.32 |
| ATOM | 1657 | CA | ARG A | 246 | 48.920 | 40.747 | 34.914 | 1.00 | 27.15 |
| ATOM | 1658 | CB | ARG A | 246 | 49.004 | 41.683 | 36.124 | 1.00 | 30.54 |
| ATOM | 1659 | CG | ARG A | 246 | 48.337 | 41.129 | 37.369 | 1.00 | 37.47 |
| ATOM | 1660 | CD | ARG A | 246 | 46.817 | 41.284 | 37.328 | 1.00 | 41.51 |
| ATOM | 1661 | NE | ARG A | 246 | 46.136 | 40.393 | 38.270 | 1.00 | 41.54 |
| ATOM | 1662 | CZ | ARG A | 246 | 46.497 | 40.210 | 39.536 | 1.00 | 40.36 |
| ATOM | 1663 | NH1 | ARG A | 246 | 47.545 | 40.851 | 40.037 | 1.00 | 39.56 |
| ATOM | 1664 | NH2 | ARG A | 246 | 45.806 | 39.382 | 40.305 | 1.00 | 41.42 |
| ATOM | 1665 | C | ARG A | 246 | 49.442 | 41.490 | 33.687 | 1.00 | 26.72 |
| ATOM | 1666 | O | ARG A | 246 | 48.677 | 41.765 | 32.762 | 1.00 | 26.83 |
| ATOM | 1667 | N | VAL A | 247 | 50.730 | 41.829 | 33.672 | 1.00 | 24.53 |
| ATOM | 1668 | CA | VAL A | 247 | 51.277 | 42.569 | 32.538 | 1.00 | 24.80 |

TABLE 29-continued

| ATOM | 1669 | CB | VAL A | 247 | 52.717 | 43.100 | 32.833 | 1.00 | 26.08 |
|---|---|---|---|---|---|---|---|---|---|
| ATOM | 1670 | CG1 | VAL A | 247 | 52.681 | 44.081 | 34.000 | 1.00 | 23.05 |
| ATOM | 1671 | CG2 | VAL A | 247 | 53.653 | 41.955 | 33.144 | 1.00 | 26.28 |
| ATOM | 1672 | C | VAL A | 247 | 51.285 | 41.778 | 31.233 | 1.00 | 24.65 |
| ATOM | 1673 | O | VAL A | 247 | 51.421 | 42.354 | 30.155 | 1.00 | 26.53 |
| ATOM | 1674 | N | HIS A | 248 | 51.117 | 40.463 | 31.331 | 1.00 | 23.77 |
| ATOM | 1675 | CA | HIS A | 248 | 51.114 | 39.592 | 30.156 | 1.00 | 22.18 |
| ATOM | 1676 | CB | HIS A | 248 | 52.113 | 38.451 | 30.365 | 1.00 | 21.01 |
| ATOM | 1677 | CG | HIS A | 248 | 53.530 | 38.911 | 30.488 | 1.00 | 21.43 |
| ATOM | 1678 | CD2 | HIS A | 248 | 54.309 | 39.116 | 31.576 | 1.00 | 21.00 |
| ATOM | 1679 | ND1 | HIS A | 248 | 54.285 | 39.292 | 29.399 | 1.00 | 20.19 |
| ATOM | 1680 | CE1 | HIS A | 248 | 55.466 | 39.715 | 29.812 | 1.00 | 21.23 |
| ATOM | 1681 | NE2 | HIS A | 248 | 55.506 | 39.619 | 31.129 | 1.00 | 21.42 |
| ATOM | 1682 | C | HIS A | 248 | 49.730 | 39.011 | 29.877 | 1.00 | 21.79 |
| ATOM | 1683 | O | HIS A | 248 | 49.606 | 37.986 | 29.205 | 1.00 | 20.09 |
| ATOM | 1684 | N | ARG A | 249 | 48.697 | 39.677 | 30.384 | 1.00 | 20.02 |
| ATOM | 1685 | CA | ARG A | 249 | 47.321 | 39.218 | 30.215 | 1.00 | 21.28 |
| ATOM | 1686 | CB | ARG A | 249 | 46.593 | 39.354 | 31.553 | 1.00 | 21.65 |
| ATOM | 1687 | CG | ARG A | 249 | 45.352 | 38.510 | 31.701 | 1.00 | 23.99 |
| ATOM | 1688 | CD | ARG A | 249 | 44.761 | 38.702 | 33.092 | 1.00 | 25.10 |
| ATOM | 1689 | NE | ARG A | 249 | 45.644 | 38.192 | 34.136 | 1.00 | 25.46 |
| ATOM | 1690 | CZ | ARG A | 249 | 45.657 | 38.631 | 35.390 | 1.00 | 26.82 |
| ATOM | 1691 | NH1 | ARG A | 249 | 44.838 | 39.601 | 35.769 | 1.00 | 26.65 |
| ATOM | 1692 | NH2 | ARG A | 249 | 46.487 | 38.092 | 36.272 | 1.00 | 28.01 |
| ATOM | 1693 | C | ARG A | 249 | 46.585 | 40.002 | 29.115 | 1.00 | 21.29 |
| ATOM | 1694 | O | ARG A | 249 | 46.166 | 41.144 | 29.315 | 1.00 | 20.84 |
| ATOM | 1695 | N | PRO A | 250 | 46.405 | 39.382 | 27.938 | 1.00 | 19.97 |
| ATOM | 1696 | CD | PRO A | 250 | 46.882 | 38.037 | 27.565 | 1.00 | 19.93 |
| ATOM | 1697 | CA | PRO A | 250 | 45.728 | 40.015 | 26.805 | 1.00 | 19.36 |
| ATOM | 1698 | CB | PRO A | 250 | 46.268 | 39.231 | 25.621 | 1.00 | 17.55 |
| ATOM | 1699 | CG | PRO A | 250 | 46.266 | 37.837 | 26.173 | 1.00 | 18.15 |
| ATOM | 1700 | C | PRO A | 250 | 44.202 | 39.976 | 26.834 | 1.00 | 19.85 |
| ATOM | 1701 | O | PRO A | 250 | 43.586 | 39.166 | 27.541 | 1.00 | 18.01 |
| ATOM | 1702 | N | ALA A | 251 | 43.603 | 40.868 | 26.052 | 1.00 | 18.13 |
| ATOM | 1703 | CA | ALA A | 251 | 42.158 | 40.914 | 25.916 | 1.00 | 17.04 |
| ATOM | 1704 | CB | ALA A | 251 | 41.730 | 42.233 | 25.293 | 1.00 | 15.49 |
| ATOM | 1705 | C | ALA A | 251 | 41.862 | 39.761 | 24.958 | 1.00 | 16.50 |
| ATOM | 1706 | O | ALA A | 251 | 42.714 | 39.395 | 24.142 | 1.00 | 15.91 |
| ATOM | 1707 | N | VAL A | 252 | 40.675 | 39.178 | 25.059 | 1.00 | 15.16 |
| ATOM | 1708 | CA | VAL A | 252 | 40.318 | 38.081 | 24.174 | 1.00 | 16.05 |
| ATOM | 1709 | CB | VAL A | 252 | 39.994 | 36.794 | 24.971 | 1.00 | 17.17 |
| ATOM | 1710 | CG1 | VAL A | 252 | 39.431 | 35.727 | 24.033 | 1.00 | 13.39 |
| ATOM | 1711 | CG2 | VAL A | 252 | 41.260 | 36.279 | 25.668 | 1.00 | 14.93 |
| ATOM | 1712 | C | VAL A | 252 | 39.121 | 38.436 | 23.296 | 1.00 | 17.27 |
| ATOM | 1713 | O | VAL A | 252 | 38.048 | 38.778 | 23.791 | 1.00 | 17.33 |
| ATOM | 1714 | N | LEU A | 253 | 39.322 | 38.370 | 21.984 | 1.00 | 17.39 |
| ATOM | 1715 | CA | LEU A | 253 | 38.261 | 38.659 | 21.030 | 1.00 | 16.46 |
| ATOM | 1716 | CB | LEU A | 253 | 38.670 | 39.792 | 20.082 | 1.00 | 16.40 |
| ATOM | 1717 | CG | LEU A | 253 | 38.850 | 41.201 | 20.660 | 1.00 | 17.88 |
| ATOM | 1718 | CD1 | LEU A | 253 | 40.172 | 41.298 | 21.409 | 1.00 | 18.95 |
| ATOM | 1719 | CD2 | LEU A | 253 | 38.818 | 42.212 | 19.530 | 1.00 | 17.21 |
| ATOM | 1720 | C | LEU A | 253 | 37.987 | 37.397 | 20.224 | 1.00 | 16.20 |
| ATOM | 1721 | O | LEU A | 253 | 38.817 | 36.489 | 20.186 | 1.00 | 15.34 |
| ATOM | 1722 | N | VAL A | 254 | 36.817 | 37.345 | 19.595 | 1.00 | 15.06 |
| ATOM | 1723 | CA | VAL A | 254 | 36.424 | 36.212 | 18.768 | 1.00 | 15.95 |
| ATOM | 1724 | CB | VAL A | 254 | 35.152 | 35.510 | 19.335 | 1.00 | 17.77 |
| ATOM | 1725 | CG1 | VAL A | 254 | 34.647 | 34.452 | 18.363 | 1.00 | 18.39 |
| ATOM | 1726 | CG2 | VAL A | 254 | 35.471 | 34.858 | 20.671 | 1.00 | 17.11 |
| ATOM | 1727 | C | VAL A | 254 | 36.136 | 36.737 | 17.363 | 1.00 | 15.21 |
| ATOM | 1728 | O | VAL A | 254 | 35.395 | 37.697 | 17.197 | 1.00 | 16.49 |
| ATOM | 1729 | N | LYS A | 255 | 36.739 | 36.120 | 16.355 | 1.00 | 15.79 |
| ATOM | 1730 | CA | LYS A | 255 | 36.526 | 36.546 | 14.978 | 1.00 | 15.67 |
| ATOM | 1731 | CB | LYS A | 255 | 37.831 | 36.464 | 14.181 | 1.00 | 14.99 |
| ATOM | 1732 | CG | LYS A | 255 | 37.716 | 36.986 | 12.763 | 1.00 | 16.27 |
| ATOM | 1733 | CD | LYS A | 255 | 39.091 | 37.270 | 12.164 | 1.00 | 17.90 |
| ATOM | 1734 | CE | LYS A | 255 | 38.977 | 37.918 | 10.785 | 1.00 | 16.12 |
| ATOM | 1735 | NZ | LYS A | 255 | 40.306 | 38.385 | 10.305 | 1.00 | 17.24 |
| ATOM | 1736 | C | LYS A | 255 | 35.464 | 35.660 | 14.343 | 1.00 | 17.11 |
| ATOM | 1737 | O | LYS A | 255 | 35.618 | 34.437 | 14.262 | 1.00 | 15.75 |
| ATOM | 1738 | N | ILE A | 256 | 34.389 | 36.288 | 13.883 | 1.00 | 15.78 |
| ATOM | 1739 | CA | ILE A | 256 | 33.284 | 35.555 | 13.294 | 1.00 | 15.09 |
| ATOM | 1740 | CB | ILE A | 256 | 31.970 | 35.932 | 13.992 | 1.00 | 14.37 |
| ATOM | 1741 | CG2 | ILE A | 256 | 32.129 | 35.743 | 15.489 | 1.00 | 14.88 |
| ATOM | 1742 | CG1 | ILE A | 256 | 31.611 | 37.391 | 13.687 | 1.00 | 13.35 |
| ATOM | 1743 | CD1 | ILE A | 256 | 30.324 | 37.871 | 14.348 | 1.00 | 10.32 |
| ATOM | 1744 | C | ILE A | 256 | 33.119 | 35.753 | 11.794 | 1.00 | 15.04 |
| ATOM | 1745 | O | ILE A | 256 | 33.681 | 36.678 | 11.203 | 1.00 | 12.31 |
| ATOM | 1746 | N | ALA A | 257 | 32.335 | 34.869 | 11.189 | 1.00 | 14.83 |
| ATOM | 1747 | CA | ALA A | 257 | 32.074 | 34.922 | 9.758 | 1.00 | 18.10 |

TABLE 29-continued

| ATOM | 1748 | CB | ALA A | 257 | 31.756 | 33.517 | 9.236 | 1.00 | 19.52 |
|------|------|-----|-------|-----|--------|--------|--------|------|-------|
| ATOM | 1749 | C | ALA A | 257 | 30.922 | 35.868 | 9.426 | 1.00 | 18.66 |
| ATOM | 1750 | O | ALA A | 257 | 30.195 | 36.328 | 10.310 | 1.00 | 18.10 |
| ATOM | 1751 | N | PRO A | 258 | 30.771 | 36.194 | 8.135 | 1.00 | 18.73 |
| ATOM | 1752 | CD | PRO A | 258 | 31.860 | 36.055 | 7.148 | 1.00 | 17.46 |
| ATOM | 1753 | CA | PRO A | 258 | 29.722 | 37.075 | 7.621 | 1.00 | 19.04 |
| ATOM | 1754 | CB | PRO A | 258 | 30.441 | 37.839 | 6.524 | 1.00 | 17.64 |
| ATOM | 1755 | CG | PRO A | 258 | 31.295 | 36.767 | 5.926 | 1.00 | 16.87 |
| ATOM | 1756 | C | PRO A | 258 | 28.571 | 36.234 | 7.059 | 1.00 | 21.92 |
| ATOM | 1757 | O | PRO A | 258 | 27.612 | 36.769 | 6.500 | 1.00 | 22.89 |
| ATOM | 1758 | N | ASP A | 259 | 28.677 | 34.915 | 7.214 | 1.00 | 21.14 |
| ATOM | 1759 | CA | ASP A | 259 | 27.668 | 33.995 | 6.699 | 1.00 | 22.52 |
| ATOM | 1760 | CB | ASP A | 259 | 28.346 | 32.914 | 5.849 | 1.00 | 20.83 |
| ATOM | 1761 | CG | ASP A | 259 | 29.371 | 33.489 | 4.889 | 1.00 | 22.44 |
| ATOM | 1762 | OD1 | ASP A | 259 | 29.029 | 34.444 | 4.159 | 1.00 | 19.29 |
| ATOM | 1763 | OD2 | ASP A | 259 | 30.518 | 32.985 | 4.861 | 1.00 | 22.71 |
| ATOM | 1764 | C | ASP A | 259 | 26.849 | 33.333 | 7.803 | 1.00 | 23.56 |
| ATOM | 1765 | O | ASP A | 259 | 26.277 | 32.265 | 7.605 | 1.00 | 24.81 |
| ATOM | 1766 | N | LEU A | 260 | 26.790 | 33.975 | 8.963 | 1.00 | 23.55 |
| ATOM | 1767 | CA | LEU A | 260 | 26.048 | 33.440 | 10.097 | 1.00 | 22.28 |
| ATOM | 1768 | CB | LEU A | 260 | 26.566 | 34.064 | 11.397 | 1.00 | 22.44 |
| ATOM | 1769 | CG | LEU A | 260 | 28.031 | 33.801 | 11.760 | 1.00 | 24.01 |
| ATOM | 1770 | CD1 | LEU A | 260 | 28.439 | 34.667 | 12.947 | 1.00 | 25.25 |
| ATOM | 1771 | CD2 | LEU A | 260 | 28.215 | 32.329 | 12.079 | 1.00 | 22.47 |
| ATOM | 1772 | C | LEU A | 260 | 24.552 | 33.705 | 9.978 | 1.00 | 21.83 |
| ATOM | 1773 | O | LEU A | 260 | 24.140 | 34.741 | 9.461 | 1.00 | 23.40 |
| ATOM | 1774 | N | THR A | 261 | 23.742 | 32.764 | 10.453 | 1.00 | 20.47 |
| ATOM | 1775 | CA | THR A | 261 | 22.291 | 32.925 | 10.433 | 1.00 | 19.70 |
| ATOM | 1776 | CB | THR A | 261 | 21.558 | 31.590 | 10.712 | 1.00 | 18.67 |
| ATOM | 1777 | OG1 | THR A | 261 | 21.930 | 31.106 | 12.011 | 1.00 | 18.39 |
| ATOM | 1778 | CG2 | THR A | 261 | 21.908 | 30.545 | 9.665 | 1.00 | 12.17 |
| ATOM | 1779 | C | THR A | 261 | 21.951 | 33.882 | 11.576 | 1.00 | 21.78 |
| ATOM | 1780 | O | THR A | 261 | 22.805 | 34.185 | 12.411 | 1.00 | 22.78 |
| ATOM | 1781 | N | SER A | 262 | 20.714 | 34.361 | 11.619 | 1.00 | 21.77 |
| ATOM | 1782 | CA | SER A | 262 | 20.312 | 35.256 | 12.696 | 1.00 | 22.54 |
| ATOM | 1783 | CB | SER A | 262 | 18.882 | 35.748 | 12.474 | 1.00 | 23.02 |
| ATOM | 1784 | OG | SER A | 262 | 18.810 | 36.562 | 11.322 | 1.00 | 26.73 |
| ATOM | 1785 | C | SER A | 262 | 20.403 | 34.525 | 14.038 | 1.00 | 22.61 |
| ATOM | 1786 | O | SER A | 262 | 20.634 | 35.143 | 15.076 | 1.00 | 21.53 |
| ATOM | 1787 | N | GLN A | 263 | 20.222 | 33.208 | 14.007 | 1.00 | 21.94 |
| ATOM | 1788 | CA | GLN A | 263 | 20.291 | 32.400 | 15.219 | 1.00 | 22.83 |
| ATOM | 1789 | CB | GLN A | 263 | 19.786 | 30.981 | 14.944 | 1.00 | 23.57 |
| ATOM | 1790 | CG | GLN A | 263 | 19.863 | 30.049 | 16.148 | 1.00 | 30.01 |
| ATOM | 1791 | CD | GLN A | 263 | 18.723 | 30.250 | 17.133 | 1.00 | 31.49 |
| ATOM | 1792 | OE1 | GLN A | 263 | 17.588 | 29.856 | 16.870 | 1.00 | 32.99 |
| ATOM | 1793 | NE2 | GLN A | 263 | 19.022 | 30.868 | 18.269 | 1.00 | 32.25 |
| ATOM | 1794 | C | GLN A | 263 | 21.723 | 32.338 | 15.756 | 1.00 | 21.26 |
| ATOM | 1795 | O | GLN A | 263 | 21.947 | 32.488 | 16.959 | 1.00 | 20.81 |
| ATOM | 1796 | N | ASP A | 264 | 22.688 | 32.119 | 14.865 | 1.00 | 21.06 |
| ATOM | 1797 | CA | ASP A | 264 | 24.088 | 32.042 | 15.270 | 1.00 | 19.84 |
| ATOM | 1798 | CB | ASP A | 264 | 25.000 | 31.772 | 14.069 | 1.00 | 22.89 |
| ATOM | 1799 | CG | ASP A | 264 | 24.752 | 30.414 | 13.431 | 1.00 | 25.22 |
| ATOM | 1800 | OD1 | ASP A | 264 | 24.372 | 29.471 | 14.158 | 1.00 | 22.28 |
| ATOM | 1801 | OD2 | ASP A | 264 | 24.954 | 30.293 | 12.201 | 1.00 | 26.91 |
| ATOM | 1802 | C | ASP A | 264 | 24.530 | 33.334 | 15.937 | 1.00 | 19.05 |
| ATOM | 1803 | O | ASP A | 264 | 25.200 | 33.315 | 16.970 | 1.00 | 19.15 |
| ATOM | 1804 | N | LYS A | 265 | 24.154 | 34.459 | 15.340 | 1.00 | 17.89 |
| ATOM | 1805 | CA | LYS A | 265 | 24.518 | 35.759 | 15.877 | 1.00 | 19.66 |
| ATOM | 1806 | CB | LYS A | 265 | 24.060 | 36.864 | 14.925 | 1.00 | 19.31 |
| ATOM | 1807 | CG | LYS A | 265 | 24.763 | 36.821 | 13.580 | 1.00 | 19.49 |
| ATOM | 1808 | CD | LYS A | 265 | 24.098 | 37.754 | 12.586 | 1.00 | 23.63 |
| ATOM | 1809 | CE | LYS A | 265 | 24.453 | 37.370 | 11.162 | 1.00 | 24.49 |
| ATOM | 1810 | NZ | LYS A | 265 | 23.506 | 37.954 | 10.171 | 1.00 | 27.62 |
| ATOM | 1811 | C | LYS A | 265 | 23.931 | 35.968 | 17.263 | 1.00 | 20.65 |
| ATOM | 1812 | O | LYS A | 265 | 24.612 | 36.470 | 18.157 | 1.00 | 21.98 |
| ATOM | 1813 | N | GLU A | 266 | 22.667 | 35.590 | 17.442 | 1.00 | 21.27 |
| ATOM | 1814 | CA | GLU A | 266 | 22.024 | 35.721 | 18.743 | 1.00 | 20.98 |
| ATOM | 1815 | CB | GLU A | 266 | 20.566 | 35.239 | 18.683 | 1.00 | 20.85 |
| ATOM | 1816 | CG | GLU A | 266 | 19.657 | 36.112 | 17.833 | 1.00 | 25.52 |
| ATOM | 1817 | CD | GLU A | 266 | 18.228 | 35.590 | 17.739 | 1.00 | 26.89 |
| ATOM | 1818 | OE1 | GLU A | 266 | 17.438 | 36.187 | 16.983 | 1.00 | 29.13 |
| ATOM | 1819 | OE2 | GLU A | 266 | 17.889 | 34.592 | 18.414 | 1.00 | 27.61 |
| ATOM | 1820 | C | GLU A | 266 | 22.798 | 34.886 | 19.766 | 1.00 | 19.97 |
| ATOM | 1821 | O | GLU A | 266 | 23.099 | 35.358 | 20.860 | 1.00 | 18.00 |
| ATOM | 1822 | N | ASP A | 267 | 23.126 | 33.647 | 19.402 | 1.00 | 20.17 |
| ATOM | 1823 | CA | ASP A | 267 | 23.860 | 32.769 | 20.310 | 1.00 | 21.48 |
| ATOM | 1824 | CB | ASP A | 267 | 24.015 | 31.365 | 19.714 | 1.00 | 21.94 |
| ATOM | 1825 | CG | ASP A | 267 | 22.695 | 30.622 | 19.619 | 1.00 | 25.04 |
| ATOM | 1826 | OD1 | ASP A | 267 | 21.762 | 30.968 | 20.376 | 1.00 | 23.89 |

TABLE 29-continued

| | | | | | | | | | |
|---|---|---|---|---|---|---|---|---|---|
| ATOM | 1827 | OD2 | ASP A | 267 | 22.592 | 29.685 | 18.797 | 1.00 | 27.05 |
| ATOM | 1828 | C | ASP A | 267 | 25.232 | 33.336 | 20.648 | 1.00 | 21.55 |
| ATOM | 1829 | O | ASP A | 267 | 25.619 | 33.386 | 21.816 | 1.00 | 22.82 |
| ATOM | 1830 | N | ILE A | 268 | 25.967 | 33.765 | 19.628 | 1.00 | 19.94 |
| ATOM | 1831 | CA | ILE A | 268 | 27.287 | 34.329 | 19.856 | 1.00 | 19.42 |
| ATOM | 1832 | CB | ILE A | 268 | 27.954 | 34.753 | 18.531 | 1.00 | 19.50 |
| ATOM | 1833 | CG2 | ILE A | 268 | 29.181 | 35.611 | 18.815 | 1.00 | 16.97 |
| ATOM | 1834 | CG1 | ILE A | 268 | 28.324 | 33.505 | 17.726 | 1.00 | 20.05 |
| ATOM | 1835 | CD1 | ILE A | 268 | 28.914 | 33.798 | 16.367 | 1.00 | 21.73 |
| ATOM | 1836 | C | ILE A | 268 | 27.201 | 35.532 | 20.784 | 1.00 | 18.16 |
| ATOM | 1837 | O | ILE A | 268 | 28.025 | 35.688 | 21.683 | 1.00 | 18.08 |
| ATOM | 1838 | N | ALA A | 269 | 26.197 | 36.376 | 20.573 | 1.00 | 17.88 |
| ATOM | 1839 | CA | ALA A | 269 | 26.023 | 37.563 | 21.405 | 1.00 | 19.04 |
| ATOM | 1840 | CB | ALA A | 269 | 24.885 | 38.414 | 20.872 | 1.00 | 17.94 |
| ATOM | 1841 | C | ALA A | 269 | 25.739 | 37.151 | 22.845 | 1.00 | 20.04 |
| ATOM | 1842 | O | ALA A | 269 | 26.225 | 37.769 | 23.791 | 1.00 | 19.17 |
| ATOM | 1843 | N | SER A | 270 | 24.951 | 36.094 | 22.999 | 1.00 | 20.63 |
| ATOM | 1844 | CA | SER A | 270 | 24.598 | 35.590 | 24.317 | 1.00 | 20.97 |
| ATOM | 1845 | CB | SER A | 270 | 23.517 | 34.514 | 24.182 | 1.00 | 20.46 |
| ATOM | 1846 | OG | SER A | 270 | 23.269 | 33.883 | 25.423 | 1.00 | 23.18 |
| ATOM | 1847 | C | SER A | 270 | 25.823 | 35.024 | 25.042 | 1.00 | 20.72 |
| ATOM | 1848 | O | SER A | 270 | 26.067 | 35.351 | 26.200 | 1.00 | 22.09 |
| ATOM | 1849 | N | VAL A | 271 | 26.590 | 34.177 | 24.361 | 1.00 | 20.12 |
| ATOM | 1850 | CA | VAL A | 271 | 27.782 | 33.582 | 24.958 | 1.00 | 20.78 |
| ATOM | 1851 | CB | VAL A | 271 | 28.432 | 32.561 | 24.004 | 1.00 | 19.82 |
| ATOM | 1852 | CG1 | VAL A | 271 | 29.748 | 32.060 | 24.592 | 1.00 | 20.03 |
| ATOM | 1853 | CG2 | VAL A | 271 | 27.487 | 31.398 | 23.773 | 1.00 | 16.90 |
| ATOM | 1854 | C | VAL A | 271 | 28.820 | 34.647 | 25.315 | 1.00 | 23.07 |
| ATOM | 1855 | O | VAL A | 271 | 29.419 | 34.614 | 26.389 | 1.00 | 21.64 |
| ATOM | 1856 | N | VAL A | 272 | 29.023 | 35.595 | 24.406 | 1.00 | 25.16 |
| ATOM | 1857 | CA | VAL A | 272 | 29.981 | 36.670 | 24.620 | 1.00 | 27.00 |
| ATOM | 1858 | CB | VAL A | 272 | 29.977 | 37.649 | 23.421 | 1.00 | 27.76 |
| ATOM | 1859 | CG1 | VAL A | 272 | 30.548 | 38.995 | 23.834 | 1.00 | 27.78 |
| ATOM | 1860 | CG2 | VAL A | 272 | 30.798 | 37.058 | 22.275 | 1.00 | 25.76 |
| ATOM | 1861 | C | VAL A | 272 | 29.710 | 37.439 | 25.911 | 1.00 | 28.67 |
| ATOM | 1862 | O | VAL A | 272 | 30.631 | 37.722 | 26.682 | 1.00 | 29.19 |
| ATOM | 1863 | N | LYS A | 273 | 28.447 | 37.767 | 26.154 | 1.00 | 29.06 |
| ATOM | 1864 | CA | LYS A | 273 | 28.086 | 38.510 | 27.356 | 1.00 | 31.31 |
| ATOM | 1865 | CB | LYS A | 273 | 26.736 | 39.211 | 27.152 | 1.00 | 31.93 |
| ATOM | 1866 | CG | LYS A | 273 | 26.814 | 40.342 | 26.115 | 1.00 | 34.44 |
| ATOM | 1867 | CD | LYS A | 273 | 25.516 | 41.133 | 26.008 | 1.00 | 36.38 |
| ATOM | 1868 | Ce | LYS A | 273 | 24.367 | 40.261 | 25.534 | 1.00 | 35.40 |
| ATOM | 1869 | NZ | LYS A | 273 | 23.122 | 41.050 | 25.352 | 1.00 | 36.63 |
| ATOM | 1870 | C | LYS A | 273 | 28.065 | 37.636 | 28.607 | 1.00 | 30.65 |
| ATOM | 1871 | O | LYS A | 273 | 28.303 | 38.115 | 29.714 | 1.00 | 30.52 |
| ATOM | 1872 | N | GLU A | 274 | 27.793 | 36.350 | 28.426 | 1.00 | 29.82 |
| ATOM | 1873 | CA | GLU A | 274 | 27.765 | 35.416 | 29.542 | 1.00 | 29.43 |
| ATOM | 1874 | CB | GLU A | 274 | 27.191 | 34.074 | 29.083 | 1.00 | 30.26 |
| ATOM | 1875 | CG | GLU A | 274 | 27.098 | 33.026 | 30.176 | 1.00 | 35.07 |
| ATOM | 1876 | CD | GLU A | 274 | 27.060 | 31.611 | 29.623 | 1.00 | 38.26 |
| ATOM | 1877 | OE1 | GLU A | 274 | 26.381 | 31.388 | 28.599 | 1.00 | 39.06 |
| ATOM | 1878 | OE2 | GLU A | 274 | 27.706 | 30.717 | 30.215 | 1.00 | 41.36 |
| ATOM | 1879 | C | GLU A | 274 | 29.179 | 35.188 | 30.094 | 1.00 | 29.77 |
| ATOM | 1880 | O | GLU A | 274 | 29.387 | 35.174 | 31.309 | 1.00 | 29.55 |
| ATOM | 1881 | N | LEU A | 275 | 30.145 | 35.021 | 29.191 | 1.00 | 27.28 |
| ATOM | 1882 | CA | LEU A | 275 | 31.531 | 34.754 | 29.574 | 1.00 | 24.61 |
| ATOM | 1883 | CB | LEU A | 275 | 32.184 | 33.835 | 28.542 | 1.00 | 22.55 |
| ATOM | 1884 | CG | LEU A | 275 | 31.489 | 32.496 | 28.298 | 1.00 | 22.58 |
| ATOM | 1885 | CD1 | LEU A | 275 | 32.236 | 31.717 | 27.224 | 1.00 | 20.96 |
| ATOM | 1886 | CD2 | LEU A | 275 | 31.435 | 31.711 | 29.600 | 1.00 | 22.06 |
| ATOM | 1887 | C | LEU A | 275 | 32.412 | 35.979 | 29.764 | 1.00 | 23.92 |
| ATOM | 1888 | O | LEU A | 275 | 33.511 | 35.873 | 30.300 | 1.00 | 24.92 |
| ATOM | 1889 | N | GLY A | 276 | 31.943 | 37.138 | 29.322 | 1.00 | 23.96 |
| ATOM | 1890 | CA | GLY A | 276 | 32.743 | 38.340 | 29.466 | 1.00 | 22.49 |
| ATOM | 1891 | C | GLY A | 276 | 33.783 | 38.516 | 28.368 | 1.00 | 24.06 |
| ATOM | 1892 | O | GLY A | 276 | 34.834 | 39.115 | 28.597 | 1.00 | 23.35 |
| ATOM | 1893 | N | ILE A | 277 | 33.504 | 37.991 | 27.176 | 1.00 | 24.12 |
| ATOM | 1894 | CA | ILE A | 277 | 34.426 | 38.138 | 26.051 | 1.00 | 22.72 |
| ATOM | 1895 | CB | ILE A | 277 | 33.814 | 37.595 | 24.744 | 1.00 | 23.36 |
| ATOM | 1896 | CG2 | ILE A | 277 | 34.734 | 37.891 | 23.570 | 1.00 | 22.55 |
| ATOM | 1897 | CG1 | ILE A | 277 | 33.609 | 36.086 | 24.863 | 1.00 | 23.90 |
| ATOM | 1898 | CD1 | ILE A | 277 | 34.891 | 35.331 | 25.133 | 1.00 | 27.10 |
| ATOM | 1899 | C | ILE A | 277 | 34.724 | 39.627 | 25.885 | 1.00 | 22.38 |
| ATOM | 1900 | O | ILE A | 277 | 33.817 | 40.461 | 25.921 | 1.00 | 20.66 |
| ATOM | 1901 | N | ASP A | 278 | 35.997 | 39.954 | 25.702 | 1.00 | 21.22 |
| ATOM | 1902 | CA | ASP A | 278 | 36.426 | 41.340 | 25.578 | 1.00 | 19.68 |
| ATOM | 1903 | CB | ASP A | 278 | 37.940 | 41.420 | 25.751 | 1.00 | 19.24 |
| ATOM | 1904 | CG | ASP A | 278 | 38.389 | 40.902 | 27.093 | 1.00 | 18.89 |
| ATOM | 1905 | OD1 | ASP A | 278 | 37.973 | 41.489 | 28.114 | 1.00 | 20.89 |

TABLE 29-continued

| ATOM | 1906 | OD2 | ASP A | 278 | 39.145 | 39.909 | 27.130 | 1.00 | 18.95 |
|---|---|---|---|---|---|---|---|---|---|
| ATOM | 1907 | C | ASP A | 278 | 36.027 | 42.056 | 24.300 | 1.00 | 19.50 |
| ATOM | 1908 | O | ASP A | 278 | 35.888 | 43.277 | 24.294 | 1.00 | 20.84 |
| ATOM | 1909 | N | GLY A | 279 | 35.844 | 41.312 | 23.216 | 1.00 | 17.90 |
| ATOM | 1910 | CA | GLY A | 279 | 35.473 | 41.961 | 21.977 | 1.00 | 17.02 |
| ATOM | 1911 | C | GLY A | 279 | 35.240 | 41.031 | 20.809 | 1.00 | 16.34 |
| ATOM | 1912 | O | GLY A | 279 | 35.461 | 39.825 | 20.896 | 1.00 | 16.62 |
| ATOM | 1913 | N | LEU A | 280 | 34.794 | 41.609 | 19.702 | 1.00 | 16.08 |
| ATOM | 1914 | CA | LEU A | 280 | 34.511 | 40.843 | 18.501 | 1.00 | 16.76 |
| ATOM | 1915 | CB | LEU A | 280 | 32.999 | 40.798 | 18.239 | 1.00 | 14.21 |
| ATOM | 1916 | CG | LEU A | 280 | 32.073 | 40.052 | 19.205 | 1.00 | 16.52 |
| ATOM | 1917 | CD1 | LEU A | 280 | 30.617 | 40.361 | 18.865 | 1.00 | 14.62 |
| ATOM | 1918 | CD2 | LEU A | 280 | 32.335 | 38.555 | 19.123 | 1.00 | 14.09 |
| ATOM | 1919 | C | LEU A | 280 | 35.190 | 41.450 | 17.284 | 1.00 | 15.76 |
| ATOM | 1920 | O | LEU A | 280 | 35.264 | 42.673 | 17.142 | 1.00 | 15.21 |
| ATOM | 1921 | N | ILE A | 281 | 35.714 | 40.586 | 16.425 | 1.00 | 13.97 |
| ATOM | 1922 | CA | ILE A | 281 | 36.316 | 41.040 | 15.188 | 1.00 | 14.74 |
| ATOM | 1923 | CB | ILE A | 281 | 37.668 | 40.375 | 14.910 | 1.00 | 12.59 |
| ATOM | 1924 | CG2 | ILE A | 281 | 38.237 | 40.914 | 13.603 | 1.00 | 13.24 |
| ATOM | 1925 | CG1 | ILE A | 281 | 38.637 | 40.691 | 16.057 | 1.00 | 11.42 |
| ATOM | 1926 | CD1 | ILE A | 281 | 40.099 | 40.695 | 15.650 | 1.00 | 9.11 |
| ATOM | 1927 | C | ILE A | 281 | 35.255 | 40.567 | 14.218 | 1.00 | 16.53 |
| ATOM | 1928 | O | ILE A | 281 | 35.042 | 39.362 | 14.036 | 1.00 | 15.17 |
| ATOM | 1929 | N | VAL A | 282 | 34.561 | 41.513 | 13.603 | 1.00 | 18.83 |
| ATOM | 1930 | CA | VAL A | 282 | 33.469 | 41.111 | 12.753 | 1.00 | 20.72 |
| ATOM | 1931 | CB | VAL A | 282 | 32.257 | 42.012 | 13.007 | 1.00 | 20.08 |
| ATOM | 1932 | CG1 | VAL A | 282 | 31.069 | 41.563 | 12.177 | 1.00 | 15.79 |
| ATOM | 1933 | CG2 | VAL A | 282 | 31.914 | 41.941 | 14.486 | 1.00 | 15.44 |
| ATOM | 1934 | C | VAL A | 282 | 33.702 | 40.896 | 11.274 | 1.00 | 23.98 |
| ATOM | 1935 | O | VAL A | 282 | 34.040 | 41.793 | 10.498 | 1.00 | 22.59 |
| ATOM | 1936 | N | THR A | 283 | 33.464 | 39.629 | 10.953 | 1.00 | 26.57 |
| ATOM | 1937 | CA | THR A | 283 | 33.562 | 38.963 | 9.669 | 1.00 | 24.80 |
| ATOM | 1938 | CB | THR A | 283 | 32.550 | 39.499 | 8.604 | 1.00 | 22.20 |
| ATOM | 1939 | OG1 | THR A | 283 | 33.258 | 39.909 | 7.430 | 1.00 | 20.11 |
| ATOM | 1940 | CG2 | THR A | 283 | 31.692 | 40.619 | 9.158 | 1.00 | 25.27 |
| ATOM | 1941 | C | THR A | 283 | 34.915 | 38.764 | 9.022 | 1.00 | 23.47 |
| ATOM | 1942 | O | THR A | 283 | 35.729 | 39.672 | 8.824 | 1.00 | 22.34 |
| ATOM | 1943 | N | ASN A | 284 | 35.117 | 37.490 | 8.739 | 1.00 | 20.14 |
| ATOM | 1944 | CA | ASN A | 284 | 36.271 | 36.955 | 8.080 | 1.00 | 17.94 |
| ATOM | 1945 | CB | ASN A | 284 | 36.427 | 35.498 | 8.507 | 1.00 | 16.23 |
| ATOM | 1946 | CG | ASN A | 284 | 37.822 | 34.989 | 8.327 | 1.00 | 15.24 |
| ATOM | 1947 | OD1 | ASN A | 284 | 38.370 | 35.042 | 7.234 | 1.00 | 16.87 |
| ATOM | 1948 | ND2 | ASN A | 284 | 38.411 | 34.484 | 9.406 | 1.00 | 15.85 |
| ATOM | 1949 | C | ASN A | 284 | 35.793 | 37.038 | 6.633 | 1.00 | 17.29 |
| ATOM | 1950 | O | ASN A | 284 | 34.912 | 37.843 | 6.314 | 1.00 | 17.42 |
| ATOM | 1951 | N | THR A | 285 | 36.346 | 36.208 | 5.762 | 1.00 | 15.65 |
| ATOM | 1952 | CA | THR A | 285 | 35.920 | 36.215 | 4.371 | 1.00 | 14.49 |
| ATOM | 1953 | CB | THR A | 285 | 36.970 | 35.548 | 3.469 | 1.00 | 13.54 |
| ATOM | 1954 | OG1 | THR A | 285 | 37.344 | 34.284 | 4.030 | 1.00 | 11.73 |
| ATOM | 1955 | CG2 | THR A | 285 | 38.205 | 36.435 | 3.348 | 1.00 | 11.58 |
| ATOM | 1956 | C | THR A | 285 | 34.600 | 35.454 | 4.268 | 1.00 | 14.94 |
| ATOM | 1957 | O | THR A | 285 | 34.250 | 34.681 | 5.164 | 1.00 | 13.05 |
| ATOM | 1958 | N | THR A | 286 | 33.872 | 35.679 | 3.177 | 1.00 | 13.81 |
| ATOM | 1959 | CA | THR A | 286 | 32.585 | 35.020 | 2.961 | 1.00 | 12.17 |
| ATOM | 1960 | CB | THR A | 286 | 31.535 | 36.022 | 2.419 | 1.00 | 10.38 |
| ATOM | 1961 | OG1 | THR A | 286 | 30.296 | 35.346 | 2.200 | 1.00 | 13.59 |
| ATOM | 1962 | CG2 | THR A | 286 | 31.996 | 36.620 | 1.096 | 1.00 | 9.39 |
| ATOM | 1963 | C | THR A | 286 | 32.679 | 33.864 | 1.965 | 1.00 | 12.82 |
| ATOM | 1964 | O | THR A | 286 | 33.406 | 33.953 | 0.969 | 1.00 | 11.73 |
| ATOM | 1965 | N | VAL A | 287 | 31.945 | 32.785 | 2.234 | 1.00 | 12.56 |
| ATOM | 1966 | CA | VAL A | 287 | 31.926 | 31.639 | 1.330 | 1.00 | 15.17 |
| ATOM | 1967 | CB | VAL A | 287 | 31.700 | 30.290 | 2.067 | 1.00 | 15.85 |
| ATOM | 1968 | CG1 | VAL A | 287 | 32.817 | 30.045 | 3.059 | 1.00 | 16.20 |
| ATOM | 1969 | CG2 | VAL A | 287 | 30.347 | 30.285 | 2.764 | 1.00 | 16.12 |
| ATOM | 1970 | C | VAL A | 287 | 30.783 | 31.846 | 0.337 | 1.00 | 16.66 |
| ATOM | 1971 | O | VAL A | 287 | 30.541 | 31.013 | −0.536 | 1.00 | 16.82 |
| ATOM | 1972 | N | SER A | 288 | 30.073 | 32.959 | 0.483 | 1.00 | 15.63 |
| ATOM | 1973 | CA | SER A | 288 | 28.985 | 33.266 | −0.432 | 1.00 | 15.70 |
| ATOM | 1974 | CB | SER A | 288 | 28.001 | 34.259 | 0.197 | 1.00 | 14.48 |
| ATOM | 1975 | OG | SER A | 288 | 28.554 | 35.568 | 0.229 | 1.00 | 13.23 |
| ATOM | 1976 | C | SER A | 288 | 29.611 | 33.903 | −1.665 | 1.00 | 16.39 |
| ATOM | 1977 | O | SER A | 288 | 30.764 | 34.334 | −1.635 | 1.00 | 15.81 |
| ATOM | 1978 | N | ARG A | 289 | 28.847 | 33.960 | −2.747 | 1.00 | 17.38 |
| ATOM | 1979 | CA | ARG A | 289 | 29.318 | 34.563 | −3.985 | 1.00 | 18.89 |
| ATOM | 1980 | CB | ARG A | 289 | 29.629 | 33.480 | −5.019 | 1.00 | 18.09 |
| ATOM | 1981 | CG | ARG A | 289 | 30.839 | 32.628 | −4.671 | 1.00 | 18.05 |
| ATOM | 1982 | CD | ARG A | 289 | 32.125 | 33.435 | −4.745 | 1.00 | 16.68 |
| ATOM | 1983 | NE | ARG A | 289 | 33.299 | 32.594 | −4.532 | 1.00 | 15.91 |
| ATOM | 1984 | CZ | ARG A | 289 | 33.787 | 32.261 | −3.340 | 1.00 | 16.31 |

TABLE 29-continued

| | | | | | | | | | |
|---|---|---|---|---|---|---|---|---|---|
| ATOM | 1985 | NH1 | ARG A | 289 | 34.858 | 31.477 | −3.261 | 1.00 | 13.06 |
| ATOM | 1986 | NH2 | ARG A | 289 | 33.220 | 32.721 | −2.229 | 1.00 | 13.64 |
| ATOM | 1987 | C | ARG A | 289 | 28.206 | 35.475 | −4.480 | 1.00 | 20.53 |
| ATOM | 1988 | O | ARG A | 289 | 27.368 | 35.079 | −5.296 | 1.00 | 21.36 |
| ATOM | 1989 | N | PRO A | 290 | 28.182 | 36.715 | −3.975 | 1.00 | 19.53 |
| ATOM | 1990 | CD | PRO A | 290 | 29.209 | 37.305 | −3.100 | 1.00 | 17.95 |
| ATOM | 1991 | CA | PRO A | 290 | 27.176 | 37.710 | −4.343 | 1.00 | 18.26 |
| ATOM | 1992 | CB | PRO A | 290 | 27.763 | 39.008 | −3.793 | 1.00 | 18.04 |
| ATOM | 1993 | CG | PRO A | 290 | 28.515 | 38.546 | −2.589 | 1.00 | 17.02 |
| ATOM | 1994 | C | PRO A | 290 | 26.964 | 37.767 | −5.845 | 1.00 | 18.99 |
| ATOM | 1995 | O | PRO A | 290 | 27.921 | 37.684 | −6.617 | 1.00 | 19.64 |
| ATOM | 1996 | N | ALA A | 291 | 25.707 | 37.889 | −6.262 | 1.00 | 18.82 |
| ATOM | 1997 | CA | ALA A | 291 | 25.405 | 37.987 | −7.685 | 1.00 | 16.85 |
| ATOM | 1998 | CB | ALA A | 291 | 23.901 | 38.084 | −7.899 | 1.00 | 14.77 |
| ATOM | 1999 | C | ALA A | 291 | 26.090 | 39.255 | −8.189 | 1.00 | 14.94 |
| ATOM | 2000 | O | ALA A | 291 | 26.138 | 40.258 | −7.482 | 1.00 | 15.17 |
| ATOM | 2001 | N | GLY A | 292 | 26.636 | 39.206 | −9.398 | 1.00 | 13.56 |
| ATOM | 2002 | CA | GLY A | 292 | 27.295 | 40.377 | −9.939 | 1.00 | 14.88 |
| ATOM | 2003 | C | GLY A | 292 | 28.797 | 40.238 | −10.102 | 1.00 | 15.80 |
| ATOM | 2004 | O | GLY A | 292 | 29.403 | 41.002 | −10.852 | 1.00 | 17.47 |
| ATOM | 2005 | N | LEU A | 293 | 29.406 | 39.286 | −9.398 | 1.00 | 15.22 |
| ATOM | 2006 | CA | LEU A | 293 | 30.846 | 39.074 | −9.520 | 1.00 | 15.55 |
| ATOM | 2007 | CB | LEU A | 293 | 31.282 | 37.831 | −8.739 | 1.00 | 15.69 |
| ATOM | 2008 | CG | LEU A | 293 | 31.174 | 37.866 | −7.210 | 1.00 | 14.60 |
| ATOM | 2009 | CD1 | LEU A | 293 | 31.673 | 36.545 | −6.650 | 1.00 | 14.40 |
| ATOM | 2010 | CD2 | LEU A | 293 | 31.995 | 39.020 | −6.647 | 1.00 | 12.10 |
| ATOM | 2011 | C | LEU A | 293 | 31.185 | 38.891 | −10.991 | 1.00 | 15.60 |
| ATOM | 2012 | O | LEU A | 293 | 30.510 | 38.147 | −11.702 | 1.00 | 16.58 |
| ATOM | 2013 | N | GLN A | 294 | 32.230 | 39.576 | −11.444 | 1.00 | 16.80 |
| ATOM | 2014 | CA | GLN A | 294 | 32.653 | 39.503 | −12.835 | 1.00 | 17.11 |
| ATOM | 2015 | CB | GLN A | 294 | 32.859 | 40.913 | −13.390 | 1.00 | 18.48 |
| ATOM | 2016 | CG | GLN A | 294 | 31.589 | 41.728 | −13.450 | 1.00 | 19.20 |
| ATOM | 2017 | CD | GLN A | 294 | 30.512 | 41.030 | −14.249 | 1.00 | 19.74 |
| ATOM | 2018 | OE1 | GLN A | 294 | 30.709 | 40.716 | −15.420 | 1.00 | 20.35 |
| ATOM | 2019 | NE2 | GLN A | 294 | 29.366 | 40.780 | −13.620 | 1.00 | 17.29 |
| ATOM | 2020 | C | GLN A | 294 | 33.929 | 38.701 | −13.029 | 1.00 | 18.33 |
| ATOM | 2021 | O | GLN A | 294 | 34.145 | 38.122 | −14.097 | 1.00 | 19.34 |
| ATOM | 2022 | N | GLY A | 295 | 34.772 | 38.678 | −11.999 | 1.00 | 16.78 |
| ATOM | 2023 | CA | GLY A | 295 | 36.029 | 37.960 | −12.076 | 1.00 | 14.58 |
| ATOM | 2024 | C | GLY A | 295 | 35.915 | 36.580 | −12.693 | 1.00 | 17.14 |
| ATOM | 2025 | O | GLY A | 295 | 34.976 | 35.828 | −12.413 | 1.00 | 15.75 |
| ATOM | 2026 | N | ALA A | 296 | 36.878 | 36.244 | −13.541 | 1.00 | 16.27 |
| ATOM | 2027 | CA | ALA A | 296 | 36.890 | 34.942 | −14.195 | 1.00 | 16.90 |
| ATOM | 2028 | CB | ALA A | 296 | 38.039 | 34.880 | −15.206 | 1.00 | 14.08 |
| ATOM | 2029 | C | ALA A | 296 | 37.030 | 33.812 | −13.175 | 1.00 | 16.05 |
| ATOM | 2030 | O | ALA A | 296 | 36.515 | 32.712 | −13.381 | 1.00 | 16.89 |
| ATOM | 2031 | N | LEU A | 297 | 37.712 | 34.101 | −12.068 | 1.00 | 15.74 |
| ATOM | 2032 | CA | LEU A | 297 | 37.967 | 33.112 | −11.019 | 1.00 | 15.01 |
| ATOM | 2033 | CB | LEU A | 297 | 39.379 | 33.327 | −10.467 | 1.00 | 12.31 |
| ATOM | 2034 | CG | LEU A | 297 | 40.468 | 33.402 | −11.544 | 1.00 | 14.81 |
| ATOM | 2035 | CD1 | LEU A | 297 | 41.783 | 33.870 | −10.927 | 1.00 | 14.19 |
| ATOM | 2036 | CD2 | LEU A | 297 | 40.627 | 32.039 | −12.214 | 1.00 | 12.20 |
| ATOM | 2037 | C | LEU A | 297 | 36.965 | 33.148 | −9.867 | 1.00 | 14.73 |
| ATOM | 2038 | O | LEU A | 297 | 37.250 | 32.650 | −8.774 | 1.00 | 14.27 |
| ATOM | 2039 | N | ARG A | 298 | 35.793 | 33.724 | −10.123 | 1.00 | 15.51 |
| ATOM | 2040 | CA | ARG A | 298 | 34.743 | 33.865 | −9.112 | 1.00 | 15.51 |
| ATOM | 2041 | CB | ARG A | 298 | 33.558 | 34.641 | −9.699 | 1.00 | 14.80 |
| ATOM | 2042 | CG | ARG A | 298 | 32.734 | 33.858 | −10.711 | 1.00 | 14.58 |
| ATOM | 2043 | CD | ARG A | 298 | 31.673 | 34.741 | −11.370 | 1.00 | 15.06 |
| ATOM | 2044 | NE | ARG A | 298 | 30.782 | 33.966 | −12.229 | 1.00 | 14.79 |
| ATOM | 2045 | CZ | ARG A | 298 | 29.917 | 34.491 | −13.093 | 1.00 | 15.35 |
| ATOM | 2046 | NH1 | ARG A | 298 | 29.151 | 33.695 | −13.828 | 1.00 | 8.68 |
| ATOM | 2047 | NH2 | ARG A | 298 | 29.822 | 35.812 | −13.233 | 1.00 | 14.16 |
| ATOM | 2048 | C | ARG A | 298 | 34.233 | 32.553 | −8.519 | 1.00 | 16.08 |
| ATOM | 2049 | O | ARG A | 298 | 33.719 | 32.537 | −7.398 | 1.00 | 16.02 |
| ATOM | 2050 | N | SER A | 299 | 34.371 | 31.458 | −9.261 | 1.00 | 15.60 |
| ATOM | 2051 | CA | SER A | 299 | 33.899 | 30.168 | −8.780 | 1.00 | 16.40 |
| ATOM | 2052 | CB | SER A | 299 | 33.206 | 29.409 | −9.910 | 1.00 | 15.38 |
| ATOM | 2053 | OG | SER A | 299 | 31.920 | 29.958 | −10.140 | 1.00 | 14.75 |
| ATOM | 2054 | C | SER A | 299 | 34.958 | 29.285 | −8.124 | 1.00 | 17.70 |
| ATOM | 2055 | O | SER A | 299 | 34.742 | 28.088 | −7.934 | 1.00 | 19.57 |
| ATOM | 2056 | N | GLU A | 300 | 36.099 | 29.873 | −7.782 | 1.00 | 15.48 |
| ATOM | 2057 | CA | GLU A | 300 | 37.153 | 29.135 | −7.096 | 1.00 | 16.69 |
| ATOM | 2058 | CB | GLU A | 300 | 38.473 | 29.921 | −7.109 | 1.00 | 15.70 |
| ATOM | 2059 | CG | GLU A | 300 | 39.177 | 29.968 | −8.460 | 1.00 | 19.09 |
| ATOM | 2060 | CD | GLU A | 300 | 39.894 | 28.668 | −8.796 | 1.00 | 19.66 |
| ATOM | 2061 | OE1 | GLU A | 300 | 40.293 | 28.485 | −9.965 | 1.00 | 21.52 |
| ATOM | 2062 | OE2 | GLU A | 300 | 40.069 | 27.831 | −7.887 | 1.00 | 20.79 |
| ATOM | 2063 | C | GLU A | 300 | 36.698 | 28.957 | −5.644 | 1.00 | 17.50 |

TABLE 29-continued

| | | | | | | | | | |
|---|---|---|---|---|---|---|---|---|---|
| ATOM | 2064 | O | GLU A | 300 | 36.012 | 29.818 | −5.085 | 1.00 | 18.25 |
| ATOM | 2065 | N | THR A | 301 | 37.075 | 27.837 | −5.043 | 1.00 | 16.77 |
| ATOM | 2066 | CA | THR A | 301 | 36.733 | 27.560 | −3.657 | 1.00 | 15.87 |
| ATOM | 2067 | CB | THR A | 301 | 37.035 | 26.089 | −3.302 | 1.00 | 16.02 |
| ATOM | 2068 | OG1 | THR A | 301 | 36.030 | 25.245 | −3.873 | 1.00 | 19.42 |
| ATOM | 2069 | CG2 | THR A | 301 | 37.077 | 25.894 | −1.798 | 1.00 | 14.14 |
| ATOM | 2070 | C | THR A | 301 | 37.564 | 28.465 | −2.747 | 1.00 | 14.56 |
| ATOM | 2071 | O | THR A | 301 | 38.729 | 28.745 | −3.037 | 1.00 | 13.06 |
| ATOM | 2072 | N | GLY A | 302 | 36.968 | 28.923 | −1.651 | 1.00 | 14.25 |
| ATOM | 2073 | CA | GLY A | 302 | 37.697 | 29.778 | −0.732 | 1.00 | 13.34 |
| ATOM | 2074 | C | GLY A | 302 | 36.874 | 30.924 | −0.184 | 1.00 | 14.22 |
| ATOM | 2075 | O | GLY A | 302 | 35.682 | 31.042 | −0.471 | 1.00 | 13.86 |
| ATOM | 2076 | N | GLY A | 303 | 37.514 | 31.769 | 0.619 | 1.00 | 14.41 |
| ATOM | 2077 | CA | GLY A | 303 | 36.829 | 32.906 | 1.199 | 1.00 | 12.84 |
| ATOM | 2078 | C | GLY A | 303 | 37.005 | 34.138 | 0.337 | 1.00 | 12.25 |
| ATOM | 2079 | O | GLY A | 303 | 38.109 | 34.439 | −0.115 | 1.00 | 12.09 |
| ATOM | 2080 | N | LEU A | 304 | 35.906 | 34.850 | 0.109 | 1.00 | 12.88 |
| ATOM | 2081 | CA | LEU A | 304 | 35.912 | 36.057 | −0.709 | 1.00 | 12.21 |
| ATOM | 2082 | CB | LEU A | 304 | 34.588 | 36.171 | −1.470 | 1.00 | 13.65 |
| ATOM | 2083 | CG | LEU A | 304 | 34.314 | 37.450 | −2.269 | 1.00 | 15.74 |
| ATOM | 2084 | CD1 | LEU A | 304 | 35.287 | 37.566 | −3.428 | 1.00 | 16.08 |
| ATOM | 2085 | CD2 | LEU A | 304 | 32.881 | 37.412 | −2.792 | 1.00 | 20.89 |
| ATOM | 2086 | C | LEU A | 304 | 36.120 | 37.301 | 0.147 | 1.00 | 12.48 |
| ATOM | 2087 | O | LEU A | 304 | 35.517 | 37.447 | 1.211 | 1.00 | 14.13 |
| ATOM | 2088 | N | SER A | 305 | 36.970 | 38.201 | −0.326 | 1.00 | 12.36 |
| ATOM | 2089 | CA | SER A | 305 | 37.253 | 39.432 | 0.396 | 1.00 | 13.71 |
| ATOM | 2090 | CB | SER A | 305 | 38.636 | 39.348 | 1.042 | 1.00 | 13.43 |
| ATOM | 2091 | OG | SER A | 305 | 39.640 | 39.207 | 0.051 | 1.00 | 13.79 |
| ATOM | 2092 | C | SER A | 305 | 37.205 | 40.615 | −0.566 | 1.00 | 13.39 |
| ATOM | 2093 | O | SER A | 305 | 37.120 | 40.428 | −1.778 | 1.00 | 14.42 |
| ATOM | 2094 | N | GLY A | 306 | 37.262 | 41.830 | −0.029 | 1.00 | 13.29 |
| ATOM | 2095 | CA | GLY A | 306 | 37.230 | 43.002 | −0.887 | 1.00 | 12.97 |
| ATOM | 2096 | C | GLY A | 306 | 35.877 | 43.690 | −0.938 | 1.00 | 14.84 |
| ATOM | 2097 | O | GLY A | 306 | 35.009 | 43.444 | −0.096 | 1.00 | 14.46 |
| ATOM | 2098 | N | LYS A | 307 | 35.686 | 44.539 | −1.945 | 1.00 | 16.17 |
| ATOM | 2099 | CA | LYS A | 307 | 34.444 | 45.290 | −2.088 | 1.00 | 16.52 |
| ATOM | 2100 | CB | LYS A | 307 | 34.460 | 46.120 | −3.385 | 1.00 | 18.40 |
| ATOM | 2101 | CG | LYS A | 307 | 33.422 | 47.261 | −3.379 | 1.00 | 25.17 |
| ATOM | 2102 | CD | LYS A | 307 | 33.336 | 48.025 | −4.705 | 1.00 | 27.88 |
| ATOM | 2103 | CE | LYS A | 307 | 34.621 | 48.787 | −5.010 | 1.00 | 29.73 |
| ATOM | 2104 | NZ | LYS A | 307 | 34.986 | 49.758 | −3.934 | 1.00 | 29.23 |
| ATOM | 2105 | C | LYS A | 307 | 33.157 | 44.466 | −2.012 | 1.00 | 15.26 |
| ATOM | 2106 | O | LYS A | 307 | 32.194 | 44.881 | −1.367 | 1.00 | 16.38 |
| ATOM | 2107 | N | PRO A | 308 | 33.114 | 43.292 | −2.663 | 1.00 | 14.54 |
| ATOM | 2108 | CD | PRO A | 308 | 34.114 | 42.680 | −3.556 | 1.00 | 14.56 |
| ATOM | 2109 | CA | PRO A | 308 | 31.894 | 42.475 | −2.613 | 1.00 | 14.08 |
| ATOM | 2110 | CB | PRO A | 308 | 32.255 | 41.259 | −3.465 | 1.00 | 14.39 |
| ATOM | 2111 | CG | PRO A | 308 | 33.248 | 41.818 | −4.448 | 1.00 | 15.27 |
| ATOM | 2112 | C | PRO A | 308 | 31.478 | 42.074 | −1.196 | 1.00 | 15.08 |
| ATOM | 2113 | O | PRO A | 308 | 30.313 | 41.764 | −0.945 | 1.00 | 16.18 |
| ATOM | 2114 | N | LEU A | 309 | 32.436 | 42.079 | −0.276 | 1.00 | 15.24 |
| ATOM | 2115 | CA | LEU A | 309 | 32.182 | 41.709 | 1.114 | 1.00 | 15.60 |
| ATOM | 2116 | CB | LEU A | 309 | 33.405 | 40.979 | 1.679 | 1.00 | 14.32 |
| ATOM | 2117 | CG | LEU A | 309 | 33.524 | 40.802 | 3.201 | 1.00 | 13.34 |
| ATOM | 2118 | CD1 | LEU A | 309 | 32.452 | 39.850 | 3.714 | 1.00 | 12.74 |
| ATOM | 2119 | CD2 | LEU A | 309 | 34.903 | 40.251 | 3.532 | 1.00 | 12.50 |
| ATOM | 2120 | C | LEU A | 309 | 31.854 | 42.890 | 2.032 | 1.00 | 16.28 |
| ATOM | 2121 | O | LEU A | 309 | 31.229 | 42.710 | 3.076 | 1.00 | 17.72 |
| ATOM | 2122 | N | ARG A | 310 | 32.264 | 44.090 | 1.633 | 1.00 | 14.78 |
| ATOM | 2123 | CA | ARG A | 310 | 32.084 | 45.286 | 2.453 | 1.00 | 15.52 |
| ATOM | 2124 | CB | ARG A | 310 | 32.340 | 46.553 | 1.623 | 1.00 | 12.86 |
| ATOM | 2125 | CG | ARG A | 310 | 32.388 | 47.832 | 2.468 | 1.00 | 14.96 |
| ATOM | 2126 | CD | ARG A | 310 | 32.520 | 49.072 | 1.597 | 1.00 | 12.65 |
| ATOM | 2127 | NE | ARG A | 310 | 31.446 | 49.104 | 0.611 | 1.00 | 14.57 |
| ATOM | 2128 | CZ | ARG A | 310 | 31.450 | 49.852 | −0.485 | 1.00 | 13.39 |
| ATOM | 2129 | NH1 | ARG A | 310 | 30.422 | 49.793 | −1.320 | 1.00 | 11.24 |
| ATOM | 2130 | NH2 | ARG A | 310 | 32.479 | 50.652 | −0.747 | 1.00 | 12.51 |
| ATOM | 2131 | C | ARG A | 310 | 30.772 | 45.455 | 3.215 | 1.00 | 16.19 |
| ATOM | 2132 | O | ARG A | 310 | 30.757 | 45.412 | 4.445 | 1.00 | 16.77 |
| ATOM | 2133 | N | ASP A | 311 | 29.675 | 45.659 | 2.496 | 1.00 | 17.50 |
| ATOM | 2134 | CA | ASP A | 311 | 28.391 | 45.878 | 3.147 | 1.00 | 17.75 |
| ATOM | 2135 | CB | ASP A | 311 | 27.381 | 46.369 | 2.109 | 1.00 | 19.42 |
| ATOM | 2136 | CG | ASP A | 311 | 27.661 | 47.809 | 1.676 | 1.00 | 21.08 |
| ATOM | 2137 | OD1 | ASP A | 311 | 28.771 | 48.309 | 1.974 | 1.00 | 20.69 |
| ATOM | 2138 | OD2 | ASP A | 311 | 26.787 | 48.441 | 1.046 | 1.00 | 20.67 |
| ATOM | 2139 | C | ASP A | 311 | 27.864 | 44.687 | 3.942 | 1.00 | 18.47 |
| ATOM | 2140 | O | ASP A | 311 | 27.205 | 44.862 | 4.969 | 1.00 | 17.98 |
| ATOM | 2141 | N | LEU A | 312 | 28.162 | 43.478 | 3.483 | 1.00 | 17.76 |
| ATOM | 2142 | CA | LEU A | 312 | 27.741 | 42.289 | 4.207 | 1.00 | 17.86 |

TABLE 29-continued

| ATOM | 2143 | CB | LEU A | 312 | 28.179 | 41.027 | 3.459 | 1.00 | 18.99 |
| ATOM | 2144 | CG | LEU A | 312 | 27.783 | 39.686 | 4.084 | 1.00 | 23.39 |
| ATOM | 2145 | CD1 | LEU A | 312 | 26.265 | 39.602 | 4.207 | 1.00 | 22.84 |
| ATOM | 2146 | CD2 | LEU A | 312 | 28.308 | 38.538 | 3.217 | 1.00 | 23.42 |
| ATOM | 2147 | C | LEU A | 312 | 28.410 | 42.346 | 5.585 | 1.00 | 17.48 |
| ATOM | 2148 | O | LEU A | 312 | 27.812 | 41.959 | 6.592 | 1.00 | 16.53 |
| ATOM | 2149 | N | SER A | 313 | 29.649 | 42.840 | 5.621 | 1.00 | 16.16 |
| ATOM | 2150 | CA | SER A | 313 | 30.397 | 42.971 | 6.873 | 1.00 | 17.10 |
| ATOM | 2151 | CB | SER A | 313 | 31.873 | 43.309 | 6.610 | 1.00 | 17.49 |
| ATOM | 2152 | OG | SER A | 313 | 32.612 | 42.163 | 6.244 | 1.00 | 23.70 |
| ATOM | 2153 | C | SER A | 313 | 29.808 | 44.067 | 7.749 | 1.00 | 15.96 |
| ATOM | 2154 | O | SER A | 313 | 29.607 | 43.875 | 8.949 | 1.00 | 16.85 |
| ATOM | 2155 | N | THR A | 314 | 29.549 | 45.221 | 7.143 | 1.00 | 13.84 |
| ATOM | 2156 | CA | THR A | 314 | 28.993 | 46.353 | 7.869 | 1.00 | 14.33 |
| ATOM | 2157 | CB | THR A | 314 | 28.745 | 47.551 | 6.934 | 1.00 | 13.64 |
| ATOM | 2158 | OG1 | THR A | 314 | 29.981 | 47.935 | 6.321 | 1.00 | 13.07 |
| ATOM | 2159 | CG2 | THR A | 314 | 28.190 | 48.731 | 7.715 | 1.00 | 12.00 |
| ATOM | 2160 | C | THR A | 314 | 27.686 | 45.969 | 8.541 | 1.00 | 14.80 |
| ATOM | 2161 | O | THR A | 314 | 27.470 | 46.292 | 9.707 | 1.00 | 16.48 |
| ATOM | 2162 | N | GLN A | 315 | 26.820 | 45.269 | 7.811 | 1.00 | 15.30 |
| ATOM | 2163 | CA | GLN A | 315 | 25.544 | 44.848 | 8.370 | 1.00 | 14.88 |
| ATOM | 2164 | CB | GLN A | 315 | 24.658 | 44.219 | 7.288 | 1.00 | 13.95 |
| ATOM | 2165 | CG | GLN A | 315 | 24.136 | 45.209 | 6.245 | 1.00 | 15.23 |
| ATOM | 2166 | CD | GLN A | 315 | 23.176 | 46.250 | 6.828 | 1.00 | 15.21 |
| ATOM | 2167 | OE1 | GLN A | 315 | 23.529 | 46.999 | 7.735 | 0.50 | 14.28 |
| ATOM | 2168 | NE2 | GLN A | 315 | 21.963 | 46.297 | 6.297 | 0.50 | 12.79 |
| ATOM | 2169 | C | GLN A | 315 | 25.743 | 43.869 | 9.523 | 1.00 | 14.34 |
| ATOM | 2170 | O | GLN A | 315 | 24.981 | 43.887 | 10.487 | 1.00 | 15.66 |
| ATOM | 2171 | N | THR A | 316 | 26.765 | 43.019 | 9.439 | 1.00 | 14.94 |
| ATOM | 2172 | CA | THR A | 316 | 27.021 | 42.062 | 10.521 | 1.00 | 13.97 |
| ATOM | 2173 | CB | THR A | 316 | 28.103 | 41.018 | 10.130 | 1.00 | 13.18 |
| ATOM | 2174 | OG1 | THR A | 316 | 27.681 | 40.314 | 8.958 | 1.00 | 14.58 |
| ATOM | 2175 | CG2 | THR A | 316 | 28.306 | 40.000 | 11.255 | 1.00 | 11.68 |
| ATOM | 2176 | C | THR A | 316 | 27.479 | 42.839 | 11.752 | 1.00 | 13.29 |
| ATOM | 2177 | O | THR A | 316 | 27.133 | 42.498 | 12.881 | 1.00 | 13.77 |
| ATOM | 2178 | N | ILE A | 317 | 28.247 | 43.897 | 11.522 | 1.00 | 13.34 |
| ATOM | 2179 | CA | ILE A | 317 | 28.728 | 44.738 | 12.609 | 1.00 | 13.60 |
| ATOM | 2180 | CB | ILE A | 317 | 29.711 | 45.803 | 12.095 | 1.00 | 12.88 |
| ATOM | 2181 | CG2 | ILE A | 317 | 29.990 | 46.820 | 13.199 | 1.00 | 12.51 |
| ATOM | 2182 | CG1 | ILE A | 317 | 30.998 | 45.132 | 11.609 | 1.00 | 8.92 |
| ATOM | 2183 | CD1 | ILE A | 317 | 31.890 | 46.038 | 10.782 | 1.00 | 8.20 |
| ATOM | 2184 | C | ILE A | 317 | 27.548 | 45.450 | 13.256 | 1.00 | 15.33 |
| ATOM | 2185 | O | ILE A | 317 | 27.442 | 45.508 | 14.482 | 1.00 | 14.07 |
| ATOM | 2186 | N | ARG A | 318 | 26.664 | 45.985 | 12.415 | 1.00 | 15.26 |
| ATOM | 2187 | CA | ARG A | 318 | 25.482 | 46.704 | 12.876 | 1.00 | 16.00 |
| ATOM | 2188 | CB | ARG A | 318 | 24.653 | 47.163 | 11.664 | 1.00 | 16.04 |
| ATOM | 2189 | CG | ARG A | 318 | 23.632 | 48.262 | 11.957 | 1.00 | 16.53 |
| ATOM | 2190 | CD | ARG A | 318 | 22.865 | 48.683 | 10.697 | 1.00 | 15.60 |
| ATOM | 2191 | NE | ARG A | 318 | 23.731 | 49.237 | 9.655 | 1.00 | 13.88 |
| ATOM | 2192 | CZ | ARG A | 318 | 24.404 | 50.379 | 9.759 | 1.00 | 13.49 |
| ATOM | 2193 | NH1 | ARG A | 318 | 24.316 | 51.104 | 10.862 | 1.00 | 12.45 |
| ATOM | 2194 | NH2 | ARG A | 318 | 25.178 | 50.792 | 8.762 | 1.00 | 11.39 |
| ATOM | 2195 | C | ARG A | 318 | 24.647 | 45.790 | 13.781 | 1.00 | 17.91 |
| ATOM | 2196 | O | ARG A | 318 | 24.223 | 46.179 | 14.874 | 1.00 | 17.43 |
| ATOM | 2197 | N | GLU A | 319 | 24.438 | 44.562 | 13.326 | 1.00 | 17.86 |
| ATOM | 2198 | CA | GLU A | 319 | 23.659 | 43.589 | 14.072 | 1.00 | 17.86 |
| ATOM | 2199 | CB | GLU A | 319 | 23.380 | 42.377 | 13.176 | 1.00 | 20.79 |
| ATOM | 2200 | CG | GLU A | 319 | 22.533 | 41.286 | 13.802 | 1.00 | 27.72 |
| ATOM | 2201 | CD | GLU A | 319 | 21.855 | 40.408 | 12.757 | 1.00 | 32.40 |
| ATOM | 2202 | OE1 | GLU A | 319 | 22.456 | 40.189 | 11.684 | 1.00 | 34.24 |
| ATOM | 2203 | OE2 | GLU A | 319 | 20.725 | 39.929 | 13.009 | 1.00 | 36.06 |
| ATOM | 2204 | C | GLU A | 319 | 24.317 | 43.156 | 15.388 | 1.00 | 17.83 |
| ATOM | 2205 | O | GLU A | 319 | 23.662 | 43.149 | 16.431 | 1.00 | 16.48 |
| ATOM | 2206 | N | MET A | 320 | 25.603 | 42.806 | 15.359 | 1.00 | 17.34 |
| ATOM | 2207 | CA | MET A | 320 | 26.273 | 42.379 | 16.590 | 1.00 | 16.86 |
| ATOM | 2208 | CB | MET A | 320 | 27.683 | 41.857 | 16.291 | 1.00 | 16.42 |
| ATOM | 2209 | CG | MET A | 320 | 27.732 | 40.636 | 15.371 | 1.00 | 13.96 |
| ATOM | 2210 | SD | MET A | 320 | 26.645 | 39.265 | 15.876 | 1.00 | 18.68 |
| ATOM | 2211 | CE | MET A | 320 | 27.333 | 38.814 | 17.496 | 1.00 | 14.45 |
| ATOM | 2212 | C | MET A | 320 | 26.340 | 43.509 | 17.627 | 1.00 | 17.09 |
| ATOM | 2213 | O | MET A | 320 | 26.256 | 43.267 | 18.833 | 1.00 | 16.35 |
| ATOM | 2214 | N | TYR A | 321 | 26.480 | 44.741 | 17.151 | 1.00 | 17.09 |
| ATOM | 2215 | CA | TYR A | 321 | 26.542 | 45.901 | 18.036 | 1.00 | 17.65 |
| ATOM | 2216 | CB | TYR A | 321 | 26.738 | 47.172 | 17.211 | 1.00 | 17.64 |
| ATOM | 2217 | CG | TYR A | 321 | 26.925 | 48.429 | 18.032 | 1.00 | 18.64 |
| ATOM | 2218 | CD1 | TYR A | 321 | 28.145 | 48.716 | 18.637 | 1.00 | 17.99 |
| ATOM | 2219 | CE1 | TYR A | 321 | 28.323 | 49.875 | 19.369 | 1.00 | 17.38 |
| ATOM | 2220 | CD2 | TYR A | 321 | 25.886 | 49.339 | 18.187 | 1.00 | 16.94 |
| ATOM | 2221 | CE2 | TYR A | 321 | 26.052 | 50.497 | 18.916 | 1.00 | 15.57 |

TABLE 29-continued

| | | | | | | | | |
|---|---|---|---|---|---|---|---|---|
| ATOM | 2222 | CZ | TYR A | 321 | 27.272 | 50.761 | 19.504 | 1.00 | 17.79 |
| ATOM | 2223 | OH | TYR A | 321 | 27.439 | 51.917 | 20.228 | 1.00 | 18.99 |
| ATOM | 2224 | C | TYR A | 321 | 25.245 | 46.012 | 18.844 | 1.00 | 18.22 |
| ATOM | 2225 | O | TYR A | 321 | 25.272 | 46.221 | 20.058 | 1.00 | 16.92 |
| ATOM | 2226 | N | ALA A | 322 | 24.115 | 45.871 | 18.154 | 1.00 | 18.07 |
| ATOM | 2227 | CA | ALA A | 322 | 22.798 | 45.951 | 18.779 | 1.00 | 18.52 |
| ATOM | 2228 | CB | ALA A | 322 | 21.708 | 46.022 | 17.698 | 1.00 | 15.28 |
| ATOM | 2229 | C | ALA A | 322 | 22.539 | 44.764 | 19.714 | 1.00 | 18.01 |
| ATOM | 2230 | O | ALA A | 322 | 21.979 | 44.929 | 20.793 | 1.00 | 19.87 |
| ATOM | 2231 | N | LEU A | 323 | 22.945 | 43.570 | 19.301 | 1.00 | 17.20 |
| ATOM | 2232 | CA | LEU A | 323 | 22.752 | 42.382 | 20.128 | 1.00 | 18.74 |
| ATOM | 2233 | CB | LEU A | 323 | 23.129 | 41.124 | 19.343 | 1.00 | 17.37 |
| ATOM | 2234 | CG | LEU A | 323 | 22.147 | 40.738 | 18.232 | 1.00 | 18.08 |
| ATOM | 2235 | CD1 | LEU A | 323 | 22.713 | 39.592 | 17.407 | 1.00 | 15.53 |
| ATOM | 2236 | CD2 | LEU A | 323 | 20.807 | 40.352 | 18.854 | 1.00 | 16.70 |
| ATOM | 2237 | C | LEU A | 323 | 23.565 | 42.446 | 21.422 | 1.00 | 19.90 |
| ATOM | 2238 | O | LEU A | 323 | 23.201 | 41.822 | 22.419 | 1.00 | 21.10 |
| ATOM | 2239 | N | THR A | 324 | 24.664 | 43.199 | 21.404 | 1.00 | 19.51 |
| ATOM | 2240 | CA | THR A | 324 | 25.509 | 43.334 | 22.585 | 1.00 | 19.82 |
| ATOM | 2241 | CB | THR A | 324 | 27.016 | 43.159 | 22.226 | 1.00 | 19.33 |
| ATOM | 2242 | OG1 | THR A | 324 | 27.408 | 44.134 | 21.250 | 1.00 | 17.08 |
| ATOM | 2243 | CG2 | THR A | 324 | 27.269 | 41.768 | 21.662 | 1.00 | 18.20 |
| ATOM | 2244 | C | THR A | 324 | 25.304 | 44.679 | 23.291 | 1.00 | 21.29 |
| ATOM | 2245 | O | THR A | 324 | 26.094 | 45.066 | 24.151 | 1.00 | 21.80 |
| ATOM | 2246 | N | GLN A | 325 | 24.242 | 45.388 | 22.920 | 1.00 | 22.83 |
| ATOM | 2247 | CA | GLN A | 325 | 23.925 | 46.679 | 23.525 | 1.00 | 24.26 |
| ATOM | 2248 | CB | GLN A | 325 | 23.529 | 46.502 | 24.995 | 1.00 | 27.36 |
| ATOM | 2249 | CG | GLN A | 325 | 22.185 | 45.830 | 25.223 | 1.00 | 30.52 |
| ATOM | 2250 | CD | GLN A | 325 | 22.121 | 44.440 | 24.633 | 1.00 | 35.25 |
| ATOM | 2251 | OE1 | GLN A | 325 | 22.909 | 43.563 | 24.991 | 1.00 | 38.03 |
| ATOM | 2252 | NE2 | GLN A | 325 | 21.178 | 44.227 | 23.721 | 1.00 | 37.42 |
| ATOM | 2253 | C | GLN A | 325 | 25.073 | 47.671 | 23.446 | 1.00 | 23.75 |
| ATOM | 2254 | O | GLN A | 325 | 25.188 | 48.557 | 24.293 | 1.00 | 23.87 |
| ATOM | 2255 | N | GLY A | 326 | 25.916 | 47.526 | 22.430 | 1.00 | 23.08 |
| ATOM | 2256 | CA | GLY A | 326 | 27.043 | 48.428 | 22.275 | 1.00 | 23.27 |
| ATOM | 2257 | C | GLY A | 326 | 28.025 | 48.394 | 23.435 | 1.00 | 22.83 |
| ATOM | 2258 | O | GLY A | 326 | 28.797 | 49.327 | 23.621 | 1.00 | 21.36 |
| ATOM | 2259 | N | ARG A | 327 | 28.006 | 47.317 | 24.213 | 1.00 | 24.94 |
| ATOM | 2260 | CA | ARG A | 327 | 28.900 | 47.192 | 25.361 | 1.00 | 27.26 |
| ATOM | 2261 | CB | ARG A | 327 | 28.134 | 46.627 | 26.559 | 1.00 | 29.79 |
| ATOM | 2262 | CG | ARG A | 327 | 27.058 | 47.569 | 27.075 | 1.00 | 36.59 |
| ATOM | 2263 | CD | ARG A | 327 | 26.163 | 46.918 | 28.119 | 1.00 | 41.47 |
| ATOM | 2264 | NE | ARG A | 327 | 25.082 | 47.821 | 28.508 | 1.00 | 48.27 |
| ATOM | 2265 | CZ | ARG A | 327 | 24.011 | 47.459 | 29.208 | 1.00 | 50.35 |
| ATOM | 2266 | NH1 | ARG A | 327 | 23.869 | 46.201 | 29.606 | 1.00 | 52.09 |
| ATOM | 2267 | NH2 | ARG A | 327 | 23.076 | 48.354 | 29.499 | 1.00 | 50.26 |
| ATOM | 2268 | C | ARG A | 327 | 30.115 | 46.320 | 25.068 | 1.00 | 26.50 |
| ATOM | 2269 | O | ARG A | 327 | 31.016 | 46.196 | 25.897 | 1.00 | 27.91 |
| ATOM | 2270 | N | VAL A | 328 | 30.137 | 45.716 | 23.887 | 1.00 | 24.28 |
| ATOM | 2271 | CA | VAL A | 328 | 31.244 | 44.860 | 23.497 | 1.00 | 21.47 |
| ATOM | 2272 | CB | VAL A | 328 | 30.749 | 43.465 | 23.088 | 1.00 | 20.24 |
| ATOM | 2273 | CG1 | VAL A | 328 | 31.923 | 42.598 | 22.686 | 1.00 | 18.37 |
| ATOM | 2274 | CG2 | VAL A | 328 | 29.973 | 42.833 | 24.236 | 1.00 | 18.95 |
| ATOM | 2275 | C | VAL A | 328 | 31.992 | 45.476 | 22.325 | 1.00 | 20.97 |
| ATOM | 2276 | O | VAL A | 328 | 31.440 | 45.624 | 21.237 | 1.00 | 21.49 |
| ATOM | 2277 | N | PRO A | 329 | 33.260 | 45.854 | 22.543 | 1.00 | 18.84 |
| ATOM | 2278 | CD | PRO A | 329 | 33.969 | 45.768 | 23.831 | 1.00 | 19.11 |
| ATOM | 2279 | CA | PRO A | 329 | 34.113 | 46.461 | 21.518 | 1.00 | 18.46 |
| ATOM | 2280 | CB | PRO A | 329 | 35.471 | 46.552 | 22.211 | 1.00 | 17.66 |
| ATOM | 2281 | CG | PRO A | 329 | 35.095 | 46.754 | 23.641 | 1.00 | 18.87 |
| ATOM | 2282 | C | PRO A | 329 | 34.168 | 45.612 | 20.246 | 1.00 | 18.00 |
| ATOM | 2283 | O | PRO A | 329 | 34.356 | 44.390 | 20.296 | 1.00 | 15.48 |
| ATOM | 2284 | N | ILE A | 330 | 34.001 | 46.268 | 19.107 | 1.00 | 15.14 |
| ATOM | 2285 | CA | ILE A | 330 | 34.038 | 45.571 | 17.835 | 1.00 | 15.79 |
| ATOM | 2286 | CB | ILE A | 330 | 32.662 | 45.635 | 17.129 | 1.00 | 15.18 |
| ATOM | 2287 | CG2 | ILE A | 330 | 32.770 | 45.067 | 15.733 | 1.00 | 13.79 |
| ATOM | 2288 | CG1 | ILE A | 330 | 31.614 | 44.869 | 17.941 | 1.00 | 15.97 |
| ATOM | 2289 | CD1 | ILE A | 330 | 30.211 | 44.945 | 17.348 | 1.00 | 16.11 |
| ATOM | 2290 | C | ILE A | 330 | 35.086 | 46.148 | 16.888 | 1.00 | 14.82 |
| ATOM | 2291 | O | ILE A | 330 | 35.266 | 47.369 | 16.796 | 1.00 | 13.07 |
| ATOM | 2292 | N | ILE A | 331 | 35.789 | 45.257 | 16.200 | 1.00 | 13.52 |
| ATOM | 2293 | CA | ILE A | 331 | 36.780 | 45.662 | 15.209 | 1.00 | 13.29 |
| ATOM | 2294 | CB | ILE A | 331 | 38.114 | 44.896 | 15.371 | 1.00 | 12.04 |
| ATOM | 2295 | CG2 | ILE A | 331 | 39.082 | 45.301 | 14.267 | 1.00 | 9.01 |
| ATOM | 2296 | CG1 | ILE A | 331 | 38.722 | 45.191 | 16.748 | 1.00 | 12.74 |
| ATOM | 2297 | CD1 | ILE A | 331 | 40.103 | 44.564 | 16.970 | 1.00 | 9.69 |
| ATOM | 2298 | C | ILE A | 331 | 36.154 | 45.300 | 13.863 | 1.00 | 13.53 |
| ATOM | 2299 | O | ILE A | 331 | 35.952 | 44.120 | 13.568 | 1.00 | 14.03 |
| ATOM | 2300 | N | GLY A | 332 | 35.825 | 46.317 | 13.069 | 1.00 | 12.79 |

TABLE 29-continued

| ATOM | 2301 | CA | GLY A | 332 | 35.209 | 46.097 | 11.770 | 1.00 | 11.23 |
| ATOM | 2302 | C | GLY A | 332 | 36.199 | 45.784 | 10.670 | 1.00 | 12.17 |
| ATOM | 2303 | O | GLY A | 332 | 37.187 | 46.495 | 10.498 | 1.00 | 15.29 |
| ATOM | 2304 | N | VAL A | 333 | 35.920 | 44.726 | 9.912 | 1.00 | 14.17 |
| ATOM | 2305 | CA | VAL A | 333 | 36.789 | 44.275 | 8.825 | 1.00 | 13.37 |
| ATOM | 2306 | CB | VAL A | 333 | 37.667 | 43.082 | 9.268 | 1.00 | 14.07 |
| ATOM | 2307 | CG1 | VAL A | 333 | 38.941 | 43.040 | 8.443 | 1.00 | 12.39 |
| ATOM | 2308 | CG2 | VAL A | 333 | 37.936 | 43.148 | 10.749 | 1.00 | 16.53 |
| ATOM | 2309 | C | VAL A | 333 | 35.962 | 43.767 | 7.646 | 1.00 | 12.46 |
| ATOM | 2310 | O | VAL A | 333 | 34.982 | 43.053 | 7.836 | 1.00 | 11.94 |
| ATOM | 2311 | N | GLY A | 334 | 36.376 | 44.104 | 6.431 | 1.00 | 12.77 |
| ATOM | 2312 | CA | GLY A | 334 | 35.651 | 43.639 | 5.264 | 1.00 | 13.14 |
| ATOM | 2313 | C | GLY A | 334 | 35.402 | 44.690 | 4.197 | 1.00 | 15.69 |
| ATOM | 2314 | O | GLY A | 334 | 34.449 | 45.473 | 4.287 | 1.00 | 14.19 |
| ATOM | 2315 | N | GLY A | 335 | 36.265 | 44.708 | 3.184 | 1.00 | 14.95 |
| ATOM | 2316 | CA | GLY A | 335 | 36.111 | 45.651 | 2.093 | 1.00 | 15.32 |
| ATOM | 2317 | C | GLY A | 335 | 36.332 | 47.119 | 2.412 | 1.00 | 16.47 |
| ATOM | 2318 | O | GLY A | 335 | 35.742 | 47.983 | 1.766 | 1.00 | 18.02 |
| ATOM | 2319 | N | VAL A | 336 | 37.162 | 47.422 | 3.403 | 1.00 | 16.45 |
| ATOM | 2320 | CA | VAL A | 336 | 37.434 | 48.817 | 3.721 | 1.00 | 15.37 |
| ATOM | 2321 | CB | VAL A | 336 | 37.868 | 48.994 | 5.185 | 1.00 | 16.95 |
| ATOM | 2322 | CG1 | VAL A | 336 | 38.430 | 50.402 | 5.396 | 1.00 | 17.10 |
| ATOM | 2323 | CG2 | VAL A | 336 | 36.681 | 48.757 | 6.104 | 1.00 | 15.58 |
| ATOM | 2324 | C | VAL A | 336 | 38.547 | 49.313 | 2.798 | 1.00 | 15.63 |
| ATOM | 2325 | O | VAL A | 336 | 39.664 | 48.788 | 2.808 | 1.00 | 12.87 |
| ATOM | 2326 | N | SER A | 337 | 38.235 | 50.323 | 1.994 | 1.00 | 15.71 |
| ATOM | 2327 | CA | SER A | 337 | 39.210 | 50.861 | 1.054 | 1.00 | 17.36 |
| ATOM | 2328 | CB | SER A | 337 | 38.909 | 50.320 | 0.348 | 1.00 | 19.55 |
| ATOM | 2329 | OG | SER A | 337 | 39.881 | 50.746 | 1.281 | 1.00 | 26.27 |
| ATOM | 2330 | C | SER A | 337 | 39.225 | 52.391 | 1.026 | 1.00 | 16.87 |
| ATOM | 2331 | O | SER A | 337 | 39.985 | 52.995 | 0.270 | 1.00 | 16.56 |
| ATOM | 2332 | N | SER A | 338 | 38.392 | 53.013 | 1.856 | 1.00 | 15.02 |
| ATOM | 2333 | CA | SER A | 338 | 38.311 | 54.466 | 1.895 | 1.00 | 14.94 |
| ATOM | 2334 | CB | SER A | 338 | 37.337 | 54.958 | 0.816 | 1.00 | 15.62 |
| ATOM | 2335 | OG | SER A | 338 | 35.993 | 54.649 | 1.163 | 1.00 | 12.43 |
| ATOM | 2336 | C | SER A | 338 | 37.836 | 54.972 | 3.257 | 1.00 | 14.83 |
| ATOM | 2337 | O | SER A | 338 | 37.402 | 54.193 | 4.108 | 1.00 | 15.32 |
| ATOM | 2338 | N | GLY A | 339 | 37.913 | 56.283 | 3.451 | 1.00 | 13.85 |
| ATOM | 2339 | CA | GLY A | 339 | 37.466 | 56.867 | 4.700 | 1.00 | 13.96 |
| ATOM | 2340 | C | GLY A | 339 | 35.992 | 56.577 | 4.911 | 1.00 | 14.77 |
| ATOM | 2341 | O | GLY A | 339 | 35.568 | 56.266 | 6.024 | 1.00 | 15.11 |
| ATOM | 2342 | N | GLN A | 340 | 35.205 | 56.675 | 3.840 | 1.00 | 13.56 |
| ATOM | 2343 | CA | GLN A | 340 | 33.775 | 56.410 | 3.929 | 1.00 | 14.73 |
| ATOM | 2344 | CB | GLN A | 340 | 33.075 | 56.650 | 2.583 | 1.00 | 14.84 |
| ATOM | 2345 | CG | GLN A | 340 | 31.606 | 56.231 | 2.606 | 1.00 | 16.68 |
| ATOM | 2346 | CD | GLN A | 340 | 30.869 | 56.527 | 1.309 | 1.00 | 17.07 |
| ATOM | 2347 | OE1 | GLN A | 340 | 30.787 | 57.678 | 0.873 | 1.00 | 17.10 |
| ATOM | 2348 | NE2 | GLN A | 340 | 30.322 | 55.487 | 0.691 | 1.00 | 15.72 |
| ATOM | 2349 | C | GLN A | 340 | 33.521 | 54.976 | 4.376 | 1.00 | 14.91 |
| ATOM | 2350 | O | GLN A | 340 | 32.690 | 54.736 | 5.258 | 1.00 | 15.89 |
| ATOM | 2351 | N | ASP A | 341 | 34.231 | 54.027 | 3.766 | 1.00 | 11.85 |
| ATOM | 2352 | CA | ASP A | 341 | 34.072 | 52.622 | 4.129 | 1.00 | 12.88 |
| ATOM | 2353 | CB | ASP A | 341 | 35.014 | 51.723 | 3.311 | 1.00 | 12.35 |
| ATOM | 2354 | CG | ASP A | 341 | 34.759 | 51.806 | 1.813 | 1.00 | 14.51 |
| ATOM | 2355 | OD1 | ASP A | 341 | 33.624 | 52.149 | 1.416 | 1.00 | 15.79 |
| ATOM | 2356 | OD2 | ASP A | 341 | 35.690 | 51.512 | 1.031 | 1.00 | 13.03 |
| ATOM | 2357 | C | ASP A | 341 | 34.385 | 52.458 | 5.613 | 1.00 | 11.93 |
| ATOM | 2358 | O | ASP A | 341 | 33.689 | 51.748 | 6.336 | 1.00 | 11.87 |
| ATOM | 2359 | N | ALA A | 342 | 35.441 | 53.124 | 6.064 | 1.00 | 11.66 |
| ATOM | 2360 | CA | ALA A | 342 | 35.843 | 53.046 | 7.460 | 1.00 | 11.86 |
| ATOM | 2361 | CB | ALA A | 342 | 37.183 | 53.751 | 7.657 | 1.00 | 11.31 |
| ATOM | 2362 | C | ALA A | 342 | 34.788 | 53.652 | 8.381 | 1.00 | 12.51 |
| ATOM | 2363 | O | ALA A | 342 | 34.421 | 53.052 | 9.390 | 1.00 | 13.16 |
| ATOM | 2364 | N | LEU A | 343 | 34.295 | 54.835 | 8.026 | 1.00 | 11.81 |
| ATOM | 2365 | CA | LEU A | 343 | 33.296 | 55.518 | 8.841 | 1.00 | 12.88 |
| ATOM | 2366 | CB | LEU A | 343 | 33.117 | 56.960 | 8.355 | 1.00 | 12.38 |
| ATOM | 2367 | CG | LEU A | 343 | 32.210 | 57.840 | 9.220 | 1.00 | 12.11 |
| ATOM | 2368 | CD1 | LEU A | 343 | 32.755 | 57.858 | 10.646 | 1.00 | 12.07 |
| ATOM | 2369 | CD2 | LEU A | 343 | 32.137 | 59.262 | 8.644 | 1.00 | 9.24 |
| ATOM | 2370 | C | LEU A | 343 | 31.935 | 54.816 | 8.893 | 1.00 | 13.84 |
| ATOM | 2371 | O | LEU A | 343 | 31.257 | 54.864 | 9.916 | 1.00 | 16.26 |
| ATOM | 2372 | N | GLU A | 344 | 31.517 | 54.178 | 7.802 | 1.00 | 14.81 |
| ATOM | 2373 | CA | GLU A | 344 | 30.234 | 53.483 | 7.821 | 1.00 | 14.29 |
| ATOM | 2374 | CB | GLU A | 344 | 29.892 | 52.902 | 6.447 | 1.00 | 15.56 |
| ATOM | 2375 | CG | GLU A | 344 | 29.631 | 53.943 | 5.363 | 1.00 | 16.52 |
| ATOM | 2376 | CD | GLU A | 344 | 29.003 | 53.345 | 4.105 | 1.00 | 17.36 |
| ATOM | 2377 | OE1 | GLU A | 344 | 29.284 | 52.169 | 3.793 | 1.00 | 17.77 |
| ATOM | 2378 | OE2 | GLU A | 344 | 28.240 | 54.056 | 3.417 | 1.00 | 15.41 |
| ATOM | 2379 | C | GLU A | 344 | 30.291 | 52.366 | 8.862 | 1.00 | 14.33 |

TABLE 29-continued

| | | | | | | | | | |
|---|---|---|---|---|---|---|---|---|---|
| ATOM | 2380 | O | GLU A | 344 | 29.335 | 52.147 | 9.608 | 1.00 | 14.20 |
| ATOM | 2381 | N | LYS A | 345 | 31.423 | 51.669 | 8.921 | 1.00 | 14.34 |
| ATOM | 2382 | CA | LYS A | 345 | 31.599 | 50.591 | 9.888 | 1.00 | 15.17 |
| ATOM | 2383 | CB | LYS A | 345 | 32.865 | 49.790 | 9.576 | 1.00 | 13.40 |
| ATOM | 2384 | CG | LYS A | 345 | 32.673 | 48.774 | 8.460 | 1.00 | 13.33 |
| ATOM | 2385 | CD | LYS A | 345 | 33.934 | 47.958 | 8.217 | 1.00 | 10.82 |
| ATOM | 2386 | CE | LYS A | 345 | 33.622 | 46.670 | 7.470 | 1.00 | 11.36 |
| ATOM | 2387 | NZ | LYS A | 345 | 32.935 | 46.896 | 6.170 | 1.00 | 11.03 |
| ATOM | 2388 | C | LYS A | 345 | 31.658 | 51.143 | 11.308 | 1.00 | 15.43 |
| ATOM | 2389 | O | LYS A | 345 | 31.113 | 50.547 | 12.237 | 1.00 | 15.78 |
| ATOM | 2390 | N | ILE A | 346 | 32.312 | 52.286 | 11.478 | 1.00 | 15.51 |
| ATOM | 2391 | CA | ILE A | 346 | 32.396 | 52.903 | 12.796 | 1.00 | 16.19 |
| ATOM | 2392 | CB | ILE A | 346 | 33.364 | 54.115 | 12.787 | 1.00 | 16.23 |
| ATOM | 2393 | CG2 | ILE A | 346 | 33.293 | 54.866 | 14.117 | 1.00 | 14.17 |
| ATOM | 2394 | CG1 | ILE A | 346 | 34.791 | 53.618 | 12.528 | 1.00 | 15.33 |
| ATOM | 2395 | CD1 | ILE A | 346 | 35.816 | 54.718 | 12.423 | 1.00 | 16.06 |
| ATOM | 2396 | C | ILE A | 346 | 30.995 | 53.344 | 13.234 | 1.00 | 16.44 |
| ATOM | 2397 | O | ILE A | 346 | 30.582 | 53.075 | 14.362 | 1.00 | 16.11 |
| ATOM | 2398 | N | ARG A | 347 | 30.256 | 54.002 | 12.343 | 1.00 | 15.77 |
| ATOM | 2399 | CA | ARG A | 347 | 28.899 | 54.435 | 12.679 | 1.00 | 16.90 |
| ATOM | 2400 | CB | ARG A | 347 | 28.298 | 55.277 | 11.548 | 1.00 | 17.76 |
| ATOM | 2401 | CG | ARG A | 347 | 28.955 | 56.649 | 11.348 | 1.00 | 18.67 |
| ATOM | 2402 | CD | ARG A | 347 | 28.227 | 57.437 | 10.259 | 1.00 | 19.78 |
| ATOM | 2403 | NE | ARG A | 347 | 26.818 | 57.633 | 10.594 | 1.00 | 22.78 |
| ATOM | 2404 | CZ | ARG A | 347 | 26.283 | 58.796 | 10.962 | 1.00 | 26.59 |
| ATOM | 2405 | NH1 | ARG A | 347 | 27.037 | 59.889 | 11.038 | 1.00 | 26.85 |
| ATOM | 2406 | NH2 | ARG A | 347 | 24.994 | 58.864 | 11.273 | 1.00 | 24.22 |
| ATOM | 2407 | C | ARG A | 347 | 28.007 | 53.220 | 12.948 | 1.00 | 15.86 |
| ATOM | 2408 | O | ARG A | 347 | 27.079 | 53.283 | 13.748 | 1.00 | 15.48 |
| ATOM | 2409 | N | ALA A | 348 | 28.296 | 52.109 | 12.278 | 1.00 | 15.92 |
| ATOM | 2410 | CA | ALA A | 348 | 27.521 | 50.892 | 12.471 | 1.00 | 15.49 |
| ATOM | 2411 | CB | ALA A | 348 | 27.792 | 49.902 | 11.333 | 1.00 | 15.25 |
| ATOM | 2412 | C | ALA A | 348 | 27.848 | 50.252 | 13.820 | 1.00 | 15.76 |
| ATOM | 2413 | O | ALA A | 348 | 27.095 | 49.401 | 14.301 | 1.00 | 16.58 |
| ATOM | 2414 | N | GLY A | 349 | 28.966 | 50.653 | 14.431 | 1.00 | 13.86 |
| ATOM | 2415 | CA | GLY A | 349 | 29.315 | 50.098 | 15.730 | 1.00 | 13.25 |
| ATOM | 2416 | C | GLY A | 349 | 30.759 | 49.684 | 15.979 | 1.00 | 14.61 |
| ATOM | 2417 | O | GLY A | 349 | 31.097 | 49.268 | 17.088 | 1.00 | 15.21 |
| ATOM | 2418 | N | ALA A | 350 | 31.617 | 49.797 | 14.972 | 1.00 | 14.16 |
| ATOM | 2419 | CA | ALA A | 350 | 33.014 | 49.418 | 15.134 | 1.00 | 16.29 |
| ATOM | 2420 | CB | ALA A | 350 | 33.637 | 49.115 | 13.774 | 1.00 | 16.52 |
| ATOM | 2421 | C | ALA A | 350 | 33.836 | 50.485 | 15.843 | 1.00 | 17.09 |
| ATOM | 2422 | O | ALA A | 350 | 33.737 | 51.674 | 15.531 | 1.00 | 17.36 |
| ATOM | 2423 | N | SER A | 351 | 34.646 | 50.051 | 16.805 | 1.00 | 17.54 |
| ATOM | 2424 | CA | SER A | 351 | 35.515 | 50.963 | 17.540 | 1.00 | 16.20 |
| ATOM | 2425 | CB | SER A | 351 | 35.821 | 50.411 | 18.932 | 1.00 | 15.23 |
| ATOM | 2426 | OG | SER A | 351 | 34.684 | 50.491 | 19.767 | 1.00 | 18.04 |
| ATOM | 2427 | C | SER A | 351 | 36.812 | 51.112 | 16.754 | 1.00 | 16.11 |
| ATOM | 2428 | O | SER A | 351 | 37.503 | 52.131 | 16.851 | 1.00 | 15.72 |
| ATOM | 2429 | N | LEU A | 352 | 37.127 | 50.078 | 15.977 | 1.00 | 14.13 |
| ATOM | 2430 | CA | LEU A | 352 | 38.328 | 50.046 | 15.149 | 1.00 | 15.05 |
| ATOM | 2431 | CB | LEU A | 352 | 39.457 | 49.286 | 15.859 | 1.00 | 13.12 |
| ATOM | 2432 | CG | LEU A | 352 | 39.909 | 49.717 | 17.254 | 1.00 | 14.84 |
| ATOM | 2433 | CD1 | LEU A | 352 | 40.771 | 48.610 | 17.869 | 1.00 | 11.84 |
| ATOM | 2434 | CD2 | LEU A | 352 | 40.674 | 51.033 | 17.171 | 1.00 | 13.14 |
| ATOM | 2435 | C | LEU A | 352 | 37.999 | 49.308 | 13.857 | 1.00 | 13.72 |
| ATOM | 2436 | O | LEU A | 352 | 37.021 | 48.565 | 13.795 | 1.00 | 11.22 |
| ATOM | 2437 | N | VAL A | 353 | 38.820 | 49.514 | 12.831 | 1.00 | 12.75 |
| ATOM | 2438 | CA | VAL A | 353 | 38.626 | 48.828 | 11.564 | 1.00 | 13.86 |
| ATOM | 2439 | CB | VAL A | 353 | 38.055 | 49.761 | 10.470 | 1.00 | 15.70 |
| ATOM | 2440 | CG1 | VAL A | 353 | 36.770 | 50.417 | 10.960 | 1.00 | 14.25 |
| ATOM | 2441 | CG2 | VAL A | 353 | 39.090 | 50.799 | 10.071 | 1.00 | 13.83 |
| ATOM | 2442 | C | VAL A | 353 | 39.962 | 48.281 | 11.081 | 1.00 | 14.67 |
| ATOM | 2443 | O | VAL A | 353 | 41.024 | 48.711 | 11.536 | 1.00 | 12.91 |
| ATOM | 2444 | N | GLN A | 354 | 39.897 | 47.316 | 10.172 | 1.00 | 14.28 |
| ATOM | 2445 | CA | GLN A | 354 | 41.089 | 46.710 | 9.596 | 1.00 | 14.04 |
| ATOM | 2446 | CB | GLN A | 354 | 41.347 | 45.307 | 10.175 | 1.00 | 14.77 |
| ATOM | 2447 | CG | GLN A | 354 | 41.594 | 45.223 | 11.678 | 1.00 | 15.51 |
| ATOM | 2448 | CD | GLN A | 354 | 41.763 | 43.774 | 12.147 | 1.00 | 18.24 |
| ATOM | 2449 | OE1 | GLN A | 354 | 41.00 | 542.888 | 11.745 | 1.00 | 16.59 |
| ATOM | 2450 | NE2 | GLN A | 354 | 42.756 | 43.534 | 13.000 | 1.00 | 16.98 |
| ATOM | 2451 | C | GLN A | 354 | 40.852 | 46.574 | 8.100 | 1.00 | 14.33 |
| ATOM | 2452 | O | GLN A | 354 | 39.715 | 46.634 | 7.626 | 1.00 | 13.37 |
| ATOM | 2453 | N | LEU A | 355 | 41.931 | 46.394 | 7.354 | 1.00 | 14.18 |
| ATOM | 2454 | CA | LEU A | 355 | 41.822 | 46.213 | 5.919 | 1.00 | 15.51 |
| ATOM | 2455 | CB | LEU A | 355 | 41.899 | 47.561 | 5.188 | 1.00 | 13.52 |
| ATOM | 2456 | CG | LEU A | 355 | 43.166 | 48.417 | 5.312 | 1.00 | 13.61 |
| ATOM | 2457 | CD1 | LEU A | 355 | 44.262 | 47.879 | 4.399 | 1.00 | 13.33 |
| ATOM | 2458 | CD2 | LEU A | 355 | 42.838 | 49.854 | 4.943 | 1.00 | 10.85 |

TABLE 29-continued

| ATOM | 2459 | C | LEU A | 355 | 42.955 | 45.306 | 5.482 | 1.00 | 16.16 |
|---|---|---|---|---|---|---|---|---|---|
| ATOM | 2460 | O | LEU A | 355 | 43.963 | 45.176 | 6.179 | 1.00 | 15.14 |
| ATOM | 2461 | N | TYR A | 356 | 42.775 | 44.657 | 4.340 | 1.00 | 17.37 |
| ATOM | 2462 | CA | TYR A | 356 | 43.805 | 43.785 | 3.804 | 1.00 | 17.28 |
| ATOM | 2463 | CB | TYR A | 356 | 43.639 | 42.352 | 4.333 | 1.00 | 16.02 |
| ATOM | 2464 | CG | TYR A | 356 | 44.703 | 41.377 | 3.852 | 1.00 | 15.51 |
| ATOM | 2465 | CD1 | TYR A | 356 | 44.774 | 40.087 | 4.363 | 1.00 | 16.04 |
| ATOM | 2466 | CE1 | TYR A | 356 | 45.714 | 39.182 | 3.897 | 1.00 | 14.34 |
| ATOM | 2467 | CD2 | TYR A | 356 | 45.611 | 41.735 | 2.862 | 1.00 | 16.62 |
| ATOM | 2468 | CE2 | TYR A | 356 | 46.551 | 40.838 | 2.387 | 1.00 | 16.21 |
| ATOM | 2469 | CZ | TYR A | 356 | 46.597 | 39.565 | 2.905 | 1.00 | 16.13 |
| ATOM | 2470 | OH | TYR A | 356 | 47.518 | 38.669 | 2.414 | 1.00 | 17.60 |
| ATOM | 2471 | C | TYR A | 356 | 43.739 | 43.803 | 2.287 | 1.00 | 17.12 |
| ATOM | 2472 | O | TYR A | 356 | 44.671 | 44.261 | 1.629 | 1.00 | 18.15 |
| ATOM | 2473 | N | THR A | 357 | 42.637 | 43.308 | 1.738 | 1.00 | 16.53 |
| ATOM | 2474 | CA | THR A | 357 | 42.472 | 43.250 | 0.292 | 1.00 | 16.40 |
| ATOM | 2475 | CB | THR A | 357 | 41.059 | 42.753 | −0.080 | 1.00 | 16.96 |
| ATOM | 2476 | OG1 | THR A | 357 | 40.868 | 41.429 | 0.439 | 1.00 | 13.18 |
| ATOM | 2477 | CG2 | THR A | 357 | 40.886 | 42.727 | −1.589 | 1.00 | 16.23 |
| ATOM | 2478 | C | THR A | 357 | 42.731 | 44.590 | −0.401 | 1.00 | 15.65 |
| ATOM | 2479 | O | THR A | 357 | 43.312 | 44.633 | −1.484 | 1.00 | 15.49 |
| ATOM | 2480 | N | ALA A | 358 | 42.307 | 45.683 | 0.223 | 1.00 | 15.19 |
| ATOM | 2481 | CA | ALA A | 358 | 42.507 | 47.002 | −0.367 | 1.00 | 15.24 |
| ATOM | 2482 | CB | ALA A | 358 | 41.921 | 48.070 | 0.534 | 1.00 | 11.12 |
| ATOM | 2483 | C | ALA A | 358 | 43.995 | 47.255 | −0.584 | 1.00 | 16.21 |
| ATOM | 2484 | O | ALA A | 358 | 44.394 | 47.872 | −1.572 | 1.00 | 15.43 |
| ATOM | 2485 | N | LEU A | 359 | 44.810 | 46.770 | 0.348 | 1.00 | 16.24 |
| ATOM | 2486 | CA | LEU A | 359 | 46.255 | 46.943 | 0.273 | 1.00 | 16.57 |
| ATOM | 2487 | CB | LEU A | 359 | 46.916 | 46.409 | 1.548 | 1.00 | 17.72 |
| ATOM | 2488 | CG | LEU A | 359 | 48.442 | 46.485 | 1.620 | 1.00 | 17.63 |
| ATOM | 2489 | CD1 | LEU A | 359 | 48.894 | 47.933 | 1.559 | 1.00 | 17.25 |
| ATOM | 2490 | CD2 | LEU A | 359 | 48.919 | 45.829 | 2.908 | 1.00 | 18.09 |
| ATOM | 2491 | C | LEU A | 359 | 46.846 | 46.239 | −0.942 | 1.00 | 15.68 |
| ATOM | 2492 | O | LEU A | 359 | 47.800 | 46.725 | −1.541 | 1.00 | 14.17 |
| ATOM | 2493 | N | THR A | 360 | 46.270 | 45.099 | −1.309 | 1.00 | 15.77 |
| ATOM | 2494 | CA | THR A | 360 | 46.762 | 44.336 | −2.450 | 1.00 | 16.61 |
| ATOM | 2495 | CB | THR A | 360 | 46.189 | 42.906 | −2.454 | 1.00 | 16.18 |
| ATOM | 2496 | OG1 | THR A | 360 | 44.804 | 42.943 | −2.829 | 1.00 | 17.30 |
| ATOM | 2497 | CG2 | THR A | 360 | 46.331 | 42.280 | −1.068 | 1.00 | 10.83 |
| ATOM | 2498 | C | THR A | 360 | 46.444 | 44.986 | −3.795 | 1.00 | 18.77 |
| ATOM | 2499 | O | THR A | 360 | 47.034 | 44.628 | −4.813 | 1.00 | 21.01 |
| ATOM | 2500 | N | PHE A | 361 | 45.516 | 45.937 | −3.810 | 1.00 | 18.81 |
| ATOM | 2501 | CA | PHE A | 361 | 45.165 | 46.606 | −5.060 | 1.00 | 20.17 |
| ATOM | 2502 | CB | PHE A | 361 | 43.644 | 46.760 | −5.197 | 1.00 | 21.09 |
| ATOM | 2503 | CG | PHE A | 361 | 42.922 | 45.482 | −5.517 | 1.00 | 22.40 |
| ATOM | 2504 | CD1 | PHE A | 361 | 42.189 | 44.821 | −4.547 | 1.00 | 19.17 |
| ATOM | 2505 | CD2 | PHE A | 361 | 42.988 | 44.935 | −6.791 | 1.00 | 24.26 |
| ATOM | 2506 | CE1 | PHE A | 361 | 41.537 | 43.641 | −4.838 | 1.00 | 22.16 |
| ATOM | 2507 | CE2 | PHE A | 361 | 42.335 | 43.748 | −7.089 | 1.00 | 23.23 |
| ATOM | 2508 | CZ | PHE A | 361 | 41.609 | 43.102 | −6.109 | 1.00 | 22.64 |
| ATOM | 2509 | C | PHE A | 361 | 45.796 | 47.988 | −5.195 | 1.00 | 20.92 |
| ATOM | 2510 | O | PHE A | 361 | 46.302 | 48.344 | −6.255 | 1.00 | 22.01 |
| ATOM | 2511 | N | TRP A | 362 | 45.769 | 48.761 | −4.116 | 1.00 | 22.57 |
| ATOM | 2512 | CA | TRP A | 362 | 46.286 | 50.122 | −4.144 | 1.00 | 23.30 |
| ATOM | 2513 | CB | TRP A | 362 | 45.259 | 51.043 | −3.480 | 1.00 | 24.63 |
| ATOM | 2514 | CG | TRP A | 362 | 43.846 | 50.707 | −3.893 | 1.00 | 28.77 |
| ATOM | 2515 | CD2 | TRP A | 362 | 43.360 | 50.512 | −5.232 | 1.00 | 30.31 |
| ATOM | 2516 | CE2 | TRP A | 362 | 42.000 | 50.158 | −5.134 | 1.00 | 30.43 |
| ATOM | 2517 | CE3 | TRP A | 362 | 43.945 | 50.600 | −6.501 | 1.00 | 30.78 |
| ATOM | 2518 | CD1 | TRP A | 362 | 42.785 | 50.474 | −3.068 | 1.00 | 28.42 |
| ATOM | 2519 | NE1 | TRP A | 362 | 41.674 | 50.141 | −3.804 | 1.00 | 28.43 |
| ATOM | 2520 | CZ2 | TRP A | 362 | 41.213 | 49.890 | −6.258 | 1.00 | 32.37 |
| ATOM | 2521 | CZ3 | TRP A | 362 | 43.163 | 50.334 | −7.616 | 1.00 | 31.79 |
| ATOM | 2522 | CH2 | TRP A | 362 | 41.812 | 49.983 | −7.487 | 1.00 | 32.17 |
| ATOM | 2523 | C | TRP A | 362 | 47.667 | 50.312 | −3.514 | 1.00 | 22.63 |
| ATOM | 2524 | O | TRP A | 362 | 48.320 | 51.334 | −3.737 | 1.00 | 22.22 |
| ATOM | 2525 | N | GLY A | 363 | 48.107 | 49.329 | −2.736 | 1.00 | 21.03 |
| ATOM | 2526 | CA | GLY A | 363 | 49.408 | 49.416 | −2.098 | 1.00 | 19.14 |
| ATOM | 2527 | C | GLY A | 363 | 49.417 | 50.228 | −0.817 | 1.00 | 19.51 |
| ATOM | 2528 | O | GLY A | 363 | 48.372 | 50.693 | −0.359 | 1.00 | 20.28 |
| ATOM | 2529 | N | PRO A | 364 | 50.601 | 50.418 | −0.214 | 1.00 | 19.32 |
| ATOM | 2530 | CD | PRO A | 364 | 51.869 | 49.874 | −0.739 | 1.00 | 19.56 |
| ATOM | 2531 | CA | PRO A | 364 | 50.831 | 51.169 | 1.026 | 1.00 | 19.42 |
| ATOM | 2532 | CB | PRO A | 364 | 52.349 | 51.331 | 1.051 | 1.00 | 18.75 |
| ATOM | 2533 | CG | PRO A | 364 | 52.816 | 50.041 | 0.441 | 1.00 | 18.97 |
| ATOM | 2534 | C | PRO A | 364 | 50.110 | 52.514 | 1.150 | 1.00 | 20.15 |
| ATOM | 2535 | O | PRO A | 364 | 49.578 | 52.837 | 2.210 | 1.00 | 21.62 |
| ATOM | 2536 | N | PRO A | 365 | 50.082 | 53.317 | 0.072 | 1.00 | 20.37 |
| ATOM | 2537 | CD | PRO A | 365 | 50.657 | 53.076 | −1.263 | 1.00 | 19.69 |

TABLE 29-continued

| | | | | | | | | | |
|---|---|---|---|---|---|---|---|---|---|
| ATOM | 2538 | CA | PRO A | 365 | 49.415 | 54.624 | 0.118 | 1.00 | 19.12 |
| ATOM | 2539 | CB | PRO A | 365 | 49.567 | 55.143 | −1.311 | 1.00 | 19.93 |
| ATOM | 2540 | CG | PRO A | 365 | 50.829 | 54.477 | −1.787 | 1.00 | 20.52 |
| ATOM | 2541 | C | PRO A | 365 | 47.950 | 54.588 | 0.551 | 1.00 | 18.92 |
| ATOM | 2542 | O | PRO A | 365 | 47.412 | 55.593 | 1.011 | 1.00 | 19.97 |
| ATOM | 2543 | N | VAL A | 366 | 47.302 | 53.437 | 0.411 | 1.00 | 18.53 |
| ATOM | 2544 | CA | VAL A | 366 | 45.895 | 53.343 | 0.779 | 1.00 | 18.39 |
| ATOM | 2545 | CB | VAL A | 366 | 45.306 | 51.950 | 0.449 | 1.00 | 18.99 |
| ATOM | 2546 | CG1 | VAL A | 366 | 45.762 | 50.925 | 1.473 | 1.00 | 17.14 |
| ATOM | 2547 | CG2 | VAL A | 366 | 43.793 | 52.032 | 0.403 | 1.00 | 18.85 |
| ATOM | 2548 | C | VAL A | 366 | 45.680 | 53.635 | 2.257 | 1.00 | 18.00 |
| ATOM | 2549 | O | VAL A | 366 | 44.627 | 54.130 | 2.653 | 1.00 | 19.45 |
| ATOM | 2550 | N | VAL A | 367 | 46.689 | 53.341 | 3.069 | 1.00 | 17.67 |
| ATOM | 2551 | CA | VAL A | 367 | 46.599 | 53.568 | 4.506 | 1.00 | 17.92 |
| ATOM | 2552 | CB | VAL A | 367 | 47.845 | 53.038 | 5.224 | 1.00 | 17.49 |
| ATOM | 2553 | CG1 | VAL A | 367 | 47.685 | 53.213 | 6.717 | 1.00 | 15.94 |
| ATOM | 2554 | CG2 | VAL A | 367 | 48.069 | 51.566 | 4.858 | 1.00 | 18.38 |
| ATOM | 2555 | C | VAL A | 367 | 46.429 | 55.050 | 4.844 | 1.00 | 18.04 |
| ATOM | 2556 | O | VAL A | 367 | 45.555 | 55.418 | 5.628 | 1.00 | 16.97 |
| ATOM | 2557 | N | GLY A | 368 | 47.269 | 55.894 | 4.254 | 1.00 | 19.26 |
| ATOM | 2558 | CA | GLY A | 368 | 47.179 | 57.320 | 4.507 | 1.00 | 19.38 |
| ATOM | 2559 | C | GLY A | 368 | 45.899 | 57.881 | 3.924 | 1.00 | 21.58 |
| ATOM | 2560 | O | GLY A | 368 | 45.281 | 58.782 | 4.500 | 1.00 | 20.55 |
| ATOM | 2561 | N | LYE A | 369 | 45.491 | 57.331 | 2.781 | 1.00 | 22.53 |
| ATOM | 2562 | CA | LYE A | 369 | 44.271 | 57.773 | 2.110 | 1.00 | 22.83 |
| ATOM | 2563 | CB | LYE A | 369 | 44.059 | 56.997 | 0.804 | 1.00 | 22.47 |
| ATOM | 2564 | CG | LYE A | 369 | 43.053 | 57.659 | −0.123 | 1.00 | 24.45 |
| ATOM | 2565 | CD | LYE A | 369 | 42.550 | 56.727 | −1.215 | 1.00 | 23.16 |
| ATOM | 2566 | CE | LYS A | 369 | 41.613 | 55.684 | −0.638 | 1.00 | 24.02 |
| ATOM | 2567 | NZ | LYS A | 369 | 40.829 | 54.997 | −1.695 | 1.00 | 24.58 |
| ATOM | 2568 | C | LYS A | 369 | 43.062 | 57.564 | 3.016 | 1.00 | 21.99 |
| ATOM | 2569 | O | LYS A | 369 | 42.264 | 58.481 | 3.231 | 1.00 | 22.20 |
| ATOM | 2570 | N | VAL A | 370 | 42.933 | 56.354 | 3.549 | 1.00 | 19.95 |
| ATOM | 2571 | CA | VAL A | 370 | 41.814 | 56.036 | 4.424 | 1.00 | 18.95 |
| ATOM | 2572 | CB | VAL A | 370 | 41.853 | 54.559 | 4.876 | 1.00 | 16.89 |
| ATOM | 2573 | CG1 | VAL A | 370 | 40.745 | 54.297 | 5.883 | 1.00 | 14.26 |
| ATOM | 2574 | CG2 | VAL A | 370 | 41.692 | 53.643 | 3.668 | 1.00 | 15.62 |
| ATOM | 2575 | C | VAL A | 370 | 41.795 | 56.936 | 5.655 | 1.00 | 19.62 |
| ATOM | 2576 | O | VAL A | 370 | 40.743 | 57.447 | 6.041 | 1.00 | 18.54 |
| ATOM | 2577 | N | LYS A | 371 | 42.957 | 57.134 | 6.268 | 1.00 | 19.57 |
| ATOM | 2578 | CA | LYS A | 371 | 43.036 | 57.982 | 7.449 | 1.00 | 20.77 |
| ATOM | 2579 | CB | LYS A | 371 | 44.437 | 57.906 | 8.068 | 1.00 | 20.80 |
| ATOM | 2580 | CG | LYS A | 371 | 44.714 | 56.573 | 8.755 | 1.00 | 20.84 |
| ATOM | 2581 | CD | LYS A | 371 | 46.007 | 56.598 | 9.547 | 1.00 | 20.94 |
| ATOM | 2582 | CE | LYS A | 371 | 47.211 | 56.772 | 8.643 | 1.00 | 20.99 |
| ATOM | 2583 | NZ | LYS A | 371 | 48.475 | 56.737 | 9.422 | 1.00 | 21.34 |
| ATOM | 2584 | C | LYS A | 371 | 42.675 | 59.433 | 7.142 | 1.00 | 20.94 |
| ATOM | 2585 | O | LYS A | 371 | 41.944 | 60.067 | 7.901 | 1.00 | 20.23 |
| ATOM | 2586 | N | ARG A | 372 | 43.181 | 59.954 | 6.029 | 1.00 | 22.39 |
| ATOM | 2587 | CA | ARG A | 372 | 42.899 | 61.332 | 5.635 | 1.00 | 24.04 |
| ATOM | 2588 | CB | ARG A | 372 | 43.711 | 61.711 | 4.392 | 1.00 | 25.41 |
| ATOM | 2589 | CG | ARG A | 372 | 43.497 | 63.151 | 3.942 | 1.00 | 30.23 |
| ATOM | 2590 | CD | ARG A | 372 | 44.290 | 63.505 | 2.680 | 1.00 | 32.89 |
| ATOM | 2591 | NE | ARG A | 372 | 43.774 | 62.832 | 1.487 | 1.00 | 37.10 |
| ATOM | 2592 | CZ | ARG A | 372 | 44.382 | 61.822 | 0.871 | 1.00 | 36.84 |
| ATOM | 2593 | NH1 | ARG A | 372 | 45.538 | 61.362 | 1.331 | 1.00 | 37.88 |
| ATOM | 2594 | NH2 | ARG A | 372 | 43.830 | 61.272 | −0.204 | 1.00 | 35.98 |
| ATOM | 2595 | C | ARG A | 372 | 41.410 | 61.554 | 5.351 | 1.00 | 23.65 |
| ATOM | 2596 | O | ARG A | 372 | 40.832 | 62.551 | 5.785 | 1.00 | 23.32 |
| ATOM | 2597 | N | GLU A | 373 | 40.793 | 60.626 | 4.624 | 1.00 | 22.04 |
| ATOM | 2598 | CA | GLU A | 373 | 39.377 | 60.748 | 4.290 | 1.00 | 21.15 |
| ATOM | 2599 | CB | GLU A | 373 | 38.990 | 59.724 | 3.214 | 1.00 | 21.21 |
| ATOM | 2600 | CG | GLU A | 373 | 39.790 | 59.861 | 1.919 | 1.00 | 21.35 |
| ATOM | 2601 | CD | GLU A | 373 | 39.474 | 58.770 | 0.908 | 1.00 | 24.25 |
| ATOM | 2602 | OE1 | GLU A | 373 | 39.337 | 57.600 | 1.318 | 1.00 | 27.16 |
| ATOM | 2603 | OE2 | GLU A | 373 | 39.376 | 59.074 | −0.299 | 1.00 | 24.09 |
| ATOM | 2604 | C | GLU A | 373 | 38.517 | 60.559 | 5.530 | 1.00 | 20.97 |
| ATOM | 2605 | O | GLU A | 373 | 37.475 | 61.196 | 5.675 | 1.00 | 23.42 |
| ATOM | 2606 | N | LEU A | 374 | 38.954 | 59.684 | 6.428 | 1.00 | 19.50 |
| ATOM | 2607 | CA | LEU A | 374 | 38.213 | 59.442 | 7.655 | 1.00 | 19.13 |
| ATOM | 2608 | CB | LEU A | 374 | 38.885 | 58.340 | 8.479 | 1.00 | 16.43 |
| ATOM | 2609 | CG | LEU A | 374 | 38.240 | 58.031 | 9.837 | 1.00 | 15.24 |
| ATOM | 2610 | CD1 | LEU A | 374 | 36.785 | 57.640 | 9.636 | 1.00 | 12.59 |
| ATOM | 2611 | CD2 | LEU A | 374 | 39.005 | 56.911 | 10.534 | 1.00 | 13.82 |
| ATOM | 2612 | C | LEU A | 374 | 38.157 | 60.729 | 8.472 | 1.00 | 20.52 |
| ATOM | 2613 | O | LEU A | 374 | 37.091 | 61.132 | 8.939 | 1.00 | 22.71 |
| ATOM | 2614 | N | GLU A | 375 | 39.310 | 61.367 | 8.641 | 1.00 | 20.39 |
| ATOM | 2615 | CA | GLU A | 375 | 39.403 | 62.609 | 9.399 | 1.00 | 23.59 |
| ATOM | 2616 | CB | GLU A | 375 | 40.846 | 63.119 | 9.404 | 1.00 | 26.05 |

TABLE 29-continued

| ATOM | 2617 | CG | GLU A | 375 | 41.083 | 64.272 | 10.360 | 1.00 | 33.07 |
| --- | --- | --- | --- | --- | --- | --- | --- | --- | --- |
| ATOM | 2618 | CD | GLU A | 375 | 42.508 | 64.792 | 10.310 | 1.00 | 37.24 |
| ATOM | 2619 | OE1 | GLU A | 375 | 43.445 | 63.966 | 10.363 | 1.00 | 39.09 |
| ATOM | 2620 | OE2 | GLU A | 375 | 42.689 | 66.027 | 10.229 | 1.00 | 41.20 |
| ATOM | 2621 | C | GLU A | 375 | 38.485 | 63.679 | 8.815 | 1.00 | 22.79 |
| ATOM | 2622 | O | GLU A | 375 | 37.710 | 64.302 | 9.537 | 1.00 | 22.67 |
| ATOM | 2623 | N | ALA A | 376 | 38.571 | 63.881 | 7.503 | 1.00 | 22.58 |
| ATOM | 2624 | CA | ALA A | 376 | 37.740 | 64.871 | 6.827 | 1.00 | 22.81 |
| ATOM | 2625 | CB | ALA A | 376 | 38.087 | 64.926 | 5.330 | 1.00 | 20.94 |
| ATOM | 2626 | C | ALA A | 376 | 36.260 | 64.557 | 7.010 | 1.00 | 23.09 |
| ATOM | 2627 | O | ALA A | 376 | 35.464 | 65.454 | 7.283 | 1.00 | 25.43 |
| ATOM | 2628 | N | LEU A | 377 | 35.890 | 63.286 | 6.859 | 1.00 | 22.26 |
| ATOM | 2629 | CA | LEU A | 377 | 34.495 | 62.881 | 7.016 | 1.00 | 21.07 |
| ATOM | 2630 | CB | LEU A | 377 | 34.316 | 61.403 | 6.661 | 1.00 | 18.38 |
| ATOM | 2631 | CG | LEU A | 377 | 34.395 | 61.099 | 5.166 | 1.00 | 19.86 |
| ATOM | 2632 | CD1 | LEU A | 377 | 34.336 | 59.603 | 4.947 | 1.00 | 17.99 |
| ATOM | 2633 | CD2 | LEU A | 377 | 33.257 | 61.809 | 4.438 | 1.00 | 15.21 |
| ATOM | 2634 | C | LEU A | 377 | 33.982 | 63.126 | 8.427 | 1.00 | 21.76 |
| ATOM | 2635 | O | LEU A | 377 | 32.835 | 63.529 | 8.610 | 1.00 | 20.90 |
| ATOM | 2636 | N | LEU A | 378 | 34.828 | 62.872 | 9.423 | 1.00 | 22.73 |
| ATOM | 2637 | CA | LEU A | 378 | 34.442 | 63.086 | 10.814 | 1.00 | 23.95 |
| ATOM | 2638 | CB | LEU A | 378 | 35.567 | 62.642 | 11.757 | 1.00 | 19.58 |
| ATOM | 2639 | CG | LEU A | 378 | 35.806 | 61.133 | 11.865 | 1.00 | 18.89 |
| ATOM | 2640 | CD1 | LEU A | 378 | 37.114 | 60.854 | 12.585 | 1.00 | 16.40 |
| ATOM | 2641 | CD2 | LEU A | 378 | 34.638 | 60.484 | 12.594 | 1.00 | 16.69 |
| ATOM | 2642 | C | LEU A | 378 | 34.114 | 64.563 | 11.048 | 1.00 | 24.69 |
| ATOM | 2643 | O | LEU A | 378 | 33.081 | 64.888 | 11.633 | 1.00 | 24.07 |
| ATOM | 2644 | N | LYS A | 379 | 34.994 | 65.449 | 10.588 | 1.00 | 25.59 |
| ATOM | 2645 | CA | LYS A | 379 | 34.783 | 66.885 | 10.747 | 1.00 | 29.22 |
| ATOM | 2646 | CB | LYS A | 379 | 35.977 | 67.667 | 10.197 | 1.00 | 30.45 |
| ATOM | 2647 | CG | LYS A | 379 | 37.288 | 67.406 | 10.926 | 1.00 | 34.68 |
| ATOM | 2648 | CD | LYS A | 379 | 38.436 | 68.182 | 10.296 | 1.00 | 36.27 |
| ATOM | 2649 | CE | LYS A | 379 | 39.747 | 67.898 | 11.010 | 1.00 | 40.47 |
| ATOM | 2650 | NZ | LYS A | 379 | 40.904 | 68.609 | 10.389 | 1.00 | 42.09 |
| ATOM | 2651 | C | LYS A | 379 | 33.528 | 67.294 | 9.993 | 1.00 | 30.46 |
| ATOM | 2652 | O | LYS A | 379 | 32.638 | 67.951 | 10.533 | 1.00 | 29.89 |
| ATOM | 2653 | N | GLU A | 380 | 33.475 | 66.888 | 8.732 | 1.00 | 31.45 |
| ATOM | 2654 | CA | GLU A | 380 | 32.358 | 67.186 | 7.853 | 1.00 | 33.02 |
| ATOM | 2655 | CB | GLU A | 380 | 32.606 | 66.511 | 6.502 | 1.00 | 34.90 |
| ATOM | 2656 | CG | GLU A | 380 | 31.467 | 66.591 | 5.519 | 1.00 | 41.07 |
| ATOM | 2657 | CD | GLU A | 380 | 31.820 | 65.940 | 4.195 | 1.00 | 44.70 |
| ATOM | 2658 | OE1 | GLU A | 380 | 30.909 | 65.725 | 3.367 | 1.00 | 47.15 |
| ATOM | 2659 | OE2 | GLU A | 380 | 33.016 | 65.649 | 3.982 | 1.00 | 46.06 |
| ATOM | 2660 | C | GLU A | 380 | 31.013 | 66.748 | 8.433 | 1.00 | 32.34 |
| ATOM | 2661 | O | GLU A | 380 | 29.979 | 67.353 | 8.144 | 1.00 | 31.13 |
| ATOM | 2662 | N | GLN A | 381 | 31.023 | 65.708 | 9.260 | 1.00 | 31.07 |
| ATOM | 2663 | CA | GLN A | 381 | 29.780 | 65.218 | 9.846 | 1.00 | 31.01 |
| ATOM | 2664 | CB | GLN A | 381 | 29.695 | 63.693 | 9.688 | 1.00 | 30.16 |
| ATOM | 2665 | CG | GLN A | 381 | 29.351 | 63.272 | 8.256 | 1.00 | 29.66 |
| ATOM | 2666 | CD | GLN A | 381 | 29.445 | 61.774 | 8.025 | 1.00 | 30.22 |
| ATOM | 2667 | OE1 | GLN A | 381 | 29.049 | 60.975 | 8.872 | 1.00 | 29.82 |
| ATOM | 2668 | NE2 | GLN A | 381 | 29.953 | 61.388 | 6.858 | 1.00 | 30.17 |
| ATOM | 2669 | C | GLN A | 381 | 29.546 | 65.632 | 11.301 | 1.00 | 30.95 |
| ATOM | 2670 | O | GLN A | 381 | 28.634 | 65.131 | 11.959 | 1.00 | 30.74 |
| ATOM | 2671 | N | GLY A | 382 | 30.375 | 66.546 | 11.796 | 1.00 | 30.35 |
| ATOM | 2672 | CA | GLY A | 382 | 30.210 | 67.043 | 13.150 | 1.00 | 30.34 |
| ATOM | 2673 | C | GLY A | 382 | 30.737 | 66.225 | 14.311 | 1.00 | 30.42 |
| ATOM | 2674 | O | GLY A | 382 | 30.443 | 66.539 | 15.463 | 1.00 | 30.46 |
| ATOM | 2675 | N | PHE A | 383 | 31.507 | 65.181 | 14.037 | 1.00 | 29.60 |
| ATOM | 2676 | CA | PHE A | 383 | 32.053 | 64.371 | 15.119 | 1.00 | 28.66 |
| ATOM | 2677 | CB | PHE A | 383 | 32.309 | 62.941 | 14.644 | 1.00 | 26.51 |
| ATOM | 2678 | CG | PHE A | 383 | 31.065 | 62.205 | 14.243 | 1.00 | 24.25 |
| ATOM | 2679 | CD1 | PHE A | 383 | 30.798 | 61.945 | 12.910 | 1.00 | 23.46 |
| ATOM | 2680 | CD2 | PHE A | 383 | 30.163 | 61.774 | 15.200 | 1.00 | 21.40 |
| ATOM | 2681 | CE1 | PHE A | 383 | 29.654 | 61.264 | 12.536 | 1.00 | 22.91 |
| ATOM | 2682 | CE2 | PHE A | 383 | 29.021 | 61.096 | 14.833 | 1.00 | 22.41 |
| ATOM | 2683 | CZ | PHE A | 383 | 28.765 | 60.839 | 13.498 | 1.00 | 22.25 |
| ATOM | 2684 | C | PHE A | 383 | 33.352 | 64.975 | 15.641 | 1.00 | 29.41 |
| ATOM | 2685 | O | PHE A | 383 | 34.237 | 65.332 | 14.864 | 1.00 | 30.63 |
| ATOM | 2686 | N | GLY A | 384 | 33.460 | 65.094 | 16.960 | 1.00 | 29.35 |
| ATOM | 2687 | CA | GLY A | 384 | 34.666 | 65.646 | 17.548 | 1.00 | 29.12 |
| ATOM | 2688 | C | GLY A | 384 | 35.834 | 64.700 | 17.353 | 1.00 | 29.26 |
| ATOM | 2689 | O | GLY A | 384 | 36.994 | 65.111 | 17.356 | 1.00 | 30.18 |
| ATOM | 2690 | N | GLY A | 385 | 35.518 | 63.422 | 17.179 | 1.00 | 28.99 |
| ATOM | 2691 | CA | GLY A | 385 | 36.546 | 62.419 | 16.978 | 1.00 | 27.13 |
| ATOM | 2692 | C | GLY A | 385 | 35.935 | 61.062 | 16.695 | 1.00 | 26.35 |
| ATOM | 2693 | O | GLY A | 385 | 34.713 | 60.913 | 16.712 | 1.00 | 26.39 |
| ATOM | 2694 | N | VAL A | 386 | 36.787 | 60.075 | 16.435 | 1.00 | 25.90 |
| ATOM | 2695 | CA | VAL A | 386 | 36.348 | 58.715 | 16.145 | 1.00 | 23.97 |

TABLE 29-continued

| ATOM | 2696 | CB | VAL A | 386 | 37.558 | 57.756 | 16.023 | 1.00 | 24.97 |
| ATOM | 2697 | CG1 | VAL A | 386 | 37.078 | 56.317 | 15.893 | 1.00 | 23.00 |
| ATOM | 2698 | CG2 | VAL A | 386 | 38.414 | 58.143 | 14.826 | 1.00 | 24.99 |
| ATOM | 2699 | C | VAL A | 386 | 35.431 | 58.187 | 17.241 | 1.00 | 24.14 |
| ATOM | 2700 | O | VAL A | 386 | 34.377 | 57.614 | 16.961 | 1.00 | 23.65 |
| ATOM | 2701 | N | THR A | 387 | 35.844 | 58.389 | 18.488 | 1.00 | 24.08 |
| ATOM | 2702 | CA | THR A | 387 | 35.090 | 57.929 | 19.649 | 1.00 | 25.04 |
| ATOM | 2703 | CB | THR A | 387 | 35.730 | 58.441 | 20.955 | 1.00 | 26.36 |
| ATOM | 2704 | OG1 | THR A | 387 | 37.126 | 58.116 | 20.960 | 1.00 | 29.95 |
| ATOM | 2705 | CG2 | THR A | 387 | 35.066 | 57.797 | 22.161 | 1.00 | 24.13 |
| ATOM | 2706 | C | THR A | 387 | 33.634 | 58.377 | 19.624 | 1.00 | 24.22 |
| ATOM | 2707 | O | THR A | 387 | 32.746 | 57.651 | 20.062 | 1.00 | 24.33 |
| ATOM | 2708 | N | ASP A | 388 | 33.400 | 59.577 | 19.106 | 1.00 | 24.01 |
| ATOM | 2709 | CA | ASP A | 388 | 32.058 | 60.142 | 19.034 | 1.00 | 23.47 |
| ATOM | 2710 | CB | ASP A | 388 | 32.150 | 61.642 | 18.747 | 1.00 | 27.09 |
| ATOM | 2711 | CG | ASP A | 388 | 32.861 | 62.399 | 19.842 | 1.00 | 30.40 |
| ATOM | 2712 | OD1 | ASP A | 388 | 33.719 | 63.251 | 19.515 | 1.00 | 33.28 |
| ATOM | 2713 | OD2 | ASP A | 388 | 32.557 | 62.147 | 21.028 | 1.00 | 32.49 |
| ATOM | 2714 | C | ASP A | 388 | 31.195 | 59.487 | 17.965 | 1.00 | 21.54 |
| ATOM | 2715 | O | ASP A | 388 | 29.975 | 59.459 | 18.079 | 1.00 | 20.53 |
| ATOM | 2716 | N | ALA A | 389 | 31.835 | 58.969 | 16.924 | 1.00 | 21.30 |
| ATOM | 2717 | CA | ALA A | 389 | 31.123 | 58.341 | 15.821 | 1.00 | 19.74 |
| ATOM | 2718 | CB | ALA A | 389 | 31.935 | 58.498 | 14.536 | 1.00 | 20.68 |
| ATOM | 2719 | C | ALA A | 389 | 30.770 | 56.873 | 16.035 | 1.00 | 18.26 |
| ATOM | 2720 | O | ALA A | 389 | 29.862 | 56.356 | 15.386 | 1.00 | 19.21 |
| ATOM | 2721 | N | ILE A | 390 | 31.485 | 56.196 | 16.930 | 1.00 | 17.78 |
| ATOM | 2722 | CA | ILE A | 390 | 31.225 | 54.778 | 17.193 | 1.00 | 15.62 |
| ATOM | 2723 | CB | ILE A | 390 | 32.106 | 54.253 | 18.358 | 1.00 | 15.31 |
| ATOM | 2724 | CG2 | ILE A | 390 | 31.813 | 52.784 | 18.613 | 1.00 | 12.29 |
| ATOM | 2725 | CG1 | ILE A | 390 | 33.588 | 54.424 | 18.013 | 1.00 | 15.83 |
| ATOM | 2726 | CD1 | ILE A | 390 | 34.527 | 54.138 | 19.169 | 1.00 | 14.86 |
| ATOM | 2727 | C | ILE A | 390 | 29.754 | 54.510 | 17.529 | 1.00 | 15.04 |
| ATOM | 2728 | O | ILE A | 390 | 29.250 | 54.962 | 18.554 | 1.00 | 16.25 |
| ATOM | 2729 | N | GLY A | 391 | 29.071 | 53.782 | 16.651 | 1.00 | 15.63 |
| ATOM | 2730 | CA | GLY A | 391 | 27.671 | 53.453 | 16.872 | 1.00 | 15.37 |
| ATOM | 2731 | C | GLY A | 391 | 26.652 | 54.560 | 16.631 | 1.00 | 15.79 |
| ATOM | 2732 | O | GLY A | 391 | 25.466 | 54.374 | 16.893 | 1.00 | 15.96 |
| ATOM | 2733 | N | ALA A | 392 | 27.097 | 55.699 | 16.114 | 1.00 | 16.55 |
| ATOM | 2734 | CA | ALA A | 392 | 26.207 | 56.836 | 15.867 | 1.00 | 18.78 |
| ATOM | 2735 | CB | ALA A | 392 | 26.968 | 57.944 | 15.133 | 1.00 | 16.54 |
| ATOM | 2736 | C | ALA A | 392 | 24.918 | 56.504 | 15.112 | 1.00 | 19.86 |
| ATOM | 2737 | O | ALA A | 392 | 23.880 | 57.119 | 15.361 | 1.00 | 19.15 |
| ATOM | 2738 | N | ASP A | 393 | 24.972 | 55.543 | 14.191 | 1.00 | 20.27 |
| ATOM | 2739 | CA | ASP A | 393 | 23.777 | 55.182 | 13.426 | 1.00 | 21.17 |
| ATOM | 2740 | CB | ASP A | 393 | 24.092 | 54.124 | 12.360 | 1.00 | 21.34 |
| ATOM | 2741 | CG | ASP A | 393 | 24.905 | 54.671 | 11.196 | 1.00 | 25.41 |
| ATOM | 2742 | OD1 | ASP A | 393 | 24.915 | 55.904 | 10.981 | 1.00 | 24.65 |
| ATOM | 2743 | OD2 | ASP A | 393 | 25.520 | 53.851 | 10.479 | 1.00 | 26.65 |
| ATOM | 2744 | C | ASP A | 393 | 22.670 | 54.642 | 14.328 | 1.00 | 22.02 |
| ATOM | 2745 | O | ASP A | 393 | 21.487 | 54.823 | 14.046 | 1.00 | 22.08 |
| ATOM | 2746 | N | HIS A | 394 | 23.062 | 53.976 | 15.410 | 1.00 | 22.05 |
| ATOM | 2747 | CA | HIS A | 394 | 22.107 | 53.383 | 16.342 | 1.00 | 23.30 |
| ATOM | 2748 | CB | HIS A | 394 | 22.818 | 52.342 | 17.212 | 1.00 | 18.42 |
| ATOM | 2749 | CG | HIS A | 394 | 23.430 | 51.219 | 16.431 | 1.00 | 18.64 |
| ATOM | 2750 | CD2 | HIS A | 394 | 24.557 | 51.165 | 15.680 | 1.00 | 15.81 |
| ATOM | 2751 | ND1 | HIS A | 394 | 22.855 | 49.968 | 16.347 | 1.00 | 15.16 |
| ATOM | 2752 | CE1 | HIS A | 394 | 23.600 | 49.193 | 15.580 | 1.00 | 15.16 |
| ATOM | 2753 | NE2 | HIS A | 394 | 24.639 | 49.895 | 15.163 | 1.00 | 16.24 |
| ATOM | 2754 | C | HIS A | 394 | 21.415 | 54.406 | 17.237 | 1.00 | 25.83 |
| ATOM | 2755 | O | HIS A | 394 | 20.373 | 54.121 | 17.821 | 1.00 | 26.50 |
| ATOM | 2756 | N | ARG A | 395 | 21.994 | 55.595 | 17.344 | 1.00 | 28.78 |
| ATOM | 2757 | CA | ARG A | 395 | 21.428 | 56.635 | 18.188 | 1.00 | 33.50 |
| ATOM | 2758 | CB | ARG A | 395 | 22.550 | 57.376 | 18.926 | 1.00 | 33.09 |
| ATOM | 2759 | CG | ARG A | 395 | 23.384 | 56.469 | 19.829 | 1.00 | 34.73 |
| ATOM | 2760 | CD | ARG A | 395 | 24.289 | 57.266 | 20.759 | 1.00 | 35.29 |
| ATOM | 2761 | NE | ARG A | 395 | 25.446 | 57.851 | 20.083 | 1.00 | 36.20 |
| ATOM | 2762 | CZ | ARG A | 395 | 26.557 | 57.184 | 19.781 | 1.00 | 36.50 |
| ATOM | 2763 | NH1 | ARG A | 395 | 27.557 | 57.804 | 19.165 | 1.00 | 35.10 |
| ATOM | 2764 | NH2 | ARG A | 395 | 26.674 | 55.900 | 20.100 | 1.00 | 35.17 |
| ATOM | 2765 | C | ARG A | 395 | 20.568 | 57.623 | 17.408 | 1.00 | 37.62 |
| ATOM | 2766 | O | ARG A | 395 | 19.865 | 58.441 | 17.996 | 1.00 | 39.11 |
| ATOM | 2767 | N | ARG A | 396 | 20.619 | 57.543 | 16.083 | 1.00 | 41.81 |
| ATOM | 2768 | CA | ARG A | 396 | 19.828 | 58.434 | 15.245 | 1.00 | 45.90 |
| ATOM | 2769 | CB | ARG A | 396 | 20.541 | 58.683 | 13.908 | 1.00 | 48.15 |
| ATOM | 2770 | CG | ARG A | 396 | 20.571 | 57.500 | 12.955 | 1.00 | 50.79 |
| ATOM | 2771 | CD | ARG A | 396 | 21.552 | 57.745 | 11.810 | 1.00 | 52.97 |
| ATOM | 2772 | NE | ARG A | 396 | 21.368 | 59.062 | 11.207 | 1.00 | 54.80 |
| ATOM | 2773 | CZ | ARG A | 396 | 20.262 | 59.449 | 10.582 | 1.00 | 56.47 |
| ATOM | 2774 | NH1 | ARG A | 396 | 20.179 | 60.669 | 10.065 | 1.00 | 57.12 |

TABLE 29-continued

| | | | | | | | | | |
|---|---|---|---|---|---|---|---|---|---|
| ATOM | 2775 | NH2 | ARG A | 396 | 19.240 | 58.614 | 10.466 | 1.00 | 57.75 |
| ATOM | 2776 | C | ARG A | 396 | 18.439 | 57.842 | 15.007 | 1.00 | 47.29 |
| ATOM | 2777 | O | ARG A | 396 | 17.445 | 58.588 | 15.139 | 1.00 | 47.81 |
| ATOM | 2778 | OXT | ARG A | 396 | 18.361 | 56.637 | 14.688 | 1.00 | 49.38 |
| THR | 1 | | ARG A | 396 | | | | | |
| END | | | | | | | | | |

TABLE 30

| | | | | | | | | | |
|---|---|---|---|---|---|---|---|---|---|
| ORIGX1 | | 1.000000 | | 0.000000 | | 0.000000 | | 0.00000 | |
| ORIGX2 | | 0.000000 | | 1.000000 | | 0.000000 | | 0.00000 | |
| ORIGX3 | | 0.000000 | | 0.000000 | | 1.000000 | | 0.00000 | |
| SCALE1 | | 0.011031 | | 0.006369 | | 0.000000 | | 0.00000 | |
| SCALE2 | | 0.000000 | | 0.012738 | | 0.000000 | | 0.00000 | |
| SCALE3 | | 0.000000 | | 0.000000 | | 0.008125 | | 0.00000 | |
| ATOM | 2779 | N1 | FMN | 398 | 41.768 | 36.138 | 8.642 | 1.00 | 13.07 |
| ATOM | 2780 | C2 | FMN | 398 | 42.156 | 35.495 | 9.777 | 1.00 | 16.23 |
| ATOM | 2781 | O2 | FMN | 398 | 41.553 | 35.602 | 10.828 | 1.00 | 15.63 |
| ATOM | 2782 | N3 | FMN | 398 | 43.332 | 34.661 | 9.720 | 1.00 | 15.17 |
| ATOM | 2783 | C4 | FMN | 398 | 44.083 | 34.463 | 8.624 | 1.00 | 14.98 |
| ATOM | 2784 | O4 | FMN | 398 | 45.078 | 33.724 | 8.673 | 1.00 | 15.42 |
| ATOM | 2785 | C4A | FMN | 398 | 43.663 | 35.157 | 7.395 | 1.00 | 13.75 |
| ATOM | 2786 | N5 | FMN | 398 | 44.353 | 35.021 | 6.251 | 1.00 | 13.73 |
| ATOM | 2787 | C5A | FMN | 398 | 43.937 | 35.699 | 5.122 | 1.00 | 11.46 |
| ATOM | 2788 | C6 | FMN | 398 | 44.677 | 35.580 | 3.868 | 1.00 | 10.75 |
| ATOM | 2789 | C7 | FMN | 398 | 44.299 | 36.258 | 2.716 | 1.00 | 11.50 |
| ATOM | 2790 | C7M | FMN | 398 | 45.115 | 36.107 | 1.416 | 1.00 | 9.29 |
| ATOM | 2791 | C8 | FMN | 398 | 43.129 | 37.121 | 2.736 | 1.00 | 11.87 |
| ATOM | 2792 | C8M | FMN | 398 | 42.661 | 37.903 | 1.514 | 1.00 | 14.22 |
| ATOM | 2793 | C9 | FMN | 398 | 42.407 | 37.240 | 3.918 | 1.00 | 11.46 |
| ATOM | 2794 | C9A | FMN | 398 | 42.774 | 36.557 | 5.116 | 1.00 | 13.45 |
| ATOM | 2795 | N10 | FMN | 398 | 42.055 | 36.664 | 6.366 | 1.00 | 13.69 |
| ATOM | 2796 | C10 | FMN | 398 | 42.452 | 36.003 | 7.508 | 1.00 | 14.43 |
| ATOM | 2797 | C1* | FMN | 398 | 40.854 | 37.510 | 6.446 | 1.00 | 12.50 |
| ATOM | 2798 | C2* | FMN | 398 | 41.120 | 39.004 | 6.623 | 1.00 | 13.52 |
| ATOM | 2799 | O2* | FMN | 398 | 41.785 | 39.192 | 7.913 | 1.00 | 13.74 |
| ATOM | 2800 | C3* | FMN | 398 | 39.791 | 39.809 | 6.666 | 1.00 | 12.06 |
| ATOM | 2801 | O3* | FMN | 398 | 38.934 | 39.288 | 7.740 | 1.00 | 12.59 |
| ATOM | 2802 | C4* | FMN | 398 | 38.960 | 39.696 | 5.359 | 1.00 | 12.31 |
| ATOM | 2803 | O4* | FMN | 398 | 39.810 | 39.464 | 4.208 | 1.00 | 11.80 |
| ATOM | 2804 | C5* | FMN | 398 | 38.118 | 40.946 | 5.100 | 1.00 | 10.70 |
| ATOM | 2805 | O5* | FMN | 398 | 38.915 | 42.126 | 4.951 | 1.00 | 14.11 |
| ATOM | 2806 | P | FMN | 398 | 39.371 | 42.728 | 3.527 | 1.00 | 13.60 |
| ATOM | 2807 | O1P | FMN | 398 | 40.438 | 41.814 | 2.959 | 1.00 | 14.55 |
| ATOM | 2808 | O2P | FMN | 398 | 39.878 | 44.114 | 3.849 | 1.00 | 12.57 |
| ATOM | 2809 | O3P | FMN | 398 | 38.126 | 42.785 | 2.627 | 1.00 | 14.12 |
| ATOM | 2810 | N1 | ORO | 399 | 41.674 | 32.379 | 4.935 | 1.00 | 16.78 |
| ATOM | 2811 | C2 | ORO | 399 | 40.657 | 33.292 | 5.240 | 1.00 | 16.40 |
| ATOM | 2812 | O2 | ORO | 399 | 40.049 | 33.934 | 4.386 | 1.00 | 20.50 |
| ATOM | 2813 | N3 | ORO | 399 | 40.350 | 33.452 | 6.592 | 1.00 | 14.80 |
| ATOM | 2814 | C4 | ORO | 399 | 40.960 | 32.786 | 7.660 | 1.00 | 15.08 |
| ATOM | 2815 | O4 | ORO | 399 | 40.634 | 32.987 | 8.809 | 1.00 | 14.56 |
| ATOM | 2816 | C5 | ORO | 399 | 42.020 | 31.838 | 7.284 | 1.00 | 14.43 |
| ATOM | 2817 | C6 | ORO | 399 | 42.319 | 31.684 | 5.976 | 1.00 | 16.70 |
| ATOM | 2818 | C7 | ORO | 399 | 43.405 | 30.715 | 5.533 | 1.00 | 17.56 |
| ATOM | 2819 | O71 | ORO | 399 | 44.524 | 30.703 | 6.023 | 1.00 | 19.26 |
| ATOM | 2820 | O72 | ORO | 399 | 42.925 | 29.978 | 4.631 | 1.00 | 18.83 |
| ATOM | 2821 | S | SO4 | 400 | 56.424 | 40.112 | 34.639 | 1.00 | 35.18 |
| ATOM | 2822 | O1 | SO4 | 400 | 56.120 | 41.429 | 35.225 | 1.00 | 35.51 |
| ATOM | 2823 | O2 | SO4 | 400 | 55.199 | 39.292 | 34.609 | 1.00 | 36.32 |
| ATOM | 2824 | O3 | SO4 | 400 | 56.937 | 40.294 | 33.270 | 1.00 | 36.60 |
| ATOM | 2825 | O4 | SO4 | 400 | 57.452 | 39.437 | 35.452 | 1.00 | 37.26 |
| ATOM | 2826 | C | ACT | 401 | 24.652 | 49.256 | 4.973 | 1.00 | 33.65 |
| ATOM | 2827 | O | ACT | 401 | 23.471 | 49.645 | 4.685 | 1.00 | 32.94 |
| ATOM | 2828 | OXT | ACT | 401 | 24.974 | 48.967 | 6.159 | 1.00 | 34.73 |
| ATOM | 2829 | CH3 | ACT | 401 | 24.990 | 48.159 | 3.937 | 1.00 | 30.22 |
| ATOM | 2830 | S | SO4 | 402 | 56.685 | 36.631 | 28.249 | 1.00 | 42.93 |
| ATOM | 2831 | O1 | SO4 | 402 | 55.412 | 37.351 | 28.128 | 1.00 | 51.57 |
| ATOM | 2832 | O2 | SO4 | 402 | 56.420 | 35.196 | 28.444 | 1.00 | 49.22 |
| ATOM | 2833 | O3 | SO4 | 402 | 57.455 | 36.828 | 27.009 | 1.00 | 51.20 |
| ATOM | 2834 | O4 | SO4 | 402 | 57.439 | 37.165 | 29.395 | 1.00 | 49.80 |
| ATOM | 2835 | S | SO4 | 403 | 48.265 | 43.940 | 28.781 | 1.00 | 91.18 |
| ATOM | 2836 | O1 | SO4 | 403 | 49.259 | 43.050 | 28.152 | 1.00 | 90.53 |
| ATOM | 2837 | O2 | SO4 | 403 | 47.958 | 43.450 | 30.139 | 1.00 | 90.33 |
| ATOM | 2838 | O3 | SO4 | 403 | 48.812 | 45.308 | 28.869 | 1.00 | 90.28 |
| ATOM | 2839 | O4 | SO4 | 403 | 47.033 | 43.952 | 27.967 | 1.00 | 90.50 |

TABLE 30-continued

| | | | | | | | | |
|---|---|---|---|---|---|---|---|---|
| ATOM | 2840 | S | SO4 | 404 | 32.854 | 23.140 | 6.523 | 1.00 | 78.69 |
| ATOM | 2841 | O1 | SO4 | 404 | 32.858 | 24.227 | 7.521 | 1.00 | 79.26 |
| ATOM | 2842 | O2 | SO4 | 404 | 31.949 | 23.493 | 5.413 | 1.00 | 78.75 |
| ATOM | 2843 | O3 | SO4 | 404 | 34.218 | 22.943 | 6.001 | 1.00 | 78.59 |
| ATOM | 2844 | O4 | SO4 | 404 | 32.383 | 21.897 | 7.160 | 1.00 | 78.61 |
| ATOM | 2845 | C1 | INH | 1 | 55.156 | 47.244 | 0.347 | 1.00 | 30.61 |
| ATOM | 2846 | C2 | INH | 1 | 55.673 | 48.190 | −0.610 | 1.00 | 30.81 |
| ATOM | 2847 | C3 | INH | 1 | 55.194 | 48.186 | −2.013 | 1.00 | 31.97 |
| ATOM | 2848 | C4 | INH | 1 | 54.168 | 47.203 | −2.451 | 1.00 | 30.44 |
| ATOM | 2849 | C5 | INH | 1 | 53.641 | 46.233 | −1.459 | 1.00 | 27.61 |
| ATOM | 2850 | C6 | INH | 1 | 52.670 | 45.202 | −1.696 | 1.00 | 26.48 |
| ATOM | 2851 | C7 | INH | 1 | 54.170 | 46.288 | −0.060 | 1.00 | 27.48 |
| ATOM | 2852 | C8 | INH | 1 | 51.525 | 45.016 | −0.763 | 1.00 | 23.90 |
| ATOM | 2853 | C9 | INH | 1 | 50.573 | 43.949 | −0.981 | 1.00 | 23.42 |
| ATOM | 2854 | F10 | INH | 1 | 49.575 | 43.791 | −0.145 | 1.00 | 23.87 |
| ATOM | 2855 | C11 | INH | 1 | 50.717 | 43.023 | −2.127 | 1.00 | 25.29 |
| ATOM | 2856 | N12 | INH | 1 | 49.793 | 41.980 | −2.283 | 1.00 | 23.77 |
| ATOM | 2857 | C13 | INH | 1 | 51.835 | 43.209 | −3.060 | 1.00 | 26.41 |
| ATOM | 2858 | F14 | INH | 1 | 52.000 | 42.413 | −4.092 | 1.00 | 28.14 |
| ATOM | 2859 | C15 | INH | 1 | 52.801 | 44.276 | −2.856 | 1.00 | 25.96 |
| ATOM | 2860 | C16 | INH | 1 | 49.489 | 40.832 | −1.506 | 1.00 | 28.49 |
| ATOM | 2861 | C17 | INH | 1 | 48.466 | 39.833 | −1.867 | 1.00 | 27.98 |
| ATOM | 2862 | O18 | INH | 1 | 50.135 | 40.651 | −0.448 | 1.00 | 29.29 |
| ATOM | 2863 | C19 | INH | 1 | 47.901 | 39.565 | −3.090 | 1.00 | 29.14 |
| ATOM | 2864 | C20 | INH | 1 | 46.915 | 38.457 | −2.940 | 1.00 | 28.65 |
| ATOM | 2865 | C21 | INH | 1 | 47.316 | 37.772 | −1.629 | 1.00 | 30.35 |
| ATOM | 2866 | C22 | INH | 1 | 47.906 | 38.930 | −0.821 | 1.00 | 26.78 |
| ATOM | 2867 | C23 | INH | 1 | 48.115 | 40.176 | −4.438 | 1.00 | 31.81 |
| ATOM | 2868 | O24 | INH | 1 | 48.914 | 41.107 | −4.671 | 1.00 | 35.53 |
| ATOM | 2869 | O25 | INH | 1 | 47.417 | 39.721 | −5.498 | 1.00 | 35.32 |
| ATOM | 2870 | O26 | INH | 1 | 55.734 | 49.119 | −2.892 | 1.00 | 38.75 |
| ATOM | 2871 | C27 | INH | 1 | 57.015 | 48.727 | −3.548 | 1.00 | 41.33 |
| ATOM | 2872 | F28 | INH | 1 | 56.944 | 47.600 | −4.240 | 1.00 | 44.03 |
| ATOM | 2873 | F29 | INH | 1 | 57.367 | 49.716 | −4.345 | 1.00 | 41.94 |
| ATOM | 2874 | F30 | INH | 1 | 57.952 | 48.575 | −2.624 | 1.00 | 42.63 |
| ATOM | 2875 | OH2 | INH | 1 | 55.935 | 42.939 | −3.322 | 1.00 | 73.19 |
| ATOM | 2876 | OH2 | TIP | 2 | 35.544 | 55.453 | −5.436 | 1.00 | 27.04 |
| ATOM | 2877 | OH2 | TIP | 3 | 38.368 | 45.691 | 5.463 | 1.00 | 9.92 |
| ATOM | 2878 | OH2 | TIP | 4 | 26.254 | 32.568 | −2.682 | 1.00 | 18.84 |
| ATOM | 2879 | OH2 | TIP | 5 | 32.726 | 49.693 | 5.055 | 1.00 | 4.99 |
| ATOM | 2880 | OH2 | TIP | 6 | 40.177 | 36.456 | 0.169 | 1.00 | 8.72 |
| ATOM | 2881 | OH2 | TIP | 7 | 28.792 | 46.338 | 21.197 | 1.00 | 9.84 |
| ATOM | 2882 | OH2 | TIP | 8 | 50.114 | 40.162 | 27.019 | 1.00 | 11.00 |
| ATOM | 2883 | OH2 | TIP | 9 | 52.707 | 35.109 | 39.872 | 1.00 | 13.09 |
| ATOM | 2884 | OH2 | TIP | 10 | 32.631 | 48.935 | 19.270 | 1.00 | 8.68 |
| ATOM | 2885 | OH2 | TIP | 11 | 31.665 | 31.398 | 6.495 | 1.00 | 16.03 |
| ATOM | 2886 | OH2 | TIP | 12 | 54.419 | 36.452 | 7.881 | 1.00 | 14.67 |
| ATOM | 2887 | OH2 | TIP | 13 | 48.765 | 30.201 | −4.577 | 1.00 | 18.66 |
| ATOM | 2888 | OH2 | TIP | 14 | 52.910 | 44.774 | 24.574 | 1.00 | 22.00 |
| ATOM | 2889 | OH2 | TIP | 15 | 56.888 | 41.478 | 19.935 | 1.00 | 12.09 |
| ATOM | 2890 | OH2 | TIP | 16 | 24.269 | 48.184 | 0.615 | 1.00 | 10.81 |
| ATOM | 2891 | OH2 | TIP | 17 | 35.600 | 30.673 | −11.563 | 1.00 | 18.80 |
| ATOM | 2892 | OH2 | TIP | 19 | 27.032 | 52.989 | 8.555 | 1.00 | 13.56 |
| ATOM | 2893 | OH2 | TIP | 20 | 33.133 | 44.845 | −12.581 | 1.00 | 21.06 |
| ATOM | 2894 | OH2 | TIP | 21 | 41.790 | 40.235 | 11.640 | 1.00 | 9.31 |
| ATOM | 2895 | OH2 | TIP | 22 | 42.183 | 27.776 | 7.444 | 1.00 | 15.77 |
| ATOM | 2896 | OH2 | TIP | 23 | 55.486 | 43.118 | 24.318 | 1.00 | 20.63 |
| ATOM | 2897 | OH2 | TIP | 24 | 22.597 | 45.848 | 3.191 | 1.00 | 20.55 |
| ATOM | 2898 | OH2 | TIP | 25 | 40.155 | 46.055 | 2.091 | 1.00 | 11.51 |
| ATOM | 2899 | OH2 | TIP | 28 | 52.870 | 40.844 | 35.692 | 1.00 | 26.47 |
| ATOM | 2900 | OH2 | TIP | 29 | 39.343 | 36.863 | −11.603 | 1.00 | 15.79 |
| ATOM | 2901 | OH2 | TIP | 30 | 29.725 | 63.303 | 4.807 | 1.00 | 30.86 |
| ATOM | 2902 | OH2 | TIP | 31 | 31.090 | 52.803 | 1.908 | 1.00 | 16.92 |
| ATOM | 2903 | OH2 | TIP | 33 | 48.470 | 40.672 | 9.314 | 1.00 | 16.35 |
| ATOM | 2904 | OH2 | TIP | 34 | 48.163 | 60.787 | −5.517 | 1.00 | 35.72 |
| ATOM | 2905 | OH2 | TIP | 35 | 33.797 | 25.032 | −2.216 | 1.00 | 28.04 |
| ATOM | 2906 | OH2 | TIP | 36 | 27.528 | 36.090 | −15.399 | 1.00 | 19.76 |
| ATOM | 2907 | OH2 | TIP | 37 | 36.123 | 58.320 | 1.544 | 1.00 | 18.50 |
| ATOM | 2908 | OH2 | TIP | 38 | 18.456 | 32.031 | 12.116 | 1.00 | 32.11 |
| ATOM | 2909 | OH2 | TIP | 39 | 30.093 | 49.596 | 4.396 | 1.00 | 26.44 |
| ATOM | 2910 | OH2 | TIP | 40 | 22.244 | 50.960 | 6.710 | 1.00 | 14.55 |
| ATOM | 2911 | OH2 | TIP | 41 | 25.186 | 53.850 | 20.632 | 1.00 | 36.61 |
| ATOM | 2912 | OH2 | TIP | 42 | 28.377 | 43.052 | 0.368 | 1.00 | 16.28 |
| ATOM | 2913 | OH2 | TIP | 43 | 48.044 | 30.947 | 8.834 | 1.00 | 23.93 |
| ATOM | 2914 | OH2 | TIP | 44 | 37.358 | 35.976 | 32.382 | 1.00 | 31.38 |
| ATOM | 2915 | OH2 | TIP | 45 | 36.077 | 52.311 | −1.386 | 1.00 | 20.23 |
| ATOM | 2916 | OH2 | TIP | 46 | 48.137 | 51.093 | 24.342 | 1.00 | 27.05 |
| ATOM | 2917 | OH2 | TIP | 47 | 31.755 | 42.556 | −7.956 | 1.00 | 13.30 |
| ATOM | 2918 | OH2 | TIP | 48 | 60.161 | 28.707 | 24.481 | 1.00 | 22.24 |

TABLE 30-continued

| ATOM | 2919 | OH2 | TIP | 49 | 39.447 | 48.502 | −3.656 | 1.00 | 28.66 |
|---|---|---|---|---|---|---|---|---|---|
| ATOM | 2920 | OH2 | TIP | 50 | 48.327 | 58.128 | 0.959 | 1.00 | 30.23 |
| ATOM | 2921 | OH2 | TIP | 51 | 55.679 | 32.342 | 25.492 | 1.00 | 27.36 |
| ATOM | 2922 | OH2 | TIP | 52 | 64.173 | 35.374 | 20.180 | 1.00 | 20.52 |
| ATOM | 2923 | OH2 | TIP | 53 | 58.849 | 49.917 | 15.132 | 1.00 | 26.47 |
| ATOM | 2924 | OH2 | TIP | 54 | 51.767 | 31.449 | 11.360 | 1.00 | 14.19 |
| ATOM | 2925 | OH2 | TIP | 55 | 39.550 | 45.797 | −2.540 | 1.00 | 15.41 |
| ATOM | 2926 | OH2 | TIP | 56 | 24.397 | 28.632 | 17.367 | 1.00 | 22.23 |
| ATOM | 2927 | OH2 | TIP | 57 | 51.705 | 20.271 | 6.838 | 1.00 | 27.23 |
| ATOM | 2928 | OH2 | TIP | 58 | 41.383 | 26.162 | −9.699 | 1.00 | 21.02 |
| ATOM | 2929 | OH2 | TIP | 59 | 25.050 | 40.672 | 6.953 | 1.00 | 20.47 |
| ATOM | 2930 | OH2 | TIP | 60 | 23.999 | 41.157 | 9.453 | 1.00 | 26.17 |
| ATOM | 2931 | OH2 | TIP | 61 | 37.989 | 29.525 | −11.423 | 1.00 | 22.38 |
| ATOM | 2932 | OH2 | TIP | 62 | 36.293 | 47.969 | −1.074 | 1.00 | 31.20 |
| ATOM | 2933 | OH2 | TIP | 63 | 38.463 | 26.067 | 1.663 | 1.00 | 29.91 |
| ATOM | 2934 | OH2 | TIP | 64 | 53.273 | 23.516 | 20.214 | 1.00 | 39.87 |
| ATOM | 2935 | OH2 | TIP | 65 | 59.232 | 43.479 | 12.582 | 1.00 | 16.61 |
| ATOM | 2936 | OH2 | TIP | 66 | 19.667 | 42.932 | 12.630 | 1.00 | 37.55 |
| ATOM | 2937 | OH2 | TIP | 67 | 34.515 | 51.648 | 22.411 | 1.00 | 33.64 |
| ATOM | 2938 | OH2 | TIP | 68 | 47.217 | 63.075 | 3.678 | 1.00 | 40.93 |
| ATOM | 2939 | OH2 | TIP | 69 | 44.997 | 42.094 | −5.482 | 1.00 | 31.45 |
| ATOM | 2940 | OH2 | TIP | 70 | 61.350 | 39.669 | 15.129 | 1.00 | 33.76 |
| ATOM | 2941 | OH2 | TIP | 71 | 63.503 | 33.512 | 24.526 | 1.00 | 30.64 |
| ATOM | 2942 | OH2 | TIP | 72 | 56.502 | 35.138 | 4.193 | 1.00 | 40.13 |
| ATOM | 2943 | OH2 | TIP | 73 | 38.388 | 59.732 | 19.181 | 1.00 | 28.57 |
| ATOM | 2944 | OH2 | TIP | 74 | 44.184 | 24.050 | 9.776 | 1.00 | 20.28 |
| ATOM | 2945 | OH2 | TIP | 75 | 59.066 | 44.574 | 9.932 | 1.00 | 18.52 |
| ATOM | 2946 | OH2 | TIP | 76 | 57.161 | 34.373 | 26.054 | 1.00 | 15.82 |
| ATOM | 2947 | OH2 | TIP | 77 | 39.582 | 50.272 | 27.336 | 1.00 | 30.32 |
| ATOM | 2948 | OH2 | TIP | 78 | 18.410 | 33.056 | 20.307 | 1.00 | 38.31 |
| ATOM | 2949 | OH2 | TIP | 80 | 46.234 | 28.316 | 18.714 | 1.00 | 22.78 |
| ATOM | 2950 | OH2 | TIP | 81 | 21.447 | 37.332 | 21.766 | 1.00 | 21.05 |
| ATOM | 2951 | OH2 | TIP | 82 | 20.551 | 32.666 | 22.014 | 1.00 | 27.65 |
| ATOM | 2952 | OH2 | TIP | 83 | 24.658 | 41.207 | −5.227 | 1.00 | 22.79 |
| ATOM | 2953 | OH2 | TIP | 84 | 55.011 | 41.531 | 26.497 | 1.00 | 25.92 |
| ATOM | 2954 | OH2 | TIP | 85 | 38.296 | 32.264 | 33.902 | 1.00 | 23.13 |
| ATOM | 2955 | OH2 | TIP | 86 | 44.369 | 24.267 | −3.546 | 1.00 | 35.96 |
| ATOM | 2956 | OH2 | TIP | 87 | 27.475 | 36.860 | 9.747 | 1.00 | 32.20 |
| ATOM | 2957 | OH2 | TIP | 88 | 31.150 | 49.186 | 21.566 | 1.00 | 26.94 |
| ATOM | 2958 | OH2 | TIP | 89 | 47.779 | 20.892 | 17.543 | 1.00 | 25.36 |
| ATOM | 2959 | OH2 | TIP | 91 | 38.494 | 53.244 | −2.751 | 1.00 | 35.05 |
| ATOM | 2960 | OH2 | TIP | 92 | 46.323 | 60.192 | 17.190 | 1.00 | 27.65 |
| ATOM | 2961 | OH2 | TIP | 93 | 28.667 | 66.884 | 4.567 | 1.00 | 40.54 |
| ATOM | 2962 | OH2 | TIP | 94 | 60.846 | 30.830 | 9.609 | 1.00 | 32.28 |
| ATOM | 2963 | OH2 | TIP | 96 | 19.909 | 46.368 | 21.678 | 1.00 | 28.96 |
| ATOM | 2964 | OH2 | TIP | 97 | 45.477 | 23.130 | 6.094 | 1.00 | 27.25 |
| ATOM | 2965 | OH2 | TIP | 98 | 55.212 | 41.460 | 21.964 | 1.00 | 16.08 |
| ATOM | 2966 | OH2 | TIP | 99 | 47.327 | 53.836 | −3.806 | 1.00 | 22.48 |
| ATOM | 2967 | OH2 | TIP | 100 | 39.042 | 57.052 | −2.132 | 1.00 | 23.68 |
| ATOM | 2968 | OH2 | TIP | 101 | 42.080 | 65.105 | 6.196 | 1.00 | 23.98 |
| ATOM | 2969 | OH2 | TIP | 102 | 50.195 | 38.982 | 37.861 | 1.00 | 33.16 |
| ATOM | 2970 | OH2 | TIP | 103 | 24.816 | 38.106 | 6.274 | 1.00 | 46.68 |
| ATOM | 2971 | OH2 | TIP | 104 | 37.606 | 19.200 | 18.942 | 1.00 | 40.91 |
| ATOM | 2972 | OH2 | TIP | 105 | 34.078 | 23.126 | 21.682 | 1.00 | 37.32 |
| ATOM | 2973 | OH2 | TIP | 106 | 50.938 | 24.646 | 25.853 | 1.00 | 23.41 |
| ATOM | 2974 | OH2 | TIP | 108 | 43.762 | 44.620 | 28.111 | 1.00 | 46.21 |
| ATOM | 2975 | OH2 | TIP | 109 | 31.113 | 28.188 | 31.316 | 1.00 | 32.77 |
| ATOM | 2976 | OH2 | TIP | 110 | 20.949 | 49.041 | 19.756 | 1.00 | 45.06 |
| ATOM | 2977 | OH2 | TIP | 111 | 52.664 | 36.212 | 5.983 | 1.00 | 26.36 |
| ATOM | 2978 | OH2 | TIP | 112 | 58.238 | 26.573 | 11.032 | 1.00 | 36.46 |
| ATOM | 2979 | OH2 | TIP | 113 | 43.014 | 36.746 | 36.299 | 1.00 | 43.53 |
| ATOM | 2980 | OH2 | TIP | 114 | 24.151 | 50.266 | 27.793 | 1.00 | 47.09 |
| ATOM | 2981 | OH2 | TIP | 115 | 30.305 | 30.980 | −7.851 | 1.00 | 30.68 |
| ATOM | 2982 | OH2 | TIP | 116 | 48.285 | 22.108 | 6.645 | 1.00 | 25.39 |
| ATOM | 2983 | OH2 | TIP | 117 | 39.224 | 37.972 | −14.257 | 1.00 | 30.69 |
| ATOM | 2984 | OH2 | TIP | 119 | 46.568 | 32.155 | −8.891 | 1.00 | 39.93 |
| ATOM | 2985 | OH2 | TIP | 121 | 20.118 | 49.260 | 17.291 | 1.00 | 30.89 |
| ATOM | 2986 | OH2 | TIP | 122 | 35.058 | 44.421 | 26.773 | 1.00 | 41.84 |
| ATOM | 2987 | OH2 | TIP | 124 | 49.192 | 64.702 | 8.137 | 1.00 | 52.76 |
| ATOM | 2988 | OH2 | TIP | 125 | 37.968 | 56.298 | 22.605 | 1.00 | 44.63 |
| ATOM | 2989 | OH2 | TIP | 126 | 35.175 | 25.867 | 8.190 | 1.00 | 40.87 |
| ATOM | 2990 | OH2 | TIP | 128 | 53.373 | 48.412 | 27.185 | 1.00 | 34.68 |
| ATOM | 2991 | OH2 | TIP | 130 | 31.753 | 41.370 | 27.331 | 1.00 | 50.15 |
| ATOM | 2992 | OH2 | TIP | 133 | 45.057 | 19.603 | 20.174 | 1.00 | 49.23 |
| ATOM | 2993 | OH2 | TIP | 135 | 62.120 | 49.293 | 13.816 | 1.00 | 51.24 |
| ATOM | 2994 | OH2 | TIP | 136 | 36.392 | 24.415 | 5.232 | 1.00 | 36.40 |
| ATOM | 2995 | OH2 | TIP | 137 | 37.190 | 47.914 | 25.973 | 1.00 | 42.47 |
| ATOM | 2996 | OH2 | TIP | 139 | 33.803 | 32.622 | 6.980 | 1.00 | 20.75 |
| ATOM | 2997 | OH2 | TIP | 140 | 37.790 | 20.683 | 21.494 | 1.00 | 33.84 |

TABLE 30-continued

| | | | | | | | | |
|---|---|---|---|---|---|---|---|---|
| ATOM | 2998 | OH2 | TIP | 141 | 27.946 | 24.070 | 16.098 | 1.00 | 35.29 |
| ATOM | 2999 | OH2 | TIP | 142 | 28.752 | 24.561 | 25.979 | 1.00 | 42.61 |
| ATOM | 3000 | OH2 | TIP | 143 | 29.987 | 30.644 | 9.290 | 1.00 | 24.83 |
| ATOM | 3001 | OH2 | TIP | 145 | 32.739 | 65.991 | 1.259 | 1.00 | 38.09 |
| ATOM | 3002 | OH2 | TIP | 146 | 43.015 | 23.319 | 7.628 | 1.00 | 40.80 |
| ATOM | 3003 | OH2 | TIP | 149 | 45.126 | 45.040 | 12.866 | 1.00 | 30.92 |
| ATOM | 3004 | OH2 | TIP | 150 | 56.775 | 54.277 | 24.966 | 1.00 | 36.42 |
| ATOM | 3005 | OH2 | TIP | 154 | 28.318 | 35.749 | −8.783 | 1.00 | 35.84 |
| ATOM | 3006 | OH2 | TIP | 157 | 49.259 | 20.639 | 1.116 | 1.00 | 39.43 |
| ATOM | 3007 | OH2 | TIP | 161 | 35.449 | 24.493 | 28.851 | 1.00 | 31.87 |
| ATOM | 3008 | OH2 | TIP | 162 | 48.248 | 19.447 | 10.858 | 1.00 | 50.81 |
| ATOM | 3009 | OH2 | TIP | 170 | 52.224 | 41.827 | 26.920 | 1.00 | 30.09 |
| ATOM | 3010 | OH2 | TIP | 171 | 43.427 | 68.248 | 20.208 | 1.00 | 50.00 |
| ATOM | 3011 | OH2 | TIP | 173 | 30.664 | 59.693 | 2.724 | 1.00 | 43.97 |
| ATOM | 3012 | OH2 | TIP | 177 | 49.139 | 23.639 | 29.923 | 1.00 | 44.34 |
| ATOM | 3013 | OH2 | TIP | 179 | 34.884 | 68.231 | 14.420 | 1.00 | 40.57 |
| ATOM | 3014 | OH2 | TIP | 180 | 34.202 | 33.407 | 32.184 | 1.00 | 40.76 |
| ATOM | 3015 | OH2 | TIP | 183 | 23.453 | 59.860 | 15.855 | 1.00 | 39.15 |
| ATOM | 3016 | OH2 | TIP | 184 | 37.128 | 22.982 | −4.060 | 1.00 | 31.12 |
| ATOM | 3017 | OH2 | TIP | 186 | 59.884 | 32.942 | 5.715 | 1.00 | 48.15 |
| ATOM | 3018 | OH2 | TIP | 187 | 38.634 | 46.165 | −0.230 | 1.00 | 13.80 |
| ATOM | 3019 | OH2 | TIP | 188 | 52.932 | 26.954 | 2.812 | 1.00 | 21.19 |
| ATOM | 3020 | OH2 | TIP | 189 | 56.883 | 26.650 | 15.220 | 1.00 | 17.90 |
| ATOM | 3021 | OH2 | TIP | 190 | 55.314 | 25.380 | 16.994 | 1.00 | 13.14 |
| ATOM | 3022 | OH2 | TIP | 191 | 51.598 | 53.602 | 12.473 | 1.00 | 17.75 |
| ATOM | 3023 | OH2 | TIP | 192 | 27.662 | 23.982 | 18.954 | 1.00 | 34.96 |
| ATOM | 3024 | OH2 | TIP | 193 | 28.692 | 32.840 | −8.937 | 1.00 | 31.39 |
| ATOM | 3025 | OH2 | TIP | 194 | 20.591 | 38.731 | 10.804 | 1.00 | 31.46 |
| ATOM | 3026 | OH2 | TIP | 195 | 24.147 | 43.407 | 2.885 | 1.00 | 28.20 |
| ATOM | 3027 | OH2 | TIP | 196 | 21.907 | 27.234 | 26.192 | 1.00 | 42.64 |
| ATOM | 3028 | OH2 | TIP | 197 | 63.736 | 33.840 | 22.009 | 1.00 | 35.07 |
| ATOM | 3029 | OH2 | TIP | 198 | 32.794 | 49.844 | 23.701 | 1.00 | 37.84 |
| ATOM | 3030 | OH2 | TIP | 199 | 58.947 | 40.782 | 13.015 | 1.00 | 31.28 |
| ATOM | 3031 | OH2 | TIP | 200 | 22.450 | 49.976 | 21.694 | 1.00 | 38.42 |
| ATOM | 3032 | OH2 | TIP | 201 | 49.606 | 32.017 | −6.528 | 1.00 | 33.11 |
| ATOM | 3033 | OH2 | TIP | 202 | 19.479 | 32.757 | 24.557 | 1.00 | 42.15 |
| ATOM | 3034 | OH2 | TIP | 203 | 18.243 | 43.892 | 25.199 | 1.00 | 34.82 |
| ATOM | 3035 | OH2 | TIP | 204 | 31.973 | 23.449 | 9.946 | 1.00 | 40.37 |
| ATOM | 3036 | OH2 | TIP | 205 | 59.437 | 39.072 | 29.736 | 1.00 | 46.69 |
| ATOM | 3037 | OH2 | TIP | 206 | 24.737 | 35.038 | −2.305 | 1.00 | 38.20 |
| ATOM | 3038 | OH2 | TIP | 207 | 51.798 | 24.226 | 23.337 | 1.00 | 43.38 |
| ATOM | 3039 | OH2 | TIP | 208 | 41.169 | 63.155 | 0.607 | 1.00 | 47.72 |
| ATOM | 3040 | OH2 | TIP | 209 | 44.987 | 24.799 | −6.919 | 1.00 | 58.95 |
| ATOM | 3041 | OH2 | TIP | 210 | 60.282 | 33.507 | 0.942 | 1.00 | 44.42 |
| ATOM | 3042 | OH2 | TIP | 211 | 55.312 | 57.953 | −5.133 | 1.00 | 61.46 |
| ATOM | 3043 | OH2 | TIP | 212 | 26.359 | 34.821 | 3.588 | 1.00 | 40.79 |
| ATOM | 3044 | OH2 | TIP | 213 | 57.280 | 58.607 | 2.155 | 1.00 | 54.60 |
| ATOM | 3045 | OH2 | TIP | 214 | 48.954 | 19.470 | 7.776 | 1.00 | 37.71 |
| ATOM | 3046 | OH2 | TIP | 215 | 18.783 | 34.339 | 22.498 | 1.00 | 38.96 |
| ATOM | 3047 | OH2 | TIP | 216 | 50.074 | 55.671 | 3.640 | 1.00 | 42.87 |
| ATOM | 3048 | OH2 | TIP | 217 | 23.725 | 39.251 | −3.750 | 1.00 | 39.29 |
| ATOM | 3049 | OH2 | TIP | 219 | 30.541 | 25.110 | 28.408 | 1.00 | 47.74 |
| ATOM | 3050 | OH2 | TIP | 220 | 26.037 | 30.541 | 16.867 | 1.00 | 34.87 |
| ATOM | 3051 | OH2 | TIP | 222 | 54.963 | 58.119 | 2.970 | 1.00 | 48.85 |
| ATOM | 3052 | OH2 | TIP | 223 | 59.416 | 53.101 | −2.816 | 1.00 | 55.72 |
| ATOM | 3053 | OH2 | TIP | 224 | 51.466 | 23.460 | 28.005 | 1.00 | 42.28 |
| ATOM | 3054 | OH2 | TIP | 225 | 37.482 | 39.527 | 29.584 | 1.00 | 30.27 |
| ATOM | 3055 | OH2 | TIP | 226 | 20.502 | 42.025 | 22.632 | 1.00 | 58.53 |
| ATOM | 3056 | OH2 | TIP | 227 | 38.047 | 51.915 | −4.933 | 1.00 | 42.64 |
| ATOM | 3057 | OH2 | TIP | 228 | 52.324 | 32.574 | 0.838 | 1.00 | 56.08 |
| ATOM | 3058 | OH2 | TIP | 229 | 58.093 | 50.903 | 12.906 | 1.00 | 32.98 |
| ATOM | 3059 | OH2 | TIP | 230 | 56.078 | 24.544 | 3.822 | 1.00 | 52.30 |
| ATOM | 3060 | OH2 | TIP | 231 | 51.692 | 20.080 | 23.166 | 1.00 | 44.78 |
| ATOM | 3061 | OH2 | TIP | 232 | 48.112 | 18.431 | 16.203 | 1.00 | 49.60 |
| ATOM | 3062 | OH2 | TIP | 233 | 49.693 | 20.764 | 19.679 | 1.00 | 38.77 |
| ATOM | 3063 | OH2 | TIP | 234 | 61.205 | 40.496 | 27.215 | 1.00 | 39.59 |
| ATOM | 3064 | OH2 | TIP | 235 | 60.244 | 28.451 | 9.868 | 1.00 | 37.16 |
| ATOM | 3065 | OH2 | TIP | 236 | 39.531 | 20.627 | 25.697 | 1.00 | 40.03 |
| ATOM | 3066 | OH2 | TIP | 237 | 21.925 | 38.965 | 24.059 | 1.00 | 48.68 |
| ATOM | 3067 | OH2 | TIP | 238 | 41.611 | 40.577 | −15.266 | 1.00 | 43.37 |
| ATOM | 3068 | OH2 | TIP | 239 | 53.812 | 60.797 | 4.864 | 1.00 | 52.56 |
| ATOM | 3069 | OH2 | TIP | 240 | 34.937 | 52.939 | −3.717 | 1.00 | 35.04 |
| ATOM | 3070 | OH2 | TIP | 241 | 55.261 | 34.522 | −10.080 | 1.00 | 38.74 |
| ATOM | 3071 | OH2 | TIP | 243 | 26.373 | 37.574 | −0.254 | 1.00 | 36.58 |
| ATOM | 3072 | OH2 | TIP | 244 | 51.004 | 60.496 | 4.046 | 1.00 | 64.83 |
| ATOM | 3073 | OH2 | TIP | 246 | 30.279 | 56.190 | 21.218 | 1.00 | 46.59 |
| ATOM | 3074 | OH2 | TIP | 247 | 25.538 | 38.352 | 8.582 | 1.00 | 38.19 |
| ATOM | 3075 | OH2 | TIP | 248 | 56.454 | 42.725 | 28.580 | 1.00 | 44.75 |
| ATOM | 3076 | OH2 | TIP | 249 | 50.714 | 57.646 | 7.941 | 1.00 | 34.81 |

TABLE 30-continued

| | | | | | | | | |
|---|---|---|---|---|---|---|---|---|
| ATOM | 3077 | OH2 | TIP | 250 | 41.382 | 43.205 | 29.087 | 1.00 | 39.12 |
| ATOM | 3078 | OH2 | TIP | 251 | 45.042 | 22.868 | 28.329 | 1.00 | 54.10 |
| ATOM | 3079 | OH2 | TIP | 252 | 20.370 | 42.693 | 15.093 | 1.00 | 54.24 |
| ATOM | 3080 | OH2 | TIP | 253 | 26.348 | 66.037 | 8.706 | 1.00 | 45.05 |
| ATOM | 3081 | OH2 | TIP | 254 | 45.856 | 38.418 | −11.622 | 1.00 | 53.29 |
| ATOM | 3082 | OH2 | TIP | 255 | 42.753 | 41.622 | 34.537 | 1.00 | 39.32 |
| ATOM | 3083 | OH2 | TIP | 256 | 48.240 | 52.734 | 26.556 | 1.00 | 43.67 |
| ATOM | 3084 | OH2 | TIP | 257 | 39.530 | 58.162 | 23.453 | 1.00 | 48.05 |
| ATOM | 3085 | OH2 | TIP | 258 | 37.524 | 57.192 | 25.020 | 1.00 | 42.73 |
| ATOM | 3086 | OH2 | TIP | 259 | 50.658 | 56.406 | 11.908 | 1.00 | 31.97 |
| ATOM | 3087 | OH2 | TIP | 260 | 59.957 | 24.763 | 12.383 | 1.00 | 36.65 |
| ATOM | 3088 | OH2 | TIP | 261 | 23.929 | 35.872 | 6.187 | 1.00 | 42.26 |
| ATOM | 3089 | OH2 | TIP | 262 | 64.700 | 52.165 | 26.674 | 1.00 | 64.00 |
| ATOM | 3090 | OH2 | TIP | 263 | 35.594 | 61.606 | 20.210 | 1.00 | 48.50 |
| ATOM | 3091 | OH2 | TIP | 264 | 43.651 | 65.314 | −7.509 | 1.00 | 43.95 |
| ATOM | 3092 | OH2 | TIP | 266 | 60.950 | 47.871 | 27.401 | 1.00 | 52.99 |
| ATOM | 3093 | OH2 | TIP | 268 | 51.791 | 34.626 | 42.320 | 1.00 | 47.15 |
| ATOM | 3094 | OH2 | TIP | 269 | 29.427 | 40.210 | 30.677 | 1.00 | 39.59 |
| ATOM | 3095 | OH2 | TIP | 270 | 22.940 | 53.289 | 8.458 | 1.00 | 42.16 |
| ATOM | 3096 | OH2 | TIP | 272 | 42.734 | 30.666 | 35.715 | 1.00 | 52.70 |
| ATOM | 3097 | OH2 | TIP | 273 | 39.864 | 24.360 | 0.437 | 1.00 | 45.07 |
| ATOM | 3098 | OH2 | TIP | 274 | 45.910 | 43.449 | 32.324 | 1.00 | 44.86 |
| ATOM | 3099 | OH2 | TIP | 276 | 60.434 | 26.488 | 22.662 | 1.00 | 54.68 |
| ATOM | 3100 | OH2 | TIP | 277 | 33.494 | 19.625 | 7.705 | 1.00 | 40.02 |
| ATOM | 3101 | OH2 | TIP | 278 | 31.089 | 37.331 | 32.964 | 1.00 | 52.04 |
| ATOM | 3102 | OH2 | TIP | 279 | 54.523 | 24.762 | 22.058 | 1.00 | 49.06 |
| ATOM | 3103 | OH2 | TIP | 280 | 47.202 | 60.156 | 19.785 | 1.00 | 46.35 |
| ATOM | 3104 | OH2 | TIP | 282 | 54.383 | 30.983 | 0.296 | 1.00 | 60.14 |
| ATOM | 3105 | OH2 | TIP | 283 | 61.892 | 32.292 | 15.089 | 1.00 | 36.30 |
| ATOM | 3106 | OH2 | TIP | 284 | 24.888 | 34.429 | −6.950 | 1.00 | 41.74 |
| ATOM | 3107 | OH2 | TIP | 285 | 24.688 | 32.139 | 26.844 | 1.00 | 41.60 |
| ATOM | 3108 | OH2 | TIP | 286 | 32.645 | 60.472 | 1.036 | 1.00 | 46.38 |
| ATOM | 3109 | OH2 | TIP | 287 | 55.123 | 56.214 | 24.983 | 1.00 | 43.87 |
| ATOM | 3110 | OH2 | TIP | 288 | 43.629 | 38.590 | 39.015 | 1.00 | 50.94 |
| ATOM | 3111 | OH2 | TIP | 292 | 20.728 | 36.639 | 8.936 | 1.00 | 42.54 |
| ATOM | 3112 | OH2 | TIP | 293 | 46.563 | 64.900 | 9.456 | 1.00 | 50.04 |
| ATOM | 3113 | OH2 | TIP | 294 | 17.012 | 60.160 | 10.502 | 1.00 | 48.90 |
| ATOM | 3114 | OH2 | TIP | 295 | 17.480 | 28.871 | 19.492 | 1.00 | 42.05 |
| ATOM | 3115 | OH2 | TIP | 297 | 36.366 | 31.406 | 32.340 | 1.00 | 42.47 |
| ATOM | 3116 | OH2 | TIP | 300 | 46.719 | 59.238 | −13.542 | 1.00 | 50.25 |
| ATOM | 3117 | OH2 | TIP | 301 | 29.641 | 25.448 | 9.713 | 1.00 | 41.77 |
| ATOM | 3118 | OH2 | TIP | 302 | 50.828 | 58.438 | 0.448 | 1.00 | 42.42 |
| ATOM | 3119 | OH2 | TIP | 303 | 29.614 | 52.009 | 22.188 | 1.00 | 37.94 |
| ATOM | 3120 | OH2 | TIP | 304 | 34.557 | 62.012 | 23.304 | 1.00 | 43.17 |
| ATOM | 3121 | OH2 | TIP | 305 | 28.994 | 20.961 | 23.471 | 1.00 | 43.02 |
| ATOM | 3122 | OH2 | TIP | 306 | 50.941 | 49.902 | 28.007 | 1.00 | 48.48 |
| ATOM | 3123 | OH2 | TIP | 307 | 18.496 | 51.343 | 16.991 | 1.00 | 44.97 |
| ATOM | 3124 | OH2 | TIP | 309 | 42.051 | 36.930 | −13.933 | 1.00 | 44.70 |
| ATOM | 3125 | OH2 | TIP | 310 | 45.128 | 42.750 | −9.449 | 1.00 | 47.67 |
| TER | 1 | | TIP | 310 | | | | | |
| ATOM | 1 | CB | MET A | 30 | 59.712 | 55.163 | −5.647 | 1.00 | 80.31 |
| ATOM | 2 | CG | MET A | 30 | 59.865 | 54.409 | −6.958 | 1.00 | 80.66 |
| ATOM | 3 | SD | MET A | 30 | 59.205 | 52.733 | −6.845 | 1.00 | 80.85 |
| ATOM | 4 | CE | MET A | 30 | 60.589 | 51.860 | −6.102 | 1.00 | 80.82 |
| ATOM | 5 | C | MET A | 30 | 58.219 | 55.645 | −3.704 | 1.00 | 79.00 |
| ATOM | 6 | O | MET A | 30 | 57.240 | 55.324 | −3.032 | 1.00 | 78.32 |
| ATOM | 7 | N | MET A | 30 | 57.620 | 56.445 | −6.003 | 1.00 | 79.37 |
| ATOM | 8 | CA | MET A | 30 | 58.259 | 55.360 | −5.203 | 1.00 | 79.50 |
| ATOM | 9 | N | ALA A | 31 | 59.288 | 56.244 | −3.187 | 1.00 | 78.38 |
| ATOM | 10 | CA | ALA A | 31 | 59.378 | 56.571 | −1.767 | 1.00 | 76.94 |
| ATOM | 11 | CB | ALA A | 31 | 60.826 | 56.867 | −1.390 | 1.00 | 77.21 |
| ATOM | 12 | C | ALA A | 31 | 58.492 | 57.763 | −1.419 | 1.00 | 75.64 |
| ATOM | 13 | O | ALA A | 31 | 58.167 | 57.987 | −0.252 | 1.00 | 75.52 |
| ATOM | 14 | N | THR A | 32 | 58.104 | 58.523 | −2.438 | 1.00 | 74.06 |
| ATOM | 15 | CA | THR A | 32 | 57.254 | 59.694 | −2.249 | 1.00 | 71.96 |
| ATOM | 16 | CB | THR A | 32 | 57.059 | 60.455 | −3.576 | 1.00 | 72.87 |
| ATOM | 17 | OG1 | THR A | 32 | 58.330 | 60.918 | −4.054 | 1.00 | 72.48 |
| ATOM | 18 | CG2 | THR A | 32 | 56.124 | 61.644 | −3.379 | 1.00 | 72.82 |
| ATOM | 19 | C | THR A | 32 | 55.887 | 59.290 | −1.703 | 1.00 | 69.77 |
| ATOM | 20 | O | THR A | 32 | 55.268 | 60.030 | −0.935 | 1.00 | 70.16 |
| ATOM | 21 | N | GLY A | 33 | 55.419 | 58.114 | −2.107 | 1.00 | 66.46 |
| ATOM | 22 | CA | GLY A | 33 | 54.136 | 57.630 | −1.637 | 1.00 | 61.99 |
| ATOM | 23 | C | GLY A | 33 | 52.945 | 58.292 | −2.296 | 1.00 | 58.74 |
| ATOM | 24 | O | GLY A | 33 | 52.090 | 58.860 | −1.617 | 1.00 | 59.57 |
| ATOM | 25 | N | ASP A | 34 | 52.881 | 58.221 | −3.621 | 1.00 | 54.17 |
| ATOM | 26 | CA | ASP A | 34 | 51.772 | 58.820 | −4.347 | 1.00 | 49.04 |
| ATOM | 27 | CB | ASP A | 34 | 52.274 | 59.467 | −5.635 | 1.00 | 48.74 |
| ATOM | 28 | CG | ASP A | 34 | 51.157 | 60.059 | −6.457 | 1.00 | 48.55 |
| ATOM | 29 | OD1 | ASP A | 34 | 50.669 | 59.367 | −7.375 | 1.00 | 48.93 |

TABLE 30-continued

| | | | | | | | | |
|---|---|---|---|---|---|---|---|---|
| ATOM | 30 | OD2 | ASP A | 34 | 50.757 | 61.211 | −6.178 | 1.00 | 49.18 |
| ATOM | 31 | C | ASP A | 34 | 50.692 | 57.784 | −4.652 | 1.00 | 46.02 |
| ATOM | 32 | O | ASP A | 34 | 50.959 | 56.738 | −5.248 | 1.00 | 43.47 |
| ATOM | 33 | N | GLU A | 35 | 49.469 | 58.095 | −4.232 | 1.00 | 43.20 |
| ATOM | 34 | CA | GLU A | 35 | 48.325 | 57.211 | −4.415 | 1.00 | 40.89 |
| ATOM | 35 | CB | GLU A | 35 | 47.077 | 57.866 | −3.811 | 1.00 | 40.86 |
| ATOM | 36 | CG | GLU A | 35 | 47.070 | 57.852 | −2.283 | 1.00 | 42.25 |
| ATOM | 37 | CD | GLU A | 35 | 46.082 | 58.836 | −1.674 | 1.00 | 43.75 |
| ATOM | 38 | OE1 | GLU A | 35 | 44.971 | 58.997 | −2.224 | 1.00 | 45.16 |
| ATOM | 39 | OE2 | GLU A | 35 | 46.416 | 59.439 | −0.631 | 1.00 | 41.85 |
| ATOM | 40 | C | GLU A | 35 | 48.063 | 56.784 | −5.858 | 1.00 | 39.00 |
| ATOM | 41 | O | GLU A | 35 | 47.816 | 55.606 | −6.114 | 1.00 | 37.91 |
| ATOM | 42 | N | ARG A | 36 | 48.122 | 57.726 | −6.799 | 1.00 | 37.60 |
| ATOM | 43 | CA | ARG A | 36 | 47.883 | 57.394 | −8.201 | 1.00 | 36.88 |
| ATOM | 44 | CB | ARG A | 36 | 47.776 | 58.651 | −9.066 | 1.00 | 40.39 |
| ATOM | 45 | CG | ARG A | 36 | 46.472 | 59.413 | −8.956 | 1.00 | 45.00 |
| ATOM | 46 | CD | ARG A | 36 | 46.295 | 60.312 | −10.173 | 1.00 | 47.46 |
| ATOM | 47 | NE | ARG A | 36 | 45.485 | 61.487 | −9.880 | 1.00 | 51.68 |
| ATOM | 48 | CZ | ARG A | 36 | 45.837 | 62.440 | −9.020 | 1.00 | 53.65 |
| ATOM | 49 | NH1 | ARG A | 36 | 46.988 | 62.355 | −8.367 | 1.00 | 54.00 |
| ATOM | 50 | NH2 | ARG A | 36 | 45.041 | 63.482 | −8.817 | 1.00 | 54.73 |
| ATOM | 51 | C | ARG A | 36 | 48.965 | 56.510 | −8.795 | 1.00 | 35.07 |
| ATOM | 52 | O | ARG A | 36 | 48.669 | 55.565 | −9.524 | 1.00 | 34.58 |
| ATOM | 53 | N | PHE A | 37 | 50.221 | 56.822 | −8.494 | 1.00 | 33.78 |
| ATOM | 54 | CA | PHE A | 37 | 51.325 | 56.042 | −9.030 | 1.00 | 33.03 |
| ATOM | 55 | CB | PHE A | 37 | 52.671 | 56.593 | −8.558 | 1.00 | 33.86 |
| ATOM | 56 | CG | PHE A | 37 | 53.846 | 55.870 | −9.146 | 1.00 | 36.09 |
| ATOM | 57 | CD1 | PHE A | 37 | 54.113 | 55.953 | −10.503 | 1.00 | 36.07 |
| ATOM | 58 | CD2 | PHE A | 37 | 54.660 | 55.077 | −8.353 | 1.00 | 37.36 |
| ATOM | 59 | CE1 | PHE A | 37 | 55.171 | 55.256 | −11.059 | 1.00 | 38.02 |
| ATOM | 60 | CE2 | PHE A | 37 | 55.720 | 54.376 | −8.903 | 1.00 | 37.55 |
| ATOM | 61 | CZ | PHE A | 37 | 55.975 | 54.466 | −10.257 | 1.00 | 38.09 |
| ATOM | 62 | C | PHE A | 37 | 51.228 | 54.575 | −8.643 | 1.00 | 30.97 |
| ATOM | 63 | O | PHE A | 37 | 51.393 | 53.693 | −9.484 | 1.00 | 30.44 |
| ATOM | 64 | N | TYR A | 38 | 50.969 | 54.311 | −7.368 | 1.00 | 30.50 |
| ATOM | 65 | CA | TYR A | 38 | 50.856 | 52.933 | −6.910 | 1.00 | 31.45 |
| ATOM | 66 | CB | TYR A | 38 | 50.826 | 52.873 | −5.381 | 1.00 | 30.08 |
| ATOM | 67 | CG | TYR A | 38 | 52.197 | 52.901 | −4.749 | 1.00 | 29.63 |
| ATOM | 68 | CD1 | TYR A | 38 | 52.936 | 54.078 | −4.693 | 1.00 | 29.71 |
| ATOM | 69 | CE1 | TYR A | 38 | 54.202 | 54.099 | −4.132 | 1.00 | 29.16 |
| ATOM | 70 | CD2 | TYR A | 38 | 52.764 | 51.742 | −4.226 | 1.00 | 26.96 |
| ATOM | 71 | CE2 | TYR A | 38 | 54.026 | 51.751 | −3.668 | 1.00 | 27.02 |
| ATOM | 72 | CZ | TYR A | 38 | 54.740 | 52.931 | −3.624 | 1.00 | 29.27 |
| ATOM | 73 | OH | TYR A | 38 | 56.001 | 52.940 | −3.086 | 1.00 | 30.40 |
| ATOM | 74 | C | TYR A | 38 | 49.619 | 52.256 | −7.474 | 1.00 | 32.16 |
| ATOM | 75 | O | TYR A | 38 | 49.684 | 51.126 | −7.953 | 1.00 | 31.25 |
| ATOM | 76 | N | ALA A | 39 | 48.494 | 52.960 | −7.425 | 1.00 | 33.95 |
| ATOM | 77 | CA | ALA A | 39 | 47.234 | 52.425 | −7.918 | 1.00 | 36.26 |
| ATOM | 78 | CB | ALA A | 39 | 46.094 | 53.349 | −7.517 | 1.00 | 36.53 |
| ATOM | 79 | C | ALA A | 39 | 47.215 | 52.209 | −9.428 | 1.00 | 37.90 |
| ATOM | 80 | O | ALA A | 39 | 46.781 | 51.158 | −9.909 | 1.00 | 37.48 |
| ATOM | 81 | N | GLU A | 40 | 47.696 | 53.201 | −10.171 | 1.00 | 40.13 |
| ATOM | 82 | CA | GLU A | 40 | 47.696 | 53.134 | −11.629 | 1.00 | 41.55 |
| ATOM | 83 | CB | GLU A | 40 | 47.512 | 54.540 | −12.215 | 1.00 | 43.53 |
| ATOM | 84 | CG | GLU A | 40 | 46.262 | 55.264 | −11.735 | 1.00 | 47.12 |
| ATOM | 85 | CD | GLU A | 40 | 46.122 | 56.651 | −12.340 | 1.00 | 49.89 |
| ATOM | 86 | OE1 | GLU A | 40 | 46.081 | 56.751 | −13.585 | 1.00 | 52.64 |
| ATOM | 87 | OE2 | GLU A | 40 | 46.051 | 57.639 | −11.574 | 1.00 | 50.61 |
| ATOM | 88 | C | GLU A | 40 | 48.911 | 52.489 | −12.286 | 1.00 | 40.57 |
| ATOM | 89 | O | GLU A | 40 | 48.785 | 51.894 | −13.354 | 1.00 | 40.85 |
| ATOM | 90 | N | HIS A | 41 | 50.083 | 52.587 | −11.664 | 1.00 | 39.75 |
| ATOM | 91 | CA | HIS A | 41 | 51.275 | 52.024 | −12.293 | 1.00 | 38.62 |
| ATOM | 92 | CB | HIS A | 41 | 52.266 | 53.146 | −12.621 | 1.00 | 40.78 |
| ATOM | 93 | CG | HIS A | 41 | 51.689 | 54.227 | −13.479 | 1.00 | 44.09 |
| ATOM | 94 | CD2 | HIS A | 41 | 51.777 | 54.451 | −14.811 | 1.00 | 45.23 |
| ATOM | 95 | ND1 | HIS A | 41 | 50.876 | 55.222 | −12.977 | 1.00 | 46.21 |
| ATOM | 96 | CE1 | HIS A | 41 | 50.488 | 56.011 | −13.963 | 1.00 | 46.60 |
| ATOM | 97 | NE2 | HIS A | 41 | 51.021 | 55.565 | −15.086 | 1.00 | 47.61 |
| ATOM | 98 | C | HIS A | 41 | 52.032 | 50.903 | −11.594 | 1.00 | 35.71 |
| ATOM | 99 | O | HIS A | 41 | 52.177 | 49.812 | −12.146 | 1.00 | 35.85 |
| ATOM | 100 | N | LEU A | 42 | 52.525 | 51.165 | −10.392 | 1.00 | 33.29 |
| ATOM | 101 | CA | LEU A | 42 | 53.311 | 50.161 | −9.682 | 1.00 | 32.13 |
| ATOM | 102 | CB | LEU A | 42 | 53.883 | 50.761 | −8.393 | 1.00 | 31.28 |
| ATOM | 103 | CG | LEU A | 42 | 55.057 | 49.987 | −7.781 | 1.00 | 34.33 |
| ATOM | 104 | CD1 | LEU A | 42 | 55.897 | 50.923 | −6.925 | 1.00 | 33.63 |
| ATOM | 105 | CD2 | LEU A | 42 | 54.542 | 48.804 | −6.967 | 1.00 | 34.74 |
| ATOM | 106 | C | LEU A | 42 | 52.581 | 48.850 | −9.382 | 1.00 | 30.26 |
| ATOM | 107 | O | LEU A | 42 | 52.981 | 47.794 | −9.871 | 1.00 | 31.23 |
| ATOM | 108 | N | MET A | 43 | 51.519 | 48.911 | −8.586 | 1.00 | 27.76 |

TABLE 30-continued

| ATOM | 109 | CA | MET A | 43 | 50.772 | 47.706 | −8.232 | 1.00 | 27.76 |
| --- | --- | --- | --- | --- | --- | --- | --- | --- | --- |
| ATOM | 110 | CB | MET A | 43 | 49.552 | 48.066 | −7.379 | 1.00 | 24.10 |
| ATOM | 111 | CG | MET A | 43 | 49.918 | 48.634 | −6.022 | 1.00 | 23.32 |
| ATOM | 112 | SD | MET A | 43 | 51.075 | 47.574 | −5.113 | 1.00 | 25.43 |
| ATOM | 113 | CE | MET A | 43 | 49.970 | 46.252 | −4.615 | 1.00 | 21.95 |
| ATOM | 114 | C | MET A | 43 | 50.343 | 46.878 | −9.440 | 1.00 | 28.21 |
| ATOM | 115 | O | MET A | 43 | 50.517 | 45.661 | −9.454 | 1.00 | 27.46 |
| ATOM | 116 | N | PRO A | 44 | 49.766 | 47.524 | −10.466 | 1.00 | 29.90 |
| ATOM | 117 | CD | PRO A | 44 | 49.323 | 48.929 | −10.518 | 1.00 | 28.73 |
| ATOM | 118 | CA | PRO A | 44 | 49.333 | 46.797 | −11.664 | 1.00 | 30.50 |
| ATOM | 119 | CB | PRO A | 44 | 48.757 | 47.902 | −12.542 | 1.00 | 30.16 |
| ATOM | 120 | CG | PRO A | 44 | 48.222 | 48.875 | −11.541 | 1.00 | 30.35 |
| ATOM | 121 | C | PRO A | 44 | 50.499 | 46.075 | −12.343 | 1.00 | 32.56 |
| ATOM | 122 | O | PRO A | 44 | 50.369 | 44.927 | −12.770 | 1.00 | 33.27 |
| ATOM | 123 | N | THR A | 45 | 51.637 | 46.756 | −12.442 | 1.00 | 33.42 |
| ATOM | 124 | CA | THR A | 45 | 52.821 | 46.180 | −13.071 | 1.00 | 34.86 |
| ATOM | 125 | CB | THR A | 45 | 53.950 | 47.225 | −13.197 | 1.00 | 36.09 |
| ATOM | 126 | OG1 | THR A | 45 | 53.499 | 48.323 | −14.001 | 1.00 | 33.74 |
| ATOM | 127 | CG2 | THR A | 45 | 55.187 | 46.599 | −13.837 | 1.00 | 35.67 |
| ATOM | 128 | C | THR A | 45 | 53.335 | 45.012 | −12.242 | 1.00 | 36.57 |
| ATOM | 129 | O | THR A | 45 | 53.717 | 43.970 | −12.774 | 1.00 | 36.59 |
| ATOM | 130 | N | LEU A | 46 | 53.342 | 45.199 | −10.928 | 1.00 | 38.25 |
| ATOM | 131 | CA | LEU A | 46 | 53.801 | 44.170 | −10.008 | 1.00 | 38.66 |
| ATOM | 132 | CB | LEU A | 46 | 53.726 | 44.694 | −8.575 | 1.00 | 39.21 |
| ATOM | 133 | CG | LEU A | 46 | 54.329 | 43.815 | −7.483 | 1.00 | 41.10 |
| ATOM | 134 | CD1 | LEU A | 46 | 55.784 | 43.519 | −7.815 | 1.00 | 43.25 |
| ATOM | 135 | CD2 | LEU A | 46 | 54.222 | 44.528 | −6.144 | 1.00 | 41.41 |
| ATOM | 136 | C | LEU A | 46 | 52.946 | 42.914 | −10.144 | 1.00 | 38.98 |
| ATOM | 137 | O | LEU A | 46 | 53.466 | 41.800 | −10.187 | 1.00 | 39.35 |
| ATOM | 138 | N | GLN A | 47 | 51.633 | 43.102 | −10.219 | 1.00 | 38.99 |
| ATOM | 139 | CA | GLN A | 47 | 50.709 | 41.981 | −10.339 | 1.00 | 40.71 |
| ATOM | 140 | CB | GLN A | 47 | 49.300 | 42.425 | −9.929 | 1.00 | 40.91 |
| ATOM | 141 | CG | GLN A | 47 | 49.228 | 42.899 | −8.478 | 1.00 | 42.99 |
| ATOM | 142 | CD | GLN A | 47 | 47.833 | 43.314 | −8.052 | 1.00 | 45.00 |
| ATOM | 143 | OE1 | GLN A | 47 | 47.222 | 44.195 | −8.657 | 1.00 | 47.02 |
| ATOM | 144 | NE2 | GLN A | 47 | 47.323 | 42.683 | −7.001 | 1.00 | 45.03 |
| ATOM | 145 | C | GLN A | 47 | 50.701 | 41.373 | −11.741 | 1.00 | 39.99 |
| ATOM | 146 | O | GLN A | 47 | 50.246 | 40.246 | −11.937 | 1.00 | 39.01 |
| ATOM | 147 | N | GLY A | 48 | 51.216 | 42.119 | −12.712 | 1.00 | 40.83 |
| ATOM | 148 | CA | GLY A | 48 | 51.276 | 41.616 | −14.073 | 1.00 | 39.56 |
| ATOM | 149 | C | GLY A | 48 | 52.526 | 40.780 | −14.291 | 1.00 | 39.27 |
| ATOM | 150 | O | GLY A | 48 | 52.678 | 40.135 | −15.327 | 1.00 | 40.98 |
| ATOM | 151 | N | LEU A | 49 | 53.422 | 40.784 | −13.308 | 1.00 | 37.67 |
| ATOM | 152 | CA | LEU A | 49 | 54.667 | 40.027 | −13.396 | 1.00 | 37.43 |
| ATOM | 153 | CB | LEU A | 49 | 55.867 | 40.954 | −13.186 | 1.00 | 38.73 |
| ATOM | 154 | CG | LEU A | 49 | 56.105 | 42.068 | −14.208 | 1.00 | 38.96 |
| ATOM | 155 | CD1 | LEU A | 49 | 57.270 | 42.932 | −13.755 | 1.00 | 38.41 |
| ATOM | 156 | CD2 | LEU A | 49 | 56.384 | 41.457 | −15.571 | 1.00 | 39.54 |
| ATOM | 157 | C | LEU A | 49 | 54.741 | 38.899 | −12.376 | 1.00 | 36.89 |
| ATOM | 158 | O | LEU A | 49 | 55.451 | 37.918 | −12.582 | 1.00 | 37.19 |
| ATOM | 159 | N | LEU A | 50 | 54.010 | 39.041 | −11.275 | 1.00 | 36.34 |
| ATOM | 160 | CA | LEU A | 50 | 54.019 | 38.038 | −10.214 | 1.00 | 34.90 |
| ATOM | 161 | CB | LEU A | 50 | 54.607 | 38.644 | −8.935 | 1.00 | 35.62 |
| ATOM | 162 | CG | LEU A | 50 | 56.057 | 39.128 | −8.994 | 1.00 | 36.46 |
| ATOM | 163 | CD1 | LEU A | 50 | 56.396 | 39.878 | −7.717 | 1.00 | 36.33 |
| ATOM | 164 | CD2 | LEU A | 50 | 56.988 | 37.937 | −9.185 | 1.00 | 35.82 |
| ATOM | 165 | C | LEU A | 50 | 52.635 | 37.484 | −9.904 | 1.00 | 34.02 |
| ATOM | 166 | O | LEU A | 50 | 51.647 | 38.219 | −9.902 | 1.00 | 34.02 |
| ATOM | 167 | N | ASP A | 51 | 52.566 | 36.183 | −9.637 | 1.00 | 32.65 |
| ATOM | 168 | CA | ASP A | 51 | 51.294 | 35.563 | −9.299 | 1.00 | 32.66 |
| ATOM | 169 | CB | ASP A | 51 | 51.403 | 34.036 | −9.364 | 1.00 | 33.88 |
| ATOM | 170 | CG | ASP A | 51 | 52.350 | 33.476 | −8.329 | 1.00 | 36.45 |
| ATOM | 171 | OD1 | ASP A | 51 | 53.554 | 33.802 | −8.389 | 1.00 | 38.39 |
| ATOM | 172 | OD2 | ASP A | 51 | 51.889 | 32.709 | −7.456 | 1.00 | 37.67 |
| ATOM | 173 | C | ASP A | 51 | 50.939 | 36.026 | −7.882 | 1.00 | 30.84 |
| ATOM | 174 | O | ASP A | 51 | 51.812 | 36.467 | −7.130 | 1.00 | 30.91 |
| ATOM | 175 | N | PRO A | 52 | 49.656 | 35.931 | −7.502 | 1.00 | 28.67 |
| ATOM | 176 | CD | PRO A | 52 | 48.574 | 35.295 | −8.273 | 1.00 | 27.32 |
| ATOM | 177 | CA | PRO A | 52 | 49.174 | 36.347 | −6.179 | 1.00 | 27.35 |
| ATOM | 178 | CB | PRO A | 52 | 47.804 | 35.684 | −6.094 | 1.00 | 28.92 |
| ATOM | 179 | CG | PRO A | 52 | 47.339 | 35.728 | −7.514 | 1.00 | 27.85 |
| ATOM | 180 | C | PRO A | 52 | 50.072 | 35.989 | −4.994 | 1.00 | 25.30 |
| ATOM | 181 | O | PRO A | 52 | 50.509 | 36.867 | −4.255 | 1.00 | 25.37 |
| ATOM | 182 | N | GLU A | 53 | 50.357 | 34.707 | −4.814 | 1.00 | 24.59 |
| ATOM | 183 | CA | GLU A | 53 | 51.190 | 34.285 | −3.696 | 1.00 | 25.59 |
| ATOM | 184 | CB | GLU A | 53 | 51.233 | 32.758 | −3.614 | 1.00 | 25.66 |
| ATOM | 185 | CG | GLU A | 53 | 51.907 | 32.257 | −2.353 | 1.00 | 27.24 |
| ATOM | 186 | CD | GLU A | 53 | 51.431 | 30.882 | −1.929 | 1.00 | 28.48 |
| ATOM | 187 | OE1 | GLU A | 53 | 51.979 | 30.357 | −0.940 | 1.00 | 31.42 |

TABLE 30-continued

| | | | | | | | | | |
|---|---|---|---|---|---|---|---|---|---|
| ATOM | 188 | OE2 | GLU A | 53 | 50.512 | 30.329 | −2.574 | 1.00 | 27.49 |
| ATOM | 189 | C | GLU A | 53 | 52.614 | 34.856 | −3.722 | 1.00 | 25.68 |
| ATOM | 190 | O | GLU A | 53 | 53.119 | 35.298 | −2.688 | 1.00 | 24.08 |
| ATOM | 191 | N | SER A | 54 | 53.259 | 34.850 | −4.887 | 1.00 | 24.37 |
| ATOM | 192 | CA | SER A | 54 | 54.609 | 35.396 | −4.996 | 1.00 | 24.85 |
| ATOM | 193 | CB | SER A | 54 | 55.175 | 35.184 | −6.404 | 1.00 | 25.94 |
| ATOM | 194 | OG | SER A | 54 | 55.400 | 33.810 | −6.667 | 1.00 | 28.92 |
| ATOM | 195 | C | SER A | 54 | 54.592 | 36.887 | −4.683 | 1.00 | 25.02 |
| ATOM | 196 | O | SER A | 54 | 55.511 | 37.408 | −4.048 | 1.00 | 25.15 |
| ATOM | 197 | N | ALA A | 55 | 53.545 | 37.570 | −5.140 | 1.00 | 23.67 |
| ATOM | 198 | CA | ALA A | 55 | 53.401 | 38.999 | −4.904 | 1.00 | 22.81 |
| ATOM | 199 | CB | ALA A | 55 | 52.155 | 39.525 | −5.617 | 1.00 | 21.78 |
| ATOM | 200 | C | ALA A | 55 | 53.290 | 39.236 | −3.400 | 1.00 | 22.62 |
| ATOM | 201 | O | ALA A | 55 | 53.913 | 40.143 | −2.850 | 1.00 | 22.65 |
| ATOM | 202 | N | HIS A | 56 | 52.492 | 38.410 | −2.737 | 1.00 | 22.22 |
| ATOM | 203 | CA | HIS A | 56 | 52.316 | 38.538 | −1.300 | 1.00 | 23.60 |
| ATOM | 204 | CB | HIS A | 56 | 51.296 | 37.523 | −0.792 | 1.00 | 19.67 |
| ATOM | 205 | CG | HIS A | 56 | 51.232 | 37.449 | 0.699 | 1.00 | 19.95 |
| ATOM | 206 | CD2 | HIS A | 56 | 51.489 | 36.432 | 1.554 | 1.00 | 17.66 |
| ATOM | 207 | ND1 | HIS A | 56 | 50.908 | 38.537 | 1.482 | 1.00 | 20.51 |
| ATOM | 208 | CE1 | HIS A | 56 | 50.969 | 38.192 | 2.754 | 1.00 | 19.63 |
| ATOM | 209 | NE2 | HIS A | 56 | 51.321 | 36.921 | 2.826 | 1.00 | 18.97 |
| ATOM | 210 | C | HIS A | 56 | 53.627 | 38.344 | −0.539 | 1.00 | 25.30 |
| ATOM | 211 | O | HIS A | 56 | 53.952 | 39.119 | 0.367 | 1.00 | 24.97 |
| ATOM | 212 | N | ARG A | 57 | 54.373 | 37.306 | −0.906 | 1.00 | 26.20 |
| ATOM | 213 | CA | ARG A | 57 | 55.641 | 37.006 | −0.253 | 1.00 | 29.31 |
| ATOM | 214 | CB | ARG A | 57 | 56.233 | 35.715 | −0.822 | 1.00 | 32.99 |
| ATOM | 215 | CG | ARG A | 57 | 55.250 | 34.553 | −0.767 | 1.00 | 40.69 |
| ATOM | 216 | CD | ARG A | 57 | 55.893 | 33.223 | −1.118 | 1.00 | 45.69 |
| ATOM | 217 | NE | ARG A | 57 | 56.865 | 32.810 | −0.111 | 1.00 | 51.83 |
| ATOM | 218 | CZ | ARG A | 57 | 57.386 | 31.591 | −0.034 | 1.00 | 54.55 |
| ATOM | 219 | NH1 | ARG A | 57 | 57.027 | 30.657 | −0.907 | 1.00 | 55.29 |
| ATOM | 220 | NH2 | ARG A | 57 | 58.264 | 31.302 | 0.920 | 1.00 | 56.65 |
| ATOM | 221 | C | ARG A | 57 | 56.630 | 38.152 | −0.400 | 1.00 | 27.88 |
| ATOM | 222 | O | ARG A | 57 | 57.344 | 38.483 | 0.543 | 1.00 | 28.70 |
| ATOM | 223 | N | LEU A | 58 | 56.665 | 38.762 | −1.579 | 1.00 | 27.01 |
| ATOM | 224 | CA | LEU A | 58 | 57.561 | 39.886 | −1.823 | 1.00 | 27.01 |
| ATOM | 225 | CB | LEU A | 58 | 57.540 | 40.266 | −3.306 | 1.00 | 29.93 |
| ATOM | 226 | CG | LEU A | 58 | 58.560 | 41.316 | −3.754 | 1.00 | 32.39 |
| ATOM | 227 | CD1 | LEU A | 58 | 59.969 | 40.741 | −3.628 | 1.00 | 33.40 |
| ATOM | 228 | CD2 | LEU A | 58 | 58.280 | 41.729 | −5.193 | 1.00 | 33.62 |
| ATOM | 229 | C | LEU A | 58 | 57.095 | 41.074 | −0.979 | 1.00 | 26.41 |
| ATOM | 230 | O | LEU A | 58 | 57.906 | 41.846 | −0.462 | 1.00 | 25.09 |
| ATOM | 231 | N | ALA A | 59 | 55.777 | 41.211 | −0.851 | 1.00 | 24.78 |
| ATOM | 232 | CA | ALA A | 59 | 55.177 | 42.286 | −0.069 | 1.00 | 22.97 |
| ATOM | 233 | CB | ALA A | 59 | 53.657 | 42.189 | −0.125 | 1.00 | 21.53 |
| ATOM | 234 | C | ALA A | 59 | 55.645 | 42.196 | 1.373 | 1.00 | 20.70 |
| ATOM | 235 | O | ALA A | 59 | 56.011 | 43.199 | 1.982 | 1.00 | 20.94 |
| ATOM | 236 | N | VAL A | 60 | 55.621 | 40.987 | 1.919 | 1.00 | 19.75 |
| ATOM | 237 | CA | VAL A | 60 | 56.053 | 40.776 | 3.292 | 1.00 | 19.54 |
| ATOM | 238 | CB | VAL A | 60 | 55.804 | 39.312 | 3.732 | 1.00 | 18.51 |
| ATOM | 239 | CG1 | VAL A | 60 | 56.381 | 39.070 | 5.125 | 1.00 | 16.83 |
| ATOM | 240 | CG2 | VAL A | 60 | 54.308 | 39.022 | 3.722 | 1.00 | 14.84 |
| ATOM | 241 | C | VAL A | 60 | 57.540 | 41.117 | 3.421 | 1.00 | 20.80 |
| ATOM | 242 | O | VAL A | 60 | 57.945 | 41.783 | 4.372 | 1.00 | 20.78 |
| ATOM | 243 | N | ARG A | 61 | 58.346 | 40.674 | 2.458 | 1.00 | 23.54 |
| ATOM | 244 | CA | ARG A | 61 | 59.782 | 40.954 | 2.477 | 1.00 | 27.19 |
| ATOM | 245 | CB | ARG A | 61 | 60.483 | 40.362 | 1.249 | 1.00 | 29.60 |
| ATOM | 246 | CG | ARG A | 61 | 60.452 | 38.847 | 1.135 | 1.00 | 38.29 |
| ATOM | 247 | CD | ARG A | 61 | 61.547 | 38.376 | 0.170 | 1.00 | 44.72 |
| ATOM | 248 | NE | ARG A | 61 | 61.507 | 36.938 | −0.097 | 1.00 | 50.19 |
| ATOM | 249 | CZ | ARG A | 61 | 60.690 | 36.356 | −0.972 | 1.00 | 51.81 |
| ATOM | 250 | NH1 | ARG A | 61 | 59.836 | 37.086 | −1.678 | 1.00 | 51.44 |
| ATOM | 251 | NH2 | ARG A | 61 | 60.728 | 35.040 | −1.143 | 1.00 | 52.85 |
| ATOM | 252 | C | ARG A | 61 | 60.056 | 42.456 | 2.503 | 1.00 | 26.67 |
| ATOM | 253 | O | ARG A | 61 | 60.766 | 42.951 | 3.380 | 1.00 | 25.34 |
| ATOM | 254 | N | PHE A | 62 | 59.496 | 43.174 | 1.534 | 1.00 | 26.17 |
| ATOM | 255 | CA | PHE A | 62 | 59.704 | 44.613 | 1.447 | 1.00 | 28.72 |
| ATOM | 256 | CB | PHE A | 62 | 58.977 | 45.187 | 0.229 | 1.00 | 31.46 |
| ATOM | 257 | CG | PHE A | 62 | 59.783 | 45.127 | −1.035 | 1.00 | 35.66 |
| ATOM | 258 | CD1 | PHE A | 62 | 60.279 | 43.921 | −1.501 | 1.00 | 36.94 |
| ATOM | 259 | CD2 | PHE A | 62 | 60.052 | 46.279 | −1.756 | 1.00 | 39.16 |
| ATOM | 260 | CE1 | PHE A | 62 | 61.029 | 43.865 | −2.663 | 1.00 | 38.76 |
| ATOM | 261 | CE2 | PHE A | 62 | 60.803 | 46.231 | −2.919 | 1.00 | 40.51 |
| ATOM | 262 | CZ | PHE A | 62 | 61.291 | 45.020 | −3.373 | 1.00 | 39.34 |
| ATOM | 263 | C | PHE A | 62 | 59.262 | 45.347 | 2.700 | 1.00 | 28.83 |
| ATOM | 264 | O | PHE A | 62 | 59.946 | 46.260 | 3.166 | 1.00 | 28.57 |
| ATOM | 265 | N | THR A | 63 | 58.117 | 44.948 | 3.244 | 1.00 | 28.55 |
| ATOM | 266 | CA | THR A | 63 | 57.594 | 45.580 | 4.444 | 1.00 | 27.95 |

TABLE 30-continued

| | | | | | | | | | |
|---|---|---|---|---|---|---|---|---|---|
| ATOM | 267 | CB | THR A | 63 | 56.193 | 45.030 | 4.800 | 1.00 | 26.73 |
| ATOM | 268 | OG1 | THR A | 63 | 55.292 | 45.280 | 3.715 | 1.00 | 25.39 |
| ATOM | 269 | CG2 | THR A | 63 | 55.656 | 45.706 | 6.048 | 1.00 | 26.61 |
| ATOM | 270 | C | THR A | 63 | 58.538 | 45.346 | 5.619 | 1.00 | 28.75 |
| ATOM | 271 | O | THR A | 63 | 58.847 | 46.272 | 6.372 | 1.00 | 27.36 |
| ATOM | 272 | N | SER A | 64 | 59.003 | 44.109 | 5.769 | 1.00 | 28.81 |
| ATOM | 273 | CA | SER A | 64 | 59.905 | 43.783 | 6.867 | 1.00 | 31.26 |
| ATOM | 274 | CB | SER A | 64 | 60.234 | 42.287 | 6.866 | 1.00 | 30.34 |
| ATOM | 275 | OG | SER A | 64 | 61.025 | 41.938 | 5.744 | 1.00 | 34.64 |
| ATOM | 276 | C | SER A | 64 | 61.193 | 44.596 | 6.771 | 1.00 | 31.63 |
| ATOM | 277 | O | SER A | 64 | 61.794 | 44.939 | 7.785 | 1.00 | 31.52 |
| ATOM | 278 | N | LEU A | 65 | 61.606 | 44.914 | 5.547 | 1.00 | 33.19 |
| ATOM | 279 | CA | LEU A | 65 | 62.828 | 45.686 | 5.332 | 1.00 | 34.17 |
| ATOM | 280 | CB | LEU A | 65 | 63.500 | 45.257 | 4.026 | 1.00 | 33.79 |
| ATOM | 281 | CG | LEU A | 65 | 63.988 | 43.807 | 3.993 | 1.00 | 36.63 |
| ATOM | 282 | CD1 | LEU A | 65 | 64.621 | 43.507 | 2.646 | 1.00 | 34.56 |
| ATOM | 283 | CD2 | LEU A | 65 | 64.990 | 43.579 | 5.124 | 1.00 | 37.33 |
| ATOM | 284 | C | LEU A | 65 | 62.596 | 47.196 | 5.316 | 1.00 | 33.85 |
| ATOM | 285 | O | LEU A | 65 | 63.542 | 47.969 | 5.195 | 1.00 | 34.26 |
| ATOM | 286 | N | GLY A | 66 | 61.341 | 47.614 | 5.430 | 1.00 | 33.45 |
| ATOM | 287 | CA | GLY A | 66 | 61.040 | 49.035 | 5.437 | 1.00 | 34.55 |
| ATOM | 288 | C | GLY A | 66 | 61.062 | 49.729 | 4.083 | 1.00 | 35.86 |
| ATOM | 289 | O | GLY A | 66 | 61.103 | 50.961 | 4.016 | 1.00 | 35.51 |
| ATOM | 290 | N | LEU A | 67 | 61.036 | 48.953 | 3.003 | 1.00 | 36.35 |
| ATOM | 291 | CA | LEU A | 67 | 61.043 | 49.522 | 1.658 | 1.00 | 37.31 |
| ATOM | 292 | CB | LEU A | 67 | 61.467 | 48.456 | 0.640 | 1.00 | 38.96 |
| ATOM | 293 | CG | LEU A | 67 | 62.781 | 47.731 | 0.967 | 1.00 | 41.48 |
| ATOM | 294 | CD1 | LEU A | 67 | 63.077 | 46.689 | −0.099 | 1.00 | 41.55 |
| ATOM | 295 | CD2 | LEU A | 67 | 63.922 | 48.739 | 1.059 | 1.00 | 42.89 |
| ATOM | 296 | C | LEU A | 67 | 59.628 | 50.012 | 1.361 | 1.00 | 36.64 |
| ATOM | 297 | O | LEU A | 67 | 58.894 | 49.406 | 0.583 | 1.00 | 35.87 |
| ATOM | 298 | N | LEU A | 68 | 59.259 | 51.119 | 1.996 | 1.00 | 37.15 |
| ATOM | 299 | CA | LEU A | 68 | 57.927 | 51.693 | 1.858 | 1.00 | 38.24 |
| ATOM | 300 | CB | LEU A | 68 | 57.184 | 51.573 | 3.188 | 1.00 | 38.62 |
| ATOM | 301 | CG | LEU A | 68 | 57.210 | 50.196 | 3.851 | 1.00 | 39.70 |
| ATOM | 302 | CD1 | LEU A | 68 | 56.699 | 50.303 | 5.275 | 1.00 | 39.82 |
| ATOM | 303 | CD2 | LEU A | 68 | 56.373 | 49.226 | 3.037 | 1.00 | 40.12 |
| ATOM | 304 | C | LEU A | 68 | 57.967 | 53.160 | 1.450 | 1.00 | 38.59 |
| ATOM | 305 | O | LEU A | 68 | 58.903 | 53.884 | 1.782 | 1.00 | 39.27 |
| ATOM | 306 | N | PRO A | 69 | 56.932 | 53.616 | 0.729 | 1.00 | 38.61 |
| ATOM | 307 | CD | PRO A | 69 | 55.779 | 52.813 | 0.291 | 1.00 | 37.91 |
| ATOM | 308 | CA | PRO A | 69 | 56.807 | 54.997 | 0.257 | 1.00 | 39.04 |
| ATOM | 309 | CB | PRO A | 69 | 55.590 | 54.932 | −0.660 | 1.00 | 38.47 |
| ATOM | 310 | CG | PRO A | 69 | 54.754 | 53.878 | −0.023 | 1.00 | 38.21 |
| ATOM | 311 | C | PRO A | 69 | 56.620 | 55.991 | 1.400 | 1.00 | 39.37 |
| ATOM | 312 | O | PRO A | 69 | 56.828 | 55.657 | 2.566 | 1.00 | 39.95 |
| ATOM | 313 | N | PHE A | 73 | 51.580 | 61.610 | 6.291 | 1.00 | 57.27 |
| ATOM | 314 | CA | PHE A | 73 | 50.360 | 61.873 | 7.047 | 1.00 | 57.38 |
| ATOM | 315 | CB | PHE A | 73 | 49.221 | 60.966 | 6.569 | 1.00 | 57.90 |
| ATOM | 316 | CG | PHE A | 73 | 47.951 | 61.126 | 7.361 | 1.00 | 58.13 |
| ATOM | 317 | CD1 | PHE A | 73 | 47.092 | 62.186 | 7.116 | 1.00 | 58.39 |
| ATOM | 318 | CD2 | PHE A | 73 | 47.638 | 60.241 | 8.381 | 1.00 | 58.13 |
| ATOM | 319 | CE1 | PHE A | 73 | 45.947 | 62.362 | 7.876 | 1.00 | 58.24 |
| ATOM | 320 | CE2 | PHE A | 73 | 46.495 | 60.412 | 9.144 | 1.00 | 57.41 |
| ATOM | 321 | CZ | PHE A | 73 | 45.649 | 61.473 | 8.891 | 1.00 | 57.23 |
| ATOM | 322 | C | PHE A | 73 | 50.553 | 61.656 | 8.543 | 1.00 | 56.41 |
| ATOM | 323 | O | PHE A | 73 | 50.901 | 60.557 | 8.979 | 1.00 | 56.28 |
| ATOM | 324 | N | GLN A | 74 | 50.320 | 62.705 | 9.326 | 1.00 | 55.49 |
| ATOM | 325 | CA | GLN A | 74 | 50.443 | 62.615 | 10.776 | 1.00 | 53.88 |
| ATOM | 326 | CB | GLN A | 74 | 51.072 | 63.883 | 11.356 | 1.00 | 55.26 |
| ATOM | 327 | CG | GLN A | 74 | 52.570 | 64.009 | 11.142 | 1.00 | 57.78 |
| ATOM | 328 | CD | GLN A | 74 | 53.176 | 65.133 | 11.970 | 1.00 | 59.54 |
| ATOM | 329 | OE1 | GLN A | 74 | 52.910 | 66.314 | 11.733 | 1.00 | 59.29 |
| ATOM | 330 | NE2 | GLN A | 74 | 53.988 | 64.767 | 12.957 | 1.00 | 59.59 |
| ATOM | 331 | C | GLN A | 74 | 49.061 | 62.421 | 11.384 | 1.00 | 51.65 |
| ATOM | 332 | O | GLN A | 74 | 48.124 | 63.149 | 11.063 | 1.00 | 50.88 |
| ATOM | 333 | N | ASP A | 75 | 48.941 | 61.430 | 12.257 | 1.00 | 49.61 |
| ATOM | 334 | CA | ASP A | 75 | 47.673 | 61.140 | 12.912 | 1.00 | 47.33 |
| ATOM | 335 | CB | ASP A | 75 | 47.786 | 59.839 | 13.712 | 1.00 | 46.31 |
| ATOM | 336 | CG | ASP A | 75 | 48.187 | 58.657 | 12.849 | 1.00 | 44.20 |
| ATOM | 337 | OD1 | ASP A | 75 | 48.706 | 57.661 | 13.399 | 1.00 | 41.48 |
| ATOM | 338 | OD2 | ASP A | 75 | 47.974 | 58.724 | 11.621 | 1.00 | 44.07 |
| ATOM | 339 | C | ASP A | 75 | 47.329 | 62.291 | 13.851 | 1.00 | 46.57 |
| ATOM | 340 | O | ASP A | 75 | 48.192 | 62.785 | 14.576 | 1.00 | 46.45 |
| ATOM | 341 | N | SER A | 76 | 46.073 | 62.724 | 13.833 | 1.00 | 45.69 |
| ATOM | 342 | CA | SER A | 76 | 45.645 | 63.809 | 14.706 | 1.00 | 44.11 |
| ATOM | 343 | CB | SER A | 76 | 44.700 | 64.758 | 13.965 | 1.00 | 44.07 |
| ATOM | 344 | OG | SER A | 76 | 43.480 | 64.113 | 13.647 | 1.00 | 46.09 |
| ATOM | 345 | C | SER A | 76 | 44.931 | 63.210 | 15.905 | 1.00 | 42.29 |

TABLE 30-continued

| | | | | | | | | |
|---|---|---|---|---|---|---|---|---|
| ATOM | 346 | O | SER A | 76 | 44.517 | 62.054 | 15.872 | 1.00 | 43.18 |
| ATOM | 347 | N | ASP A | 77 | 44.793 | 63.997 | 16.964 | 1.00 | 41.16 |
| ATOM | 348 | CA | ASP A | 77 | 44.122 | 63.541 | 18.174 | 1.00 | 41.04 |
| ATOM | 349 | CB | ASP A | 77 | 43.962 | 64.709 | 19.150 | 1.00 | 43.43 |
| ATOM | 350 | CG | ASP A | 77 | 45.296 | 65.278 | 19.605 | 1.00 | 47.07 |
| ATOM | 351 | OD1 | ASP A | 77 | 45.294 | 66.321 | 20.293 | 1.00 | 48.75 |
| ATOM | 352 | OD2 | ASP A | 77 | 46.347 | 64.682 | 19.281 | 1.00 | 48.82 |
| ATOM | 353 | C | ASP A | 77 | 42.753 | 62.939 | 17.861 | 1.00 | 39.12 |
| ATOM | 354 | O | ASP A | 77 | 42.286 | 62.045 | 18.564 | 1.00 | 38.74 |
| ATOM | 355 | N | MET A | 78 | 42.118 | 63.435 | 16.802 | 1.00 | 37.74 |
| ATOM | 356 | CA | MET A | 78 | 40.797 | 62.961 | 16.385 | 1.00 | 36.19 |
| ATOM | 357 | CB | MET A | 78 | 40.349 | 63.676 | 15.109 | 1.00 | 37.19 |
| ATOM | 358 | CG | MET A | 78 | 40.014 | 65.135 | 15.267 | 1.00 | 39.81 |
| ATOM | 359 | SD | MET A | 78 | 39.364 | 65.773 | 13.711 | 1.00 | 44.22 |
| ATOM | 360 | CE | MET A | 78 | 37.676 | 65.136 | 13.771 | 1.00 | 41.40 |
| ATOM | 361 | C | MET A | 78 | 40.737 | 61.460 | 16.118 | 1.00 | 33.43 |
| ATOM | 362 | O | MET A | 78 | 39.739 | 60.807 | 16.423 | 1.00 | 32.83 |
| ATOM | 363 | N | LEU A | 79 | 41.803 | 60.923 | 15.534 | 1.00 | 29.93 |
| ATOM | 364 | CA | LEU A | 79 | 41.847 | 59.508 | 15.201 | 1.00 | 28.79 |
| ATOM | 365 | CB | LEU A | 79 | 42.839 | 59.273 | 14.059 | 1.00 | 26.98 |
| ATOM | 366 | CG | LEU A | 79 | 42.524 | 60.001 | 12.745 | 1.00 | 28.06 |
| ATOM | 367 | CD1 | LEU A | 79 | 43.498 | 59.551 | 11.662 | 1.00 | 25.66 |
| ATOM | 368 | CD2 | LEU A | 79 | 41.085 | 59.712 | 12.321 | 1.00 | 25.01 |
| ATOM | 369 | C | LEU A | 79 | 42.186 | 58.599 | 16.375 | 1.00 | 28.13 |
| ATOM | 370 | O | LEU A | 79 | 42.097 | 57.377 | 16.258 | 1.00 | 27.01 |
| ATOM | 371 | N | GLU A | 80 | 42.562 | 59.187 | 17.505 | 1.00 | 27.26 |
| ATOM | 372 | CA | GLU A | 80 | 42.909 | 58.392 | 18.672 | 1.00 | 28.24 |
| ATOM | 373 | CB | GLU A | 80 | 43.622 | 59.248 | 19.724 | 1.00 | 30.41 |
| ATOM | 374 | CG | GLU A | 80 | 43.753 | 58.555 | 21.080 | 1.00 | 36.61 |
| ATOM | 375 | CD | GLU A | 80 | 44.624 | 59.320 | 22.067 | 1.00 | 40.69 |
| ATOM | 376 | OE1 | GLU A | 80 | 44.508 | 59.059 | 23.284 | 1.00 | 41.38 |
| ATOM | 377 | OE2 | GLU A | 80 | 45.432 | 60.171 | 21.630 | 1.00 | 43.40 |
| ATOM | 378 | C | GLU A | 80 | 41.686 | 57.735 | 19.291 | 1.00 | 27.76 |
| ATOM | 379 | O | GLU A | 80 | 40.636 | 58.356 | 19.437 | 1.00 | 29.08 |
| ATOM | 380 | N | VAL A | 81 | 41.831 | 56.469 | 19.652 | 1.00 | 26.18 |
| ATOM | 381 | CA | VAL A | 81 | 40.747 | 55.717 | 20.258 | 1.00 | 26.74 |
| ATOM | 382 | CB | VAL A | 81 | 40.134 | 54.702 | 19.259 | 1.00 | 27.51 |
| ATOM | 383 | CG1 | VAL A | 81 | 38.943 | 53.996 | 19.895 | 1.00 | 26.14 |
| ATOM | 384 | CG2 | VAL A | 81 | 39.723 | 55.407 | 17.981 | 1.00 | 27.18 |
| ATOM | 385 | C | VAL A | 81 | 41.292 | 54.936 | 21.441 | 1.00 | 26.74 |
| ATOM | 386 | O | VAL A | 81 | 42.455 | 54.525 | 21.441 | 1.00 | 27.00 |
| ATOM | 387 | N | ARG A | 82 | 40.457 | 54.735 | 22.452 | 1.00 | 27.63 |
| ATOM | 388 | CA | ARG A | 82 | 40.878 | 53.971 | 23.613 | 1.00 | 29.47 |
| ATOM | 389 | CB | ARG A | 82 | 40.960 | 54.852 | 24.862 | 1.00 | 32.41 |
| ATOM | 390 | CG | ARG A | 82 | 42.027 | 54.360 | 25.826 | 1.00 | 40.18 |
| ATOM | 391 | CD | ARG A | 82 | 41.648 | 54.500 | 27.294 | 1.00 | 45.31 |
| ATOM | 392 | NE | ARG A | 82 | 42.675 | 53.907 | 28.156 | 1.00 | 48.83 |
| ATOM | 393 | CZ | ARG A | 82 | 43.075 | 52.639 | 28.082 | 1.00 | 48.91 |
| ATOM | 394 | NH1 | ARG A | 82 | 42.538 | 51.818 | 27.188 | 1.00 | 49.58 |
| ATOM | 395 | NH2 | ARG A | 82 | 44.021 | 52.192 | 28.895 | 1.00 | 50.35 |
| ATOM | 396 | C | ARG A | 82 | 39.898 | 52.835 | 23.855 | 1.00 | 28.41 |
| ATOM | 397 | O | ARG A | 82 | 38.730 | 53.070 | 24.154 | 1.00 | 29.65 |
| ATOM | 398 | N | VAL A | 83 | 40.382 | 51.604 | 23.713 | 1.00 | 28.37 |
| ATOM | 399 | CA | VAL A | 83 | 39.570 | 50.407 | 23.918 | 1.00 | 28.82 |
| ATOM | 400 | CB | VAL A | 83 | 38.745 | 50.038 | 22.662 | 1.00 | 29.44 |
| ATOM | 401 | CG1 | VAL A | 83 | 37.511 | 50.915 | 22.570 | 1.00 | 30.89 |
| ATOM | 402 | CG2 | VAL A | 83 | 39.608 | 50.181 | 21.413 | 1.00 | 25.04 |
| ATOM | 403 | C | VAL A | 83 | 40.457 | 49.217 | 24.235 | 1.00 | 29.77 |
| ATOM | 404 | O | VAL A | 83 | 41.673 | 49.281 | 24.066 | 1.00 | 29.28 |
| ATOM | 405 | N | LEU A | 84 | 39.836 | 48.130 | 24.688 | 1.00 | 31.31 |
| ATOM | 406 | CA | LEU A | 84 | 40.559 | 46.902 | 25.009 | 1.00 | 32.35 |
| ATOM | 407 | CB | LEU A | 84 | 41.071 | 46.250 | 23.714 | 1.00 | 31.07 |
| ATOM | 408 | CG | LEU A | 84 | 40.002 | 45.965 | 22.649 | 1.00 | 31.01 |
| ATOM | 409 | CD1 | LEU A | 84 | 40.659 | 45.510 | 21.363 | 1.00 | 30.37 |
| ATOM | 410 | CD2 | LEU A | 84 | 39.028 | 44.917 | 23.160 | 1.00 | 26.83 |
| ATOM | 411 | C | LEU A | 84 | 41.731 | 47.144 | 25.961 | 1.00 | 33.06 |
| ATOM | 412 | O | LEU A | 84 | 42.730 | 46.424 | 25.914 | 1.00 | 34.52 |
| ATOM | 413 | N | GLY A | 85 | 41.602 | 48.154 | 26.819 | 1.00 | 33.14 |
| ATOM | 414 | CA | GLY A | 85 | 42.655 | 48.469 | 27.774 | 1.00 | 31.49 |
| ATOM | 415 | C | GLY A | 85 | 43.893 | 49.069 | 27.133 | 1.00 | 31.37 |
| ATOM | 416 | O | GLY A | 85 | 44.996 | 48.980 | 27.680 | 1.00 | 29.38 |
| ATOM | 417 | N | HIS A | 86 | 43.713 | 49.691 | 25.972 | 1.00 | 30.74 |
| ATOM | 418 | CA | HIS A | 86 | 44.827 | 50.294 | 25.255 | 1.00 | 31.19 |
| ATOM | 419 | CB | HIS A | 86 | 45.421 | 49.287 | 24.261 | 1.00 | 33.63 |
| ATOM | 420 | CG | HIS A | 86 | 45.956 | 48.046 | 24.903 | 1.00 | 36.97 |
| ATOM | 421 | CD2 | HIS A | 86 | 45.488 | 46.775 | 24.913 | 1.00 | 38.23 |
| ATOM | 422 | ND1 | HIS A | 86 | 47.100 | 48.039 | 25.672 | 1.00 | 38.35 |
| ATOM | 423 | CE1 | HIS A | 86 | 47.313 | 46.817 | 26.130 | 1.00 | 38.39 |
| ATOM | 424 | NE2 | HIS A | 86 | 46.349 | 46.031 | 25.685 | 1.00 | 40.10 |

TABLE 30-continued

| | | | | | | | | | |
|---|---|---|---|---|---|---|---|---|---|
| ATOM | 425 | C | HIS A | 86 | 44.442 | 51.556 | 24.493 | 1.00 | 30.01 |
| ATOM | 426 | O | HIS A | 86 | 43.268 | 51.837 | 24.249 | 1.00 | 29.30 |
| ATOM | 427 | N | LYS A | 87 | 45.459 | 52.315 | 24.116 | 1.00 | 29.25 |
| ATOM | 428 | CA | LYS A | 87 | 45.266 | 53.528 | 23.350 | 1.00 | 28.62 |
| ATOM | 429 | CB | LYS A | 87 | 46.126 | 54.656 | 23.921 | 1.00 | 31.36 |
| ATOM | 430 | CG | LYS A | 87 | 46.098 | 55.934 | 23.105 | 1.00 | 36.49 |
| ATOM | 431 | CD | LYS A | 87 | 47.040 | 56.982 | 23.680 | 1.00 | 40.20 |
| ATOM | 432 | CE | LYS A | 87 | 48.488 | 56.523 | 23.617 | 1.00 | 42.08 |
| ATOM | 433 | NZ | LYS A | 87 | 49.419 | 57.556 | 24.157 | 1.00 | 44.04 |
| ATOM | 434 | C | LYS A | 87 | 45.710 | 53.205 | 21.928 | 1.00 | 26.31 |
| ATOM | 435 | O | LYS A | 87 | 46.727 | 52.532 | 21.729 | 1.00 | 25.00 |
| ATOM | 436 | N | PHE A | 88 | 44.932 | 53.655 | 20.948 | 1.00 | 22.41 |
| ATOM | 437 | CA | PHE A | 88 | 45.260 | 53.440 | 19.543 | 1.00 | 21.20 |
| ATOM | 438 | CB | PHE A | 88 | 44.160 | 52.635 | 18.839 | 1.00 | 18.24 |
| ATOM | 439 | CG | PHE A | 88 | 43.981 | 51.235 | 19.369 | 1.00 | 17.32 |
| ATOM | 440 | CD1 | PHE A | 88 | 43.462 | 51.014 | 20.637 | 1.00 | 15.98 |
| ATOM | 441 | CD2 | PHE A | 88 | 44.315 | 50.139 | 18.588 | 1.00 | 14.22 |
| ATOM | 442 | CE1 | PHE A | 88 | 43.277 | 49.730 | 21.114 | 1.00 | 15.75 |
| ATOM | 443 | CE2 | PHE A | 88 | 44.134 | 48.857 | 19.057 | 1.00 | 14.62 |
| ATOM | 444 | CZ | PHE A | 88 | 43.614 | 48.649 | 20.321 | 1.00 | 16.23 |
| ATOM | 445 | C | PHE A | 88 | 45.359 | 54.828 | 18.912 | 1.00 | 21.47 |
| ATOM | 446 | O | PHE A | 88 | 44.371 | 55.563 | 18.897 | 1.00 | 21.28 |
| ATOM | 447 | N | ARG A | 89 | 46.531 | 55.195 | 18.395 | 1.00 | 21.89 |
| ATOM | 448 | CA | ARG A | 89 | 46.683 | 56.522 | 17.797 | 1.00 | 24.22 |
| ATOM | 449 | CB | ARG A | 89 | 48.145 | 56.814 | 17.437 | 1.00 | 27.64 |
| ATOM | 450 | CG | ARG A | 89 | 48.743 | 55.954 | 16.360 | 1.00 | 34.35 |
| ATOM | 451 | CD | ARG A | 89 | 50.110 | 56.502 | 15.978 | 1.00 | 39.78 |
| ATOM | 452 | NE | ARG A | 89 | 50.936 | 56.747 | 17.157 | 1.00 | 43.12 |
| ATOM | 453 | CZ | ARG A | 89 | 52.226 | 57.066 | 17.115 | 1.00 | 45.70 |
| ATOM | 454 | NH1 | ARG A | 89 | 52.846 | 57.180 | 15.946 | 1.00 | 46.09 |
| ATOM | 455 | NH2 | ARG A | 89 | 52.898 | 57.264 | 18.242 | 1.00 | 46.23 |
| ATOM | 456 | C | ARG A | 89 | 45.774 | 56.724 | 16.586 | 1.00 | 21.57 |
| ATOM | 457 | O | ARG A | 89 | 45.382 | 57.846 | 16.289 | 1.00 | 20.90 |
| ATOM | 458 | N | ASN A | 90 | 45.461 | 55.644 | 15.878 | 1.00 | 19.52 |
| ATOM | 459 | CA | ASN A | 90 | 44.525 | 55.712 | 14.756 | 1.00 | 19.26 |
| ATOM | 460 | CB | ASN A | 90 | 45.227 | 56.049 | 13.419 | 1.00 | 17.47 |
| ATOM | 461 | CG | ASN A | 90 | 45.921 | 54.873 | 12.783 | 1.00 | 17.14 |
| ATOM | 462 | OD1 | ASN A | 90 | 45.286 | 53.893 | 12.402 | 1.00 | 19.02 |
| ATOM | 463 | ND2 | ASN A | 90 | 47.239 | 54.973 | 12.641 | 1.00 | 18.11 |
| ATOM | 464 | C | ASN A | 90 | 43.816 | 54.359 | 14.759 | 1.00 | 18.80 |
| ATOM | 465 | O | ASN A | 90 | 44.381 | 53.354 | 15.198 | 1.00 | 20.27 |
| ATOM | 466 | N | PRO A | 91 | 42.558 | 54.323 | 14.304 | 1.00 | 17.37 |
| ATOM | 467 | CD | PRO A | 91 | 41.808 | 55.489 | 13.797 | 1.00 | 17.95 |
| ATOM | 468 | CA | PRO A | 91 | 41.725 | 53.119 | 14.258 | 1.00 | 16.60 |
| ATOM | 469 | CB | PRO A | 91 | 40.323 | 53.702 | 14.336 | 1.00 | 17.12 |
| ATOM | 470 | CG | PRO A | 91 | 40.447 | 54.890 | 13.434 | 1.00 | 14.17 |
| ATOM | 471 | C | PRO A | 91 | 41.876 | 52.188 | 13.062 | 1.00 | 17.11 |
| ATOM | 472 | O | PRO A | 91 | 41.084 | 51.260 | 12.903 | 1.00 | 16.80 |
| ATOM | 473 | N | VAL A | 92 | 42.885 | 52.423 | 12.230 | 1.00 | 17.06 |
| ATOM | 474 | CA | VAL A | 92 | 43.085 | 51.606 | 11.034 | 1.00 | 17.33 |
| ATOM | 475 | CB | VAL A | 92 | 43.397 | 52.506 | 9.813 | 1.00 | 17.14 |
| ATOM | 476 | CG1 | VAL A | 92 | 43.517 | 51.672 | 8.551 | 1.00 | 13.98 |
| ATOM | 477 | CG2 | VAL A | 92 | 42.314 | 53.559 | 9.666 | 1.00 | 16.18 |
| ATOM | 478 | C | VAL A | 92 | 44.204 | 50.584 | 11.201 | 1.00 | 17.94 |
| ATOM | 479 | O | VAL A | 92 | 45.376 | 50.942 | 11.278 | 1.00 | 18.09 |
| ATOM | 480 | N | GLY A | 93 | 43.836 | 49.308 | 11.251 | 1.00 | 17.48 |
| ATOM | 481 | CA | GLY A | 93 | 44.833 | 48.270 | 11.410 | 1.00 | 16.24 |
| ATOM | 482 | C | GLY A | 93 | 44.900 | 47.330 | 10.227 | 1.00 | 16.29 |
| ATOM | 483 | O | GLY A | 93 | 44.035 | 47.356 | 9.355 | 1.00 | 17.30 |
| ATOM | 484 | N | ILE A | 94 | 45.947 | 46.512 | 10.185 | 1.00 | 15.88 |
| ATOM | 485 | CA | ILE A | 94 | 46.113 | 45.536 | 9.114 | 1.00 | 13.94 |
| ATOM | 486 | CB | ILE A | 94 | 47.612 | 45.320 | 8.770 | 1.00 | 14.90 |
| ATOM | 487 | CG2 | ILE A | 94 | 48.408 | 44.996 | 10.024 | 1.00 | 13.27 |
| ATOM | 488 | CG1 | ILE A | 94 | 47.756 | 44.209 | 7.726 | 1.00 | 14.95 |
| ATOM | 489 | CD1 | ILE A | 94 | 47.281 | 44.608 | 6.336 | 1.00 | 14.84 |
| ATOM | 490 | C | ILE A | 94 | 45.492 | 44.227 | 9.603 | 1.00 | 14.64 |
| ATOM | 491 | O | ILE A | 94 | 45.872 | 43.698 | 10.647 | 1.00 | 14.21 |
| ATOM | 492 | N | ALA A | 95 | 44.520 | 43.717 | 8.856 | 1.00 | 14.20 |
| ATOM | 493 | CA | ALA A | 95 | 43.840 | 42.487 | 9.233 | 1.00 | 14.41 |
| ATOM | 494 | CB | ALA A | 95 | 42.675 | 42.227 | 8.279 | 1.00 | 14.00 |
| ATOM | 495 | C | ALA A | 95 | 44.778 | 41.282 | 9.255 | 1.00 | 14.74 |
| ATOM | 496 | O | ALA A | 95 | 45.885 | 41.333 | 8.724 | 1.00 | 13.48 |
| ATOM | 497 | N | ALA A | 96 | 44.327 | 40.204 | 9.887 | 1.00 | 13.92 |
| ATOM | 498 | CA | ALA A | 96 | 45.111 | 38.982 | 9.964 | 1.00 | 16.74 |
| ATOM | 499 | CB | ALA A | 96 | 44.417 | 37.967 | 10.867 | 1.00 | 15.50 |
| ATOM | 500 | C | ALA A | 96 | 45.254 | 38.415 | 8.557 | 1.00 | 17.13 |
| ATOM | 501 | O | ALA A | 96 | 44.393 | 38.634 | 7.703 | 1.00 | 18.95 |
| ATOM | 502 | N | GLY A | 97 | 46.343 | 37.695 | 8.312 | 1.00 | 17.82 |
| ATOM | 503 | CA | GLY A | 97 | 46.546 | 37.112 | 6.999 | 1.00 | 16.65 |

TABLE 30-continued

| ATOM | 504 | C | GLY A | 97 | 47.708 | 37.683 | 6.212 | 1.00 | 15.52 |
|---|---|---|---|---|---|---|---|---|---|
| ATOM | 505 | O | GLY A | 97 | 48.423 | 36.936 | 5.553 | 1.00 | 16.01 |
| ATOM | 506 | N | PHE A | 98 | 47.903 | 38.998 | 6.255 | 1.00 | 15.36 |
| ATOM | 507 | CA | PHE A | 98 | 49.014 | 39.583 | 5.515 | 1.00 | 16.42 |
| ATOM | 508 | CB | PHE A | 98 | 48.962 | 41.112 | 5.519 | 1.00 | 16.50 |
| ATOM | 509 | CG | PHE A | 98 | 50.095 | 41.739 | 4.761 | 1.00 | 18.21 |
| ATOM | 510 | CD1 | PHE A | 98 | 50.149 | 41.650 | 3.376 | 1.00 | 19.68 |
| ATOM | 511 | CD2 | PHE A | 98 | 51.140 | 42.355 | 5.431 | 1.00 | 18.88 |
| ATOM | 512 | CE1 | PHE A | 98 | 51.225 | 42.159 | 2.674 | 1.00 | 19.14 |
| ATOM | 513 | CE2 | PHE A | 98 | 52.223 | 42.868 | 4.735 | 1.00 | 19.22 |
| ATOM | 514 | CZ | PHE A | 98 | 52.266 | 42.770 | 3.355 | 1.00 | 20.69 |
| ATOM | 515 | C | PHE A | 98 | 50.325 | 39.129 | 6.149 | 1.00 | 15.73 |
| ATOM | 516 | O | PHE A | 98 | 51.219 | 38.636 | 5.467 | 1.00 | 15.56 |
| ATOM | 517 | N | ASP A | 99 | 50.434 | 39.312 | 7.459 | 1.00 | 15.88 |
| ATOM | 518 | CA | ASP A | 99 | 51.627 | 38.898 | 8.193 | 1.00 | 15.70 |
| ATOM | 519 | CB | ASP A | 99 | 52.156 | 40.068 | 9.025 | 1.00 | 15.27 |
| ATOM | 520 | CG | ASP A | 99 | 53.534 | 39.800 | 9.607 | 1.00 | 17.99 |
| ATOM | 521 | OD1 | ASP A | 99 | 54.160 | 38.786 | 9.234 | 1.00 | 16.77 |
| ATOM | 522 | OD2 | ASP A | 99 | 53.996 | 40.616 | 10.432 | 1.00 | 19.28 |
| ATOM | 523 | C | ASP A | 99 | 51.233 | 37.723 | 9.096 | 1.00 | 16.32 |
| ATOM | 524 | O | ASP A | 99 | 51.003 | 37.891 | 10.295 | 1.00 | 14.93 |
| ATOM | 525 | N | LYS A | 100 | 51.138 | 36.538 | 8.498 | 1.00 | 16.61 |
| ATOM | 526 | CA | LYS A | 100 | 50.756 | 35.330 | 9.220 | 1.00 | 17.25 |
| ATOM | 527 | CB | LYS A | 100 | 50.490 | 34.187 | 8.231 | 1.00 | 19.41 |
| ATOM | 528 | CG | LYS A | 100 | 49.159 | 34.247 | 7.483 | 1.00 | 20.97 |
| ATOM | 529 | CD | LYS A | 100 | 49.092 | 33.131 | 6.437 | 1.00 | 23.93 |
| ATOM | 530 | CE | LYS A | 100 | 47.732 | 33.042 | 5.730 | 1.00 | 25.43 |
| ATOM | 531 | NZ | LYS A | 100 | 46.656 | 32.457 | 6.595 | 1.00 | 22.86 |
| ATOM | 532 | C | LYS A | 100 | 51.774 | 34.848 | 10.253 | 1.00 | 18.16 |
| ATOM | 533 | O | LYS A | 100 | 51.398 | 34.268 | 11.274 | 1.00 | 18.89 |
| ATOM | 534 | N | HIS A | 101 | 53.058 | 35.084 | 10.000 | 1.00 | 17.48 |
| ATOM | 535 | CA | HIS A | 101 | 54.095 | 34.603 | 10.911 | 1.00 | 19.25 |
| ATOM | 536 | CB | HIS A | 101 | 55.114 | 33.779 | 10.118 | 1.00 | 16.89 |
| ATOM | 537 | CG | HIS A | 101 | 54.516 | 33.041 | 8.961 | 1.00 | 18.72 |
| ATOM | 538 | CD2 | HIS A | 101 | 54.771 | 33.111 | 7.632 | 1.00 | 17.76 |
| ATOM | 539 | ND1 | HIS A | 101 | 53.504 | 32.115 | 9.108 | 1.00 | 18.28 |
| ATOM | 540 | CE1 | HIS A | 101 | 53.162 | 31.648 | 7.920 | 1.00 | 17.69 |
| ATOM | 541 | NE2 | HIS A | 101 | 53.916 | 32.235 | 7.007 | 1.00 | 16.65 |
| ATOM | 542 | C | HIS A | 101 | 54.826 | 35.679 | 11.712 | 1.00 | 19.41 |
| ATOM | 543 | O | HIS A | 101 | 55.871 | 35.407 | 12.296 | 1.00 | 21.11 |
| ATOM | 544 | N | GLY A | 102 | 54.281 | 36.892 | 11.736 | 1.00 | 20.30 |
| ATOM | 545 | CA | GLY A | 102 | 54.904 | 37.977 | 12.478 | 1.00 | 20.25 |
| ATOM | 546 | C | GLY A | 102 | 56.284 | 38.376 | 11.984 | 1.00 | 20.48 |
| ATOM | 547 | O | GLY A | 102 | 57.188 | 38.599 | 12.781 | 1.00 | 21.67 |
| ATOM | 548 | N | GLU A | 103 | 56.445 | 38.491 | 10.670 | 1.00 | 22.35 |
| ATOM | 549 | CA | GLU A | 103 | 57.732 | 38.855 | 10.076 | 1.00 | 21.64 |
| ATOM | 550 | CB | GLU A | 103 | 57.964 | 38.041 | 8.804 | 1.00 | 20.45 |
| ATOM | 551 | CG | GLU A | 103 | 58.008 | 36.546 | 9.009 | 1.00 | 23.87 |
| ATOM | 552 | CD | GLU A | 103 | 58.054 | 35.792 | 7.697 | 1.00 | 26.38 |
| ATOM | 553 | OE1 | GLU A | 103 | 57.019 | 35.749 | 6.993 | 1.00 | 26.70 |
| ATOM | 554 | OE2 | GLU A | 103 | 59.130 | 35.251 | 7.365 | 1.00 | 28.54 |
| ATOM | 555 | C | GLU A | 103 | 57.884 | 40.329 | 9.719 | 1.00 | 21.18 |
| ATOM | 556 | O | GLU A | 103 | 58.997 | 40.797 | 9.493 | 1.00 | 22.35 |
| ATOM | 557 | N | ALA A | 104 | 56.782 | 41.067 | 9.665 | 1.00 | 20.64 |
| ATOM | 558 | CA | ALA A | 104 | 56.858 | 42.471 | 9.274 | 1.00 | 19.54 |
| ATOM | 559 | CB | ALA A | 104 | 56.348 | 42.618 | 7.851 | 1.00 | 16.12 |
| ATOM | 560 | C | ALA A | 104 | 56.111 | 43.435 | 10.181 | 1.00 | 19.23 |
| ATOM | 561 | O | ALA A | 104 | 55.690 | 44.502 | 9.741 | 1.00 | 18.91 |
| ATOM | 562 | N | VAL A | 105 | 55.955 | 43.074 | 11.446 | 1.00 | 19.88 |
| ATOM | 563 | CA | VAL A | 105 | 55.231 | 43.924 | 12.384 | 1.00 | 19.66 |
| ATOM | 564 | CB | VAL A | 105 | 55.361 | 43.389 | 13.814 | 1.00 | 19.24 |
| ATOM | 565 | CG1 | VAL A | 105 | 54.667 | 44.328 | 14.781 | 1.00 | 18.21 |
| ATOM | 566 | CG2 | VAL A | 105 | 54.767 | 41.990 | 13.892 | 1.00 | 17.39 |
| ATOM | 567 | C | VAL A | 105 | 55.669 | 45.389 | 12.372 | 1.00 | 20.45 |
| ATOM | 568 | O | VAL A | 105 | 54.836 | 46.294 | 12.292 | 1.00 | 21.75 |
| ATOM | 569 | N | ASP A | 106 | 56.974 | 45.622 | 12.444 | 1.00 | 18.45 |
| ATOM | 570 | CA | ASP A | 106 | 57.493 | 46.984 | 12.467 | 1.00 | 19.17 |
| ATOM | 571 | CB | ASP A | 106 | 58.967 | 46.970 | 12.880 | 1.00 | 18.60 |
| ATOM | 572 | CG | ASP A | 106 | 59.154 | 46.476 | 14.297 | 1.00 | 19.83 |
| ATOM | 573 | OD1 | ASP A | 106 | 59.731 | 45.382 | 14.485 | 1.00 | 21.21 |
| ATOM | 574 | OD2 | ASP A | 106 | 58.701 | 47.179 | 15.225 | 1.00 | 19.11 |
| ATOM | 575 | C | ASP A | 106 | 57.313 | 47.739 | 11.159 | 1.00 | 18.26 |
| ATOM | 576 | O | ASP A | 106 | 57.040 | 48.941 | 11.164 | 1.00 | 18.22 |
| ATOM | 577 | N | GLY A | 107 | 57.468 | 47.039 | 10.043 | 1.00 | 16.23 |
| ATOM | 578 | CA | GLY A | 107 | 57.288 | 47.677 | 8.755 | 1.00 | 17.23 |
| ATOM | 579 | C | GLY A | 107 | 55.832 | 48.061 | 8.554 | 1.00 | 18.78 |
| ATOM | 580 | O | GLY A | 107 | 55.521 | 48.958 | 7.770 | 1.00 | 20.34 |
| ATOM | 581 | N | LEU A | 108 | 54.934 | 47.383 | 9.267 | 1.00 | 17.72 |
| ATOM | 582 | CA | LEU A | 108 | 53.507 | 47.668 | 9.166 | 1.00 | 17.68 |

TABLE 30-continued

| | | | | | | | | |
|---|---|---|---|---|---|---|---|---|
| ATOM | 583 | CB | LEU A | 108 | 52.690 | 46.463 | 9.650 | 1.00 | 18.56 |
| ATOM | 584 | CG | LEU A | 108 | 52.748 | 45.288 | 8.665 | 1.00 | 17.20 |
| ATOM | 585 | CD1 | LEU A | 108 | 52.205 | 44.023 | 9.300 | 1.00 | 15.49 |
| ATOM | 586 | CD2 | LEU A | 108 | 51.964 | 45.654 | 7.413 | 1.00 | 18.33 |
| ATOM | 587 | C | LEU A | 108 | 53.140 | 48.930 | 9.943 | 1.00 | 17.62 |
| ATOM | 588 | O | LEU A | 108 | 52.320 | 49.718 | 9.482 | 1.00 | 17.86 |
| ATOM | 589 | N | TYR A | 109 | 53.734 | 49.127 | 11.118 | 1.00 | 17.88 |
| ATOM | 590 | CA | TYR A | 109 | 53.464 | 50.347 | 11.883 | 1.00 | 19.37 |
| ATOM | 591 | CB | TYR A | 109 | 54.179 | 50.335 | 13.246 | 1.00 | 17.43 |
| ATOM | 592 | CG | TYR A | 109 | 53.573 | 49.401 | 14.273 | 1.00 | 15.80 |
| ATOM | 593 | CD1 | TYR A | 109 | 54.324 | 48.381 | 14.840 | 1.00 | 14.92 |
| ATOM | 594 | CE1 | TYR A | 109 | 53.767 | 47.507 | 15.760 | 1.00 | 16.08 |
| ATOM | 595 | CD2 | TYR A | 109 | 52.243 | 49.529 | 14.660 | 1.00 | 14.37 |
| ATOM | 596 | CE2 | TYR A | 109 | 51.677 | 48.663 | 15.580 | 1.00 | 14.70 |
| ATOM | 597 | CZ | TYR A | 109 | 52.443 | 47.651 | 16.125 | 1.00 | 15.77 |
| ATOM | 598 | OH | TYR A | 109 | 51.880 | 46.769 | 17.019 | 1.00 | 15.33 |
| ATOM | 599 | C | TYR A | 109 | 54.006 | 51.509 | 11.053 | 1.00 | 20.25 |
| ATOM | 600 | O | TYR A | 109 | 53.430 | 52.598 | 11.023 | 1.00 | 20.30 |
| ATOM | 601 | N | LYS A | 110 | 55.125 | 51.265 | 10.378 | 1.00 | 20.12 |
| ATOM | 602 | CA | LYS A | 110 | 55.747 | 52.287 | 9.551 | 1.00 | 22.39 |
| ATOM | 603 | CB | LYS A | 110 | 57.123 | 51.821 | 9.074 | 1.00 | 23.00 |
| ATOM | 604 | CG | LYS A | 110 | 57.804 | 52.825 | 8.169 | 1.00 | 26.93 |
| ATOM | 605 | CD | LYS A | 110 | 59.140 | 52.328 | 7.667 | 1.00 | 31.08 |
| ATOM | 606 | CE | LYS A | 110 | 59.795 | 53.371 | 6.769 | 1.00 | 33.97 |
| ATOM | 607 | NZ | LYS A | 110 | 61.123 | 52.922 | 6.263 | 1.00 | 37.79 |
| ATOM | 608 | C | LYS A | 110 | 54.880 | 52.635 | 8.342 | 1.00 | 22.91 |
| ATOM | 609 | O | LYS A | 110 | 55.002 | 53.722 | 7.772 | 1.00 | 21.83 |
| ATOM | 610 | N | MET A | 111 | 54.009 | 51.706 | 7.955 | 1.00 | 22.68 |
| ATOM | 611 | CA | MET A | 111 | 53.123 | 51.912 | 6.814 | 1.00 | 21.52 |
| ATOM | 612 | CB | MET A | 111 | 52.576 | 50.565 | 6.331 | 1.00 | 22.57 |
| ATOM | 613 | CG | MET A | 111 | 52.097 | 50.560 | 4.885 | 1.00 | 23.41 |
| ATOM | 614 | SD | MET A | 111 | 51.657 | 48.907 | 4.289 | 1.00 | 22.54 |
| ATOM | 615 | CE | MET A | 111 | 53.262 | 48.165 | 4.105 | 1.00 | 21.48 |
| ATOM | 616 | C | MET A | 111 | 51.976 | 52.850 | 7.201 | 1.00 | 21.63 |
| ATOM | 617 | O | MET A | 111 | 51.250 | 53.352 | 6.341 | 1.00 | 21.82 |
| ATOM | 618 | N | GLY A | 112 | 51.817 | 53.084 | 8.500 | 1.00 | 20.62 |
| ATOM | 619 | CA | GLY A | 112 | 50.768 | 53.980 | 8.955 | 1.00 | 18.24 |
| ATOM | 620 | C | GLY A | 112 | 49.644 | 53.347 | 9.752 | 1.00 | 17.64 |
| ATOM | 621 | O | GLY A | 112 | 48.736 | 54.048 | 10.198 | 1.00 | 18.17 |
| ATOM | 622 | N | PHE A | 113 | 49.691 | 52.032 | 9.941 | 1.00 | 16.29 |
| ATOM | 623 | CA | PHE A | 113 | 48.644 | 51.344 | 10.693 | 1.00 | 15.85 |
| ATOM | 624 | CB | PHE A | 113 | 48.769 | 49.829 | 10.520 | 1.00 | 15.16 |
| ATOM | 625 | CG | PHE A | 113 | 48.390 | 49.346 | 9.153 | 1.00 | 15.73 |
| ATOM | 626 | CD1 | PHE A | 113 | 49.355 | 48.898 | 8.269 | 1.00 | 15.73 |
| ATOM | 627 | CD2 | PHE A | 113 | 47.062 | 49.334 | 8.755 | 1.00 | 15.52 |
| ATOM | 628 | CE1 | PHE A | 113 | 49.003 | 48.442 | 7.007 | 1.00 | 18.04 |
| ATOM | 629 | CE2 | PHE A | 113 | 46.699 | 48.881 | 7.498 | 1.00 | 15.62 |
| ATOM | 630 | CZ | PHE A | 113 | 47.669 | 48.433 | 6.621 | 1.00 | 17.05 |
| ATOM | 631 | C | PHE A | 113 | 48.662 | 51.690 | 12.175 | 1.00 | 14.70 |
| ATOM | 632 | O | PHE A | 113 | 49.722 | 51.759 | 12.788 | 1.00 | 15.50 |
| ATOM | 633 | N | GLY A | 114 | 47.477 | 51.911 | 12.738 | 1.00 | 13.84 |
| ATOM | 634 | CA | GLY A | 114 | 47.361 | 52.248 | 14.148 | 1.00 | 13.69 |
| ATOM | 635 | C | GLY A | 114 | 47.578 | 51.041 | 15.042 | 1.00 | 14.92 |
| ATOM | 636 | O | GLY A | 114 | 47.813 | 51.174 | 16.240 | 1.00 | 16.13 |
| ATOM | 637 | N | PHE A | 115 | 47.470 | 49.852 | 14.463 | 1.00 | 15.20 |
| ATOM | 638 | CA | PHE A | 115 | 47.690 | 48.624 | 15.209 | 1.00 | 15.32 |
| ATOM | 639 | CB | PHE A | 115 | 46.547 | 48.364 | 16.206 | 1.00 | 15.74 |
| ATOM | 640 | CG | PHE A | 115 | 45.214 | 48.071 | 15.575 | 1.00 | 14.70 |
| ATOM | 641 | CD1 | PHE A | 115 | 44.715 | 46.778 | 15.553 | 1.00 | 14.33 |
| ATOM | 642 | CD2 | PHE A | 115 | 44.430 | 49.095 | 15.061 | 1.00 | 14.87 |
| ATOM | 643 | CE1 | PHE A | 115 | 43.456 | 46.507 | 15.034 | 1.00 | 13.48 |
| ATOM | 644 | CE2 | PHE A | 115 | 43.170 | 48.831 | 14.539 | 1.00 | 15.39 |
| ATOM | 645 | CZ | PHE A | 115 | 42.684 | 47.533 | 14.528 | 1.00 | 14.35 |
| ATOM | 646 | C | PHE A | 115 | 47.871 | 47.464 | 14.247 | 1.00 | 15.52 |
| ATOM | 647 | O | PHE A | 115 | 47.350 | 47.481 | 13.136 | 1.00 | 15.04 |
| ATOM | 648 | N | VAL A | 116 | 48.638 | 46.468 | 14.675 | 1.00 | 16.15 |
| ATOM | 649 | CA | VAL A | 116 | 48.931 | 45.311 | 13.845 | 1.00 | 14.61 |
| ATOM | 650 | CB | VAL A | 116 | 50.464 | 45.183 | 13.615 | 1.00 | 15.46 |
| ATOM | 651 | CG1 | VAL A | 116 | 50.782 | 43.920 | 12.803 | 1.00 | 10.90 |
| ATOM | 652 | CG2 | VAL A | 116 | 50.991 | 46.434 | 12.912 | 1.00 | 12.53 |
| ATOM | 653 | C | VAL A | 116 | 48.431 | 44.006 | 14.448 | 1.00 | 15.98 |
| ATOM | 654 | O | VAL A | 116 | 48.469 | 43.817 | 15.664 | 1.00 | 16.18 |
| ATOM | 655 | N | GLU A | 117 | 47.955 | 43.113 | 13.584 | 1.00 | 15.89 |
| ATOM | 656 | CA | GLU A | 117 | 47.490 | 41.796 | 14.009 | 1.00 | 17.58 |
| ATOM | 657 | CB | GLU A | 117 | 45.977 | 41.668 | 13.845 | 1.00 | 16.28 |
| ATOM | 658 | CG | GLU A | 117 | 45.442 | 40.307 | 14.263 | 1.00 | 16.44 |
| ATOM | 659 | CD | GLU A | 117 | 43.929 | 40.257 | 14.255 | 1.00 | 17.58 |
| ATOM | 660 | OE1 | GLU A | 117 | 43.366 | 39.304 | 13.671 | 1.00 | 16.31 |
| ATOM | 661 | OE2 | GLU A | 117 | 43.309 | 41.173 | 14.837 | 1.00 | 14.25 |

TABLE 30-continued

| | | | | | | | | |
|---|---|---|---|---|---|---|---|---|
| ATOM | 662 | C | GLU A | 117 | 48.190 | 40.782 | 13.115 | 1.00 | 17.75 |
| ATOM | 663 | O | GLU A | 117 | 48.077 | 40.853 | 11.892 | 1.00 | 19.22 |
| ATOM | 664 | N | ILE A | 118 | 48.917 | 39.840 | 13.706 | 1.00 | 17.57 |
| ATOM | 665 | CA | ILE A | 118 | 49.619 | 38.870 | 12.882 | 1.00 | 20.33 |
| ATOM | 666 | CB | ILE A | 118 | 50.981 | 38.473 | 13.503 | 1.00 | 18.22 |
| ATOM | 667 | CG2 | ILE A | 118 | 51.869 | 39.704 | 13.594 | 1.00 | 20.47 |
| ATOM | 668 | CG1 | ILE A | 118 | 50.801 | 37.879 | 14.893 | 1.00 | 18.20 |
| ATOM | 669 | CD1 | ILE A | 118 | 52.101 | 37.437 | 15.500 | 1.00 | 18.29 |
| ATOM | 670 | C | ILE A | 118 | 48.777 | 37.643 | 12.566 | 1.00 | 21.46 |
| ATOM | 671 | O | ILE A | 118 | 48.183 | 37.032 | 13.453 | 1.00 | 18.99 |
| ATOM | 672 | N | GLY A | 119 | 48.729 | 37.336 | 11.266 | 1.00 | 26.74 |
| ATOM | 673 | CA | GLY A | 119 | 47.955 | 36.234 | 10.707 | 1.00 | 23.10 |
| ATOM | 674 | C | GLY A | 119 | 47.785 | 35.068 | 11.633 | 1.00 | 24.55 |
| ATOM | 675 | O | GLY A | 119 | 48.548 | 34.923 | 12.591 | 1.00 | 25.31 |
| ATOM | 676 | N | SER A | 120 | 46.793 | 34.229 | 11.345 | 1.00 | 21.80 |
| ATOM | 677 | CA | SER A | 120 | 46.529 | 33.069 | 12.185 | 1.00 | 20.39 |
| ATOM | 678 | CB | SER A | 120 | 45.371 | 32.243 | 11.623 | 1.00 | 19.81 |
| ATOM | 679 | OG | SER A | 120 | 44.128 | 32.878 | 11.874 | 1.00 | 18.88 |
| ATOM | 680 | C | SER A | 120 | 47.750 | 32.187 | 12.352 | 1.00 | 19.19 |
| ATOM | 681 | O | SER A | 120 | 48.453 | 31.881 | 11.389 | 1.00 | 19.54 |
| ATOM | 682 | N | VAL A | 121 | 47.992 | 31.785 | 13.594 | 1.00 | 18.84 |
| ATOM | 683 | CA | VAL A | 121 | 49.115 | 30.924 | 13.936 | 1.00 | 15.63 |
| ATOM | 684 | CB | VAL A | 121 | 50.007 | 31.580 | 15.023 | 1.00 | 15.71 |
| ATOM | 685 | CG1 | VAL A | 121 | 51.322 | 30.801 | 15.174 | 1.00 | 10.48 |
| ATOM | 686 | CG2 | VAL A | 121 | 50.268 | 33.045 | 14.670 | 1.00 | 12.14 |
| ATOM | 687 | C | VAL A | 121 | 48.538 | 29.622 | 14.488 | 1.00 | 16.66 |
| ATOM | 688 | O | VAL A | 121 | 47.610 | 29.641 | 15.302 | 1.00 | 15.77 |
| ATOM | 689 | N | THR A | 122 | 49.071 | 28.496 | 14.028 | 1.00 | 15.22 |
| ATOM | 690 | CA | THR A | 122 | 48.619 | 27.192 | 14.493 | 1.00 | 16.76 |
| ATOM | 691 | CB | THR A | 122 | 48.448 | 26.211 | 13.304 | 1.00 | 15.90 |
| ATOM | 692 | OG1 | THR A | 122 | 49.666 | 26.132 | 12.557 | 1.00 | 16.51 |
| ATOM | 693 | CG2 | THR A | 122 | 47.343 | 26.693 | 12.378 | 1.00 | 16.10 |
| ATOM | 694 | C | THR A | 122 | 49.668 | 26.677 | 15.480 | 1.00 | 16.25 |
| ATOM | 695 | O | THR A | 122 | 50.814 | 27.112 | 15.443 | 1.00 | 17.59 |
| ATOM | 696 | N | PRO A | 123 | 49.285 | 25.770 | 16.393 | 1.00 | 17.47 |
| ATOM | 697 | CD | PRO A | 123 | 47.920 | 25.301 | 16.691 | 1.00 | 16.85 |
| ATOM | 698 | CA | PRO A | 123 | 50.244 | 25.236 | 17.373 | 1.00 | 18.92 |
| ATOM | 699 | CB | PRO A | 123 | 49.420 | 24.203 | 18.128 | 1.00 | 17.69 |
| ATOM | 700 | CG | PRO A | 123 | 48.052 | 24.841 | 18.132 | 1.00 | 17.76 |
| ATOM | 701 | C | PRO A | 123 | 51.499 | 24.642 | 16.736 | 1.00 | 20.99 |
| ATOM | 702 | O | PRO A | 123 | 52.621 | 25.028 | 17.074 | 1.00 | 21.78 |
| ATOM | 703 | N | LYS A | 124 | 51.305 | 23.701 | 15.819 | 1.00 | 21.75 |
| ATOM | 704 | CA | LYS A | 124 | 52.420 | 23.079 | 15.119 | 1.00 | 23.14 |
| ATOM | 705 | CB | LYS A | 124 | 52.202 | 21.563 | 14.973 | 1.00 | 25.62 |
| ATOM | 706 | CG | LYS A | 124 | 51.920 | 20.840 | 16.279 | 1.00 | 30.22 |
| ATOM | 707 | CD | LYS A | 124 | 52.985 | 21.160 | 17.320 | 1.00 | 36.14 |
| ATOM | 708 | CE | LYS A | 124 | 52.562 | 20.694 | 18.707 | 1.00 | 40.67 |
| ATOM | 709 | NZ | LYS A | 124 | 53.568 | 21.045 | 19.751 | 1.00 | 42.17 |
| ATOM | 710 | C | LYS A | 124 | 52.488 | 23.707 | 13.736 | 1.00 | 23.21 |
| ATOM | 711 | O | LYS A | 124 | 51.504 | 24.267 | 13.245 | 1.00 | 23.64 |
| ATOM | 712 | N | PRO A | 125 | 53.660 | 23.644 | 13.095 | 1.00 | 21.67 |
| ATOM | 713 | CD | PRO A | 125 | 54.966 | 23.207 | 13.623 | 1.00 | 21.13 |
| ATOM | 714 | CA | PRO A | 125 | 53.790 | 24.220 | 11.756 | 1.00 | 20.12 |
| ATOM | 715 | CB | PRO A | 125 | 55.292 | 24.112 | 11.473 | 1.00 | 20.06 |
| ATOM | 716 | CG | PRO A | 125 | 55.924 | 24.057 | 12.844 | 1.00 | 19.41 |
| ATOM | 717 | C | PRO A | 125 | 52.976 | 23.368 | 10.775 | 1.00 | 20.04 |
| ATOM | 718 | O | PRO A | 125 | 52.738 | 22.187 | 11.024 | 1.00 | 19.30 |
| ATOM | 719 | N | GLN A | 126 | 52.536 | 23.965 | 9.674 | 1.00 | 19.35 |
| ATOM | 720 | CA | GLN A | 126 | 51.801 | 23.229 | 8.650 | 1.00 | 20.20 |
| ATOM | 721 | CB | GLN A | 126 | 50.352 | 22.926 | 9.078 | 1.00 | 21.37 |
| ATOM | 722 | CG | GLN A | 126 | 49.441 | 24.118 | 9.337 | 1.00 | 20.47 |
| ATOM | 723 | CD | GLN A | 126 | 47.993 | 23.689 | 9.578 | 1.00 | 21.76 |
| ATOM | 724 | OE1 | GLN A | 126 | 47.725 | 22.742 | 10.330 | 1.00 | 19.13 |
| ATOM | 725 | NE2 | GLN A | 126 | 47.056 | 24.391 | 8.949 | 1.00 | 19.73 |
| ATOM | 726 | C | GLN A | 126 | 51.844 | 24.027 | 7.357 | 1.00 | 20.40 |
| ATOM | 727 | O | GLN A | 126 | 51.827 | 25.255 | 7.375 | 1.00 | 20.14 |
| ATOM | 728 | N | GLU A | 127 | 51.914 | 23.323 | 6.234 | 1.00 | 22.71 |
| ATOM | 729 | CA | GLU A | 127 | 52.018 | 23.970 | 4.933 | 1.00 | 26.01 |
| ATOM | 730 | CB | GLU A | 127 | 52.622 | 22.989 | 3.922 | 1.00 | 29.64 |
| ATOM | 731 | CG | GLU A | 127 | 53.987 | 22.463 | 4.345 | 1.00 | 37.72 |
| ATOM | 732 | CD | GLU A | 127 | 54.735 | 21.770 | 3.220 | 1.00 | 43.15 |
| ATOM | 733 | OE1 | GLU A | 127 | 54.150 | 20.871 | 2.574 | 1.00 | 46.06 |
| ATOM | 734 | OE2 | GLU A | 127 | 55.914 | 22.120 | 2.986 | 1.00 | 45.97 |
| ATOM | 735 | C | GLU A | 127 | 50.752 | 24.584 | 4.352 | 1.00 | 24.16 |
| ATOM | 736 | O | GLU A | 127 | 50.832 | 25.468 | 3.503 | 1.00 | 22.80 |
| ATOM | 737 | N | GLY A | 128 | 49.589 | 24.133 | 4.805 | 1.00 | 23.12 |
| ATOM | 738 | CA | GLY A | 128 | 48.353 | 24.669 | 4.267 | 1.00 | 23.32 |
| ATOM | 739 | C | GLY A | 128 | 48.007 | 23.957 | 2.972 | 1.00 | 25.32 |
| ATOM | 740 | O | GLY A | 128 | 48.637 | 22.951 | 2.629 | 1.00 | 24.84 |

TABLE 30-continued

| | | | | | | | | |
|---|---|---|---|---|---|---|---|---|
| ATOM | 741 | N | ASN A | 129 | 47.013 | 24.465 | 2.247 | 1.00 | 25.42 |
| ATOM | 742 | CA | ASN A | 129 | 46.602 | 23.847 | 0.992 | 1.00 | 25.80 |
| ATOM | 743 | CB | ASN A | 129 | 45.256 | 24.411 | 0.530 | 1.00 | 24.97 |
| ATOM | 744 | CG | ASN A | 129 | 44.122 | 24.051 | 1.466 | 1.00 | 25.95 |
| ATOM | 745 | OD1 | ASN A | 129 | 44.069 | 22.938 | 1.988 | 1.00 | 27.09 |
| ATOM | 746 | ND2 | ASN A | 129 | 43.198 | 24.985 | 1.670 | 1.00 | 21.37 |
| ATOM | 747 | C | ASN A | 129 | 47.631 | 24.031 | −0.118 | 1.00 | 26.37 |
| ATOM | 748 | O | ASN A | 129 | 48.474 | 24.927 | −0.065 | 1.00 | 25.71 |
| ATOM | 749 | N | PRO A | 130 | 47.577 | 23.167 | −1.141 | 1.00 | 26.97 |
| ATOM | 750 | CD | PRO A | 130 | 46.708 | 21.978 | −1.222 | 1.00 | 25.53 |
| ATOM | 751 | CA | PRO A | 130 | 48.501 | 23.228 | −2.279 | 1.00 | 27.02 |
| ATOM | 752 | CB | PRO A | 130 | 48.271 | 21.888 | −2.979 | 1.00 | 26.16 |
| ATOM | 753 | CG | PRO A | 130 | 46.835 | 21.584 | −2.672 | 1.00 | 25.45 |
| ATOM | 754 | C | PRO A | 130 | 48.213 | 24.422 | −3.188 | 1.00 | 28.78 |
| ATOM | 755 | O | PRO A | 130 | 47.072 | 24.874 | −3.278 | 1.00 | 29.43 |
| ATOM | 756 | N | ARG A | 131 | 49.250 | 24.933 | −3.849 | 1.00 | 29.59 |
| ATOM | 757 | CA | ARG A | 131 | 49.113 | 26.073 | −4.754 | 1.00 | 31.09 |
| ATOM | 758 | CB | ARG A | 131 | 50.475 | 26.715 | −5.026 | 1.00 | 32.79 |
| ATOM | 759 | CG | ARG A | 131 | 51.191 | 27.347 | −3.841 | 1.00 | 35.14 |
| ATOM | 760 | CD | ARG A | 131 | 52.247 | 28.306 | −4.389 | 1.00 | 40.85 |
| ATOM | 761 | NE | ARG A | 131 | 53.156 | 28.865 | −3.389 | 1.00 | 45.50 |
| ATOM | 762 | CZ | ARG A | 131 | 53.991 | 29.877 | −3.630 | 1.00 | 45.91 |
| ATOM | 763 | NH1 | ARG A | 131 | 54.024 | 30.440 | −4.834 | 1.00 | 44.20 |
| ATOM | 764 | NH2 | ARG A | 131 | 54.801 | 30.322 | −2.676 | 1.00 | 45.31 |
| ATOM | 765 | C | ARG A | 131 | 48.517 | 25.640 | −6.096 | 1.00 | 31.92 |
| ATOM | 766 | O | ARG A | 131 | 48.732 | 24.516 | −6.542 | 1.00 | 33.62 |
| ATOM | 767 | N | PRO A | 132 | 47.764 | 26.533 | −6.762 | 1.00 | 30.70 |
| ATOM | 768 | CD | PRO A | 132 | 47.273 | 26.311 | −8.134 | 1.00 | 31.37 |
| ATOM | 769 | CA | PRO A | 132 | 47.455 | 27.896 | −6.321 | 1.00 | 28.34 |
| ATOM | 770 | CB | PRO A | 132 | 47.035 | 28.583 | −7.617 | 1.00 | 28.99 |
| ATOM | 771 | CG | PRO A | 132 | 46.335 | 27.486 | −8.341 | 1.00 | 30.32 |
| ATOM | 772 | C | PRO A | 132 | 46.350 | 27.900 | −5.265 | 1.00 | 24.58 |
| ATOM | 773 | O | PRO A | 132 | 45.461 | 27.052 | −5.282 | 1.00 | 22.71 |
| ATOM | 774 | N | ARG A | 133 | 46.411 | 28.860 | −4.350 | 1.00 | 21.45 |
| ATOM | 775 | CA | ARG A | 133 | 45.426 | 28.948 | −3.288 | 1.00 | 19.40 |
| ATOM | 776 | CB | ARG A | 133 | 46.003 | 28.314 | −2.020 | 1.00 | 20.88 |
| ATOM | 777 | CG | ARG A | 133 | 47.407 | 28.788 | −1.693 | 1.00 | 18.79 |
| ATOM | 778 | CD | ARG A | 133 | 48.079 | 27.880 | −0.680 | 1.00 | 16.96 |
| ATOM | 779 | NE | ARG A | 133 | 49.405 | 28.380 | −0.333 | 1.00 | 17.39 |
| ATOM | 780 | CZ | ARG A | 133 | 50.178 | 27.861 | 0.614 | 1.00 | 15.76 |
| ATOM | 781 | NH1 | ARG A | 133 | 51.367 | 28.387 | 0.862 | 1.00 | 13.75 |
| ATOM | 782 | NH2 | ARG A | 133 | 49.761 | 26.816 | 1.311 | 1.00 | 15.94 |
| ATOM | 783 | C | ARG A | 133 | 44.959 | 30.377 | −3.019 | 1.00 | 19.15 |
| ATOM | 784 | O | ARG A | 133 | 44.253 | 30.634 | −2.044 | 1.00 | 18.90 |
| ATOM | 785 | N | VAL A | 134 | 45.360 | 31.304 | −3.884 | 1.00 | 18.67 |
| ATOM | 786 | CA | VAL A | 134 | 44.954 | 32.702 | −3.768 | 1.00 | 19.00 |
| ATOM | 787 | CB | VAL A | 134 | 46.082 | 33.609 | −3.230 | 1.00 | 19.66 |
| ATOM | 788 | CG1 | VAL A | 134 | 45.482 | 34.904 | −2.693 | 1.00 | 16.74 |
| ATOM | 789 | CG2 | VAL A | 134 | 46.868 | 32.889 | −2.168 | 1.00 | 19.63 |
| ATOM | 790 | C | VAL A | 134 | 44.621 | 33.162 | −5.178 | 1.00 | 19.08 |
| ATOM | 791 | O | VAL A | 134 | 45.318 | 32.807 | −6.124 | 1.00 | 19.65 |
| ATOM | 792 | N | PHE A | 135 | 43.565 | 33.951 | −5.324 | 1.00 | 19.21 |
| ATOM | 793 | CA | PHE A | 135 | 43.165 | 34.409 | −6.645 | 1.00 | 17.86 |
| ATOM | 794 | CB | PHE A | 135 | 42.074 | 33.489 | −7.198 | 1.00 | 17.21 |
| ATOM | 795 | CG | PHE A | 135 | 42.393 | 32.023 | −7.056 | 1.00 | 17.38 |
| ATOM | 796 | CD1 | PHE A | 135 | 42.116 | 31.349 | −5.876 | 1.00 | 15.76 |
| ATOM | 797 | CD2 | PHE A | 135 | 43.022 | 31.332 | −8.087 | 1.00 | 18.52 |
| ATOM | 798 | CE1 | PHE A | 135 | 42.462 | 30.012 | −5.721 | 1.00 | 17.54 |
| ATOM | 799 | CE2 | PHE A | 135 | 43.372 | 29.995 | −7.941 | 1.00 | 16.71 |
| ATOM | 800 | CZ | PHE A | 135 | 43.091 | 29.335 | −6.756 | 1.00 | 16.55 |
| ATOM | 801 | C | PHE A | 135 | 42.680 | 35.852 | −6.650 | 1.00 | 18.55 |
| ATOM | 802 | O | PHE A | 135 | 42.010 | 36.302 | −5.718 | 1.00 | 17.50 |
| ATOM | 803 | N | ARG A | 136 | 43.038 | 36.575 | −7.705 | 1.00 | 17.21 |
| ATOM | 804 | CA | ARG A | 136 | 42.634 | 37.960 | −7.852 | 1.00 | 17.96 |
| ATOM | 805 | CB | ARG A | 136 | 43.732 | 38.785 | −8.532 | 1.00 | 19.09 |
| ATOM | 806 | CG | ARG A | 136 | 45.099 | 38.812 | −7.862 | 1.00 | 21.38 |
| ATOM | 807 | CD | ARG A | 136 | 46.005 | 39.773 | −8.631 | 1.00 | 23.13 |
| ATOM | 808 | NE | ARG A | 136 | 47.367 | 39.847 | −8.108 | 1.00 | 28.99 |
| ATOM | 809 | CZ | ARG A | 136 | 48.424 | 39.246 | −8.653 | 1.00 | 30.96 |
| ATOM | 810 | NE1 | ARG A | 136 | 49.621 | 39.379 | −8.097 | 1.00 | 30.96 |
| ATOM | 811 | NH2 | ARG A | 136 | 48.291 | 38.516 | −9.754 | 1.00 | 31.45 |
| ATOM | 812 | C | ARG A | 136 | 41.382 | 38.045 | −8.724 | 1.00 | 18.26 |
| ATOM | 813 | O | ARG A | 136 | 41.231 | 37.280 | −9.684 | 1.00 | 18.07 |
| ATOM | 814 | N | LEU A | 137 | 40.487 | 38.965 | −8.366 | 1.00 | 16.02 |
| ATOM | 815 | CA | LEU A | 137 | 39.264 | 39.245 | −9.124 | 1.00 | 14.64 |
| ATOM | 816 | CB | LEU A | 137 | 38.005 | 38.850 | −8.348 | 1.00 | 14.99 |
| ATOM | 817 | CG | LEU A | 137 | 37.568 | 37.381 | −8.289 | 1.00 | 16.86 |
| ATOM | 818 | CD1 | LEU A | 137 | 38.611 | 36.533 | −7.567 | 1.00 | 16.16 |
| ATOM | 819 | CD2 | LEU A | 137 | 36.234 | 37.302 | −7.572 | 1.00 | 12.39 |

TABLE 30-continued

| ATOM | 820 | C | LEU A | 137 | 39.312 | 40.762 | −9.270 | 1.00 | 15.43 |
|---|---|---|---|---|---|---|---|---|---|
| ATOM | 821 | O | LEU A | 137 | 38.557 | 41.487 | −8.619 | 1.00 | 13.75 |
| ATOM | 822 | N | PRO A | 138 | 40.230 | 41.261 | −10.114 | 1.00 | 15.66 |
| ATOM | 823 | CD | PRO A | 138 | 41.182 | 40.481 | −10.927 | 1.00 | 15.43 |
| ATOM | 824 | CA | PRO A | 138 | 40.389 | 42.701 | −10.339 | 1.00 | 16.74 |
| ATOM | 825 | CB | PRO A | 138 | 41.536 | 42.776 | −11.359 | 1.00 | 16.03 |
| ATOM | 826 | CG | PRO A | 138 | 41.505 | 41.426 | −12.042 | 1.00 | 16.02 |
| ATOM | 827 | C | PRO A | 138 | 39.133 | 43.455 | −10.778 | 1.00 | 16.37 |
| ATOM | 828 | O | PRO A | 138 | 38.947 | 44.611 | −10.407 | 1.00 | 17.51 |
| ATOM | 829 | N | GLU A | 139 | 38.267 | 42.812 | −11.551 | 1.00 | 16.27 |
| ATOM | 830 | CA | GLU A | 139 | 37.044 | 43.478 | −11.988 | 1.00 | 17.29 |
| ATOM | 831 | CB | GLU A | 139 | 36.312 | 42.646 | −13.049 | 1.00 | 17.90 |
| ATOM | 832 | CG | GLU A | 139 | 37.056 | 42.476 | −14.371 | 1.00 | 21.52 |
| ATOM | 833 | CD | GLU A | 139 | 38.072 | 41.341 | −14.353 | 1.00 | 24.56 |
| ATOM | 834 | OE1 | GLU A | 139 | 38.733 | 41.139 | −15.393 | 1.00 | 28.04 |
| ATOM | 835 | OE2 | GLU A | 139 | 38.211 | 40.652 | −13.314 | 1.00 | 23.31 |
| ATOM | 836 | C | GLU A | 139 | 36.097 | 43.717 | −10.811 | 1.00 | 17.97 |
| ATOM | 837 | O | GLU A | 139 | 35.181 | 44.538 | −10.899 | 1.00 | 18.18 |
| ATOM | 838 | N | ASP A | 140 | 36.317 | 43.000 | −9.712 | 1.00 | 15.32 |
| ATOM | 839 | CA | ASP A | 140 | 35.462 | 43.125 | −8.535 | 1.00 | 13.52 |
| ATOM | 840 | CB | ASP A | 140 | 34.958 | 41.745 | −8.099 | 1.00 | 11.56 |
| ATOM | 841 | CG | ASP A | 140 | 34.317 | 40.965 | −9.235 | 1.00 | 14.42 |
| ATOM | 842 | OD1 | ASP A | 140 | 33.256 | 41.394 | −9.737 | 1.00 | 12.89 |
| ATOM | 843 | OD2 | ASP A | 140 | 34.875 | 39.916 | −9.626 | 1.00 | 14.92 |
| ATOM | 844 | C | ASP A | 140 | 36.205 | 43.756 | −7.368 | 1.00 | 14.63 |
| ATOM | 845 | O | ASP A | 140 | 35.629 | 43.958 | −6.292 | 1.00 | 13.69 |
| ATOM | 846 | N | GLN A | 141 | 37.480 | 44.071 | −7.580 | 1.00 | 15.16 |
| ATOM | 847 | CA | GLN A | 141 | 38.302 | 44.629 | −6.516 | 1.00 | 15.06 |
| ATOM | 848 | CB | GLN A | 141 | 37.812 | 46.028 | −6.139 | 1.00 | 16.60 |
| ATOM | 849 | CG | GLN A | 141 | 38.184 | 47.085 | −7.174 | 1.00 | 23.33 |
| ATOM | 850 | CD | GLN A | 141 | 37.655 | 48.473 | −6.843 | 1.00 | 25.68 |
| ATOM | 851 | OE1 | GLN A | 141 | 37.850 | 48.983 | −5.734 | 1.00 | 29.01 |
| ATOM | 852 | NE2 | GLN A | 141 | 36.991 | 49.098 | −7.812 | 1.00 | 26.01 |
| ATOM | 853 | C | GLN A | 141 | 38.179 | 43.665 | −5.340 | 1.00 | 14.75 |
| ATOM | 854 | O | GLN A | 141 | 38.013 | 44.069 | −4.187 | 1.00 | 15.25 |
| ATOM | 855 | N | ALA A | 142 | 38.250 | 42.376 | −5.660 | 1.00 | 13.65 |
| ATOM | 856 | CA | ALA A | 142 | 38.140 | 41.322 | −4.663 | 1.00 | 13.75 |
| ATOM | 857 | CB | ALA A | 142 | 36.773 | 40.647 | −4.773 | 1.00 | 11.94 |
| ATOM | 858 | C | ALA A | 142 | 39.246 | 40.274 | −4.793 | 1.00 | 13.78 |
| ATOM | 859 | O | ALA A | 142 | 39.999 | 40.248 | −5.769 | 1.00 | 12.61 |
| ATOM | 860 | N | VAL A | 143 | 39.326 | 39.411 | −3.786 | 1.00 | 13.55 |
| ATOM | 861 | CA | VAL A | 143 | 40.298 | 38.333 | −3.743 | 1.00 | 12.13 |
| ATOM | 862 | CB | VAL A | 143 | 41.522 | 38.688 | −2.836 | 1.00 | 13.66 |
| ATOM | 863 | CG1 | VAL A | 143 | 42.332 | 37.430 | −2.521 | 1.00 | 9.03 |
| ATOM | 864 | CG2 | VAL A | 143 | 42.419 | 39.713 | −3.528 | 1.00 | 8.76 |
| ATOM | 865 | C | VAL A | 143 | 39.604 | 37.110 | −3.156 | 1.00 | 14.44 |
| ATOM | 866 | O | VAL A | 143 | 38.669 | 37.234 | −2.365 | 1.00 | 16.13 |
| ATOM | 867 | N | ILE A | 144 | 40.041 | 35.930 | −3.574 | 1.00 | 14.55 |
| ATOM | 868 | CA | ILE A | 144 | 39.507 | 34.683 | −3.050 | 1.00 | 13.21 |
| ATOM | 869 | CB | ILE A | 144 | 38.725 | 33.884 | −4.116 | 1.00 | 13.83 |
| ATOM | 870 | CG2 | ILE A | 144 | 38.563 | 32.426 | −3.673 | 1.00 | 10.86 |
| ATOM | 871 | CG1 | ILE A | 144 | 37.348 | 34.514 | −4.329 | 1.00 | 11.70 |
| ATOM | 872 | CD1 | ILE A | 144 | 36.505 | 33.768 | −5.324 | 1.00 | 14.85 |
| ATOM | 873 | C | ILE A | 144 | 40.729 | 33.893 | −2.627 | 1.00 | 14.02 |
| ATOM | 874 | O | ILE A | 144 | 41.700 | 33.795 | −3.382 | 1.00 | 14.77 |
| ATOM | 875 | N | ASN A | 145 | 40.700 | 33.341 | −1.421 | 1.00 | 14.01 |
| ATOM | 876 | CA | ASN A | 145 | 41.841 | 32.575 | −0.945 | 1.00 | 13.47 |
| ATOM | 877 | CB | ASN A | 145 | 42.717 | 33.455 | −0.046 | 1.00 | 13.34 |
| ATOM | 878 | CG | ASN A | 145 | 42.256 | 33.451 | 1.407 | 1.00 | 16.62 |
| ATOM | 879 | OD1 | ASN A | 145 | 42.562 | 32.525 | 2.161 | 1.00 | 14.82 |
| ATOM | 880 | ND2 | ASN A | 145 | 41.507 | 34.481 | 1.801 | 1.00 | 15.48 |
| ATOM | 881 | C | ASN A | 145 | 41.423 | 31.330 | −0.176 | 1.00 | 14.78 |
| ATOM | 882 | O | ASN A | 145 | 40.369 | 31.299 | 0.468 | 1.00 | 13.11 |
| ATOM | 883 | N | ARG A | 146 | 42.258 | 30.300 | −0.257 | 1.00 | 14.90 |
| ATOM | 884 | CA | ARG A | 146 | 42.025 | 29.057 | 0.461 | 1.00 | 16.46 |
| ATOM | 885 | CB | ARG A | 146 | 41.335 | 28.021 | −0.435 | 1.00 | 15.83 |
| ATOM | 886 | CG | ARG A | 146 | 41.964 | 27.806 | −1.803 | 1.00 | 15.41 |
| ATOM | 887 | CD | ARG A | 146 | 41.394 | 26.539 | −2.428 | 1.00 | 16.11 |
| ATOM | 888 | NE | ARG A | 146 | 41.950 | 26.245 | −3.747 | 1.00 | 16.55 |
| ATOM | 889 | CZ | ARG A | 146 | 41.419 | 26.640 | −4.902 | 1.00 | 17.12 |
| ATOM | 890 | NH1 | ARG A | 146 | 40.303 | 27.357 | −4.922 | 1.00 | 16.98 |
| ATOM | 891 | NH2 | ARG A | 146 | 42.004 | 26.308 | −6.045 | 1.00 | 19.03 |
| ATOM | 892 | C | ARG A | 146 | 43.368 | 28.527 | 0.963 | 1.00 | 18.74 |
| ATOM | 893 | O | ARG A | 146 | 43.712 | 27.363 | 0.752 | 1.00 | 18.99 |
| ATOM | 894 | N | TYR A | 147 | 44.122 | 29.401 | 1.630 | 1.00 | 18.17 |
| ATOM | 895 | CA | TYR A | 147 | 45.429 | 29.043 | 2.165 | 1.00 | 18.86 |
| ATOM | 896 | CB | TYR A | 147 | 46.020 | 30.205 | 2.964 | 1.00 | 18.76 |
| ATOM | 897 | CG | TYR A | 147 | 46.884 | 31.127 | 2.146 | 1.00 | 18.93 |
| ATOM | 898 | CD1 | TYR A | 147 | 46.428 | 32.377 | 1.754 | 1.00 | 19.69 |

TABLE 30-continued

| ATOM | 899 | CE1 | TYR A | 147 | 47.220 | 33.216 | 0.987 | 1.00 | 22.27 |
| --- | --- | --- | --- | --- | --- | --- | --- | --- | --- |
| ATOM | 900 | CD2 | TYR A | 147 | 48.160 | 30.736 | 1.748 | 1.00 | 20.18 |
| ATOM | 901 | CE2 | TYR A | 147 | 48.958 | 31.565 | 0.981 | 1.00 | 21.33 |
| ATOM | 902 | CZ | TYR A | 147 | 48.483 | 32.802 | 0.604 | 1.00 | 22.73 |
| ATOM | 903 | OH | TYR A | 147 | 49.271 | 33.626 | −0.164 | 1.00 | 28.16 |
| ATOM | 904 | C | TYR A | 147 | 45.393 | 27.806 | 3.047 | 1.00 | 19.56 |
| ATOM | 905 | O | TYR A | 147 | 46.249 | 26.930 | 2.928 | 1.00 | 21.06 |
| ATOM | 906 | N | GLY A | 148 | 44.408 | 27.746 | 3.937 | 1.00 | 19.63 |
| ATOM | 907 | CA | GLY A | 148 | 44.280 | 26.611 | 4.831 | 1.00 | 17.88 |
| ATOM | 908 | C | GLY A | 148 | 45.174 | 26.702 | 6.055 | 1.00 | 19.35 |
| ATOM | 909 | O | GLY A | 148 | 45.677 | 25.687 | 6.538 | 1.00 | 20.24 |
| ATOM | 910 | N | PHE A | 149 | 45.385 | 27.913 | 6.558 | 1.00 | 19.11 |
| ATOM | 911 | CA | PHE A | 149 | 46.216 | 28.106 | 7.746 | 1.00 | 19.25 |
| ATOM | 912 | CB | PHE A | 149 | 45.629 | 27.343 | 8.942 | 1.00 | 18.52 |
| ATOM | 913 | CG | PHE A | 149 | 44.462 | 28.026 | 9.603 | 1.00 | 19.93 |
| ATOM | 914 | CD1 | PHE A | 149 | 43.605 | 27.308 | 10.431 | 1.00 | 21.48 |
| ATOM | 915 | CD2 | PHE A | 149 | 44.224 | 29.377 | 9.415 | 1.00 | 20.70 |
| ATOM | 916 | CE1 | PHE A | 149 | 42.530 | 27.928 | 11.058 | 1.00 | 22.80 |
| ATOM | 917 | CE2 | PHE A | 149 | 43.151 | 30.005 | 10.039 | 1.00 | 21.90 |
| ATOM | 918 | CZ | PHE A | 149 | 42.303 | 29.281 | 10.860 | 1.00 | 22.32 |
| ATOM | 919 | C | PHE A | 149 | 47.674 | 27.677 | 7.577 | 1.00 | 19.22 |
| ATOM | 920 | O | PHE A | 149 | 48.185 | 26.895 | 8.376 | 1.00 | 20.27 |
| ATOM | 921 | N | ASN A | 150 | 48.343 | 28.155 | 6.536 | 1.00 | 17.52 |
| ATOM | 922 | CA | ASN A | 150 | 49.748 | 27.822 | 6.375 | 1.00 | 18.34 |
| ATOM | 923 | CB | ASN A | 150 | 50.269 | 28.307 | 5.018 | 1.00 | 16.68 |
| ATOM | 924 | CG | ASN A | 150 | 49.967 | 29.769 | 4.765 | 1.00 | 18.37 |
| ATOM | 925 | OD1 | ASN A | 150 | 48.819 | 30.205 | 4.866 | 1.00 | 18.33 |
| ATOM | 926 | ND2 | ASN A | 150 | 50.996 | 30.536 | 4.423 | 1.00 | 17.29 |
| ATOM | 927 | C | ASN A | 150 | 50.385 | 28.604 | 7.525 | 1.00 | 19.77 |
| ATOM | 928 | O | ASN A | 150 | 50.135 | 29.800 | 7.673 | 1.00 | 20.24 |
| ATOM | 929 | N | SER A | 151 | 51.185 | 27.936 | 8.349 | 1.00 | 18.05 |
| ATOM | 930 | CA | SER A | 151 | 51.779 | 28.604 | 9.497 | 1.00 | 18.67 |
| ATOM | 931 | CB | SER A | 151 | 50.774 | 28.580 | 10.654 | 1.00 | 17.61 |
| ATOM | 932 | OG | SER A | 151 | 51.380 | 28.930 | 11.884 | 1.00 | 16.00 |
| ATOM | 933 | C | SER A | 151 | 53.111 | 28.029 | 9.977 | 1.00 | 19.35 |
| ATOM | 934 | O | SER A | 151 | 53.329 | 26.812 | 9.940 | 1.00 | 18.88 |
| ATOM | 935 | N | HIS A | 152 | 53.987 | 28.920 | 10.440 | 1.00 | 18.69 |
| ATOM | 936 | CA | HIS A | 152 | 55.300 | 28.539 | 10.960 | 1.00 | 18.85 |
| ATOM | 937 | CB | HIS A | 152 | 56.208 | 29.770 | 11.094 | 1.00 | 18.68 |
| ATOM | 938 | CG | HIS A | 152 | 56.662 | 30.341 | 9.785 | 1.00 | 20.96 |
| ATOM | 939 | CD2 | HIS A | 152 | 56.389 | 29.978 | 8.508 | 1.00 | 20.68 |
| ATOM | 940 | ND1 | HIS A | 152 | 57.513 | 31.422 | 9.701 | 1.00 | 22.15 |
| ATOM | 941 | CE1 | HIS A | 152 | 57.746 | 31.700 | 8.430 | 1.00 | 20.45 |
| ATOM | 942 | NE2 | HIS A | 152 | 57.075 | 30.839 | 7.686 | 1.00 | 21.40 |
| ATOM | 943 | C | HIS A | 152 | 55.154 | 27.875 | 12.329 | 1.00 | 18.49 |
| ATOM | 944 | O | HIS A | 152 | 56.082 | 27.224 | 12.815 | 1.00 | 17.98 |
| ATOM | 945 | N | GLY A | 153 | 53.991 | 28.050 | 12.954 | 1.00 | 17.52 |
| ATOM | 946 | CA | GLY A | 153 | 53.764 | 27.451 | 14.256 | 1.00 | 16.27 |
| ATOM | 947 | C | GLY A | 153 | 54.047 | 28.392 | 15.412 | 1.00 | 15.14 |
| ATOM | 948 | O | GLY A | 153 | 54.711 | 29.411 | 15.248 | 1.00 | 13.16 |
| ATOM | 949 | N | LEU A | 154 | 53.546 | 28.035 | 16.589 | 1.00 | 15.48 |
| ATOM | 950 | CA | LEU A | 154 | 53.717 | 28.845 | 17.791 | 1.00 | 16.27 |
| ATOM | 951 | CB | LEU A | 154 | 52.982 | 28.184 | 18.966 | 1.00 | 12.85 |
| ATOM | 952 | CG | LEU A | 154 | 51.455 | 28.194 | 18.838 | 1.00 | 14.19 |
| ATOM | 953 | CD1 | LEU A | 154 | 50.811 | 27.354 | 19.940 | 1.00 | 9.42 |
| ATOM | 954 | CD2 | LEU A | 154 | 50.965 | 29.638 | 18.898 | 1.00 | 11.87 |
| ATOM | 955 | C | LEU A | 154 | 55.168 | 29.136 | 18.187 | 1.00 | 17.92 |
| ATOM | 956 | O | LEU A | 154 | 55.520 | 30.295 | 18.425 | 1.00 | 18.40 |
| ATOM | 957 | N | SER A | 155 | 56.001 | 28.096 | 18.266 | 1.00 | 18.05 |
| ATOM | 958 | CA | SER A | 155 | 57.408 | 28.268 | 18.647 | 1.00 | 19.71 |
| ATOM | 959 | CB | SER A | 155 | 58.173 | 26.946 | 18.528 | 1.00 | 18.07 |
| ATOM | 960 | OG | SER A | 155 | 57.775 | 26.035 | 19.528 | 1.00 | 26.58 |
| ATOM | 961 | C | SER A | 155 | 58.143 | 29.319 | 17.820 | 1.00 | 19.87 |
| ATOM | 962 | O | SER A | 155 | 58.706 | 30.272 | 18.368 | 1.00 | 19.91 |
| ATOM | 963 | N | VAL A | 156 | 58.158 | 29.134 | 16.503 | 1.00 | 18.27 |
| ATOM | 964 | CA | VAL A | 156 | 58.846 | 30.077 | 15.637 | 1.00 | 19.17 |
| ATOM | 965 | CB | VAL A | 156 | 58.723 | 29.672 | 14.153 | 1.00 | 19.48 |
| ATOM | 966 | CG1 | VAL A | 156 | 59.158 | 30.829 | 13.264 | 1.00 | 18.32 |
| ATOM | 967 | CG2 | VAL A | 156 | 59.597 | 28.452 | 13.880 | 1.00 | 15.72 |
| ATOM | 968 | C | VAL A | 156 | 58.346 | 31.508 | 15.817 | 1.00 | 18.93 |
| ATOM | 969 | O | VAL A | 156 | 59.146 | 32.435 | 15.936 | 1.00 | 21.37 |
| ATOM | 970 | N | VAL A | 157 | 57.030 | 31.691 | 15.848 | 1.00 | 17.16 |
| ATOM | 971 | CA | VAL A | 157 | 56.470 | 33.027 | 16.013 | 1.00 | 17.31 |
| ATOM | 972 | CB | VAL A | 157 | 54.936 | 33.021 | 15.790 | 1.00 | 18.26 |
| ATOM | 973 | CG1 | VAL A | 157 | 54.368 | 34.417 | 16.001 | 1.00 | 15.69 |
| ATOM | 974 | CG2 | VAL A | 157 | 54.620 | 32.532 | 14.380 | 1.00 | 15.91 |
| ATOM | 975 | C | VAL A | 157 | 56.785 | 33.562 | 17.408 | 1.00 | 16.86 |
| ATOM | 976 | O | VAL A | 157 | 57.047 | 34.750 | 17.584 | 1.00 | 16.79 |
| ATOM | 977 | N | GLU A | 158 | 56.771 | 32.670 | 18.394 | 1.00 | 17.65 |

TABLE 30-continued

| | | | | | | | | |
|---|---|---|---|---|---|---|---|---|
| ATOM | 978 | CA | GLU A | 158 | 57.065 | 33.034 | 19.774 | 1.00 | 16.94 |
| ATOM | 979 | CB | GLU A | 158 | 57.009 | 31.790 | 20.661 | 1.00 | 17.93 |
| ATOM | 980 | CG | GLU A | 158 | 57.397 | 32.041 | 22.110 | 1.00 | 20.56 |
| ATOM | 981 | CD | GLU A | 158 | 57.966 | 30.802 | 22.779 | 1.00 | 22.55 |
| ATOM | 982 | OE1 | GLU A | 158 | 57.274 | 29.769 | 22.816 | 1.00 | 26.93 |
| ATOM | 983 | OE2 | GLU A | 158 | 59.110 | 30.857 | 23.269 | 1.00 | 24.61 |
| ATOM | 984 | C | GLU A | 158 | 58.449 | 33.675 | 19.887 | 1.00 | 16.25 |
| ATOM | 985 | O | GLU A | 158 | 58.600 | 34.760 | 20.450 | 1.00 | 14.87 |
| ATOM | 986 | N | HIS A | 159 | 59.458 | 33.000 | 19.350 | 1.00 | 15.71 |
| ATOM | 987 | CA | HIS A | 159 | 60.823 | 33.515 | 19.402 | 1.00 | 18.49 |
| ATOM | 988 | CB | HIS A | 159 | 61.808 | 32.435 | 18.945 | 1.00 | 20.42 |
| ATOM | 989 | CG | HIS A | 159 | 61.867 | 31.260 | 19.868 | 1.00 | 25.61 |
| ATOM | 990 | CD2 | HIS A | 159 | 62.134 | 31.183 | 21.193 | 1.00 | 26.32 |
| ATOM | 991 | ND1 | HIS A | 159 | 61.582 | 29.974 | 19.460 | 1.00 | 28.74 |
| ATOM | 992 | CE1 | HIS A | 159 | 61.669 | 29.156 | 20.494 | 1.00 | 28.74 |
| ATOM | 993 | NE2 | HIS A | 159 | 62.002 | 29.865 | 21.558 | 1.00 | 29.76 |
| ATOM | 994 | C | HIS A | 159 | 60.988 | 34.768 | 18.557 | 1.00 | 17.35 |
| ATOM | 995 | O | HIS A | 159 | 61.779 | 35.648 | 18.884 | 1.00 | 18.51 |
| ATOM | 996 | N | ARG A | 160 | 60.227 | 34.846 | 17.474 | 1.00 | 17.65 |
| ATOM | 997 | CA | ARG A | 160 | 60.278 | 35.992 | 16.579 | 1.00 | 19.47 |
| ATOM | 998 | CB | ARG A | 160 | 59.514 | 35.655 | 15.297 | 1.00 | 20.64 |
| ATOM | 999 | CG | ARG A | 160 | 59.535 | 36.710 | 14.214 | 1.00 | 21.36 |
| ATOM | 1000 | CD | ARG A | 160 | 58.908 | 36.135 | 12.943 | 1.00 | 24.65 |
| ATOM | 1001 | NE | ARG A | 160 | 59.770 | 35.132 | 12.317 | 1.00 | 24.10 |
| ATOM | 1002 | CZ | ARG A | 160 | 59.334 | 34.096 | 11.602 | 1.00 | 24.79 |
| ATOM | 1003 | NH1 | ARG A | 160 | 58.034 | 33.901 | 11.420 | 1.00 | 21.67 |
| ATOM | 1004 | NH2 | ARG A | 160 | 60.206 | 33.260 | 11.051 | 1.00 | 22.81 |
| ATOM | 1005 | C | ARG A | 160 | 59.696 | 37.235 | 17.266 | 1.00 | 20.02 |
| ATOM | 1006 | O | ARG A | 160 | 60.174 | 38.351 | 17.057 | 1.00 | 21.08 |
| ATOM | 1007 | N | LEU A | 161 | 58.673 | 37.046 | 18.093 | 1.00 | 19.43 |
| ATOM | 1008 | CA | LEU A | 161 | 58.079 | 38.172 | 18.812 | 1.00 | 19.27 |
| ATOM | 1009 | CB | LEU A | 161 | 56.638 | 37.853 | 19.224 | 1.00 | 19.24 |
| ATOM | 1010 | CG | LEU A | 161 | 55.611 | 37.741 | 18.090 | 1.00 | 19.93 |
| ATOM | 1011 | CD1 | LEU A | 161 | 54.227 | 37.519 | 18.685 | 1.00 | 18.11 |
| ATOM | 1012 | CD2 | LEU A | 161 | 55.626 | 39.012 | 17.245 | 1.00 | 16.76 |
| ATOM | 1013 | C | LEU A | 161 | 58.912 | 38.510 | 20.051 | 1.00 | 18.22 |
| ATOM | 1014 | O | LEU A | 161 | 58.995 | 39.667 | 20.457 | 1.00 | 17.78 |
| ATOM | 1015 | N | ARG A | 162 | 59.533 | 37.497 | 20.648 | 1.00 | 17.88 |
| ATOM | 1016 | CA | ARG A | 162 | 60.370 | 37.715 | 21.826 | 1.00 | 17.59 |
| ATOM | 1017 | CB | ARG A | 162 | 60.843 | 36.385 | 22.412 | 1.00 | 16.52 |
| ATOM | 1018 | CG | ARG A | 162 | 59.806 | 35.670 | 23.257 | 1.00 | 16.27 |
| ATOM | 1019 | CD | ARG A | 162 | 60.424 | 34.465 | 23.941 | 1.00 | 15.33 |
| ATOM | 1020 | NE | ARG A | 162 | 59.500 | 33.825 | 24.871 | 1.00 | 15.04 |
| ATOM | 1021 | CZ | ARG A | 162 | 59.804 | 32.759 | 25.602 | 1.00 | 15.93 |
| ATOM | 1022 | NH1 | ARG A | 162 | 61.013 | 32.217 | 25.508 | 1.00 | 14.79 |
| ATOM | 1023 | NH2 | ARG A | 162 | 58.902 | 32.231 | 26.422 | 1.00 | 14.97 |
| ATOM | 1024 | C | ARG A | 162 | 61.586 | 38.566 | 21.490 | 1.00 | 17.29 |
| ATOM | 1025 | O | ARG A | 162 | 62.058 | 39.338 | 22.322 | 1.00 | 16.65 |
| ATOM | 1026 | N | ALA A | 163 | 62.084 | 38.423 | 20.265 | 1.00 | 16.93 |
| ATOM | 1027 | CA | ALA A | 163 | 63.250 | 39.175 | 19.816 | 1.00 | 16.63 |
| ATOM | 1028 | CB | ALA A | 163 | 63.685 | 38.689 | 18.440 | 1.00 | 15.17 |
| ATOM | 1029 | C | ALA A | 163 | 62.983 | 40.677 | 19.775 | 1.00 | 17.05 |
| ATOM | 1030 | O | ALA A | 163 | 63.917 | 41.470 | 19.668 | 1.00 | 14.83 |
| ATOM | 1031 | N | ARG A | 164 | 61.709 | 41.061 | 19.860 | 1.00 | 17.20 |
| ATOM | 1032 | CA | ARG A | 164 | 61.329 | 42.471 | 19.827 | 1.00 | 18.88 |
| ATOM | 1033 | CB | ARG A | 164 | 60.772 | 42.841 | 18.446 | 1.00 | 18.87 |
| ATOM | 1034 | CG | ARG A | 164 | 59.504 | 42.079 | 18.063 | 1.00 | 19.81 |
| ATOM | 1035 | CD | ARG A | 164 | 59.017 | 42.460 | 16.670 | 1.00 | 17.62 |
| ATOM | 1036 | NE | ARG A | 164 | 58.529 | 43.835 | 16.611 | 1.00 | 17.21 |
| ATOM | 1037 | CZ | ARG A | 164 | 57.354 | 44.237 | 17.087 | 1.00 | 18.36 |
| ATOM | 1038 | NH1 | ARG A | 164 | 56.532 | 43.366 | 17.663 | 1.00 | 17.29 |
| ATOM | 1039 | NH2 | ARG A | 164 | 56.995 | 45.511 | 16.984 | 1.00 | 16.99 |
| ATOM | 1040 | C | ARG A | 164 | 60.279 | 42.785 | 20.878 | 1.00 | 19.51 |
| ATOM | 1041 | O | ARG A | 164 | 59.604 | 43.812 | 20.796 | 1.00 | 19.66 |
| ATOM | 1042 | N | GLN A | 165 | 60.151 | 41.907 | 21.870 | 1.00 | 20.83 |
| ATOM | 1043 | CA | GLN A | 165 | 59.158 | 42.079 | 22.924 | 1.00 | 20.81 |
| ATOM | 1044 | CB | GLN A | 165 | 59.280 | 40.942 | 23.952 | 1.00 | 20.22 |
| ATOM | 1045 | CG | GLN A | 165 | 58.312 | 41.047 | 25.136 | 1.00 | 22.04 |
| ATOM | 1046 | CD | GLN A | 165 | 58.155 | 39.735 | 25.903 | 1.00 | 22.82 |
| ATOM | 1047 | OE1 | GLN A | 165 | 59.083 | 38.932 | 25.987 | 1.00 | 22.86 |
| ATOM | 1048 | NE2 | GLN A | 165 | 56.975 | 39.523 | 26.476 | 1.00 | 21.38 |
| ATOM | 1049 | C | GLN A | 165 | 59.208 | 43.437 | 23.626 | 1.00 | 22.14 |
| ATOM | 1050 | O | GLN A | 165 | 58.164 | 44.037 | 23.897 | 1.00 | 22.79 |
| ATOM | 1051 | N | GLN A | 166 | 60.409 | 43.930 | 23.914 | 1.00 | 22.12 |
| ATOM | 1052 | CA | GLN A | 166 | 60.537 | 45.212 | 24.598 | 1.00 | 22.70 |
| ATOM | 1053 | CB | GLN A | 166 | 61.937 | 45.371 | 25.188 | 1.00 | 25.51 |
| ATOM | 1054 | CG | GLN A | 166 | 62.201 | 44.385 | 26.301 | 1.00 | 27.11 |
| ATOM | 1055 | CD | GLN A | 166 | 61.020 | 44.285 | 27.244 | 1.00 | 28.49 |
| ATOM | 1056 | OE1 | GLN A | 166 | 60.591 | 45.282 | 27.823 | 1.00 | 28.75 |

TABLE 30-continued

| ATOM | 1057 | NE2 | GLN A | 166 | 60.480 | 43.081 | 27.394 | 1.00 | 29.17 |
|------|------|-----|-------|-----|--------|--------|--------|------|-------|
| ATOM | 1058 | C | GLN A | 166 | 60.217 | 46.381 | 23.696 | 1.00 | 21.88 |
| ATOM | 1059 | O | GLN A | 166 | 59.636 | 47.372 | 24.140 | 1.00 | 20.81 |
| ATOM | 1060 | N | LYS A | 167 | 60.601 | 46.272 | 22.429 | 1.00 | 21.75 |
| ATOM | 1061 | CA | LYS A | 167 | 60.308 | 47.331 | 21.480 | 1.00 | 21.20 |
| ATOM | 1062 | CB | LYS A | 167 | 60.888 | 47.002 | 20.105 | 1.00 | 20.78 |
| ATOM | 1063 | CG | LYS A | 167 | 60.386 | 47.931 | 19.023 | 1.00 | 25.29 |
| ATOM | 1064 | CD | LYS A | 167 | 60.917 | 47.567 | 17.651 | 1.00 | 29.48 |
| ATOM | 1065 | CE | LYS A | 167 | 62.372 | 47.952 | 17.502 | 1.00 | 33.26 |
| ATOM | 1066 | NZ | LYS A | 167 | 62.806 | 47.876 | 16.078 | 1.00 | 36.00 |
| ATOM | 1067 | C | LYS A | 167 | 58.788 | 47.459 | 21.380 | 1.00 | 20.64 |
| ATOM | 1068 | O | LYS A | 167 | 58.246 | 48.565 | 21.406 | 1.00 | 20.50 |
| ATOM | 1069 | N | GLN A | 168 | 58.105 | 46.320 | 21.278 | 1.00 | 19.29 |
| ATOM | 1070 | CA | GLN A | 168 | 56.649 | 46.318 | 21.175 | 1.00 | 18.72 |
| ATOM | 1071 | CB | GLN A | 168 | 56.117 | 44.894 | 20.986 | 1.00 | 17.31 |
| ATOM | 1072 | CG | GLN A | 168 | 54.598 | 44.820 | 20.821 | 1.00 | 17.69 |
| ATOM | 1073 | CD | GLN A | 168 | 54.086 | 45.620 | 19.624 | 1.00 | 18.27 |
| ATOM | 1074 | OE1 | GLN A | 168 | 54.449 | 45.349 | 18.474 | 1.00 | 16.59 |
| ATOM | 1075 | NE2 | GLN A | 168 | 53.239 | 46.610 | 19.894 | 1.00 | 16.80 |
| ATOM | 1076 | C | GLN A | 168 | 56.028 | 46.944 | 22.416 | 1.00 | 17.89 |
| ATOM | 1077 | O | GLN A | 168 | 55.043 | 47.669 | 22.318 | 1.00 | 17.45 |
| ATOM | 1078 | N | ALA A | 169 | 56.615 | 46.680 | 23.581 | 1.00 | 17.92 |
| ATOM | 1079 | CA | ALA A | 169 | 56.098 | 47.247 | 24.825 | 1.00 | 18.33 |
| ATOM | 1080 | CB | ALA A | 169 | 56.972 | 46.831 | 26.006 | 1.00 | 17.47 |
| ATOM | 1081 | C | ALA A | 169 | 56.043 | 48.770 | 24.722 | 1.00 | 18.61 |
| ATOM | 1082 | O | ALA A | 169 | 55.075 | 49.394 | 25.159 | 1.00 | 19.23 |
| ATOM | 1083 | N | LYS A | 170 | 57.082 | 49.368 | 24.146 | 1.00 | 19.44 |
| ATOM | 1084 | CA | LYS A | 170 | 57.121 | 50.818 | 23.986 | 1.00 | 21.87 |
| ATOM | 1085 | CB | LYS A | 170 | 58.535 | 51.290 | 23.629 | 1.00 | 23.58 |
| ATOM | 1086 | CG | LYS A | 170 | 59.517 | 51.205 | 24.793 | 1.00 | 28.39 |
| ATOM | 1087 | CD | LYS A | 170 | 60.837 | 51.900 | 24.472 | 1.00 | 30.60 |
| ATOM | 1088 | CE | LYS A | 170 | 61.785 | 51.860 | 25.663 | 1.00 | 31.30 |
| ATOM | 1089 | NZ | LYS A | 170 | 62.110 | 50.456 | 26.065 | 1.00 | 35.39 |
| ATOM | 1090 | C | LYS A | 170 | 56.136 | 51.284 | 22.919 | 1.00 | 20.75 |
| ATOM | 1091 | O | LYS A | 170 | 55.505 | 52.328 | 23.068 | 1.00 | 21.15 |
| ATOM | 1092 | N | LEU A | 171 | 56.011 | 50.511 | 21.844 | 1.00 | 19.14 |
| ATOM | 1093 | CA | LEU A | 171 | 55.078 | 50.851 | 20.771 | 1.00 | 18.56 |
| ATOM | 1094 | CB | LEU A | 171 | 55.186 | 49.835 | 19.633 | 1.00 | 17.57 |
| ATOM | 1095 | CG | LEU A | 171 | 56.467 | 49.956 | 18.807 | 1.00 | 17.13 |
| ATOM | 1096 | CD1 | LEU A | 171 | 56.664 | 48.719 | 17.947 | 1.00 | 13.91 |
| ATOM | 1097 | CD2 | LEU A | 171 | 56.385 | 51.217 | 17.954 | 1.00 | 14.77 |
| ATOM | 1098 | C | LEU A | 171 | 53.650 | 50.878 | 21.311 | 1.00 | 17.89 |
| ATOM | 1099 | O | LEU A | 171 | 52.891 | 51.810 | 21.041 | 1.00 | 15.97 |
| ATOM | 1100 | N | THR A | 172 | 53.294 | 49.850 | 22.078 | 1.00 | 18.22 |
| ATOM | 1101 | CA | THR A | 172 | 51.965 | 49.758 | 22.669 | 1.00 | 19.38 |
| ATOM | 1102 | CB | THR A | 172 | 51.805 | 48.444 | 23.467 | 1.00 | 17.92 |
| ATOM | 1103 | OG1 | THR A | 172 | 51.885 | 47.330 | 22.566 | 1.00 | 16.29 |
| ATOM | 1104 | CG2 | THR A | 172 | 50.465 | 48.412 | 24.188 | 1.00 | 14.36 |
| ATOM | 1105 | C | THR A | 172 | 51.708 | 50.956 | 23.587 | 1.00 | 21.01 |
| ATOM | 1106 | O | THR A | 172 | 50.659 | 51.598 | 23.507 | 1.00 | 19.74 |
| ATOM | 1107 | N | GLU A | 173 | 52.674 | 51.261 | 24.447 | 1.00 | 23.19 |
| ATOM | 1108 | CA | GLU A | 173 | 52.551 | 52.395 | 25.356 | 1.00 | 26.29 |
| ATOM | 1109 | CB | GLU A | 173 | 53.800 | 52.506 | 26.235 | 1.00 | 30.21 |
| ATOM | 1110 | CG | GLU A | 173 | 53.738 | 53.624 | 27.267 | 1.00 | 38.62 |
| ATOM | 1111 | CD | GLU A | 173 | 52.659 | 53.398 | 28.323 | 1.00 | 43.67 |
| ATOM | 1112 | OE1 | GLU A | 173 | 52.386 | 54.338 | 29.103 | 1.00 | 44.97 |
| ATOM | 1113 | OE2 | GLU A | 173 | 52.089 | 52.283 | 28.380 | 1.00 | 45.74 |
| ATOM | 1114 | C | GLU A | 173 | 52.387 | 53.667 | 24.524 | 1.00 | 26.14 |
| ATOM | 1115 | O | GLU A | 173 | 51.782 | 54.643 | 24.964 | 1.00 | 25.40 |
| ATOM | 1116 | N | ASP A | 174 | 52.926 | 53.636 | 23.311 | 1.00 | 26.93 |
| ATOM | 1117 | CA | ASP A | 174 | 52.855 | 54.766 | 22.395 | 1.00 | 27.97 |
| ATOM | 1118 | CB | ASP A | 174 | 54.062 | 54.748 | 21.462 | 1.00 | 32.88 |
| ATOM | 1119 | CG | ASP A | 174 | 54.992 | 55.914 | 21.696 | 1.00 | 38.17 |
| ATOM | 1120 | OD1 | ASP A | 174 | 54.577 | 57.066 | 21.429 | 1.00 | 39.41 |
| ATOM | 1121 | OD2 | ASP A | 174 | 56.133 | 55.675 | 22.150 | 1.00 | 40.28 |
| ATOM | 1122 | C | ASP A | 174 | 51.576 | 54.795 | 21.556 | 1.00 | 26.80 |
| ATOM | 1123 | O | ASP A | 174 | 51.448 | 55.620 | 20.653 | 1.00 | 26.81 |
| ATOM | 1124 | N | GLY A | 175 | 50.642 | 53.891 | 21.841 | 1.00 | 24.53 |
| ATOM | 1125 | CA | GLY A | 175 | 49.397 | 53.864 | 21.092 | 1.00 | 23.66 |
| ATOM | 1126 | C | GLY A | 175 | 49.402 | 52.979 | 19.856 | 1.00 | 23.36 |
| ATOM | 1127 | O | GLY A | 175 | 48.568 | 53.153 | 18.967 | 1.00 | 23.88 |
| ATOM | 1128 | N | LEU A | 176 | 50.332 | 52.026 | 19.799 | 1.00 | 22.36 |
| ATOM | 1129 | CA | LEU A | 176 | 50.440 | 51.116 | 18.657 | 1.00 | 20.26 |
| ATOM | 1130 | CB | LEU A | 176 | 51.730 | 51.411 | 17.886 | 1.00 | 19.38 |
| ATOM | 1131 | CG | LEU A | 176 | 51.783 | 52.791 | 17.220 | 1.00 | 20.05 |
| ATOM | 1132 | CD1 | LEU A | 176 | 53.163 | 53.045 | 16.621 | 1.00 | 19.87 |
| ATOM | 1133 | CD2 | LEU A | 176 | 50.706 | 52.866 | 16.142 | 1.00 | 20.92 |
| ATOM | 1134 | C | LEU A | 176 | 50.419 | 49.654 | 19.110 | 1.00 | 19.21 |
| ATOM | 1135 | O | LEU A | 176 | 51.443 | 48.967 | 19.083 | 1.00 | 18.80 |

TABLE 30-continued

| | | | | | | | | |
|---|---|---|---|---|---|---|---|---|
| ATOM | 1136 | N | PRO A | 177 | 49.235 | 49.160 | 19.515 | 1.00 | 17.06 |
| ATOM | 1137 | CD | PRO A | 177 | 48.000 | 49.955 | 19.595 | 1.00 | 14.58 |
| ATOM | 1138 | CA | PRO A | 177 | 48.994 | 47.795 | 19.995 | 1.00 | 16.17 |
| ATOM | 1139 | CB | PRO A | 177 | 47.529 | 47.834 | 20.437 | 1.00 | 16.09 |
| ATOM | 1140 | CG | PRO A | 177 | 47.276 | 49.277 | 20.718 | 1.00 | 15.02 |
| ATOM | 1141 | C | PRO A | 177 | 49.252 | 46.660 | 18.998 | 1.00 | 16.11 |
| ATOM | 1142 | O | PRO A | 177 | 49.238 | 46.851 | 17.780 | 1.00 | 15.91 |
| ATOM | 1143 | N | LEU A | 178 | 49.469 | 45.471 | 19.549 | 1.00 | 14.60 |
| ATOM | 1144 | CA | LEU A | 178 | 49.725 | 44.272 | 18.768 | 1.00 | 15.30 |
| ATOM | 1145 | CB | LEU A | 178 | 51.126 | 43.735 | 19.072 | 1.00 | 13.15 |
| ATOM | 1146 | CG | LEU A | 178 | 51.497 | 42.403 | 18.417 | 1.00 | 14.53 |
| ATOM | 1147 | CD1 | LEU A | 178 | 51.552 | 42.587 | 16.908 | 1.00 | 13.70 |
| ATOM | 1148 | CD2 | LEU A | 178 | 52.843 | 41.914 | 18.945 | 1.00 | 10.81 |
| ATOM | 1149 | C | LEU A | 178 | 48.700 | 43.197 | 19.109 | 1.00 | 14.34 |
| ATOM | 1150 | O | LEU A | 178 | 48.451 | 42.913 | 20.277 | 1.00 | 16.02 |
| ATOM | 1151 | N | GLY A | 179 | 48.100 | 42.606 | 18.086 | 1.00 | 14.80 |
| ATOM | 1152 | CA | GLY A | 179 | 47.134 | 41.551 | 18.312 | 1.00 | 11.92 |
| ATOM | 1153 | C | GLY A | 179 | 47.677 | 40.287 | 17.677 | 1.00 | 13.13 |
| ATOM | 1154 | O | GLY A | 179 | 48.431 | 40.358 | 16.703 | 1.00 | 11.81 |
| ATOM | 1155 | N | VAL A | 180 | 47.320 | 39.136 | 18.237 | 1.00 | 12.90 |
| ATOM | 1156 | CA | VAL A | 180 | 47.758 | 37.855 | 17.701 | 1.00 | 12.61 |
| ATOM | 1157 | CB | VAL A | 180 | 48.702 | 37.128 | 18.671 | 1.00 | 13.26 |
| ATOM | 1158 | CG1 | VAL A | 180 | 49.023 | 35.738 | 18.132 | 1.00 | 11.53 |
| ATOM | 1159 | CG2 | VAL A | 180 | 49.983 | 37.938 | 18.846 | 1.00 | 14.43 |
| ATOM | 1160 | C | VAL A | 180 | 46.534 | 36.986 | 17.436 | 1.00 | 14.18 |
| ATOM | 1161 | O | VAL A | 180 | 45.710 | 36.758 | 18.326 | 1.00 | 14.98 |
| ATOM | 1162 | N | ASN A | 181 | 46.421 | 36.513 | 16.200 | 1.00 | 14.07 |
| ATOM | 1163 | CA | ASN A | 181 | 45.293 | 35.696 | 15.774 | 1.00 | 15.82 |
| ATOM | 1164 | CB | ASN A | 181 | 44.929 | 36.081 | 14.335 | 1.00 | 16.86 |
| ATOM | 1165 | CG | ASN A | 181 | 43.629 | 35.469 | 13.868 | 1.00 | 18.54 |
| ATOM | 1166 | OD1 | ASN A | 181 | 43.430 | 34.254 | 13.948 | 1.00 | 16.81 |
| ATOM | 1167 | ND2 | ASN A | 181 | 42.734 | 36.313 | 13.356 | 1.00 | 18.07 |
| ATOM | 1168 | C | ASN A | 181 | 45.656 | 34.209 | 15.870 | 1.00 | 16.41 |
| ATOM | 1169 | O | ASN A | 181 | 46.649 | 33.767 | 15.290 | 1.00 | 16.63 |
| ATOM | 1170 | N | LEU A | 182 | 44.838 | 33.448 | 16.595 | 1.00 | 15.13 |
| ATOM | 1171 | CA | LEU A | 182 | 45.070 | 32.023 | 16.807 | 1.00 | 16.25 |
| ATOM | 1172 | CB | LEU A | 182 | 44.865 | 31.684 | 18.284 | 1.00 | 15.13 |
| ATOM | 1173 | CG | LEU A | 182 | 45.680 | 32.500 | 19.285 | 1.00 | 16.55 |
| ATOM | 1174 | CD1 | LEU A | 182 | 45.267 | 32.128 | 20.704 | 1.00 | 14.83 |
| ATOM | 1175 | CD2 | LEU A | 182 | 47.163 | 32.246 | 19.060 | 1.00 | 15.51 |
| ATOM | 1176 | C | LEU A | 182 | 44.185 | 31.102 | 15.970 | 1.00 | 16.80 |
| ATOM | 1177 | O | LEU A | 182 | 42.981 | 31.307 | 15.857 | 1.00 | 18.12 |
| ATOM | 1178 | N | GLY A | 183 | 44.802 | 30.078 | 15.397 | 1.00 | 17.17 |
| ATOM | 1179 | CA | GLY A | 183 | 44.073 | 29.118 | 14.594 | 1.00 | 17.88 |
| ATOM | 1180 | C | GLY A | 183 | 44.345 | 27.738 | 15.160 | 1.00 | 19.65 |
| ATOM | 1181 | O | GLY A | 183 | 44.918 | 27.605 | 16.244 | 1.00 | 18.50 |
| ATOM | 1182 | N | LYS A | 184 | 43.939 | 26.702 | 14.441 | 1.00 | 20.40 |
| ATOM | 1183 | CA | LYS A | 184 | 44.174 | 25.353 | 14.921 | 1.00 | 22.00 |
| ATOM | 1184 | CB | LYS A | 184 | 42.895 | 24.767 | 15.529 | 1.00 | 23.77 |
| ATOM | 1185 | CG | LYS A | 184 | 41.908 | 24.238 | 14.518 | 1.00 | 27.06 |
| ATOM | 1186 | CD | LYS A | 184 | 40.885 | 23.350 | 15.198 | 1.00 | 31.45 |
| ATOM | 1187 | CE | LYS A | 184 | 40.161 | 22.473 | 14.186 | 1.00 | 34.64 |
| ATOM | 1188 | NZ | LYS A | 184 | 41.100 | 21.535 | 13.509 | 1.00 | 34.99 |
| ATOM | 1189 | C | LYS A | 184 | 44.677 | 24.470 | 13.791 | 1.00 | 20.60 |
| ATOM | 1190 | O | LYS A | 184 | 44.382 | 24.705 | 12.624 | 1.00 | 21.08 |
| ATOM | 1191 | N | ASN A | 185 | 45.449 | 23.454 | 14.146 | 1.00 | 21.53 |
| ATOM | 1192 | CA | ASN A | 185 | 46.000 | 22.545 | 13.157 | 1.00 | 22.66 |
| ATOM | 1193 | CB | ASN A | 185 | 47.050 | 21.643 | 13.804 | 1.00 | 20.05 |
| ATOM | 1194 | CG | ASN A | 185 | 48.367 | 22.358 | 14.035 | 1.00 | 19.87 |
| ATOM | 1195 | OD1 | ASN A | 185 | 48.806 | 22.523 | 15.172 | 1.00 | 20.27 |
| ATOM | 1196 | ND2 | ASN A | 185 | 49.006 | 22.781 | 12.952 | 1.00 | 18.79 |
| ATOM | 1197 | C | ASN A | 185 | 44.945 | 21.689 | 12.464 | 1.00 | 24.39 |
| ATOM | 1198 | O | ASN A | 185 | 43.932 | 21.308 | 13.058 | 1.00 | 23.03 |
| ATOM | 1199 | N | LYS A | 186 | 45.209 | 21.385 | 11.198 | 1.00 | 27.14 |
| ATOM | 1200 | CA | LYS A | 186 | 44.319 | 20.572 | 10.385 | 1.00 | 29.82 |
| ATOM | 1201 | CB | LYS A | 186 | 44.908 | 20.425 | 8.982 | 1.00 | 30.42 |
| ATOM | 1202 | CG | LYS A | 186 | 44.080 | 19.567 | 8.044 | 1.00 | 33.06 |
| ATOM | 1203 | CD | LYS A | 186 | 44.744 | 19.470 | 6.687 | 1.00 | 35.37 |
| ATOM | 1204 | CE | LYS A | 186 | 43.899 | 18.682 | 5.706 | 1.00 | 36.58 |
| ATOM | 1205 | NZ | LYS A | 186 | 44.566 | 18.585 | 4.374 | 1.00 | 38.37 |
| ATOM | 1206 | C | LYS A | 186 | 44.061 | 19.184 | 10.980 | 1.00 | 31.17 |
| ATOM | 1207 | O | LYS A | 186 | 42.924 | 18.719 | 11.006 | 1.00 | 31.03 |
| ATOM | 1208 | N | THR A | 187 | 45.113 | 18.527 | 11.460 | 1.00 | 33.25 |
| ATOM | 1209 | CA | THR A | 187 | 44.974 | 17.186 | 12.027 | 1.00 | 36.04 |
| ATOM | 1210 | CB | THR A | 187 | 46.211 | 16.316 | 11.719 | 1.00 | 36.38 |
| ATOM | 1211 | OG1 | THR A | 187 | 47.351 | 16.838 | 12.416 | 1.00 | 35.74 |
| ATOM | 1212 | CG2 | THR A | 187 | 46.489 | 16.300 | 10.216 | 1.00 | 35.36 |
| ATOM | 1213 | C | THR A | 187 | 44.755 | 17.181 | 13.537 | 1.00 | 37.75 |
| ATOM | 1214 | O | THR A | 187 | 44.844 | 16.134 | 14.182 | 1.00 | 39.15 |

TABLE 30-continued

| | | | | | | | | |
|---|---|---|---|---|---|---|---|---|
| ATOM | 1215 | N | SER A | 188 | 44.474 | 18.349 | 14.100 | 1.00 | 38.10 |
| ATOM | 1216 | CA | SER A | 188 | 44.233 | 18.451 | 15.530 | 1.00 | 37.99 |
| ATOM | 1217 | CB | SER A | 188 | 44.062 | 19.915 | 15.929 | 1.00 | 37.74 |
| ATOM | 1218 | OG | SER A | 188 | 43.772 | 20.028 | 17.309 | 1.00 | 39.67 |
| ATOM | 1219 | C | SER A | 188 | 42.977 | 17.666 | 15.899 | 1.00 | 38.60 |
| ATOM | 1220 | O | SER A | 188 | 42.034 | 17.586 | 15.113 | 1.00 | 37.87 |
| ATOM | 1221 | N | VAL A | 189 | 42.971 | 17.088 | 17.097 | 1.00 | 39.17 |
| ATOM | 1222 | CA | VAL A | 189 | 41.830 | 16.313 | 17.576 | 1.00 | 40.90 |
| ATOM | 1223 | CB | VAL A | 189 | 42.290 | 14.987 | 18.225 | 1.00 | 42.04 |
| ATOM | 1224 | CG1 | VAL A | 189 | 41.117 | 14.308 | 18.903 | 1.00 | 42.79 |
| ATOM | 1225 | CG2 | VAL A | 189 | 42.890 | 14.068 | 17.168 | 1.00 | 41.83 |
| ATOM | 1226 | C | VAL A | 189 | 41.024 | 17.101 | 18.607 | 1.00 | 41.62 |
| ATOM | 1227 | O | VAL A | 189 | 39.803 | 16.950 | 18.708 | 1.00 | 43.26 |
| ATOM | 1228 | N | ASP A | 190 | 41.714 | 17.947 | 19.366 | 1.00 | 40.63 |
| ATOM | 1229 | CA | ASP A | 190 | 41.078 | 18.761 | 20.396 | 1.00 | 39.16 |
| ATOM | 1230 | CB | ASP A | 190 | 41.755 | 18.507 | 21.745 | 1.00 | 41.81 |
| ATOM | 1231 | CG | ASP A | 190 | 40.974 | 19.080 | 22.907 | 1.00 | 44.27 |
| ATOM | 1232 | OD1 | ASP A | 190 | 40.345 | 20.147 | 22.741 | 1.00 | 44.15 |
| ATOM | 1233 | OD2 | ASP A | 190 | 41.000 | 18.468 | 23.995 | 1.00 | 48.15 |
| ATOM | 1234 | C | ASP A | 190 | 41.201 | 20.242 | 20.036 | 1.00 | 37.02 |
| ATOM | 1235 | O | ASP A | 190 | 42.176 | 20.899 | 20.409 | 1.00 | 36.48 |
| ATOM | 1236 | N | ALA A | 191 | 40.210 | 20.763 | 19.318 | 1.00 | 33.89 |
| ATOM | 1237 | CA | ALA A | 191 | 40.214 | 22.162 | 18.899 | 1.00 | 30.62 |
| ATOM | 1238 | CB | ALA A | 191 | 38.896 | 22.505 | 18.218 | 1.00 | 30.65 |
| ATOM | 1239 | C | ALA A | 191 | 40.458 | 23.120 | 20.055 | 1.00 | 28.69 |
| ATOM | 1240 | O | ALA A | 191 | 41.217 | 24.077 | 19.926 | 1.00 | 26.95 |
| ATOM | 1241 | N | ALA A | 192 | 39.809 | 22.860 | 21.185 | 1.00 | 27.16 |
| ATOM | 1242 | CA | ALA A | 192 | 39.952 | 23.713 | 22.359 | 1.00 | 25.90 |
| ATOM | 1243 | CB | ALA A | 192 | 39.019 | 23.237 | 23.467 | 1.00 | 23.51 |
| ATOM | 1244 | C | ALA A | 192 | 41.389 | 23.758 | 22.866 | 1.00 | 25.40 |
| ATOM | 1245 | O | ALA A | 192 | 41.880 | 24.821 | 23.231 | 1.00 | 27.26 |
| ATOM | 1246 | N | GLU A | 193 | 42.062 | 22.610 | 22.890 | 1.00 | 25.06 |
| ATOM | 1247 | CA | GLU A | 193 | 43.442 | 22.555 | 23.359 | 1.00 | 25.56 |
| ATOM | 1248 | CB | GLU A | 193 | 43.925 | 21.103 | 23.449 | 1.00 | 28.82 |
| ATOM | 1249 | CG | GLU A | 193 | 45.366 | 20.970 | 23.923 | 1.00 | 33.91 |
| ATOM | 1250 | CD | GLU A | 193 | 45.599 | 21.600 | 25.290 | 1.00 | 38.03 |
| ATOM | 1251 | OE1 | GLU A | 193 | 46.776 | 21.781 | 25.672 | 1.00 | 40.48 |
| ATOM | 1252 | OE2 | GLU A | 193 | 44.607 | 21.909 | 25.986 | 1.00 | 40.31 |
| ATOM | 1253 | C | GLU A | 193 | 44.371 | 23.363 | 22.451 | 1.00 | 24.11 |
| ATOM | 1254 | O | GLU A | 193 | 45.293 | 24.025 | 22.931 | 1.00 | 23.27 |
| ATOM | 1255 | N | ASP A | 194 | 44.124 | 23.308 | 21.145 | 1.00 | 21.29 |
| ATOM | 1256 | CA | ASP A | 194 | 44.919 | 24.062 | 20.179 | 1.00 | 21.47 |
| ATOM | 1257 | CB | ASP A | 194 | 44.370 | 23.860 | 18.762 | 1.00 | 22.50 |
| ATOM | 1258 | CG | ASP A | 194 | 45.052 | 22.725 | 18.025 | 1.00 | 22.41 |
| ATOM | 1259 | OD1 | ASP A | 194 | 45.566 | 21.806 | 18.686 | 1.00 | 25.90 |
| ATOM | 1260 | OD2 | ASP A | 194 | 45.068 | 22.746 | 16.776 | 1.00 | 24.02 |
| ATOM | 1261 | C | ASP A | 194 | 44.905 | 25.554 | 20.523 | 1.00 | 21.24 |
| ATOM | 1262 | O | ASP A | 194 | 45.957 | 26.199 | 20.556 | 1.00 | 21.63 |
| ATOM | 1263 | N | TYR A | 195 | 43.718 | 26.104 | 20.773 | 1.00 | 19.11 |
| ATOM | 1264 | CA | TYR A | 195 | 43.615 | 27.517 | 21.118 | 1.00 | 19.37 |
| ATOM | 1265 | CB | TYR A | 195 | 42.157 | 27.996 | 21.078 | 1.00 | 18.34 |
| ATOM | 1266 | CG | TYR A | 195 | 41.555 | 27.995 | 19.692 | 1.00 | 19.08 |
| ATOM | 1267 | CD1 | TYR A | 195 | 40.775 | 26.935 | 19.252 | 1.00 | 18.54 |
| ATOM | 1268 | CE1 | TYR A | 195 | 40.267 | 26.906 | 17.972 | 1.00 | 19.33 |
| ATOM | 1269 | CD2 | TYR A | 195 | 41.808 | 29.034 | 18.806 | 1.00 | 19.55 |
| ATOM | 1270 | CE2 | TYR A | 195 | 41.303 | 29.013 | 17.518 | 1.00 | 19.90 |
| ATOM | 1271 | CZ | TYR A | 195 | 40.535 | 27.946 | 17.108 | 1.00 | 20.74 |
| ATOM | 1272 | OH | TYR A | 195 | 40.041 | 27.910 | 15.823 | 1.00 | 21.90 |
| ATOM | 1273 | C | TYR A | 195 | 44.197 | 27.759 | 22.500 | 1.00 | 18.97 |
| ATOM | 1274 | O | TYR A | 195 | 44.819 | 28.791 | 22.745 | 1.00 | 19.13 |
| ATOM | 1275 | N | ALA A | 196 | 43.993 | 26.806 | 23.404 | 1.00 | 18.98 |
| ATOM | 1276 | CA | ALA A | 196 | 44.518 | 26.925 | 24.759 | 1.00 | 19.56 |
| ATOM | 1277 | CB | ALA A | 196 | 44.132 | 25.705 | 25.581 | 1.00 | 19.04 |
| ATOM | 1278 | C | ALA A | 196 | 46.040 | 27.062 | 24.699 | 1.00 | 19.48 |
| ATOM | 1279 | O | ALA A | 196 | 46.625 | 27.874 | 25.419 | 1.00 | 19.62 |
| ATOM | 1280 | N | GLU A | 197 | 46.670 | 26.271 | 23.834 | 1.00 | 18.28 |
| ATOM | 1281 | CA | GLU A | 197 | 48.120 | 26.312 | 23.671 | 1.00 | 21.11 |
| ATOM | 1282 | CB | GLU A | 197 | 48.592 | 25.208 | 22.716 | 1.00 | 25.12 |
| ATOM | 1283 | CG | GLU A | 197 | 48.254 | 23.800 | 23.169 | 1.00 | 34.80 |
| ATOM | 1284 | CD | GLU A | 197 | 48.965 | 22.741 | 22.346 | 1.00 | 40.02 |
| ATOM | 1285 | OE1 | GLU A | 197 | 48.613 | 21.546 | 22.466 | 1.00 | 41.16 |
| ATOM | 1286 | OE2 | GLU A | 197 | 49.885 | 23.106 | 21.583 | 1.00 | 44.59 |
| ATOM | 1287 | C | GLU A | 197 | 48.557 | 27.668 | 23.129 | 1.00 | 19.25 |
| ATOM | 1288 | O | GLU A | 197 | 49.545 | 28.242 | 23.595 | 1.00 | 17.18 |
| ATOM | 1289 | N | GLY A | 198 | 47.819 | 28.170 | 22.141 | 1.00 | 16.72 |
| ATOM | 1290 | CA | GLY A | 198 | 48.136 | 29.461 | 21.560 | 1.00 | 16.16 |
| ATOM | 1291 | C | GLY A | 198 | 48.061 | 30.570 | 22.594 | 1.00 | 15.20 |
| ATOM | 1292 | O | GLY A | 198 | 48.885 | 31.485 | 22.603 | 1.00 | 14.79 |
| ATOM | 1293 | N | VAL A | 199 | 47.063 | 30.489 | 23.466 | 1.00 | 15.52 |

TABLE 30-continued

| | | | | | | | | |
|---|---|---|---|---|---|---|---|---|
| ATOM | 1294 | CA | VAL A | 199 | 46.884 | 31.477 | 24.520 | 1.00 | 15.90 |
| ATOM | 1295 | CB | VAL A | 199 | 45.622 | 31.184 | 25.361 | 1.00 | 16.38 |
| ATOM | 1296 | CG1 | VAL A | 199 | 45.625 | 32.046 | 26.619 | 1.00 | 12.29 |
| ATOM | 1297 | CG2 | VAL A | 199 | 44.368 | 31.442 | 24.530 | 1.00 | 16.31 |
| ATOM | 1298 | C | VAL A | 199 | 48.085 | 31.465 | 25.458 | 1.00 | 18.10 |
| ATOM | 1299 | O | VAL A | 199 | 48.575 | 32.519 | 25.867 | 1.00 | 19.32 |
| ATOM | 1300 | N | ARG A | 200 | 48.564 | 30.269 | 25.786 | 1.00 | 17.75 |
| ATOM | 1301 | CA | ARG A | 200 | 49.699 | 30.129 | 26.691 | 1.00 | 20.29 |
| ATOM | 1302 | CB | ARG A | 200 | 49.814 | 28.683 | 27.186 | 1.00 | 22.43 |
| ATOM | 1303 | CG | ARG A | 200 | 48.752 | 28.276 | 28.191 | 1.00 | 25.39 |
| ATOM | 1304 | CD | ARG A | 200 | 49.160 | 27.005 | 28.914 | 1.00 | 26.71 |
| ATOM | 1305 | NE | ARG A | 200 | 49.080 | 25.828 | 28.060 | 1.00 | 28.79 |
| ATOM | 1306 | CZ | ARG A | 200 | 47.967 | 25.134 | 27.859 | 1.00 | 30.88 |
| ATOM | 1307 | NH1 | ARG A | 200 | 46.846 | 25.505 | 28.457 | 1.00 | 32.47 |
| ATOM | 1308 | NH2 | ARG A | 200 | 47.973 | 24.071 | 27.063 | 1.00 | 31.75 |
| ATOM | 1309 | C | ARG A | 200 | 51.039 | 30.551 | 26.106 | 1.00 | 19.06 |
| ATOM | 1310 | O | ARG A | 200 | 51.873 | 31.128 | 26.805 | 1.00 | 19.67 |
| ATOM | 1311 | N | VAL A | 201 | 51.249 | 30.267 | 24.826 | 1.00 | 17.35 |
| ATOM | 1312 | CA | VAL A | 201 | 52.514 | 30.599 | 24.189 | 1.00 | 14.77 |
| ATOM | 1313 | CB | VAL A | 201 | 52.828 | 29.606 | 23.044 | 1.00 | 15.43 |
| ATOM | 1314 | CG1 | VAL A | 201 | 54.145 | 29.990 | 22.369 | 1.00 | 13.31 |
| ATOM | 1315 | CG2 | VAL A | 201 | 52.906 | 28.177 | 23.596 | 1.00 | 9.07 |
| ATOM | 1316 | C | VAL A | 201 | 52.618 | 32.027 | 23.652 | 1.00 | 16.34 |
| ATOM | 1317 | O | VAL A | 201 | 53.651 | 32.680 | 23.826 | 1.00 | 13.79 |
| ATOM | 1318 | N | LEU A | 202 | 51.556 | 32.520 | 23.016 | 1.00 | 16.01 |
| ATOM | 1319 | CA | LEU A | 202 | 51.590 | 33.867 | 22.453 | 1.00 | 14.71 |
| ATOM | 1320 | CB | LEU A | 202 | 51.104 | 33.840 | 21.003 | 1.00 | 15.87 |
| ATOM | 1321 | CG | LEU A | 202 | 51.994 | 33.063 | 20.029 | 1.00 | 16.57 |
| ATOM | 1322 | CD1 | LEU A | 202 | 51.515 | 33.304 | 18.603 | 1.00 | 15.39 |
| ATOM | 1323 | CD2 | LEU A | 202 | 53.444 | 33.510 | 20.185 | 1.00 | 15.53 |
| ATOM | 1324 | C | LEU A | 202 | 50.815 | 34.924 | 23.235 | 1.00 | 15.25 |
| ATOM | 1325 | O | LEU A | 202 | 51.056 | 36.117 | 23.070 | 1.00 | 14.50 |
| ATOM | 1326 | N | GLY A | 203 | 49.890 | 34.492 | 24.084 | 1.00 | 15.32 |
| ATOM | 1327 | CA | GLY A | 203 | 49.128 | 35.441 | 24.873 | 1.00 | 16.45 |
| ATOM | 1328 | C | GLY A | 203 | 49.993 | 36.407 | 25.672 | 1.00 | 16.99 |
| ATOM | 1329 | O | GLY A | 203 | 49.628 | 37.574 | 25.838 | 1.00 | 14.26 |
| ATOM | 1330 | N | PRO A | 204 | 51.145 | 35.954 | 26.193 | 1.00 | 18.28 |
| ATOM | 1331 | CD | PRO A | 204 | 51.566 | 34.547 | 26.321 | 1.00 | 17.79 |
| ATOM | 1332 | CA | PRO A | 204 | 52.029 | 36.831 | 26.975 | 1.00 | 18.93 |
| ATOM | 1333 | CB | PRO A | 204 | 53.021 | 35.849 | 27.608 | 1.00 | 16.96 |
| ATOM | 1334 | CG | PRO A | 204 | 52.257 | 34.552 | 27.654 | 1.00 | 17.70 |
| ATOM | 1335 | C | PRO A | 204 | 52.744 | 37.892 | 26.132 | 1.00 | 18.89 |
| ATOM | 1336 | O | PRO A | 204 | 53.331 | 38.836 | 26.672 | 1.00 | 20.25 |
| ATOM | 1337 | N | LEU A | 205 | 52.689 | 37.736 | 24.812 | 1.00 | 17.55 |
| ATOM | 1338 | CA | LEU A | 205 | 53.351 | 38.669 | 23.898 | 1.00 | 16.80 |
| ATOM | 1339 | CB | LEU A | 205 | 54.220 | 37.883 | 22.910 | 1.00 | 16.30 |
| ATOM | 1340 | CG | LEU A | 205 | 55.394 | 37.098 | 23.508 | 1.00 | 18.10 |
| ATOM | 1341 | CD1 | LEU A | 205 | 55.731 | 35.902 | 22.640 | 1.00 | 15.74 |
| ATOM | 1342 | CD2 | LEU A | 205 | 56.589 | 38.023 | 23.657 | 1.00 | 17.13 |
| ATOM | 1343 | C | LEU A | 205 | 52.389 | 39.562 | 23.113 | 1.00 | 17.23 |
| ATOM | 1344 | O | LEU A | 205 | 52.815 | 40.337 | 22.256 | 1.00 | 16.66 |
| ATOM | 1345 | N | ALA A | 206 | 51.097 | 39.471 | 23.413 | 1.00 | 16.47 |
| ATOM | 1346 | CA | ALA A | 206 | 50.111 | 40.254 | 22.684 | 1.00 | 16.01 |
| ATOM | 1347 | CB | ALA A | 206 | 49.215 | 39.315 | 21.890 | 1.00 | 16.02 |
| ATOM | 1348 | C | ALA A | 206 | 49.253 | 41.173 | 23.536 | 1.00 | 16.71 |
| ATOM | 1349 | O | ALA A | 206 | 49.019 | 40.921 | 24.715 | 1.00 | 17.69 |
| ATOM | 1350 | N | ASP A | 207 | 48.782 | 42.253 | 22.928 | 1.00 | 17.04 |
| ATOM | 1351 | CA | ASP A | 207 | 47.909 | 43.171 | 23.635 | 1.00 | 17.84 |
| ATOM | 1352 | CB | ASP A | 207 | 47.940 | 44.546 | 22.977 | 1.00 | 17.96 |
| ATOM | 1353 | CG | ASP A | 207 | 49.256 | 45.264 | 23.222 | 1.00 | 20.68 |
| ATOM | 1354 | OD1 | ASP A | 207 | 49.642 | 45.391 | 24.403 | 1.00 | 22.88 |
| ATOM | 1355 | OD2 | ASP A | 207 | 49.907 | 45.698 | 22.250 | 1.00 | 20.09 |
| ATOM | 1356 | C | ASP A | 207 | 46.515 | 42.552 | 23.601 | 1.00 | 16.42 |
| ATOM | 1357 | O | ASP A | 207 | 45.732 | 42.708 | 24.530 | 1.00 | 16.76 |
| ATOM | 1358 | N | TYR A | 208 | 46.217 | 41.833 | 22.525 | 1.00 | 15.49 |
| ATOM | 1359 | CA | TYR A | 208 | 44.941 | 41.145 | 22.412 | 1.00 | 15.74 |
| ATOM | 1360 | CB | TYR A | 208 | 43.844 | 42.052 | 21.815 | 1.00 | 15.84 |
| ATOM | 1361 | CG | TYR A | 208 | 43.919 | 42.333 | 20.326 | 1.00 | 16.08 |
| ATOM | 1362 | CD1 | TYR A | 208 | 44.387 | 43.558 | 19.852 | 1.00 | 16.67 |
| ATOM | 1363 | CE1 | TYR A | 208 | 44.400 | 43.846 | 18.496 | 1.00 | 16.45 |
| ATOM | 1364 | CD2 | TYR A | 208 | 43.471 | 41.399 | 19.396 | 1.00 | 15.39 |
| ATOM | 1365 | CE2 | TYR A | 208 | 43.483 | 41.675 | 18.037 | 1.00 | 14.91 |
| ATOM | 1366 | CZ | TYR A | 208 | 43.947 | 42.900 | 17.593 | 1.00 | 18.55 |
| ATOM | 1367 | OH | TYR A | 208 | 43.966 | 43.179 | 16.243 | 1.00 | 18.49 |
| ATOM | 1368 | C | TYR A | 208 | 45.106 | 39.887 | 21.575 | 1.00 | 15.90 |
| ATOM | 1369 | O | TYR A | 208 | 45.915 | 39.845 | 20.646 | 1.00 | 15.17 |
| ATOM | 1370 | N | LEU A | 209 | 44.355 | 38.853 | 21.940 | 1.00 | 16.34 |
| ATOM | 1371 | CA | LEU A | 209 | 44.382 | 37.580 | 21.235 | 1.00 | 17.24 |
| ATOM | 1372 | CB | LEU A | 209 | 44.520 | 36.418 | 22.217 | 1.00 | 16.47 |

TABLE 30-continued

| ATOM | 1373 | CG  | LEU A | 209 | 45.855 | 36.203 | 22.920 | 1.00 | 17.92 |
| ---- | ---- | --- | ----- | --- | ------ | ------ | ------ | ---- | ----- |
| ATOM | 1374 | CD1 | LEU A | 209 | 45.716 | 35.042 | 23.899 | 1.00 | 18.62 |
| ATOM | 1375 | CD2 | LEU A | 209 | 46.942 | 35.917 | 21.889 | 1.00 | 15.83 |
| ATOM | 1376 | C   | LEU A | 209 | 43.077 | 37.420 | 20.472 | 1.00 | 16.93 |
| ATOM | 1377 | O   | LEU A | 209 | 42.031 | 37.890 | 20.914 | 1.00 | 16.94 |
| ATOM | 1378 | N   | VAL A | 210 | 43.142 | 36.749 | 19.330 | 1.00 | 18.06 |
| ATOM | 1379 | CA  | VAL A | 210 | 41.955 | 36.527 | 18.523 | 1.00 | 16.88 |
| ATOM | 1380 | CB  | VAL A | 210 | 42.096 | 37.153 | 17.119 | 1.00 | 16.81 |
| ATOM | 1381 | CG1 | VAL A | 210 | 40.811 | 36.928 | 16.310 | 1.00 | 14.14 |
| ATOM | 1382 | CG2 | VAL A | 210 | 42.414 | 38.631 | 17.239 | 1.00 | 12.93 |
| ATOM | 1383 | C   | VAL A | 210 | 41.683 | 35.045 | 18.338 | 1.00 | 17.75 |
| ATOM | 1384 | O   | VAL A | 210 | 42.509 | 34.318 | 17.794 | 1.00 | 18.14 |
| ATOM | 1385 | N   | VAL A | 211 | 40.531 | 34.592 | 18.813 | 1.00 | 18.47 |
| ATOM | 1386 | CA  | VAL A | 211 | 40.155 | 33.199 | 18.629 | 1.00 | 18.41 |
| ATOM | 1387 | CB  | VAL A | 211 | 39.128 | 32.731 | 19.682 | 1.00 | 16.92 |
| ATOM | 1388 | CG1 | VAL A | 211 | 38.707 | 31.304 | 19.389 | 1.00 | 13.30 |
| ATOM | 1389 | CG2 | VAL A | 211 | 39.725 | 32.832 | 21.079 | 1.00 | 16.37 |
| ATOM | 1390 | C   | VAL A | 211 | 39.501 | 33.158 | 17.247 | 1.00 | 19.20 |
| ATOM | 1391 | O   | VAL A | 211 | 38.338 | 33.534 | 17.090 | 1.00 | 17.95 |
| ATOM | 1392 | N   | ASN A | 212 | 40.258 | 32.729 | 16.243 | 1.00 | 19.49 |
| ATOM | 1393 | CA  | ASN A | 212 | 39.721 | 32.661 | 14.896 | 1.00 | 20.70 |
| ATOM | 1394 | CB  | ASN A | 212 | 40.834 | 32.722 | 13.854 | 1.00 | 19.05 |
| ATOM | 1395 | CG  | ASN A | 212 | 40.291 | 32.666 | 12.444 | 1.00 | 18.45 |
| ATOM | 1396 | OD1 | ASN A | 212 | 39.081 | 32.697 | 12.243 | 1.00 | 19.17 |
| ATOM | 1397 | ND2 | ASN A | 212 | 41.177 | 32.585 | 11.463 | 1.00 | 18.72 |
| ATOM | 1398 | C   | ASN A | 212 | 38.925 | 31.381 | 14.712 | 1.00 | 22.66 |
| ATOM | 1399 | O   | ASN A | 212 | 39.484 | 30.282 | 14.621 | 1.00 | 23.43 |
| ATOM | 1400 | N   | VAL A | 213 | 37.611 | 31.529 | 14.646 | 1.00 | 21.15 |
| ATOM | 1401 | CA  | VAL A | 213 | 36.745 | 30.379 | 14.489 | 1.00 | 22.75 |
| ATOM | 1402 | CB  | VAL A | 213 | 35.893 | 30.194 | 15.760 | 1.00 | 23.97 |
| ATOM | 1403 | CG1 | VAL A | 213 | 34.781 | 31.241 | 15.810 | 1.00 | 23.80 |
| ATOM | 1404 | CG2 | VAL A | 213 | 35.341 | 28.810 | 15.799 | 1.00 | 27.69 |
| ATOM | 1405 | C   | VAL A | 213 | 35.841 | 30.572 | 13.272 | 1.00 | 21.59 |
| ATOM | 1406 | O   | VAL A | 213 | 34.820 | 29.893 | 13.120 | 1.00 | 21.53 |
| ATOM | 1407 | N   | SER A | 214 | 36.242 | 31.492 | 12.397 | 1.00 | 20.91 |
| ATOM | 1408 | CA  | SER A | 214 | 35.469 | 31.813 | 11.206 | 1.00 | 19.69 |
| ATOM | 1409 | CB  | SER A | 214 | 35.015 | 33.275 | 11.267 | 1.00 | 19.18 |
| ATOM | 1410 | OG  | SER A | 214 | 36.110 | 34.144 | 11.508 | 1.00 | 14.56 |
| ATOM | 1411 | C   | SER A | 214 | 36.180 | 31.556 | 9.881  | 1.00 | 20.92 |
| ATOM | 1412 | O   | SER A | 214 | 35.712 | 31.996 | 8.832  | 1.00 | 19.05 |
| ATOM | 1413 | N   | SER A | 215 | 37.309 | 30.856 | 9.914  | 1.00 | 22.56 |
| ATOM | 1414 | CA  | SER A | 215 | 38.010 | 30.563 | 8.672  | 1.00 | 23.82 |
| ATOM | 1415 | CB  | SER A | 215 | 39.385 | 29.968 | 8.945  | 1.00 | 25.73 |
| ATOM | 1416 | OG  | SER A | 215 | 40.010 | 29.597 | 7.726  | 1.00 | 25.27 |
| ATOM | 1417 | C   | SER A | 215 | 37.186 | 29.564 | 7.867  | 1.00 | 24.98 |
| ATOM | 1418 | O   | SER A | 215 | 36.744 | 28.539 | 8.387  | 1.00 | 25.15 |
| ATOM | 1419 | N   | PRO A | 216 | 36.961 | 29.857 | 6.582  | 1.00 | 26.90 |
| ATOM | 1420 | CD  | PRO A | 216 | 37.238 | 31.138 | 5.900  | 1.00 | 24.99 |
| ATOM | 1421 | CA  | PRO A | 216 | 36.182 | 28.963 | 5.721  | 1.00 | 27.74 |
| ATOM | 1422 | CB  | PRO A | 216 | 35.606 | 29.920 | 4.690  | 1.00 | 27.00 |
| ATOM | 1423 | CG  | PRO A | 216 | 36.755 | 30.872 | 4.482  | 1.00 | 25.45 |
| ATOM | 1424 | C   | PRO A | 216 | 37.045 | 27.895 | 5.066  | 1.00 | 29.18 |
| ATOM | 1425 | O   | PRO A | 216 | 36.531 | 27.026 | 4.368  | 1.00 | 30.98 |
| ATOM | 1426 | N   | ASN A | 217 | 38.353 | 27.958 | 5.302  | 1.00 | 30.72 |
| ATOM | 1427 | CA  | ASN A | 217 | 39.283 | 27.022 | 4.679  | 1.00 | 32.10 |
| ATOM | 1428 | CB  | ASN A | 217 | 40.446 | 27.804 | 4.072  | 1.00 | 31.89 |
| ATOM | 1429 | CG  | ASN A | 217 | 39.971 | 28.926 | 3.170  | 1.00 | 33.35 |
| ATOM | 1430 | OD1 | ASN A | 217 | 39.220 | 28.696 | 2.220  | 1.00 | 33.84 |
| ATOM | 1431 | ND2 | ASN A | 217 | 40.400 | 30.149 | 3.465  | 1.00 | 32.31 |
| ATOM | 1432 | C   | ASN A | 217 | 39.814 | 25.889 | 5.548  | 1.00 | 33.08 |
| ATOM | 1433 | O   | ASN A | 217 | 40.812 | 25.250 | 5.204  | 1.00 | 32.64 |
| ATOM | 1434 | N   | THR A | 218 | 39.149 | 25.644 | 6.671  | 1.00 | 34.23 |
| ATOM | 1435 | CA  | THR A | 218 | 39.523 | 24.556 | 7.570  | 1.00 | 35.11 |
| ATOM | 1436 | CB  | THR A | 218 | 40.191 | 25.073 | 8.867  | 1.00 | 35.66 |
| ATOM | 1437 | OG1 | THR A | 218 | 41.508 | 25.556 | 8.568  | 1.00 | 34.06 |
| ATOM | 1438 | CG2 | THR A | 218 | 40.293 | 23.956 | 9.895  | 1.00 | 33.99 |
| ATOM | 1439 | C   | THR A | 218 | 38.243 | 23.801 | 7.915  | 1.00 | 35.83 |
| ATOM | 1440 | O   | THR A | 218 | 37.315 | 24.367 | 8.497  | 1.00 | 36.15 |
| ATOM | 1441 | N   | ALA A | 219 | 38.200 | 22.526 | 7.532  | 1.00 | 36.11 |
| ATOM | 1442 | CA  | ALA A | 219 | 37.041 | 21.666 | 7.760  | 1.00 | 35.60 |
| ATOM | 1443 | CB  | ALA A | 219 | 37.372 | 20.234 | 7.347  | 1.00 | 33.81 |
| ATOM | 1444 | C   | ALA A | 219 | 36.502 | 21.678 | 9.187  | 1.00 | 35.62 |
| ATOM | 1445 | O   | ALA A | 219 | 37.232 | 21.414 | 10.143 | 1.00 | 36.09 |
| ATOM | 1446 | N   | GLY A | 220 | 35.214 | 21.992 | 9.313  | 1.00 | 35.71 |
| ATOM | 1447 | CA  | GLY A | 220 | 34.556 | 22.014 | 10.609 | 1.00 | 35.84 |
| ATOM | 1448 | C   | GLY A | 220 | 34.916 | 23.111 | 11.596 | 1.00 | 35.60 |
| ATOM | 1449 | O   | GLY A | 220 | 34.418 | 23.100 | 12.720 | 1.00 | 36.18 |
| ATOM | 1450 | N   | LEU A | 221 | 35.759 | 24.058 | 11.197 | 1.00 | 34.93 |
| ATOM | 1451 | CA  | LEU A | 221 | 36.162 | 25.135 | 12.099 | 1.00 | 34.46 |

TABLE 30-continued

| | | | | | | | | |
|---|---|---|---|---|---|---|---|---|
| ATOM | 1452 | CB | LEU A | 221 | 37.307 | 25.951 | 11.489 | 1.00 | 34.46 |
| ATOM | 1453 | CG | LEU A | 221 | 37.951 | 26.938 | 12.470 | 1.00 | 34.17 |
| ATOM | 1454 | CD1 | LEU A | 221 | 38.908 | 26.171 | 13.375 | 1.00 | 35.09 |
| ATOM | 1455 | CD2 | LEU A | 221 | 38.693 | 28.035 | 11.725 | 1.00 | 33.10 |
| ATOM | 1456 | C | LEU A | 221 | 35.013 | 26.080 | 12.451 | 1.00 | 34.14 |
| ATOM | 1457 | O | LEU A | 221 | 34.823 | 26.438 | 13.615 | 1.00 | 34.17 |
| ATOM | 1458 | N | ARG A | 222 | 34.248 | 26.483 | 11.444 | 1.00 | 34.57 |
| ATOM | 1459 | CA | ARG A | 222 | 33.130 | 27.395 | 11.654 | 1.00 | 34.52 |
| ATOM | 1460 | CB | ARG A | 222 | 32.554 | 27.826 | 10.307 | 1.00 | 35.12 |
| ATOM | 1461 | CG | ARG A | 222 | 33.462 | 28.768 | 9.529 | 1.00 | 36.10 |
| ATOM | 1462 | CD | ARG A | 222 | 32.904 | 29.017 | 8.143 | 1.00 | 38.44 |
| ATOM | 1463 | NE | ARG A | 222 | 32.993 | 27.822 | 7.306 | 1.00 | 39.22 |
| ATOM | 1464 | CZ | ARG A | 222 | 32.290 | 27.634 | 6.194 | 1.00 | 39.46 |
| ATOM | 1465 | NH1 | ARG A | 222 | 31.435 | 28.564 | 5.784 | 1.00 | 37.86 |
| ATOM | 1466 | NH2 | ARG A | 222 | 32.447 | 26.521 | 5.490 | 1.00 | 38.60 |
| ATOM | 1467 | C | ARG A | 222 | 32.019 | 26.831 | 12.538 | 1.00 | 34.35 |
| ATOM | 1468 | O | ARG A | 222 | 31.231 | 27.589 | 13.108 | 1.00 | 32.92 |
| ATOM | 1469 | N | SER A | 223 | 31.953 | 25.507 | 12.658 | 1.00 | 34.08 |
| ATOM | 1470 | CA | SER A | 223 | 30.928 | 24.888 | 13.490 | 1.00 | 33.94 |
| ATOM | 1471 | CB | SER A | 223 | 30.913 | 23.366 | 13.304 | 1.00 | 32.78 |
| ATOM | 1472 | OG | SER A | 223 | 32.095 | 22.769 | 13.808 | 1.00 | 35.71 |
| ATOM | 1473 | C | SER A | 223 | 31.206 | 25.234 | 14.949 | 1.00 | 33.87 |
| ATOM | 1474 | O | SER A | 223 | 30.325 | 25.123 | 15.803 | 1.00 | 33.34 |
| ATOM | 1475 | N | LEU A | 224 | 32.435 | 25.660 | 15.227 | 1.00 | 33.97 |
| ATOM | 1476 | CA | LEU A | 224 | 32.817 | 26.038 | 16.584 | 1.00 | 34.45 |
| ATOM | 1477 | CB | LEU A | 224 | 34.340 | 26.172 | 16.697 | 1.00 | 33.66 |
| ATOM | 1478 | CG | LEU A | 224 | 35.194 | 24.915 | 16.507 | 1.00 | 34.95 |
| ATOM | 1479 | CD1 | LEU A | 224 | 36.670 | 25.288 | 16.515 | 1.00 | 31.91 |
| ATOM | 1480 | CD2 | LEU A | 224 | 34.883 | 23.913 | 17.612 | 1.00 | 31.97 |
| ATOM | 1481 | C | LEU A | 224 | 32.146 | 27.358 | 16.967 | 1.00 | 34.39 |
| ATOM | 1482 | O | LEU A | 224 | 32.243 | 27.807 | 18.109 | 1.00 | 33.98 |
| ATOM | 1483 | N | GLN A | 225 | 31.474 | 27.984 | 16.004 | 1.00 | 35.00 |
| ATOM | 1484 | CA | GLN A | 225 | 30.774 | 29.237 | 16.271 | 1.00 | 35.56 |
| ATOM | 1485 | CB | GLN A | 225 | 30.571 | 30.043 | 14.976 | 1.00 | 34.95 |
| ATOM | 1486 | CG | GLN A | 225 | 31.863 | 30.374 | 14.230 | 1.00 | 35.29 |
| ATOM | 1487 | CD | GLN A | 225 | 31.628 | 31.191 | 12.966 | 1.00 | 34.79 |
| ATOM | 1488 | OE1 | GLN A | 225 | 31.617 | 32.425 | 12.997 | 1.00 | 32.25 |
| ATOM | 1489 | NE2 | GLN A | 225 | 31.427 | 30.501 | 11.846 | 1.00 | 32.30 |
| ATOM | 1490 | C | GLN A | 225 | 29.421 | 28.905 | 16.904 | 1.00 | 34.76 |
| ATOM | 1491 | O | GLN A | 225 | 28.710 | 29.793 | 17.371 | 1.00 | 34.05 |
| ATOM | 1492 | N | GLY A | 226 | 29.076 | 27.618 | 16.916 | 1.00 | 34.83 |
| ATOM | 1493 | CA | GLY A | 226 | 27.822 | 27.183 | 17.512 | 1.00 | 35.53 |
| ATOM | 1494 | C | GLY A | 226 | 27.803 | 27.504 | 18.997 | 1.00 | 36.05 |
| ATOM | 1495 | O | GLY A | 226 | 28.852 | 27.509 | 19.641 | 1.00 | 37.13 |
| ATOM | 1496 | N | LYS A | 227 | 26.616 | 27.754 | 19.546 | 1.00 | 35.45 |
| ATOM | 1497 | CA | LYS A | 227 | 26.465 | 28.116 | 20.957 | 1.00 | 34.81 |
| ATOM | 1498 | CB | LYS A | 227 | 24.980 | 28.242 | 21.313 | 1.00 | 33.35 |
| ATOM | 1499 | CG | LYS A | 227 | 24.723 | 28.929 | 22.652 | 1.00 | 32.92 |
| ATOM | 1500 | CD | LYS A | 227 | 23.244 | 29.219 | 22.853 | 1.00 | 32.63 |
| ATOM | 1501 | CE | LYS A | 227 | 22.980 | 29.911 | 24.182 | 1.00 | 34.34 |
| ATOM | 1502 | NZ | LYS A | 227 | 23.617 | 31.256 | 24.261 | 1.00 | 36.79 |
| ATOM | 1503 | C | LYS A | 227 | 27.150 | 27.204 | 21.974 | 1.00 | 35.00 |
| ATOM | 1504 | O | LYS A | 227 | 27.985 | 27.663 | 22.755 | 1.00 | 33.88 |
| ATOM | 1505 | N | ALA A | 228 | 26.797 | 25.922 | 21.975 | 1.00 | 34.83 |
| ATOM | 1506 | CA | ALA A | 228 | 27.390 | 24.978 | 22.924 | 1.00 | 35.86 |
| ATOM | 1507 | CB | ALA A | 228 | 26.719 | 23.615 | 22.795 | 1.00 | 33.42 |
| ATOM | 1508 | C | ALA A | 228 | 28.897 | 24.837 | 22.723 | 1.00 | 35.90 |
| ATOM | 1509 | O | ALA A | 228 | 29.674 | 24.941 | 23.671 | 1.00 | 34.64 |
| ATOM | 1510 | N | GLU A | 229 | 29.301 | 24.597 | 21.481 | 1.00 | 37.47 |
| ATOM | 1511 | CA | GLU A | 229 | 30.711 | 24.443 | 21.141 | 1.00 | 38.72 |
| ATOM | 1512 | CB | GLU A | 229 | 30.852 | 24.145 | 19.644 | 1.00 | 42.88 |
| ATOM | 1513 | CG | GLU A | 229 | 31.409 | 22.766 | 19.319 | 1.00 | 49.61 |
| ATOM | 1514 | CD | GLU A | 229 | 31.311 | 22.429 | 17.838 | 1.00 | 53.45 |
| ATOM | 1515 | OE1 | GLU A | 229 | 30.180 | 22.205 | 17.350 | 1.00 | 56.34 |
| ATOM | 1516 | OE2 | GLU A | 229 | 32.361 | 22.393 | 17.159 | 1.00 | 55.01 |
| ATOM | 1517 | C | GLU A | 229 | 31.498 | 25.704 | 21.490 | 1.00 | 36.50 |
| ATOM | 1518 | O | GLU A | 229 | 32.584 | 25.632 | 22.061 | 1.00 | 37.17 |
| ATOM | 1519 | N | LEU A | 230 | 30.935 | 26.860 | 21.152 | 1.00 | 33.85 |
| ATOM | 1520 | CA | LEU A | 230 | 31.588 | 28.135 | 21.409 | 1.00 | 30.53 |
| ATOM | 1521 | CB | LEU A | 230 | 30.795 | 29.281 | 20.766 | 1.00 | 28.19 |
| ATOM | 1522 | CG | LEU A | 230 | 31.417 | 30.680 | 20.851 | 1.00 | 26.88 |
| ATOM | 1523 | CD1 | LEU A | 230 | 32.750 | 30.701 | 20.106 | 1.00 | 24.02 |
| ATOM | 1524 | CD2 | LEU A | 230 | 30.466 | 31.701 | 20.253 | 1.00 | 26.26 |
| ATOM | 1525 | C | LEU A | 230 | 31.761 | 28.414 | 22.895 | 1.00 | 29.06 |
| ATOM | 1526 | O | LEU A | 230 | 32.795 | 28.935 | 23.312 | 1.00 | 28.63 |
| ATOM | 1527 | N | ARG A | 231 | 30.753 | 28.076 | 23.693 | 1.00 | 28.59 |
| ATOM | 1528 | CA | ARG A | 231 | 30.826 | 28.324 | 25.128 | 1.00 | 28.19 |
| ATOM | 1529 | CB | ARG A | 231 | 29.484 | 28.021 | 25.803 | 1.00 | 29.46 |
| ATOM | 1530 | CG | ARG A | 231 | 29.462 | 28.385 | 27.285 | 1.00 | 32.38 |

TABLE 30-continued

| | | | | | | | | |
|---|---|---|---|---|---|---|---|---|
| ATOM | 1531 | CD  | ARG A | 231 | 28.201 | 27.903 | 27.986 | 1.00 | 36.36 |
| ATOM | 1532 | NE  | ARG A | 231 | 27.009 | 28.660 | 27.608 | 1.00 | 39.08 |
| ATOM | 1533 | CZ  | ARG A | 231 | 25.952 | 28.134 | 26.995 | 1.00 | 39.48 |
| ATOM | 1534 | NH1 | ARG A | 231 | 25.938 | 26.845 | 26.684 | 1.00 | 40.17 |
| ATOM | 1535 | NH2 | ARG A | 231 | 24.901 | 28.893 | 26.710 | 1.00 | 39.24 |
| ATOM | 1536 | C   | ARG A | 231 | 31.931 | 27.503 | 25.793 | 1.00 | 27.19 |
| ATOM | 1537 | O   | ARG A | 231 | 32.689 | 28.024 | 26.605 | 1.00 | 25.57 |
| ATOM | 1538 | N   | ARG A | 232 | 32.018 | 26.222 | 25.450 | 1.00 | 27.04 |
| ATOM | 1539 | CA  | ARG A | 232 | 33.042 | 25.355 | 26.022 | 1.00 | 28.55 |
| ATOM | 1540 | CB  | ARG A | 232 | 32.820 | 23.900 | 25.598 | 1.00 | 31.40 |
| ATOM | 1541 | CG  | ARG A | 232 | 33.906 | 22.951 | 26.097 | 1.00 | 37.46 |
| ATOM | 1542 | CD  | ARG A | 232 | 33.651 | 21.497 | 25.697 | 1.00 | 41.98 |
| ATOM | 1543 | NE  | ARG A | 232 | 32.314 | 21.050 | 26.084 | 1.00 | 46.56 |
| ATOM | 1544 | CZ  | ARG A | 232 | 31.240 | 21.146 | 25.305 | 1.00 | 49.01 |
| ATOM | 1545 | NH1 | ARG A | 232 | 31.345 | 21.669 | 24.089 | 1.00 | 49.17 |
| ATOM | 1546 | NH2 | ARG A | 232 | 30.057 | 20.732 | 25.746 | 1.00 | 49.45 |
| ATOM | 1547 | C   | ARG A | 232 | 34.428 | 25.807 | 25.579 | 1.00 | 27.29 |
| ATOM | 1548 | O   | ARG A | 232 | 35.377 | 25.795 | 26.361 | 1.00 | 26.97 |
| ATOM | 1549 | N   | LEU A | 233 | 34.538 | 26.203 | 24.318 | 1.00 | 25.58 |
| ATOM | 1550 | CA  | LEU A | 233 | 35.806 | 26.664 | 23.777 | 1.00 | 25.13 |
| ATOM | 1551 | CB  | LEU A | 233 | 35.669 | 26.912 | 22.275 | 1.00 | 26.34 |
| ATOM | 1552 | CG  | LEU A | 233 | 36.840 | 27.630 | 21.604 | 1.00 | 27.27 |
| ATOM | 1553 | CD1 | LEU A | 233 | 38.097 | 26.800 | 21.736 | 1.00 | 29.09 |
| ATOM | 1554 | CD2 | LEU A | 233 | 36.514 | 27.875 | 20.146 | 1.00 | 29.53 |
| ATOM | 1555 | C   | LEU A | 233 | 36.295 | 27.942 | 24.467 | 1.00 | 24.39 |
| ATOM | 1556 | O   | LEU A | 233 | 37.436 | 28.010 | 24.927 | 1.00 | 22.15 |
| ATOM | 1557 | N   | LEU A | 234 | 35.424 | 28.945 | 24.547 | 1.00 | 22.75 |
| ATOM | 1558 | CA  | LEU A | 234 | 35.774 | 30.228 | 25.154 | 1.00 | 22.29 |
| ATOM | 1559 | CB  | LEU A | 234 | 34.725 | 31.283 | 24.788 | 1.00 | 23.57 |
| ATOM | 1560 | CG  | LEU A | 234 | 34.647 | 31.536 | 23.280 | 1.00 | 26.28 |
| ATOM | 1561 | CD1 | LEU A | 234 | 33.539 | 32.528 | 22.960 | 1.00 | 27.43 |
| ATOM | 1562 | CD2 | LEU A | 234 | 35.995 | 32.047 | 22.794 | 1.00 | 26.22 |
| ATOM | 1563 | C   | LEU A | 234 | 35.963 | 30.180 | 26.663 | 1.00 | 21.30 |
| ATOM | 1564 | O   | LEU A | 234 | 36.710 | 30.980 | 27.223 | 1.00 | 20.43 |
| ATOM | 1565 | N   | THR A | 235 | 35.285 | 29.256 | 27.330 | 1.00 | 21.31 |
| ATOM | 1566 | CA  | THR A | 235 | 35.444 | 29.135 | 28.772 | 1.00 | 22.40 |
| ATOM | 1567 | CB  | THR A | 235 | 34.468 | 28.104 | 29.367 | 1.00 | 22.83 |
| ATOM | 1568 | OG1 | THR A | 235 | 33.137 | 28.632 | 29.324 | 1.00 | 23.92 |
| ATOM | 1569 | CG2 | THR A | 235 | 34.842 | 27.789 | 30.809 | 1.00 | 20.20 |
| ATOM | 1570 | C   | THR A | 235 | 36.877 | 28.691 | 29.069 | 1.00 | 21.59 |
| ATOM | 1571 | O   | THR A | 235 | 37.524 | 29.213 | 29.977 | 1.00 | 21.97 |
| ATOM | 1572 | N   | LYS A | 236 | 37.367 | 27.735 | 28.285 | 1.00 | 18.98 |
| ATOM | 1573 | CA  | LYS A | 236 | 38.720 | 27.227 | 28.451 | 1.00 | 20.97 |
| ATOM | 1574 | CB  | LYS A | 236 | 38.905 | 25.951 | 27.632 | 1.00 | 22.57 |
| ATOM | 1575 | CG  | LYS A | 236 | 40.256 | 25.283 | 27.844 | 1.00 | 29.29 |
| ATOM | 1576 | CD  | LYS A | 236 | 40.284 | 23.874 | 27.266 | 1.00 | 31.20 |
| ATOM | 1577 | CE  | LYS A | 236 | 41.588 | 23.177 | 27.602 | 1.00 | 34.02 |
| ATOM | 1578 | NZ  | LYS A | 236 | 41.554 | 21.739 | 27.212 | 1.00 | 37.66 |
| ATOM | 1579 | C   | LYS A | 236 | 39.758 | 28.273 | 28.036 | 1.00 | 20.11 |
| ATOM | 1580 | O   | LYS A | 236 | 40.773 | 28.454 | 28.710 | 1.00 | 18.99 |
| ATOM | 1581 | N   | VAL A | 237 | 39.500 | 28.963 | 26.931 | 1.00 | 19.39 |
| ATOM | 1582 | CA  | VAL A | 237 | 40.410 | 29.995 | 26.449 | 1.00 | 19.41 |
| ATOM | 1583 | CB  | VAL A | 237 | 39.892 | 30.619 | 25.137 | 1.00 | 19.28 |
| ATOM | 1584 | CG1 | VAL A | 237 | 40.631 | 31.923 | 24.840 | 1.00 | 15.51 |
| ATOM | 1585 | CG2 | VAL A | 237 | 40.078 | 29.630 | 23.997 | 1.00 | 17.43 |
| ATOM | 1586 | C   | VAL A | 237 | 40.582 | 31.098 | 27.489 | 1.00 | 20.27 |
| ATOM | 1587 | O   | VAL A | 237 | 41.705 | 31.484 | 27.817 | 1.00 | 20.76 |
| ATOM | 1588 | N   | LEU A | 238 | 39.462 | 31.597 | 28.007 | 1.00 | 21.31 |
| ATOM | 1589 | CA  | LEU A | 238 | 39.470 | 32.660 | 29.010 | 1.00 | 21.14 |
| ATOM | 1590 | CB  | LEU A | 238 | 38.042 | 33.127 | 29.295 | 1.00 | 19.77 |
| ATOM | 1591 | CG  | LEU A | 238 | 37.364 | 33.913 | 28.168 | 1.00 | 22.01 |
| ATOM | 1592 | CD1 | LEU A | 238 | 35.894 | 34.143 | 28.506 | 1.00 | 21.78 |
| ATOM | 1593 | CD2 | LEU A | 238 | 38.083 | 35.244 | 27.974 | 1.00 | 21.85 |
| ATOM | 1594 | C   | LEU A | 238 | 40.138 | 32.233 | 30.314 | 1.00 | 21.63 |
| ATOM | 1595 | O   | LEU A | 238 | 40.774 | 33.047 | 30.989 | 1.00 | 20.14 |
| ATOM | 1596 | N   | GLN A | 239 | 39.993 | 30.960 | 30.670 | 1.00 | 21.99 |
| ATOM | 1597 | CA  | GLN A | 239 | 40.609 | 30.458 | 31.891 | 1.00 | 22.84 |
| ATOM | 1598 | CB  | GLN A | 239 | 40.126 | 29.039 | 32.200 | 1.00 | 25.02 |
| ATOM | 1599 | CG  | GLN A | 239 | 40.681 | 28.489 | 33.504 | 1.00 | 29.97 |
| ATOM | 1600 | CD  | GLN A | 239 | 40.153 | 27.103 | 33.828 | 1.00 | 37.06 |
| ATOM | 1601 | OE1 | GLN A | 239 | 38.940 | 26.895 | 33.941 | 1.00 | 40.00 |
| ATOM | 1602 | NE2 | GLN A | 239 | 41.063 | 26.145 | 33.982 | 1.00 | 36.33 |
| ATOM | 1603 | C   | GLN A | 239 | 42.129 | 30.468 | 31.743 | 1.00 | 20.31 |
| ATOM | 1604 | O   | GLN A | 239 | 42.847 | 30.888 | 32.648 | 1.00 | 20.83 |
| ATOM | 1605 | N   | GLU A | 240 | 42.617 | 29.999 | 30.601 | 1.00 | 19.91 |
| ATOM | 1606 | CA  | GLU A | 240 | 44.054 | 29.985 | 30.348 | 1.00 | 20.13 |
| ATOM | 1607 | CB  | GLU A | 240 | 44.348 | 29.345 | 28.992 | 1.00 | 21.91 |
| ATOM | 1608 | CG  | GLU A | 240 | 44.002 | 27.868 | 28.918 | 1.00 | 28.96 |
| ATOM | 1609 | CD  | GLU A | 240 | 44.945 | 26.992 | 29.735 | 1.00 | 33.18 |

TABLE 30-continued

| | | | | | | | | |
|---|---|---|---|---|---|---|---|---|
| ATOM | 1610 | OE1 | GLU A | 240 | 44.662 | 25.782 | 29.865 | 1.00 | 37.45 |
| ATOM | 1611 | OE2 | GLU A | 240 | 45.973 | 27.501 | 30.237 | 1.00 | 33.72 |
| ATOM | 1612 | C | GLU A | 240 | 44.570 | 31.423 | 30.363 | 1.00 | 19.32 |
| ATOM | 1613 | O | GLU A | 240 | 45.656 | 31.695 | 30.871 | 1.00 | 20.24 |
| ATOM | 1614 | N | ARG A | 241 | 43.775 | 32.337 | 29.812 | 1.00 | 17.22 |
| ATOM | 1615 | CA | ARG A | 241 | 44.131 | 33.751 | 29.755 | 1.00 | 17.57 |
| ATOM | 1616 | CB | ARG A | 241 | 43.094 | 34.509 | 28.915 | 1.00 | 15.94 |
| ATOM | 1617 | CG | ARG A | 241 | 43.423 | 35.971 | 28.625 | 1.00 | 16.24 |
| ATOM | 1618 | CD | ARG A | 241 | 43.210 | 36.882 | 29.829 | 1.00 | 13.73 |
| ATOM | 1619 | NE | ARG A | 241 | 41.826 | 36.914 | 30.293 | 1.00 | 15.88 |
| ATOM | 1620 | CZ | ARG A | 241 | 40.845 | 37.616 | 29.726 | 1.00 | 17.28 |
| ATOM | 1621 | NH1 | ARG A | 241 | 39.620 | 37.568 | 30.235 | 1.00 | 15.42 |
| ATOM | 1622 | NH2 | ARG A | 241 | 41.082 | 38.374 | 28.661 | 1.00 | 14.65 |
| ATOM | 1623 | C | ARG A | 241 | 44.227 | 34.371 | 31.150 | 1.00 | 18.35 |
| ATOM | 1624 | O | ARG A | 241 | 45.174 | 35.102 | 31.442 | 1.00 | 17.69 |
| ATOM | 1625 | N | ASP A | 242 | 43.248 | 34.082 | 32.007 | 1.00 | 19.04 |
| ATOM | 1626 | CA | ASP A | 242 | 43.247 | 34.631 | 33.362 | 1.00 | 19.06 |
| ATOM | 1627 | CB | ASP A | 242 | 41.914 | 34.344 | 34.073 | 1.00 | 18.23 |
| ATOM | 1628 | CG | ASP A | 242 | 40.726 | 35.019 | 33.397 | 1.00 | 20.68 |
| ATOM | 1629 | OD1 | ASP A | 242 | 40.913 | 36.078 | 32.761 | 1.00 | 20.74 |
| ATOM | 1630 | OD2 | ASP A | 242 | 39.596 | 34.499 | 33.516 | 1.00 | 19.78 |
| ATOM | 1631 | C | ASP A | 242 | 44.404 | 34.085 | 34.201 | 1.00 | 18.63 |
| ATOM | 1632 | O | ASP A | 242 | 44.793 | 34.695 | 35.195 | 1.00 | 18.12 |
| ATOM | 1633 | N | GLY A | 243 | 44.952 | 32.944 | 33.794 | 1.00 | 17.67 |
| ATOM | 1634 | CA | GLY A | 243 | 46.061 | 32.353 | 34.526 | 1.00 | 17.88 |
| ATOM | 1635 | C | GLY A | 243 | 47.407 | 32.997 | 34.216 | 1.00 | 18.89 |
| ATOM | 1636 | O | GLY A | 243 | 48.429 | 32.641 | 34.807 | 1.00 | 18.71 |
| ATOM | 1637 | N | LEU A | 244 | 47.421 | 33.945 | 33.286 | 1.00 | 18.25 |
| ATOM | 1638 | CA | LEU A | 244 | 48.666 | 34.622 | 32.933 | 1.00 | 19.00 |
| ATOM | 1639 | CB | LEU A | 244 | 48.613 | 35.126 | 31.485 | 1.00 | 17.15 |
| ATOM | 1640 | CG | LEU A | 244 | 48.385 | 34.081 | 30.392 | 1.00 | 17.74 |
| ATOM | 1641 | CD1 | LEU A | 244 | 48.274 | 34.772 | 29.044 | 1.00 | 16.09 |
| ATOM | 1642 | CD2 | LEU A | 244 | 49.526 | 33.074 | 30.400 | 1.00 | 18.11 |
| ATOM | 1643 | C | LEU A | 244 | 48.912 | 35.801 | 33.868 | 1.00 | 18.91 |
| ATOM | 1644 | O | LEU A | 244 | 47.970 | 36.388 | 34.401 | 1.00 | 18.13 |
| ATOM | 1645 | N | ARG A | 245 | 50.180 | 36.143 | 34.067 | 1.00 | 19.32 |
| ATOM | 1646 | CA | ARG A | 245 | 50.529 | 37.269 | 34.924 | 1.00 | 20.36 |
| ATOM | 1647 | CB | ARG A | 245 | 52.051 | 37.346 | 35.085 | 1.00 | 19.37 |
| ATOM | 1648 | CG | ARG A | 245 | 52.601 | 36.269 | 36.035 | 1.00 | 19.13 |
| ATOM | 1649 | CD | ARG A | 245 | 54.072 | 35.967 | 35.805 | 1.00 | 18.27 |
| ATOM | 1650 | NE | ARG A | 245 | 54.965 | 37.032 | 36.254 | 1.00 | 19.00 |
| ATOM | 1651 | CZ | ARG A | 245 | 55.396 | 37.178 | 37.504 | 1.00 | 19.64 |
| ATOM | 1652 | NH1 | ARG A | 245 | 56.211 | 38.181 | 37.811 | 1.00 | 16.23 |
| ATOM | 1653 | NH2 | ARG A | 245 | 55.021 | 36.318 | 38.447 | 1.00 | 17.19 |
| ATOM | 1654 | C | ARG A | 245 | 49.958 | 38.569 | 34.349 | 1.00 | 22.32 |
| ATOM | 1655 | O | ARG A | 245 | 49.910 | 38.758 | 33.130 | 1.00 | 20.59 |
| ATOM | 1656 | N | ARG A | 246 | 49.517 | 39.446 | 35.249 | 1.00 | 25.41 |
| ATOM | 1657 | CA | ARG A | 246 | 48.906 | 40.737 | 34.920 | 1.00 | 26.97 |
| ATOM | 1658 | CB | ARG A | 246 | 48.979 | 41.664 | 36.137 | 1.00 | 30.43 |
| ATOM | 1659 | CG | ARG A | 246 | 48.315 | 41.093 | 37.380 | 1.00 | 37.76 |
| ATOM | 1660 | CD | ARG A | 246 | 46.792 | 41.252 | 37.353 | 1.00 | 41.81 |
| ATOM | 1661 | NE | ARG A | 246 | 46.113 | 40.366 | 38.302 | 1.00 | 42.05 |
| ATOM | 1662 | CZ | ARG A | 246 | 46.468 | 40.202 | 39.573 | 1.00 | 40.82 |
| ATOM | 1663 | NH1 | ARG A | 246 | 47.505 | 40.859 | 40.073 | 1.00 | 40.20 |
| ATOM | 1664 | NH2 | ARG A | 246 | 45.779 | 39.377 | 40.348 | 1.00 | 41.81 |
| ATOM | 1665 | C | ARG A | 246 | 49.429 | 41.490 | 33.698 | 1.00 | 26.71 |
| ATOM | 1666 | O | ARG A | 246 | 48.659 | 41.784 | 32.781 | 1.00 | 26.44 |
| ATOM | 1667 | N | VAL A | 247 | 50.720 | 41.816 | 33.678 | 1.00 | 24.35 |
| ATOM | 1668 | CA | VAL A | 247 | 51.268 | 42.561 | 32.548 | 1.00 | 24.81 |
| ATOM | 1669 | CB | VAL A | 247 | 52.703 | 43.101 | 32.853 | 1.00 | 26.12 |
| ATOM | 1670 | CG1 | VAL A | 247 | 52.655 | 44.084 | 34.018 | 1.00 | 23.20 |
| ATOM | 1671 | CG2 | VAL A | 247 | 53.644 | 41.962 | 33.171 | 1.00 | 26.44 |
| ATOM | 1672 | C | VAL A | 247 | 51.290 | 41.768 | 31.244 | 1.00 | 24.54 |
| ATOM | 1673 | O | VAL A | 247 | 51.443 | 42.341 | 30.167 | 1.00 | 26.25 |
| ATOM | 1674 | N | HIS A | 248 | 51.116 | 40.453 | 31.342 | 1.00 | 23.59 |
| ATOM | 1675 | CA | HIS A | 248 | 51.123 | 39.580 | 30.169 | 1.00 | 21.97 |
| ATOM | 1676 | CB | HIS A | 248 | 52.118 | 38.438 | 30.387 | 1.00 | 20.64 |
| ATOM | 1677 | CG | HIS A | 248 | 53.536 | 38.897 | 30.510 | 1.00 | 21.01 |
| ATOM | 1678 | CD2 | HIS A | 248 | 54.312 | 39.108 | 31.598 | 1.00 | 20.81 |
| ATOM | 1679 | ND1 | HIS A | 248 | 54.293 | 39.270 | 29.421 | 1.00 | 20.08 |
| ATOM | 1680 | CE1 | HIS A | 248 | 55.474 | 39.696 | 29.833 | 1.00 | 20.69 |
| ATOM | 1681 | NE2 | HIS A | 248 | 55.510 | 39.608 | 31.150 | 1.00 | 21.17 |
| ATOM | 1682 | C | HIS A | 248 | 49.741 | 38.999 | 29.884 | 1.00 | 21.65 |
| ATOM | 1683 | O | HIS A | 248 | 49.620 | 37.980 | 29.205 | 1.00 | 19.83 |
| ATOM | 1684 | N | ARG A | 249 | 48.705 | 39.658 | 30.395 | 1.00 | 20.25 |
| ATOM | 1685 | CA | ARG A | 249 | 47.332 | 39.196 | 30.219 | 1.00 | 21.40 |
| ATOM | 1686 | CB | ARG A | 249 | 46.598 | 39.334 | 31.553 | 1.00 | 21.77 |
| ATOM | 1687 | CG | ARG A | 249 | 45.363 | 38.482 | 31.700 | 1.00 | 24.08 |
| ATOM | 1688 | CD | ARG A | 249 | 44.769 | 38.681 | 33.090 | 1.00 | 25.21 |

TABLE 30-continued

| | | | | | | | | |
|---|---|---|---|---|---|---|---|---|
| ATOM | 1689 | NE | ARG A | 249 | 45.655 | 38.177 | 34.132 | 1.00 | 25.36 |
| ATOM | 1690 | CZ | ARG A | 249 | 45.674 | 38.624 | 35.384 | 1.00 | 26.64 |
| ATOM | 1691 | NH1 | ARG A | 249 | 44.858 | 39.598 | 35.760 | 1.00 | 26.33 |
| ATOM | 1692 | NH2 | ARG A | 249 | 46.507 | 38.087 | 36.265 | 1.00 | 27.83 |
| ATOM | 1693 | C | ARG A | 249 | 46.600 | 39.975 | 29.113 | 1.00 | 21.27 |
| ATOM | 1694 | O | ARG A | 249 | 46.192 | 41.122 | 29.304 | 1.00 | 21.00 |
| ATOM | 1695 | N | PRO A | 250 | 46.410 | 39.345 | 27.941 | 1.00 | 19.96 |
| ATOM | 1696 | CD | PRO A | 250 | 46.878 | 37.994 | 27.575 | 1.00 | 19.81 |
| ATOM | 1697 | CA | PRO A | 250 | 45.735 | 39.977 | 26.807 | 1.00 | 19.13 |
| ATOM | 1698 | CB | PRO A | 250 | 46.266 | 39.185 | 25.625 | 1.00 | 17.18 |
| ATOM | 1699 | CG | PRO A | 250 | 46.263 | 37.792 | 26.184 | 1.00 | 18.21 |
| ATOM | 1700 | C | PRO A | 250 | 44.208 | 39.953 | 26.837 | 1.00 | 19.62 |
| ATOM | 1701 | O | PRO A | 250 | 43.587 | 39.152 | 27.546 | 1.00 | 17.65 |
| ATOM | 1702 | N | ALA A | 251 | 43.616 | 40.850 | 26.054 | 1.00 | 18.39 |
| ATOM | 1703 | CA | ALA A | 251 | 42.171 | 40.904 | 25.918 | 1.00 | 17.20 |
| ATOM | 1704 | CB | ALA A | 251 | 41.747 | 42.226 | 25.296 | 1.00 | 15.99 |
| ATOM | 1705 | C | ALA A | 251 | 41.874 | 39.756 | 24.957 | 1.00 | 16.57 |
| ATOM | 1706 | O | ALA A | 251 | 42.723 | 39.398 | 24.133 | 1.00 | 16.08 |
| ATOM | 1707 | N | VAL A | 252 | 40.691 | 39.167 | 25.063 | 1.00 | 15.31 |
| ATOM | 1708 | CA | VAL A | 252 | 40.332 | 38.073 | 24.176 | 1.00 | 15.76 |
| ATOM | 1709 | CB | VAL A | 252 | 40.008 | 36.787 | 24.972 | 1.00 | 16.54 |
| ATOM | 1710 | CG1 | VAL A | 252 | 39.416 | 35.731 | 24.040 | 1.00 | 13.14 |
| ATOM | 1711 | CG2 | VAL A | 252 | 41.279 | 36.254 | 25.644 | 1.00 | 14.05 |
| ATOM | 1712 | C | VAL A | 252 | 39.135 | 38.434 | 23.297 | 1.00 | 17.13 |
| ATOM | 1713 | O | VAL A | 252 | 38.062 | 38.774 | 23.793 | 1.00 | 17.25 |
| ATOM | 1714 | N | LEU A | 253 | 39.337 | 38.376 | 21.985 | 1.00 | 17.15 |
| ATOM | 1715 | CA | LEU A | 253 | 38.275 | 38.667 | 21.033 | 1.00 | 16.03 |
| ATOM | 1716 | CB | LEU A | 253 | 38.682 | 39.802 | 20.086 | 1.00 | 16.00 |
| ATOM | 1717 | CG | LEU A | 253 | 38.871 | 41.205 | 20.673 | 1.00 | 17.12 |
| ATOM | 1718 | CD1 | LEU A | 253 | 40.194 | 41.292 | 21.418 | 1.00 | 18.46 |
| ATOM | 1719 | CD2 | LEU A | 253 | 38.840 | 42.222 | 19.550 | 1.00 | 16.89 |
| ATOM | 1720 | C | LEU A | 253 | 37.999 | 37.406 | 20.225 | 1.00 | 15.90 |
| ATOM | 1721 | O | LEU A | 253 | 38.829 | 36.497 | 20.182 | 1.00 | 14.68 |
| ATOM | 1722 | N | VAL A | 254 | 36.827 | 37.355 | 19.600 | 1.00 | 15.02 |
| ATOM | 1723 | CA | VAL A | 254 | 36.428 | 36.222 | 18.775 | 1.00 | 15.71 |
| ATOM | 1724 | CB | VAL A | 254 | 35.158 | 35.531 | 19.351 | 1.00 | 17.13 |
| ATOM | 1725 | CG1 | VAL A | 254 | 34.663 | 34.449 | 18.404 | 1.00 | 17.46 |
| ATOM | 1726 | CG2 | VAL A | 254 | 35.473 | 34.915 | 20.706 | 1.00 | 16.81 |
| ATOM | 1727 | C | VAL A | 254 | 36.142 | 36.741 | 17.367 | 1.00 | 15.10 |
| ATOM | 1728 | O | VAL A | 254 | 35.406 | 37.704 | 17.195 | 1.00 | 16.08 |
| ATOM | 1729 | N | LYS A | 255 | 36.738 | 36.116 | 16.361 | 1.00 | 15.28 |
| ATOM | 1730 | CA | LYS A | 255 | 36.521 | 36.541 | 14.985 | 1.00 | 15.28 |
| ATOM | 1731 | CB | LYS A | 255 | 37.826 | 36.463 | 14.186 | 1.00 | 14.88 |
| ATOM | 1732 | CG | LYS A | 255 | 37.714 | 36.994 | 12.770 | 1.00 | 15.89 |
| ATOM | 1733 | CD | LYS A | 255 | 39.092 | 37.270 | 12.172 | 1.00 | 16.96 |
| ATOM | 1734 | CE | LYS A | 255 | 38.985 | 37.946 | 10.804 | 1.00 | 15.29 |
| ATOM | 1735 | NZ | LYS A | 255 | 40.316 | 38.399 | 10.320 | 1.00 | 15.29 |
| ATOM | 1736 | C | LYS A | 255 | 35.458 | 35.656 | 14.349 | 1.00 | 16.78 |
| ATOM | 1737 | O | LYS A | 255 | 35.611 | 34.433 | 14.269 | 1.00 | 15.57 |
| ATOM | 1738 | N | ILE A | 256 | 34.384 | 36.284 | 13.888 | 1.00 | 15.73 |
| ATOM | 1739 | CA | ILE A | 256 | 33.280 | 35.553 | 13.295 | 1.00 | 15.18 |
| ATOM | 1740 | CB | ILE A | 256 | 31.963 | 35.924 | 13.993 | 1.00 | 14.40 |
| ATOM | 1741 | CG2 | ILE A | 256 | 32.115 | 35.716 | 15.485 | 1.00 | 14.47 |
| ATOM | 1742 | CG1 | ILE A | 256 | 31.607 | 37.387 | 13.703 | 1.00 | 13.65 |
| ATOM | 1743 | CD1 | ILE A | 256 | 30.305 | 37.857 | 14.348 | 1.00 | 10.70 |
| ATOM | 1744 | C | ILE A | 256 | 33.118 | 35.758 | 11.795 | 1.00 | 15.17 |
| ATOM | 1745 | O | ILE A | 256 | 33.677 | 36.688 | 11.210 | 1.00 | 12.59 |
| ATOM | 1746 | N | ALA A | 257 | 32.340 | 34.873 | 11.181 | 1.00 | 15.08 |
| ATOM | 1747 | CA | ALA A | 257 | 32.084 | 34.934 | 9.750 | 1.00 | 18.08 |
| ATOM | 1748 | CB | ALA A | 257 | 31.766 | 33.533 | 9.221 | 1.00 | 19.52 |
| ATOM | 1749 | C | ALA A | 257 | 30.934 | 35.881 | 9.418 | 1.00 | 18.32 |
| ATOM | 1750 | O | ALA A | 257 | 30.208 | 36.344 | 10.303 | 1.00 | 17.66 |
| ATOM | 1751 | N | PRO A | 258 | 30.781 | 36.206 | 8.128 | 1.00 | 18.01 |
| ATOM | 1752 | CD | PRO A | 258 | 31.867 | 36.066 | 7.138 | 1.00 | 16.50 |
| ATOM | 1753 | CA | PRO A | 258 | 29.732 | 37.089 | 7.615 | 1.00 | 18.62 |
| ATOM | 1754 | CB | PRO A | 258 | 30.449 | 37.850 | 6.515 | 1.00 | 16.96 |
| ATOM | 1755 | CG | PRO A | 258 | 31.298 | 36.776 | 5.918 | 1.00 | 16.10 |
| ATOM | 1756 | C | PRO A | 258 | 28.578 | 36.248 | 7.057 | 1.00 | 21.75 |
| ATOM | 1757 | O | PRO A | 258 | 27.619 | 36.785 | 6.498 | 1.00 | 23.00 |
| ATOM | 1758 | N | ASP A | 259 | 28.682 | 34.930 | 7.218 | 1.00 | 20.77 |
| ATOM | 1759 | CA | ASP A | 259 | 27.675 | 34.007 | 6.705 | 1.00 | 22.20 |
| ATOM | 1760 | CB | ASP A | 259 | 28.355 | 32.919 | 5.867 | 1.00 | 20.49 |
| ATOM | 1761 | CG | ASP A | 259 | 29.382 | 33.485 | 4.900 | 1.00 | 22.19 |
| ATOM | 1762 | OD1 | ASP A | 259 | 29.043 | 34.442 | 4.170 | 1.00 | 19.06 |
| ATOM | 1763 | OD2 | ASP A | 259 | 30.524 | 32.970 | 4.868 | 1.00 | 21.62 |
| ATOM | 1764 | C | ASP A | 259 | 26.849 | 33.351 | 7.808 | 1.00 | 23.62 |
| ATOM | 1765 | O | ASP A | 259 | 26.272 | 32.286 | 7.606 | 1.00 | 25.15 |
| ATOM | 1766 | N | LEU A | 260 | 26.787 | 33.991 | 8.969 | 1.00 | 23.63 |
| ATOM | 1767 | CA | LEU A | 260 | 26.039 | 33.454 | 10.097 | 1.00 | 22.23 |

TABLE 30-continued

| ATOM | 1768 | CB  | LEU A | 260 | 26.549 | 34.075 | 11.400 | 1.00 | 22.52 |
| ATOM | 1769 | CG  | LEU A | 260 | 28.015 | 33.815 | 11.761 | 1.00 | 23.59 |
| ATOM | 1770 | CD1 | LEU A | 260 | 28.418 | 34.668 | 12.958 | 1.00 | 25.06 |
| ATOM | 1771 | CD2 | LEU A | 260 | 28.205 | 32.341 | 12.063 | 1.00 | 21.98 |
| ATOM | 1772 | C   | LEU A | 260 | 24.544 | 33.715 | 9.973  | 1.00 | 22.15 |
| ATOM | 1773 | O   | LEU A | 260 | 24.131 | 34.749 | 9.454  | 1.00 | 23.71 |
| ATOM | 1774 | N   | THR A | 261 | 23.736 | 32.769 | 10.444 | 1.00 | 20.79 |
| ATOM | 1775 | CA  | THR A | 261 | 22.285 | 32.926 | 10.419 | 1.00 | 19.86 |
| ATOM | 1776 | CB  | THR A | 261 | 21.556 | 31.590 | 10.694 | 1.00 | 19.22 |
| ATOM | 1777 | OG1 | THR A | 261 | 21.909 | 31.118 | 12.003 | 1.00 | 18.63 |
| ATOM | 1778 | CG2 | THR A | 261 | 21.933 | 30.539 | 9.661  | 1.00 | 12.85 |
| ATOM | 1779 | C   | THR A | 261 | 21.946 | 33.876 | 11.567 | 1.00 | 22.13 |
| ATOM | 1780 | O   | THR A | 261 | 22.800 | 34.166 | 12.407 | 1.00 | 23.22 |
| ATOM | 1781 | N   | SER A | 262 | 20.712 | 34.364 | 11.611 | 1.00 | 22.17 |
| ATOM | 1782 | CA  | SER A | 262 | 20.316 | 35.256 | 12.696 | 1.00 | 22.97 |
| ATOM | 1783 | CB  | SER A | 262 | 18.886 | 35.748 | 12.484 | 1.00 | 22.97 |
| ATOM | 1784 | OG  | SER A | 262 | 18.791 | 36.509 | 11.298 | 1.00 | 26.68 |
| ATOM | 1785 | C   | SER A | 262 | 20.413 | 34.521 | 14.036 | 1.00 | 23.06 |
| ATOM | 1786 | O   | SER A | 262 | 20.653 | 35.136 | 15.075 | 1.00 | 22.02 |
| ATOM | 1787 | N   | GLN A | 263 | 20.227 | 33.204 | 14.004 | 1.00 | 22.11 |
| ATOM | 1788 | CA  | GLN A | 263 | 20.297 | 32.393 | 15.215 | 1.00 | 23.04 |
| ATOM | 1789 | CB  | GLN A | 263 | 19.794 | 30.974 | 14.935 | 1.00 | 24.15 |
| ATOM | 1790 | CG  | GLN A | 263 | 19.870 | 30.039 | 16.136 | 1.00 | 30.55 |
| ATOM | 1791 | CD  | GLN A | 263 | 18.717 | 30.225 | 17.108 | 1.00 | 32.21 |
| ATOM | 1792 | OE1 | GLN A | 263 | 17.581 | 29.856 | 16.815 | 1.00 | 33.90 |
| ATOM | 1793 | NE2 | GLN A | 263 | 19.005 | 30.805 | 18.267 | 1.00 | 33.03 |
| ATOM | 1794 | C   | GLN A | 263 | 21.727 | 32.331 | 15.753 | 1.00 | 21.52 |
| ATOM | 1795 | O   | GLN A | 263 | 21.951 | 32.483 | 16.956 | 1.00 | 21.15 |
| ATOM | 1796 | N   | ASP A | 264 | 22.692 | 32.109 | 14.863 | 1.00 | 20.97 |
| ATOM | 1797 | CA  | ASP A | 264 | 24.090 | 32.034 | 15.272 | 1.00 | 19.77 |
| ATOM | 1798 | CB  | ASP A | 264 | 25.007 | 31.755 | 14.076 | 1.00 | 22.91 |
| ATOM | 1799 | CG  | ASP A | 264 | 24.750 | 30.398 | 13.437 | 1.00 | 25.44 |
| ATOM | 1800 | OD1 | ASP A | 264 | 24.364 | 29.457 | 14.163 | 1.00 | 23.04 |
| ATOM | 1801 | OD2 | ASP A | 264 | 24.952 | 30.276 | 12.206 | 1.00 | 26.99 |
| ATOM | 1802 | C   | ASP A | 264 | 24.530 | 33.330 | 15.931 | 1.00 | 18.65 |
| ATOM | 1803 | O   | ASP A | 264 | 25.201 | 33.315 | 16.962 | 1.00 | 18.71 |
| ATOM | 1804 | N   | LYS A | 265 | 24.149 | 34.453 | 15.333 | 1.00 | 17.32 |
| ATOM | 1805 | CA  | LYS A | 265 | 24.514 | 35.754 | 15.868 | 1.00 | 19.13 |
| ATOM | 1806 | CB  | LYS A | 265 | 24.063 | 36.860 | 14.915 | 1.00 | 19.32 |
| ATOM | 1807 | CG  | LYS A | 265 | 24.772 | 36.820 | 13.573 | 1.00 | 19.57 |
| ATOM | 1808 | CD  | LYS A | 265 | 24.127 | 37.779 | 12.589 | 1.00 | 23.29 |
| ATOM | 1809 | CE  | LYS A | 265 | 24.425 | 37.366 | 11.160 | 1.00 | 24.36 |
| ATOM | 1810 | NZ  | LYS A | 265 | 23.497 | 38.006 | 10.187 | 1.00 | 27.53 |
| ATOM | 1811 | C   | LYS A | 265 | 23.927 | 35.971 | 17.253 | 1.00 | 20.16 |
| ATOM | 1812 | O   | LYS A | 265 | 24.611 | 36.473 | 18.144 | 1.00 | 21.28 |
| ATOM | 1813 | N   | GLU A | 266 | 22.661 | 35.598 | 17.434 | 1.00 | 20.98 |
| ATOM | 1814 | CA  | GLU A | 266 | 22.014 | 35.734 | 18.736 | 1.00 | 20.75 |
| ATOM | 1815 | CB  | GLU A | 266 | 20.558 | 35.247 | 18.677 | 1.00 | 20.43 |
| ATOM | 1816 | CG  | GLU A | 266 | 19.640 | 36.121 | 17.839 | 1.00 | 25.19 |
| ATOM | 1817 | CD  | GLU A | 266 | 18.213 | 35.587 | 17.743 | 1.00 | 26.74 |
| ATOM | 1818 | OE1 | GLU A | 266 | 17.414 | 36.194 | 17.003 | 1.00 | 28.84 |
| ATOM | 1819 | OE2 | GLU A | 266 | 17.886 | 34.573 | 18.399 | 1.00 | 27.22 |
| ATOM | 1820 | C   | GLU A | 266 | 22.787 | 34.905 | 19.763 | 1.00 | 19.77 |
| ATOM | 1821 | O   | GLU A | 266 | 23.080 | 35.378 | 20.858 | 1.00 | 17.93 |
| ATOM | 1822 | N   | ASP A | 267 | 23.120 | 33.668 | 19.400 | 1.00 | 20.25 |
| ATOM | 1823 | CA  | ASP A | 267 | 23.854 | 32.790 | 20.305 | 1.00 | 21.56 |
| ATOM | 1824 | CB  | ASP A | 267 | 24.000 | 31.385 | 19.707 | 1.00 | 22.05 |
| ATOM | 1825 | CG  | ASP A | 267 | 22.674 | 30.651 | 19.611 | 1.00 | 25.11 |
| ATOM | 1826 | OD1 | ASP A | 267 | 21.737 | 31.015 | 20.353 | 1.00 | 24.11 |
| ATOM | 1827 | OD2 | ASP A | 267 | 22.570 | 29.701 | 18.803 | 1.00 | 26.91 |
| ATOM | 1828 | C   | ASP A | 267 | 25.229 | 33.352 | 20.640 | 1.00 | 21.65 |
| ATOM | 1829 | O   | ASP A | 267 | 25.618 | 33.404 | 21.808 | 1.00 | 22.61 |
| ATOM | 1830 | N   | ILE A | 268 | 25.965 | 33.776 | 19.619 | 1.00 | 20.24 |
| ATOM | 1831 | CA  | ILE A | 268 | 27.287 | 34.336 | 19.843 | 1.00 | 19.65 |
| ATOM | 1832 | CB  | ILE A | 268 | 27.949 | 34.762 | 18.517 | 1.00 | 19.77 |
| ATOM | 1833 | CG2 | ILE A | 268 | 29.181 | 35.615 | 18.796 | 1.00 | 18.25 |
| ATOM | 1834 | CG1 | ILE A | 268 | 28.312 | 33.516 | 17.706 | 1.00 | 20.48 |
| ATOM | 1835 | CD1 | ILE A | 268 | 28.903 | 33.813 | 16.347 | 1.00 | 21.71 |
| ATOM | 1836 | C   | ILE A | 268 | 27.209 | 35.538 | 20.774 | 1.00 | 18.66 |
| ATOM | 1837 | O   | ILE A | 268 | 28.037 | 35.689 | 21.671 | 1.00 | 18.66 |
| ATOM | 1838 | N   | ALA A | 269 | 26.208 | 36.386 | 20.567 | 1.00 | 18.12 |
| ATOM | 1839 | CA  | ALA A | 269 | 26.042 | 37.573 | 21.401 | 1.00 | 19.02 |
| ATOM | 1840 | CB  | ALA A | 269 | 24.906 | 38.429 | 20.872 | 1.00 | 17.83 |
| ATOM | 1841 | C   | ALA A | 269 | 25.760 | 37.165 | 22.842 | 1.00 | 19.92 |
| ATOM | 1842 | O   | ALA A | 269 | 26.246 | 37.785 | 23.786 | 1.00 | 19.07 |
| ATOM | 1843 | N   | SER A | 270 | 24.971 | 36.108 | 22.998 | 1.00 | 20.50 |
| ATOM | 1844 | CA  | SER A | 270 | 24.616 | 35.604 | 24.314 | 1.00 | 20.79 |
| ATOM | 1845 | CB  | SER A | 270 | 23.528 | 34.536 | 24.175 | 1.00 | 20.34 |
| ATOM | 1846 | OG  | SER A | 270 | 23.261 | 33.914 | 25.417 | 1.00 | 22.74 |

TABLE 30-continued

| ATOM | 1847 | C | SER A | 270 | 25.837 | 35.031 | 25.039 | 1.00 | 20.69 |
|------|------|------|-------|-----|--------|--------|--------|------|-------|
| ATOM | 1848 | O | SER A | 270 | 26.084 | 35.356 | 26.198 | 1.00 | 22.32 |
| ATOM | 1849 | N | VAL A | 271 | 26.596 | 34.178 | 24.358 | 1.00 | 20.01 |
| ATOM | 1850 | CA | VAL A | 271 | 27.786 | 33.578 | 24.955 | 1.00 | 20.35 |
| ATOM | 1851 | CB | VAL A | 271 | 28.435 | 32.556 | 23.998 | 1.00 | 19.34 |
| ATOM | 1852 | CG1 | VAL A | 271 | 29.753 | 32.056 | 24.584 | 1.00 | 19.49 |
| ATOM | 1853 | CG2 | VAL A | 271 | 27.491 | 31.390 | 23.767 | 1.00 | 15.58 |
| ATOM | 1854 | C | VAL A | 271 | 28.819 | 34.649 | 25.308 | 1.00 | 22.65 |
| ATOM | 1855 | O | VAL A | 271 | 29.420 | 34.621 | 26.382 | 1.00 | 21.15 |
| ATOM | 1856 | N | VAL A | 272 | 29.015 | 35.597 | 24.398 | 1.00 | 24.64 |
| ATOM | 1857 | CA | VAL A | 272 | 29.968 | 36.677 | 24.609 | 1.00 | 26.34 |
| ATOM | 1858 | CB | VAL A | 272 | 29.957 | 37.656 | 23.411 | 1.00 | 27.45 |
| ATOM | 1859 | CG1 | VAL A | 272 | 30.522 | 39.005 | 23.824 | 1.00 | 27.55 |
| ATOM | 1860 | CG2 | VAL A | 272 | 30.780 | 37.070 | 22.264 | 1.00 | 25.36 |
| ATOM | 1861 | C | VAL A | 272 | 29.691 | 37.446 | 25.897 | 1.00 | 27.85 |
| ATOM | 1862 | O | VAL A | 272 | 30.610 | 37.748 | 26.662 | 1.00 | 28.31 |
| ATOM | 1863 | N | LYS A | 273 | 28.424 | 37.750 | 26.146 | 1.00 | 28.61 |
| ATOM | 1864 | CA | LYS A | 273 | 28.054 | 38.491 | 27.345 | 1.00 | 30.76 |
| ATOM | 1865 | CB | LYS A | 273 | 26.695 | 39.173 | 27.137 | 1.00 | 31.43 |
| ATOM | 1866 | CG | LYS A | 273 | 26.759 | 40.293 | 26.087 | 1.00 | 34.55 |
| ATOM | 1867 | CD | LYS A | 273 | 25.463 | 41.089 | 25.987 | 1.00 | 36.45 |
| ATOM | 1868 | CE | LYS A | 273 | 24.312 | 40.229 | 25.501 | 1.00 | 36.17 |
| ATOM | 1869 | NZ | LYS A | 273 | 23.073 | 41.031 | 25.320 | 1.00 | 38.03 |
| ATOM | 1870 | C | LYS A | 273 | 28.042 | 37.615 | 28.595 | 1.00 | 30.26 |
| ATOM | 1871 | O | LYS A | 273 | 28.295 | 38.091 | 29.701 | 1.00 | 30.38 |
| ATOM | 1872 | N | GLU A | 274 | 27.765 | 36.331 | 28.414 | 1.00 | 29.22 |
| ATOM | 1873 | CA | GLU A | 274 | 27.745 | 35.396 | 29.527 | 1.00 | 28.71 |
| ATOM | 1874 | CB | GLU A | 274 | 27.184 | 34.051 | 29.064 | 1.00 | 29.65 |
| ATOM | 1875 | CG | GLU A | 274 | 27.100 | 32.996 | 30.152 | 1.00 | 34.63 |
| ATOM | 1876 | CD | GLU A | 274 | 27.077 | 31.583 | 29.590 | 1.00 | 37.55 |
| ATOM | 1877 | OE1 | GLU A | 274 | 26.405 | 31.360 | 28.562 | 1.00 | 38.36 |
| ATOM | 1878 | OE2 | GLU A | 274 | 27.727 | 30.691 | 30.180 | 1.00 | 40.62 |
| ATOM | 1879 | C | GLU A | 274 | 29.159 | 35.179 | 30.084 | 1.00 | 29.15 |
| ATOM | 1880 | O | GLU A | 274 | 29.361 | 35.158 | 31.300 | 1.00 | 28.97 |
| ATOM | 1881 | N | LEU A | 275 | 30.135 | 35.032 | 29.185 | 1.00 | 26.95 |
| ATOM | 1882 | CA | LEU A | 275 | 31.522 | 34.772 | 29.575 | 1.00 | 24.76 |
| ATOM | 1883 | CB | LEU A | 275 | 32.181 | 33.842 | 28.556 | 1.00 | 22.52 |
| ATOM | 1884 | CG | LEU A | 275 | 31.494 | 32.500 | 28.313 | 1.00 | 22.79 |
| ATOM | 1885 | CD1 | LEU A | 275 | 32.250 | 31.719 | 27.247 | 1.00 | 21.36 |
| ATOM | 1886 | CD2 | LEU A | 275 | 31.436 | 31.721 | 29.617 | 1.00 | 22.41 |
| ATOM | 1887 | C | LEU A | 275 | 32.413 | 35.992 | 29.761 | 1.00 | 24.23 |
| ATOM | 1888 | O | LEU A | 275 | 33.522 | 35.874 | 30.276 | 1.00 | 25.42 |
| ATOM | 1889 | N | GLY A | 276 | 31.944 | 37.158 | 29.338 | 1.00 | 24.12 |
| ATOM | 1890 | CA | GLY A | 276 | 32.758 | 38.351 | 29.479 | 1.00 | 22.44 |
| ATOM | 1891 | C | GLY A | 276 | 33.796 | 38.517 | 28.378 | 1.00 | 23.67 |
| ATOM | 1892 | O | GLY A | 276 | 34.851 | 39.110 | 28.605 | 1.00 | 23.44 |
| ATOM | 1893 | N | ILE A | 277 | 33.515 | 37.992 | 27.186 | 1.00 | 23.83 |
| ATOM | 1894 | CA | ILE A | 277 | 34.440 | 38.134 | 26.062 | 1.00 | 22.17 |
| ATOM | 1895 | CB | ILE A | 277 | 33.829 | 37.586 | 24.754 | 1.00 | 22.72 |
| ATOM | 1896 | CG2 | ILE A | 277 | 34.746 | 37.888 | 23.577 | 1.00 | 21.72 |
| ATOM | 1897 | CG1 | ILE A | 277 | 33.635 | 36.077 | 24.871 | 1.00 | 22.65 |
| ATOM | 1898 | CD1 | ILE A | 277 | 34.926 | 35.332 | 25.123 | 1.00 | 26.25 |
| ATOM | 1899 | C | ILE A | 277 | 34.735 | 39.623 | 25.899 | 1.00 | 22.15 |
| ATOM | 1900 | O | ILE A | 277 | 33.828 | 40.456 | 25.949 | 1.00 | 20.17 |
| ATOM | 1901 | N | ASP A | 278 | 36.006 | 39.953 | 25.701 | 1.00 | 20.80 |
| ATOM | 1902 | CA | ASP A | 278 | 36.431 | 41.340 | 25.578 | 1.00 | 19.25 |
| ATOM | 1903 | CB | ASP A | 278 | 37.945 | 41.421 | 25.753 | 1.00 | 18.89 |
| ATOM | 1904 | CG | ASP A | 278 | 38.392 | 40.898 | 27.094 | 1.00 | 18.41 |
| ATOM | 1905 | OD1 | ASP A | 278 | 37.974 | 41.485 | 28.115 | 1.00 | 20.16 |
| ATOM | 1906 | OD2 | ASP A | 278 | 39.147 | 39.903 | 27.131 | 1.00 | 17.97 |
| ATOM | 1907 | C | ASP A | 278 | 36.029 | 42.062 | 24.303 | 1.00 | 19.25 |
| ATOM | 1908 | O | ASP A | 278 | 35.907 | 43.286 | 24.299 | 1.00 | 20.39 |
| ATOM | 1909 | N | GLY A | 279 | 35.825 | 41.320 | 23.221 | 1.00 | 17.95 |
| ATOM | 1910 | CA | GLY A | 279 | 35.451 | 41.970 | 21.981 | 1.00 | 16.99 |
| ATOM | 1911 | C | GLY A | 279 | 35.229 | 41.038 | 20.812 | 1.00 | 16.55 |
| ATOM | 1912 | O | GLY A | 279 | 35.455 | 39.833 | 20.902 | 1.00 | 16.99 |
| ATOM | 1913 | N | LEU A | 280 | 34.788 | 41.613 | 19.700 | 1.00 | 16.23 |
| ATOM | 1914 | CA | LEU A | 280 | 34.515 | 40.848 | 18.495 | 1.00 | 16.29 |
| ATOM | 1915 | CB | LEU A | 280 | 33.006 | 40.804 | 18.222 | 1.00 | 14.21 |
| ATOM | 1916 | CG | LEU A | 280 | 32.071 | 40.069 | 19.187 | 1.00 | 16.53 |
| ATOM | 1917 | CD1 | LEU A | 280 | 30.623 | 40.395 | 18.840 | 1.00 | 14.51 |
| ATOM | 1918 | CD2 | LEU A | 280 | 32.315 | 38.568 | 19.110 | 1.00 | 14.28 |
| ATOM | 1919 | C | LEU A | 280 | 35.197 | 41.457 | 17.283 | 1.00 | 15.25 |
| ATOM | 1920 | O | LEU A | 280 | 35.274 | 42.681 | 17.145 | 1.00 | 14.60 |
| ATOM | 1921 | N | ILE A | 281 | 35.718 | 40.596 | 16.420 | 1.00 | 13.70 |
| ATOM | 1922 | CA | ILE A | 281 | 36.325 | 41.051 | 15.186 | 1.00 | 14.56 |
| ATOM | 1923 | CB | ILE A | 281 | 37.675 | 40.382 | 14.911 | 1.00 | 12.34 |
| ATOM | 1924 | CG2 | ILE A | 281 | 38.259 | 40.937 | 13.619 | 1.00 | 12.73 |
| ATOM | 1925 | CG1 | ILE A | 281 | 38.640 | 40.684 | 16.065 | 1.00 | 11.34 |

TABLE 30-continued

| | | | | | | | | |
|---|---|---|---|---|---|---|---|---|
| ATOM | 1926 | CD1 | ILE A | 281 | 40.103 | 40.703 | 15.660 | 1.00 | 9.52 |
| ATOM | 1927 | C | ILE A | 281 | 35.264 | 40.584 | 14.213 | 1.00 | 16.31 |
| ATOM | 1928 | O | ILE A | 281 | 35.038 | 39.382 | 14.036 | 1.00 | 15.34 |
| ATOM | 1929 | N | VAL A | 282 | 34.584 | 41.535 | 13.590 | 1.00 | 18.61 |
| ATOM | 1930 | CA | VAL A | 282 | 33.493 | 41.138 | 12.738 | 1.00 | 20.29 |
| ATOM | 1931 | CB | VAL A | 282 | 32.273 | 42.022 | 13.010 | 1.00 | 19.32 |
| ATOM | 1932 | CG1 | VAL A | 282 | 31.089 | 41.577 | 12.175 | 1.00 | 15.46 |
| ATOM | 1933 | CG2 | VAL A | 282 | 31.931 | 41.917 | 14.484 | 1.00 | 14.77 |
| ATOM | 1934 | C | VAL A | 282 | 33.718 | 40.940 | 11.257 | 1.00 | 23.76 |
| ATOM | 1935 | O | VAL A | 282 | 34.031 | 41.849 | 10.483 | 1.00 | 21.79 |
| ATOM | 1936 | N | THR A | 283 | 33.500 | 39.669 | 10.937 | 1.00 | 26.44 |
| ATOM | 1937 | CA | THR A | 283 | 33.591 | 38.994 | 9.657 | 1.00 | 24.63 |
| ATOM | 1938 | CB | THR A | 283 | 32.573 | 39.520 | 8.593 | 1.00 | 22.04 |
| ATOM | 1939 | OG1 | THR A | 283 | 33.276 | 39.969 | 7.431 | 1.00 | 20.72 |
| ATOM | 1940 | CG2 | THR A | 283 | 31.680 | 40.606 | 9.165 | 1.00 | 24.57 |
| ATOM | 1941 | C | THR A | 283 | 34.939 | 38.783 | 9.006 | 1.00 | 23.16 |
| ATOM | 1942 | O | THR A | 283 | 35.758 | 39.683 | 8.794 | 1.00 | 22.01 |
| ATOM | 1943 | N | ASN A | 284 | 35.133 | 37.504 | 8.741 | 1.00 | 19.80 |
| ATOM | 1944 | CA | ASN A | 284 | 36.279 | 36.955 | 8.085 | 1.00 | 17.61 |
| ATOM | 1945 | CB | ASN A | 284 | 36.417 | 35.497 | 8.515 | 1.00 | 15.52 |
| ATOM | 1946 | CG | ASN A | 284 | 37.812 | 34.981 | 8.365 | 1.00 | 14.49 |
| ATOM | 1947 | OD1 | ASN A | 284 | 38.384 | 35.036 | 7.285 | 1.00 | 15.69 |
| ATOM | 1948 | ND2 | ASN A | 284 | 38.375 | 34.467 | 9.453 | 1.00 | 14.96 |
| ATOM | 1949 | C | ASN A | 284 | 35.796 | 37.043 | 6.641 | 1.00 | 16.90 |
| ATOM | 1950 | O | ASN A | 284 | 34.917 | 37.850 | 6.326 | 1.00 | 17.24 |
| ATOM | 1951 | N | THR A | 285 | 36.344 | 36.214 | 5.766 | 1.00 | 15.67 |
| ATOM | 1952 | CA | THR A | 285 | 35.914 | 36.225 | 4.377 | 1.00 | 14.29 |
| ATOM | 1953 | CB | THR A | 285 | 36.971 | 35.569 | 3.468 | 1.00 | 13.61 |
| ATOM | 1954 | OG1 | THR A | 285 | 37.347 | 34.296 | 4.012 | 1.00 | 11.23 |
| ATOM | 1955 | CG2 | THR A | 285 | 38.206 | 36.462 | 3.366 | 1.00 | 10.88 |
| ATOM | 1956 | C | THR A | 285 | 34.593 | 35.461 | 4.274 | 1.00 | 14.86 |
| ATOM | 1957 | O | THR A | 285 | 34.238 | 34.697 | 5.176 | 1.00 | 12.89 |
| ATOM | 1958 | N | THR A | 286 | 33.868 | 35.676 | 3.179 | 1.00 | 14.02 |
| ATOM | 1959 | CA | THR A | 286 | 32.582 | 35.016 | 2.960 | 1.00 | 11.85 |
| ATOM | 1960 | CB | THR A | 286 | 31.533 | 36.015 | 2.411 | 1.00 | 9.54 |
| ATOM | 1961 | OG1 | THR A | 286 | 30.298 | 35.335 | 2.179 | 1.00 | 12.88 |
| ATOM | 1962 | CG2 | THR A | 286 | 32.000 | 36.614 | 1.091 | 1.00 | 8.80 |
| ATOM | 1963 | C | THR A | 286 | 32.682 | 33.861 | 1.964 | 1.00 | 12.60 |
| ATOM | 1964 | O | THR A | 286 | 33.413 | 33.953 | 0.970 | 1.00 | 11.62 |
| ATOM | 1965 | N | VAL A | 287 | 31.951 | 32.778 | 2.230 | 1.00 | 12.37 |
| ATOM | 1966 | CA | VAL A | 287 | 31.939 | 31.636 | 1.320 | 1.00 | 14.81 |
| ATOM | 1967 | CB | VAL A | 287 | 31.725 | 30.281 | 2.047 | 1.00 | 15.55 |
| ATOM | 1968 | CG1 | VAL A | 287 | 32.846 | 30.035 | 3.035 | 1.00 | 16.38 |
| ATOM | 1969 | CG2 | VAL A | 287 | 30.372 | 30.261 | 2.748 | 1.00 | 16.45 |
| ATOM | 1970 | C | VAL A | 287 | 30.789 | 31.844 | 0.336 | 1.00 | 16.38 |
| ATOM | 1971 | O | VAL A | 287 | 30.525 | 31.001 | −0.521 | 1.00 | 16.63 |
| ATOM | 1972 | N | SER A | 288 | 30.096 | 32.969 | 0.473 | 1.00 | 15.25 |
| ATOM | 1973 | CA | SER A | 288 | 29.001 | 33.278 | −0.433 | 1.00 | 15.37 |
| ATOM | 1974 | CB | SER A | 288 | 28.026 | 34.275 | 0.202 | 1.00 | 14.24 |
| ATOM | 1975 | OG | SER A | 288 | 28.580 | 35.583 | 0.215 | 1.00 | 13.66 |
| ATOM | 1976 | C | SER A | 288 | 29.620 | 33.910 | −1.672 | 1.00 | 15.99 |
| ATOM | 1977 | O | SER A | 288 | 30.772 | 34.339 | −1.653 | 1.00 | 15.45 |
| ATOM | 1978 | N | ARG A | 289 | 28.848 | 33.965 | −2.749 | 1.00 | 17.27 |
| ATOM | 1979 | CA | ARG A | 289 | 29.312 | 34.562 | −3.992 | 1.00 | 19.15 |
| ATOM | 1980 | CB | ARG A | 289 | 29.620 | 33.473 | −5.022 | 1.00 | 18.24 |
| ATOM | 1981 | CG | ARG A | 289 | 30.830 | 32.621 | −4.669 | 1.00 | 18.25 |
| ATOM | 1982 | CD | ARG A | 289 | 32.121 | 33.425 | −4.740 | 1.00 | 16.51 |
| ATOM | 1983 | NE | ARG A | 289 | 33.291 | 32.580 | −4.521 | 1.00 | 15.70 |
| ATOM | 1984 | CZ | ARG A | 289 | 33.785 | 32.259 | −3.328 | 1.00 | 15.56 |
| ATOM | 1985 | NH1 | ARG A | 289 | 34.850 | 31.469 | −3.246 | 1.00 | 12.48 |
| ATOM | 1986 | NH2 | ARG A | 289 | 33.230 | 32.736 | −2.219 | 1.00 | 13.20 |
| ATOM | 1987 | C | ARG A | 289 | 28.198 | 35.472 | −4.488 | 1.00 | 20.73 |
| ATOM | 1988 | O | ARG A | 289 | 27.361 | 35.073 | −5.305 | 1.00 | 21.86 |
| ATOM | 1989 | N | PRO A | 290 | 28.172 | 36.714 | −3.985 | 1.00 | 19.73 |
| ATOM | 1990 | CD | PRO A | 290 | 29.204 | 37.305 | −3.117 | 1.00 | 17.99 |
| ATOM | 1991 | CA | PRO A | 290 | 27.165 | 37.710 | −4.349 | 1.00 | 18.33 |
| ATOM | 1992 | CB | PRO A | 290 | 27.754 | 39.008 | −3.799 | 1.00 | 18.12 |
| ATOM | 1993 | CG | PRO A | 290 | 28.512 | 38.545 | −2.599 | 1.00 | 16.66 |
| ATOM | 1994 | C | PRO A | 290 | 26.952 | 37.769 | −5.850 | 1.00 | 18.94 |
| ATOM | 1995 | O | PRO A | 290 | 27.910 | 37.702 | −6.623 | 1.00 | 19.73 |
| ATOM | 1996 | N | ALA A | 291 | 25.694 | 37.876 | −6.267 | 1.00 | 18.87 |
| ATOM | 1997 | CA | ALA A | 291 | 25.392 | 37.974 | −7.691 | 1.00 | 16.81 |
| ATOM | 1998 | CB | ALA A | 291 | 23.890 | 38.075 | −7.905 | 1.00 | 14.68 |
| ATOM | 1999 | C | ALA A | 291 | 26.082 | 39.244 | −8.191 | 1.00 | 15.05 |
| ATOM | 2000 | O | ALA A | 291 | 26.121 | 40.247 | −7.484 | 1.00 | 15.36 |
| ATOM | 2001 | N | GLY A | 292 | 26.640 | 39.196 | −9.394 | 1.00 | 13.71 |
| ATOM | 2002 | CA | GLY A | 292 | 27.302 | 40.370 | −9.925 | 1.00 | 14.53 |
| ATOM | 2003 | C | GLY A | 292 | 28.803 | 40.235 | −10.097 | 1.00 | 15.49 |
| ATOM | 2004 | O | GLY A | 292 | 29.400 | 40.997 | −10.857 | 1.00 | 17.37 |

TABLE 30-continued

| | | | | | | | | |
|---|---|---|---|---|---|---|---|---|
| ATOM | 2005 | N    | LEU A | 293 | 29.422 | 39.291 | −9.392  | 1.00 | 14.91 |
| ATOM | 2006 | CA   | LEU A | 293 | 30.862 | 39.082 | −9.521  | 1.00 | 15.19 |
| ATOM | 2007 | CB   | LEU A | 293 | 31.304 | 37.838 | −8.746  | 1.00 | 15.22 |
| ATOM | 2008 | CG   | LEU A | 293 | 31.184 | 37.854 | −7.218  | 1.00 | 13.79 |
| ATOM | 2009 | CD1  | LEU A | 293 | 31.680 | 36.528 | −6.668  | 1.00 | 13.53 |
| ATOM | 2010 | CD2  | LEU A | 293 | 31.997 | 39.001 | −6.637  | 1.00 | 11.50 |
| ATOM | 2011 | C    | LEU A | 293 | 31.199 | 38.904 | −10.994 | 1.00 | 15.17 |
| ATOM | 2012 | O    | LEU A | 293 | 30.523 | 38.162 | −11.708 | 1.00 | 16.42 |
| ATOM | 2013 | N    | GLN A | 294 | 32.243 | 39.589 | −11.446 | 1.00 | 16.27 |
| ATOM | 2014 | CA   | GLN A | 294 | 32.660 | 39.517 | −12.838 | 1.00 | 16.80 |
| ATOM | 2015 | CB   | GLN A | 294 | 32.865 | 40.929 | −13.391 | 1.00 | 17.50 |
| ATOM | 2016 | CG   | GLN A | 294 | 31.593 | 41.745 | −13.445 | 1.00 | 18.23 |
| ATOM | 2017 | CD   | GLN A | 294 | 30.511 | 41.048 | −14.238 | 1.00 | 18.91 |
| ATOM | 2018 | OE1  | GLN A | 294 | 30.707 | 40.720 | −15.404 | 1.00 | 20.05 |
| ATOM | 2019 | NE2  | GLN A | 294 | 29.362 | 40.812 | −13.607 | 1.00 | 16.51 |
| ATOM | 2020 | C    | GLN A | 294 | 33.936 | 38.712 | −13.038 | 1.00 | 18.25 |
| ATOM | 2021 | O    | GLN A | 294 | 34.154 | 38.143 | −14.111 | 1.00 | 18.99 |
| ATOM | 2022 | N    | GLY A | 295 | 34.774 | 38.675 | −12.004 | 1.00 | 16.83 |
| ATOM | 2023 | CA   | GLY A | 295 | 36.029 | 37.954 | −12.083 | 1.00 | 15.09 |
| ATOM | 2024 | C    | GLY A | 295 | 35.916 | 36.574 | −12.704 | 1.00 | 17.40 |
| ATOM | 2025 | O    | GLY A | 295 | 34.975 | 35.823 | −12.431 | 1.00 | 15.89 |
| ATOM | 2026 | N    | ALA A | 296 | 36.884 | 36.238 | −13.546 | 1.00 | 16.27 |
| ATOM | 2027 | CA   | ALA A | 296 | 36.894 | 34.936 | −14.201 | 1.00 | 17.04 |
| ATOM | 2028 | CB   | ALA A | 296 | 38.046 | 34.870 | −15.208 | 1.00 | 14.05 |
| ATOM | 2029 | C    | ALA A | 296 | 37.030 | 33.808 | −13.179 | 1.00 | 16.37 |
| ATOM | 2030 | O    | ALA A | 296 | 36.512 | 32.709 | −13.383 | 1.00 | 17.15 |
| ATOM | 2031 | N    | LEU A | 297 | 37.710 | 34.098 | −12.072 | 1.00 | 16.31 |
| ATOM | 2032 | CA   | LEU A | 297 | 37.964 | 33.113 | −11.019 | 1.00 | 14.92 |
| ATOM | 2033 | CB   | LEU A | 297 | 39.375 | 33.333 | −10.467 | 1.00 | 12.34 |
| ATOM | 2034 | CG   | LEU A | 297 | 40.466 | 33.409 | −11.544 | 1.00 | 14.84 |
| ATOM | 2035 | CD1  | LEU A | 297 | 41.782 | 33.872 | −10.924 | 1.00 | 14.02 |
| ATOM | 2036 | CD2  | LEU A | 297 | 40.625 | 32.047 | −12.216 | 1.00 | 12.49 |
| ATOM | 2037 | C    | LEU A | 297 | 36.962 | 33.148 | −9.867  | 1.00 | 14.64 |
| ATOM | 2038 | O    | LEU A | 297 | 37.247 | 32.650 | −8.774  | 1.00 | 14.34 |
| ATOM | 2039 | N    | ARG A | 298 | 35.789 | 33.722 | −10.122 | 1.00 | 15.32 |
| ATOM | 2040 | CA   | ARG A | 298 | 34.742 | 33.858 | −9.109  | 1.00 | 15.13 |
| ATOM | 2041 | CB   | ARG A | 298 | 33.557 | 34.642 | −9.687  | 1.00 | 14.29 |
| ATOM | 2042 | CG   | ARG A | 298 | 32.751 | 33.880 | −10.727 | 1.00 | 14.22 |
| ATOM | 2043 | CD   | ARG A | 298 | 31.674 | 34.763 | −11.358 | 1.00 | 14.90 |
| ATOM | 2044 | NE   | ARG A | 298 | 30.796 | 33.992 | −12.234 | 1.00 | 14.82 |
| ATOM | 2045 | CZ   | ARG A | 298 | 29.930 | 34.523 | −13.094 | 1.00 | 15.76 |
| ATOM | 2046 | NH1  | ARG A | 298 | 29.177 | 33.731 | −13.845 | 1.00 | 9.49  |
| ATOM | 2047 | NH2  | ARG A | 298 | 29.823 | 35.844 | −13.213 | 1.00 | 14.55 |
| ATOM | 2048 | C    | ARG A | 298 | 34.230 | 32.544 | −8.517  | 1.00 | 15.68 |
| ATOM | 2049 | O    | ARG A | 298 | 33.714 | 32.527 | −7.397  | 1.00 | 15.39 |
| ATOM | 2050 | N    | SER A | 299 | 34.367 | 31.448 | −9.259  | 1.00 | 15.50 |
| ATOM | 2051 | CA   | SER A | 299 | 33.893 | 30.160 | −8.773  | 1.00 | 16.47 |
| ATOM | 2052 | CB   | SER A | 299 | 33.196 | 29.397 | −9.898  | 1.00 | 15.50 |
| ATOM | 2053 | OG   | SER A | 299 | 31.911 | 29.949 | −10.126 | 1.00 | 15.72 |
| ATOM | 2054 | C    | SER A | 299 | 34.951 | 29.280 | −8.117  | 1.00 | 17.56 |
| ATOM | 2055 | O    | SER A | 299 | 34.733 | 28.085 | −7.916  | 1.00 | 19.41 |
| ATOM | 2056 | N    | GLU A | 300 | 36.095 | 29.869 | −7.786  | 1.00 | 15.71 |
| ATOM | 2057 | CA   | GLU A | 300 | 37.151 | 29.135 | −7.100  | 1.00 | 16.76 |
| ATOM | 2058 | CB   | GLU A | 300 | 38.469 | 29.926 | −7.116  | 1.00 | 15.74 |
| ATOM | 2059 | CG   | GLU A | 300 | 39.165 | 29.978 | −8.471  | 1.00 | 18.89 |
| ATOM | 2060 | CD   | GLU A | 300 | 39.888 | 28.684 | −8.808  | 1.00 | 19.42 |
| ATOM | 2061 | OE1  | GLU A | 300 | 40.297 | 28.509 | −9.975  | 1.00 | 21.22 |
| ATOM | 2062 | OE2  | GLU A | 300 | 40.057 | 27.844 | −7.902  | 1.00 | 20.90 |
| ATOM | 2063 | C    | GLU A | 300 | 36.700 | 28.958 | −5.648  | 1.00 | 17.51 |
| ATOM | 2064 | O    | GLU A | 300 | 36.012 | 29.818 | −5.087  | 1.00 | 18.05 |
| ATOM | 2065 | N    | THR A | 301 | 37.080 | 27.838 | −5.050  | 1.00 | 16.82 |
| ATOM | 2066 | CA   | THR A | 301 | 36.744 | 27.556 | −3.664  | 1.00 | 15.60 |
| ATOM | 2067 | CB   | THR A | 301 | 37.055 | 26.084 | −3.318  | 1.00 | 15.47 |
| ATOM | 2068 | OG1  | THR A | 301 | 36.037 | 25.241 | −3.867  | 1.00 | 18.75 |
| ATOM | 2069 | CG2  | THR A | 301 | 37.132 | 25.886 | −1.816  | 1.00 | 13.34 |
| ATOM | 2070 | C    | THR A | 301 | 37.571 | 28.462 | −2.753  | 1.00 | 14.33 |
| ATOM | 2071 | O    | THR A | 301 | 38.739 | 28.735 | −3.034  | 1.00 | 13.01 |
| ATOM | 2072 | N    | GLY A | 302 | 36.968 | 28.929 | −1.663  | 1.00 | 14.07 |
| ATOM | 2073 | CA   | GLY A | 302 | 37.697 | 29.783 | −0.743  | 1.00 | 13.12 |
| ATOM | 2074 | C    | GLY A | 302 | 36.880 | 30.929 | −0.186  | 1.00 | 14.13 |
| ATOM | 2075 | O    | GLY A | 302 | 35.687 | 31.054 | −0.468  | 1.00 | 13.77 |
| ATOM | 2076 | N    | GLY A | 303 | 37.529 | 31.764 | 0.619   | 1.00 | 14.37 |
| ATOM | 2077 | CA   | GLY A | 303 | 36.855 | 32.902 | 1.210   | 1.00 | 12.82 |
| ATOM | 2078 | C    | GLY A | 303 | 37.024 | 34.135 | 0.347   | 1.00 | 12.16 |
| ATOM | 2079 | O    | GLY A | 303 | 38.127 | 34.440 | −0.105  | 1.00 | 12.51 |
| ATOM | 2080 | N    | LEU A | 304 | 35.921 | 34.842 | 0.122   | 1.00 | 12.72 |
| ATOM | 2081 | CA   | LEU A | 304 | 35.916 | 36.049 | −0.694  | 1.00 | 11.93 |
| ATOM | 2082 | CB   | LEU A | 304 | 34.591 | 36.149 | −1.457  | 1.00 | 13.90 |
| ATOM | 2083 | CG   | LEU A | 304 | 34.302 | 37.429 | −2.248  | 1.00 | 16.01 |

TABLE 30-continued

| ATOM | 2084 | CD1 | LEU A | 304 | 35.263 | 37.557 | -3.414 | 1.00 | 16.08 |
| --- | --- | --- | --- | --- | --- | --- | --- | --- | --- |
| ATOM | 2085 | CD2 | LEU A | 304 | 32.865 | 37.382 | -2.756 | 1.00 | 20.99 |
| ATOM | 2086 | C | LEU A | 304 | 36.110 | 37.295 | 0.162 | 1.00 | 12.47 |
| ATOM | 2087 | O | LEU A | 304 | 35.500 | 37.438 | 1.225 | 1.00 | 13.78 |
| ATOM | 2088 | N | SER A | 305 | 36.957 | 38.199 | -0.313 | 1.00 | 12.54 |
| ATOM | 2089 | CA | SER A | 305 | 37.239 | 39.434 | 0.402 | 1.00 | 13.57 |
| ATOM | 2090 | CB | SER A | 305 | 38.617 | 39.349 | 1.056 | 1.00 | 13.12 |
| ATOM | 2091 | OG | SER A | 305 | 39.626 | 39.209 | 0.068 | 1.00 | 13.73 |
| ATOM | 2092 | C | SER A | 305 | 37.201 | 40.615 | -0.563 | 1.00 | 13.51 |
| ATOM | 2093 | O | SER A | 305 | 37.114 | 40.428 | -1.775 | 1.00 | 14.24 |
| ATOM | 2094 | N | GLY A | 306 | 37.273 | 41.829 | -0.026 | 1.00 | 13.39 |
| ATOM | 2095 | CA | GLY A | 306 | 37.250 | 43.002 | -0.884 | 1.00 | 13.15 |
| ATOM | 2096 | C | GLY A | 306 | 35.896 | 43.685 | -0.937 | 1.00 | 15.03 |
| ATOM | 2097 | O | GLY A | 306 | 35.028 | 43.435 | -0.096 | 1.00 | 14.92 |
| ATOM | 2098 | N | LYS A | 307 | 35.704 | 44.532 | -1.944 | 1.00 | 16.11 |
| ATOM | 2099 | CA | LYS A | 307 | 34.461 | 45.281 | -2.089 | 1.00 | 16.67 |
| ATOM | 2100 | CB | LYS A | 307 | 34.479 | 46.114 | -3.385 | 1.00 | 18.76 |
| ATOM | 2101 | CG | LYS A | 307 | 33.436 | 47.248 | -3.381 | 1.00 | 25.21 |
| ATOM | 2102 | CD | LYS A | 307 | 33.375 | 48.040 | -4.692 | 1.00 | 28.15 |
| ATOM | 2103 | CE | LYS A | 307 | 34.659 | 48.824 | -4.944 | 1.00 | 29.58 |
| ATOM | 2104 | NZ | LYS A | 307 | 35.009 | 49.744 | -3.819 | 1.00 | 29.15 |
| ATOM | 2105 | C | LYS A | 307 | 33.173 | 44.458 | -2.014 | 1.00 | 15.62 |
| ATOM | 2106 | O | LYS A | 307 | 32.211 | 44.872 | -1.365 | 1.00 | 16.68 |
| ATOM | 2107 | N | PRO A | 308 | 33.129 | 43.285 | -2.670 | 1.00 | 14.78 |
| ATOM | 2108 | CD | PRO A | 308 | 34.126 | 42.668 | -3.562 | 1.00 | 14.76 |
| ATOM | 2109 | CA | PRO A | 308 | 31.905 | 42.473 | -2.617 | 1.00 | 14.19 |
| ATOM | 2110 | CB | PRO A | 308 | 32.261 | 41.252 | -3.466 | 1.00 | 14.85 |
| ATOM | 2111 | CG | PRO A | 308 | 33.257 | 41.804 | -4.452 | 1.00 | 15.81 |
| ATOM | 2112 | C | PRO A | 308 | 31.492 | 42.079 | -1.198 | 1.00 | 15.30 |
| ATOM | 2113 | O | PRO A | 308 | 30.324 | 41.786 | -0.941 | 1.00 | 16.37 |
| ATOM | 2114 | N | LEU A | 309 | 32.454 | 42.072 | -0.281 | 1.00 | 15.32 |
| ATOM | 2115 | CA | LEU A | 309 | 32.202 | 41.706 | 1.111 | 1.00 | 15.37 |
| ATOM | 2116 | CB | LEU A | 309 | 33.434 | 40.995 | 1.682 | 1.00 | 13.97 |
| ATOM | 2117 | CG | LEU A | 309 | 33.538 | 40.793 | 3.201 | 1.00 | 12.70 |
| ATOM | 2118 | CD1 | LEU A | 309 | 32.468 | 39.821 | 3.683 | 1.00 | 12.47 |
| ATOM | 2119 | CD2 | LEU A | 309 | 34.920 | 40.250 | 3.541 | 1.00 | 11.41 |
| ATOM | 2120 | C | LEU A | 309 | 31.855 | 42.887 | 2.023 | 1.00 | 16.22 |
| ATOM | 2121 | O | LEU A | 309 | 31.211 | 42.707 | 3.056 | 1.00 | 17.60 |
| ATOM | 2122 | N | ARG A | 310 | 32.269 | 44.087 | 1.632 | 1.00 | 14.52 |
| ATOM | 2123 | CA | ARG A | 310 | 32.076 | 45.283 | 2.448 | 1.00 | 15.17 |
| ATOM | 2124 | CB | ARG A | 310 | 32.323 | 46.548 | 1.614 | 1.00 | 12.82 |
| ATOM | 2125 | CG | ARG A | 310 | 32.391 | 47.825 | 2.458 | 1.00 | 14.88 |
| ATOM | 2126 | CD | ARG A | 310 | 32.530 | 49.062 | 1.582 | 1.00 | 12.41 |
| ATOM | 2127 | NE | ARG A | 310 | 31.453 | 49.099 | 0.600 | 1.00 | 14.40 |
| ATOM | 2128 | CZ | ARG A | 310 | 31.454 | 49.851 | -0.492 | 1.00 | 12.91 |
| ATOM | 2129 | NH1 | ARG A | 310 | 30.422 | 49.797 | -1.323 | 1.00 | 10.64 |
| ATOM | 2130 | NH2 | ARG A | 310 | 32.482 | 50.652 | -0.753 | 1.00 | 12.19 |
| ATOM | 2131 | C | ARG A | 310 | 30.766 | 45.448 | 3.214 | 1.00 | 16.11 |
| ATOM | 2132 | O | ARG A | 310 | 30.753 | 45.395 | 4.444 | 1.00 | 17.04 |
| ATOM | 2133 | N | ASP A | 311 | 29.668 | 45.663 | 2.499 | 1.00 | 17.60 |
| ATOM | 2134 | CA | ASP A | 311 | 28.385 | 45.880 | 3.153 | 1.00 | 17.43 |
| ATOM | 2135 | CB | ASP A | 311 | 27.374 | 46.374 | 2.117 | 1.00 | 18.97 |
| ATOM | 2136 | CG | ASP A | 311 | 27.651 | 47.817 | 1.689 | 1.00 | 20.40 |
| ATOM | 2137 | OD1 | ASP A | 311 | 28.760 | 48.320 | 1.985 | 1.00 | 19.94 |
| ATOM | 2138 | OD2 | ASP A | 311 | 26.774 | 48.447 | 1.060 | 1.00 | 19.67 |
| ATOM | 2139 | C | ASP A | 311 | 27.855 | 44.688 | 3.945 | 1.00 | 18.29 |
| ATOM | 2140 | O | ASP A | 311 | 27.188 | 44.862 | 4.969 | 1.00 | 17.82 |
| ATOM | 2141 | N | LEU A | 312 | 28.156 | 43.480 | 3.485 | 1.00 | 17.49 |
| ATOM | 2142 | CA | LEU A | 312 | 27.734 | 42.290 | 4.204 | 1.00 | 17.70 |
| ATOM | 2143 | CB | LEU A | 312 | 28.172 | 41.033 | 3.451 | 1.00 | 18.87 |
| ATOM | 2144 | CG | LEU A | 312 | 27.778 | 39.688 | 4.066 | 1.00 | 23.26 |
| ATOM | 2145 | CD1 | LEU A | 312 | 26.260 | 39.596 | 4.183 | 1.00 | 22.82 |
| ATOM | 2146 | CD2 | LEU A | 312 | 28.312 | 38.549 | 3.193 | 1.00 | 23.37 |
| ATOM | 2147 | C | LEU A | 312 | 28.409 | 42.349 | 5.578 | 1.00 | 17.59 |
| ATOM | 2148 | O | LEU A | 312 | 27.818 | 41.959 | 6.588 | 1.00 | 16.95 |
| ATOM | 2149 | N | SER A | 313 | 29.646 | 42.851 | 5.607 | 1.00 | 16.39 |
| ATOM | 2150 | CA | SER A | 313 | 30.405 | 42.992 | 6.853 | 1.00 | 16.85 |
| ATOM | 2151 | CB | SER A | 313 | 31.869 | 43.359 | 6.575 | 1.00 | 17.49 |
| ATOM | 2152 | OG | SER A | 313 | 32.646 | 42.218 | 6.280 | 1.00 | 23.42 |
| ATOM | 2153 | C | SER A | 313 | 29.811 | 44.079 | 7.736 | 1.00 | 15.83 |
| ATOM | 2154 | O | SER A | 313 | 29.612 | 43.878 | 8.936 | 1.00 | 16.72 |
| ATOM | 2155 | N | THR A | 314 | 29.549 | 45.236 | 7.136 | 1.00 | 13.67 |
| ATOM | 2156 | CA | THR A | 314 | 28.989 | 46.362 | 7.866 | 1.00 | 13.92 |
| ATOM | 2157 | CB | THR A | 314 | 28.752 | 47.567 | 6.938 | 1.00 | 13.42 |
| ATOM | 2158 | OG1 | THR A | 314 | 29.990 | 47.938 | 6.323 | 1.00 | 13.10 |
| ATOM | 2159 | CG2 | THR A | 314 | 28.215 | 48.748 | 7.726 | 1.00 | 11.72 |
| ATOM | 2160 | C | THR A | 314 | 27.678 | 45.978 | 8.534 | 1.00 | 14.57 |
| ATOM | 2161 | O | THR A | 314 | 27.453 | 46.317 | 9.693 | 1.00 | 16.40 |
| ATOM | 2162 | N | GLN A | 315 | 26.823 | 45.259 | 7.811 | 1.00 | 14.98 |

TABLE 30-continued

| | | | | | | | |
|---|---|---|---|---|---|---|---|
| ATOM | 2163 CA | GLN A | 315 | 25.546 | 44.836 | 8.371 | 1.00 14.55 |
| ATOM | 2164 CB | GLN A | 315 | 24.656 | 44.215 | 7.288 | 1.00 13.68 |
| ATOM | 2165 CG | GLN A | 315 | 24.143 | 45.209 | 6.244 | 1.00 14.38 |
| ATOM | 2166 CD | GLN A | 315 | 23.178 | 46.249 | 6.821 | 1.00 14.67 |
| ATOM | 2167 OE1 | GLN A | 315 | 23.518 | 46.986 | 7.743 | 0.50 13.22 |
| ATOM | 2168 NE2 | GLN A | 315 | 21.975 | 46.310 | 6.268 | 0.50 11.94 |
| ATOM | 2169 C | GLN A | 315 | 25.741 | 43.852 | 9.522 | 1.00 13.89 |
| ATOM | 2170 O | GLN A | 315 | 24.962 | 43.853 | 10.472 | 1.00 15.26 |
| ATOM | 2171 N | THR A | 316 | 26.777 | 43.017 | 9.451 | 1.00 14.65 |
| ATOM | 2172 CA | THR A | 316 | 27.032 | 42.059 | 10.534 | 1.00 14.00 |
| ATOM | 2173 CB | THR A | 316 | 28.114 | 41.012 | 10.150 | 1.00 13.24 |
| ATOM | 2174 OG1 | THR A | 316 | 27.691 | 40.295 | 8.986 | 1.00 14.44 |
| ATOM | 2175 CG2 | THR A | 316 | 28.321 | 40.005 | 11.284 | 1.00 11.52 |
| ATOM | 2176 C | THR A | 316 | 27.489 | 42.835 | 11.767 | 1.00 13.16 |
| ATOM | 2177 O | THR A | 316 | 27.143 | 42.492 | 12.896 | 1.00 13.83 |
| ATOM | 2178 N | ILE A | 317 | 28.255 | 43.895 | 11.537 | 1.00 13.37 |
| ATOM | 2179 CA | ILE A | 317 | 28.736 | 44.741 | 12.622 | 1.00 13.69 |
| ATOM | 2180 CB | ILE A | 317 | 29.716 | 45.810 | 12.103 | 1.00 12.91 |
| ATOM | 2181 CG2 | ILE A | 317 | 30.004 | 46.824 | 13.206 | 1.00 11.97 |
| ATOM | 2182 CG1 | ILE A | 317 | 31.001 | 45.141 | 11.605 | 1.00 9.12 |
| ATOM | 2183 CD1 | ILE A | 317 | 31.901 | 46.053 | 10.797 | 1.00 7.71 |
| ATOM | 2184 C | ILE A | 317 | 27.554 | 45.452 | 13.268 | 1.00 15.49 |
| ATOM | 2185 O | ILE A | 317 | 27.451 | 45.522 | 14.494 | 1.00 14.24 |
| ATOM | 2186 N | ARG A | 318 | 26.662 | 45.971 | 12.424 | 1.00 15.63 |
| ATOM | 2187 CA | ARG A | 318 | 25.477 | 46.689 | 12.880 | 1.00 16.16 |
| ATOM | 2188 CB | ARG A | 318 | 24.657 | 47.153 | 11.664 | 1.00 16.16 |
| ATOM | 2189 CG | ARG A | 318 | 23.631 | 48.248 | 11.955 | 1.00 16.61 |
| ATOM | 2190 CD | ARG A | 318 | 22.868 | 48.675 | 10.694 | 1.00 15.44 |
| ATOM | 2191 NE | ARG A | 318 | 23.738 | 49.227 | 9.653 | 1.00 13.75 |
| ATOM | 2192 CZ | ARG A | 318 | 24.409 | 50.371 | 9.753 | 1.00 13.69 |
| ATOM | 2193 NH1 | ARG A | 318 | 24.318 | 51.105 | 10.851 | 1.00 12.53 |
| ATOM | 2194 NH2 | ARG A | 318 | 25.184 | 50.780 | 8.755 | 1.00 11.64 |
| ATOM | 2195 C | ARG A | 318 | 24.636 | 45.776 | 13.782 | 1.00 17.52 |
| ATOM | 2196 O | ARG A | 318 | 24.204 | 46.167 | 14.869 | 1.00 17.25 |
| ATOM | 2197 N | GLU A | 319 | 24.432 | 44.546 | 13.331 | 1.00 17.44 |
| ATOM | 2198 CA | GLU A | 319 | 23.651 | 43.577 | 14.081 | 1.00 17.47 |
| ATOM | 2199 CB | GLU A | 319 | 23.373 | 42.360 | 13.190 | 1.00 20.17 |
| ATOM | 2200 CG | GLU A | 319 | 22.491 | 41.289 | 13.803 | 1.00 26.82 |
| ATOM | 2201 CD | GLU A | 319 | 21.819 | 40.419 | 12.747 | 1.00 31.60 |
| ATOM | 2202 OE1 | GLU A | 319 | 22.427 | 40.206 | 11.677 | 1.00 33.28 |
| ATOM | 2203 OE2 | GLU A | 319 | 20.686 | 39.940 | 12.988 | 1.00 35.27 |
| ATOM | 2204 C | GLU A | 319 | 24.311 | 43.153 | 15.398 | 1.00 17.42 |
| ATOM | 2205 O | GLU A | 319 | 23.662 | 43.160 | 16.443 | 1.00 16.52 |
| ATOM | 2206 N | MET A | 320 | 25.596 | 42.797 | 15.368 | 1.00 17.15 |
| ATOM | 2207 CA | MET A | 320 | 26.272 | 42.378 | 16.599 | 1.00 16.53 |
| ATOM | 2208 CB | MET A | 320 | 27.685 | 41.865 | 16.298 | 1.00 16.03 |
| ATOM | 2209 CG | MET A | 320 | 27.739 | 40.641 | 15.383 | 1.00 13.63 |
| ATOM | 2210 SD | MET A | 320 | 26.655 | 39.271 | 15.894 | 1.00 18.40 |
| ATOM | 2211 CE | MET A | 320 | 27.359 | 38.810 | 17.506 | 1.00 13.96 |
| ATOM | 2212 C | MET A | 320 | 26.338 | 43.509 | 17.632 | 1.00 16.54 |
| ATOM | 2213 O | MET A | 320 | 26.255 | 43.270 | 18.838 | 1.00 16.13 |
| ATOM | 2214 N | TYR A | 321 | 26.478 | 44.740 | 17.153 | 1.00 16.60 |
| ATOM | 2215 CA | TYR A | 321 | 26.541 | 45.901 | 18.034 | 1.00 17.25 |
| ATOM | 2216 CB | TYR A | 321 | 26.734 | 47.171 | 17.207 | 1.00 16.92 |
| ATOM | 2217 CG | TYR A | 321 | 26.919 | 48.428 | 18.029 | 1.00 18.08 |
| ATOM | 2218 CD1 | TYR A | 321 | 28.139 | 48.716 | 18.633 | 1.00 17.27 |
| ATOM | 2219 CE1 | TYR A | 321 | 28.313 | 49.874 | 19.368 | 1.00 17.13 |
| ATOM | 2220 CD2 | TYR A | 321 | 25.877 | 49.334 | 18.189 | 1.00 16.65 |
| ATOM | 2221 CE2 | TYR A | 321 | 26.039 | 50.491 | 18.922 | 1.00 14.99 |
| ATOM | 2222 CZ | TYR A | 321 | 27.260 | 50.756 | 19.508 | 1.00 17.32 |
| ATOM | 2223 OH | TYR A | 321 | 27.429 | 51.912 | 20.232 | 1.00 18.90 |
| ATOM | 2224 C | TYR A | 321 | 25.247 | 46.013 | 18.845 | 1.00 17.69 |
| ATOM | 2225 O | TYR A | 321 | 25.279 | 46.220 | 20.059 | 1.00 16.80 |
| ATOM | 2226 N | ALA A | 322 | 24.115 | 45.872 | 18.159 | 1.00 17.52 |
| ATOM | 2227 CA | ALA A | 322 | 22.800 | 45.951 | 18.787 | 1.00 18.13 |
| ATOM | 2228 CB | ALA A | 322 | 21.708 | 46.037 | 17.709 | 1.00 14.74 |
| ATOM | 2229 C | ALA A | 322 | 22.537 | 44.757 | 19.713 | 1.00 18.09 |
| ATOM | 2230 O | ALA A | 322 | 21.958 | 44.914 | 20.783 | 1.00 20.05 |
| ATOM | 2231 N | LEU A | 323 | 22.957 | 43.566 | 19.303 | 1.00 17.18 |
| ATOM | 2232 CA | LEU A | 323 | 22.759 | 42.377 | 20.128 | 1.00 18.68 |
| ATOM | 2233 CB | LEU A | 323 | 23.137 | 41.117 | 19.344 | 1.00 17.23 |
| ATOM | 2234 CG | LEU A | 323 | 22.151 | 40.724 | 18.239 | 1.00 17.86 |
| ATOM | 2235 CD1 | LEU A | 323 | 22.725 | 39.591 | 17.402 | 1.00 15.10 |
| ATOM | 2236 CD2 | LEU A | 323 | 20.821 | 40.316 | 18.869 | 1.00 16.30 |
| ATOM | 2237 C | LEU A | 323 | 23.571 | 42.441 | 21.422 | 1.00 19.74 |
| ATOM | 2238 O | LEU A | 323 | 23.206 | 41.819 | 22.419 | 1.00 20.81 |
| ATOM | 2239 N | THR A | 324 | 24.669 | 43.194 | 21.404 | 1.00 19.53 |
| ATOM | 2240 CA | THR A | 324 | 25.515 | 43.330 | 22.584 | 1.00 20.06 |
| ATOM | 2241 CB | THR A | 324 | 27.023 | 43.166 | 22.223 | 1.00 19.26 |

TABLE 30-continued

| | | | | | | | | |
|---|---|---|---|---|---|---|---|---|
| ATOM | 2242 | OG1 | THR A | 324 | 27.408 | 44.147 | 21.249 | 1.00 | 17.20 |
| ATOM | 2243 | CG2 | THR A | 324 | 27.285 | 41.778 | 21.654 | 1.00 | 17.70 |
| ATOM | 2244 | C | THR A | 324 | 25.302 | 44.672 | 23.295 | 1.00 | 21.64 |
| ATOM | 2245 | O | THR A | 324 | 26.085 | 45.055 | 24.163 | 1.00 | 22.12 |
| ATOM | 2246 | N | GLN A | 325 | 24.241 | 45.381 | 22.921 | 1.00 | 22.94 |
| ATOM | 2247 | CA | GLN A | 325 | 23.919 | 46.670 | 23.528 | 1.00 | 24.57 |
| ATOM | 2248 | CB | GLN A | 325 | 23.522 | 46.491 | 24.999 | 1.00 | 27.95 |
| ATOM | 2249 | CG | GLN A | 325 | 22.175 | 45.828 | 25.230 | 1.00 | 30.78 |
| ATOM | 2250 | CD | GLN A | 325 | 22.100 | 44.441 | 24.636 | 1.00 | 35.70 |
| ATOM | 2251 | OE1 | GLN A | 325 | 22.901 | 43.565 | 24.967 | 1.00 | 38.45 |
| ATOM | 2252 | NE2 | GLN A | 325 | 21.131 | 44.229 | 23.751 | 1.00 | 38.29 |
| ATOM | 2253 | C | GLN A | 325 | 25.063 | 47.668 | 23.453 | 1.00 | 23.94 |
| ATOM | 2254 | O | GLN A | 325 | 25.177 | 48.548 | 24.306 | 1.00 | 23.91 |
| ATOM | 2255 | N | GLY A | 326 | 25.904 | 47.534 | 22.434 | 1.00 | 23.24 |
| ATOM | 2256 | CA | GLY A | 326 | 27.027 | 48.443 | 22.282 | 1.00 | 23.28 |
| ATOM | 2257 | C | GLY A | 326 | 28.016 | 48.409 | 23.436 | 1.00 | 22.96 |
| ATOM | 2258 | O | GLY A | 326 | 28.793 | 49.339 | 23.614 | 1.00 | 21.52 |
| ATOM | 2259 | N | ARG A | 327 | 27.999 | 47.334 | 24.217 | 1.00 | 25.30 |
| ATOM | 2260 | CA | ARG A | 327 | 28.899 | 47.206 | 25.361 | 1.00 | 27.57 |
| ATOM | 2261 | CB | ARG A | 327 | 28.138 | 46.638 | 26.562 | 1.00 | 30.57 |
| ATOM | 2262 | CG | ARG A | 327 | 27.083 | 47.587 | 27.105 | 1.00 | 37.38 |
| ATOM | 2263 | CD | ARG A | 327 | 26.178 | 46.924 | 28.131 | 1.00 | 42.63 |
| ATOM | 2264 | NE | ARG A | 327 | 25.129 | 47.846 | 28.565 | 1.00 | 49.69 |
| ATOM | 2265 | CZ | ARG A | 327 | 24.028 | 47.483 | 29.217 | 1.00 | 51.85 |
| ATOM | 2266 | NH1 | ARG A | 327 | 23.823 | 46.207 | 29.521 | 1.00 | 53.56 |
| ATOM | 2267 | NH2 | ARG A | 327 | 23.126 | 48.397 | 29.554 | 1.00 | 52.17 |
| ATOM | 2268 | C | ARG A | 327 | 30.116 | 46.335 | 25.068 | 1.00 | 26.53 |
| ATOM | 2269 | O | ARG A | 327 | 31.021 | 46.222 | 25.893 | 1.00 | 27.60 |
| ATOM | 2270 | N | VAL A | 328 | 30.133 | 45.720 | 23.892 | 1.00 | 24.01 |
| ATOM | 2271 | CA | VAL A | 328 | 31.240 | 44.864 | 23.504 | 1.00 | 21.11 |
| ATOM | 2272 | CB | VAL A | 328 | 30.744 | 43.469 | 23.096 | 1.00 | 19.81 |
| ATOM | 2273 | CG1 | VAL A | 328 | 31.914 | 42.606 | 22.672 | 1.00 | 17.59 |
| ATOM | 2274 | CG2 | VAL A | 328 | 29.987 | 42.831 | 24.255 | 1.00 | 17.80 |
| ATOM | 2275 | C | VAL A | 328 | 31.991 | 45.481 | 22.334 | 1.00 | 20.87 |
| ATOM | 2276 | O | VAL A | 328 | 31.442 | 45.632 | 21.246 | 1.00 | 21.52 |
| ATOM | 2277 | N | PRO A | 329 | 33.258 | 45.856 | 22.553 | 1.00 | 18.86 |
| ATOM | 2278 | CD | PRO A | 329 | 33.971 | 45.781 | 23.840 | 1.00 | 19.19 |
| ATOM | 2279 | CA | PRO A | 329 | 34.105 | 46.463 | 21.524 | 1.00 | 18.28 |
| ATOM | 2280 | CB | PRO A | 329 | 35.465 | 46.562 | 22.212 | 1.00 | 17.54 |
| ATOM | 2281 | CG | PRO A | 329 | 35.091 | 46.773 | 23.641 | 1.00 | 18.63 |
| ATOM | 2282 | C | PRO A | 329 | 34.160 | 45.615 | 20.250 | 1.00 | 17.72 |
| ATOM | 2283 | O | PRO A | 329 | 34.349 | 44.392 | 20.298 | 1.00 | 15.04 |
| ATOM | 2284 | N | ILE A | 330 | 33.990 | 46.273 | 19.112 | 1.00 | 14.63 |
| ATOM | 2285 | CA | ILE A | 330 | 34.029 | 45.580 | 17.838 | 1.00 | 15.12 |
| ATOM | 2286 | CB | ILE A | 330 | 32.657 | 45.651 | 17.123 | 1.00 | 14.81 |
| ATOM | 2287 | CG2 | ILE A | 330 | 32.768 | 45.073 | 15.732 | 1.00 | 13.87 |
| ATOM | 2288 | CG1 | ILE A | 330 | 31.598 | 44.895 | 17.928 | 1.00 | 15.39 |
| ATOM | 2289 | CD1 | ILE A | 330 | 30.206 | 44.971 | 17.315 | 1.00 | 15.21 |
| ATOM | 2290 | C | ILE A | 330 | 35.085 | 46.158 | 16.898 | 1.00 | 14.12 |
| ATOM | 2291 | O | ILE A | 330 | 35.274 | 47.377 | 16.816 | 1.00 | 12.39 |
| ATOM | 2292 | N | ILE A | 331 | 35.786 | 45.267 | 16.207 | 1.00 | 13.16 |
| ATOM | 2293 | CA | ILE A | 331 | 36.781 | 45.671 | 15.220 | 1.00 | 12.79 |
| ATOM | 2294 | CB | ILE A | 331 | 38.109 | 44.896 | 15.382 | 1.00 | 11.95 |
| ATOM | 2295 | CG2 | ILE A | 331 | 39.078 | 45.288 | 14.274 | 1.00 | 8.71 |
| ATOM | 2296 | CG1 | ILE A | 331 | 38.723 | 45.190 | 16.755 | 1.00 | 12.47 |
| ATOM | 2297 | CD1 | ILE A | 331 | 40.105 | 44.566 | 16.970 | 1.00 | 10.17 |
| ATOM | 2298 | C | ILE A | 331 | 36.153 | 45.306 | 13.875 | 1.00 | 13.43 |
| ATOM | 2299 | O | ILE A | 331 | 35.949 | 44.125 | 13.584 | 1.00 | 14.21 |
| ATOM | 2300 | N | GLY A | 332 | 35.824 | 46.319 | 13.077 | 1.00 | 12.41 |
| ATOM | 2301 | CA | GLY A | 332 | 35.206 | 46.086 | 11.782 | 1.00 | 11.36 |
| ATOM | 2302 | C | GLY A | 332 | 36.193 | 45.783 | 10.675 | 1.00 | 12.22 |
| ATOM | 2303 | O | GLY A | 332 | 37.166 | 46.510 | 10.493 | 1.00 | 15.34 |
| ATOM | 2304 | N | VAL A | 333 | 35.925 | 44.718 | 9.921 | 1.00 | 14.28 |
| ATOM | 2305 | CA | VAL A | 333 | 36.793 | 44.280 | 8.826 | 1.00 | 13.45 |
| ATOM | 2306 | CB | VAL A | 333 | 37.684 | 43.091 | 9.256 | 1.00 | 14.21 |
| ATOM | 2307 | CG1 | VAL A | 333 | 38.950 | 43.057 | 8.412 | 1.00 | 12.25 |
| ATOM | 2308 | CG2 | VAL A | 333 | 37.971 | 43.157 | 10.734 | 1.00 | 16.51 |
| ATOM | 2309 | C | VAL A | 333 | 35.961 | 43.770 | 7.649 | 1.00 | 12.59 |
| ATOM | 2310 | O | VAL A | 333 | 34.980 | 43.058 | 7.845 | 1.00 | 12.06 |
| ATOM | 2311 | N | GLY A | 334 | 36.373 | 44.103 | 6.431 | 1.00 | 12.29 |
| ATOM | 2312 | CA | GLY A | 334 | 35.643 | 43.639 | 5.266 | 1.00 | 12.70 |
| ATOM | 2313 | C | GLY A | 334 | 35.389 | 44.687 | 4.198 | 1.00 | 15.26 |
| ATOM | 2314 | O | GLY A | 334 | 34.428 | 45.458 | 4.284 | 1.00 | 13.77 |
| ATOM | 2315 | N | GLY A | 335 | 36.256 | 44.715 | 3.187 | 1.00 | 14.74 |
| ATOM | 2316 | CA | GLY A | 335 | 36.098 | 45.658 | 2.095 | 1.00 | 15.16 |
| ATOM | 2317 | C | GLY A | 335 | 36.323 | 47.127 | 2.409 | 1.00 | 16.18 |
| ATOM | 2318 | O | GLY A | 335 | 35.736 | 47.992 | 1.760 | 1.00 | 17.52 |
| ATOM | 2319 | N | VAL A | 336 | 37.154 | 47.429 | 3.400 | 1.00 | 16.08 |
| ATOM | 2320 | CA | VAL A | 336 | 37.434 | 48.822 | 3.723 | 1.00 | 14.99 |

TABLE 30-continued

| | | | | | | | | |
|---|---|---|---|---|---|---|---|---|
| ATOM | 2321 | CB | VAL A | 336 | 37.869 | 48.991 | 5.187 | 1.00 | 16.76 |
| ATOM | 2322 | CG1 | VAL A | 336 | 38.404 | 50.408 | 5.411 | 1.00 | 16.87 |
| ATOM | 2323 | CG2 | VAL A | 336 | 36.690 | 48.720 | 6.107 | 1.00 | 15.70 |
| ATOM | 2324 | C | VAL A | 336 | 38.547 | 49.319 | 2.801 | 1.00 | 15.40 |
| ATOM | 2325 | O | VAL A | 336 | 39.670 | 48.805 | 2.821 | 1.00 | 12.42 |
| ATOM | 2326 | N | SER A | 337 | 38.230 | 50.321 | 1.990 | 1.00 | 15.42 |
| ATOM | 2327 | CA | SER A | 337 | 39.204 | 50.859 | 1.051 | 1.00 | 17.10 |
| ATOM | 2328 | CB | SER A | 337 | 38.895 | 50.322 | −0.351 | 1.00 | 19.36 |
| ATOM | 2329 | OG | SER A | 337 | 39.848 | 50.768 | −1.295 | 1.00 | 25.95 |
| ATOM | 2330 | C | SER A | 337 | 39.225 | 52.388 | 1.030 | 1.00 | 16.56 |
| ATOM | 2331 | O | SER A | 337 | 39.991 | 52.992 | 0.280 | 1.00 | 16.38 |
| ATOM | 2332 | N | SER A | 338 | 38.393 | 53.012 | 1.860 | 1.00 | 14.64 |
| ATOM | 2333 | CA | SER A | 338 | 38.320 | 54.465 | 1.899 | 1.00 | 14.67 |
| ATOM | 2334 | CB | SER A | 338 | 37.349 | 54.961 | 0.819 | 1.00 | 14.99 |
| ATOM | 2335 | OG | SER A | 338 | 36.003 | 54.656 | 1.164 | 1.00 | 12.44 |
| ATOM | 2336 | C | SER A | 338 | 37.848 | 54.977 | 3.258 | 1.00 | 14.59 |
| ATOM | 2337 | O | SER A | 338 | 37.415 | 54.201 | 4.112 | 1.00 | 15.42 |
| ATOM | 2338 | N | GLY A | 339 | 37.922 | 56.289 | 3.446 | 1.00 | 13.82 |
| ATOM | 2339 | CA | GLY A | 339 | 37.478 | 56.877 | 4.694 | 1.00 | 13.48 |
| ATOM | 2340 | C | GLY A | 339 | 36.003 | 56.588 | 4.906 | 1.00 | 14.71 |
| ATOM | 2341 | O | GLY A | 339 | 35.578 | 56.290 | 6.023 | 1.00 | 15.22 |
| ATOM | 2342 | N | GLN A | 340 | 35.217 | 56.674 | 3.834 | 1.00 | 13.41 |
| ATOM | 2343 | CA | GLN A | 340 | 33.786 | 56.410 | 3.925 | 1.00 | 14.35 |
| ATOM | 2344 | CB | GLN A | 340 | 33.085 | 56.650 | 2.581 | 1.00 | 14.35 |
| ATOM | 2345 | CG | GLN A | 340 | 31.618 | 56.236 | 2.611 | 1.00 | 16.02 |
| ATOM | 2346 | CD | GLN A | 340 | 30.880 | 56.527 | 1.314 | 1.00 | 16.82 |
| ATOM | 2347 | OE1 | GLN A | 340 | 30.797 | 57.676 | 0.873 | 1.00 | 16.80 |
| ATOM | 2348 | NE2 | GLN A | 340 | 30.333 | 55.484 | 0.701 | 1.00 | 15.54 |
| ATOM | 2349 | C | GLN A | 340 | 33.529 | 54.978 | 4.372 | 1.00 | 14.64 |
| ATOM | 2350 | O | GLN A | 340 | 32.696 | 54.741 | 5.253 | 1.00 | 16.30 |
| ATOM | 2351 | N | ASP A | 341 | 34.237 | 54.028 | 3.763 | 1.00 | 11.52 |
| ATOM | 2352 | CA | ASP A | 341 | 34.078 | 52.623 | 4.127 | 1.00 | 12.53 |
| ATOM | 2353 | CB | ASP A | 341 | 35.023 | 51.726 | 3.310 | 1.00 | 11.88 |
| ATOM | 2354 | CG | ASP A | 341 | 34.767 | 51.803 | 1.813 | 1.00 | 13.90 |
| ATOM | 2355 | OD1 | ASP A | 341 | 33.638 | 52.168 | 1.416 | 1.00 | 15.59 |
| ATOM | 2356 | OD2 | ASP A | 341 | 35.689 | 51.483 | 1.029 | 1.00 | 12.73 |
| ATOM | 2357 | C | ASP A | 341 | 34.388 | 52.456 | 5.611 | 1.00 | 11.81 |
| ATOM | 2358 | O | ASP A | 341 | 33.694 | 51.742 | 6.332 | 1.00 | 11.96 |
| ATOM | 2359 | N | ALA A | 342 | 35.439 | 53.126 | 6.067 | 1.00 | 11.76 |
| ATOM | 2360 | CA | ALA A | 342 | 35.833 | 53.044 | 7.465 | 1.00 | 11.81 |
| ATOM | 2361 | CB | ALA A | 342 | 37.176 | 53.738 | 7.667 | 1.00 | 11.59 |
| ATOM | 2362 | C | ALA A | 342 | 34.780 | 53.655 | 8.385 | 1.00 | 12.36 |
| ATOM | 2363 | O | ALA A | 342 | 34.412 | 53.057 | 9.396 | 1.00 | 12.99 |
| ATOM | 2364 | N | LEU A | 343 | 34.288 | 54.840 | 8.029 | 1.00 | 11.54 |
| ATOM | 2365 | CA | LEU A | 343 | 33.291 | 55.524 | 8.845 | 1.00 | 12.58 |
| ATOM | 2366 | CB | LEU A | 343 | 33.119 | 56.971 | 8.367 | 1.00 | 12.32 |
| ATOM | 2367 | CG | LEU A | 343 | 32.194 | 57.846 | 9.219 | 1.00 | 11.92 |
| ATOM | 2368 | CD1 | LEU A | 343 | 32.722 | 57.868 | 10.649 | 1.00 | 12.03 |
| ATOM | 2369 | CD2 | LEU A | 343 | 32.115 | 59.269 | 8.648 | 1.00 | 8.59 |
| ATOM | 2370 | C | LEU A | 343 | 31.928 | 54.829 | 8.891 | 1.00 | 13.74 |
| ATOM | 2371 | O | LEU A | 343 | 31.238 | 54.894 | 9.905 | 1.00 | 16.00 |
| ATOM | 2372 | N | GLU A | 344 | 31.521 | 54.178 | 7.803 | 1.00 | 14.78 |
| ATOM | 2373 | CA | GLU A | 344 | 30.237 | 53.485 | 7.817 | 1.00 | 14.04 |
| ATOM | 2374 | CB | GLU A | 344 | 29.900 | 52.905 | 6.440 | 1.00 | 15.85 |
| ATOM | 2375 | CG | GLU A | 344 | 29.651 | 53.948 | 5.354 | 1.00 | 17.05 |
| ATOM | 2376 | CD | GLU A | 344 | 29.008 | 53.356 | 4.101 | 1.00 | 17.77 |
| ATOM | 2377 | OE1 | GLU A | 344 | 29.281 | 52.178 | 3.784 | 1.00 | 18.22 |
| ATOM | 2378 | OE2 | GLU A | 344 | 28.239 | 54.071 | 3.423 | 1.00 | 15.65 |
| ATOM | 2379 | C | GLU A | 344 | 30.291 | 52.365 | 8.855 | 1.00 | 14.33 |
| ATOM | 2380 | O | GLU A | 344 | 29.325 | 52.135 | 9.589 | 1.00 | 14.32 |
| ATOM | 2381 | N | LYS A | 345 | 31.429 | 51.678 | 8.925 | 1.00 | 14.23 |
| ATOM | 2382 | CA | LYS A | 345 | 31.607 | 50.597 | 9.891 | 1.00 | 14.82 |
| ATOM | 2383 | CB | LYS A | 345 | 32.874 | 49.798 | 9.577 | 1.00 | 13.09 |
| ATOM | 2384 | CG | LYS A | 345 | 32.684 | 48.787 | 8.455 | 1.00 | 13.42 |
| ATOM | 2385 | CD | LYS A | 345 | 33.950 | 47.983 | 8.198 | 1.00 | 11.05 |
| ATOM | 2386 | CE | LYS A | 345 | 33.644 | 46.692 | 7.449 | 1.00 | 11.82 |
| ATOM | 2387 | NZ | LYS A | 345 | 32.954 | 46.910 | 6.149 | 1.00 | 11.61 |
| ATOM | 2388 | C | LYS A | 345 | 31.668 | 51.150 | 11.310 | 1.00 | 14.91 |
| ATOM | 2389 | O | LYS A | 345 | 31.127 | 50.554 | 12.240 | 1.00 | 15.66 |
| ATOM | 2390 | N | ILE A | 346 | 32.320 | 52.295 | 11.478 | 1.00 | 14.92 |
| ATOM | 2391 | CA | ILE A | 346 | 32.402 | 52.911 | 12.796 | 1.00 | 15.79 |
| ATOM | 2392 | CB | ILE A | 346 | 33.369 | 54.121 | 12.789 | 1.00 | 16.10 |
| ATOM | 2393 | CG2 | ILE A | 346 | 33.290 | 54.875 | 14.116 | 1.00 | 14.25 |
| ATOM | 2394 | CG1 | ILE A | 346 | 34.797 | 53.623 | 12.538 | 1.00 | 14.97 |
| ATOM | 2395 | CD1 | ILE A | 346 | 35.817 | 54.721 | 12.416 | 1.00 | 16.00 |
| ATOM | 2396 | C | ILE A | 346 | 31.001 | 53.350 | 13.234 | 1.00 | 16.25 |
| ATOM | 2397 | O | ILE A | 346 | 30.591 | 53.083 | 14.363 | 1.00 | 16.13 |
| ATOM | 2398 | N | ARG A | 347 | 30.260 | 54.007 | 12.342 | 1.00 | 15.62 |
| ATOM | 2399 | CA | ARG A | 347 | 28.902 | 54.438 | 12.679 | 1.00 | 16.59 |

TABLE 30-continued

| | | | | | | | | |
|---|---|---|---|---|---|---|---|---|
| ATOM | 2400 | CB | ARG A | 347 | 28.295 | 55.277 | 11.548 | 1.00 | 17.49 |
| ATOM | 2401 | CG | ARG A | 347 | 28.941 | 56.653 | 11.343 | 1.00 | 18.28 |
| ATOM | 2402 | CD | ARG A | 347 | 28.202 | 57.433 | 10.253 | 1.00 | 19.60 |
| ATOM | 2403 | NE | ARG A | 347 | 26.798 | 57.641 | 10.603 | 1.00 | 22.54 |
| ATOM | 2404 | CZ | ARG A | 347 | 26.277 | 58.810 | 10.972 | 1.00 | 26.53 |
| ATOM | 2405 | NH1 | ARG A | 347 | 27.041 | 59.897 | 11.035 | 1.00 | 26.79 |
| ATOM | 2406 | NH2 | ARG A | 347 | 24.991 | 58.890 | 11.298 | 1.00 | 24.26 |
| ATOM | 2407 | C | ARG A | 347 | 28.012 | 53.219 | 12.946 | 1.00 | 15.67 |
| ATOM | 2408 | O | ARG A | 347 | 27.085 | 53.279 | 13.747 | 1.00 | 15.54 |
| ATOM | 2409 | N | ALA A | 348 | 28.301 | 52.110 | 12.272 | 1.00 | 15.61 |
| ATOM | 2410 | CA | ALA A | 348 | 27.526 | 50.891 | 12.464 | 1.00 | 15.15 |
| ATOM | 2411 | CB | ALA A | 348 | 27.797 | 49.900 | 11.325 | 1.00 | 14.45 |
| ATOM | 2412 | C | ALA A | 348 | 27.850 | 50.250 | 13.813 | 1.00 | 15.53 |
| ATOM | 2413 | O | ALA A | 348 | 27.090 | 49.407 | 14.295 | 1.00 | 16.19 |
| ATOM | 2414 | N | GLY A | 349 | 28.973 | 50.642 | 14.423 | 1.00 | 13.70 |
| ATOM | 2415 | CA | GLY A | 349 | 29.320 | 50.084 | 15.722 | 1.00 | 12.86 |
| ATOM | 2416 | C | GLY A | 349 | 30.763 | 49.672 | 15.980 | 1.00 | 14.30 |
| ATOM | 2417 | O | GLY A | 349 | 31.101 | 49.272 | 17.096 | 1.00 | 14.51 |
| ATOM | 2418 | N | ALA A | 350 | 31.621 | 49.770 | 14.971 | 1.00 | 13.70 |
| ATOM | 2419 | CA | ALA A | 350 | 33.019 | 49.392 | 15.136 | 1.00 | 15.96 |
| ATOM | 2420 | CB | ALA A | 350 | 33.643 | 49.085 | 13.777 | 1.00 | 16.02 |
| ATOM | 2421 | C | ALA A | 350 | 33.836 | 50.463 | 15.841 | 1.00 | 16.80 |
| ATOM | 2422 | O | ALA A | 350 | 33.729 | 51.652 | 15.527 | 1.00 | 17.12 |
| ATOM | 2423 | N | SER A | 351 | 34.651 | 50.034 | 16.801 | 1.00 | 17.39 |
| ATOM | 2424 | CA | SER A | 351 | 35.520 | 50.950 | 17.534 | 1.00 | 16.33 |
| ATOM | 2425 | CB | SER A | 351 | 35.833 | 50.400 | 18.926 | 1.00 | 15.21 |
| ATOM | 2426 | OG | SER A | 351 | 34.706 | 50.492 | 19.773 | 1.00 | 17.81 |
| ATOM | 2427 | C | SER A | 351 | 36.817 | 51.109 | 16.748 | 1.00 | 16.42 |
| ATOM | 2428 | O | SER A | 351 | 37.501 | 52.131 | 16.847 | 1.00 | 16.42 |
| ATOM | 2429 | N | LEU A | 352 | 37.141 | 50.076 | 15.971 | 1.00 | 14.86 |
| ATOM | 2430 | CA | LEU A | 352 | 38.343 | 50.051 | 15.142 | 1.00 | 15.16 |
| ATOM | 2431 | CB | LEU A | 352 | 39.475 | 49.292 | 15.849 | 1.00 | 12.61 |
| ATOM | 2432 | CG | LEU A | 352 | 39.911 | 49.711 | 17.252 | 1.00 | 14.17 |
| ATOM | 2433 | CD1 | LEU A | 352 | 40.762 | 48.598 | 17.870 | 1.00 | 10.97 |
| ATOM | 2434 | CD2 | LEU A | 352 | 40.676 | 51.026 | 17.187 | 1.00 | 12.18 |
| ATOM | 2435 | C | LEU A | 352 | 38.013 | 49.313 | 13.851 | 1.00 | 13.91 |
| ATOM | 2436 | O | LEU A | 352 | 37.037 | 48.564 | 13.792 | 1.00 | 11.65 |
| ATOM | 2437 | N | VAL A | 353 | 38.829 | 49.523 | 12.823 | 1.00 | 13.16 |
| ATOM | 2438 | CA | VAL A | 353 | 38.631 | 48.835 | 11.558 | 1.00 | 14.12 |
| ATOM | 2439 | CB | VAL A | 353 | 38.062 | 49.767 | 10.463 | 1.00 | 15.89 |
| ATOM | 2440 | CG1 | VAL A | 353 | 36.764 | 50.405 | 10.946 | 1.00 | 14.47 |
| ATOM | 2441 | CG2 | VAL A | 353 | 39.090 | 50.819 | 10.078 | 1.00 | 13.72 |
| ATOM | 2442 | C | VAL A | 353 | 39.966 | 48.288 | 11.082 | 1.00 | 14.87 |
| ATOM | 2443 | O | VAL A | 353 | 41.026 | 48.706 | 11.554 | 1.00 | 13.31 |
| ATOM | 2444 | N | GLN A | 354 | 39.902 | 47.336 | 10.158 | 1.00 | 14.46 |
| ATOM | 2445 | CA | GLN A | 354 | 41.092 | 46.725 | 9.586 | 1.00 | 14.10 |
| ATOM | 2446 | CB | GLN A | 354 | 41.343 | 45.324 | 10.168 | 1.00 | 14.76 |
| ATOM | 2447 | CG | GLN A | 354 | 41.579 | 45.243 | 11.671 | 1.00 | 15.41 |
| ATOM | 2448 | CD | GLN A | 354 | 41.760 | 43.796 | 12.139 | 1.00 | 18.05 |
| ATOM | 2449 | OE1 | GLN A | 354 | 41.012 | 42.904 | 11.732 | 1.00 | 16.89 |
| ATOM | 2450 | NE2 | GLN A | 354 | 42.750 | 43.564 | 12.997 | 1.00 | 17.31 |
| ATOM | 2451 | C | GLN A | 354 | 40.861 | 46.586 | 8.088 | 1.00 | 14.25 |
| ATOM | 2452 | O | GLN A | 354 | 39.726 | 46.651 | 7.608 | 1.00 | 13.09 |
| ATOM | 2453 | N | LEU A | 355 | 41.942 | 46.395 | 7.349 | 1.00 | 14.08 |
| ATOM | 2454 | CA | LEU A | 355 | 41.835 | 46.209 | 5.914 | 1.00 | 15.37 |
| ATOM | 2455 | CB | LEU A | 355 | 41.910 | 47.555 | 5.180 | 1.00 | 13.53 |
| ATOM | 2456 | CG | LEU A | 355 | 43.170 | 48.420 | 5.302 | 1.00 | 13.38 |
| ATOM | 2457 | CD1 | LEU A | 355 | 44.270 | 47.896 | 4.383 | 1.00 | 13.17 |
| ATOM | 2458 | CD2 | LEU A | 355 | 42.825 | 49.855 | 4.938 | 1.00 | 10.64 |
| ATOM | 2459 | C | LEU A | 355 | 42.965 | 45.302 | 5.478 | 1.00 | 15.97 |
| ATOM | 2460 | O | LEU A | 355 | 43.971 | 45.169 | 6.175 | 1.00 | 15.47 |
| ATOM | 2461 | N | TYR A | 356 | 42.786 | 44.656 | 4.334 | 1.00 | 16.99 |
| ATOM | 2462 | CA | TYR A | 356 | 43.815 | 43.784 | 3.802 | 1.00 | 16.94 |
| ATOM | 2463 | CB | TYR A | 356 | 43.645 | 42.351 | 4.334 | 1.00 | 15.18 |
| ATOM | 2464 | CG | TYR A | 356 | 44.707 | 41.373 | 3.857 | 1.00 | 14.99 |
| ATOM | 2465 | CD1 | TYR A | 356 | 44.767 | 40.080 | 4.362 | 1.00 | 15.31 |
| ATOM | 2466 | CE1 | TYR A | 356 | 45.700 | 39.171 | 3.893 | 1.00 | 13.63 |
| ATOM | 2467 | CD2 | TYR A | 356 | 45.620 | 41.728 | 2.869 | 1.00 | 15.99 |
| ATOM | 2468 | CE2 | TYR A | 356 | 46.553 | 40.826 | 2.391 | 1.00 | 15.09 |
| ATOM | 2469 | CZ | TYR A | 356 | 46.588 | 39.551 | 2.904 | 1.00 | 15.51 |
| ATOM | 2470 | OH | TYR A | 356 | 47.502 | 38.651 | 2.408 | 1.00 | 17.24 |
| ATOM | 2471 | C | TYR A | 356 | 43.747 | 43.805 | 2.285 | 1.00 | 16.84 |
| ATOM | 2472 | O | TYR A | 356 | 44.675 | 44.272 | 1.628 | 1.00 | 17.11 |
| ATOM | 2473 | N | THR A | 357 | 42.646 | 43.305 | 1.735 | 1.00 | 16.44 |
| ATOM | 2474 | CA | THR A | 357 | 42.478 | 43.251 | 0.289 | 1.00 | 16.13 |
| ATOM | 2475 | CB | THR A | 357 | 41.066 | 42.747 | −0.080 | 1.00 | 16.57 |
| ATOM | 2476 | OG1 | THR A | 357 | 40.874 | 41.433 | 0.460 | 1.00 | 13.38 |
| ATOM | 2477 | CG2 | THR A | 357 | 40.899 | 42.689 | −1.588 | 1.00 | 16.25 |
| ATOM | 2478 | C | THR A | 357 | 42.727 | 44.596 | −0.400 | 1.00 | 15.53 |

TABLE 30-continued

| | | | | | | | | |
|---|---|---|---|---|---|---|---|---|
| ATOM | 2479 | O | THR A | 357 | 43.292 | 44.640 | −1.491 | 1.00 | 15.19 |
| ATOM | 2480 | N | ALA A | 358 | 42.314 | 45.689 | 0.233 | 1.00 | 14.89 |
| ATOM | 2481 | CA | ALA A | 358 | 42.508 | 47.012 | −0.356 | 1.00 | 15.09 |
| ATOM | 2482 | CB | ALA A | 358 | 41.917 | 48.075 | 0.546 | 1.00 | 11.21 |
| ATOM | 2483 | C | ALA A | 358 | 43.993 | 47.277 | −0.572 | 1.00 | 16.40 |
| ATOM | 2484 | O | ALA A | 358 | 44.389 | 47.910 | −1.551 | 1.00 | 15.75 |
| ATOM | 2485 | N | LEU A | 359 | 44.810 | 46.786 | 0.355 | 1.00 | 16.78 |
| ATOM | 2486 | CA | LEU A | 359 | 46.254 | 46.967 | 0.284 | 1.00 | 17.50 |
| ATOM | 2487 | CB | LEU A | 359 | 46.912 | 46.440 | 1.566 | 1.00 | 18.55 |
| ATOM | 2488 | CG | LEU A | 359 | 48.438 | 46.517 | 1.659 | 1.00 | 19.27 |
| ATOM | 2489 | CD1 | LEU A | 359 | 48.888 | 47.968 | 1.604 | 1.00 | 17.73 |
| ATOM | 2490 | CD2 | LEU A | 359 | 48.897 | 45.862 | 2.955 | 1.00 | 18.92 |
| ATOM | 2491 | C | LEU A | 359 | 46.844 | 46.258 | −0.932 | 1.00 | 16.82 |
| ATOM | 2492 | O | LEU A | 359 | 47.773 | 46.762 | −1.558 | 1.00 | 15.67 |
| ATOM | 2493 | N | THR A | 360 | 46.293 | 45.096 | −1.269 | 1.00 | 16.87 |
| ATOM | 2494 | CA | THR A | 360 | 46.783 | 44.325 | −2.406 | 1.00 | 17.52 |
| ATOM | 2495 | CB | THR A | 360 | 46.203 | 42.896 | −2.402 | 1.00 | 17.31 |
| ATOM | 2496 | OG1 | THR A | 360 | 44.839 | 42.927 | −2.843 | 1.00 | 16.95 |
| ATOM | 2497 | CG2 | THR A | 360 | 46.262 | 42.310 | −0.993 | 1.00 | 13.68 |
| ATOM | 2498 | C | THR A | 360 | 46.474 | 44.971 | −3.757 | 1.00 | 19.33 |
| ATOM | 2499 | O | THR A | 360 | 47.081 | 44.616 | −4.768 | 1.00 | 21.20 |
| ATOM | 2500 | N | PHE A | 361 | 45.538 | 45.916 | −3.783 | 1.00 | 19.66 |
| ATOM | 2501 | CA | PHE A | 361 | 45.186 | 46.590 | −5.034 | 1.00 | 20.68 |
| ATOM | 2502 | CB | PHE A | 361 | 43.663 | 46.753 | −5.171 | 1.00 | 21.37 |
| ATOM | 2503 | CG | PHE A | 361 | 42.933 | 45.484 | −5.510 | 1.00 | 22.02 |
| ATOM | 2504 | CD1 | PHE A | 361 | 42.179 | 44.825 | −4.554 | 1.00 | 18.66 |
| ATOM | 2505 | CD2 | PHE A | 361 | 43.012 | 44.944 | −6.786 | 1.00 | 23.48 |
| ATOM | 2506 | CE1 | PHE A | 361 | 41.520 | 43.653 | −4.861 | 1.00 | 21.36 |
| ATOM | 2507 | CE2 | PHE A | 361 | 42.353 | 43.764 | −7.099 | 1.00 | 22.19 |
| ATOM | 2508 | CZ | PHE A | 361 | 41.607 | 43.119 | −6.134 | 1.00 | 21.74 |
| ATOM | 2509 | C | PHE A | 361 | 45.814 | 47.973 | −5.168 | 1.00 | 21.60 |
| ATOM | 2510 | O | PHE A | 361 | 46.323 | 48.330 | −6.226 | 1.00 | 23.15 |
| ATOM | 2511 | N | TRP A | 362 | 45.777 | 48.750 | −4.091 | 1.00 | 23.22 |
| ATOM | 2512 | CA | TRP A | 362 | 46.291 | 50.113 | −4.118 | 1.00 | 23.91 |
| ATOM | 2513 | CB | TRP A | 362 | 45.264 | 51.031 | −3.449 | 1.00 | 25.18 |
| ATOM | 2514 | CG | TRP A | 362 | 43.854 | 50.699 | −3.871 | 1.00 | 29.81 |
| ATOM | 2515 | CD2 | TRP A | 362 | 43.375 | 50.514 | −5.214 | 1.00 | 31.67 |
| ATOM | 2516 | CE2 | TRP A | 362 | 42.015 | 50.155 | −5.126 | 1.00 | 31.90 |
| ATOM | 2517 | CE3 | TRP A | 362 | 43.966 | 50.614 | −6.480 | 1.00 | 32.33 |
| ATOM | 2518 | CD1 | TRP A | 362 | 42.789 | 50.457 | −3.053 | 1.00 | 29.44 |
| ATOM | 2519 | NE1 | TRP A | 362 | 41.683 | 50.128 | −3.798 | 1.00 | 29.93 |
| ATOM | 2520 | CZ2 | TRP A | 362 | 41.234 | 49.895 | −6.257 | 1.00 | 33.85 |
| ATOM | 2521 | CZ3 | TRP A | 362 | 43.190 | 50.355 | −7.601 | 1.00 | 33.08 |
| ATOM | 2522 | CH2 | TRP A | 362 | 41.839 | 50.000 | −7.481 | 1.00 | 33.33 |
| ATOM | 2523 | C | TRP A | 362 | 47.671 | 50.307 | −3.494 | 1.00 | 22.99 |
| ATOM | 2524 | O | TRP A | 362 | 48.318 | 51.334 | −3.713 | 1.00 | 22.54 |
| ATOM | 2525 | N | GLY A | 363 | 48.119 | 49.321 | −2.725 | 1.00 | 21.66 |
| ATOM | 2526 | CA | GLY A | 363 | 49.422 | 49.408 | −2.094 | 1.00 | 20.23 |
| ATOM | 2527 | C | GLY A | 363 | 49.423 | 50.222 | −0.815 | 1.00 | 20.57 |
| ATOM | 2528 | O | GLY A | 363 | 48.373 | 50.675 | −0.358 | 1.00 | 20.51 |
| ATOM | 2529 | N | PRO A | 364 | 50.606 | 50.428 | −0.215 | 1.00 | 20.18 |
| ATOM | 2530 | CD | PRO A | 364 | 51.880 | 49.909 | −0.750 | 1.00 | 20.17 |
| ATOM | 2531 | CA | PRO A | 364 | 50.833 | 51.183 | 1.024 | 1.00 | 20.20 |
| ATOM | 2532 | CB | PRO A | 364 | 52.353 | 51.338 | 1.057 | 1.00 | 19.15 |
| ATOM | 2533 | CG | PRO A | 364 | 52.820 | 50.058 | 0.437 | 1.00 | 19.46 |
| ATOM | 2534 | C | PRO A | 364 | 50.118 | 52.533 | 1.143 | 1.00 | 20.39 |
| ATOM | 2535 | O | PRO A | 364 | 49.604 | 52.870 | 2.209 | 1.00 | 22.16 |
| ATOM | 2536 | N | PRO A | 365 | 50.079 | 53.327 | 0.058 | 1.00 | 20.34 |
| ATOM | 2537 | CD | PRO A | 365 | 50.655 | 53.090 | −1.277 | 1.00 | 19.58 |
| ATOM | 2538 | CA | PRO A | 365 | 49.414 | 54.635 | 0.110 | 1.00 | 18.92 |
| ATOM | 2539 | CB | PRO A | 365 | 49.568 | 55.161 | −1.318 | 1.00 | 19.47 |
| ATOM | 2540 | CG | PRO A | 365 | 50.826 | 54.495 | −1.798 | 1.00 | 20.15 |
| ATOM | 2541 | C | PRO A | 365 | 47.950 | 54.601 | 0.542 | 1.00 | 18.73 |
| ATOM | 2542 | O | PRO A | 365 | 47.409 | 55.610 | 0.994 | 1.00 | 20.00 |
| ATOM | 2543 | N | VAL A | 366 | 47.304 | 53.447 | 0.411 | 1.00 | 18.05 |
| ATOM | 2544 | CA | VAL A | 366 | 45.898 | 53.351 | 0.779 | 1.00 | 18.28 |
| ATOM | 2545 | CB | VAL A | 366 | 45.315 | 51.954 | 0.450 | 1.00 | 18.78 |
| ATOM | 2546 | CG1 | VAL A | 366 | 45.801 | 50.926 | 1.455 | 1.00 | 16.44 |
| ATOM | 2547 | CG2 | VAL A | 366 | 43.800 | 52.024 | 0.432 | 1.00 | 18.48 |
| ATOM | 2548 | C | VAL A | 366 | 45.674 | 53.645 | 2.257 | 1.00 | 17.96 |
| ATOM | 2549 | O | VAL A | 366 | 44.621 | 54.152 | 2.645 | 1.00 | 19.15 |
| ATOM | 2550 | N | VAL A | 367 | 46.673 | 53.340 | 3.076 | 1.00 | 17.52 |
| ATOM | 2551 | CA | VAL A | 367 | 46.576 | 53.566 | 4.512 | 1.00 | 17.49 |
| ATOM | 2552 | CB | VAL A | 367 | 47.814 | 53.021 | 5.234 | 1.00 | 16.98 |
| ATOM | 2553 | CG1 | VAL A | 367 | 47.646 | 53.187 | 6.728 | 1.00 | 14.72 |
| ATOM | 2554 | CG2 | VAL A | 367 | 48.028 | 51.551 | 4.857 | 1.00 | 17.23 |
| ATOM | 2555 | C | VAL A | 367 | 46.415 | 55.046 | 4.859 | 1.00 | 17.78 |
| ATOM | 2556 | O | VAL A | 367 | 45.553 | 55.413 | 5.655 | 1.00 | 17.04 |
| ATOM | 2557 | N | GLY A | 368 | 47.252 | 55.891 | 4.264 | 1.00 | 19.06 |

TABLE 30-continued

| ATOM | 2558 | CA | GLY A | 368 | 47.169 | 57.316 | 4.525 | 1.00 | 19.05 |
|---|---|---|---|---|---|---|---|---|---|
| ATOM | 2559 | C | GLY A | 368 | 45.890 | 57.877 | 3.942 | 1.00 | 21.25 |
| ATOM | 2560 | O | GLY A | 368 | 45.269 | 58.774 | 4.522 | 1.00 | 20.35 |
| ATOM | 2561 | N | LYS A | 369 | 45.488 | 57.332 | 2.795 | 1.00 | 22.08 |
| ATOM | 2562 | CA | LYS A | 369 | 44.270 | 57.771 | 2.118 | 1.00 | 22.27 |
| ATOM | 2563 | CB | LYS A | 369 | 44.063 | 56.989 | 0.813 | 1.00 | 21.63 |
| ATOM | 2564 | CG | LYS A | 369 | 43.072 | 57.652 | −0.132 | 1.00 | 23.91 |
| ATOM | 2565 | CD | LYS A | 369 | 42.558 | 56.712 | −1.216 | 1.00 | 22.29 |
| ATOM | 2566 | CE | LYS A | 369 | 41.611 | 55.682 | −0.630 | 1.00 | 23.00 |
| ATOM | 2567 | NZ | LYS A | 369 | 40.826 | 54.976 | −1.675 | 1.00 | 23.30 |
| ATOM | 2568 | C | LYS A | 369 | 43.060 | 57.561 | 3.022 | 1.00 | 21.33 |
| ATOM | 2569 | O | LYS A | 369 | 42.255 | 58.474 | 3.228 | 1.00 | 21.31 |
| ATOM | 2570 | N | VAL A | 370 | 42.936 | 56.353 | 3.563 | 1.00 | 19.60 |
| ATOM | 2571 | CA | VAL A | 370 | 41.816 | 56.032 | 4.436 | 1.00 | 18.55 |
| ATOM | 2572 | CB | VAL A | 370 | 41.855 | 54.555 | 4.889 | 1.00 | 16.90 |
| ATOM | 2573 | CG1 | VAL A | 370 | 40.748 | 54.295 | 5.897 | 1.00 | 14.02 |
| ATOM | 2574 | CG2 | VAL A | 370 | 41.693 | 53.636 | 3.682 | 1.00 | 15.42 |
| ATOM | 2575 | C | VAL A | 370 | 41.794 | 56.930 | 5.667 | 1.00 | 19.20 |
| ATOM | 2576 | O | VAL A | 370 | 40.740 | 57.439 | 6.054 | 1.00 | 18.26 |
| ATOM | 2577 | N | LYS A | 371 | 42.956 | 57.128 | 6.280 | 1.00 | 19.20 |
| ATOM | 2578 | CA | LYS A | 371 | 43.040 | 57.974 | 7.462 | 1.00 | 20.21 |
| ATOM | 2579 | CB | LYS A | 371 | 44.444 | 57.897 | 8.075 | 1.00 | 20.24 |
| ATOM | 2580 | CG | LYS A | 371 | 44.726 | 56.563 | 8.759 | 1.00 | 19.89 |
| ATOM | 2581 | CD | LYS A | 371 | 46.018 | 56.590 | 9.551 | 1.00 | 19.73 |
| ATOM | 2582 | CE | LYS A | 371 | 47.218 | 56.781 | 8.647 | 1.00 | 20.14 |
| ATOM | 2583 | NZ | LYS A | 371 | 48.488 | 56.743 | 9.416 | 1.00 | 20.57 |
| ATOM | 2584 | C | LYS A | 371 | 42.678 | 59.426 | 7.155 | 1.00 | 20.46 |
| ATOM | 2585 | O | LYS A | 371 | 41.956 | 60.063 | 7.917 | 1.00 | 19.82 |
| ATOM | 2586 | N | ARG A | 372 | 43.177 | 59.943 | 6.036 | 1.00 | 21.92 |
| ATOM | 2587 | CA | ARG A | 372 | 42.895 | 61.319 | 5.639 | 1.00 | 23.46 |
| ATOM | 2588 | CB | ARG A | 372 | 43.702 | 61.689 | 4.390 | 1.00 | 24.84 |
| ATOM | 2589 | CG | ARG A | 372 | 43.493 | 63.125 | 3.930 | 1.00 | 29.50 |
| ATOM | 2590 | CD | ARG A | 372 | 44.269 | 63.452 | 2.649 | 1.00 | 32.37 |
| ATOM | 2591 | NE | ARG A | 372 | 43.723 | 62.769 | 1.475 | 1.00 | 36.28 |
| ATOM | 2592 | CZ | ARG A | 372 | 44.333 | 61.781 | 0.829 | 1.00 | 36.09 |
| ATOM | 2593 | NH1 | ARG A | 372 | 45.519 | 61.352 | 1.240 | 1.00 | 36.80 |
| ATOM | 2594 | NH2 | ARG A | 372 | 43.755 | 61.220 | −0.227 | 1.00 | 35.12 |
| ATOM | 2595 | C | ARG A | 372 | 41.405 | 61.541 | 5.360 | 1.00 | 23.29 |
| ATOM | 2596 | O | ARG A | 372 | 40.823 | 62.530 | 5.809 | 1.00 | 22.86 |
| ATOM | 2597 | N | GLU A | 373 | 40.791 | 60.622 | 4.619 | 1.00 | 21.51 |
| ATOM | 2598 | CA | GLU A | 373 | 39.376 | 60.744 | 4.288 | 1.00 | 20.70 |
| ATOM | 2599 | CB | GLU A | 373 | 38.987 | 59.727 | 3.206 | 1.00 | 21.22 |
| ATOM | 2600 | CG | GLU A | 373 | 39.796 | 59.863 | 1.918 | 1.00 | 21.34 |
| ATOM | 2601 | CD | GLU A | 373 | 39.475 | 58.778 | 0.904 | 1.00 | 24.10 |
| ATOM | 2602 | OE1 | GLU A | 373 | 39.326 | 57.609 | 1.313 | 1.00 | 26.50 |
| ATOM | 2603 | OE2 | GLU A | 373 | 39.385 | 59.085 | −0.302 | 1.00 | 24.10 |
| ATOM | 2604 | C | GLU A | 373 | 38.516 | 60.548 | 5.525 | 1.00 | 20.60 |
| ATOM | 2605 | O | GLU A | 373 | 37.472 | 61.181 | 5.671 | 1.00 | 23.32 |
| ATOM | 2606 | N | LEU A | 374 | 38.951 | 59.671 | 6.420 | 1.00 | 19.33 |
| ATOM | 2607 | CA | LEU A | 374 | 38.203 | 59.429 | 7.643 | 1.00 | 19.28 |
| ATOM | 2608 | CB | LEU A | 374 | 38.860 | 58.314 | 8.462 | 1.00 | 16.56 |
| ATOM | 2609 | CG | LEU A | 374 | 38.206 | 58.007 | 9.816 | 1.00 | 15.77 |
| ATOM | 2610 | CD1 | LEU A | 374 | 36.750 | 57.618 | 9.607 | 1.00 | 12.63 |
| ATOM | 2611 | CD2 | LEU A | 374 | 38.968 | 56.885 | 10.520 | 1.00 | 14.15 |
| ATOM | 2612 | C | LEU A | 374 | 38.153 | 60.713 | 8.468 | 1.00 | 20.85 |
| ATOM | 2613 | O | LEU A | 374 | 37.091 | 61.114 | 8.943 | 1.00 | 23.22 |
| ATOM | 2614 | N | GLU A | 375 | 39.306 | 61.353 | 8.635 | 1.00 | 20.32 |
| ATOM | 2615 | CA | GLU A | 375 | 39.398 | 62.592 | 9.399 | 1.00 | 23.08 |
| ATOM | 2616 | CB | GLU A | 375 | 40.840 | 63.099 | 9.412 | 1.00 | 25.75 |
| ATOM | 2617 | CG | GLU A | 375 | 41.075 | 64.247 | 10.371 | 1.00 | 32.67 |
| ATOM | 2618 | CD | GLU A | 375 | 42.494 | 64.777 | 10.308 | 1.00 | 37.01 |
| ATOM | 2619 | OE1 | GLU A | 375 | 43.438 | 63.960 | 10.365 | 1.00 | 39.17 |
| ATOM | 2620 | OE2 | GLU A | 375 | 42.664 | 66.012 | 10.209 | 1.00 | 41.03 |
| ATOM | 2621 | C | GLU A | 375 | 38.487 | 63.667 | 8.813 | 1.00 | 22.51 |
| ATOM | 2622 | O | GLU A | 375 | 37.720 | 64.300 | 9.536 | 1.00 | 22.31 |
| ATOM | 2623 | N | ALA A | 376 | 38.571 | 63.865 | 7.501 | 1.00 | 22.41 |
| ATOM | 2624 | CA | ALA A | 376 | 37.746 | 64.859 | 6.822 | 1.00 | 22.75 |
| ATOM | 2625 | CB | ALA A | 376 | 38.096 | 64.910 | 5.325 | 1.00 | 21.03 |
| ATOM | 2626 | C | ALA A | 376 | 36.262 | 64.556 | 7.003 | 1.00 | 23.07 |
| ATOM | 2627 | O | ALA A | 376 | 35.470 | 65.461 | 7.258 | 1.00 | 25.45 |
| ATOM | 2628 | N | LEU A | 377 | 35.885 | 63.285 | 6.868 | 1.00 | 22.11 |
| ATOM | 2629 | CA | LEU A | 377 | 34.487 | 62.890 | 7.022 | 1.00 | 20.80 |
| ATOM | 2630 | CB | LEU A | 377 | 34.298 | 61.417 | 6.655 | 1.00 | 18.44 |
| ATOM | 2631 | CG | LEU A | 377 | 34.362 | 61.131 | 5.155 | 1.00 | 19.93 |
| ATOM | 2632 | CD1 | LEU A | 377 | 34.310 | 59.637 | 4.918 | 1.00 | 18.66 |
| ATOM | 2633 | CD2 | LEU A | 377 | 33.212 | 61.842 | 4.449 | 1.00 | 15.51 |
| ATOM | 2634 | C | LEU A | 377 | 33.973 | 63.131 | 8.433 | 1.00 | 21.64 |
| ATOM | 2635 | O | LEU A | 377 | 32.826 | 63.536 | 8.615 | 1.00 | 20.67 |
| ATOM | 2636 | N | LEU A | 378 | 34.816 | 62.870 | 9.430 | 1.00 | 22.64 |

TABLE 30-continued

| ATOM | 2637 | CA | LEU A | 378 | 34.429 | 63.081 | 10.822 | 1.00 | 23.81 |
| ATOM | 2638 | CB | LEU A | 378 | 35.555 | 62.637 | 11.764 | 1.00 | 19.85 |
| ATOM | 2639 | CG | LEU A | 378 | 35.811 | 61.131 | 11.866 | 1.00 | 18.67 |
| ATOM | 2640 | CD1 | LEU A | 378 | 37.123 | 60.867 | 12.585 | 1.00 | 16.23 |
| ATOM | 2641 | CD2 | LEU A | 378 | 34.650 | 60.466 | 12.592 | 1.00 | 16.80 |
| ATOM | 2642 | C | LEU A | 378 | 34.104 | 64.558 | 11.059 | 1.00 | 24.84 |
| ATOM | 2643 | O | LEU A | 378 | 33.079 | 64.884 | 11.658 | 1.00 | 24.64 |
| ATOM | 2644 | N | LYS A | 379 | 34.979 | 65.443 | 10.587 | 1.00 | 25.82 |
| ATOM | 2645 | CA | LYS A | 379 | 34.775 | 66.880 | 10.745 | 1.00 | 29.39 |
| ATOM | 2646 | CB | LYS A | 379 | 35.972 | 67.656 | 10.191 | 1.00 | 30.69 |
| ATOM | 2647 | CG | LYS A | 379 | 37.283 | 67.388 | 10.916 | 1.00 | 34.84 |
| ATOM | 2648 | CD | LYS A | 379 | 38.430 | 68.176 | 10.299 | 1.00 | 36.48 |
| ATOM | 2649 | CE | LYS A | 379 | 39.740 | 67.884 | 11.014 | 1.00 | 40.34 |
| ATOM | 2650 | NZ | LYS A | 379 | 40.898 | 68.607 | 10.410 | 1.00 | 42.08 |
| ATOM | 2651 | C | LYS A | 379 | 33.524 | 67.295 | 9.991 | 1.00 | 30.60 |
| ATOM | 2652 | O | LYS A | 379 | 32.634 | 67.950 | 10.531 | 1.00 | 30.06 |
| ATOM | 2653 | N | GLU A | 380 | 33.476 | 66.892 | 8.729 | 1.00 | 31.82 |
| ATOM | 2654 | CA | GLU A | 380 | 32.365 | 67.193 | 7.845 | 1.00 | 33.48 |
| ATOM | 2655 | CB | GLU A | 380 | 32.618 | 66.512 | 6.499 | 1.00 | 35.73 |
| ATOM | 2656 | CG | GLU A | 380 | 31.528 | 66.676 | 5.475 | 1.00 | 42.73 |
| ATOM | 2657 | CD | GLU A | 380 | 31.886 | 66.003 | 4.164 | 1.00 | 46.67 |
| ATOM | 2658 | OE1 | GLU A | 380 | 31.007 | 65.891 | 3.284 | 1.00 | 49.93 |
| ATOM | 2659 | OE2 | GLU A | 380 | 33.055 | 65.588 | 4.016 | 1.00 | 48.55 |
| ATOM | 2660 | C | GLU A | 380 | 31.020 | 66.757 | 8.424 | 1.00 | 32.66 |
| ATOM | 2661 | O | GLU A | 380 | 29.984 | 67.357 | 8.131 | 1.00 | 31.37 |
| ATOM | 2662 | N | GLN A | 381 | 31.032 | 65.721 | 9.256 | 1.00 | 31.27 |
| ATOM | 2663 | CA | GLN A | 381 | 29.790 | 65.231 | 9.844 | 1.00 | 30.92 |
| ATOM | 2664 | CB | GLN A | 381 | 29.709 | 63.706 | 9.693 | 1.00 | 30.23 |
| ATOM | 2665 | CG | GLN A | 381 | 29.397 | 63.274 | 8.258 | 1.00 | 29.83 |
| ATOM | 2666 | CD | GLN A | 381 | 29.461 | 61.772 | 8.047 | 1.00 | 30.64 |
| ATOM | 2667 | OE1 | GLN A | 381 | 29.032 | 60.993 | 8.897 | 1.00 | 30.52 |
| ATOM | 2668 | NE2 | GLN A | 381 | 29.982 | 61.359 | 6.894 | 1.00 | 30.34 |
| ATOM | 2669 | C | GLN A | 381 | 29.561 | 65.652 | 11.296 | 1.00 | 30.74 |
| ATOM | 2670 | O | GLN A | 381 | 28.644 | 65.164 | 11.956 | 1.00 | 30.23 |
| ATOM | 2671 | N | GLY A | 382 | 30.401 | 66.559 | 11.786 | 1.00 | 30.20 |
| ATOM | 2672 | CA | GLY A | 382 | 30.244 | 67.065 | 13.138 | 1.00 | 30.10 |
| ATOM | 2673 | C | GLY A | 382 | 30.755 | 66.241 | 14.302 | 1.00 | 30.25 |
| ATOM | 2674 | O | GLY A | 382 | 30.454 | 66.554 | 15.452 | 1.00 | 30.34 |
| ATOM | 2675 | N | PHE A | 383 | 31.520 | 65.192 | 14.033 | 1.00 | 29.37 |
| ATOM | 2676 | CA | PHE A | 383 | 32.051 | 64.377 | 15.118 | 1.00 | 28.29 |
| ATOM | 2677 | CB | PHE A | 383 | 32.310 | 62.948 | 14.641 | 1.00 | 26.27 |
| ATOM | 2678 | CG | PHE A | 383 | 31.068 | 62.210 | 14.240 | 1.00 | 24.23 |
| ATOM | 2679 | CD1 | PHE A | 383 | 30.803 | 61.945 | 12.908 | 1.00 | 23.49 |
| ATOM | 2680 | CD2 | PHE A | 383 | 30.164 | 61.784 | 15.197 | 1.00 | 21.41 |
| ATOM | 2681 | CE1 | PHE A | 383 | 29.658 | 61.264 | 12.535 | 1.00 | 22.95 |
| ATOM | 2682 | CE2 | PHE A | 383 | 29.021 | 61.106 | 14.830 | 1.00 | 22.42 |
| ATOM | 2683 | CZ | PHE A | 383 | 28.767 | 60.845 | 13.496 | 1.00 | 22.22 |
| ATOM | 2684 | C | PHE A | 383 | 33.346 | 64.978 | 15.652 | 1.00 | 29.12 |
| ATOM | 2685 | O | PHE A | 383 | 34.229 | 65.354 | 14.882 | 1.00 | 30.28 |
| ATOM | 2686 | N | GLY A | 384 | 33.452 | 65.073 | 16.973 | 1.00 | 28.98 |
| ATOM | 2687 | CA | GLY A | 384 | 34.655 | 65.619 | 17.573 | 1.00 | 29.01 |
| ATOM | 2688 | C | GLY A | 384 | 35.827 | 64.681 | 17.363 | 1.00 | 29.23 |
| ATOM | 2689 | O | GLY A | 384 | 36.983 | 65.101 | 17.345 | 1.00 | 30.19 |
| ATOM | 2690 | N | GLY A | 385 | 35.518 | 63.399 | 17.198 | 1.00 | 28.93 |
| ATOM | 2691 | CA | GLY A | 385 | 36.548 | 62.402 | 16.983 | 1.00 | 27.17 |
| ATOM | 2692 | C | GLY A | 385 | 35.933 | 61.048 | 16.690 | 1.00 | 26.43 |
| ATOM | 2693 | O | GLY A | 385 | 34.712 | 60.903 | 16.701 | 1.00 | 26.73 |
| ATOM | 2694 | N | VAL A | 386 | 36.781 | 60.057 | 16.430 | 1.00 | 25.91 |
| ATOM | 2695 | CA | VAL A | 386 | 36.336 | 58.700 | 16.132 | 1.00 | 23.85 |
| ATOM | 2696 | CB | VAL A | 386 | 37.545 | 57.736 | 16.010 | 1.00 | 24.56 |
| ATOM | 2697 | CG1 | VAL A | 386 | 37.061 | 56.300 | 15.881 | 1.00 | 22.43 |
| ATOM | 2698 | CG2 | VAL A | 386 | 38.400 | 58.119 | 14.812 | 1.00 | 24.35 |
| ATOM | 2699 | C | VAL A | 386 | 35.413 | 58.174 | 17.224 | 1.00 | 24.03 |
| ATOM | 2700 | O | VAL A | 386 | 34.355 | 57.608 | 16.940 | 1.00 | 23.33 |
| ATOM | 2701 | N | THR A | 387 | 35.825 | 58.368 | 18.473 | 1.00 | 23.99 |
| ATOM | 2702 | CA | THR A | 387 | 35.068 | 57.909 | 19.632 | 1.00 | 24.92 |
| ATOM | 2703 | CB | THR A | 387 | 35.716 | 58.406 | 20.939 | 1.00 | 26.36 |
| ATOM | 2704 | OG1 | THR A | 387 | 37.104 | 58.047 | 20.950 | 1.00 | 30.29 |
| ATOM | 2705 | CG2 | THR A | 387 | 35.034 | 57.782 | 22.144 | 1.00 | 24.51 |
| ATOM | 2706 | C | THR A | 387 | 33.616 | 58.369 | 19.612 | 1.00 | 24.16 |
| ATOM | 2707 | O | THR A | 387 | 32.723 | 57.652 | 20.057 | 1.00 | 24.55 |
| ATOM | 2708 | N | ASP A | 388 | 33.389 | 59.570 | 19.094 | 1.00 | 23.85 |
| ATOM | 2709 | CA | ASP A | 388 | 32.052 | 60.144 | 19.024 | 1.00 | 23.14 |
| ATOM | 2710 | CB | ASP A | 388 | 32.154 | 61.640 | 18.724 | 1.00 | 26.77 |
| ATOM | 2711 | CG | ASP A | 388 | 32.878 | 62.399 | 19.806 | 1.00 | 30.24 |
| ATOM | 2712 | OD1 | ASP A | 388 | 33.722 | 63.260 | 19.469 | 1.00 | 33.20 |
| ATOM | 2713 | OD2 | ASP A | 388 | 32.597 | 62.138 | 20.996 | 1.00 | 33.14 |
| ATOM | 2714 | C | ASP A | 388 | 31.187 | 59.486 | 17.960 | 1.00 | 21.34 |
| ATOM | 2715 | O | ASP A | 388 | 29.968 | 59.454 | 18.077 | 1.00 | 19.97 |

TABLE 30-continued

| ATOM | 2716 | N | ALA A | 389 | 31.828 | 58.968 | 16.918 | 1.00 | 20.96 |
|---|---|---|---|---|---|---|---|---|---|
| ATOM | 2717 | CA | ALA A | 389 | 31.122 | 58.335 | 15.815 | 1.00 | 19.43 |
| ATOM | 2718 | CB | ALA A | 389 | 31.944 | 58.481 | 14.536 | 1.00 | 20.22 |
| ATOM | 2719 | C | ALA A | 389 | 30.762 | 56.870 | 16.036 | 1.00 | 18.17 |
| ATOM | 2720 | O | ALA A | 389 | 29.841 | 56.357 | 15.399 | 1.00 | 19.04 |
| ATOM | 2721 | N | ILE A | 390 | 31.485 | 56.191 | 16.923 | 1.00 | 17.77 |
| ATOM | 2722 | CA | ILE A | 390 | 31.222 | 54.774 | 17.193 | 1.00 | 15.58 |
| ATOM | 2723 | CB | ILE A | 390 | 32.105 | 54.251 | 18.355 | 1.00 | 15.12 |
| ATOM | 2724 | CG2 | ILE A | 390 | 31.802 | 52.784 | 18.617 | 1.00 | 12.26 |
| ATOM | 2725 | CG1 | ILE A | 390 | 33.589 | 54.412 | 18.005 | 1.00 | 15.87 |
| ATOM | 2726 | CD1 | ILE A | 390 | 34.530 | 54.143 | 19.163 | 1.00 | 13.96 |
| ATOM | 2727 | C | ILE A | 390 | 29.753 | 54.514 | 17.539 | 1.00 | 15.15 |
| ATOM | 2728 | O | ILE A | 390 | 29.254 | 54.982 | 18.561 | 1.00 | 16.23 |
| ATOM | 2729 | N | GLY A | 391 | 29.066 | 53.774 | 16.676 | 1.00 | 15.83 |
| ATOM | 2730 | CA | GLY A | 391 | 27.665 | 53.450 | 16.907 | 1.00 | 15.35 |
| ATOM | 2731 | C | GLY A | 391 | 26.649 | 54.555 | 16.651 | 1.00 | 15.84 |
| ATOM | 2732 | O | GLY A | 391 | 25.460 | 54.366 | 16.896 | 1.00 | 15.88 |
| ATOM | 2733 | N | ALA A | 392 | 27.100 | 55.695 | 16.139 | 1.00 | 16.70 |
| ATOM | 2734 | CA | ALA A | 392 | 26.214 | 56.832 | 15.877 | 1.00 | 18.63 |
| ATOM | 2735 | CB | ALA A | 392 | 26.985 | 57.936 | 15.145 | 1.00 | 16.34 |
| ATOM | 2736 | C | ALA A | 392 | 24.928 | 56.505 | 15.114 | 1.00 | 19.71 |
| ATOM | 2737 | O | ALA A | 392 | 23.893 | 57.130 | 15.355 | 1.00 | 19.45 |
| ATOM | 2738 | N | ASP A | 393 | 24.980 | 55.541 | 14.196 | 1.00 | 20.17 |
| ATOM | 2739 | CA | ASP A | 393 | 23.786 | 55.187 | 13.424 | 1.00 | 20.89 |
| ATOM | 2740 | CB | ASP A | 393 | 24.099 | 54.129 | 12.356 | 1.00 | 21.04 |
| ATOM | 2741 | CG | ASP A | 393 | 24.899 | 54.680 | 11.185 | 1.00 | 25.12 |
| ATOM | 2742 | OD1 | ASP A | 393 | 24.911 | 55.914 | 10.973 | 1.00 | 24.48 |
| ATOM | 2743 | OD2 | ASP A | 393 | 25.505 | 53.860 | 10.459 | 1.00 | 26.24 |
| ATOM | 2744 | C | ASP A | 393 | 22.678 | 54.646 | 14.321 | 1.00 | 21.66 |
| ATOM | 2745 | O | ASP A | 393 | 21.495 | 54.824 | 14.034 | 1.00 | 21.79 |
| ATOM | 2746 | N | HIS A | 394 | 23.068 | 53.980 | 15.404 | 1.00 | 21.55 |
| ATOM | 2747 | CA | HIS A | 394 | 22.113 | 53.388 | 16.334 | 1.00 | 22.75 |
| ATOM | 2748 | CB | HIS A | 394 | 22.825 | 52.353 | 17.208 | 1.00 | 17.96 |
| ATOM | 2749 | CG | HIS A | 394 | 23.439 | 51.228 | 16.430 | 1.00 | 18.66 |
| ATOM | 2750 | CD2 | HIS A | 394 | 24.567 | 51.172 | 15.683 | 1.00 | 15.93 |
| ATOM | 2751 | ND1 | HIS A | 394 | 22.860 | 49.979 | 16.342 | 1.00 | 15.56 |
| ATOM | 2752 | CE1 | HIS A | 394 | 23.605 | 49.204 | 15.576 | 1.00 | 15.23 |
| ATOM | 2753 | NE2 | HIS A | 394 | 24.647 | 49.903 | 15.163 | 1.00 | 16.20 |
| ATOM | 2754 | C | HIS A | 394 | 21.415 | 54.414 | 17.222 | 1.00 | 25.26 |
| ATOM | 2755 | O | HIS A | 394 | 20.369 | 54.132 | 17.798 | 1.00 | 26.08 |
| ATOM | 2756 | N | ARG A | 395 | 21.996 | 55.602 | 17.332 | 1.00 | 28.23 |
| ATOM | 2757 | CA | ARG A | 395 | 21.426 | 56.647 | 18.170 | 1.00 | 32.93 |
| ATOM | 2758 | CB | ARG A | 395 | 22.545 | 57.387 | 18.911 | 1.00 | 32.49 |
| ATOM | 2759 | CG | ARG A | 395 | 23.385 | 56.481 | 19.809 | 1.00 | 34.34 |
| ATOM | 2760 | CD | ARG A | 395 | 24.306 | 57.282 | 20.723 | 1.00 | 34.96 |
| ATOM | 2761 | NE | ARG A | 395 | 25.452 | 57.866 | 20.029 | 1.00 | 36.24 |
| ATOM | 2762 | CZ | ARG A | 395 | 26.561 | 57.199 | 19.715 | 1.00 | 36.79 |
| ATOM | 2763 | NH1 | ARG A | 395 | 27.552 | 57.817 | 19.083 | 1.00 | 35.26 |
| ATOM | 2764 | NH2 | ARG A | 395 | 26.684 | 55.916 | 20.038 | 1.00 | 35.52 |
| ATOM | 2765 | C | ARG A | 395 | 20.577 | 57.637 | 17.377 | 1.00 | 36.89 |
| ATOM | 2766 | O | ARG A | 395 | 19.863 | 58.453 | 17.956 | 1.00 | 38.27 |
| ATOM | 2767 | N | ARG A | 396 | 20.650 | 57.561 | 16.053 | 1.00 | 41.09 |
| ATOM | 2768 | CA | ARG A | 396 | 19.876 | 58.454 | 15.202 | 1.00 | 45.29 |
| ATOM | 2769 | CB | ARG A | 396 | 20.594 | 58.671 | 13.862 | 1.00 | 47.75 |
| ATOM | 2770 | CG | ARG A | 396 | 20.593 | 57.476 | 12.923 | 1.00 | 50.83 |
| ATOM | 2771 | CD | ARG A | 396 | 21.562 | 57.692 | 11.761 | 1.00 | 53.11 |
| ATOM | 2772 | NE | ARG A | 396 | 21.411 | 59.015 | 11.162 | 1.00 | 55.40 |
| ATOM | 2773 | CZ | ARG A | 396 | 20.296 | 59.453 | 10.587 | 1.00 | 57.11 |
| ATOM | 2774 | NH1 | ARG A | 396 | 20.246 | 60.674 | 10.069 | 1.00 | 57.93 |
| ATOM | 2775 | NH2 | ARG A | 396 | 19.231 | 58.668 | 10.524 | 1.00 | 58.62 |
| ATOM | 2776 | C | ARG A | 396 | 18.478 | 57.885 | 14.970 | 1.00 | 46.68 |
| ATOM | 2777 | O | ARG A | 396 | 17.498 | 58.657 | 15.061 | 1.00 | 47.16 |
| ATOM | 2778 | OXT | ARG A | 396 | 18.379 | 56.671 | 14.696 | 1.00 | 48.86 |
| TER | 1 | | ARG A | 396 | | | | | |
| END | | | | | | | | | |

TABLE 31

| CRYST1 | 90.692 | 90.692 | 123.221 | 90.00 | 90.00 | 120.00 | P 32 2 1 | 12 |
|---|---|---|---|---|---|---|---|---|
| ORIGX1 | 1.000000 | 0.000000 | 0.000000 | | | 0.00000 | | |
| ORIGX2 | 0.000000 | 1.000000 | 0.000000 | | | 0.00000 | | |
| ORIGX3 | 0.000000 | 0.000000 | 1.000000 | | | 0.00000 | | |
| SCALE1 | 0.011026 | 0.006366 | 0.000000 | | | 0.00000 | | |
| SCALE2 | 0.000000 | 0.012732 | 0.000000 | | | 0.00000 | | |
| SCALE3 | 0.000000 | 0.000000 | 0.008115 | | | 0.00000 | | |

TABLE 31-continued

| | | | | | | | | |
|---|---|---|---|---|---|---|---|---|
| ATOM | 2779 | N1 | FMN | 398 | 48.982 | 36.086 | 32.351 | 1.00 | 13.65 |
| ATOM | 2780 | C2 | FMN | 398 | 48.621 | 35.465 | 31.196 | 1.00 | 15.79 |
| ATOM | 2781 | O2 | FMN | 398 | 49.207 | 35.572 | 30.149 | 1.00 | 16.16 |
| ATOM | 2782 | N3 | FMN | 398 | 47.453 | 34.623 | 31.236 | 1.00 | 15.84 |
| ATOM | 2783 | C4 | FMN | 398 | 46.691 | 34.411 | 32.352 | 1.00 | 15.69 |
| ATOM | 2784 | O4 | FMN | 398 | 45.690 | 33.661 | 32.297 | 1.00 | 18.13 |
| ATOM | 2785 | C4A | FMN | 398 | 47.084 | 35.083 | 33.587 | 1.00 | 14.70 |
| ATOM | 2786 | N5 | FMN | 398 | 46.390 | 34.934 | 34.726 | 1.00 | 16.27 |
| ATOM | 2787 | C5A | FMN | 398 | 46.793 | 35.607 | 35.867 | 1.00 | 13.36 |
| ATOM | 2788 | C6 | FMN | 398 | 46.064 | 35.496 | 37.124 | 1.00 | 10.34 |
| ATOM | 2789 | C7 | FMN | 398 | 46.419 | 36.162 | 38.280 | 1.00 | 11.27 |
| ATOM | 2790 | C7M | FMN | 398 | 45.627 | 36.037 | 39.591 | 1.00 | 12.50 |
| ATOM | 2791 | C8 | FMN | 398 | 47.597 | 37.031 | 38.258 | 1.00 | 12.24 |
| ATOM | 2792 | C8M | FMN | 398 | 48.067 | 37.811 | 39.455 | 1.00 | 12.12 |
| ATOM | 2793 | C9 | FMN | 398 | 48.309 | 37.142 | 37.069 | 1.00 | 11.89 |
| ATOM | 2794 | C9A | FMN | 398 | 47.965 | 36.475 | 35.873 | 1.00 | 13.80 |
| ATOM | 2795 | N10 | FMN | 398 | 48.680 | 36.591 | 34.639 | 1.00 | 15.34 |
| ATOM | 2796 | C10 | FMN | 398 | 48.300 | 35.943 | 33.489 | 1.00 | 15.60 |
| ATOM | 2797 | C1* | FMN | 398 | 49.889 | 37.455 | 34.581 | 1.00 | 13.44 |
| ATOM | 2798 | C2* | FMN | 398 | 49.650 | 38.935 | 34.357 | 1.00 | 13.38 |
| ATOM | 2799 | O2* | FMN | 398 | 49.014 | 39.163 | 33.083 | 1.00 | 14.11 |
| ATOM | 2800 | C3* | FMN | 398 | 50.988 | 39.727 | 34.356 | 1.00 | 12.71 |
| ATOM | 2801 | O3* | FMN | 398 | 51.831 | 39.225 | 33.274 | 1.00 | 11.59 |
| ATOM | 2802 | C4* | FMN | 398 | 51.799 | 39.592 | 35.655 | 1.00 | 12.19 |
| ATOM | 2803 | O4* | FMN | 398 | 50.908 | 39.382 | 36.778 | 1.00 | 9.70 |
| ATOM | 2804 | C5* | FMN | 398 | 52.667 | 40.790 | 35.978 | 1.00 | 13.16 |
| ATOM | 2805 | O5* | FMN | 398 | 51.923 | 42.012 | 36.092 | 1.00 | 14.37 |
| ATOM | 2806 | P | FMN | 398 | 51.422 | 42.666 | 37.461 | 1.00 | 15.94 |
| ATOM | 2807 | O1P | FMN | 398 | 50.317 | 41.745 | 37.973 | 1.00 | 15.70 |
| ATOM | 2808 | O2P | FMN | 398 | 50.895 | 44.013 | 37.089 | 1.00 | 15.09 |
| ATOM | 2809 | O3P | FMN | 398 | 52.652 | 42.679 | 38.391 | 1.00 | 16.83 |
| ATOM | 2810 | N1 | ORO | 399 | 49.032 | 32.288 | 36.152 | 1.00 | 18.25 |
| ATOM | 2811 | C2 | ORO | 399 | 50.025 | 33.225 | 35.839 | 1.00 | 17.42 |
| ATOM | 2812 | O3 | ORO | 399 | 50.604 | 33.882 | 36.700 | 1.00 | 19.91 |
| ATOM | 2813 | N4 | ORO | 399 | 50.326 | 33.372 | 34.500 | 1.00 | 15.40 |
| ATOM | 2814 | C5 | ORO | 399 | 49.749 | 32.688 | 33.445 | 1.00 | 16.04 |
| ATOM | 2815 | O6 | ORO | 399 | 50.091 | 32.895 | 32.302 | 1.00 | 15.47 |
| ATOM | 2816 | C7 | ORO | 399 | 48.718 | 31.722 | 33.822 | 1.00 | 15.22 |
| ATOM | 2817 | C8 | ORO | 399 | 48.415 | 31.571 | 35.132 | 1.00 | 18.83 |
| ATOM | 2818 | C9 | ORO | 399 | 47.365 | 30.573 | 35.616 | 1.00 | 19.59 |
| ATOM | 2819 | O10 | ORO | 399 | 47.594 | 29.817 | 36.545 | 1.00 | 21.79 |
| ATOM | 2820 | O11 | ORO | 399 | 46.323 | 30.677 | 34.919 | 1.00 | 21.84 |
| ATOM | 2821 | C1 | INH | 400 | 35.607 | 47.222 | 40.518 | 1.00 | 24.78 |
| ATOM | 2822 | C2 | INH | 400 | 35.062 | 48.080 | 41.508 | 1.00 | 23.86 |
| ATOM | 2823 | C3 | INH | 400 | 35.535 | 48.013 | 42.863 | 1.00 | 24.02 |
| ATOM | 2824 | C4 | INH | 400 | 36.569 | 47.072 | 43.218 | 1.00 | 24.44 |
| ATOM | 2825 | C5 | INH | 400 | 37.128 | 46.196 | 42.209 | 1.00 | 22.48 |
| ATOM | 2826 | C6 | INH | 400 | 38.133 | 45.216 | 42.490 | 1.00 | 22.48 |
| ATOM | 2827 | C7 | INH | 400 | 36.623 | 46.291 | 40.860 | 1.00 | 22.67 |
| ATOM | 2828 | C8 | INH | 400 | 38.032 | 44.391 | 43.667 | 1.00 | 20.92 |
| ATOM | 2829 | C9 | INH | 400 | 38.992 | 43.378 | 43.923 | 1.00 | 22.05 |
| ATOM | 2830 | C10 | INH | 400 | 40.088 | 43.146 | 43.018 | 1.00 | 21.93 |
| ATOM | 2831 | N11 | INH | 400 | 40.994 | 42.107 | 43.283 | 1.00 | 19.47 |
| ATOM | 2832 | C12 | INH | 400 | 40.206 | 43.966 | 41.854 | 1.00 | 20.67 |
| ATOM | 2833 | F13 | INH | 400 | 41.192 | 43.777 | 40.999 | 1.00 | 23.37 |
| ATOM | 2834 | C14 | INH | 400 | 39.242 | 44.990 | 41.586 | 1.00 | 21.17 |
| ATOM | 2835 | C15 | INH | 400 | 41.311 | 41.338 | 44.410 | 1.00 | 21.10 |
| ATOM | 2836 | C16 | INH | 400 | 42.300 | 40.258 | 44.384 | 1.00 | 18.97 |
| ATOM | 2837 | O17 | INH | 400 | 40.713 | 41.559 | 45.466 | 1.00 | 24.88 |
| ATOM | 2838 | C18 | INH | 400 | 42.725 | 39.520 | 43.331 | 1.00 | 18.81 |
| ATOM | 2839 | C19 | INH | 400 | 43.719 | 38.514 | 43.792 | 1.00 | 18.57 |
| ATOM | 2840 | C20 | INH | 400 | 44.202 | 39.048 | 45.143 | 1.00 | 18.27 |
| ATOM | 2841 | C21 | INH | 400 | 42.981 | 39.825 | 45.638 | 1.00 | 16.93 |
| ATOM | 2842 | C22 | INH | 400 | 42.339 | 39.571 | 41.901 | 1.00 | 19.11 |
| ATOM | 2843 | O23 | INH | 400 | 41.535 | 40.384 | 41.444 | 1.00 | 20.87 |
| ATOM | 2844 | O24 | INH | 400 | 42.882 | 38.689 | 41.022 | 1.00 | 19.27 |
| ATOM | 2845 | O25 | INH | 400 | 34.997 | 48.846 | 43.813 | 1.00 | 26.96 |
| ATOM | 2846 | C26 | INH | 400 | 33.649 | 48.435 | 44.070 | 1.00 | 28.19 |
| ATOM | 2847 | C | ACT | 401 | 66.322 | 48.953 | 35.993 | 1.00 | 31.77 |
| ATOM | 2848 | O | ACT | 401 | 67.328 | 49.644 | 36.341 | 1.00 | 30.18 |
| ATOM | 2849 | OXT | ACT | 401 | 65.833 | 48.910 | 34.832 | 1.00 | 32.50 |
| ATOM | 2850 | CH3 | ACT | 401 | 65.696 | 48.119 | 37.112 | 1.00 | 30.07 |
| ATOM | 2851 | S | SO4 | 402 | 34.333 | 40.203 | 6.362 | 1.00 | 35.89 |
| ATOM | 2852 | O1 | SO4 | 402 | 34.721 | 41.545 | 5.893 | 1.00 | 38.88 |
| ATOM | 2853 | O2 | SO4 | 402 | 35.521 | 39.335 | 6.395 | 1.00 | 37.76 |
| ATOM | 2854 | O3 | SO4 | 402 | 33.760 | 40.298 | 7.717 | 1.00 | 39.48 |
| ATOM | 2855 | O4 | SO4 | 402 | 33.326 | 39.642 | 5.444 | 1.00 | 38.73 |
| ATOM | 2856 | S | SO4 | 403 | 36.080 | 30.092 | 37.260 | 1.00 | 59.73 |
| ATOM | 2857 | O1 | SO4 | 403 | 36.357 | 31.501 | 36.909 | 1.00 | 59.29 |

TABLE 31-continued

| | | | | | | | | |
|---|---|---|---|---|---|---|---|---|
| ATOM | 2858 | O2 | SO4 | 403 | 37.023 | 29.206 | 36.551 | 1.00 57.64 |
| ATOM | 2859 | O3 | SO4 | 403 | 36.237 | 29.908 | 38.718 | 1.00 59.62 |
| ATOM | 2860 | O4 | SO4 | 403 | 34.697 | 29.758 | 36.868 | 1.00 59.77 |
| ATOM | 2861 | OH2 | TIP | 1 | 60.060 | 30.725 | 53.700 | 1.00 3.85 |
| ATOM | 2862 | OH2 | TIP | 2 | 52.367 | 45.630 | 35.605 | 1.00 9.31 |
| ATOM | 2863 | OH2 | TIP | 3 | 58.030 | 49.528 | 35.970 | 1.00 11.67 |
| ATOM | 2864 | OH2 | TIP | 4 | 50.550 | 36.383 | 40.910 | 1.00 9.15 |
| ATOM | 2865 | OH2 | TIP | 5 | 58.035 | 48.907 | 21.969 | 1.00 15.13 |
| ATOM | 2866 | OH2 | TIP | 6 | 49.097 | 40.172 | 29.373 | 1.00 13.46 |
| ATOM | 2867 | OH2 | TIP | 7 | 56.666 | 28.089 | 42.316 | 1.00 12.52 |
| ATOM | 2868 | OH2 | TIP | 8 | 37.855 | 27.076 | 38.255 | 1.00 22.25 |
| ATOM | 2869 | OH2 | TIP | 9 | 59.045 | 31.393 | 34.498 | 1.00 17.43 |
| ATOM | 2870 | OH2 | TIP | 10 | 61.985 | 46.199 | 19.869 | 1.00 20.90 |
| ATOM | 2871 | OH2 | TIP | 11 | 33.724 | 41.447 | 21.286 | 1.00 16.51 |
| ATOM | 2872 | OH2 | TIP | 12 | 64.454 | 32.508 | 43.713 | 1.00 25.03 |
| ATOM | 2873 | OH2 | TIP | 13 | 35.247 | 43.126 | 16.686 | 1.00 22.09 |
| ATOM | 2874 | OH2 | TIP | 14 | 58.994 | 42.404 | 49.027 | 1.00 12.52 |
| ATOM | 2875 | OH2 | TIP | 15 | 57.581 | 44.787 | 53.944 | 1.00 22.80 |
| ATOM | 2876 | OH2 | TIP | 16 | 39.067 | 31.534 | 29.620 | 1.00 16.07 |
| ATOM | 2877 | OH2 | TIP | 17 | 42.346 | 60.681 | 46.719 | 1.00 34.08 |
| ATOM | 2878 | OH2 | TIP | 18 | 36.301 | 36.571 | 33.168 | 1.00 15.41 |
| ATOM | 2879 | OH2 | TIP | 19 | 41.935 | 30.030 | 45.729 | 1.00 19.39 |
| ATOM | 2880 | OH2 | TIP | 20 | 42.353 | 40.596 | 31.923 | 1.00 13.54 |
| ATOM | 2881 | OH2 | TIP | 21 | 40.520 | 40.057 | 13.943 | 1.00 15.83 |
| ATOM | 2882 | OH2 | TIP | 22 | 39.285 | 53.585 | 28.554 | 1.00 17.52 |
| ATOM | 2883 | OH2 | TIP | 23 | 35.343 | 25.302 | 23.916 | 1.00 17.49 |
| ATOM | 2884 | OH2 | TIP | 24 | 60.804 | 49.477 | 36.760 | 1.00 18.25 |
| ATOM | 2885 | OH2 | TIP | 25 | 39.416 | 24.528 | 14.376 | 1.00 27.09 |
| ATOM | 2886 | OH2 | TIP | 26 | 50.670 | 45.964 | 38.922 | 1.00 12.31 |
| ATOM | 2887 | OH2 | TIP | 27 | 51.502 | 36.631 | 52.577 | 1.00 18.23 |
| ATOM | 2888 | OH2 | TIP | 28 | 54.818 | 42.146 | 42.516 | 1.00 22.73 |
| ATOM | 2889 | OH2 | TIP | 29 | 33.864 | 26.690 | 25.789 | 1.00 19.94 |
| ATOM | 2890 | OH2 | TIP | 30 | 65.696 | 40.626 | 33.942 | 1.00 21.89 |
| ATOM | 2891 | OH2 | TIP | 31 | 56.168 | 56.708 | 18.745 | 1.00 29.01 |
| ATOM | 2892 | OH2 | TIP | 32 | 54.982 | 30.599 | 52.611 | 1.00 18.21 |
| ATOM | 2893 | OH2 | TIP | 33 | 38.144 | 40.983 | 5.331 | 1.00 31.87 |
| ATOM | 2894 | OH2 | TIP | 34 | 33.676 | 34.519 | 15.071 | 1.00 23.56 |
| ATOM | 2895 | OH2 | TIP | 35 | 62.221 | 42.445 | 44.141 | 1.00 20.83 |
| ATOM | 2896 | OH2 | TIP | 36 | 59.679 | 52.708 | 39.168 | 1.00 20.48 |
| ATOM | 2897 | OH2 | TIP | 37 | 51.513 | 48.458 | 44.581 | 1.00 28.15 |
| ATOM | 2898 | OH2 | TIP | 38 | 51.079 | 45.614 | 43.529 | 1.00 16.70 |
| ATOM | 2899 | OH2 | TIP | 39 | 32.029 | 49.946 | 26.001 | 1.00 26.17 |
| ATOM | 2900 | OH2 | TIP | 40 | 35.203 | 32.402 | 15.435 | 1.00 26.10 |
| ATOM | 2901 | OH2 | TIP | 41 | 68.467 | 50.979 | 34.362 | 1.00 21.55 |
| ATOM | 2902 | OH2 | TIP | 42 | 52.544 | 29.461 | 52.556 | 1.00 23.72 |
| ATOM | 2903 | OH2 | TIP | 43 | 48.533 | 27.810 | 33.536 | 1.00 19.98 |
| ATOM | 2904 | OH2 | TIP | 44 | 63.782 | 52.953 | 32.497 | 1.00 19.82 |
| ATOM | 2905 | OH2 | TIP | 45 | 66.426 | 48.144 | 40.544 | 1.00 15.64 |
| ATOM | 2906 | OH2 | TIP | 46 | 63.396 | 36.742 | 31.190 | 1.00 34.59 |
| ATOM | 2907 | OH2 | TIP | 47 | 65.569 | 53.618 | 20.355 | 1.00 33.40 |
| ATOM | 2908 | OH2 | TIP | 48 | 43.542 | 29.587 | 9.732 | 1.00 24.10 |
| ATOM | 2909 | OH2 | TIP | 49 | 72.437 | 31.865 | 28.980 | 1.00 27.82 |
| ATOM | 2910 | OH2 | TIP | 50 | 38.905 | 23.141 | 44.956 | 1.00 37.59 |
| ATOM | 2911 | OH2 | TIP | 51 | 42.809 | 30.953 | 32.234 | 1.00 27.21 |
| ATOM | 2912 | OH2 | TIP | 52 | 43.248 | 53.783 | 44.946 | 1.00 21.23 |
| ATOM | 2913 | OH2 | TIP | 53 | 53.351 | 36.194 | 8.506 | 1.00 36.32 |
| ATOM | 2914 | OH2 | TIP | 54 | 56.693 | 24.667 | 43.143 | 1.00 39.40 |
| ATOM | 2915 | OH2 | TIP | 55 | 66.806 | 41.088 | 31.475 | 1.00 30.36 |
| ATOM | 2916 | OH2 | TIP | 56 | 37.574 | 23.750 | 20.244 | 1.00 41.77 |
| ATOM | 2917 | OH2 | TIP | 57 | 70.299 | 32.603 | 18.834 | 1.00 32.10 |
| ATOM | 2918 | OH2 | TIP | 58 | 54.515 | 58.147 | 39.651 | 1.00 28.68 |
| ATOM | 2919 | OH2 | TIP | 59 | 51.721 | 56.894 | 43.342 | 1.00 19.99 |
| ATOM | 2920 | OH2 | TIP | 60 | 38.442 | 41.829 | 13.935 | 1.00 25.07 |
| ATOM | 2921 | OH2 | TIP | 61 | 43.655 | 62.897 | 37.603 | 1.00 43.03 |
| ATOM | 2922 | OH2 | TIP | 62 | 45.750 | 42.115 | 46.652 | 1.00 26.72 |
| ATOM | 2923 | OH2 | TIP | 63 | 69.417 | 37.196 | 19.214 | 1.00 23.58 |
| ATOM | 2924 | OH2 | TIP | 64 | 31.743 | 44.583 | 31.047 | 1.00 22.02 |
| ATOM | 2925 | OH2 | TIP | 65 | 31.729 | 43.466 | 28.354 | 1.00 20.77 |
| ATOM | 2926 | OH2 | TIP | 66 | 49.885 | 61.184 | 42.216 | 1.00 36.18 |
| ATOM | 2927 | OH2 | TIP | 67 | 34.384 | 35.165 | 36.872 | 1.00 40.36 |
| ATOM | 2928 | OH2 | TIP | 68 | 51.653 | 37.967 | 55.085 | 1.00 22.01 |
| ATOM | 2929 | OH2 | TIP | 69 | 29.355 | 39.640 | 25.875 | 1.00 26.40 |
| ATOM | 2930 | OH2 | TIP | 70 | 42.464 | 21.852 | 34.480 | 1.00 28.86 |
| ATOM | 2931 | OH2 | TIP | 71 | 45.229 | 22.919 | 34.845 | 1.00 31.09 |
| ATOM | 2932 | OH2 | TIP | 72 | 42.964 | 20.824 | 23.475 | 1.00 27.79 |
| ATOM | 2933 | OH2 | TIP | 73 | 60.952 | 63.544 | 36.337 | 1.00 27.14 |
| ATOM | 2934 | OH2 | TIP | 74 | 63.312 | 23.939 | 22.011 | 1.00 37.06 |
| ATOM | 2935 | OH2 | TIP | 75 | 66.301 | 28.555 | 23.465 | 1.00 28.01 |
| ATOM | 2936 | OH2 | TIP | 76 | 60.676 | 38.163 | 57.470 | 1.00 34.78 |

TABLE 31-continued

| | | | | | | | | |
|---|---|---|---|---|---|---|---|---|
| ATOM | 2937 | OH2 | TIP | 77 | 52.460 | 26.054 | 39.635 | 1.00 40.06 |
| ATOM | 2938 | OH2 | TIP | 78 | 62.406 | 35.903 | 49.759 | 1.00 27.79 |
| ATOM | 2939 | OH2 | TIP | 79 | 52.178 | 53.523 | 44.125 | 1.00 35.13 |
| ATOM | 2940 | OH2 | TIP | 80 | 42.554 | 58.098 | 40.280 | 1.00 33.38 |
| ATOM | 2941 | OH2 | TIP | 81 | 58.030 | 41.857 | 58.164 | 1.00 30.26 |
| ATOM | 2942 | OH2 | TIP | 82 | 59.733 | 49.051 | 19.405 | 1.00 27.97 |
| ATOM | 2943 | OH2 | TIP | 83 | 36.034 | 27.617 | 34.567 | 1.00 34.15 |
| ATOM | 2944 | OH2 | TIP | 84 | 26.557 | 35.421 | 20.896 | 1.00 29.67 |
| ATOM | 2945 | OH2 | TIP | 85 | 55.473 | 51.440 | 48.459 | 1.00 33.01 |
| ATOM | 2946 | OH2 | TIP | 86 | 42.649 | 50.960 | 16.828 | 1.00 31.38 |
| ATOM | 2947 | OH2 | TIP | 87 | 66.170 | 32.041 | 14.438 | 1.00 35.56 |
| ATOM | 2948 | OH2 | TIP | 88 | 70.923 | 46.419 | 19.569 | 1.00 29.27 |
| ATOM | 2949 | OH2 | TIP | 89 | 56.751 | 32.577 | 34.130 | 1.00 25.63 |
| ATOM | 2950 | OH2 | TIP | 90 | 42.493 | 35.941 | 41.050 | 1.00 33.08 |
| ATOM | 2951 | OH2 | TIP | 91 | 30.681 | 28.816 | 16.556 | 1.00 27.33 |
| ATOM | 2952 | OH2 | TIP | 92 | 46.460 | 24.293 | 44.169 | 1.00 34.16 |
| ATOM | 2953 | OH2 | TIP | 93 | 48.432 | 24.353 | 11.034 | 1.00 34.69 |
| ATOM | 2954 | OH2 | TIP | 94 | 52.557 | 59.642 | 21.794 | 1.00 25.61 |
| ATOM | 2955 | OH2 | TIP | 95 | 41.084 | 32.123 | 47.677 | 1.00 29.77 |
| ATOM | 2956 | OH2 | TIP | 96 | 46.793 | 44.614 | 13.529 | 1.00 44.70 |
| ATOM | 2957 | OH2 | TIP | 97 | 53.521 | 22.830 | 45.046 | 1.00 29.14 |
| ATOM | 2958 | OH2 | TIP | 98 | 29.812 | 30.485 | 31.098 | 1.00 33.09 |
| ATOM | 2959 | OH2 | TIP | 99 | 32.089 | 40.898 | 27.978 | 1.00 25.82 |
| ATOM | 2960 | OH2 | TIP | 100 | 52.375 | 32.327 | 7.043 | 1.00 32.25 |
| ATOM | 2961 | OH2 | TIP | 101 | 62.327 | 42.900 | 40.662 | 1.00 22.77 |
| ATOM | 2962 | OH2 | TIP | 102 | 64.175 | 37.371 | 41.404 | 1.00 35.08 |
| ATOM | 2963 | OH2 | TIP | 103 | 59.638 | 59.791 | 38.765 | 1.00 31.48 |
| ATOM | 2964 | OH2 | TIP | 104 | 32.709 | 26.673 | 29.792 | 1.00 28.88 |
| ATOM | 2965 | OH2 | TIP | 105 | 51.017 | 50.179 | 13.353 | 1.00 42.02 |
| ATOM | 2966 | OH2 | TIP | 106 | 44.398 | 28.252 | 22.452 | 1.00 27.78 |
| ATOM | 2967 | OH2 | TIP | 107 | 47.749 | 23.069 | 33.446 | 1.00 41.42 |
| ATOM | 2968 | OH2 | TIP | 108 | 45.086 | 48.695 | 49.919 | 1.00 43.00 |
| ATOM | 2969 | OH2 | TIP | 109 | 44.998 | 67.007 | 24.798 | 1.00 47.56 |
| ATOM | 2970 | OH2 | TIP | 110 | 54.365 | 45.236 | 14.693 | 1.00 40.44 |
| ATOM | 2971 | OH2 | TIP | 111 | 53.518 | 47.725 | 14.954 | 1.00 35.35 |
| ATOM | 2972 | OH2 | TIP | 112 | 59.581 | 28.126 | 10.019 | 1.00 33.27 |
| ATOM | 2973 | OH2 | TIP | 113 | 64.379 | 34.664 | 37.556 | 1.00 37.42 |
| ATOM | 2974 | OH2 | TIP | 114 | 35.688 | 41.444 | 14.660 | 1.00 30.13 |
| ATOM | 2975 | OH2 | TIP | 115 | 37.327 | 48.122 | 13.936 | 1.00 33.07 |
| ATOM | 2976 | OH2 | TIP | 116 | 39.099 | 24.372 | 17.130 | 1.00 44.61 |
| ATOM | 2977 | OH2 | TIP | 117 | 66.062 | 41.012 | 46.358 | 1.00 29.39 |
| ATOM | 2978 | OH2 | TIP | 118 | 47.642 | 36.763 | 4.574 | 1.00 35.65 |
| ATOM | 2979 | OH2 | TIP | 119 | 65.270 | 38.095 | 32.836 | 1.00 41.52 |
| ATOM | 2980 | OH2 | TIP | 120 | 48.628 | 65.085 | 34.950 | 1.00 37.26 |
| ATOM | 2981 | OH2 | TIP | 121 | 25.753 | 46.099 | 24.755 | 1.00 44.46 |
| ATOM | 2982 | OH2 | TIP | 122 | 37.685 | 32.073 | 40.100 | 1.00 37.09 |
| ATOM | 2983 | OH2 | TIP | 123 | 63.723 | 66.856 | 33.778 | 1.00 37.70 |
| ATOM | 2984 | OH2 | TIP | 124 | 61.504 | 51.786 | 18.568 | 1.00 41.55 |
| ATOM | 2985 | OH2 | TIP | 125 | 46.476 | 24.073 | 31.375 | 1.00 23.40 |
| ATOM | 2986 | OH2 | TIP | 126 | 60.304 | 30.723 | 48.847 | 1.00 32.91 |
| ATOM | 2987 | OH2 | TIP | 127 | 54.304 | 24.230 | 35.850 | 1.00 41.67 |
| ATOM | 2988 | OH2 | TIP | 129 | 66.979 | 38.849 | 45.036 | 1.00 41.82 |
| ATOM | 2989 | OH2 | TIP | 130 | 42.233 | 35.385 | 38.170 | 1.00 27.93 |
| ATOM | 2990 | OH2 | TIP | 131 | 60.719 | 30.545 | 31.856 | 1.00 38.36 |
| ATOM | 2991 | OH2 | TIP | 132 | 40.738 | 39.057 | 2.892 | 1.00 32.59 |
| ATOM | 2992 | OH2 | TIP | 133 | 62.708 | 23.986 | 25.043 | 1.00 42.43 |
| ATOM | 2993 | OH2 | TIP | 134 | 35.497 | 41.399 | 19.114 | 1.00 25.27 |
| ATOM | 2994 | OH2 | TIP | 135 | 53.296 | 39.609 | 11.264 | 1.00 38.06 |
| ATOM | 2995 | OH2 | TIP | 136 | 32.634 | 36.735 | 38.827 | 1.00 45.72 |
| ATOM | 2996 | OH2 | TIP | 137 | 51.884 | 57.784 | 17.735 | 1.00 44.09 |
| ATOM | 2997 | OH2 | TIP | 138 | 52.590 | 51.257 | 45.492 | 1.00 41.96 |
| ATOM | 2998 | OH2 | TIP | 139 | 69.561 | 35.796 | 14.477 | 1.00 45.47 |
| ATOM | 2999 | OH2 | TIP | 140 | 43.069 | 52.778 | 14.466 | 1.00 38.58 |
| ATOM | 3000 | OH2 | TIP | 141 | 44.350 | 60.071 | 23.707 | 1.00 34.18 |
| ATOM | 3001 | OH2 | TIP | 142 | 40.145 | 56.197 | 29.092 | 1.00 32.21 |
| ATOM | 3002 | OH2 | TIP | 143 | 68.741 | 38.750 | 17.070 | 1.00 47.07 |
| ATOM | 3003 | OH2 | TIP | 144 | 42.642 | 19.568 | 29.836 | 1.00 36.77 |
| ATOM | 3004 | OH2 | TIP | 145 | 40.366 | 33.392 | 37.870 | 1.00 31.48 |
| ATOM | 3005 | OH2 | TIP | 146 | 71.730 | 51.850 | 23.663 | 1.00 42.26 |
| ATOM | 3006 | OH2 | TIP | 147 | 49.116 | 40.579 | 56.678 | 1.00 46.10 |
| ATOM | 3007 | OH2 | TIP | 148 | 47.913 | 30.808 | 5.178 | 1.00 46.45 |
| ATOM | 3008 | OH2 | TIP | 149 | 38.099 | 34.045 | 36.957 | 1.00 42.98 |
| ATOM | 3009 | OH2 | TIP | 150 | 64.592 | 30.466 | 24.304 | 1.00 40.67 |
| ATOM | 3010 | OH2 | TIP | 151 | 28.792 | 49.500 | 27.018 | 1.00 47.07 |
| ATOM | 3011 | OH2 | TIP | 152 | 38.062 | 36.480 | 35.087 | 1.00 34.16 |
| ATOM | 3012 | OH2 | TIP | 153 | 55.920 | 46.433 | 49.521 | 1.00 45.73 |
| ATOM | 3013 | OH2 | TIP | 154 | 44.328 | 37.046 | 1.316 | 1.00 46.31 |
| TER | 1 | | TIP | 154 | | | | |
| ATOM | 1 | CB | MET A | 30 | 31.574 | 53.310 | 46.169 | 1.00 84.87 |

TABLE 31-continued

| | | | | | | | | | |
|---|---|---|---|---|---|---|---|---|---|
| ATOM | 2 | CG | MET A | 30 | 31.623 | 52.655 | 47.538 | 1.00 | 86.03 |
| ATOM | 3 | SD | MET A | 30 | 30.794 | 51.051 | 47.554 | 1.00 | 88.57 |
| ATOM | 4 | CE | MET A | 30 | 29.099 | 51.544 | 47.904 | 1.00 | 88.24 |
| ATOM | 5 | C | MET A | 30 | 32.230 | 55.176 | 44.652 | 1.00 | 83.28 |
| ATOM | 6 | O | MET A | 30 | 33.176 | 55.117 | 43.866 | 1.00 | 82.94 |
| ATOM | 7 | N | MET A | 30 | 31.862 | 55.601 | 47.078 | 1.00 | 84.20 |
| ATOM | 8 | CA | MET A | 30 | 32.359 | 54.621 | 46.067 | 1.00 | 84.06 |
| ATOM | 9 | N | ALA A | 31 | 31.054 | 55.713 | 44.336 | 1.00 | 82.18 |
| ATOM | 10 | CA | ALA A | 31 | 30.785 | 56.279 | 43.017 | 1.00 | 80.47 |
| ATOM | 11 | CB | ALA A | 31 | 29.325 | 56.713 | 42.925 | 1.00 | 80.79 |
| ATOM | 12 | C | ALA A | 31 | 31.701 | 57.461 | 42.704 | 1.00 | 79.07 |
| ATOM | 13 | O | ALA A | 31 | 32.146 | 57.628 | 41.567 | 1.00 | 78.92 |
| ATOM | 14 | N | THR A | 32 | 31.976 | 58.280 | 43.716 | 1.00 | 77.24 |
| ATOM | 15 | CA | THR A | 32 | 32.841 | 59.446 | 43.550 | 1.00 | 74.71 |
| ATOM | 16 | CB | THR A | 32 | 33.148 | 60.116 | 44.908 | 1.00 | 75.25 |
| ATOM | 17 | OG1 | THR A | 32 | 31.953 | 60.706 | 45.435 | 1.00 | 74.93 |
| ATOM | 18 | CG2 | THR A | 32 | 34.216 | 61.190 | 44.743 | 1.00 | 75.54 |
| ATOM | 19 | C | THR A | 32 | 34.163 | 59.066 | 42.892 | 1.00 | 71.95 |
| ATOM | 20 | O | THR A | 32 | 34.569 | 59.666 | 41.896 | 1.00 | 72.33 |
| ATOM | 21 | N | GLY A | 33 | 34.831 | 58.065 | 43.457 | 1.00 | 68.40 |
| ATOM | 22 | CA | GLY A | 33 | 36.100 | 57.626 | 42.908 | 1.00 | 63.03 |
| ATOM | 23 | C | GLY A | 33 | 37.268 | 58.373 | 43.508 | 1.00 | 58.58 |
| ATOM | 24 | O | GLY A | 33 | 37.724 | 59.370 | 42.951 | 1.00 | 59.69 |
| ATOM | 25 | N | ASP A | 34 | 37.758 | 57.889 | 44.643 | 1.00 | 53.42 |
| ATOM | 26 | CA | ASP A | 34 | 38.876 | 58.532 | 45.315 | 1.00 | 47.16 |
| ATOM | 27 | CB | ASP A | 34 | 38.365 | 59.272 | 46.551 | 1.00 | 46.88 |
| ATOM | 28 | CG | ASP A | 34 | 39.476 | 59.876 | 47.365 | 1.00 | 45.83 |
| ATOM | 29 | OD1 | ASP A | 34 | 40.058 | 59.148 | 48.193 | 1.00 | 46.55 |
| ATOM | 30 | OD2 | ASP A | 34 | 39.772 | 61.075 | 47.172 | 1.00 | 46.46 |
| ATOM | 31 | C | ASP A | 34 | 39.979 | 57.542 | 45.687 | 1.00 | 44.21 |
| ATOM | 32 | O | ASP A | 34 | 39.731 | 56.508 | 46.310 | 1.00 | 40.97 |
| ATOM | 33 | N | GLU A | 35 | 41.202 | 57.878 | 45.290 | 1.00 | 41.79 |
| ATOM | 34 | CA | GLU A | 35 | 42.369 | 57.041 | 45.536 | 1.00 | 39.52 |
| ATOM | 35 | CB | GLU A | 35 | 43.618 | 57.733 | 44.988 | 1.00 | 39.60 |
| ATOM | 36 | CG | GLU A | 35 | 43.639 | 57.855 | 43.471 | 1.00 | 41.54 |
| ATOM | 37 | CD | GLU A | 35 | 44.721 | 58.798 | 42.973 | 1.00 | 43.04 |
| ATOM | 38 | OE1 | GLU A | 35 | 45.780 | 58.884 | 43.631 | 1.00 | 44.35 |
| ATOM | 39 | OE2 | GLU A | 35 | 44.519 | 59.441 | 41.919 | 1.00 | 42.18 |
| ATOM | 40 | C | GLU A | 35 | 42.587 | 56.669 | 46.998 | 1.00 | 37.40 |
| ATOM | 41 | O | GLU A | 35 | 42.891 | 55.518 | 47.308 | 1.00 | 36.91 |
| ATOM | 42 | N | ARG A | 36 | 42.428 | 57.634 | 47.896 | 1.00 | 36.05 |
| ATOM | 43 | CA | ARG A | 36 | 42.636 | 57.377 | 49.315 | 1.00 | 34.31 |
| ATOM | 44 | CB | ARG A | 36 | 42.756 | 58.699 | 50.077 | 1.00 | 38.49 |
| ATOM | 45 | CG | ARG A | 36 | 44.042 | 58.824 | 50.893 | 1.00 | 43.28 |
| ATOM | 46 | CD | ARG A | 36 | 44.289 | 60.252 | 51.356 | 1.00 | 47.33 |
| ATOM | 47 | NE | ARG A | 36 | 44.557 | 61.139 | 50.225 | 1.00 | 52.51 |
| ATOM | 48 | CZ | ARG A | 36 | 44.701 | 62.459 | 50.316 | 1.00 | 54.87 |
| ATOM | 49 | NH1 | ARG A | 36 | 44.603 | 63.067 | 51.492 | 1.00 | 56.47 |
| ATOM | 50 | NH2 | ARG A | 36 | 44.948 | 63.173 | 49.225 | 1.00 | 55.27 |
| ATOM | 51 | C | ARG A | 36 | 41.534 | 56.517 | 49.920 | 1.00 | 31.92 |
| ATOM | 52 | O | ARG A | 36 | 41.799 | 55.667 | 50.771 | 1.00 | 31.50 |
| ATOM | 53 | N | PHE A | 37 | 40.301 | 56.721 | 49.472 | 1.00 | 29.13 |
| ATOM | 54 | CA | PHE A | 37 | 39.185 | 55.945 | 49.996 | 1.00 | 27.89 |
| ATOM | 55 | CB | PHE A | 37 | 37.853 | 56.469 | 49.451 | 1.00 | 28.59 |
| ATOM | 56 | CG | PHE A | 37 | 36.673 | 55.643 | 49.867 | 1.00 | 30.69 |
| ATOM | 57 | CD1 | PHE A | 37 | 36.289 | 55.582 | 51.197 | 1.00 | 32.45 |
| ATOM | 58 | CD2 | PHE A | 37 | 35.977 | 54.885 | 48.938 | 1.00 | 31.58 |
| ATOM | 59 | CE1 | PHE A | 37 | 35.234 | 54.778 | 51.594 | 1.00 | 32.16 |
| ATOM | 60 | CE2 | PHE A | 37 | 34.921 | 54.078 | 49.329 | 1.00 | 32.49 |
| ATOM | 61 | CZ | PHE A | 37 | 34.551 | 54.025 | 50.659 | 1.00 | 31.20 |
| ATOM | 62 | C | PHE A | 37 | 39.314 | 54.463 | 49.660 | 1.00 | 26.36 |
| ATOM | 63 | O | PHE A | 37 | 39.115 | 53.603 | 50.516 | 1.00 | 25.18 |
| ATOM | 64 | N | TYR A | 38 | 39.638 | 54.164 | 48.408 | 1.00 | 25.54 |
| ATOM | 65 | CA | TYR A | 38 | 39.778 | 52.777 | 47.992 | 1.00 | 25.07 |
| ATOM | 66 | CB | TYR A | 38 | 39.877 | 52.682 | 46.471 | 1.00 | 24.76 |
| ATOM | 67 | CG | TYR A | 38 | 38.533 | 52.662 | 45.790 | 1.00 | 23.78 |
| ATOM | 68 | CD1 | TYR A | 38 | 37.778 | 53.820 | 45.660 | 1.00 | 22.64 |
| ATOM | 69 | CE1 | TYR A | 38 | 36.536 | 53.792 | 45.061 | 1.00 | 23.66 |
| ATOM | 70 | CD2 | TYR A | 38 | 38.007 | 51.473 | 45.301 | 1.00 | 20.64 |
| ATOM | 71 | CE2 | TYR A | 38 | 36.771 | 51.433 | 44.706 | 1.00 | 21.87 |
| ATOM | 72 | CZ | TYR A | 38 | 36.039 | 52.591 | 44.588 | 1.00 | 23.46 |
| ATOM | 73 | OH | TYR A | 38 | 34.804 | 52.542 | 44.000 | 1.00 | 25.38 |
| ATOM | 74 | C | TYR A | 38 | 40.982 | 52.105 | 48.622 | 1.00 | 25.60 |
| ATOM | 75 | O | TYR A | 38 | 40.892 | 50.976 | 49.105 | 1.00 | 23.56 |
| ATOM | 76 | N | ALA A | 39 | 42.106 | 52.814 | 48.617 | 1.00 | 27.30 |
| ATOM | 77 | CA | ALA A | 39 | 43.350 | 52.299 | 49.172 | 1.00 | 29.38 |
| ATOM | 78 | CB | ALA A | 39 | 44.489 | 53.265 | 48.860 | 1.00 | 29.11 |
| ATOM | 79 | C | ALA A | 39 | 43.288 | 52.045 | 50.673 | 1.00 | 31.61 |
| ATOM | 80 | O | ALA A | 39 | 43.717 | 50.992 | 51.153 | 1.00 | 31.66 |

TABLE 31-continued

| | | | | | | | | | |
|---|---|---|---|---|---|---|---|---|---|
| ATOM | 81 | N | GLU | A | 40 | 42.745 | 53.006 | 51.414 | 1.00 34.51 |
| ATOM | 82 | CA | GLU | A | 40 | 42.670 | 52.889 | 52.867 | 1.00 36.59 |
| ATOM | 83 | CB | GLU | A | 40 | 42.856 | 54.268 | 53.511 | 1.00 37.79 |
| ATOM | 84 | CG | GLU | A | 40 | 44.205 | 54.910 | 53.224 | 1.00 40.73 |
| ATOM | 85 | CD | GLU | A | 40 | 44.332 | 56.299 | 53.821 | 1.00 43.21 |
| ATOM | 86 | OE1 | GLU | A | 40 | 44.189 | 56.439 | 55.057 | 1.00 44.07 |
| ATOM | 87 | OE2 | GLU | A | 40 | 44.579 | 57.252 | 53.055 | 1.00 42.96 |
| ATOM | 88 | C | GLU | A | 40 | 41.415 | 52.246 | 53.443 | 1.00 36.74 |
| ATOM | 89 | O | GLU | A | 40 | 41.452 | 51.743 | 54.567 | 1.00 37.63 |
| ATOM | 90 | N | HIS | A | 41 | 40.310 | 52.242 | 52.700 | 1.00 35.29 |
| ATOM | 91 | CA | HIS | A | 41 | 39.088 | 51.664 | 53.253 | 1.00 33.66 |
| ATOM | 92 | CB | HIS | A | 41 | 38.084 | 52.777 | 53.566 | 1.00 34.87 |
| ATOM | 93 | CG | HIS | A | 41 | 38.580 | 53.754 | 54.581 | 1.00 36.99 |
| ATOM | 94 | CD2 | HIS | A | 41 | 38.568 | 53.714 | 55.934 | 1.00 37.45 |
| ATOM | 95 | ND1 | HIS | A | 41 | 39.253 | 54.907 | 54.237 | 1.00 38.03 |
| ATOM | 96 | CE1 | HIS | A | 41 | 39.636 | 55.534 | 55.334 | 1.00 38.68 |
| ATOM | 97 | NE2 | HIS | A | 41 | 39.234 | 54.831 | 56.378 | 1.00 39.29 |
| ATOM | 98 | C | HIS | A | 41 | 38.372 | 50.557 | 52.497 | 1.00 31.54 |
| ATOM | 99 | O | HIS | A | 41 | 38.222 | 49.450 | 53.016 | 1.00 31.30 |
| ATOM | 100 | N | LEU | A | 42 | 37.917 | 50.843 | 51.285 | 1.00 29.85 |
| ATOM | 101 | CA | LEU | A | 42 | 37.186 | 49.839 | 50.533 | 1.00 28.77 |
| ATOM | 102 | CB | LEU | A | 42 | 36.677 | 50.426 | 49.208 | 1.00 28.98 |
| ATOM | 103 | CG | LEU | A | 42 | 35.637 | 49.562 | 48.477 | 1.00 29.95 |
| ATOM | 104 | CD1 | LEU | A | 42 | 34.785 | 50.431 | 47.569 | 1.00 29.75 |
| ATOM | 105 | CD2 | LEU | A | 42 | 36.336 | 48.459 | 47.687 | 1.00 29.98 |
| ATOM | 106 | C | LEU | A | 42 | 37.970 | 48.552 | 50.278 | 1.00 27.67 |
| ATOM | 107 | O | LEU | A | 42 | 37.522 | 47.470 | 50.662 | 1.00 28.28 |
| ATOM | 108 | N | MET | A | 43 | 39.133 | 48.655 | 49.643 | 1.00 25.24 |
| ATOM | 109 | CA | MET | A | 43 | 39.919 | 47.457 | 49.347 | 1.00 24.82 |
| ATOM | 110 | CB | MET | A | 43 | 41.166 | 47.820 | 48.535 | 1.00 22.03 |
| ATOM | 111 | CG | MET | A | 43 | 40.856 | 48.385 | 47.150 | 1.00 20.76 |
| ATOM | 112 | SD | MET | A | 43 | 39.792 | 47.312 | 46.142 | 1.00 22.83 |
| ATOM | 113 | CE | MET | A | 43 | 40.970 | 46.112 | 45.560 | 1.00 16.61 |
| ATOM | 114 | C | MET | A | 43 | 40.311 | 46.660 | 50.593 | 1.00 24.94 |
| ATOM | 115 | O | MET | A | 43 | 40.160 | 45.441 | 50.627 | 1.00 24.63 |
| ATOM | 116 | N | PRO | A | 44 | 40.822 | 47.335 | 51.632 | 1.00 26.27 |
| ATOM | 117 | CD | PRO | A | 44 | 41.271 | 48.738 | 51.698 | 1.00 25.74 |
| ATOM | 118 | CA | PRO | A | 44 | 41.204 | 46.603 | 52.844 | 1.00 27.11 |
| ATOM | 119 | CB | PRO | A | 44 | 41.767 | 47.700 | 53.742 | 1.00 27.91 |
| ATOM | 120 | CG | PRO | A | 44 | 42.352 | 48.671 | 52.747 | 1.00 27.46 |
| ATOM | 121 | C | PRO | A | 44 | 40.016 | 45.877 | 53.483 | 1.00 28.57 |
| ATOM | 122 | O | PRO | A | 44 | 40.156 | 44.762 | 53.984 | 1.00 29.09 |
| ATOM | 123 | N | THR | A | 45 | 38.848 | 46.510 | 53.463 | 1.00 29.17 |
| ATOM | 124 | CA | THR | A | 45 | 37.651 | 45.903 | 54.038 | 1.00 30.69 |
| ATOM | 125 | CB | THR | A | 45 | 36.456 | 46.884 | 54.021 | 1.00 31.67 |
| ATOM | 126 | OG1 | THR | A | 45 | 36.729 | 47.984 | 54.897 | 1.00 32.25 |
| ATOM | 127 | CG2 | THR | A | 45 | 35.180 | 46.182 | 54.469 | 1.00 29.83 |
| ATOM | 128 | C | THR | A | 45 | 37.270 | 44.660 | 53.244 | 1.00 30.58 |
| ATOM | 129 | O | THR | A | 45 | 36.945 | 43.617 | 53.808 | 1.00 31.05 |
| ATOM | 130 | N | LEU | A | 46 | 37.316 | 44.782 | 51.925 | 1.00 30.78 |
| ATOM | 131 | CA | LEU | A | 46 | 36.982 | 43.677 | 51.041 | 1.00 31.05 |
| ATOM | 132 | CB | LEU | A | 46 | 37.128 | 44.127 | 49.587 | 1.00 30.41 |
| ATOM | 133 | CG | LEU | A | 46 | 36.837 | 43.103 | 48.493 | 1.00 32.94 |
| ATOM | 134 | CD1 | LEU | A | 46 | 35.421 | 42.563 | 48.647 | 1.00 33.88 |
| ATOM | 135 | CD2 | LEU | A | 46 | 37.010 | 43.761 | 47.133 | 1.00 33.97 |
| ATOM | 136 | C | LEU | A | 46 | 37.878 | 42.466 | 51.305 | 1.00 31.41 |
| ATOM | 137 | O | LEU | A | 46 | 37.402 | 41.332 | 51.363 | 1.00 31.43 |
| ATOM | 138 | N | GLN | A | 47 | 39.175 | 42.711 | 51.472 | 1.00 31.41 |
| ATOM | 139 | CA | GLN | A | 47 | 40.133 | 41.635 | 51.717 | 1.00 33.75 |
| ATOM | 140 | CB | GLN | A | 47 | 41.565 | 42.151 | 51.542 | 1.00 34.91 |
| ATOM | 141 | CG | GLN | A | 47 | 41.812 | 42.791 | 50.186 | 1.00 38.32 |
| ATOM | 142 | CD | GLN | A | 47 | 41.505 | 41.859 | 49.019 | 1.00 39.37 |
| ATOM | 143 | OE1 | GLN | A | 47 | 41.452 | 42.296 | 47.870 | 1.00 41.29 |
| ATOM | 144 | NE2 | GLN | A | 47 | 41.311 | 40.573 | 49.307 | 1.00 37.71 |
| ATOM | 145 | C | GLN | A | 47 | 39.981 | 40.999 | 53.094 | 1.00 33.50 |
| ATOM | 146 | O | GLN | A | 47 | 40.391 | 39.861 | 53.306 | 1.00 32.66 |
| ATOM | 147 | N | GLY | A | 48 | 39.393 | 41.739 | 54.027 | 1.00 34.33 |
| ATOM | 148 | CA | GLY | A | 48 | 39.193 | 41.209 | 55.361 | 1.00 34.12 |
| ATOM | 149 | C | GLY | A | 48 | 37.925 | 40.379 | 55.422 | 1.00 34.95 |
| ATOM | 150 | O | GLY | A | 48 | 37.744 | 39.576 | 56.336 | 1.00 36.30 |
| ATOM | 151 | N | LEU | A | 49 | 37.049 | 40.562 | 54.438 | 1.00 33.88 |
| ATOM | 152 | CA | LEU | A | 49 | 35.785 | 39.829 | 54.399 | 1.00 33.94 |
| ATOM | 153 | CB | LEU | A | 49 | 34.644 | 40.762 | 53.979 | 1.00 34.56 |
| ATOM | 154 | CG | LEU | A | 49 | 34.289 | 41.903 | 54.934 | 1.00 35.63 |
| ATOM | 155 | CD1 | LEU | A | 49 | 33.179 | 42.746 | 54.335 | 1.00 33.76 |
| ATOM | 156 | CD2 | LEU | A | 49 | 33.862 | 41.324 | 56.277 | 1.00 35.21 |
| ATOM | 157 | C | LEU | A | 49 | 35.794 | 38.627 | 53.469 | 1.00 32.93 |
| ATOM | 158 | O | LEU | A | 49 | 35.129 | 37.629 | 53.734 | 1.00 34.79 |
| ATOM | 159 | N | LEU | A | 50 | 36.542 | 38.719 | 52.377 | 1.00 31.80 |

TABLE 31-continued

| | | | | | | | | | |
|---|---|---|---|---|---|---|---|---|---|
| ATOM | 160 | CA  | LEU A | 50 | 36.590 | 37.633 | 51.405 | 1.00 | 30.50 |
| ATOM | 161 | CB  | LEU A | 50 | 35.997 | 38.106 | 50.074 | 1.00 | 31.09 |
| ATOM | 162 | CG  | LEU A | 50 | 34.525 | 38.517 | 50.048 | 1.00 | 32.47 |
| ATOM | 163 | CD1 | LEU A | 50 | 34.219 | 39.247 | 48.745 | 1.00 | 32.88 |
| ATOM | 164 | CD2 | LEU A | 50 | 33.651 | 37.283 | 50.193 | 1.00 | 30.73 |
| ATOM | 165 | C   | LEU A | 50 | 37.991 | 37.107 | 51.146 | 1.00 | 29.49 |
| ATOM | 166 | O   | LEU A | 50 | 38.979 | 37.818 | 51.326 | 1.00 | 29.57 |
| ATOM | 167 | N   | ASP A | 51 | 38.068 | 35.852 | 50.717 | 1.00 | 28.16 |
| ATOM | 168 | CA  | ASP A | 51 | 39.346 | 35.250 | 50.384 | 1.00 | 27.52 |
| ATOM | 169 | CB  | ASP A | 51 | 39.212 | 33.727 | 50.313 | 1.00 | 29.07 |
| ATOM | 170 | CG  | ASP A | 51 | 38.180 | 33.279 | 49.300 | 1.00 | 33.09 |
| ATOM | 171 | OD1 | ASP A | 51 | 36.984 | 33.589 | 49.495 | 1.00 | 35.70 |
| ATOM | 172 | OD2 | ASP A | 51 | 38.565 | 32.621 | 48.308 | 1.00 | 33.73 |
| ATOM | 173 | C   | ASP A | 51 | 39.723 | 35.833 | 49.015 | 1.00 | 26.45 |
| ATOM | 174 | O   | ASP A | 51 | 38.863 | 36.344 | 48.292 | 1.00 | 25.84 |
| ATOM | 175 | N   | PRO A | 52 | 41.009 | 35.764 | 48.643 | 1.00 | 24.56 |
| ATOM | 176 | CD  | PRO A | 52 | 42.083 | 35.090 | 49.390 | 1.00 | 22.91 |
| ATOM | 177 | CA  | PRO A | 52 | 41.519 | 36.286 | 47.371 | 1.00 | 23.09 |
| ATOM | 178 | CB  | PRO A | 52 | 42.928 | 35.707 | 47.308 | 1.00 | 23.93 |
| ATOM | 179 | CG  | PRO A | 52 | 43.319 | 35.645 | 48.731 | 1.00 | 23.45 |
| ATOM | 180 | C   | PRO A | 52 | 40.698 | 35.940 | 46.129 | 1.00 | 21.14 |
| ATOM | 181 | O   | PRO A | 52 | 40.314 | 36.828 | 45.370 | 1.00 | 20.30 |
| ATOM | 182 | N   | GLU A | 53 | 40.424 | 34.658 | 45.918 | 1.00 | 19.62 |
| ATOM | 183 | CA  | GLU A | 53 | 39.664 | 34.265 | 44.739 | 1.00 | 20.75 |
| ATOM | 184 | CB  | GLU A | 53 | 39.626 | 32.741 | 44.597 | 1.00 | 20.17 |
| ATOM | 185 | CG  | GLU A | 53 | 38.933 | 32.290 | 43.320 | 1.00 | 21.25 |
| ATOM | 186 | CD  | GLU A | 53 | 39.243 | 30.855 | 42.944 | 1.00 | 22.83 |
| ATOM | 187 | OE1 | GLU A | 53 | 38.632 | 30.361 | 41.975 | 1.00 | 25.63 |
| ATOM | 188 | OE2 | GLU A | 53 | 40.093 | 30.220 | 43.603 | 1.00 | 23.30 |
| ATOM | 189 | C   | GLU A | 53 | 38.245 | 34.833 | 44.734 | 1.00 | 21.37 |
| ATOM | 190 | O   | GLU A | 53 | 37.789 | 35.355 | 43.712 | 1.00 | 20.91 |
| ATOM | 191 | N   | SER A | 54 | 37.552 | 34.745 | 45.867 | 1.00 | 20.10 |
| ATOM | 192 | CA  | SER A | 54 | 36.196 | 35.274 | 45.951 | 1.00 | 20.81 |
| ATOM | 193 | CB  | SER A | 54 | 35.588 | 34.995 | 47.327 | 1.00 | 21.56 |
| ATOM | 194 | OG  | SER A | 54 | 35.420 | 33.606 | 47.532 | 1.00 | 23.22 |
| ATOM | 195 | C   | SER A | 54 | 36.208 | 36.776 | 45.698 | 1.00 | 20.03 |
| ATOM | 196 | O   | SER A | 54 | 35.305 | 37.314 | 45.055 | 1.00 | 19.91 |
| ATOM | 197 | N   | ALA A | 55 | 37.237 | 37.448 | 46.206 | 1.00 | 18.25 |
| ATOM | 198 | CA  | ALA A | 55 | 37.363 | 38.887 | 46.027 | 1.00 | 17.25 |
| ATOM | 199 | CB  | ALA A | 55 | 38.584 | 39.404 | 46.781 | 1.00 | 18.23 |
| ATOM | 200 | C   | ALA A | 55 | 37.491 | 39.191 | 44.540 | 1.00 | 17.58 |
| ATOM | 201 | O   | ALA A | 55 | 36.888 | 40.136 | 44.038 | 1.00 | 18.04 |
| ATOM | 202 | N   | HIS A | 56 | 38.279 | 38.382 | 43.837 | 1.00 | 17.22 |
| ATOM | 203 | CA  | HIS A | 56 | 38.466 | 38.563 | 42.404 | 1.00 | 18.71 |
| ATOM | 204 | CB  | HIS A | 56 | 39.509 | 37.575 | 41.875 | 1.00 | 17.37 |
| ATOM | 205 | CG  | HIS A | 56 | 39.537 | 37.479 | 40.383 | 1.00 | 16.55 |
| ATOM | 206 | CD2 | HIS A | 56 | 39.262 | 36.449 | 39.551 | 1.00 | 17.62 |
| ATOM | 207 | ND1 | HIS A | 56 | 39.827 | 38.558 | 39.575 | 1.00 | 20.55 |
| ATOM | 208 | CE1 | HIS A | 56 | 39.729 | 38.196 | 38.309 | 1.00 | 17.33 |
| ATOM | 209 | NE2 | HIS A | 56 | 39.387 | 36.921 | 38.267 | 1.00 | 19.33 |
| ATOM | 210 | C   | HIS A | 56 | 37.146 | 38.368 | 41.646 | 1.00 | 20.76 |
| ATOM | 211 | O   | HIS A | 56 | 36.775 | 39.196 | 40.806 | 1.00 | 20.87 |
| ATOM | 212 | N   | ARG A | 57 | 36.444 | 37.275 | 41.943 | 1.00 | 21.25 |
| ATOM | 213 | CA  | ARG A | 57 | 35.172 | 36.988 | 41.287 | 1.00 | 23.72 |
| ATOM | 214 | CB  | ARG A | 57 | 34.548 | 35.704 | 41.846 | 1.00 | 27.11 |
| ATOM | 215 | CG  | ARG A | 57 | 35.395 | 34.453 | 41.619 | 1.00 | 33.78 |
| ATOM | 216 | CD  | ARG A | 57 | 34.691 | 33.191 | 42.119 | 1.00 | 38.40 |
| ATOM | 217 | NE  | ARG A | 57 | 33.504 | 32.870 | 41.328 | 1.00 | 44.51 |
| ATOM | 218 | CZ  | ARG A | 57 | 33.536 | 32.421 | 40.074 | 1.00 | 47.98 |
| ATOM | 219 | NH1 | ARG A | 57 | 34.699 | 32.231 | 39.460 | 1.00 | 48.55 |
| ATOM | 220 | NH2 | ARG A | 57 | 32.404 | 32.169 | 39.426 | 1.00 | 49.25 |
| ATOM | 221 | C   | ARG A | 57 | 34.198 | 38.148 | 41.458 | 1.00 | 22.08 |
| ATOM | 222 | O   | ARG A | 57 | 33.547 | 38.561 | 40.503 | 1.00 | 22.37 |
| ATOM | 223 | N   | LEU A | 58 | 34.103 | 38.676 | 42.674 | 1.00 | 22.22 |
| ATOM | 224 | CA  | LEU A | 58 | 33.206 | 39.798 | 42.941 | 1.00 | 21.56 |
| ATOM | 225 | CB  | LEU A | 58 | 33.211 | 40.140 | 44.434 | 1.00 | 22.30 |
| ATOM | 226 | CG  | LEU A | 58 | 32.224 | 41.206 | 44.926 | 1.00 | 23.79 |
| ATOM | 227 | CD1 | LEU A | 58 | 30.798 | 40.778 | 44.615 | 1.00 | 21.41 |
| ATOM | 228 | CD2 | LEU A | 58 | 32.400 | 41.405 | 46.430 | 1.00 | 24.56 |
| ATOM | 229 | C   | LEU A | 58 | 33.660 | 41.006 | 42.121 | 1.00 | 21.85 |
| ATOM | 230 | O   | LEU A | 58 | 32.839 | 41.785 | 41.636 | 1.00 | 21.96 |
| ATOM | 231 | N   | ALA A | 59 | 34.973 | 41.150 | 41.964 | 1.00 | 21.62 |
| ATOM | 232 | CA  | ALA A | 59 | 35.548 | 42.251 | 41.191 | 1.00 | 21.13 |
| ATOM | 233 | CB  | ALA A | 59 | 37.063 | 42.195 | 41.256 | 1.00 | 19.47 |
| ATOM | 234 | C   | ALA A | 59 | 35.097 | 42.166 | 39.738 | 1.00 | 20.15 |
| ATOM | 235 | O   | ALA A | 59 | 34.778 | 43.178 | 39.110 | 1.00 | 20.52 |
| ATOM | 236 | N   | VAL A | 60 | 35.090 | 40.952 | 39.202 | 1.00 | 19.14 |
| ATOM | 237 | CA  | VAL A | 60 | 34.674 | 40.742 | 37.826 | 1.00 | 19.94 |
| ATOM | 238 | CB  | VAL A | 60 | 34.888 | 39.266 | 37.395 | 1.00 | 20.28 |

TABLE 31-continued

| | | | | | | | | | |
|---|---|---|---|---|---|---|---|---|---|
| ATOM | 239 | CG1 | VAL A | 60 | 34.306 | 39.029 | 35.995 | 1.00 | 17.45 |
| ATOM | 240 | CG2 | VAL A | 60 | 36.377 | 38.941 | 37.401 | 1.00 | 16.77 |
| ATOM | 241 | C | VAL A | 60 | 33.206 | 41.118 | 37.678 | 1.00 | 21.14 |
| ATOM | 242 | O | VAL A | 60 | 32.827 | 41.770 | 36.709 | 1.00 | 21.64 |
| ATOM | 243 | N | ARG A | 61 | 32.386 | 40.718 | 38.646 | 1.00 | 23.53 |
| ATOM | 244 | CA | ARG A | 61 | 30.958 | 41.024 | 38.614 | 1.00 | 26.90 |
| ATOM | 245 | CB | ARG A | 61 | 30.233 | 40.410 | 39.821 | 1.00 | 28.84 |
| ATOM | 246 | CG | ARG A | 61 | 30.228 | 38.890 | 39.867 | 1.00 | 37.63 |
| ATOM | 247 | CD | ARG A | 61 | 29.007 | 38.376 | 40.646 | 1.00 | 43.68 |
| ATOM | 248 | NE | ARG A | 61 | 28.948 | 36.915 | 40.714 | 1.00 | 48.20 |
| ATOM | 249 | CZ | ARG A | 61 | 29.617 | 36.174 | 41.595 | 1.00 | 50.86 |
| ATOM | 250 | NH1 | ARG A | 61 | 30.401 | 36.753 | 42.500 | 1.00 | 50.24 |
| ATOM | 251 | NH2 | ARG A | 61 | 29.503 | 34.850 | 41.568 | 1.00 | 51.48 |
| ATOM | 252 | C | ARG A | 61 | 30.698 | 42.530 | 38.605 | 1.00 | 26.52 |
| ATOM | 253 | O | ARG A | 61 | 30.004 | 43.043 | 37.727 | 1.00 | 25.59 |
| ATOM | 254 | N | PHE A | 62 | 31.250 | 43.230 | 39.592 | 1.00 | 26.34 |
| ATOM | 255 | CA | PHE A | 62 | 31.061 | 44.670 | 39.697 | 1.00 | 28.44 |
| ATOM | 256 | CB | PHE A | 62 | 31.812 | 45.227 | 40.910 | 1.00 | 29.57 |
| ATOM | 257 | CG | PHE A | 62 | 31.012 | 45.197 | 42.182 | 1.00 | 33.68 |
| ATOM | 258 | CD1 | PHE A | 62 | 30.562 | 43.997 | 42.709 | 1.00 | 34.80 |
| ATOM | 259 | CD2 | PHE A | 62 | 30.699 | 46.373 | 42.844 | 1.00 | 35.83 |
| ATOM | 260 | CE1 | PHE A | 62 | 29.813 | 43.970 | 43.876 | 1.00 | 35.32 |
| ATOM | 261 | CE2 | PHE A | 62 | 29.950 | 46.353 | 44.011 | 1.00 | 38.21 |
| ATOM | 262 | CZ | PHE A | 62 | 29.507 | 45.146 | 44.526 | 1.00 | 36.55 |
| ATOM | 263 | C | PHE A | 62 | 31.523 | 45.388 | 38.445 | 1.00 | 28.73 |
| ATOM | 264 | O | PHE A | 62 | 30.866 | 46.318 | 37.974 | 1.00 | 29.92 |
| ATOM | 265 | N | THR A | 63 | 32.657 | 44.952 | 37.908 | 1.00 | 27.65 |
| ATOM | 266 | CA | THR A | 63 | 33.205 | 45.569 | 36.715 | 1.00 | 26.81 |
| ATOM | 267 | CB | THR A | 63 | 34.612 | 45.017 | 36.408 | 1.00 | 26.29 |
| ATOM | 268 | OG1 | THR A | 63 | 35.493 | 45.331 | 37.494 | 1.00 | 23.98 |
| ATOM | 269 | CG2 | THR A | 63 | 35.154 | 45.626 | 35.129 | 1.00 | 23.92 |
| ATOM | 270 | C | THR A | 63 | 32.296 | 45.342 | 35.513 | 1.00 | 27.15 |
| ATOM | 271 | O | THR A | 63 | 32.031 | 46.268 | 34.750 | 1.00 | 26.07 |
| ATOM | 272 | N | SER A | 64 | 31.812 | 44.116 | 35.350 | 1.00 | 27.56 |
| ATOM | 273 | CA | SER A | 64 | 30.938 | 43.802 | 34.224 | 1.00 | 30.29 |
| ATOM | 274 | CB | SER A | 64 | 30.608 | 42.311 | 34.204 | 1.00 | 29.40 |
| ATOM | 275 | OG | SER A | 64 | 29.850 | 41.959 | 35.345 | 1.00 | 32.57 |
| ATOM | 276 | C | SER A | 64 | 29.646 | 44.606 | 34.312 | 1.00 | 31.20 |
| ATOM | 277 | O | SER A | 64 | 29.007 | 44.880 | 33.297 | 1.00 | 30.61 |
| ATOM | 278 | N | LEU A | 65 | 29.273 | 44.984 | 35.532 | 1.00 | 31.93 |
| ATOM | 279 | CA | LEU A | 65 | 28.057 | 45.756 | 35.766 | 1.00 | 33.43 |
| ATOM | 280 | CB | LEU A | 65 | 27.416 | 45.335 | 37.093 | 1.00 | 32.99 |
| ATOM | 281 | CG | LEU A | 65 | 26.891 | 43.899 | 37.148 | 1.00 | 35.43 |
| ATOM | 282 | CD1 | LEU A | 65 | 26.483 | 43.545 | 38.573 | 1.00 | 33.63 |
| ATOM | 283 | CD2 | LEU A | 65 | 25.712 | 43.756 | 36.189 | 1.00 | 34.95 |
| ATOM | 284 | C | LEU A | 65 | 28.318 | 47.263 | 35.781 | 1.00 | 33.55 |
| ATOM | 285 | O | LEU A | 65 | 27.397 | 48.057 | 35.964 | 1.00 | 34.23 |
| ATOM | 286 | N | GLY A | 66 | 29.573 | 47.654 | 35.599 | 1.00 | 32.60 |
| ATOM | 287 | CA | GLY A | 66 | 29.901 | 49.068 | 35.592 | 1.00 | 33.27 |
| ATOM | 288 | C | GLY A | 66 | 29.833 | 49.755 | 36.948 | 1.00 | 34.31 |
| ATOM | 289 | O | GLY A | 66 | 29.785 | 50.983 | 37.017 | 1.00 | 34.03 |
| ATOM | 290 | N | LEU A | 67 | 29.823 | 48.975 | 38.027 | 1.00 | 33.85 |
| ATOM | 291 | CA | LEU A | 67 | 29.776 | 49.542 | 39.372 | 1.00 | 34.20 |
| ATOM | 292 | CB | LEU A | 67 | 29.338 | 48.476 | 40.383 | 1.00 | 35.31 |
| ATOM | 293 | CG | LEU A | 67 | 27.989 | 47.797 | 40.101 | 1.00 | 37.76 |
| ATOM | 294 | CD1 | LEU A | 67 | 27.648 | 46.833 | 41.231 | 1.00 | 37.88 |
| ATOM | 295 | CD2 | LEU A | 67 | 26.894 | 48.850 | 39.959 | 1.00 | 37.81 |
| ATOM | 296 | C | LEU A | 67 | 31.181 | 50.044 | 39.699 | 1.00 | 33.76 |
| ATOM | 297 | O | LEU A | 67 | 31.889 | 49.467 | 40.527 | 1.00 | 31.48 |
| ATOM | 298 | N | LEU A | 68 | 31.568 | 51.128 | 39.035 | 1.00 | 34.01 |
| ATOM | 299 | CA | LEU A | 68 | 32.894 | 51.713 | 39.189 | 1.00 | 34.57 |
| ATOM | 300 | CB | LEU A | 68 | 33.635 | 51.632 | 37.856 | 1.00 | 33.46 |
| ATOM | 301 | CG | LEU A | 68 | 33.665 | 50.257 | 37.193 | 1.00 | 33.94 |
| ATOM | 302 | CD1 | LEU A | 68 | 34.112 | 50.389 | 35.752 | 1.00 | 35.15 |
| ATOM | 303 | CD2 | LEU A | 68 | 34.596 | 49.347 | 37.966 | 1.00 | 32.93 |
| ATOM | 304 | C | LEU A | 68 | 32.858 | 53.166 | 39.641 | 1.00 | 35.27 |
| ATOM | 305 | O | LEU A | 68 | 31.884 | 53.880 | 39.411 | 1.00 | 36.69 |
| ATOM | 306 | N | PRO A | 69 | 33.937 | 53.622 | 40.291 | 1.00 | 35.09 |
| ATOM | 307 | CD | PRO A | 69 | 35.096 | 52.799 | 40.678 | 1.00 | 35.32 |
| ATOM | 308 | CA | PRO A | 69 | 34.084 | 54.987 | 40.795 | 1.00 | 35.10 |
| ATOM | 309 | CB | PRO A | 69 | 35.296 | 54.876 | 41.711 | 1.00 | 35.36 |
| ATOM | 310 | CG | PRO A | 69 | 36.126 | 53.847 | 41.031 | 1.00 | 35.57 |
| ATOM | 311 | C | PRO A | 69 | 34.298 | 55.987 | 39.664 | 1.00 | 34.95 |
| ATOM | 312 | O | PRO A | 69 | 34.206 | 55.632 | 38.488 | 1.00 | 35.36 |
| ATOM | 313 | N | PHE A | 73 | 39.366 | 61.866 | 34.983 | 1.00 | 57.11 |
| ATOM | 314 | CA | PHE A | 73 | 40.556 | 62.093 | 34.169 | 1.00 | 56.79 |
| ATOM | 315 | CB | PHE A | 73 | 41.700 | 61.180 | 34.627 | 1.00 | 57.43 |
| ATOM | 316 | CG | PHE A | 73 | 42.919 | 61.254 | 33.747 | 1.00 | 58.50 |
| ATOM | 317 | CD1 | PHE A | 73 | 43.795 | 62.325 | 33.837 | 1.00 | 59.04 |

TABLE 31-continued

| | | | | | | | | |
|---|---|---|---|---|---|---|---|---|
| ATOM | 318 | CD2 | PHE A | 73 | 43.162 | 60.276 | 32.793 | 1.00 | 58.27 |
| ATOM | 319 | CE1 | PHE A | 73 | 44.891 | 62.421 | 32.990 | 1.00 | 58.38 |
| ATOM | 320 | CE2 | PHE A | 73 | 44.254 | 60.368 | 31.944 | 1.00 | 58.17 |
| ATOM | 321 | CZ | PHE A | 73 | 45.119 | 61.442 | 32.042 | 1.00 | 57.71 |
| ATOM | 322 | C | PHE A | 73 | 40.302 | 61.851 | 32.681 | 1.00 | 55.94 |
| ATOM | 323 | O | PHE A | 73 | 39.909 | 60.755 | 32.279 | 1.00 | 55.31 |
| ATOM | 324 | N | GLN A | 74 | 40.534 | 62.875 | 31.866 | 1.00 | 54.83 |
| ATOM | 325 | CA | GLN A | 74 | 40.352 | 62.752 | 30.425 | 1.00 | 53.34 |
| ATOM | 326 | CB | GLN A | 74 | 39.707 | 64.013 | 29.848 | 1.00 | 55.61 |
| ATOM | 327 | CG | GLN A | 74 | 38.222 | 64.153 | 30.133 | 1.00 | 57.81 |
| ATOM | 328 | CD | GLN A | 74 | 37.578 | 65.243 | 29.291 | 1.00 | 59.81 |
| ATOM | 329 | OE1 | GLN A | 74 | 37.852 | 66.432 | 29.472 | 1.00 | 60.73 |
| ATOM | 330 | NE2 | GLN A | 74 | 36.725 | 64.840 | 28.353 | 1.00 | 59.42 |
| ATOM | 331 | C | GLN A | 74 | 41.698 | 62.517 | 29.749 | 1.00 | 51.28 |
| ATOM | 332 | O | GLN A | 74 | 42.650 | 63.267 | 29.964 | 1.00 | 50.95 |
| ATOM | 333 | N | ASP A | 75 | 41.774 | 61.471 | 28.935 | 1.00 | 48.79 |
| ATOM | 334 | CA | ASP A | 75 | 43.006 | 61.145 | 28.229 | 1.00 | 46.68 |
| ATOM | 335 | CB | ASP A | 75 | 42.824 | 59.856 | 27.421 | 1.00 | 45.00 |
| ATOM | 336 | CG | ASP A | 75 | 42.570 | 58.642 | 28.299 | 1.00 | 43.45 |
| ATOM | 337 | OD1 | ASP A | 75 | 42.067 | 57.627 | 27.770 | 1.00 | 41.56 |
| ATOM | 338 | OD2 | ASP A | 75 | 42.881 | 58.696 | 29.508 | 1.00 | 41.80 |
| ATOM | 339 | C | ASP A | 75 | 43.378 | 62.286 | 27.288 | 1.00 | 46.07 |
| ATOM | 340 | O | ASP A | 75 | 42.529 | 62.798 | 26.558 | 1.00 | 45.66 |
| ATOM | 341 | N | SER A | 76 | 44.645 | 62.688 | 27.308 | 1.00 | 45.37 |
| ATOM | 342 | CA | SER A | 76 | 45.105 | 63.763 | 26.437 | 1.00 | 44.09 |
| ATOM | 343 | CB | SER A | 76 | 46.045 | 64.706 | 27.193 | 1.00 | 44.35 |
| ATOM | 344 | OG | SER A | 76 | 47.276 | 64.074 | 27.492 | 1.00 | 45.29 |
| ATOM | 345 | C | SER A | 76 | 45.830 | 63.171 | 25.236 | 1.00 | 42.66 |
| ATOM | 346 | O | SER A | 76 | 46.194 | 61.997 | 25.240 | 1.00 | 42.40 |
| ATOM | 347 | N | ASP A | 77 | 46.033 | 63.987 | 24.209 | 1.00 | 42.12 |
| ATOM | 348 | CA | ASP A | 77 | 46.719 | 63.545 | 23.001 | 1.00 | 41.76 |
| ATOM | 349 | CB | ASP A | 77 | 46.909 | 64.727 | 22.047 | 1.00 | 44.71 |
| ATOM | 350 | CG | ASP A | 77 | 45.595 | 65.295 | 21.551 | 1.00 | 47.31 |
| ATOM | 351 | OD1 | ASP A | 77 | 45.623 | 66.334 | 20.859 | 1.00 | 50.25 |
| ATOM | 352 | OD2 | ASP A | 77 | 44.535 | 64.702 | 21.846 | 1.00 | 48.62 |
| ATOM | 353 | C | ASP A | 77 | 48.080 | 62.931 | 23.318 | 1.00 | 40.11 |
| ATOM | 354 | O | ASP A | 77 | 48.532 | 62.019 | 22.627 | 1.00 | 39.81 |
| ATOM | 355 | N | MET A | 78 | 48.728 | 63.440 | 24.361 | 1.00 | 37.97 |
| ATOM | 356 | CA | MET A | 78 | 50.044 | 62.949 | 24.769 | 1.00 | 36.17 |
| ATOM | 357 | CB | MET A | 78 | 50.517 | 63.660 | 26.036 | 1.00 | 37.17 |
| ATOM | 358 | CG | MET A | 78 | 50.848 | 65.124 | 25.881 | 1.00 | 39.57 |
| ATOM | 359 | SD | MET A | 78 | 51.536 | 65.736 | 27.440 | 1.00 | 42.24 |
| ATOM | 360 | CE | MET A | 78 | 53.252 | 65.210 | 27.264 | 1.00 | 41.08 |
| ATOM | 361 | C | MET A | 78 | 50.067 | 61.452 | 25.044 | 1.00 | 32.99 |
| ATOM | 362 | O | MET A | 78 | 51.070 | 60.786 | 24.799 | 1.00 | 31.46 |
| ATOM | 363 | N | LEU A | 79 | 48.965 | 60.927 | 25.567 | 1.00 | 30.29 |
| ATOM | 364 | CA | LEU A | 79 | 48.899 | 59.512 | 25.893 | 1.00 | 29.12 |
| ATOM | 365 | CB | LEU A | 79 | 47.916 | 59.285 | 27.045 | 1.00 | 27.76 |
| ATOM | 366 | CG | LEU A | 79 | 48.297 | 59.972 | 28.363 | 1.00 | 27.32 |
| ATOM | 367 | CD1 | LEU A | 79 | 47.400 | 59.469 | 29.489 | 1.00 | 25.53 |
| ATOM | 368 | CD2 | LEU A | 79 | 49.756 | 59.681 | 28.687 | 1.00 | 23.95 |
| ATOM | 369 | C | LEU A | 79 | 48.545 | 58.604 | 24.721 | 1.00 | 28.57 |
| ATOM | 370 | O | LEU A | 79 | 48.563 | 57.379 | 24.863 | 1.00 | 28.17 |
| ATOM | 371 | N | GLU A | 80 | 48.238 | 59.188 | 23.567 | 1.00 | 26.89 |
| ATOM | 372 | CA | GLU A | 80 | 47.890 | 58.382 | 22.407 | 1.00 | 27.84 |
| ATOM | 373 | CB | GLU A | 80 | 47.230 | 59.221 | 21.309 | 1.00 | 29.86 |
| ATOM | 374 | CG | GLU A | 80 | 46.633 | 58.344 | 20.206 | 1.00 | 36.28 |
| ATOM | 375 | CD | GLU A | 80 | 46.323 | 59.094 | 18.918 | 1.00 | 39.58 |
| ATOM | 376 | OE1 | GLU A | 80 | 47.270 | 59.411 | 18.165 | 1.00 | 40.87 |
| ATOM | 377 | OE2 | GLU A | 80 | 45.129 | 59.362 | 18.659 | 1.00 | 41.08 |
| ATOM | 378 | C | GLU A | 80 | 49.118 | 57.705 | 21.822 | 1.00 | 27.25 |
| ATOM | 379 | O | GLU A | 80 | 50.192 | 58.298 | 21.748 | 1.00 | 26.76 |
| ATOM | 380 | N | VAL A | 81 | 48.949 | 56.461 | 21.395 | 1.00 | 26.60 |
| ATOM | 381 | CA | VAL A | 81 | 50.040 | 55.701 | 20.810 | 1.00 | 26.88 |
| ATOM | 382 | CB | VAL A | 81 | 50.640 | 54.702 | 21.830 | 1.00 | 27.64 |
| ATOM | 383 | CG1 | VAL A | 81 | 51.781 | 53.927 | 21.190 | 1.00 | 27.14 |
| ATOM | 384 | CG2 | VAL A | 81 | 51.114 | 55.435 | 23.066 | 1.00 | 27.80 |
| ATOM | 385 | C | VAL A | 81 | 49.515 | 54.900 | 19.634 | 1.00 | 27.49 |
| ATOM | 386 | O | VAL A | 81 | 48.376 | 54.442 | 19.651 | 1.00 | 29.86 |
| ATOM | 387 | N | ARG A | 82 | 50.337 | 54.741 | 18.605 | 1.00 | 28.74 |
| ATOM | 388 | CA | ARG A | 82 | 49.936 | 53.947 | 17.453 | 1.00 | 30.33 |
| ATOM | 389 | CB | ARG A | 82 | 49.821 | 54.804 | 16.186 | 1.00 | 32.47 |
| ATOM | 390 | CG | ARG A | 82 | 49.899 | 53.969 | 14.905 | 1.00 | 38.74 |
| ATOM | 391 | CD | ARG A | 82 | 49.248 | 54.638 | 13.697 | 1.00 | 44.42 |
| ATOM | 392 | NE | ARG A | 82 | 47.836 | 54.269 | 13.548 | 1.00 | 48.91 |
| ATOM | 393 | CZ | ARG A | 82 | 47.397 | 53.029 | 13.330 | 1.00 | 48.71 |
| ATOM | 394 | NH1 | ARG A | 82 | 48.252 | 52.018 | 13.233 | 1.00 | 47.85 |
| ATOM | 395 | NH2 | ARG A | 82 | 46.096 | 52.799 | 13.205 | 1.00 | 50.04 |
| ATOM | 396 | C | ARG A | 82 | 50.939 | 52.822 | 17.228 | 1.00 | 29.93 |

TABLE 31-continued

| | | | | | | | | | |
|---|---|---|---|---|---|---|---|---|---|
| ATOM | 397 | O | ARG A | 82 | 52.115 | 53.068 | 16.972 | 1.00 | 29.16 |
| ATOM | 398 | N | VAL A | 83 | 50.461 | 51.587 | 17.347 | 1.00 | 29.81 |
| ATOM | 399 | CA | VAL A | 83 | 51.281 | 50.394 | 17.157 | 1.00 | 31.73 |
| ATOM | 400 | CB | VAL A | 83 | 52.080 | 50.023 | 18.432 | 1.00 | 32.09 |
| ATOM | 401 | CG1 | VAL A | 83 | 53.222 | 50.992 | 18.638 | 1.00 | 34.42 |
| ATOM | 402 | CG2 | VAL A | 83 | 51.154 | 50.021 | 19.640 | 1.00 | 30.34 |
| ATOM | 403 | C | VAL A | 83 | 50.370 | 49.218 | 16.838 | 1.00 | 32.50 |
| ATOM | 404 | O | VAL A | 83 | 49.155 | 49.307 | 17.005 | 1.00 | 31.46 |
| ATOM | 405 | N | LEU A | 84 | 50.968 | 48.119 | 16.384 | 1.00 | 33.48 |
| ATOM | 406 | CA | LEU A | 84 | 50.223 | 46.906 | 16.062 | 1.00 | 33.72 |
| ATOM | 407 | CB | LEU A | 84 | 49.674 | 46.274 | 17.350 | 1.00 | 32.58 |
| ATOM | 408 | CG | LEU A | 84 | 50.683 | 45.955 | 18.458 | 1.00 | 32.62 |
| ATOM | 409 | CD1 | LEU A | 84 | 49.948 | 45.447 | 19.680 | 1.00 | 31.27 |
| ATOM | 410 | CD2 | LEU A | 84 | 51.692 | 44.926 | 17.974 | 1.00 | 30.95 |
| ATOM | 411 | C | LEU A | 84 | 49.072 | 47.158 | 15.089 | 1.00 | 33.95 |
| ATOM | 412 | O | LEU A | 84 | 48.077 | 46.429 | 15.097 | 1.00 | 34.81 |
| ATOM | 413 | N | GLY A | 85 | 49.210 | 48.191 | 14.259 | 1.00 | 34.10 |
| ATOM | 414 | CA | GLY A | 85 | 48.177 | 48.517 | 13.286 | 1.00 | 33.41 |
| ATOM | 415 | C | GLY A | 85 | 46.908 | 49.089 | 13.895 | 1.00 | 34.00 |
| ATOM | 416 | O | GLY A | 85 | 45.814 | 48.929 | 13.346 | 1.00 | 32.49 |
| ATOM | 417 | N | HIS A | 86 | 47.056 | 49.765 | 15.032 | 1.00 | 33.02 |
| ATOM | 418 | CA | HIS A | 86 | 45.922 | 50.356 | 15.729 | 1.00 | 32.41 |
| ATOM | 419 | CB | HIS A | 86 | 45.284 | 49.323 | 16.669 | 1.00 | 35.18 |
| ATOM | 420 | CG | HIS A | 86 | 44.707 | 48.131 | 15.968 | 1.00 | 37.48 |
| ATOM | 421 | CD2 | HIS A | 86 | 45.181 | 46.872 | 15.816 | 1.00 | 38.23 |
| ATOM | 422 | ND1 | HIS A | 86 | 43.504 | 48.171 | 15.298 | 1.00 | 38.86 |
| ATOM | 423 | CE1 | HIS A | 86 | 43.260 | 46.988 | 14.763 | 1.00 | 38.09 |
| ATOM | 424 | NE2 | HIS A | 86 | 44.263 | 46.182 | 15.062 | 1.00 | 39.89 |
| ATOM | 425 | C | HIS A | 86 | 46.331 | 51.577 | 16.552 | 1.00 | 31.23 |
| ATOM | 426 | O | HIS A | 86 | 47.505 | 51.788 | 16.854 | 1.00 | 29.77 |
| ATOM | 427 | N | LYS A | 87 | 45.343 | 52.383 | 16.912 | 1.00 | 30.25 |
| ATOM | 428 | CA | LYS A | 87 | 45.586 | 53.554 | 17.734 | 1.00 | 29.97 |
| ATOM | 429 | CB | LYS A | 87 | 44.787 | 54.748 | 17.211 | 1.00 | 32.13 |
| ATOM | 430 | CG | LYS A | 87 | 44.628 | 55.873 | 18.224 | 1.00 | 36.96 |
| ATOM | 431 | CD | LYS A | 87 | 43.748 | 56.993 | 17.684 | 1.00 | 41.35 |
| ATOM | 432 | CE | LYS A | 87 | 42.362 | 56.487 | 17.312 | 1.00 | 43.33 |
| ATOM | 433 | NZ | LYS A | 87 | 41.497 | 57.581 | 16.779 | 1.00 | 46.62 |
| ATOM | 434 | C | LYS A | 87 | 45.135 | 53.214 | 19.154 | 1.00 | 28.11 |
| ATOM | 435 | O | LYS A | 87 | 44.115 | 52.545 | 19.342 | 1.00 | 27.33 |
| ATOM | 436 | N | PHE A | 88 | 45.909 | 53.650 | 20.144 | 1.00 | 23.77 |
| ATOM | 437 | CA | PHE A | 88 | 45.573 | 53.423 | 21.544 | 1.00 | 22.55 |
| ATOM | 438 | CB | PHE A | 88 | 46.655 | 52.587 | 22.239 | 1.00 | 20.08 |
| ATOM | 439 | CG | PHE A | 88 | 46.807 | 51.192 | 21.687 | 1.00 | 19.53 |
| ATOM | 440 | CD1 | PHE A | 88 | 47.346 | 50.981 | 20.426 | 1.00 | 18.13 |
| ATOM | 441 | CD2 | PHE A | 88 | 46.427 | 50.090 | 22.442 | 1.00 | 16.88 |
| ATOM | 442 | CE1 | PHE A | 88 | 47.506 | 49.698 | 19.929 | 1.00 | 17.99 |
| ATOM | 443 | CE2 | PHE A | 88 | 46.583 | 48.806 | 21.953 | 1.00 | 16.38 |
| ATOM | 444 | CZ | PHE A | 88 | 47.122 | 48.608 | 20.696 | 1.00 | 17.99 |
| ATOM | 445 | C | PHE A | 88 | 45.497 | 54.804 | 22.185 | 1.00 | 22.18 |
| ATOM | 446 | O | PHE A | 88 | 46.494 | 55.520 | 22.225 | 1.00 | 21.05 |
| ATOM | 447 | N | ARG A | 89 | 44.324 | 55.184 | 22.683 | 1.00 | 23.63 |
| ATOM | 448 | CA | ARG A | 89 | 44.175 | 56.506 | 23.284 | 1.00 | 25.47 |
| ATOM | 449 | CB | ARG A | 89 | 42.700 | 56.800 | 23.577 | 1.00 | 28.55 |
| ATOM | 450 | CG | ARG A | 89 | 42.038 | 55.912 | 24.596 | 1.00 | 35.93 |
| ATOM | 451 | CD | ARG A | 89 | 40.528 | 56.029 | 24.444 | 1.00 | 41.44 |
| ATOM | 452 | NE | ARG A | 89 | 40.131 | 57.382 | 24.066 | 1.00 | 44.82 |
| ATOM | 453 | CZ | ARG A | 89 | 38.899 | 57.725 | 23.701 | 1.00 | 47.58 |
| ATOM | 454 | NH1 | ARG A | 89 | 37.934 | 56.813 | 23.666 | 1.00 | 46.73 |
| ATOM | 455 | NH2 | ARG A | 89 | 38.635 | 58.981 | 23.358 | 1.00 | 48.84 |
| ATOM | 456 | C | ARG A | 89 | 45.049 | 56.721 | 24.522 | 1.00 | 23.67 |
| ATOM | 457 | O | ARG A | 89 | 45.374 | 57.854 | 24.859 | 1.00 | 22.06 |
| ATOM | 458 | N | ASN A | 90 | 45.413 | 55.637 | 25.204 | 1.00 | 21.74 |
| ATOM | 459 | CA | ASN A | 90 | 46.322 | 55.709 | 26.348 | 1.00 | 20.23 |
| ATOM | 460 | CB | ASN A | 90 | 45.590 | 56.038 | 27.671 | 1.00 | 20.14 |
| ATOM | 461 | CG | ASN A | 90 | 44.945 | 54.836 | 28.327 | 1.00 | 20.24 |
| ATOM | 462 | OD1 | ASN A | 90 | 45.623 | 53.893 | 28.744 | 1.00 | 20.28 |
| ATOM | 463 | ND2 | ASN A | 90 | 43.621 | 54.877 | 28.449 | 1.00 | 19.47 |
| ATOM | 464 | C | ASN A | 90 | 47.025 | 54.356 | 26.353 | 1.00 | 20.03 |
| ATOM | 465 | O | ASN A | 90 | 46.446 | 53.348 | 25.943 | 1.00 | 21.07 |
| ATOM | 466 | N | PRO A | 91 | 48.293 | 54.323 | 26.783 | 1.00 | 19.07 |
| ATOM | 467 | CD | PRO A | 91 | 49.025 | 55.490 | 27.309 | 1.00 | 19.27 |
| ATOM | 468 | CA | PRO A | 91 | 49.137 | 53.127 | 26.837 | 1.00 | 17.79 |
| ATOM | 469 | CB | PRO A | 91 | 50.532 | 53.720 | 26.810 | 1.00 | 18.33 |
| ATOM | 470 | CG | PRO A | 91 | 50.367 | 54.889 | 27.730 | 1.00 | 17.60 |
| ATOM | 471 | C | PRO A | 91 | 48.966 | 52.189 | 28.014 | 1.00 | 17.38 |
| ATOM | 472 | O | PRO A | 91 | 49.753 | 51.252 | 28.170 | 1.00 | 16.67 |
| ATOM | 473 | N | VAL A | 92 | 47.953 | 52.430 | 28.838 | 1.00 | 16.23 |
| ATOM | 474 | CA | VAL A | 92 | 47.736 | 51.601 | 30.019 | 1.00 | 16.20 |
| ATOM | 475 | CB | VAL A | 92 | 47.444 | 52.487 | 31.249 | 1.00 | 15.65 |

TABLE 31-continued

| ATOM | 476 | CG1 | VAL A | 92 | 47.342 | 51.635 | 32.500 | 1.00 | 14.38 |
| --- | --- | --- | --- | --- | --- | --- | --- | --- | --- |
| ATOM | 477 | CG2 | VAL A | 92 | 48.538 | 53.535 | 31.394 | 1.00 | 14.11 |
| ATOM | 478 | C | VAL A | 92 | 46.602 | 50.591 | 29.852 | 1.00 | 16.68 |
| ATOM | 479 | O | VAL A | 92 | 45.433 | 50.966 | 29.778 | 1.00 | 16.63 |
| ATOM | 480 | N | GLY A | 93 | 46.955 | 49.309 | 29.800 | 1.00 | 15.93 |
| ATOM | 481 | CA | GLY A | 93 | 45.945 | 48.276 | 29.645 | 1.00 | 13.68 |
| ATOM | 482 | C | GLY A | 93 | 45.845 | 47.336 | 30.833 | 1.00 | 14.71 |
| ATOM | 483 | O | GLY A | 93 | 46.692 | 47.349 | 31.721 | 1.00 | 15.24 |
| ATOM | 484 | N | ILE A | 94 | 44.788 | 46.532 | 30.865 | 1.00 | 15.38 |
| ATOM | 485 | CA | ILE A | 94 | 44.606 | 45.560 | 31.937 | 1.00 | 15.09 |
| ATOM | 486 | CB | ILE A | 94 | 43.103 | 45.352 | 32.267 | 1.00 | 15.86 |
| ATOM | 487 | CG2 | ILE A | 94 | 42.326 | 44.977 | 31.008 | 1.00 | 15.73 |
| ATOM | 488 | CG1 | ILE A | 94 | 42.945 | 44.275 | 33.341 | 1.00 | 16.69 |
| ATOM | 489 | CD1 | ILE A | 94 | 43.321 | 44.733 | 34.740 | 1.00 | 15.99 |
| ATOM | 490 | C | ILE A | 94 | 45.218 | 44.251 | 31.436 | 1.00 | 15.45 |
| ATOM | 491 | O | ILE A | 94 | 44.815 | 43.724 | 30.397 | 1.00 | 16.68 |
| ATOM | 492 | N | ALA A | 95 | 46.207 | 43.744 | 32.166 | 1.00 | 15.14 |
| ATOM | 493 | CA | ALA A | 95 | 46.894 | 42.508 | 31.802 | 1.00 | 14.33 |
| ATOM | 494 | CB | ALA A | 95 | 48.074 | 42.274 | 32.746 | 1.00 | 11.97 |
| ATOM | 495 | C | ALA A | 95 | 45.986 | 41.282 | 31.807 | 1.00 | 15.28 |
| ATOM | 496 | O | ALA A | 95 | 44.927 | 41.275 | 32.437 | 1.00 | 14.75 |
| ATOM | 497 | N | ALA A | 96 | 46.418 | 40.245 | 31.097 | 1.00 | 14.38 |
| ATOM | 498 | CA | ALA A | 96 | 45.673 | 38.996 | 31.022 | 1.00 | 15.14 |
| ATOM | 499 | CB | ALA A | 96 | 46.389 | 38.014 | 30.096 | 1.00 | 12.19 |
| ATOM | 500 | C | ALA A | 96 | 45.556 | 38.399 | 32.417 | 1.00 | 16.35 |
| ATOM | 501 | O | ALA A | 96 | 46.460 | 38.549 | 33.250 | 1.00 | 16.20 |
| ATOM | 502 | N | GLY A | 97 | 44.441 | 37.723 | 32.675 | 1.00 | 16.89 |
| ATOM | 503 | CA | GLY A | 97 | 44.250 | 37.110 | 33.977 | 1.00 | 16.58 |
| ATOM | 504 | C | GLY A | 97 | 43.097 | 37.675 | 34.780 | 1.00 | 16.24 |
| ATOM | 505 | O | GLY A | 97 | 42.389 | 36.925 | 35.445 | 1.00 | 18.73 |
| ATOM | 506 | N | PHE A | 98 | 42.903 | 38.989 | 34.741 | 1.00 | 15.41 |
| ATOM | 507 | CA | PHE A | 98 | 41.805 | 39.573 | 35.490 | 1.00 | 14.93 |
| ATOM | 508 | CB | PHE A | 98 | 41.879 | 41.098 | 35.501 | 1.00 | 15.74 |
| ATOM | 509 | CG | PHE A | 98 | 40.754 | 41.736 | 36.260 | 1.00 | 17.64 |
| ATOM | 510 | CD1 | PHE A | 98 | 40.677 | 41.611 | 37.642 | 1.00 | 16.91 |
| ATOM | 511 | CD2 | PHE A | 98 | 39.736 | 42.402 | 35.592 | 1.00 | 17.91 |
| ATOM | 512 | CE1 | PHE A | 98 | 39.607 | 42.134 | 38.344 | 1.00 | 16.70 |
| ATOM | 513 | CE2 | PHE A | 98 | 38.656 | 42.930 | 36.290 | 1.00 | 17.89 |
| ATOM | 514 | CZ | PHE A | 98 | 38.592 | 42.794 | 37.667 | 1.00 | 17.68 |
| ATOM | 515 | C | PHE A | 98 | 40.483 | 39.145 | 34.867 | 1.00 | 15.52 |
| ATOM | 516 | O | PHE A | 98 | 39.554 | 38.756 | 35.572 | 1.00 | 16.20 |
| ATOM | 517 | N | ASP A | 99 | 40.398 | 39.232 | 33.543 | 1.00 | 15.16 |
| ATOM | 518 | CA | ASP A | 99 | 39.187 | 38.834 | 32.827 | 1.00 | 15.45 |
| ATOM | 519 | CB | ASP A | 99 | 38.647 | 40.008 | 31.990 | 1.00 | 14.91 |
| ATOM | 520 | CG | ASP A | 99 | 37.235 | 39.753 | 31.452 | 1.00 | 18.47 |
| ATOM | 521 | OD1 | ASP A | 99 | 36.640 | 38.706 | 31.793 | 1.00 | 18.16 |
| ATOM | 522 | OD2 | ASP A | 99 | 36.712 | 40.604 | 30.692 | 1.00 | 17.82 |
| ATOM | 523 | C | ASP A | 99 | 39.553 | 37.654 | 31.926 | 1.00 | 15.19 |
| ATOM | 524 | O | ASP A | 99 | 39.735 | 37.811 | 30.720 | 1.00 | 14.17 |
| ATOM | 525 | N | LYS A | 100 | 39.671 | 36.474 | 32.527 | 1.00 | 14.99 |
| ATOM | 526 | CA | LYS A | 100 | 40.030 | 35.269 | 31.793 | 1.00 | 15.35 |
| ATOM | 527 | CB | LYS A | 100 | 40.278 | 34.113 | 32.772 | 1.00 | 17.26 |
| ATOM | 528 | CG | LYS A | 100 | 41.615 | 34.153 | 33.517 | 1.00 | 18.99 |
| ATOM | 529 | CD | LYS A | 100 | 41.680 | 33.041 | 34.571 | 1.00 | 22.00 |
| ATOM | 530 | CE | LYS A | 100 | 43.053 | 32.945 | 35.250 | 1.00 | 22.40 |
| ATOM | 531 | NZ | LYS A | 100 | 44.125 | 32.441 | 34.326 | 1.00 | 21.47 |
| ATOM | 532 | C | LYS A | 100 | 39.012 | 34.813 | 30.743 | 1.00 | 16.92 |
| ATOM | 533 | O | LYS A | 100 | 39.394 | 34.243 | 29.716 | 1.00 | 15.83 |
| ATOM | 534 | N | HIS A | 101 | 37.729 | 35.075 | 30.981 | 1.00 | 16.62 |
| ATOM | 535 | CA | HIS A | 101 | 36.684 | 34.616 | 30.060 | 1.00 | 19.07 |
| ATOM | 536 | CB | HIS A | 101 | 35.668 | 33.777 | 30.842 | 1.00 | 16.73 |
| ATOM | 537 | CG | HIS A | 101 | 36.265 | 33.037 | 32.000 | 1.00 | 17.69 |
| ATOM | 538 | CD2 | HIS A | 101 | 36.040 | 33.138 | 33.333 | 1.00 | 17.45 |
| ATOM | 539 | ND1 | HIS A | 101 | 37.242 | 32.075 | 31.849 | 1.00 | 18.04 |
| ATOM | 540 | CE1 | HIS A | 101 | 37.592 | 31.615 | 33.038 | 1.00 | 17.28 |
| ATOM | 541 | NE2 | HIS A | 101 | 36.878 | 32.244 | 33.956 | 1.00 | 16.78 |
| ATOM | 542 | C | HIS A | 101 | 35.945 | 35.698 | 29.265 | 1.00 | 20.21 |
| ATOM | 543 | O | HIS A | 101 | 34.887 | 35.434 | 28.686 | 1.00 | 20.90 |
| ATOM | 544 | N | GLY A | 102 | 36.497 | 36.908 | 29.240 | 1.00 | 21.33 |
| ATOM | 545 | CA | GLY A | 102 | 35.878 | 37.998 | 28.505 | 1.00 | 20.61 |
| ATOM | 546 | C | GLY A | 102 | 34.498 | 38.398 | 28.997 | 1.00 | 21.28 |
| ATOM | 547 | O | GLY A | 102 | 33.588 | 38.595 | 28.201 | 1.00 | 21.11 |
| ATOM | 548 | N | GLU A | 103 | 34.341 | 38.545 | 30.307 | 1.00 | 22.37 |
| ATOM | 549 | CA | GLU A | 103 | 33.046 | 38.913 | 30.874 | 1.00 | 22.31 |
| ATOM | 550 | CB | GLU A | 103 | 32.763 | 38.062 | 32.112 | 1.00 | 21.38 |
| ATOM | 551 | CG | GLU A | 103 | 32.758 | 36.577 | 31.849 | 1.00 | 23.32 |
| ATOM | 552 | CD | GLU A | 103 | 32.669 | 35.773 | 33.124 | 1.00 | 23.87 |
| ATOM | 553 | OE1 | GLU A | 103 | 33.622 | 35.821 | 33.929 | 1.00 | 23.22 |
| ATOM | 554 | OE2 | GLU A | 103 | 31.642 | 35.094 | 33.323 | 1.00 | 27.00 |

TABLE 31-continued

| | | | | | | | | | |
|---|---|---|---|---|---|---|---|---|---|
| ATOM | 555 | C | GLU | A | 103 | 32.914 | 40.377 | 31.270 | 1.00 | 21.22 |
| ATOM | 556 | O | GLU | A | 103 | 31.805 | 40.870 | 31.462 | 1.00 | 22.46 |
| ATOM | 557 | N | ALA | A | 104 | 34.033 | 41.078 | 31.388 | 1.00 | 20.39 |
| ATOM | 558 | CA | ALA | A | 104 | 33.983 | 42.468 | 31.828 | 1.00 | 19.96 |
| ATOM | 559 | CB | ALA | A | 104 | 34.494 | 42.554 | 33.259 | 1.00 | 17.08 |
| ATOM | 560 | C | ALA | A | 104 | 34.734 | 43.458 | 30.955 | 1.00 | 18.70 |
| ATOM | 561 | O | ALA | A | 104 | 35.166 | 44.505 | 31.432 | 1.00 | 18.68 |
| ATOM | 562 | N | VAL | A | 105 | 34.869 | 43.139 | 29.675 | 1.00 | 19.67 |
| ATOM | 563 | CA | VAL | A | 105 | 35.585 | 44.004 | 28.747 | 1.00 | 18.98 |
| ATOM | 564 | CB | VAL | A | 105 | 35.482 | 43.473 | 27.309 | 1.00 | 18.35 |
| ATOM | 565 | CG1 | VAL | A | 105 | 36.203 | 44.413 | 26.361 | 1.00 | 17.12 |
| ATOM | 566 | CG2 | VAL | A | 105 | 36.077 | 42.076 | 27.230 | 1.00 | 17.81 |
| ATOM | 567 | C | VAL | A | 105 | 35.113 | 45.458 | 28.753 | 1.00 | 20.21 |
| ATOM | 568 | O | VAL | A | 105 | 35.927 | 46.384 | 28.840 | 1.00 | 21.83 |
| ATOM | 569 | N | ASP | A | 106 | 33.805 | 45.667 | 28.654 | 1.00 | 17.79 |
| ATOM | 570 | CA | ASP | A | 106 | 33.286 | 47.024 | 28.633 | 1.00 | 19.14 |
| ATOM | 571 | CB | ASP | A | 106 | 31.800 | 47.026 | 28.256 | 1.00 | 18.51 |
| ATOM | 572 | CG | ASP | A | 106 | 31.569 | 46.509 | 26.853 | 1.00 | 21.68 |
| ATOM | 573 | OD1 | ASP | A | 106 | 31.007 | 45.402 | 26.704 | 1.00 | 23.82 |
| ATOM | 574 | OD2 | ASP | A | 106 | 31.968 | 47.204 | 25.894 | 1.00 | 21.96 |
| ATOM | 575 | C | ASP | A | 106 | 33.511 | 47.737 | 29.960 | 1.00 | 17.72 |
| ATOM | 576 | O | ASP | A | 106 | 33.881 | 48.907 | 29.981 | 1.00 | 17.97 |
| ATOM | 577 | N | GLY | A | 107 | 33.301 | 47.035 | 31.065 | 1.00 | 16.46 |
| ATOM | 578 | CA | GLY | A | 107 | 33.526 | 47.656 | 32.359 | 1.00 | 17.38 |
| ATOM | 579 | C | GLY | A | 107 | 34.971 | 48.111 | 32.495 | 1.00 | 17.35 |
| ATOM | 580 | O | GLY | A | 107 | 35.255 | 49.153 | 33.084 | 1.00 | 19.25 |
| ATOM | 581 | N | LEU | A | 108 | 35.890 | 47.326 | 31.942 | 1.00 | 16.97 |
| ATOM | 582 | CA | LEU | A | 108 | 37.309 | 47.650 | 31.996 | 1.00 | 17.36 |
| ATOM | 583 | CB | LEU | A | 108 | 38.125 | 46.437 | 31.529 | 1.00 | 17.86 |
| ATOM | 584 | CG | LEU | A | 108 | 38.062 | 45.272 | 32.526 | 1.00 | 17.10 |
| ATOM | 585 | CD1 | LEU | A | 108 | 38.470 | 43.978 | 31.867 | 1.00 | 15.95 |
| ATOM | 586 | CD2 | LEU | A | 108 | 38.968 | 45.584 | 33.715 | 1.00 | 18.93 |
| ATOM | 587 | C | LEU | A | 108 | 37.660 | 48.912 | 31.184 | 1.00 | 17.60 |
| ATOM | 588 | O | LEU | A | 108 | 38.488 | 49.713 | 31.617 | 1.00 | 17.54 |
| ATOM | 589 | N | TYR | A | 109 | 37.049 | 49.091 | 30.014 | 1.00 | 17.36 |
| ATOM | 590 | CA | TYR | A | 109 | 37.308 | 50.300 | 29.226 | 1.00 | 18.50 |
| ATOM | 591 | CB | TYR | A | 109 | 36.579 | 50.270 | 27.873 | 1.00 | 16.29 |
| ATOM | 592 | CG | TYR | A | 109 | 37.220 | 49.373 | 26.842 | 1.00 | 15.60 |
| ATOM | 593 | CD1 | TYR | A | 109 | 36.483 | 48.389 | 26.196 | 1.00 | 13.47 |
| ATOM | 594 | CE1 | TYR | A | 109 | 37.074 | 47.542 | 25.273 | 1.00 | 14.70 |
| ATOM | 595 | CD2 | TYR | A | 109 | 38.568 | 49.494 | 26.531 | 1.00 | 15.56 |
| ATOM | 596 | CE2 | TYR | A | 109 | 39.169 | 48.657 | 25.605 | 1.00 | 15.08 |
| ATOM | 597 | CZ | TYR | A | 109 | 38.416 | 47.682 | 24.982 | 1.00 | 15.11 |
| ATOM | 598 | OH | TYR | A | 109 | 39.008 | 46.842 | 24.073 | 1.00 | 14.37 |
| ATOM | 599 | C | TYR | A | 109 | 36.781 | 51.476 | 30.038 | 1.00 | 19.94 |
| ATOM | 600 | O | TYR | A | 109 | 37.402 | 52.538 | 30.099 | 1.00 | 19.20 |
| ATOM | 601 | N | LYS | A | 110 | 35.627 | 51.274 | 30.665 | 1.00 | 19.60 |
| ATOM | 602 | CA | LYS | A | 110 | 35.026 | 52.316 | 31.478 | 1.00 | 22.98 |
| ATOM | 603 | CB | LYS | A | 110 | 33.652 | 51.869 | 31.984 | 1.00 | 22.64 |
| ATOM | 604 | CG | LYS | A | 110 | 32.978 | 52.883 | 32.884 | 1.00 | 25.49 |
| ATOM | 605 | CD | LYS | A | 110 | 31.614 | 52.398 | 33.349 | 1.00 | 28.43 |
| ATOM | 606 | CE | LYS | A | 110 | 30.978 | 53.387 | 34.316 | 1.00 | 29.85 |
| ATOM | 607 | NZ | LYS | A | 110 | 29.639 | 52.924 | 34.779 | 1.00 | 32.33 |
| ATOM | 608 | C | LYS | A | 110 | 35.931 | 52.656 | 32.660 | 1.00 | 23.71 |
| ATOM | 609 | O | LYS | A | 110 | 35.911 | 53.779 | 33.159 | 1.00 | 24.86 |
| ATOM | 610 | N | MET | A | 111 | 36.724 | 51.683 | 33.105 | 1.00 | 23.14 |
| ATOM | 611 | CA | MET | A | 111 | 37.635 | 51.896 | 34.227 | 1.00 | 22.28 |
| ATOM | 612 | CB | MET | A | 111 | 38.200 | 50.556 | 34.710 | 1.00 | 23.75 |
| ATOM | 613 | CG | MET | A | 111 | 38.638 | 50.548 | 36.169 | 1.00 | 22.53 |
| ATOM | 614 | SD | MET | A | 111 | 39.196 | 48.918 | 36.741 | 1.00 | 22.26 |
| ATOM | 615 | CE | MET | A | 111 | 37.667 | 48.079 | 37.039 | 1.00 | 21.23 |
| ATOM | 616 | C | MET | A | 111 | 38.775 | 52.825 | 33.802 | 1.00 | 22.11 |
| ATOM | 617 | O | MET | A | 111 | 39.489 | 53.375 | 34.641 | 1.00 | 22.69 |
| ATOM | 618 | N | GLY | A | 112 | 38.949 | 52.995 | 32.496 | 1.00 | 20.34 |
| ATOM | 619 | CA | GLY | A | 112 | 39.991 | 53.883 | 32.015 | 1.00 | 18.15 |
| ATOM | 620 | C | GLY | A | 112 | 41.119 | 53.247 | 31.226 | 1.00 | 18.34 |
| ATOM | 621 | O | GLY | A | 112 | 42.003 | 53.956 | 30.741 | 1.00 | 18.29 |
| ATOM | 622 | N | PHE | A | 113 | 41.105 | 51.924 | 31.083 | 1.00 | 16.38 |
| ATOM | 623 | CA | PHE | A | 113 | 42.169 | 51.256 | 30.341 | 1.00 | 16.66 |
| ATOM | 624 | CB | PHE | A | 113 | 42.085 | 49.736 | 30.519 | 1.00 | 15.73 |
| ATOM | 625 | CG | PHE | A | 113 | 42.439 | 49.268 | 31.907 | 1.00 | 15.86 |
| ATOM | 626 | CD1 | PHE | A | 113 | 41.461 | 48.785 | 32.763 | 1.00 | 13.52 |
| ATOM | 627 | CD2 | PHE | A | 113 | 43.750 | 49.325 | 32.358 | 1.00 | 15.66 |
| ATOM | 628 | CE1 | PHE | A | 113 | 41.783 | 48.366 | 34.049 | 1.00 | 16.31 |
| ATOM | 629 | CE2 | PHE | A | 113 | 44.082 | 48.911 | 33.640 | 1.00 | 15.91 |
| ATOM | 630 | CZ | PHE | A | 113 | 43.097 | 48.430 | 34.488 | 1.00 | 17.25 |
| ATOM | 631 | C | PHE | A | 113 | 42.123 | 51.613 | 28.860 | 1.00 | 17.48 |
| ATOM | 632 | O | PHE | A | 113 | 41.050 | 51.697 | 28.262 | 1.00 | 18.96 |
| ATOM | 633 | N | GLY | A | 114 | 43.298 | 51.833 | 28.280 | 1.00 | 17.21 |

TABLE 31-continued

| | | | | | | | | | |
|---|---|---|---|---|---|---|---|---|---|
| ATOM | 634 | CA | GLY A | 114 | 43.387 | 52.183 | 26.875 | 1.00 | 17.10 |
| ATOM | 635 | C | GLY A | 114 | 43.185 | 50.974 | 25.983 | 1.00 | 17.43 |
| ATOM | 636 | O | GLY A | 114 | 42.940 | 51.105 | 24.781 | 1.00 | 18.13 |
| ATOM | 637 | N | PHE A | 115 | 43.321 | 49.790 | 26.567 | 1.00 | 15.88 |
| ATOM | 638 | CA | PHE A | 115 | 43.118 | 48.554 | 25.827 | 1.00 | 15.94 |
| ATOM | 639 | CB | PHE A | 115 | 44.278 | 48.279 | 24.855 | 1.00 | 14.80 |
| ATOM | 640 | CG | PHE A | 115 | 45.594 | 47.961 | 25.516 | 1.00 | 15.10 |
| ATOM | 641 | CD1 | PHE A | 115 | 46.118 | 46.678 | 25.455 | 1.00 | 13.34 |
| ATOM | 642 | CD2 | PHE A | 115 | 46.352 | 48.960 | 26.114 | 1.00 | 15.38 |
| ATOM | 643 | CE1 | PHE A | 115 | 47.375 | 46.391 | 25.968 | 1.00 | 13.45 |
| ATOM | 644 | CE2 | PHE A | 115 | 47.613 | 48.684 | 26.631 | 1.00 | 15.60 |
| ATOM | 645 | CZ | PHE A | 115 | 48.126 | 47.394 | 26.556 | 1.00 | 16.23 |
| ATOM | 646 | C | PHE A | 115 | 42.924 | 47.404 | 26.797 | 1.00 | 15.57 |
| ATOM | 647 | O | PHE A | 115 | 43.407 | 47.441 | 27.925 | 1.00 | 15.80 |
| ATOM | 648 | N | VAL A | 116 | 42.195 | 46.391 | 26.350 | 1.00 | 14.53 |
| ATOM | 649 | CA | VAL A | 116 | 41.886 | 45.245 | 27.184 | 1.00 | 13.55 |
| ATOM | 650 | CB | VAL A | 116 | 40.352 | 45.155 | 27.428 | 1.00 | 12.30 |
| ATOM | 651 | CG1 | VAL A | 116 | 39.999 | 43.863 | 28.178 | 1.00 | 11.26 |
| ATOM | 652 | CG2 | VAL A | 116 | 39.888 | 46.366 | 28.199 | 1.00 | 9.84 |
| ATOM | 653 | C | VAL A | 116 | 42.342 | 43.936 | 26.573 | 1.00 | 13.19 |
| ATOM | 654 | O | VAL A | 116 | 42.195 | 43.716 | 25.371 | 1.00 | 13.44 |
| ATOM | 655 | N | GLU A | 117 | 42.896 | 43.070 | 27.411 | 1.00 | 13.85 |
| ATOM | 656 | CA | GLU A | 117 | 43.342 | 41.752 | 26.972 | 1.00 | 15.89 |
| ATOM | 657 | CB | GLU A | 117 | 44.856 | 41.608 | 27.145 | 1.00 | 15.80 |
| ATOM | 658 | CG | GLU A | 117 | 45.399 | 40.231 | 26.767 | 1.00 | 16.39 |
| ATOM | 659 | CD | GLU A | 117 | 46.916 | 40.177 | 26.798 | 1.00 | 18.77 |
| ATOM | 660 | OE1 | GLU A | 117 | 47.467 | 39.207 | 27.369 | 1.00 | 16.54 |
| ATOM | 661 | OE2 | GLU A | 117 | 47.553 | 41.101 | 26.245 | 1.00 | 15.23 |
| ATOM | 662 | C | GLU A | 117 | 42.611 | 40.759 | 27.867 | 1.00 | 16.46 |
| ATOM | 663 | O | GLU A | 117 | 42.710 | 40.840 | 29.088 | 1.00 | 17.95 |
| ATOM | 664 | N | ILE A | 118 | 41.864 | 39.831 | 27.283 | 1.00 | 18.07 |
| ATOM | 665 | CA | ILE A | 118 | 41.139 | 38.885 | 28.117 | 1.00 | 19.92 |
| ATOM | 666 | CB | ILE A | 118 | 39.789 | 38.483 | 27.484 | 1.00 | 18.14 |
| ATOM | 667 | CG2 | ILE A | 118 | 38.863 | 39.685 | 27.481 | 1.00 | 16.23 |
| ATOM | 668 | CG1 | ILE A | 118 | 39.990 | 37.954 | 26.066 | 1.00 | 18.31 |
| ATOM | 669 | CD1 | ILE A | 118 | 38.708 | 37.447 | 25.441 | 1.00 | 19.68 |
| ATOM | 670 | C | ILE A | 118 | 41.964 | 37.656 | 28.465 | 1.00 | 21.94 |
| ATOM | 671 | O | ILE A | 118 | 42.582 | 37.044 | 27.597 | 1.00 | 20.77 |
| ATOM | 672 | N | GLY A | 119 | 41.971 | 37.348 | 29.766 | 1.00 | 26.52 |
| ATOM | 673 | CA | GLY A | 119 | 42.725 | 36.240 | 30.343 | 1.00 | 23.76 |
| ATOM | 674 | C | GLY A | 119 | 42.913 | 35.080 | 29.411 | 1.00 | 24.45 |
| ATOM | 675 | O | GLY A | 119 | 42.145 | 34.933 | 28.455 | 1.00 | 22.92 |
| ATOM | 676 | N | SER A | 120 | 43.921 | 34.254 | 29.691 | 1.00 | 21.74 |
| ATOM | 677 | CA | SER A | 120 | 44.207 | 33.102 | 28.843 | 1.00 | 20.99 |
| ATOM | 678 | CB | SER A | 120 | 45.383 | 32.290 | 29.396 | 1.00 | 21.02 |
| ATOM | 679 | OG | SER A | 120 | 46.621 | 32.902 | 29.074 | 1.00 | 21.19 |
| ATOM | 680 | C | SER A | 120 | 43.004 | 32.195 | 28.669 | 1.00 | 19.92 |
| ATOM | 681 | O | SER A | 120 | 42.319 | 31.853 | 29.637 | 1.00 | 19.73 |
| ATOM | 682 | N | VAL A | 121 | 42.761 | 31.817 | 27.420 | 1.00 | 18.41 |
| ATOM | 683 | CA | VAL A | 121 | 41.652 | 30.945 | 27.064 | 1.00 | 17.15 |
| ATOM | 684 | CB | VAL A | 121 | 40.762 | 31.588 | 25.973 | 1.00 | 17.17 |
| ATOM | 685 | CG1 | VAL A | 121 | 39.474 | 30.770 | 25.791 | 1.00 | 15.03 |
| ATOM | 686 | CG2 | VAL A | 121 | 40.451 | 33.036 | 26.337 | 1.00 | 15.07 |
| ATOM | 687 | C | VAL A | 121 | 42.216 | 29.637 | 26.510 | 1.00 | 17.36 |
| ATOM | 688 | O | VAL A | 121 | 43.129 | 29.649 | 25.685 | 1.00 | 17.64 |
| ATOM | 689 | N | THR A | 122 | 41.679 | 28.516 | 26.977 | 1.00 | 15.93 |
| ATOM | 690 | CA | THR A | 122 | 42.112 | 27.204 | 26.513 | 1.00 | 18.45 |
| ATOM | 691 | CB | THR A | 122 | 42.255 | 26.209 | 27.692 | 1.00 | 18.19 |
| ATOM | 692 | OG1 | THR A | 122 | 41.041 | 26.182 | 28.446 | 1.00 | 20.07 |
| ATOM | 693 | CG2 | THR A | 122 | 43.385 | 26.624 | 28.607 | 1.00 | 17.93 |
| ATOM | 694 | C | THR A | 122 | 41.056 | 26.694 | 25.532 | 1.00 | 19.33 |
| ATOM | 695 | O | THR A | 122 | 39.897 | 27.099 | 25.595 | 1.00 | 20.13 |
| ATOM | 696 | N | PRO A | 123 | 41.447 | 25.817 | 24.599 | 1.00 | 19.88 |
| ATOM | 697 | CD | PRO A | 123 | 42.813 | 25.347 | 24.312 | 1.00 | 20.45 |
| ATOM | 698 | CA | PRO A | 123 | 40.495 | 25.283 | 23.618 | 1.00 | 21.16 |
| ATOM | 699 | CB | PRO A | 123 | 41.326 | 24.252 | 22.864 | 1.00 | 20.64 |
| ATOM | 700 | CG | PRO A | 123 | 42.693 | 24.893 | 22.870 | 1.00 | 20.94 |
| ATOM | 701 | C | PRO A | 123 | 39.244 | 24.684 | 24.259 | 1.00 | 22.19 |
| ATOM | 702 | O | PRO A | 123 | 38.122 | 25.084 | 23.948 | 1.00 | 21.78 |
| ATOM | 703 | N | LYS A | 124 | 39.439 | 23.727 | 25.155 | 1.00 | 22.48 |
| ATOM | 704 | CA | LYS A | 124 | 38.314 | 23.107 | 25.834 | 1.00 | 24.61 |
| ATOM | 705 | CB | LYS A | 124 | 38.518 | 21.589 | 25.943 | 1.00 | 26.75 |
| ATOM | 706 | CG | LYS A | 124 | 38.853 | 20.915 | 24.624 | 1.00 | 31.52 |
| ATOM | 707 | CD | LYS A | 124 | 37.838 | 21.287 | 23.548 | 1.00 | 36.94 |
| ATOM | 708 | CE | LYS A | 124 | 38.268 | 20.790 | 22.173 | 1.00 | 39.83 |
| ATOM | 709 | NZ | LYS A | 124 | 37.347 | 21.270 | 21.104 | 1.00 | 41.97 |
| ATOM | 710 | C | LYS A | 124 | 38.214 | 23.710 | 27.226 | 1.00 | 24.06 |
| ATOM | 711 | O | LYS A | 124 | 39.197 | 24.224 | 27.760 | 1.00 | 24.29 |
| ATOM | 712 | N | PRO A | 125 | 37.016 | 23.679 | 27.823 | 1.00 | 23.56 |

TABLE 31-continued

| | | | | | | | | | |
|---|---|---|---|---|---|---|---|---|---|
| ATOM | 713 | CD | PRO A | 125 | 35.731 | 23.209 | 27.272 | 1.00 | 22.50 |
| ATOM | 714 | CA | PRO A | 125 | 36.849 | 24.235 | 29.169 | 1.00 | 22.94 |
| ATOM | 715 | CB | PRO A | 125 | 35.345 | 24.099 | 29.424 | 1.00 | 23.90 |
| ATOM | 716 | CG | PRO A | 125 | 34.736 | 24.031 | 28.039 | 1.00 | 23.27 |
| ATOM | 717 | C | PRO A | 125 | 37.652 | 23.386 | 30.156 | 1.00 | 23.04 |
| ATOM | 718 | O | PRO A | 125 | 37.809 | 22.183 | 29.955 | 1.00 | 22.12 |
| ATOM | 719 | N | GLN A | 126 | 38.173 | 24.012 | 31.204 | 1.00 | 22.29 |
| ATOM | 720 | CA | GLN A | 126 | 38.908 | 23.286 | 32.235 | 1.00 | 22.14 |
| ATOM | 721 | CB | GLN A | 126 | 40.345 | 22.953 | 31.794 | 1.00 | 23.41 |
| ATOM | 722 | CG | GLN A | 126 | 41.271 | 24.132 | 31.558 | 1.00 | 21.69 |
| ATOM | 723 | CD | GLN A | 126 | 42.719 | 23.691 | 31.384 | 1.00 | 21.50 |
| ATOM | 724 | OE1 | GLN A | 126 | 43.012 | 22.748 | 30.640 | 1.00 | 17.39 |
| ATOM | 725 | NE2 | GLN A | 126 | 43.633 | 24.376 | 32.067 | 1.00 | 19.78 |
| ATOM | 726 | C | GLN A | 126 | 38.907 | 24.109 | 33.516 | 1.00 | 22.34 |
| ATOM | 727 | O | GLN A | 126 | 39.050 | 25.329 | 33.485 | 1.00 | 21.16 |
| ATOM | 728 | N | GLU A | 127 | 38.742 | 23.421 | 34.640 | 1.00 | 23.72 |
| ATOM | 729 | CA | GLU A | 127 | 38.657 | 24.053 | 35.950 | 1.00 | 26.48 |
| ATOM | 730 | CB | GLU A | 127 | 38.023 | 23.071 | 36.940 | 1.00 | 30.25 |
| ATOM | 731 | CG | GLU A | 127 | 36.718 | 22.476 | 36.444 | 1.00 | 38.37 |
| ATOM | 732 | CD | GLU A | 127 | 35.966 | 21.732 | 37.527 | 1.00 | 43.74 |
| ATOM | 733 | OE1 | GLU A | 127 | 36.591 | 20.898 | 38.223 | 1.00 | 46.79 |
| ATOM | 734 | OE2 | GLU A | 127 | 34.748 | 21.979 | 37.678 | 1.00 | 45.76 |
| ATOM | 735 | C | GLU A | 127 | 39.936 | 24.614 | 36.559 | 1.00 | 24.46 |
| ATOM | 736 | O | GLU A | 127 | 39.874 | 25.515 | 37.395 | 1.00 | 21.80 |
| ATOM | 737 | N | GLY A | 128 | 41.085 | 24.083 | 36.158 | 1.00 | 23.10 |
| ATOM | 738 | CA | GLY A | 128 | 42.337 | 24.559 | 36.715 | 1.00 | 23.08 |
| ATOM | 739 | C | GLY A | 128 | 42.681 | 23.831 | 38.005 | 1.00 | 24.88 |
| ATOM | 740 | O | GLY A | 128 | 42.088 | 22.794 | 38.317 | 1.00 | 22.39 |
| ATOM | 741 | N | ASN A | 129 | 43.635 | 24.371 | 38.761 | 1.00 | 25.51 |
| ATOM | 742 | CA | ASN A | 129 | 44.060 | 23.752 | 40.013 | 1.00 | 26.86 |
| ATOM | 743 | CB | ASN A | 129 | 45.401 | 24.333 | 40.475 | 1.00 | 26.95 |
| ATOM | 744 | CG | ASN A | 129 | 46.545 | 23.948 | 39.564 | 1.00 | 29.42 |
| ATOM | 745 | OD1 | ASN A | 129 | 46.684 | 22.784 | 39.191 | 1.00 | 29.57 |
| ATOM | 746 | ND2 | ASN A | 129 | 47.379 | 24.922 | 39.206 | 1.00 | 27.28 |
| ATOM | 747 | C | ASN A | 129 | 43.044 | 23.916 | 41.130 | 1.00 | 27.75 |
| ATOM | 748 | O | ASN A | 129 | 42.222 | 24.832 | 41.112 | 1.00 | 28.72 |
| ATOM | 749 | N | PRO A | 130 | 43.090 | 23.016 | 42.123 | 1.00 | 28.29 |
| ATOM | 750 | CD | PRO A | 130 | 43.976 | 21.840 | 42.196 | 1.00 | 28.29 |
| ATOM | 751 | CA | PRO A | 130 | 42.176 | 23.057 | 43.266 | 1.00 | 28.70 |
| ATOM | 752 | CB | PRO A | 130 | 42.415 | 21.708 | 43.943 | 1.00 | 28.73 |
| ATOM | 753 | CG | PRO A | 130 | 43.849 | 21.432 | 43.648 | 1.00 | 28.52 |
| ATOM | 754 | C | PRO A | 130 | 42.519 | 24.238 | 44.170 | 1.00 | 30.37 |
| ATOM | 755 | O | PRO A | 130 | 43.658 | 24.703 | 44.181 | 1.00 | 30.70 |
| ATOM | 756 | N | ARG A | 131 | 41.535 | 24.728 | 44.916 | 1.00 | 31.62 |
| ATOM | 757 | CA | ARG A | 131 | 41.753 | 25.857 | 45.813 | 1.00 | 33.50 |
| ATOM | 758 | CB | ARG A | 131 | 40.420 | 26.515 | 46.178 | 1.00 | 35.74 |
| ATOM | 759 | CG | ARG A | 131 | 39.613 | 27.089 | 45.017 | 1.00 | 38.80 |
| ATOM | 760 | CD | ARG A | 131 | 38.514 | 27.985 | 45.580 | 1.00 | 42.56 |
| ATOM | 761 | NE | ARG A | 131 | 37.622 | 28.555 | 44.573 | 1.00 | 47.82 |
| ATOM | 762 | CZ | ARG A | 131 | 36.761 | 29.545 | 44.818 | 1.00 | 49.92 |
| ATOM | 763 | NH1 | ARG A | 131 | 36.682 | 30.074 | 46.035 | 1.00 | 48.66 |
| ATOM | 764 | NH2 | ARG A | 131 | 35.974 | 30.006 | 43.853 | 1.00 | 49.91 |
| ATOM | 765 | C | ARG A | 131 | 42.461 | 25.422 | 47.103 | 1.00 | 33.57 |
| ATOM | 766 | O | ARG A | 131 | 42.376 | 24.265 | 47.515 | 1.00 | 34.25 |
| ATOM | 767 | N | PRO A | 132 | 43.194 | 26.345 | 47.743 | 1.00 | 31.72 |
| ATOM | 768 | CD | PRO A | 132 | 43.813 | 26.140 | 49.065 | 1.00 | 32.80 |
| ATOM | 769 | CA | PRO A | 132 | 43.370 | 27.730 | 47.297 | 1.00 | 29.67 |
| ATOM | 770 | CB | PRO A | 132 | 43.810 | 28.437 | 48.572 | 1.00 | 30.49 |
| ATOM | 771 | CG | PRO A | 132 | 44.655 | 27.389 | 49.233 | 1.00 | 31.39 |
| ATOM | 772 | C | PRO A | 132 | 44.432 | 27.774 | 46.198 | 1.00 | 26.70 |
| ATOM | 773 | O | PRO A | 132 | 45.304 | 26.907 | 46.143 | 1.00 | 25.75 |
| ATOM | 774 | N | ARG A | 133 | 44.363 | 28.779 | 45.329 | 1.00 | 23.15 |
| ATOM | 775 | CA | ARG A | 133 | 45.315 | 28.882 | 44.232 | 1.00 | 20.71 |
| ATOM | 776 | CB | ARG A | 133 | 44.701 | 28.268 | 42.972 | 1.00 | 20.72 |
| ATOM | 777 | CG | ARG A | 133 | 43.273 | 28.731 | 42.700 | 1.00 | 19.27 |
| ATOM | 778 | CD | ARG A | 133 | 42.596 | 27.848 | 41.651 | 1.00 | 19.00 |
| ATOM | 779 | NE | ARG A | 133 | 41.216 | 28.261 | 41.400 | 1.00 | 17.68 |
| ATOM | 780 | CZ | ARG A | 133 | 40.462 | 27.779 | 40.418 | 1.00 | 16.01 |
| ATOM | 781 | NH1 | ARG A | 133 | 39.221 | 28.209 | 40.258 | 1.00 | 13.83 |
| ATOM | 782 | NH2 | ARG A | 133 | 40.952 | 26.866 | 39.592 | 1.00 | 16.14 |
| ATOM | 783 | C | ARG A | 133 | 45.789 | 30.303 | 43.952 | 1.00 | 20.50 |
| ATOM | 784 | O | ARG A | 133 | 46.444 | 30.562 | 42.941 | 1.00 | 20.67 |
| ATOM | 785 | N | VAL A | 134 | 45.447 | 31.225 | 44.842 | 1.00 | 19.19 |
| ATOM | 786 | CA | VAL A | 134 | 45.876 | 32.609 | 44.702 | 1.00 | 18.94 |
| ATOM | 787 | CB | VAL A | 134 | 44.805 | 33.483 | 43.977 | 1.00 | 18.31 |
| ATOM | 788 | CG1 | VAL A | 134 | 43.524 | 33.555 | 44.790 | 1.00 | 17.25 |
| ATOM | 789 | CG2 | VAL A | 134 | 45.366 | 34.876 | 43.720 | 1.00 | 16.42 |
| ATOM | 790 | C | VAL A | 134 | 46.136 | 33.109 | 46.121 | 1.00 | 19.93 |
| ATOM | 791 | O | VAL A | 134 | 45.393 | 32.784 | 47.044 | 1.00 | 21.00 |

TABLE 31-continued

| ATOM | 792 | N | PHE A | 135 | 47.208 | 33.870 | 46.303 | 1.00 | 19.43 |
| ATOM | 793 | CA | PHE A | 135 | 47.558 | 34.352 | 47.630 | 1.00 | 18.68 |
| ATOM | 794 | CB | PHE A | 135 | 48.619 | 33.437 | 48.244 | 1.00 | 18.25 |
| ATOM | 795 | CG | PHE A | 135 | 48.311 | 31.968 | 48.099 | 1.00 | 17.64 |
| ATOM | 796 | CD1 | PHE A | 135 | 48.567 | 31.305 | 46.909 | 1.00 | 17.96 |
| ATOM | 797 | CD2 | PHE A | 135 | 47.730 | 31.262 | 49.142 | 1.00 | 18.54 |
| ATOM | 798 | CE1 | PHE A | 135 | 48.248 | 29.963 | 46.758 | 1.00 | 17.71 |
| ATOM | 799 | CE2 | PHE A | 135 | 47.407 | 29.921 | 49.001 | 1.00 | 17.69 |
| ATOM | 800 | CZ | PHE A | 135 | 47.667 | 29.272 | 47.804 | 1.00 | 18.64 |
| ATOM | 801 | C | PHE A | 135 | 48.060 | 35.791 | 47.635 | 1.00 | 19.58 |
| ATOM | 802 | O | PHE A | 135 | 48.769 | 36.227 | 46.724 | 1.00 | 19.26 |
| ATOM | 803 | N | ARG A | 136 | 47.684 | 36.522 | 48.676 | 1.00 | 18.78 |
| ATOM | 804 | CA | ARG A | 136 | 48.087 | 37.907 | 48.821 | 1.00 | 18.85 |
| ATOM | 805 | CB | ARG A | 136 | 46.945 | 38.734 | 49.440 | 1.00 | 18.08 |
| ATOM | 806 | CG | ARG A | 136 | 45.648 | 38.704 | 48.639 | 1.00 | 21.63 |
| ATOM | 807 | CD | ARG A | 136 | 44.493 | 39.450 | 49.317 | 1.00 | 22.90 |
| ATOM | 808 | NE | ARG A | 136 | 44.669 | 40.900 | 49.298 | 1.00 | 31.55 |
| ATOM | 809 | CZ | ARG A | 136 | 45.236 | 41.604 | 50.277 | 1.00 | 34.11 |
| ATOM | 810 | NH1 | ARG A | 136 | 45.358 | 42.922 | 50.170 | 1.00 | 33.96 |
| ATOM | 811 | NH2 | ARG A | 136 | 45.663 | 40.995 | 51.374 | 1.00 | 36.33 |
| ATOM | 812 | C | ARG A | 136 | 49.319 | 37.991 | 49.714 | 1.00 | 18.61 |
| ATOM | 813 | O | ARG A | 136 | 49.460 | 37.220 | 50.663 | 1.00 | 16.80 |
| ATOM | 814 | N | LEU A | 137 | 50.214 | 38.918 | 49.376 | 1.00 | 17.15 |
| ATOM | 815 | CA | LEU A | 137 | 51.432 | 39.182 | 50.141 | 1.00 | 15.58 |
| ATOM | 816 | CB | LEU A | 137 | 52.685 | 38.735 | 49.383 | 1.00 | 14.90 |
| ATOM | 817 | CG | LEU A | 137 | 53.070 | 37.252 | 49.326 | 1.00 | 16.15 |
| ATOM | 818 | CD1 | LEU A | 137 | 52.002 | 36.449 | 48.591 | 1.00 | 14.54 |
| ATOM | 819 | CD2 | LEU A | 137 | 54.416 | 37.119 | 48.613 | 1.00 | 14.08 |
| ATOM | 820 | C | LEU A | 137 | 51.442 | 40.700 | 50.288 | 1.00 | 16.26 |
| ATOM | 821 | O | LEU A | 137 | 52.240 | 41.396 | 49.653 | 1.00 | 14.07 |
| ATOM | 822 | N | PRO A | 138 | 50.524 | 41.229 | 51.113 | 1.00 | 15.45 |
| ATOM | 823 | CD | PRO A | 138 | 49.555 | 40.439 | 51.895 | 1.00 | 15.39 |
| ATOM | 824 | CA | PRO A | 138 | 50.371 | 42.661 | 51.379 | 1.00 | 15.67 |
| ATOM | 825 | CB | PRO A | 138 | 49.263 | 42.711 | 52.442 | 1.00 | 16.12 |
| ATOM | 826 | CG | PRO A | 138 | 49.300 | 41.332 | 53.076 | 1.00 | 16.29 |
| ATOM | 827 | C | PRO A | 138 | 51.642 | 43.386 | 51.806 | 1.00 | 16.69 |
| ATOM | 828 | O | PRO A | 138 | 51.878 | 44.518 | 51.382 | 1.00 | 16.05 |
| ATOM | 829 | N | GLU A | 139 | 52.460 | 42.750 | 52.638 | 1.00 | 16.00 |
| ATOM | 830 | CA | GLU A | 139 | 53.694 | 43.391 | 53.072 | 1.00 | 18.28 |
| ATOM | 831 | CB | GLU A | 139 | 54.414 | 42.551 | 54.135 | 1.00 | 19.48 |
| ATOM | 832 | CG | GLU A | 139 | 53.660 | 42.377 | 55.455 | 1.00 | 21.64 |
| ATOM | 833 | CD | GLU A | 139 | 52.648 | 41.240 | 55.418 | 1.00 | 23.74 |
| ATOM | 834 | OE1 | GLU A | 139 | 51.996 | 41.000 | 56.460 | 1.00 | 24.15 |
| ATOM | 835 | OE2 | GLU A | 139 | 52.504 | 40.589 | 54.356 | 1.00 | 21.93 |
| ATOM | 836 | C | GLU A | 139 | 54.640 | 43.610 | 51.890 | 1.00 | 19.58 |
| ATOM | 837 | O | GLU A | 139 | 55.566 | 44.423 | 51.974 | 1.00 | 20.31 |
| ATOM | 838 | N | ASP A | 140 | 54.406 | 42.892 | 50.792 | 1.00 | 16.14 |
| ATOM | 839 | CA | ASP A | 140 | 55.256 | 43.010 | 49.608 | 1.00 | 15.71 |
| ATOM | 840 | CB | ASP A | 140 | 55.743 | 41.628 | 49.155 | 1.00 | 14.25 |
| ATOM | 841 | CG | ASP A | 140 | 56.369 | 40.833 | 50.277 | 1.00 | 16.28 |
| ATOM | 842 | OD1 | ASP A | 140 | 57.398 | 41.284 | 50.819 | 1.00 | 15.84 |
| ATOM | 843 | OD2 | ASP A | 140 | 55.829 | 39.755 | 50.618 | 1.00 | 17.81 |
| ATOM | 844 | C | ASP A | 140 | 54.522 | 43.649 | 48.448 | 1.00 | 15.94 |
| ATOM | 845 | O | ASP A | 140 | 55.112 | 43.886 | 47.387 | 1.00 | 15.41 |
| ATOM | 846 | N | GLN A | 141 | 53.237 | 43.928 | 48.645 | 1.00 | 16.39 |
| ATOM | 847 | CA | GLN A | 141 | 52.424 | 44.492 | 47.576 | 1.00 | 16.60 |
| ATOM | 848 | CB | GLN A | 141 | 52.891 | 45.907 | 47.239 | 1.00 | 17.74 |
| ATOM | 849 | CG | GLN A | 141 | 52.463 | 46.925 | 48.283 | 1.00 | 21.42 |
| ATOM | 850 | CD | GLN A | 141 | 52.966 | 48.321 | 47.992 | 1.00 | 22.86 |
| ATOM | 851 | OE1 | GLN A | 141 | 52.811 | 48.829 | 46.879 | 1.00 | 25.58 |
| ATOM | 852 | NE2 | GLN A | 141 | 53.560 | 48.961 | 48.999 | 1.00 | 20.82 |
| ATOM | 853 | C | GLN A | 141 | 52.584 | 43.563 | 46.379 | 1.00 | 16.15 |
| ATOM | 854 | O | GLN A | 141 | 52.779 | 44.000 | 45.243 | 1.00 | 16.04 |
| ATOM | 855 | N | ALA A | 142 | 52.502 | 42.265 | 46.664 | 1.00 | 15.11 |
| ATOM | 856 | CA | ALA A | 142 | 52.639 | 41.230 | 45.655 | 1.00 | 16.24 |
| ATOM | 857 | CB | ALA A | 142 | 54.011 | 40.566 | 45.776 | 1.00 | 14.95 |
| ATOM | 858 | C | ALA A | 142 | 51.543 | 40.173 | 45.790 | 1.00 | 16.14 |
| ATOM | 859 | O | ALA A | 142 | 50.822 | 40.128 | 46.786 | 1.00 | 16.05 |
| ATOM | 860 | N | VAL A | 143 | 51.434 | 39.327 | 44.770 | 1.00 | 14.61 |
| ATOM | 861 | CA | VAL A | 143 | 50.463 | 38.248 | 44.751 | 1.00 | 13.30 |
| ATOM | 862 | CB | VAL A | 143 | 49.232 | 38.585 | 43.848 | 1.00 | 15.01 |
| ATOM | 863 | CG1 | VAL A | 143 | 48.372 | 37.345 | 43.658 | 1.00 | 12.24 |
| ATOM | 864 | CG2 | VAL A | 143 | 48.392 | 39.705 | 44.469 | 1.00 | 12.72 |
| ATOM | 865 | C | VAL A | 143 | 51.153 | 37.022 | 44.169 | 1.00 | 15.22 |
| ATOM | 866 | O | VAL A | 143 | 52.098 | 37.140 | 43.386 | 1.00 | 17.23 |
| ATOM | 867 | N | ILE A | 144 | 50.702 | 35.845 | 44.581 | 1.00 | 15.07 |
| ATOM | 868 | CA | ILE A | 144 | 51.228 | 34.597 | 44.050 | 1.00 | 14.14 |
| ATOM | 869 | CB | ILE A | 144 | 51.994 | 33.783 | 45.113 | 1.00 | 15.13 |
| ATOM | 870 | CG2 | ILE A | 144 | 52.184 | 32.340 | 44.627 | 1.00 | 12.58 |

TABLE 31-continued

| | | | | | | | | | |
|---|---|---|---|---|---|---|---|---|---|
| ATOM | 871 | CG1 | ILE | A | 144 | 53.357 | 34.429 | 45.382 | 1.00 | 14.50 |
| ATOM | 872 | CD1 | ILE | A | 144 | 54.167 | 33.719 | 46.437 | 1.00 | 15.10 |
| ATOM | 873 | C | ILE | A | 144 | 50.007 | 33.812 | 43.597 | 1.00 | 15.18 |
| ATOM | 874 | O | ILE | A | 144 | 49.014 | 33.728 | 44.325 | 1.00 | 14.61 |
| ATOM | 875 | N | ASN | A | 145 | 50.063 | 33.247 | 42.397 | 1.00 | 14.87 |
| ATOM | 876 | CA | ASN | A | 145 | 48.926 | 32.492 | 41.896 | 1.00 | 14.98 |
| ATOM | 877 | CB | ASN | A | 145 | 48.079 | 33.381 | 40.981 | 1.00 | 14.70 |
| ATOM | 878 | CG | ASN | A | 145 | 48.613 | 33.431 | 39.558 | 1.00 | 16.21 |
| ATOM | 879 | OD1 | ASN | A | 145 | 48.327 | 32.549 | 38.747 | 1.00 | 15.94 |
| ATOM | 880 | ND2 | ASN | A | 145 | 49.404 | 34.457 | 39.253 | 1.00 | 15.29 |
| ATOM | 881 | C | ASN | A | 145 | 49.326 | 31.228 | 41.139 | 1.00 | 16.34 |
| ATOM | 882 | O | ASN | A | 145 | 50.392 | 31.163 | 40.515 | 1.00 | 14.81 |
| ATOM | 883 | N | ARG | A | 146 | 48.457 | 30.224 | 41.207 | 1.00 | 15.88 |
| ATOM | 884 | CA | ARG | A | 146 | 48.667 | 28.965 | 40.512 | 1.00 | 16.71 |
| ATOM | 885 | CB | ARG | A | 146 | 49.355 | 27.941 | 41.429 | 1.00 | 17.60 |
| ATOM | 886 | CG | ARG | A | 146 | 48.672 | 27.686 | 42.775 | 1.00 | 16.03 |
| ATOM | 887 | CD | ARG | A | 146 | 49.242 | 26.427 | 43.427 | 1.00 | 16.96 |
| ATOM | 888 | NE | ARG | A | 146 | 48.682 | 26.156 | 44.751 | 1.00 | 18.10 |
| ATOM | 889 | CZ | ARG | A | 146 | 49.201 | 26.585 | 45.900 | 1.00 | 18.95 |
| ATOM | 890 | NH1 | ARG | A | 146 | 50.311 | 27.316 | 45.910 | 1.00 | 16.91 |
| ATOM | 891 | NH2 | ARG | A | 146 | 48.609 | 26.275 | 47.048 | 1.00 | 18.90 |
| ATOM | 892 | C | ARG | A | 146 | 47.317 | 28.429 | 40.026 | 1.00 | 17.77 |
| ATOM | 893 | O | ARG | A | 146 | 46.987 | 27.260 | 40.226 | 1.00 | 18.14 |
| ATOM | 894 | N | TYR | A | 147 | 46.540 | 29.296 | 39.381 | 1.00 | 16.93 |
| ATOM | 895 | CA | TYR | A | 147 | 45.232 | 28.913 | 38.866 | 1.00 | 17.10 |
| ATOM | 896 | CB | TYR | A | 147 | 44.583 | 30.088 | 38.131 | 1.00 | 16.67 |
| ATOM | 897 | CG | TYR | A | 147 | 43.797 | 31.015 | 39.033 | 1.00 | 16.52 |
| ATOM | 898 | CD1 | TYR | A | 147 | 44.347 | 32.200 | 39.502 | 1.00 | 15.84 |
| ATOM | 899 | CE1 | TYR | A | 147 | 43.618 | 33.051 | 40.323 | 1.00 | 17.11 |
| ATOM | 900 | CD2 | TYR | A | 147 | 42.496 | 30.699 | 39.413 | 1.00 | 17.14 |
| ATOM | 901 | CE2 | TYR | A | 147 | 41.761 | 31.540 | 40.233 | 1.00 | 17.07 |
| ATOM | 902 | CZ | TYR | A | 147 | 42.326 | 32.714 | 40.681 | 1.00 | 16.99 |
| ATOM | 903 | OH | TYR | A | 147 | 41.586 | 33.557 | 41.475 | 1.00 | 19.36 |
| ATOM | 904 | C | TYR | A | 147 | 45.289 | 27.704 | 37.937 | 1.00 | 18.90 |
| ATOM | 905 | O | TYR | A | 147 | 44.454 | 26.799 | 38.030 | 1.00 | 19.56 |
| ATOM | 906 | N | GLY | A | 148 | 46.272 | 27.693 | 37.040 | 1.00 | 17.53 |
| ATOM | 907 | CA | GLY | A | 148 | 46.418 | 26.586 | 36.114 | 1.00 | 18.26 |
| ATOM | 908 | C | GLY | A | 148 | 45.518 | 26.661 | 34.892 | 1.00 | 18.89 |
| ATOM | 909 | O | GLY | A | 148 | 45.036 | 25.635 | 34.409 | 1.00 | 18.59 |
| ATOM | 910 | N | PHE | A | 149 | 45.292 | 27.869 | 34.387 | 1.00 | 18.08 |
| ATOM | 911 | CA | PHE | A | 149 | 44.454 | 28.060 | 33.209 | 1.00 | 18.01 |
| ATOM | 912 | CB | PHE | A | 149 | 45.024 | 27.286 | 32.012 | 1.00 | 17.90 |
| ATOM | 913 | CG | PHE | A | 149 | 46.184 | 27.962 | 31.334 | 1.00 | 19.93 |
| ATOM | 914 | CD1 | PHE | A | 149 | 47.006 | 27.250 | 30.469 | 1.00 | 20.61 |
| ATOM | 915 | CD2 | PHE | A | 149 | 46.450 | 29.307 | 31.545 | 1.00 | 19.87 |
| ATOM | 916 | CE1 | PHE | A | 149 | 48.074 | 27.868 | 29.829 | 1.00 | 21.56 |
| ATOM | 917 | CE2 | PHE | A | 149 | 47.511 | 29.929 | 30.912 | 1.00 | 20.39 |
| ATOM | 918 | CZ | PHE | A | 149 | 48.326 | 29.211 | 30.053 | 1.00 | 21.63 |
| ATOM | 919 | C | PHE | A | 149 | 42.989 | 27.658 | 33.393 | 1.00 | 18.19 |
| ATOM | 920 | O | PHE | A | 149 | 42.459 | 26.885 | 32.598 | 1.00 | 16.88 |
| ATOM | 921 | N | ASN | A | 150 | 42.338 | 28.154 | 34.440 | 1.00 | 17.39 |
| ATOM | 922 | CA | ASN | A | 150 | 40.921 | 27.859 | 34.617 | 1.00 | 18.20 |
| ATOM | 923 | CB | ASN | A | 150 | 40.426 | 28.360 | 35.978 | 1.00 | 16.86 |
| ATOM | 924 | CG | ASN | A | 150 | 40.861 | 29.778 | 36.272 | 1.00 | 19.11 |
| ATOM | 925 | OD1 | ASN | A | 150 | 42.042 | 30.119 | 36.151 | 1.00 | 18.63 |
| ATOM | 926 | ND2 | ASN | A | 150 | 39.913 | 30.612 | 36.679 | 1.00 | 18.23 |
| ATOM | 927 | C | ASN | A | 150 | 40.296 | 28.653 | 33.469 | 1.00 | 18.25 |
| ATOM | 928 | O | ASN | A | 150 | 40.556 | 29.849 | 33.329 | 1.00 | 17.98 |
| ATOM | 929 | N | SER | A | 151 | 39.495 | 27.994 | 32.636 | 1.00 | 17.60 |
| ATOM | 930 | CA | SER | A | 151 | 38.924 | 28.669 | 31.479 | 1.00 | 17.42 |
| ATOM | 931 | CB | SER | A | 151 | 39.948 | 28.625 | 30.337 | 1.00 | 16.39 |
| ATOM | 932 | OG | SER | A | 151 | 39.383 | 29.008 | 29.094 | 1.00 | 16.77 |
| ATOM | 933 | C | SER | A | 151 | 37.589 | 28.125 | 30.981 | 1.00 | 18.29 |
| ATOM | 934 | O | SER | A | 151 | 37.367 | 26.912 | 30.950 | 1.00 | 19.11 |
| ATOM | 935 | N | HIS | A | 152 | 36.706 | 29.036 | 30.580 | 1.00 | 17.96 |
| ATOM | 936 | CA | HIS | A | 152 | 35.399 | 28.655 | 30.051 | 1.00 | 18.60 |
| ATOM | 937 | CB | HIS | A | 152 | 34.502 | 29.887 | 29.899 | 1.00 | 18.50 |
| ATOM | 938 | CG | HIS | A | 152 | 34.020 | 30.450 | 31.200 | 1.00 | 20.25 |
| ATOM | 939 | CD2 | HIS | A | 152 | 34.271 | 30.083 | 32.480 | 1.00 | 21.79 |
| ATOM | 940 | ND1 | HIS | A | 152 | 33.157 | 31.523 | 31.271 | 1.00 | 21.65 |
| ATOM | 941 | CE1 | HIS | A | 152 | 32.896 | 31.791 | 32.538 | 1.00 | 20.98 |
| ATOM | 942 | NE2 | HIS | A | 152 | 33.559 | 30.932 | 33.292 | 1.00 | 21.39 |
| ATOM | 943 | C | HIS | A | 152 | 35.557 | 27.974 | 28.687 | 1.00 | 18.05 |
| ATOM | 944 | O | HIS | A | 152 | 34.641 | 27.302 | 28.207 | 1.00 | 16.86 |
| ATOM | 945 | N | GLY | A | 153 | 36.721 | 28.149 | 28.064 | 1.00 | 16.67 |
| ATOM | 946 | CA | GLY | A | 153 | 36.953 | 27.536 | 26.766 | 1.00 | 15.79 |
| ATOM | 947 | C | GLY | A | 153 | 36.671 | 28.464 | 25.599 | 1.00 | 14.76 |
| ATOM | 948 | O | GLY | A | 153 | 35.935 | 29.442 | 25.727 | 1.00 | 13.73 |
| ATOM | 949 | N | LEU | A | 154 | 37.254 | 28.147 | 24.450 | 1.00 | 16.63 |

TABLE 31-continued

| | | | | | | | | | |
|---|---|---|---|---|---|---|---|---|---|
| ATOM | 950 | CA | LEU A | 154 | 37.095 | 28.958 | 23.246 | 1.00 | 18.43 |
| ATOM | 951 | CB | LEU A | 154 | 37.831 | 28.297 | 22.074 | 1.00 | 15.94 |
| ATOM | 952 | CG | LEU A | 154 | 39.356 | 28.283 | 22.137 | 1.00 | 16.17 |
| ATOM | 953 | CD1 | LEU A | 154 | 39.925 | 27.439 | 21.003 | 1.00 | 11.50 |
| ATOM | 954 | CD2 | LEU A | 154 | 39.863 | 29.713 | 22.061 | 1.00 | 15.25 |
| ATOM | 955 | C | LEU A | 154 | 35.640 | 29.198 | 22.847 | 1.00 | 20.28 |
| ATOM | 956 | O | LEU A | 154 | 35.227 | 30.337 | 22.613 | 1.00 | 20.49 |
| ATOM | 957 | N | SER A | 155 | 34.872 | 28.118 | 22.768 | 1.00 | 20.71 |
| ATOM | 958 | CA | SER A | 155 | 33.473 | 28.194 | 22.369 | 1.00 | 23.17 |
| ATOM | 959 | CB | SER A | 155 | 32.824 | 26.818 | 22.520 | 1.00 | 24.18 |
| ATOM | 960 | OG | SER A | 155 | 31.494 | 26.838 | 22.053 | 1.00 | 31.05 |
| ATOM | 961 | C | SER A | 155 | 32.674 | 29.240 | 23.147 | 1.00 | 22.07 |
| ATOM | 962 | O | SER A | 155 | 32.091 | 30.153 | 22.562 | 1.00 | 21.98 |
| ATOM | 963 | N | VAL A | 156 | 32.648 | 29.110 | 24.468 | 1.00 | 22.13 |
| ATOM | 964 | CA | VAL A | 156 | 31.915 | 30.054 | 25.297 | 1.00 | 20.80 |
| ATOM | 965 | CB | VAL A | 156 | 31.977 | 29.643 | 26.779 | 1.00 | 22.11 |
| ATOM | 966 | CG1 | VAL A | 156 | 31.467 | 30.777 | 27.661 | 1.00 | 21.20 |
| ATOM | 967 | CG2 | VAL A | 156 | 31.137 | 28.386 | 26.993 | 1.00 | 18.95 |
| ATOM | 968 | C | VAL A | 156 | 32.433 | 31.486 | 25.136 | 1.00 | 20.60 |
| ATOM | 969 | O | VAL A | 156 | 31.647 | 32.424 | 25.025 | 1.00 | 20.47 |
| ATOM | 970 | N | VAL A | 157 | 33.751 | 31.655 | 25.106 | 1.00 | 17.60 |
| ATOM | 971 | CA | VAL A | 157 | 34.325 | 32.983 | 24.955 | 1.00 | 16.63 |
| ATOM | 972 | CB | VAL A | 157 | 35.854 | 32.953 | 25.181 | 1.00 | 16.62 |
| ATOM | 973 | CG1 | VAL A | 157 | 36.459 | 34.308 | 24.880 | 1.00 | 14.21 |
| ATOM | 974 | CG2 | VAL A | 157 | 36.149 | 32.556 | 26.616 | 1.00 | 16.01 |
| ATOM | 975 | C | VAL A | 157 | 34.015 | 33.539 | 23.564 | 1.00 | 16.34 |
| ATOM | 976 | O | VAL A | 157 | 33.786 | 34.738 | 23.401 | 1.00 | 15.07 |
| ATOM | 977 | N | GLU A | 158 | 34.001 | 32.658 | 22.568 | 1.00 | 17.68 |
| ATOM | 978 | CA | GLU A | 158 | 33.703 | 33.050 | 21.194 | 1.00 | 18.02 |
| ATOM | 979 | CB | GLU A | 158 | 33.724 | 31.823 | 20.278 | 1.00 | 18.61 |
| ATOM | 980 | CG | GLU A | 158 | 33.372 | 32.118 | 18.826 | 1.00 | 20.67 |
| ATOM | 981 | CD | GLU A | 158 | 32.777 | 30.909 | 18.115 | 1.00 | 24.47 |
| ATOM | 982 | OE1 | GLU A | 158 | 33.444 | 29.860 | 18.042 | 1.00 | 29.63 |
| ATOM | 983 | OE2 | GLU A | 158 | 31.633 | 31.003 | 17.629 | 1.00 | 26.66 |
| ATOM | 984 | C | GLU A | 158 | 32.323 | 33.708 | 21.121 | 1.00 | 18.60 |
| ATOM | 985 | O | GLU A | 158 | 32.176 | 34.816 | 20.602 | 1.00 | 18.32 |
| ATOM | 986 | N | HIS A | 159 | 31.315 | 33.022 | 21.648 | 1.00 | 18.17 |
| ATOM | 987 | CA | HIS A | 159 | 29.951 | 33.543 | 21.621 | 1.00 | 21.55 |
| ATOM | 988 | CB | HIS A | 159 | 28.970 | 32.459 | 22.078 | 1.00 | 21.45 |
| ATOM | 989 | CG | HIS A | 159 | 28.883 | 31.307 | 21.127 | 1.00 | 26.95 |
| ATOM | 990 | CD2 | HIS A | 159 | 28.642 | 31.271 | 19.794 | 1.00 | 25.37 |
| ATOM | 991 | ND1 | HIS A | 159 | 29.117 | 30.002 | 21.509 | 1.00 | 29.08 |
| ATOM | 992 | CE1 | HIS A | 159 | 29.027 | 29.214 | 20.452 | 1.00 | 28.39 |
| ATOM | 993 | NE2 | HIS A | 159 | 28.741 | 29.960 | 19.399 | 1.00 | 27.32 |
| ATOM | 994 | C | HIS A | 159 | 29.791 | 34.796 | 22.464 | 1.00 | 21.09 |
| ATOM | 995 | O | HIS A | 159 | 28.996 | 35.679 | 22.141 | 1.00 | 20.90 |
| ATOM | 996 | N | ARG A | 160 | 30.565 | 34.874 | 23.538 | 1.00 | 21.00 |
| ATOM | 997 | CA | ARG A | 160 | 30.519 | 36.020 | 24.429 | 1.00 | 22.35 |
| ATOM | 998 | CB | ARG A | 160 | 31.346 | 35.714 | 25.684 | 1.00 | 22.67 |
| ATOM | 999 | CG | ARG A | 160 | 31.199 | 36.704 | 26.824 | 1.00 | 23.49 |
| ATOM | 1000 | CD | ARG A | 160 | 31.778 | 36.108 | 28.107 | 1.00 | 24.33 |
| ATOM | 1001 | NE | ARG A | 160 | 30.914 | 35.082 | 28.688 | 1.00 | 22.62 |
| ATOM | 1002 | CZ | ARG A | 160 | 31.348 | 34.044 | 29.399 | 1.00 | 24.90 |
| ATOM | 1003 | NH1 | ARG A | 160 | 32.648 | 33.878 | 29.615 | 1.00 | 23.96 |
| ATOM | 1004 | NH2 | ARG A | 160 | 30.480 | 33.183 | 29.921 | 1.00 | 23.86 |
| ATOM | 1005 | C | ARG A | 160 | 31.056 | 37.256 | 23.701 | 1.00 | 21.87 |
| ATOM | 1006 | O | ARG A | 160 | 30.532 | 38.357 | 23.861 | 1.00 | 22.45 |
| ATOM | 1007 | N | LEU A | 161 | 32.096 | 37.073 | 22.892 | 1.00 | 20.79 |
| ATOM | 1008 | CA | LEU A | 161 | 32.665 | 38.195 | 22.153 | 1.00 | 20.55 |
| ATOM | 1009 | CB | LEU A | 161 | 34.105 | 37.890 | 21.726 | 1.00 | 19.07 |
| ATOM | 1010 | CG | LEU A | 161 | 35.109 | 37.731 | 22.873 | 1.00 | 20.07 |
| ATOM | 1011 | CD1 | LEU A | 161 | 36.506 | 37.526 | 22.299 | 1.00 | 17.41 |
| ATOM | 1012 | CD2 | LEU A | 161 | 35.074 | 38.967 | 23.773 | 1.00 | 14.84 |
| ATOM | 1013 | C | LEU A | 161 | 31.815 | 38.538 | 20.932 | 1.00 | 19.72 |
| ATOM | 1014 | O | LEU A | 161 | 31.718 | 39.702 | 20.543 | 1.00 | 18.72 |
| ATOM | 1015 | N | ARG A | 162 | 31.192 | 37.530 | 20.329 | 1.00 | 18.38 |
| ATOM | 1016 | CA | ARG A | 162 | 30.345 | 37.781 | 19.166 | 1.00 | 19.35 |
| ATOM | 1017 | CB | ARG A | 162 | 29.871 | 36.469 | 18.543 | 1.00 | 17.39 |
| ATOM | 1018 | CG | ARG A | 162 | 30.917 | 35.783 | 17.676 | 1.00 | 18.97 |
| ATOM | 1019 | CD | ARG A | 162 | 30.314 | 34.562 | 17.002 | 1.00 | 19.54 |
| ATOM | 1020 | NE | ARG A | 162 | 31.228 | 33.917 | 16.068 | 1.00 | 19.77 |
| ATOM | 1021 | CZ | ARG A | 162 | 30.929 | 32.814 | 15.395 | 1.00 | 20.70 |
| ATOM | 1022 | NH1 | ARG A | 162 | 29.741 | 32.248 | 15.564 | 1.00 | 21.29 |
| ATOM | 1023 | NH2 | ARG A | 162 | 31.808 | 32.277 | 14.560 | 1.00 | 19.65 |
| ATOM | 1024 | C | ARG A | 162 | 29.133 | 38.631 | 19.535 | 1.00 | 18.62 |
| ATOM | 1025 | O | ARG A | 162 | 28.631 | 39.396 | 18.716 | 1.00 | 18.15 |
| ATOM | 1026 | N | ALA A | 163 | 28.675 | 38.498 | 20.773 | 1.00 | 18.36 |
| ATOM | 1027 | CA | ALA A | 163 | 27.518 | 39.251 | 21.248 | 1.00 | 19.15 |
| ATOM | 1028 | CB | ALA A | 163 | 27.121 | 38.765 | 22.644 | 1.00 | 17.76 |

TABLE 31-continued

| | | | | | | | | | |
|---|---|---|---|---|---|---|---|---|---|
| ATOM | 1029 | C | ALA A | 163 | 27.770 | 40.758 | 21.275 | 1.00 | 19.03 |
| ATOM | 1030 | O | ALA A | 163 | 26.829 | 41.544 | 21.340 | 1.00 | 17.57 |
| ATOM | 1031 | N | ARG A | 164 | 29.041 | 41.152 | 21.221 | 1.00 | 19.26 |
| ATOM | 1032 | CA | ARG A | 164 | 29.414 | 42.565 | 21.254 | 1.00 | 20.90 |
| ATOM | 1033 | CB | ARG A | 164 | 29.975 | 42.924 | 22.637 | 1.00 | 21.75 |
| ATOM | 1034 | CG | ARG A | 164 | 31.237 | 42.143 | 23.013 | 1.00 | 20.72 |
| ATOM | 1035 | CD | ARG A | 164 | 31.734 | 42.494 | 24.411 | 1.00 | 18.57 |
| ATOM | 1036 | NE | ARG A | 164 | 32.268 | 43.851 | 24.502 | 1.00 | 16.65 |
| ATOM | 1037 | CZ | ARG A | 164 | 33.417 | 44.250 | 23.962 | 1.00 | 17.53 |
| ATOM | 1038 | NH1 | ARG A | 164 | 34.174 | 43.398 | 23.281 | 1.00 | 15.56 |
| ATOM | 1039 | NH2 | ARG A | 164 | 33.819 | 45.506 | 24.115 | 1.00 | 17.21 |
| ATOM | 1040 | C | ARG A | 164 | 30.462 | 42.885 | 20.194 | 1.00 | 21.89 |
| ATOM | 1041 | O | ARG A | 164 | 31.128 | 43.919 | 20.260 | 1.00 | 21.63 |
| ATOM | 1042 | N | GLN A | 165 | 30.595 | 41.995 | 19.216 | 1.00 | 22.72 |
| ATOM | 1043 | CA | GLN A | 165 | 31.576 | 42.151 | 18.157 | 1.00 | 23.14 |
| ATOM | 1044 | CB | GLN A | 165 | 31.411 | 41.026 | 17.128 | 1.00 | 24.10 |
| ATOM | 1045 | CG | GLN A | 165 | 32.334 | 41.139 | 15.926 | 1.00 | 26.13 |
| ATOM | 1046 | CD | GLN A | 165 | 32.461 | 39.833 | 15.158 | 1.00 | 27.06 |
| ATOM | 1047 | OE1 | GLN A | 165 | 31.513 | 39.057 | 15.068 | 1.00 | 27.74 |
| ATOM | 1048 | NE2 | GLN A | 165 | 33.637 | 39.593 | 14.590 | 1.00 | 29.00 |
| ATOM | 1049 | C | GLN A | 165 | 31.538 | 43.507 | 17.462 | 1.00 | 24.15 |
| ATOM | 1050 | O | GLN A | 165 | 32.587 | 44.092 | 17.189 | 1.00 | 23.74 |
| ATOM | 1051 | N | GLN A | 166 | 30.343 | 44.013 | 17.178 | 1.00 | 23.33 |
| ATOM | 1052 | CA | GLN A | 166 | 30.239 | 45.298 | 16.505 | 1.00 | 24.01 |
| ATOM | 1053 | CB | GLN A | 166 | 28.863 | 45.464 | 15.855 | 1.00 | 25.30 |
| ATOM | 1054 | CG | GLN A | 166 | 28.623 | 44.498 | 14.703 | 1.00 | 26.42 |
| ATOM | 1055 | CD | GLN A | 166 | 29.765 | 44.486 | 13.703 | 1.00 | 28.04 |
| ATOM | 1056 | OE1 | GLN A | 166 | 30.215 | 45.538 | 13.241 | 1.00 | 29.98 |
| ATOM | 1057 | NE2 | GLN A | 166 | 30.234 | 43.291 | 13.356 | 1.00 | 28.88 |
| ATOM | 1058 | C | GLN A | 166 | 30.522 | 46.450 | 17.451 | 1.00 | 22.96 |
| ATOM | 1059 | O | GLN A | 166 | 31.075 | 47.471 | 17.042 | 1.00 | 22.74 |
| ATOM | 1060 | N | LYS A | 167 | 30.147 | 46.298 | 18.715 | 1.00 | 22.13 |
| ATOM | 1061 | CA | LYS A | 167 | 30.432 | 47.347 | 19.681 | 1.00 | 21.57 |
| ATOM | 1062 | CB | LYS A | 167 | 29.868 | 47.004 | 21.060 | 1.00 | 21.33 |
| ATOM | 1063 | CG | LYS A | 167 | 30.360 | 47.954 | 22.141 | 1.00 | 26.86 |
| ATOM | 1064 | CD | LYS A | 167 | 29.860 | 47.587 | 23.528 | 1.00 | 30.91 |
| ATOM | 1065 | CE | LYS A | 167 | 28.377 | 47.871 | 23.681 | 1.00 | 34.06 |
| ATOM | 1066 | NZ | LYS A | 167 | 27.936 | 47.697 | 25.092 | 1.00 | 36.77 |
| ATOM | 1067 | C | LYS A | 167 | 31.951 | 47.478 | 19.773 | 1.00 | 21.05 |
| ATOM | 1068 | O | LYS A | 167 | 32.486 | 48.586 | 19.789 | 1.00 | 22.09 |
| ATOM | 1069 | N | GLN A | 168 | 32.642 | 46.340 | 19.818 | 1.00 | 19.71 |
| ATOM | 1070 | CA | GLN A | 168 | 34.100 | 46.339 | 19.909 | 1.00 | 18.61 |
| ATOM | 1071 | CB | GLN A | 168 | 34.630 | 44.914 | 20.104 | 1.00 | 17.41 |
| ATOM | 1072 | CG | GLN A | 168 | 36.150 | 44.837 | 20.262 | 1.00 | 16.23 |
| ATOM | 1073 | CD | GLN A | 168 | 36.658 | 45.632 | 21.465 | 1.00 | 17.12 |
| ATOM | 1074 | OE1 | GLN A | 168 | 36.286 | 45.356 | 22.609 | 1.00 | 16.33 |
| ATOM | 1075 | NE2 | GLN A | 168 | 37.505 | 46.624 | 21.208 | 1.00 | 15.46 |
| ATOM | 1076 | C | GLN A | 168 | 34.732 | 46.957 | 18.669 | 1.00 | 18.91 |
| ATOM | 1077 | O | GLN A | 168 | 35.774 | 47.600 | 18.755 | 1.00 | 18.77 |
| ATOM | 1078 | N | ALA A | 169 | 34.102 | 46.771 | 17.514 | 1.00 | 19.76 |
| ATOM | 1079 | CA | ALA A | 169 | 34.643 | 47.341 | 16.282 | 1.00 | 20.87 |
| ATOM | 1080 | CB | ALA A | 169 | 33.802 | 46.913 | 15.083 | 1.00 | 20.96 |
| ATOM | 1081 | C | ALA A | 169 | 34.691 | 48.867 | 16.378 | 1.00 | 21.41 |
| ATOM | 1082 | O | ALA A | 169 | 35.629 | 49.498 | 15.890 | 1.00 | 21.80 |
| ATOM | 1083 | N | LYS A | 170 | 33.682 | 49.459 | 17.009 | 1.00 | 22.29 |
| ATOM | 1084 | CA | LYS A | 170 | 33.642 | 50.909 | 17.158 | 1.00 | 23.95 |
| ATOM | 1085 | CB | LYS A | 170 | 32.227 | 51.382 | 17.512 | 1.00 | 24.74 |
| ATOM | 1086 | CG | LYS A | 170 | 31.236 | 51.279 | 16.347 | 1.00 | 29.74 |
| ATOM | 1087 | CD | LYS A | 170 | 29.874 | 51.874 | 16.705 | 1.00 | 30.85 |
| ATOM | 1088 | CE | LYS A | 170 | 28.915 | 51.843 | 15.512 | 1.00 | 33.49 |
| ATOM | 1089 | NZ | LYS A | 170 | 28.547 | 50.458 | 15.087 | 1.00 | 32.56 |
| ATOM | 1090 | C | LYS A | 170 | 34.629 | 51.372 | 18.223 | 1.00 | 23.26 |
| ATOM | 1091 | O | LYS A | 170 | 35.224 | 52.441 | 18.099 | 1.00 | 23.47 |
| ATOM | 1092 | N | LEU A | 171 | 34.802 | 50.570 | 19.268 | 1.00 | 22.26 |
| ATOM | 1093 | CA | LEU A | 171 | 35.742 | 50.921 | 20.328 | 1.00 | 22.16 |
| ATOM | 1094 | CB | LEU A | 171 | 35.634 | 49.925 | 21.485 | 1.00 | 20.03 |
| ATOM | 1095 | CG | LEU A | 171 | 34.340 | 50.039 | 22.300 | 1.00 | 20.45 |
| ATOM | 1096 | CD1 | LEU A | 171 | 34.112 | 48.782 | 23.127 | 1.00 | 15.47 |
| ATOM | 1097 | CD2 | LEU A | 171 | 34.418 | 51.280 | 23.188 | 1.00 | 20.39 |
| ATOM | 1098 | C | LEU A | 171 | 37.161 | 50.926 | 19.757 | 1.00 | 21.88 |
| ATOM | 1099 | O | LEU A | 171 | 37.925 | 51.867 | 19.977 | 1.00 | 19.98 |
| ATOM | 1100 | N | THR A | 172 | 37.500 | 49.877 | 19.013 | 1.00 | 22.29 |
| ATOM | 1101 | CA | THR A | 172 | 38.821 | 49.763 | 18.396 | 1.00 | 22.96 |
| ATOM | 1102 | CB | THR A | 172 | 38.940 | 48.457 | 17.581 | 1.00 | 21.62 |
| ATOM | 1103 | OG1 | THR A | 172 | 38.883 | 47.335 | 18.474 | 1.00 | 21.62 |
| ATOM | 1104 | CG2 | THR A | 172 | 40.249 | 48.424 | 16.799 | 1.00 | 19.50 |
| ATOM | 1105 | C | THR A | 172 | 39.076 | 50.955 | 17.473 | 1.00 | 23.87 |
| ATOM | 1106 | O | THR A | 172 | 40.133 | 51.588 | 17.528 | 1.00 | 23.14 |
| ATOM | 1107 | N | GLU A | 173 | 38.100 | 51.257 | 16.628 | 1.00 | 24.87 |

TABLE 31-continued

| | | | | | | | | | |
|---|---|---|---|---|---|---|---|---|---|
| ATOM | 1108 | CA | GLU A | 173 | 38.215 | 52.382 | 15.710 | 1.00 | 27.68 |
| ATOM | 1109 | CB | GLU A | 173 | 36.962 | 52.477 | 14.835 | 1.00 | 31.02 |
| ATOM | 1110 | CG | GLU A | 173 | 37.047 | 53.531 | 13.743 | 1.00 | 39.64 |
| ATOM | 1111 | CD | GLU A | 173 | 38.105 | 53.207 | 12.696 | 1.00 | 43.67 |
| ATOM | 1112 | OE1 | GLU A | 173 | 38.366 | 54.069 | 11.828 | 1.00 | 45.72 |
| ATOM | 1113 | OE2 | GLU A | 173 | 38.669 | 52.089 | 12.736 | 1.00 | 46.35 |
| ATOM | 1114 | C | GLU A | 173 | 38.371 | 53.666 | 16.528 | 1.00 | 27.22 |
| ATOM | 1115 | O | GLU A | 173 | 38.926 | 54.655 | 16.057 | 1.00 | 27.62 |
| ATOM | 1116 | N | ASP A | 174 | 37.884 | 53.633 | 17.762 | 1.00 | 26.71 |
| ATOM | 1117 | CA | ASP A | 174 | 37.959 | 54.781 | 18.652 | 1.00 | 27.64 |
| ATOM | 1118 | CB | ASP A | 174 | 36.736 | 54.803 | 19.564 | 1.00 | 32.56 |
| ATOM | 1119 | CG | ASP A | 174 | 35.901 | 56.045 | 19.380 | 1.00 | 38.04 |
| ATOM | 1120 | OD1 | ASP A | 174 | 36.428 | 57.159 | 19.615 | 1.00 | 39.70 |
| ATOM | 1121 | OD2 | ASP A | 174 | 34.718 | 55.907 | 18.997 | 1.00 | 41.14 |
| ATOM | 1122 | C | ASP A | 174 | 39.224 | 54.814 | 19.512 | 1.00 | 26.26 |
| ATOM | 1123 | O | ASP A | 174 | 39.353 | 55.667 | 20.382 | 1.00 | 25.02 |
| ATOM | 1124 | N | GLY A | 175 | 40.143 | 53.879 | 19.281 | 1.00 | 24.50 |
| ATOM | 1125 | CA | GLY A | 175 | 41.377 | 53.854 | 20.052 | 1.00 | 23.56 |
| ATOM | 1126 | C | GLY A | 175 | 41.362 | 52.979 | 21.297 | 1.00 | 22.22 |
| ATOM | 1127 | O | GLY A | 175 | 42.154 | 53.190 | 22.210 | 1.00 | 22.02 |
| ATOM | 1128 | N | LEU A | 176 | 40.469 | 51.996 | 21.332 | 1.00 | 21.00 |
| ATOM | 1129 | CA | LEU A | 176 | 40.355 | 51.089 | 22.474 | 1.00 | 19.94 |
| ATOM | 1130 | CB | LEU A | 176 | 39.066 | 51.392 | 23.245 | 1.00 | 17.55 |
| ATOM | 1131 | CG | LEU A | 176 | 39.050 | 52.786 | 23.882 | 1.00 | 16.90 |
| ATOM | 1132 | CD1 | LEU A | 176 | 37.707 | 53.069 | 24.539 | 1.00 | 16.22 |
| ATOM | 1133 | CD2 | LEU A | 176 | 40.170 | 52.863 | 24.913 | 1.00 | 17.20 |
| ATOM | 1134 | C | LEU A | 176 | 40.351 | 49.641 | 21.979 | 1.00 | 19.32 |
| ATOM | 1135 | O | LEU A | 176 | 39.322 | 48.964 | 22.011 | 1.00 | 20.05 |
| ATOM | 1136 | N | PRO A | 177 | 41.517 | 49.152 | 21.522 | 1.00 | 16.90 |
| ATOM | 1137 | CD | PRO A | 177 | 42.774 | 49.917 | 21.486 | 1.00 | 15.26 |
| ATOM | 1138 | CA | PRO A | 177 | 41.722 | 47.797 | 20.997 | 1.00 | 16.11 |
| ATOM | 1139 | CB | PRO A | 177 | 43.185 | 47.814 | 20.534 | 1.00 | 16.45 |
| ATOM | 1140 | CG | PRO A | 177 | 43.491 | 49.272 | 20.340 | 1.00 | 15.90 |
| ATOM | 1141 | C | PRO A | 177 | 41.466 | 46.673 | 21.995 | 1.00 | 16.18 |
| ATOM | 1142 | O | PRO A | 177 | 41.512 | 46.870 | 23.211 | 1.00 | 16.44 |
| ATOM | 1143 | N | LEU A | 178 | 41.216 | 45.485 | 21.459 | 1.00 | 15.12 |
| ATOM | 1144 | CA | LEU A | 178 | 40.958 | 44.303 | 22.268 | 1.00 | 15.59 |
| ATOM | 1145 | CB | LEU A | 178 | 39.567 | 43.744 | 21.957 | 1.00 | 15.24 |
| ATOM | 1146 | CG | LEU A | 178 | 39.190 | 42.414 | 22.620 | 1.00 | 15.95 |
| ATOM | 1147 | CD1 | LEU A | 178 | 39.216 | 42.567 | 24.138 | 1.00 | 14.48 |
| ATOM | 1148 | CD2 | LEU A | 178 | 37.804 | 41.986 | 22.152 | 1.00 | 14.88 |
| ATOM | 1149 | C | LEU A | 178 | 42.006 | 43.239 | 21.965 | 1.00 | 14.93 |
| ATOM | 1150 | O | LEU A | 178 | 42.315 | 42.977 | 20.804 | 1.00 | 14.69 |
| ATOM | 1151 | N | GLY A | 179 | 42.559 | 42.639 | 23.013 | 1.00 | 15.57 |
| ATOM | 1152 | CA | GLY A | 179 | 43.546 | 41.592 | 22.832 | 1.00 | 13.53 |
| ATOM | 1153 | C | GLY A | 179 | 43.036 | 40.292 | 23.430 | 1.00 | 13.94 |
| ATOM | 1154 | O | GLY A | 179 | 42.314 | 40.313 | 24.427 | 1.00 | 12.42 |
| ATOM | 1155 | N | VAL A | 180 | 43.391 | 39.164 | 22.818 | 1.00 | 13.58 |
| ATOM | 1156 | CA | VAL A | 180 | 42.985 | 37.856 | 23.326 | 1.00 | 13.10 |
| ATOM | 1157 | CB | VAL A | 180 | 42.060 | 37.114 | 22.348 | 1.00 | 12.34 |
| ATOM | 1158 | CG1 | VAL A | 180 | 41.785 | 35.713 | 22.872 | 1.00 | 10.35 |
| ATOM | 1159 | CG2 | VAL A | 180 | 40.762 | 37.880 | 22.176 | 1.00 | 13.73 |
| ATOM | 1160 | C | VAL A | 180 | 44.223 | 36.995 | 23.566 | 1.00 | 13.99 |
| ATOM | 1161 | O | VAL A | 180 | 45.028 | 36.769 | 22.658 | 1.00 | 14.16 |
| ATOM | 1162 | N | ASN A | 181 | 44.360 | 36.519 | 24.797 | 1.00 | 14.29 |
| ATOM | 1163 | CA | ASN A | 181 | 45.494 | 35.701 | 25.204 | 1.00 | 15.91 |
| ATOM | 1164 | CB | ASN A | 181 | 45.891 | 36.089 | 26.632 | 1.00 | 16.63 |
| ATOM | 1165 | CG | ASN A | 181 | 47.170 | 35.433 | 27.086 | 1.00 | 17.72 |
| ATOM | 1166 | OD1 | ASN A | 181 | 47.332 | 34.214 | 26.986 | 1.00 | 16.04 |
| ATOM | 1167 | ND2 | ASN A | 181 | 48.092 | 36.241 | 27.606 | 1.00 | 18.08 |
| ATOM | 1168 | C | ASN A | 181 | 45.118 | 34.215 | 25.126 | 1.00 | 16.42 |
| ATOM | 1169 | O | ASN A | 181 | 44.143 | 33.775 | 25.744 | 1.00 | 14.66 |
| ATOM | 1170 | N | LEU A | 182 | 45.903 | 33.456 | 24.366 | 1.00 | 16.83 |
| ATOM | 1171 | CA | LEU A | 182 | 45.665 | 32.030 | 24.158 | 1.00 | 17.66 |
| ATOM | 1172 | CB | LEU A | 182 | 45.895 | 31.683 | 22.688 | 1.00 | 16.07 |
| ATOM | 1173 | CG | LEU A | 182 | 45.063 | 32.452 | 21.667 | 1.00 | 17.09 |
| ATOM | 1174 | CD1 | LEU A | 182 | 45.506 | 32.068 | 20.259 | 1.00 | 15.57 |
| ATOM | 1175 | CD2 | LEU A | 182 | 43.585 | 32.135 | 21.876 | 1.00 | 16.09 |
| ATOM | 1176 | C | LEU A | 182 | 46.536 | 31.112 | 25.007 | 1.00 | 17.78 |
| ATOM | 1177 | O | LEU A | 182 | 47.742 | 31.310 | 25.121 | 1.00 | 19.45 |
| ATOM | 1178 | N | GLY A | 183 | 45.913 | 30.091 | 25.581 | 1.00 | 19.38 |
| ATOM | 1179 | CA | GLY A | 183 | 46.636 | 29.132 | 26.395 | 1.00 | 20.04 |
| ATOM | 1180 | C | GLY A | 183 | 46.373 | 27.736 | 25.863 | 1.00 | 21.64 |
| ATOM | 1181 | O | GLY A | 183 | 45.763 | 27.580 | 24.805 | 1.00 | 20.21 |
| ATOM | 1182 | N | LYS A | 184 | 46.823 | 26.716 | 26.584 | 1.00 | 22.24 |
| ATOM | 1183 | CA | LYS A | 184 | 46.608 | 25.345 | 26.141 | 1.00 | 23.65 |
| ATOM | 1184 | CB | LYS A | 184 | 47.910 | 24.746 | 25.599 | 1.00 | 25.57 |
| ATOM | 1185 | CG | LYS A | 184 | 48.874 | 24.293 | 26.670 | 1.00 | 28.71 |
| ATOM | 1186 | CD | LYS A | 184 | 49.505 | 22.955 | 26.300 | 1.00 | 32.25 |

TABLE 31-continued

| | | | | | | | | | |
|---|---|---|---|---|---|---|---|---|---|
| ATOM | 1187 | CE | LYS A | 184 | 50.079 | 22.260 | 27.534 | 1.00 | 35.22 |
| ATOM | 1188 | NZ | LYS A | 184 | 50.604 | 20.898 | 27.229 | 1.00 | 37.42 |
| ATOM | 1189 | C | LYS A | 184 | 46.067 | 24.466 | 27.266 | 1.00 | 23.40 |
| ATOM | 1190 | O | LYS A | 184 | 46.339 | 24.699 | 28.443 | 1.00 | 23.34 |
| ATOM | 1191 | N | ASN A | 185 | 45.293 | 23.455 | 26.893 | 1.00 | 24.12 |
| ATOM | 1192 | CA | ASN A | 185 | 44.712 | 22.542 | 27.866 | 1.00 | 24.81 |
| ATOM | 1193 | CB | ASN A | 185 | 43.674 | 21.640 | 27.194 | 1.00 | 22.02 |
| ATOM | 1194 | CG | ASN A | 185 | 42.349 | 22.341 | 26.979 | 1.00 | 21.04 |
| ATOM | 1195 | OD1 | ASN A | 185 | 41.860 | 22.442 | 25.853 | 1.00 | 18.81 |
| ATOM | 1196 | ND2 | ASN A | 185 | 41.758 | 22.830 | 28.064 | 1.00 | 19.40 |
| ATOM | 1197 | C | ASN A | 185 | 45.758 | 21.684 | 28.567 | 1.00 | 26.33 |
| ATOM | 1198 | O | ASN A | 185 | 46.753 | 21.271 | 27.970 | 1.00 | 26.09 |
| ATOM | 1199 | N | LYS A | 186 | 45.502 | 21.411 | 29.841 | 1.00 | 28.32 |
| ATOM | 1200 | CA | LYS A | 186 | 46.389 | 20.610 | 30.672 | 1.00 | 31.00 |
| ATOM | 1201 | CB | LYS A | 186 | 45.758 | 20.442 | 32.057 | 1.00 | 31.57 |
| ATOM | 1202 | CG | LYS A | 186 | 46.588 | 19.640 | 33.039 | 1.00 | 34.30 |
| ATOM | 1203 | CD | LYS A | 186 | 45.932 | 19.624 | 34.412 | 1.00 | 36.90 |
| ATOM | 1204 | CE | LYS A | 186 | 46.830 | 18.965 | 35.444 | 1.00 | 38.54 |
| ATOM | 1205 | NZ | LYS A | 186 | 46.265 | 19.074 | 36.824 | 1.00 | 42.77 |
| ATOM | 1206 | C | LYS A | 186 | 46.707 | 19.236 | 30.080 | 1.00 | 31.61 |
| ATOM | 1207 | O | LYS A | 186 | 47.846 | 18.781 | 30.131 | 1.00 | 30.28 |
| ATOM | 1208 | N | THR A | 187 | 45.696 | 18.584 | 29.516 | 1.00 | 33.93 |
| ATOM | 1209 | CA | THR A | 187 | 45.868 | 17.253 | 28.944 | 1.00 | 36.41 |
| ATOM | 1210 | CB | THR A | 187 | 44.687 | 16.339 | 29.318 | 1.00 | 36.67 |
| ATOM | 1211 | OG1 | THR A | 187 | 43.495 | 16.815 | 28.678 | 1.00 | 35.00 |
| ATOM | 1212 | CG2 | THR A | 187 | 44.479 | 16.335 | 30.830 | 1.00 | 36.74 |
| ATOM | 1213 | C | THR A | 187 | 46.005 | 17.243 | 27.427 | 1.00 | 37.64 |
| ATOM | 1214 | O | THR A | 187 | 45.789 | 16.214 | 26.788 | 1.00 | 38.91 |
| ATOM | 1215 | N | SER A | 188 | 46.359 | 18.382 | 26.847 | 1.00 | 38.56 |
| ATOM | 1216 | CA | SER A | 188 | 46.524 | 18.457 | 25.402 | 1.00 | 38.88 |
| ATOM | 1217 | CB | SER A | 188 | 46.703 | 19.908 | 24.962 | 1.00 | 39.09 |
| ATOM | 1218 | OG | SER A | 188 | 46.982 | 19.984 | 23.576 | 1.00 | 39.52 |
| ATOM | 1219 | C | SER A | 188 | 47.738 | 17.639 | 24.971 | 1.00 | 39.36 |
| ATOM | 1220 | O | SER A | 188 | 48.759 | 17.621 | 25.655 | 1.00 | 39.30 |
| ATOM | 1221 | N | VAL A | 189 | 47.619 | 16.967 | 23.832 | 1.00 | 39.91 |
| ATOM | 1222 | CA | VAL A | 189 | 48.702 | 16.146 | 23.302 | 1.00 | 41.03 |
| ATOM | 1223 | CB | VAL A | 189 | 48.152 | 14.828 | 22.714 | 1.00 | 42.23 |
| ATOM | 1224 | CG1 | VAL A | 189 | 49.287 | 14.003 | 22.127 | 1.00 | 43.91 |
| ATOM | 1225 | CG2 | VAL A | 189 | 47.421 | 14.040 | 23.794 | 1.00 | 42.66 |
| ATOM | 1226 | C | VAL A | 189 | 49.466 | 16.881 | 22.203 | 1.00 | 40.93 |
| ATOM | 1227 | O | VAL A | 189 | 50.556 | 16.469 | 21.807 | 1.00 | 42.30 |
| ATOM | 1228 | N | ASP A | 190 | 48.891 | 17.979 | 21.721 | 1.00 | 39.41 |
| ATOM | 1229 | CA | ASP A | 190 | 49.493 | 18.764 | 20.649 | 1.00 | 36.64 |
| ATOM | 1230 | CB | ASP A | 190 | 48.748 | 18.467 | 19.344 | 1.00 | 38.93 |
| ATOM | 1231 | CG | ASP A | 190 | 49.462 | 19.001 | 18.120 | 1.00 | 40.37 |
| ATOM | 1232 | OD1 | ASP A | 190 | 50.152 | 20.038 | 18.225 | 1.00 | 40.59 |
| ATOM | 1233 | OD2 | ASP A | 190 | 49.314 | 18.382 | 17.045 | 1.00 | 42.48 |
| ATOM | 1234 | C | ASP A | 190 | 49.392 | 20.258 | 20.981 | 1.00 | 34.58 |
| ATOM | 1235 | O | ASP A | 190 | 48.405 | 20.913 | 20.639 | 1.00 | 33.67 |
| ATOM | 1236 | N | ALA A | 191 | 50.416 | 20.792 | 21.642 | 1.00 | 31.42 |
| ATOM | 1237 | CA | ALA A | 191 | 50.432 | 22.200 | 22.033 | 1.00 | 27.87 |
| ATOM | 1238 | CB | ALA A | 191 | 51.759 | 22.539 | 22.708 | 1.00 | 27.00 |
| ATOM | 1239 | C | ALA A | 191 | 50.199 | 23.138 | 20.857 | 1.00 | 26.64 |
| ATOM | 1240 | O | ALA A | 191 | 49.386 | 24.059 | 20.932 | 1.00 | 24.74 |
| ATOM | 1241 | N | ALA A | 192 | 50.925 | 22.906 | 19.772 | 1.00 | 25.42 |
| ATOM | 1242 | CA | ALA A | 192 | 50.796 | 23.739 | 18.590 | 1.00 | 25.28 |
| ATOM | 1243 | CB | ALA A | 192 | 51.725 | 23.233 | 17.487 | 1.00 | 24.03 |
| ATOM | 1244 | C | ALA A | 192 | 49.356 | 23.769 | 18.096 | 1.00 | 24.83 |
| ATOM | 1245 | O | ALA A | 192 | 48.840 | 24.829 | 17.761 | 1.00 | 25.43 |
| ATOM | 1246 | N | GLU A | 193 | 48.704 | 22.611 | 18.052 | 1.00 | 24.14 |
| ATOM | 1247 | CA | GLU A | 193 | 47.325 | 22.565 | 17.587 | 1.00 | 24.59 |
| ATOM | 1248 | CB | GLU A | 193 | 46.840 | 21.117 | 17.459 | 1.00 | 27.03 |
| ATOM | 1249 | CG | GLU A | 193 | 45.429 | 20.999 | 16.885 | 1.00 | 31.53 |
| ATOM | 1250 | CD | GLU A | 193 | 45.284 | 21.623 | 15.496 | 1.00 | 35.25 |
| ATOM | 1251 | OE1 | GLU A | 193 | 44.134 | 21.818 | 15.051 | 1.00 | 36.27 |
| ATOM | 1252 | OE2 | GLU A | 193 | 46.312 | 21.911 | 14.842 | 1.00 | 37.72 |
| ATOM | 1253 | C | GLU A | 193 | 46.407 | 23.356 | 18.522 | 1.00 | 24.21 |
| ATOM | 1254 | O | GLU A | 193 | 45.480 | 24.022 | 18.059 | 1.00 | 23.61 |
| ATOM | 1255 | N | ASP A | 194 | 46.664 | 23.292 | 19.828 | 1.00 | 21.48 |
| ATOM | 1256 | CA | ASP A | 194 | 45.861 | 24.047 | 20.791 | 1.00 | 22.74 |
| ATOM | 1257 | CB | ASP A | 194 | 46.396 | 23.855 | 22.214 | 1.00 | 21.86 |
| ATOM | 1258 | CG | ASP A | 194 | 45.696 | 22.732 | 22.952 | 1.00 | 23.25 |
| ATOM | 1259 | OD1 | ASP A | 194 | 45.166 | 21.826 | 22.282 | 1.00 | 26.44 |
| ATOM | 1260 | OD2 | ASP A | 194 | 45.680 | 22.747 | 24.203 | 1.00 | 23.07 |
| ATOM | 1261 | C | ASP A | 194 | 45.876 | 25.537 | 20.430 | 1.00 | 23.39 |
| ATOM | 1262 | O | ASP A | 194 | 44.822 | 26.167 | 20.304 | 1.00 | 24.67 |
| ATOM | 1263 | N | TYR A | 195 | 47.066 | 26.102 | 20.255 | 1.00 | 20.91 |
| ATOM | 1264 | CA | TYR A | 195 | 47.154 | 27.507 | 19.900 | 1.00 | 21.95 |
| ATOM | 1265 | CB | TYR A | 195 | 48.609 | 27.981 | 19.918 | 1.00 | 22.02 |

TABLE 31-continued

| | | | | | | | | | |
|---|---|---|---|---|---|---|---|---|---|
| ATOM | 1266 | CG | TYR A | 195 | 49.211 | 27.972 | 21.304 | 1.00 | 22.80 |
| ATOM | 1267 | CD1 | TYR A | 195 | 50.009 | 26.921 | 21.732 | 1.00 | 25.25 |
| ATOM | 1268 | CE1 | TYR A | 195 | 50.518 | 26.887 | 23.020 | 1.00 | 24.25 |
| ATOM | 1269 | CD2 | TYR A | 195 | 48.939 | 28.992 | 22.202 | 1.00 | 22.50 |
| ATOM | 1270 | CE2 | TYR A | 195 | 49.442 | 28.968 | 23.491 | 1.00 | 23.44 |
| ATOM | 1271 | CZ | TYR A | 195 | 50.229 | 27.913 | 23.895 | 1.00 | 23.86 |
| ATOM | 1272 | OH | TYR A | 195 | 50.721 | 27.882 | 25.181 | 1.00 | 26.06 |
| ATOM | 1273 | C | TYR A | 195 | 46.531 | 27.748 | 18.532 | 1.00 | 21.73 |
| ATOM | 1274 | O | TYR A | 195 | 45.922 | 28.788 | 18.300 | 1.00 | 20.92 |
| ATOM | 1275 | N | ALA A | 196 | 46.676 | 26.776 | 17.635 | 1.00 | 22.63 |
| ATOM | 1276 | CA | ALA A | 196 | 46.114 | 26.882 | 16.291 | 1.00 | 22.46 |
| ATOM | 1277 | CB | ALA A | 196 | 46.454 | 25.641 | 15.477 | 1.00 | 21.74 |
| ATOM | 1278 | C | ALA A | 196 | 44.599 | 27.057 | 16.366 | 1.00 | 22.46 |
| ATOM | 1279 | O | ALA A | 196 | 44.031 | 27.903 | 15.672 | 1.00 | 22.82 |
| ATOM | 1280 | N | GLU A | 197 | 43.950 | 26.252 | 17.204 | 1.00 | 21.69 |
| ATOM | 1281 | CA | GLU A | 197 | 42.501 | 26.342 | 17.364 | 1.00 | 23.49 |
| ATOM | 1282 | CB | GLU A | 197 | 41.985 | 25.303 | 18.370 | 1.00 | 26.37 |
| ATOM | 1283 | CG | GLU A | 197 | 42.357 | 23.863 | 18.050 | 1.00 | 35.55 |
| ATOM | 1284 | CD | GLU A | 197 | 41.608 | 22.855 | 18.917 | 1.00 | 40.35 |
| ATOM | 1285 | OE1 | GLU A | 197 | 42.041 | 21.682 | 18.981 | 1.00 | 40.76 |
| ATOM | 1286 | OE2 | GLU A | 197 | 40.579 | 23.235 | 19.524 | 1.00 | 43.83 |
| ATOM | 1287 | C | GLU A | 197 | 42.162 | 27.737 | 17.869 | 1.00 | 21.55 |
| ATOM | 1288 | O | GLU A | 197 | 41.214 | 28.368 | 17.396 | 1.00 | 20.17 |
| ATOM | 1289 | N | GLY A | 198 | 42.955 | 28.208 | 18.831 | 1.00 | 19.05 |
| ATOM | 1290 | CA | GLY A | 198 | 42.744 | 29.522 | 19.401 | 1.00 | 16.82 |
| ATOM | 1291 | C | GLY A | 198 | 42.790 | 30.622 | 18.362 | 1.00 | 16.04 |
| ATOM | 1292 | O | GLY A | 198 | 41.967 | 31.538 | 18.381 | 1.00 | 13.85 |
| ATOM | 1293 | N | VAL A | 199 | 43.757 | 30.538 | 17.455 | 1.00 | 16.13 |
| ATOM | 1294 | CA | VAL A | 199 | 43.894 | 31.534 | 16.403 | 1.00 | 15.39 |
| ATOM | 1295 | CB | VAL A | 199 | 45.144 | 31.268 | 15.543 | 1.00 | 15.53 |
| ATOM | 1296 | CG1 | VAL A | 199 | 45.175 | 32.225 | 14.351 | 1.00 | 12.07 |
| ATOM | 1297 | CG2 | VAL A | 199 | 46.400 | 31.424 | 16.393 | 1.00 | 14.66 |
| ATOM | 1298 | C | VAL A | 199 | 42.666 | 31.502 | 15.500 | 1.00 | 16.99 |
| ATOM | 1299 | O | VAL A | 199 | 42.127 | 32.544 | 15.126 | 1.00 | 15.25 |
| ATOM | 1300 | N | ARG A | 200 | 42.219 | 30.296 | 15.167 | 1.00 | 18.08 |
| ATOM | 1301 | CA | ARG A | 200 | 41.062 | 30.119 | 14.296 | 1.00 | 20.59 |
| ATOM | 1302 | CB | ARG A | 200 | 40.949 | 28.656 | 13.851 | 1.00 | 21.75 |
| ATOM | 1303 | CG | ARG A | 200 | 42.052 | 28.201 | 12.911 | 1.00 | 25.45 |
| ATOM | 1304 | CD | ARG A | 200 | 41.661 | 26.913 | 12.209 | 1.00 | 26.76 |
| ATOM | 1305 | NE | ARG A | 200 | 41.756 | 25.748 | 13.079 | 1.00 | 27.81 |
| ATOM | 1306 | CZ | ARG A | 200 | 42.857 | 25.022 | 13.229 | 1.00 | 31.77 |
| ATOM | 1307 | NH1 | ARG A | 200 | 43.957 | 25.343 | 12.562 | 1.00 | 32.51 |
| ATOM | 1308 | NH2 | ARG A | 200 | 42.861 | 23.974 | 14.045 | 1.00 | 32.64 |
| ATOM | 1309 | C | ARG A | 200 | 39.730 | 30.546 | 14.900 | 1.00 | 19.16 |
| ATOM | 1310 | O | ARG A | 200 | 38.882 | 31.105 | 14.207 | 1.00 | 19.15 |
| ATOM | 1311 | N | VAL A | 201 | 39.541 | 30.288 | 16.188 | 1.00 | 18.46 |
| ATOM | 1312 | CA | VAL A | 201 | 38.276 | 30.624 | 16.825 | 1.00 | 16.58 |
| ATOM | 1313 | CB | VAL A | 201 | 37.964 | 29.635 | 17.981 | 1.00 | 16.58 |
| ATOM | 1314 | CG1 | VAL A | 201 | 36.661 | 30.031 | 18.685 | 1.00 | 13.59 |
| ATOM | 1315 | CG2 | VAL A | 201 | 37.853 | 28.212 | 17.424 | 1.00 | 12.80 |
| ATOM | 1316 | C | VAL A | 201 | 38.161 | 32.053 | 17.342 | 1.00 | 17.72 |
| ATOM | 1317 | O | VAL A | 201 | 37.132 | 32.702 | 17.138 | 1.00 | 17.43 |
| ATOM | 1318 | N | LEU A | 202 | 39.208 | 32.555 | 17.994 | 1.00 | 16.85 |
| ATOM | 1319 | CA | LEU A | 202 | 39.156 | 33.906 | 18.544 | 1.00 | 16.20 |
| ATOM | 1320 | CB | LEU A | 202 | 39.657 | 33.895 | 19.990 | 1.00 | 16.83 |
| ATOM | 1321 | CG | LEU A | 202 | 38.747 | 33.119 | 20.947 | 1.00 | 18.98 |
| ATOM | 1322 | CD1 | LEU A | 202 | 39.256 | 33.246 | 22.379 | 1.00 | 16.76 |
| ATOM | 1323 | CD2 | LEU A | 202 | 37.325 | 33.664 | 20.831 | 1.00 | 16.77 |
| ATOM | 1324 | C | LEU A | 202 | 39.903 | 34.962 | 17.741 | 1.00 | 16.51 |
| ATOM | 1325 | O | LEU A | 202 | 39.632 | 36.157 | 17.872 | 1.00 | 15.03 |
| ATOM | 1326 | N | GLY A | 203 | 40.839 | 34.521 | 16.909 | 1.00 | 16.09 |
| ATOM | 1327 | CA | GLY A | 203 | 41.597 | 35.453 | 16.100 | 1.00 | 16.71 |
| ATOM | 1328 | C | GLY A | 203 | 40.737 | 36.446 | 15.338 | 1.00 | 16.82 |
| ATOM | 1329 | O | GLY A | 203 | 41.079 | 37.626 | 15.261 | 1.00 | 15.75 |
| ATOM | 1330 | N | PRO A | 204 | 39.611 | 36.003 | 14.760 | 1.00 | 17.04 |
| ATOM | 1331 | CD | PRO A | 204 | 39.177 | 34.601 | 14.618 | 1.00 | 17.18 |
| ATOM | 1332 | CA | PRO A | 204 | 38.729 | 36.900 | 14.003 | 1.00 | 17.32 |
| ATOM | 1333 | CB | PRO A | 204 | 37.713 | 35.941 | 13.371 | 1.00 | 16.93 |
| ATOM | 1334 | CG | PRO A | 204 | 38.451 | 34.630 | 13.306 | 1.00 | 17.12 |
| ATOM | 1335 | C | PRO A | 204 | 38.043 | 37.955 | 14.869 | 1.00 | 17.63 |
| ATOM | 1336 | O | PRO A | 204 | 37.494 | 38.928 | 14.354 | 1.00 | 17.99 |
| ATOM | 1337 | N | LEU A | 205 | 38.079 | 37.759 | 16.184 | 1.00 | 17.45 |
| ATOM | 1338 | CA | LEU A | 205 | 37.433 | 38.682 | 17.116 | 1.00 | 16.83 |
| ATOM | 1339 | CB | LEU A | 205 | 36.565 | 37.888 | 18.101 | 1.00 | 16.28 |
| ATOM | 1340 | CG | LEU A | 205 | 35.394 | 37.106 | 17.488 | 1.00 | 20.11 |
| ATOM | 1341 | CD1 | LEU A | 205 | 35.041 | 35.896 | 18.335 | 1.00 | 17.62 |
| ATOM | 1342 | CD2 | LEU A | 205 | 34.203 | 38.035 | 17.350 | 1.00 | 20.89 |
| ATOM | 1343 | C | LEU A | 205 | 38.420 | 39.546 | 17.900 | 1.00 | 17.46 |
| ATOM | 1344 | O | LEU A | 205 | 38.015 | 40.316 | 18.772 | 1.00 | 16.55 |

TABLE 31-continued

| | | | | | | | | | |
|---|---|---|---|---|---|---|---|---|---|
| ATOM | 1345 | N | ALA | A | 206 | 39.706 | 39.443 | 17.580 | 1.00 15.70 |
| ATOM | 1346 | CA | ALA | A | 206 | 40.707 | 40.200 | 18.318 | 1.00 16.71 |
| ATOM | 1347 | CB | ALA | A | 206 | 41.608 | 39.229 | 19.077 | 1.00 17.67 |
| ATOM | 1348 | C | ALA | A | 206 | 41.563 | 41.150 | 17.494 | 1.00 18.08 |
| ATOM | 1349 | O | ALA | A | 206 | 41.810 | 40.926 | 16.313 | 1.00 20.90 |
| ATOM | 1350 | N | ASP | A | 207 | 42.015 | 42.225 | 18.123 | 1.00 17.59 |
| ATOM | 1351 | CA | ASP | A | 207 | 42.877 | 43.159 | 17.431 | 1.00 18.07 |
| ATOM | 1352 | CB | ASP | A | 207 | 42.816 | 44.532 | 18.090 | 1.00 17.18 |
| ATOM | 1353 | CG | ASP | A | 207 | 41.508 | 45.246 | 17.787 | 1.00 18.63 |
| ATOM | 1354 | OD1 | ASP | A | 207 | 41.170 | 45.360 | 16.594 | 1.00 19.40 |
| ATOM | 1355 | OD2 | ASP | A | 207 | 40.813 | 45.684 | 18.725 | 1.00 19.83 |
| ATOM | 1356 | C | ASP | A | 207 | 44.270 | 42.553 | 17.470 | 1.00 18.03 |
| ATOM | 1357 | O | ASP | A | 207 | 45.050 | 42.708 | 16.533 | 1.00 17.72 |
| ATOM | 1358 | N | TYR | A | 208 | 44.572 | 41.843 | 18.554 | 1.00 17.96 |
| ATOM | 1359 | CA | TYR | A | 208 | 45.850 | 41.150 | 18.662 | 1.00 17.00 |
| ATOM | 1360 | CB | TYR | A | 208 | 46.946 | 42.049 | 19.267 | 1.00 17.79 |
| ATOM | 1361 | CG | TYR | A | 208 | 46.848 | 42.358 | 20.750 | 1.00 17.93 |
| ATOM | 1362 | CD1 | TYR | A | 208 | 46.344 | 43.577 | 21.197 | 1.00 18.65 |
| ATOM | 1363 | CE1 | TYR | A | 208 | 46.324 | 43.897 | 22.546 | 1.00 17.54 |
| ATOM | 1364 | CD2 | TYR | A | 208 | 47.324 | 41.461 | 21.699 | 1.00 16.58 |
| ATOM | 1365 | CE2 | TYR | A | 208 | 47.306 | 41.768 | 23.052 | 1.00 18.19 |
| ATOM | 1366 | CZ | TYR | A | 208 | 46.806 | 42.986 | 23.471 | 1.00 19.57 |
| ATOM | 1367 | OH | TYR | A | 208 | 46.776 | 43.286 | 24.817 | 1.00 18.19 |
| ATOM | 1368 | C | TYR | A | 208 | 45.691 | 39.866 | 19.475 | 1.00 16.78 |
| ATOM | 1369 | O | TYR | A | 208 | 44.864 | 39.790 | 20.389 | 1.00 15.50 |
| ATOM | 1370 | N | LEU | A | 209 | 46.460 | 38.849 | 19.101 | 1.00 15.49 |
| ATOM | 1371 | CA | LEU | A | 209 | 46.437 | 37.562 | 19.783 | 1.00 17.52 |
| ATOM | 1372 | CB | LEU | A | 209 | 46.324 | 36.413 | 18.778 | 1.00 17.27 |
| ATOM | 1373 | CG | LEU | A | 209 | 44.998 | 36.199 | 18.047 | 1.00 18.45 |
| ATOM | 1374 | CD1 | LEU | A | 209 | 45.167 | 35.096 | 17.003 | 1.00 18.80 |
| ATOM | 1375 | CD2 | LEU | A | 209 | 43.916 | 35.825 | 19.044 | 1.00 16.66 |
| ATOM | 1376 | C | LEU | A | 209 | 47.729 | 37.400 | 20.570 | 1.00 17.91 |
| ATOM | 1377 | O | LEU | A | 209 | 48.780 | 37.893 | 20.160 | 1.00 17.96 |
| ATOM | 1378 | N | VAL | A | 210 | 47.653 | 36.701 | 21.695 | 1.00 17.39 |
| ATOM | 1379 | CA | VAL | A | 210 | 48.833 | 36.483 | 22.518 | 1.00 17.32 |
| ATOM | 1380 | CB | VAL | A | 210 | 48.673 | 37.088 | 23.933 | 1.00 17.21 |
| ATOM | 1381 | CG1 | VAL | A | 210 | 49.973 | 36.919 | 24.714 | 1.00 15.24 |
| ATOM | 1382 | CG2 | VAL | A | 210 | 48.279 | 38.559 | 23.840 | 1.00 16.48 |
| ATOM | 1383 | C | VAL | A | 210 | 49.109 | 35.003 | 22.695 | 1.00 17.74 |
| ATOM | 1384 | O | VAL | A | 210 | 48.290 | 34.276 | 23.257 | 1.00 18.14 |
| ATOM | 1385 | N | VAL | A | 211 | 50.256 | 34.552 | 22.204 | 1.00 18.02 |
| ATOM | 1386 | CA | VAL | A | 211 | 50.630 | 33.159 | 22.373 | 1.00 18.15 |
| ATOM | 1387 | CB | VAL | A | 211 | 51.608 | 32.682 | 21.271 | 1.00 17.93 |
| ATOM | 1388 | CG1 | VAL | A | 211 | 51.994 | 31.226 | 21.508 | 1.00 17.07 |
| ATOM | 1389 | CG2 | VAL | A | 211 | 50.953 | 32.819 | 19.905 | 1.00 17.85 |
| ATOM | 1390 | C | VAL | A | 211 | 51.318 | 33.115 | 23.734 | 1.00 18.99 |
| ATOM | 1391 | O | VAL | A | 211 | 52.486 | 33.486 | 23.868 | 1.00 18.16 |
| ATOM | 1392 | N | ASN | A | 212 | 50.569 | 32.695 | 24.750 | 1.00 19.69 |
| ATOM | 1393 | CA | ASN | A | 212 | 51.100 | 32.615 | 26.098 | 1.00 19.88 |
| ATOM | 1394 | CB | ASN | A | 212 | 49.972 | 32.681 | 27.128 | 1.00 20.27 |
| ATOM | 1395 | CG | ASN | A | 212 | 50.492 | 32.616 | 28.547 | 1.00 18.89 |
| ATOM | 1396 | OD1 | ASN | A | 212 | 51.694 | 32.723 | 28.770 | 1.00 21.39 |
| ATOM | 1397 | ND2 | ASN | A | 212 | 49.597 | 32.444 | 29.511 | 1.00 17.08 |
| ATOM | 1398 | C | ASN | A | 212 | 51.899 | 31.333 | 26.279 | 1.00 21.25 |
| ATOM | 1399 | O | ASN | A | 212 | 51.346 | 30.238 | 26.408 | 1.00 21.20 |
| ATOM | 1400 | N | VAL | A | 213 | 53.214 | 31.489 | 26.305 | 1.00 20.47 |
| ATOM | 1401 | CA | VAL | A | 213 | 54.113 | 30.362 | 26.442 | 1.00 21.67 |
| ATOM | 1402 | CB | VAL | A | 213 | 55.010 | 30.280 | 25.182 | 1.00 23.71 |
| ATOM | 1403 | CG1 | VAL | A | 213 | 55.981 | 31.460 | 25.150 | 1.00 23.82 |
| ATOM | 1404 | CG2 | VAL | A | 213 | 55.748 | 28.982 | 25.152 | 1.00 27.31 |
| ATOM | 1405 | C | VAL | A | 213 | 54.975 | 30.539 | 27.698 | 1.00 21.91 |
| ATOM | 1406 | O | VAL | A | 213 | 56.029 | 29.908 | 27.843 | 1.00 22.46 |
| ATOM | 1407 | N | SER | A | 214 | 54.506 | 31.384 | 28.614 | 1.00 20.82 |
| ATOM | 1408 | CA | SER | A | 214 | 55.255 | 31.684 | 29.829 | 1.00 20.65 |
| ATOM | 1409 | CB | SER | A | 214 | 55.741 | 33.136 | 29.782 | 1.00 20.36 |
| ATOM | 1410 | OG | SER | A | 214 | 54.666 | 34.034 | 29.547 | 1.00 15.52 |
| ATOM | 1411 | C | SER | A | 214 | 54.531 | 31.442 | 31.150 | 1.00 22.40 |
| ATOM | 1412 | O | SER | A | 214 | 54.998 | 31.881 | 32.207 | 1.00 19.56 |
| ATOM | 1413 | N | SER | A | 215 | 53.390 | 30.763 | 31.106 | 1.00 22.46 |
| ATOM | 1414 | CA | SER | A | 215 | 52.683 | 30.482 | 32.344 | 1.00 23.77 |
| ATOM | 1415 | CB | SER | A | 215 | 51.326 | 29.839 | 32.071 | 1.00 25.30 |
| ATOM | 1416 | OG | SER | A | 215 | 50.707 | 29.476 | 33.296 | 1.00 24.25 |
| ATOM | 1417 | C | SER | A | 215 | 53.531 | 29.518 | 33.168 | 1.00 23.82 |
| ATOM | 1418 | O | SER | A | 215 | 53.986 | 28.488 | 32.673 | 1.00 23.43 |
| ATOM | 1419 | N | PRO | A | 216 | 53.763 | 29.845 | 34.438 | 1.00 24.01 |
| ATOM | 1420 | CD | PRO | A | 216 | 53.529 | 31.120 | 35.142 | 1.00 22.46 |
| ATOM | 1421 | CA | PRO | A | 216 | 54.572 | 28.931 | 35.244 | 1.00 25.17 |
| ATOM | 1422 | CB | PRO | A | 216 | 55.177 | 29.857 | 36.287 | 1.00 24.52 |
| ATOM | 1423 | CG | PRO | A | 216 | 54.042 | 30.826 | 36.538 | 1.00 23.00 |

TABLE 31-continued

| | | | | | | | | |
|---|---|---|---|---|---|---|---|---|
| ATOM | 1424 | C | PRO A | 216 | 53.712 | 27.841 | 35.881 | 1.00 26.39 |
| ATOM | 1425 | O | PRO A | 216 | 54.233 | 26.928 | 36.518 | 1.00 26.20 |
| ATOM | 1426 | N | ASN A | 217 | 52.397 | 27.923 | 35.685 | 1.00 27.51 |
| ATOM | 1427 | CA | ASN A | 217 | 51.485 | 26.964 | 36.304 | 1.00 29.22 |
| ATOM | 1428 | CB | ASN A | 217 | 50.343 | 27.732 | 36.966 | 1.00 28.29 |
| ATOM | 1429 | CG | ASN A | 217 | 50.851 | 28.799 | 37.913 | 1.00 29.28 |
| ATOM | 1430 | OD1 | ASN A | 217 | 51.615 | 28.507 | 38.836 | 1.00 29.47 |
| ATOM | 1431 | ND2 | ASN A | 217 | 50.440 | 30.046 | 37.686 | 1.00 27.94 |
| ATOM | 1432 | C | ASN A | 217 | 50.931 | 25.825 | 35.452 | 1.00 30.25 |
| ATOM | 1433 | O | ASN A | 217 | 49.928 | 25.204 | 35.808 | 1.00 29.74 |
| ATOM | 1434 | N | THR A | 218 | 51.584 | 25.550 | 34.331 | 1.00 31.98 |
| ATOM | 1435 | CA | THR A | 218 | 51.178 | 24.451 | 33.462 | 1.00 33.25 |
| ATOM | 1436 | CB | THR A | 218 | 50.484 | 24.949 | 32.177 | 1.00 33.36 |
| ATOM | 1437 | OG1 | THR A | 218 | 49.194 | 25.481 | 32.507 | 1.00 31.23 |
| ATOM | 1438 | CG2 | THR A | 218 | 50.317 | 23.800 | 31.187 | 1.00 31.71 |
| ATOM | 1439 | C | THR A | 218 | 52.440 | 23.680 | 33.096 | 1.00 33.78 |
| ATOM | 1440 | O | THR A | 218 | 53.319 | 24.198 | 32.406 | 1.00 35.20 |
| ATOM | 1441 | N | ALA A | 219 | 52.522 | 22.445 | 33.579 | 1.00 34.20 |
| ATOM | 1442 | CA | ALA A | 219 | 53.675 | 21.578 | 33.353 | 1.00 34.19 |
| ATOM | 1443 | CB | ALA A | 219 | 53.323 | 20.146 | 33.750 | 1.00 33.41 |
| ATOM | 1444 | C | ALA A | 219 | 54.256 | 21.593 | 31.939 | 1.00 34.71 |
| ATOM | 1445 | O | ALA A | 219 | 53.581 | 21.240 | 30.970 | 1.00 34.13 |
| ATOM | 1446 | N | GLY A | 220 | 55.517 | 22.010 | 31.839 | 1.00 34.72 |
| ATOM | 1447 | CA | GLY A | 220 | 56.212 | 22.041 | 30.562 | 1.00 35.48 |
| ATOM | 1448 | C | GLY A | 220 | 55.842 | 23.107 | 29.544 | 1.00 35.40 |
| ATOM | 1449 | O | GLY A | 220 | 56.396 | 23.117 | 28.446 | 1.00 35.16 |
| ATOM | 1450 | N | LEU A | 221 | 54.924 | 24.005 | 29.888 | 1.00 35.62 |
| ATOM | 1451 | CA | LEU A | 221 | 54.518 | 25.049 | 28.949 | 1.00 36.17 |
| ATOM | 1452 | CB | LEU A | 221 | 53.333 | 25.845 | 29.506 | 1.00 37.59 |
| ATOM | 1453 | CG | LEU A | 221 | 52.702 | 26.794 | 28.481 | 1.00 37.81 |
| ATOM | 1454 | CD1 | LEU A | 221 | 51.886 | 25.973 | 27.495 | 1.00 38.01 |
| ATOM | 1455 | CD2 | LEU A | 221 | 51.822 | 27.822 | 29.167 | 1.00 37.63 |
| ATOM | 1456 | C | LEU A | 221 | 55.652 | 26.019 | 28.614 | 1.00 36.27 |
| ATOM | 1457 | O | LEU A | 221 | 55.829 | 26.407 | 27.457 | 1.00 36.24 |
| ATOM | 1458 | N | ARG A | 222 | 56.415 | 26.410 | 29.630 | 1.00 35.57 |
| ATOM | 1459 | CA | ARG A | 222 | 57.516 | 27.350 | 29.441 | 1.00 35.99 |
| ATOM | 1460 | CB | ARG A | 222 | 58.064 | 27.787 | 30.801 | 1.00 35.50 |
| ATOM | 1461 | CG | ARG A | 222 | 57.107 | 28.675 | 31.588 | 1.00 35.37 |
| ATOM | 1462 | CD | ARG A | 222 | 57.621 | 28.891 | 32.997 | 1.00 37.33 |
| ATOM | 1463 | NE | ARG A | 222 | 57.660 | 27.637 | 33.746 | 1.00 37.02 |
| ATOM | 1464 | CZ | ARG A | 222 | 58.429 | 27.427 | 34.808 | 1.00 37.78 |
| ATOM | 1465 | NH1 | ARG A | 222 | 59.228 | 28.391 | 35.246 | 1.00 37.31 |
| ATOM | 1466 | NH2 | ARG A | 222 | 58.401 | 26.255 | 35.430 | 1.00 36.46 |
| ATOM | 1467 | C | ARG A | 222 | 58.650 | 26.820 | 28.565 | 1.00 35.63 |
| ATOM | 1468 | O | ARG A | 222 | 59.436 | 27.599 | 28.021 | 1.00 34.70 |
| ATOM | 1469 | N | SER A | 223 | 58.732 | 25.501 | 28.419 | 1.00 35.11 |
| ATOM | 1470 | CA | SER A | 223 | 59.775 | 24.910 | 27.591 | 1.00 34.96 |
| ATOM | 1471 | CB | SER A | 223 | 59.838 | 23.393 | 27.797 | 1.00 34.78 |
| ATOM | 1472 | OG | SER A | 223 | 58.724 | 22.749 | 27.205 | 1.00 35.91 |
| ATOM | 1473 | C | SER A | 223 | 59.491 | 25.222 | 26.123 | 1.00 34.64 |
| ATOM | 1474 | O | SER A | 223 | 60.346 | 25.025 | 25.261 | 1.00 34.71 |
| ATOM | 1475 | N | LEU A | 224 | 58.286 | 25.709 | 25.839 | 1.00 34.48 |
| ATOM | 1476 | CA | LEU A | 224 | 57.922 | 26.060 | 24.468 | 1.00 34.31 |
| ATOM | 1477 | CB | LEU A | 224 | 56.401 | 26.201 | 24.328 | 1.00 33.45 |
| ATOM | 1478 | CG | LEU A | 224 | 55.538 | 24.957 | 24.545 | 1.00 34.69 |
| ATOM | 1479 | CD1 | LEU A | 224 | 54.063 | 25.342 | 24.517 | 1.00 33.25 |
| ATOM | 1480 | CD2 | LEU A | 224 | 55.852 | 23.923 | 23.469 | 1.00 33.41 |
| ATOM | 1481 | C | LEU A | 224 | 58.611 | 27.363 | 24.060 | 1.00 32.98 |
| ATOM | 1482 | O | LEU A | 224 | 58.511 | 27.800 | 22.914 | 1.00 32.26 |
| ATOM | 1483 | N | GLN A | 225 | 59.302 | 27.987 | 25.012 | 1.00 33.62 |
| ATOM | 1484 | CA | GLN A | 225 | 60.037 | 29.223 | 24.740 | 1.00 33.44 |
| ATOM | 1485 | CB | GLN A | 225 | 60.248 | 30.028 | 26.034 | 1.00 32.87 |
| ATOM | 1486 | CG | GLN A | 225 | 58.958 | 30.580 | 26.637 | 1.00 32.65 |
| ATOM | 1487 | CD | GLN A | 225 | 59.166 | 31.235 | 27.994 | 1.00 31.96 |
| ATOM | 1488 | OE1 | GLN A | 225 | 59.017 | 32.450 | 28.142 | 1.00 30.99 |
| ATOM | 1489 | NE2 | GLN A | 225 | 59.513 | 30.428 | 28.993 | 1.00 30.44 |
| ATOM | 1490 | C | GLN A | 225 | 61.390 | 28.869 | 24.110 | 1.00 32.02 |
| ATOM | 1491 | O | GLN A | 225 | 62.107 | 29.746 | 23.630 | 1.00 30.91 |
| ATOM | 1492 | N | GLY A | 226 | 61.725 | 27.578 | 24.119 | 1.00 31.76 |
| ATOM | 1493 | CA | GLY A | 226 | 62.973 | 27.117 | 23.528 | 1.00 32.16 |
| ATOM | 1494 | C | GLY A | 226 | 62.982 | 27.411 | 22.037 | 1.00 32.87 |
| ATOM | 1495 | O | GLY A | 226 | 61.932 | 27.372 | 21.390 | 1.00 33.10 |
| ATOM | 1496 | N | LYS A | 227 | 64.161 | 27.685 | 21.483 | 1.00 31.88 |
| ATOM | 1497 | CA | LYS A | 227 | 64.279 | 28.027 | 20.069 | 1.00 31.63 |
| ATOM | 1498 | CB | LYS A | 227 | 65.750 | 28.190 | 19.673 | 1.00 29.76 |
| ATOM | 1499 | CG | LYS A | 227 | 65.909 | 28.842 | 18.309 | 1.00 30.36 |
| ATOM | 1500 | CD | LYS A | 227 | 67.320 | 29.337 | 18.047 | 1.00 31.75 |
| ATOM | 1501 | CE | LYS A | 227 | 67.360 | 30.139 | 16.750 | 1.00 33.43 |
| ATOM | 1502 | NZ | LYS A | 227 | 68.702 | 30.723 | 16.462 | 1.00 35.16 |

TABLE 31-continued

| | | | | | | | | | |
|---|---|---|---|---|---|---|---|---|---|
| ATOM | 1503 | C | LYS A | 227 | 63.593 | 27.099 | 19.068 | 1.00 | 31.84 |
| ATOM | 1504 | O | LYS A | 227 | 62.752 | 27.549 | 18.287 | 1.00 | 31.56 |
| ATOM | 1505 | N | ALA A | 228 | 63.945 | 25.818 | 19.081 | 1.00 | 31.83 |
| ATOM | 1506 | CA | ALA A | 228 | 63.357 | 24.862 | 18.141 | 1.00 | 33.57 |
| ATOM | 1507 | CB | ALA A | 228 | 63.962 | 23.479 | 18.353 | 1.00 | 32.38 |
| ATOM | 1508 | C | ALA A | 228 | 61.832 | 24.776 | 18.218 | 1.00 | 34.39 |
| ATOM | 1509 | O | ALA A | 228 | 61.149 | 24.865 | 17.197 | 1.00 | 34.34 |
| ATOM | 1510 | N | GLU A | 229 | 61.305 | 24.598 | 19.426 | 1.00 | 35.55 |
| ATOM | 1511 | CA | GLU A | 229 | 59.861 | 24.496 | 19.617 | 1.00 | 37.25 |
| ATOM | 1512 | CB | GLU A | 229 | 59.540 | 23.960 | 21.017 | 1.00 | 40.77 |
| ATOM | 1513 | CG | GLU A | 229 | 59.922 | 22.501 | 21.212 | 1.00 | 46.52 |
| ATOM | 1514 | CD | GLU A | 229 | 59.367 | 21.915 | 22.496 | 1.00 | 51.23 |
| ATOM | 1515 | OE1 | GLU A | 229 | 59.608 | 20.712 | 22.748 | 1.00 | 53.05 |
| ATOM | 1516 | OE2 | GLU A | 229 | 58.692 | 22.652 | 23.251 | 1.00 | 52.90 |
| ATOM | 1517 | C | GLU A | 229 | 59.123 | 25.812 | 19.399 | 1.00 | 35.01 |
| ATOM | 1518 | O | GLU A | 229 | 57.995 | 25.817 | 18.911 | 1.00 | 35.28 |
| ATOM | 1519 | N | LEU A | 230 | 59.749 | 26.926 | 19.759 | 1.00 | 31.93 |
| ATOM | 1520 | CA | LEU A | 230 | 59.105 | 28.214 | 19.578 | 1.00 | 29.21 |
| ATOM | 1521 | CB | LEU A | 230 | 59.935 | 29.341 | 20.210 | 1.00 | 27.50 |
| ATOM | 1522 | CG | LEU A | 230 | 59.254 | 30.717 | 20.189 | 1.00 | 25.31 |
| ATOM | 1523 | CD1 | LEU A | 230 | 57.949 | 30.639 | 20.966 | 1.00 | 22.54 |
| ATOM | 1524 | CD2 | LEU A | 230 | 60.166 | 31.775 | 20.791 | 1.00 | 25.43 |
| ATOM | 1525 | C | LEU A | 230 | 58.939 | 28.473 | 18.087 | 1.00 | 28.35 |
| ATOM | 1526 | O | LEU A | 230 | 57.897 | 28.959 | 17.645 | 1.00 | 28.45 |
| ATOM | 1527 | N | ARG A | 231 | 59.966 | 28.139 | 17.313 | 1.00 | 26.82 |
| ATOM | 1528 | CA | ARG A | 231 | 59.923 | 28.349 | 15.875 | 1.00 | 26.87 |
| ATOM | 1529 | CB | ARG A | 231 | 61.260 | 27.965 | 15.232 | 1.00 | 27.39 |
| ATOM | 1530 | CG | ARG A | 231 | 61.280 | 28.158 | 13.722 | 1.00 | 29.23 |
| ATOM | 1531 | CD | ARG A | 231 | 62.568 | 27.648 | 13.079 | 1.00 | 32.62 |
| ATOM | 1532 | NE | ARG A | 231 | 63.730 | 28.479 | 13.388 | 1.00 | 35.22 |
| ATOM | 1533 | CZ | ARG A | 231 | 64.755 | 28.084 | 14.139 | 1.00 | 35.71 |
| ATOM | 1534 | NH1 | ARG A | 231 | 64.764 | 26.866 | 14.665 | 1.00 | 35.83 |
| ATOM | 1535 | NH2 | ARG A | 231 | 65.777 | 28.902 | 14.355 | 1.00 | 35.67 |
| ATOM | 1536 | C | ARG A | 231 | 58.796 | 27.547 | 15.230 | 1.00 | 26.27 |
| ATOM | 1537 | O | ARG A | 231 | 58.007 | 28.083 | 14.452 | 1.00 | 24.54 |
| ATOM | 1538 | N | ARG A | 232 | 58.723 | 26.264 | 15.563 | 1.00 | 26.74 |
| ATOM | 1539 | CA | ARG A | 232 | 57.701 | 25.386 | 15.010 | 1.00 | 28.61 |
| ATOM | 1540 | CB | ARG A | 232 | 57.938 | 23.948 | 15.481 | 1.00 | 31.33 |
| ATOM | 1541 | CG | ARG A | 232 | 56.989 | 22.931 | 14.872 | 1.00 | 36.52 |
| ATOM | 1542 | CD | ARG A | 232 | 57.345 | 21.497 | 15.274 | 1.00 | 40.85 |
| ATOM | 1543 | NE | ARG A | 232 | 58.727 | 21.154 | 14.936 | 1.00 | 45.04 |
| ATOM | 1544 | CZ | ARG A | 232 | 59.747 | 21.220 | 15.788 | 1.00 | 46.48 |
| ATOM | 1545 | NH1 | ARG A | 232 | 59.548 | 21.611 | 17.041 | 1.00 | 47.37 |
| ATOM | 1546 | NH2 | ARG A | 232 | 60.971 | 20.899 | 15.387 | 1.00 | 45.94 |
| ATOM | 1547 | C | ARG A | 232 | 56.311 | 25.860 | 15.426 | 1.00 | 28.53 |
| ATOM | 1548 | O | ARG A | 232 | 55.395 | 25.942 | 14.603 | 1.00 | 29.20 |
| ATOM | 1549 | N | LEU A | 233 | 56.162 | 26.184 | 16.706 | 1.00 | 26.18 |
| ATOM | 1550 | CA | LEU A | 233 | 54.891 | 26.659 | 17.229 | 1.00 | 24.46 |
| ATOM | 1551 | CB | LEU A | 233 | 55.008 | 26.890 | 18.737 | 1.00 | 23.72 |
| ATOM | 1552 | CG | LEU A | 233 | 53.841 | 27.633 | 19.387 | 1.00 | 25.00 |
| ATOM | 1553 | CD1 | LEU A | 233 | 52.574 | 26.806 | 19.272 | 1.00 | 26.45 |
| ATOM | 1554 | CD2 | LEU A | 233 | 54.168 | 27.907 | 20.842 | 1.00 | 27.05 |
| ATOM | 1555 | C | LEU A | 233 | 54.409 | 27.948 | 16.544 | 1.00 | 24.04 |
| ATOM | 1556 | O | LEU A | 233 | 53.270 | 28.024 | 16.083 | 1.00 | 22.35 |
| ATOM | 1557 | N | LEU A | 234 | 55.279 | 28.952 | 16.470 | 1.00 | 23.30 |
| ATOM | 1558 | CA | LEU A | 234 | 54.911 | 30.231 | 15.864 | 1.00 | 24.03 |
| ATOM | 1559 | CB | LEU A | 234 | 55.935 | 31.308 | 16.235 | 1.00 | 24.63 |
| ATOM | 1560 | CG | LEU A | 234 | 56.001 | 31.602 | 17.736 | 1.00 | 27.77 |
| ATOM | 1561 | CD1 | LEU A | 234 | 56.990 | 32.737 | 18.006 | 1.00 | 29.67 |
| ATOM | 1562 | CD2 | LEU A | 234 | 54.612 | 31.965 | 18.237 | 1.00 | 26.11 |
| ATOM | 1563 | C | LEU A | 234 | 54.731 | 30.183 | 14.352 | 1.00 | 23.42 |
| ATOM | 1564 | O | LEU A | 234 | 53.975 | 30.974 | 13.790 | 1.00 | 24.20 |
| ATOM | 1565 | N | THR A | 235 | 55.427 | 29.269 | 13.688 | 1.00 | 23.68 |
| ATOM | 1566 | CA | THR A | 235 | 55.285 | 29.139 | 12.242 | 1.00 | 23.60 |
| ATOM | 1567 | CB | THR A | 235 | 56.254 | 28.084 | 11.671 | 1.00 | 22.71 |
| ATOM | 1568 | OG1 | THR A | 235 | 57.600 | 28.546 | 11.819 | 1.00 | 24.30 |
| ATOM | 1569 | CG2 | THR A | 235 | 55.966 | 27.833 | 10.196 | 1.00 | 21.44 |
| ATOM | 1570 | C | THR A | 235 | 53.846 | 28.699 | 11.959 | 1.00 | 23.27 |
| ATOM | 1571 | O | THR A | 235 | 53.188 | 29.221 | 11.060 | 1.00 | 22.47 |
| ATOM | 1572 | N | LYS A | 236 | 53.364 | 27.745 | 12.750 | 1.00 | 21.09 |
| ATOM | 1573 | CA | LYS A | 236 | 52.011 | 27.235 | 12.597 | 1.00 | 22.24 |
| ATOM | 1574 | CB | LYS A | 236 | 51.827 | 25.988 | 13.468 | 1.00 | 23.70 |
| ATOM | 1575 | CG | LYS A | 236 | 50.541 | 25.236 | 13.196 | 1.00 | 30.31 |
| ATOM | 1576 | CD | LYS A | 236 | 50.512 | 23.894 | 13.916 | 1.00 | 33.61 |
| ATOM | 1577 | CE | LYS A | 236 | 49.235 | 23.136 | 13.588 | 1.00 | 34.03 |
| ATOM | 1578 | NZ | LYS A | 236 | 49.184 | 21.805 | 14.253 | 1.00 | 39.23 |
| ATOM | 1579 | C | LYS A | 236 | 50.980 | 28.309 | 12.966 | 1.00 | 21.56 |
| ATOM | 1580 | O | LYS A | 236 | 49.988 | 28.500 | 12.258 | 1.00 | 20.17 |
| ATOM | 1581 | N | VAL A | 237 | 51.223 | 29.015 | 14.068 | 1.00 | 19.27 |

TABLE 31-continued

| | | | | | | | | |
|---|---|---|---|---|---|---|---|---|
| ATOM | 1582 | CA | VAL A | 237 | 50.320 | 30.075 | 14.502 | 1.00 | 19.15 |
| ATOM | 1583 | CB | VAL A | 237 | 50.792 | 30.714 | 15.829 | 1.00 | 18.47 |
| ATOM | 1584 | CG1 | VAL A | 237 | 50.037 | 32.014 | 16.080 | 1.00 | 13.34 |
| ATOM | 1585 | CG2 | VAL A | 237 | 50.562 | 29.741 | 16.981 | 1.00 | 15.49 |
| ATOM | 1586 | C | VAL A | 237 | 50.199 | 31.176 | 13.454 | 1.00 | 20.61 |
| ATOM | 1587 | O | VAL A | 237 | 49.091 | 31.571 | 13.089 | 1.00 | 21.34 |
| ATOM | 1588 | N | LEU A | 238 | 51.336 | 31.671 | 12.970 | 1.00 | 22.56 |
| ATOM | 1589 | CA | LEU A | 238 | 51.337 | 32.729 | 11.960 | 1.00 | 23.63 |
| ATOM | 1590 | CB | LEU A | 238 | 52.771 | 33.179 | 11.658 | 1.00 | 23.97 |
| ATOM | 1591 | CG | LEU A | 238 | 53.528 | 33.907 | 12.780 | 1.00 | 26.60 |
| ATOM | 1592 | CD1 | LEU A | 238 | 54.919 | 34.302 | 12.291 | 1.00 | 25.27 |
| ATOM | 1593 | CD2 | LEU A | 238 | 52.757 | 35.147 | 13.205 | 1.00 | 24.92 |
| ATOM | 1594 | C | LEU A | 238 | 50.656 | 32.270 | 10.668 | 1.00 | 23.77 |
| ATOM | 1595 | O | LEU A | 238 | 50.020 | 33.066 | 9.967 | 1.00 | 22.47 |
| ATOM | 1596 | N | GLN A | 239 | 50.785 | 30.983 | 10.363 | 1.00 | 23.65 |
| ATOM | 1597 | CA | GLN A | 239 | 50.181 | 30.415 | 9.163 | 1.00 | 25.14 |
| ATOM | 1598 | CB | GLN A | 239 | 50.674 | 28.981 | 8.971 | 1.00 | 28.29 |
| ATOM | 1599 | CG | GLN A | 239 | 50.626 | 28.477 | 7.541 | 1.00 | 35.77 |
| ATOM | 1600 | CD | GLN A | 239 | 51.286 | 27.113 | 7.398 | 1.00 | 41.56 |
| ATOM | 1601 | OE1 | GLN A | 239 | 52.403 | 26.895 | 7.886 | 1.00 | 42.96 |
| ATOM | 1602 | NE2 | GLN A | 239 | 50.601 | 26.187 | 6.726 | 1.00 | 40.56 |
| ATOM | 1603 | C | GLN A | 239 | 48.657 | 30.441 | 9.305 | 1.00 | 23.70 |
| ATOM | 1604 | O | GLN A | 239 | 47.941 | 30.845 | 8.385 | 1.00 | 23.65 |
| ATOM | 1605 | N | GLU A | 240 | 48.167 | 30.013 | 10.465 | 1.00 | 21.97 |
| ATOM | 1606 | CA | GLU A | 240 | 46.734 | 30.010 | 10.730 | 1.00 | 20.44 |
| ATOM | 1607 | CB | GLU A | 240 | 46.448 | 29.386 | 12.095 | 1.00 | 22.95 |
| ATOM | 1608 | CG | GLU A | 240 | 46.828 | 27.919 | 12.198 | 1.00 | 29.40 |
| ATOM | 1609 | CD | GLU A | 240 | 45.887 | 26.998 | 11.430 | 1.00 | 33.44 |
| ATOM | 1610 | OE1 | GLU A | 240 | 46.180 | 25.782 | 11.370 | 1.00 | 35.38 |
| ATOM | 1611 | OE2 | GLU A | 240 | 44.855 | 27.476 | 10.900 | 1.00 | 32.33 |
| ATOM | 1612 | C | GLU A | 240 | 46.221 | 31.447 | 10.701 | 1.00 | 19.08 |
| ATOM | 1613 | O | GLU A | 240 | 45.164 | 31.725 | 10.139 | 1.00 | 19.25 |
| ATOM | 1614 | N | ARG A | 241 | 46.983 | 32.357 | 11.302 | 1.00 | 16.60 |
| ATOM | 1615 | CA | ARG A | 241 | 46.618 | 33.770 | 11.342 | 1.00 | 16.03 |
| ATOM | 1616 | CB | ARG A | 241 | 47.645 | 34.546 | 12.184 | 1.00 | 14.90 |
| ATOM | 1617 | CG | ARG A | 241 | 47.330 | 36.025 | 12.422 | 1.00 | 14.73 |
| ATOM | 1618 | CD | ARG A | 241 | 47.582 | 36.887 | 11.187 | 1.00 | 14.81 |
| ATOM | 1619 | NE | ARG A | 241 | 48.978 | 36.867 | 10.751 | 1.00 | 16.28 |
| ATOM | 1620 | CZ | ARG A | 241 | 49.961 | 37.579 | 11.303 | 1.00 | 18.91 |
| ATOM | 1621 | NH1 | ARG A | 241 | 51.195 | 37.478 | 10.824 | 1.00 | 19.86 |
| ATOM | 1622 | NH2 | ARG A | 241 | 49.719 | 38.400 | 12.321 | 1.00 | 15.94 |
| ATOM | 1623 | C | ARG A | 241 | 46.529 | 34.366 | 9.934 | 1.00 | 16.63 |
| ATOM | 1624 | O | ARG A | 241 | 45.598 | 35.116 | 9.631 | 1.00 | 15.25 |
| ATOM | 1625 | N | ASP A | 242 | 47.492 | 34.037 | 9.074 | 1.00 | 18.61 |
| ATOM | 1626 | CA | ASP A | 242 | 47.494 | 34.565 | 7.708 | 1.00 | 19.30 |
| ATOM | 1627 | CB | ASP A | 242 | 48.831 | 34.274 | 7.012 | 1.00 | 19.94 |
| ATOM | 1628 | CG | ASP A | 242 | 49.997 | 35.047 | 7.626 | 1.00 | 22.29 |
| ATOM | 1629 | OD1 | ASP A | 242 | 49.753 | 36.079 | 8.285 | 1.00 | 22.41 |
| ATOM | 1630 | OD2 | ASP A | 242 | 51.158 | 34.631 | 7.438 | 1.00 | 21.78 |
| ATOM | 1631 | C | ASP A | 242 | 46.344 | 34.020 | 6.860 | 1.00 | 19.63 |
| ATOM | 1632 | O | ASP A | 242 | 45.960 | 34.630 | 5.860 | 1.00 | 19.11 |
| ATOM | 1633 | N | GLY A | 243 | 45.792 | 32.879 | 7.261 | 1.00 | 18.88 |
| ATOM | 1634 | CA | GLY A | 243 | 44.690 | 32.299 | 6.516 | 1.00 | 18.95 |
| ATOM | 1635 | C | GLY A | 243 | 43.362 | 32.995 | 6.781 | 1.00 | 20.52 |
| ATOM | 1636 | O | GLY A | 243 | 42.352 | 32.681 | 6.145 | 1.00 | 20.72 |
| ATOM | 1637 | N | LEU A | 244 | 43.354 | 33.943 | 7.714 | 1.00 | 18.75 |
| ATOM | 1638 | CA | LEU A | 244 | 42.127 | 34.665 | 8.044 | 1.00 | 20.57 |
| ATOM | 1639 | CB | LEU A | 244 | 42.165 | 35.141 | 9.504 | 1.00 | 18.57 |
| ATOM | 1640 | CG | LEU A | 244 | 42.365 | 34.061 | 10.570 | 1.00 | 20.12 |
| ATOM | 1641 | CD1 | LEU A | 244 | 42.432 | 34.710 | 11.947 | 1.00 | 17.77 |
| ATOM | 1642 | CD2 | LEU A | 244 | 41.228 | 33.051 | 10.500 | 1.00 | 17.79 |
| ATOM | 1643 | C | LEU A | 244 | 41.893 | 35.870 | 7.131 | 1.00 | 20.23 |
| ATOM | 1644 | O | LEU A | 244 | 42.840 | 36.505 | 6.673 | 1.00 | 19.19 |
| ATOM | 1645 | N | ARG A | 245 | 40.626 | 36.180 | 6.872 | 1.00 | 20.66 |
| ATOM | 1646 | CA | ARG A | 245 | 40.283 | 37.325 | 6.036 | 1.00 | 21.47 |
| ATOM | 1647 | CB | ARG A | 245 | 38.759 | 37.419 | 5.884 | 1.00 | 20.91 |
| ATOM | 1648 | CG | ARG A | 245 | 38.193 | 36.330 | 4.950 | 1.00 | 20.87 |
| ATOM | 1649 | CD | ARG A | 245 | 36.720 | 36.044 | 5.198 | 1.00 | 21.09 |
| ATOM | 1650 | NE | ARG A | 245 | 35.835 | 37.118 | 4.758 | 1.00 | 22.13 |
| ATOM | 1651 | CZ | ARG A | 245 | 35.416 | 37.283 | 3.506 | 1.00 | 23.36 |
| ATOM | 1652 | NH1 | ARG A | 245 | 34.606 | 38.293 | 3.208 | 1.00 | 21.07 |
| ATOM | 1653 | NH2 | ARG A | 245 | 35.798 | 36.438 | 2.553 | 1.00 | 20.90 |
| ATOM | 1654 | C | ARG A | 245 | 40.875 | 38.593 | 6.662 | 1.00 | 23.84 |
| ATOM | 1655 | O | ARG A | 245 | 40.956 | 38.720 | 7.893 | 1.00 | 20.34 |
| ATOM | 1656 | N | ARG A | 246 | 41.291 | 39.523 | 5.803 | 1.00 | 25.07 |
| ATOM | 1657 | CA | ARG A | 246 | 41.939 | 40.756 | 6.232 | 1.00 | 26.56 |
| ATOM | 1658 | CB | ARG A | 246 | 42.161 | 41.672 | 5.025 | 1.00 | 29.73 |
| ATOM | 1659 | CG | ARG A | 246 | 43.280 | 41.141 | 4.145 | 1.00 | 37.20 |
| ATOM | 1660 | CD | ARG A | 246 | 43.693 | 42.065 | 3.006 | 1.00 | 41.04 |

TABLE 31-continued

| | | | | | | | | | |
|---|---|---|---|---|---|---|---|---|---|
| ATOM | 1661 | NE | ARG A | 246 | 44.801 | 41.472 | 2.258 | 1.00 | 40.54 |
| ATOM | 1662 | CZ | ARG A | 246 | 44.727 | 40.307 | 1.624 | 1.00 | 40.16 |
| ATOM | 1663 | NH1 | ARG A | 246 | 43.599 | 39.615 | 1.640 | 1.00 | 40.31 |
| ATOM | 1664 | NH2 | ARG A | 246 | 45.787 | 39.821 | 0.996 | 1.00 | 41.87 |
| ATOM | 1665 | C | ARG A | 246 | 41.371 | 41.555 | 7.394 | 1.00 | 25.25 |
| ATOM | 1666 | O | ARG A | 246 | 42.111 | 41.875 | 8.323 | 1.00 | 23.36 |
| ATOM | 1667 | N | VAL A | 247 | 40.083 | 41.881 | 7.370 | 1.00 | 24.09 |
| ATOM | 1668 | CA | VAL A | 247 | 39.527 | 42.654 | 8.473 | 1.00 | 24.28 |
| ATOM | 1669 | CB | VAL A | 247 | 38.099 | 43.170 | 8.149 | 1.00 | 26.35 |
| ATOM | 1670 | CG1 | VAL A | 247 | 38.126 | 43.983 | 6.861 | 1.00 | 25.68 |
| ATOM | 1671 | CG2 | VAL A | 247 | 37.130 | 42.017 | 8.029 | 1.00 | 27.49 |
| ATOM | 1672 | C | VAL A | 247 | 39.509 | 41.850 | 9.775 | 1.00 | 24.03 |
| ATOM | 1673 | O | VAL A | 247 | 39.357 | 42.413 | 10.857 | 1.00 | 23.84 |
| ATOM | 1674 | N | HIS A | 248 | 39.695 | 40.536 | 9.665 | 1.00 | 23.16 |
| ATOM | 1675 | CA | HIS A | 248 | 39.696 | 39.653 | 10.829 | 1.00 | 22.42 |
| ATOM | 1676 | CB | HIS A | 248 | 38.703 | 38.506 | 10.606 | 1.00 | 23.50 |
| ATOM | 1677 | CG | HIS A | 248 | 37.275 | 38.950 | 10.536 | 1.00 | 25.02 |
| ATOM | 1678 | CD2 | HIS A | 248 | 36.461 | 39.171 | 9.476 | 1.00 | 25.76 |
| ATOM | 1679 | ND1 | HIS A | 248 | 36.541 | 39.273 | 11.657 | 1.00 | 24.47 |
| ATOM | 1680 | CE1 | HIS A | 248 | 35.337 | 39.675 | 11.291 | 1.00 | 25.12 |
| ATOM | 1681 | NE2 | HIS A | 248 | 35.263 | 39.624 | 9.973 | 1.00 | 25.47 |
| ATOM | 1682 | C | HIS A | 248 | 41.083 | 39.076 | 11.113 | 1.00 | 20.89 |
| ATOM | 1683 | O | HIS A | 248 | 41.216 | 38.084 | 11.831 | 1.00 | 18.62 |
| ATOM | 1684 | N | ARG A | 249 | 42.110 | 39.708 | 10.559 | 1.00 | 19.69 |
| ATOM | 1685 | CA | ARG A | 249 | 43.484 | 39.242 | 10.730 | 1.00 | 20.69 |
| ATOM | 1686 | CB | ARG A | 249 | 44.226 | 39.385 | 9.399 | 1.00 | 20.68 |
| ATOM | 1687 | CG | ARG A | 249 | 45.425 | 38.475 | 9.227 | 1.00 | 24.73 |
| ATOM | 1688 | CD | ARG A | 249 | 46.029 | 38.640 | 7.830 | 1.00 | 24.81 |
| ATOM | 1689 | NE | ARG A | 249 | 45.120 | 38.193 | 6.778 | 1.00 | 24.85 |
| ATOM | 1690 | CZ | ARG A | 249 | 45.081 | 38.707 | 5.553 | 1.00 | 26.85 |
| ATOM | 1691 | NH1 | ARG A | 249 | 45.899 | 39.695 | 5.220 | 1.00 | 27.97 |
| ATOM | 1692 | NH2 | ARG A | 249 | 44.226 | 38.230 | 4.654 | 1.00 | 26.76 |
| ATOM | 1693 | C | ARG A | 249 | 44.193 | 40.043 | 11.830 | 1.00 | 19.79 |
| ATOM | 1694 | O | ARG A | 249 | 44.579 | 41.194 | 11.626 | 1.00 | 19.90 |
| ATOM | 1695 | N | PRO A | 250 | 44.371 | 39.437 | 13.014 | 1.00 | 18.06 |
| ATOM | 1696 | CD | PRO A | 250 | 43.843 | 38.125 | 13.435 | 1.00 | 16.95 |
| ATOM | 1697 | CA | PRO A | 250 | 45.029 | 40.112 | 14.136 | 1.00 | 18.31 |
| ATOM | 1698 | CB | PRO A | 250 | 44.465 | 39.376 | 15.343 | 1.00 | 16.97 |
| ATOM | 1699 | CG | PRO A | 250 | 44.438 | 37.960 | 14.837 | 1.00 | 17.39 |
| ATOM | 1700 | C | PRO A | 250 | 46.551 | 40.055 | 14.125 | 1.00 | 18.15 |
| ATOM | 1701 | O | PRO A | 250 | 47.160 | 39.265 | 13.396 | 1.00 | 18.56 |
| ATOM | 1702 | N | ALA A | 251 | 47.155 | 40.911 | 14.940 | 1.00 | 17.21 |
| ATOM | 1703 | CA | ALA A | 251 | 48.600 | 40.928 | 15.092 | 1.00 | 16.57 |
| ATOM | 1704 | CB | ALA A | 251 | 49.050 | 42.240 | 15.712 | 1.00 | 15.93 |
| ATOM | 1705 | C | ALA A | 251 | 48.861 | 39.775 | 16.056 | 1.00 | 15.37 |
| ATOM | 1706 | O | ALA A | 251 | 47.978 | 39.414 | 16.839 | 1.00 | 13.89 |
| ATOM | 1707 | N | VAL A | 252 | 50.051 | 39.185 | 15.986 | 1.00 | 15.17 |
| ATOM | 1708 | CA | VAL A | 252 | 50.405 | 38.076 | 16.864 | 1.00 | 15.31 |
| ATOM | 1709 | CB | VAL A | 252 | 50.732 | 36.796 | 16.060 | 1.00 | 16.18 |
| ATOM | 1710 | CG1 | VAL A | 252 | 51.332 | 35.733 | 16.983 | 1.00 | 13.26 |
| ATOM | 1711 | CG2 | VAL A | 252 | 49.455 | 36.255 | 15.397 | 1.00 | 15.46 |
| ATOM | 1712 | C | VAL A | 252 | 51.601 | 38.422 | 17.747 | 1.00 | 17.46 |
| ATOM | 1713 | O | VAL A | 252 | 52.667 | 38.806 | 17.258 | 1.00 | 16.99 |
| ATOM | 1714 | N | LEU A | 253 | 51.407 | 38.287 | 19.054 | 1.00 | 17.27 |
| ATOM | 1715 | CA | LEU A | 253 | 52.454 | 38.569 | 20.020 | 1.00 | 17.95 |
| ATOM | 1716 | CB | LEU A | 253 | 52.044 | 39.727 | 20.936 | 1.00 | 18.28 |
| ATOM | 1717 | CG | LEU A | 253 | 51.981 | 41.133 | 20.330 | 1.00 | 19.28 |
| ATOM | 1718 | CD1 | LEU A | 253 | 50.743 | 41.285 | 19.464 | 1.00 | 20.31 |
| ATOM | 1719 | CD2 | LEU A | 253 | 51.956 | 42.153 | 21.448 | 1.00 | 20.44 |
| ATOM | 1720 | C | LEU A | 253 | 52.738 | 37.332 | 20.865 | 1.00 | 19.31 |
| ATOM | 1721 | O | LEU A | 253 | 51.900 | 36.439 | 20.985 | 1.00 | 18.01 |
| ATOM | 1722 | N | VAL A | 254 | 53.932 | 37.283 | 21.440 | 1.00 | 19.14 |
| ATOM | 1723 | CA | VAL A | 254 | 54.319 | 36.171 | 22.290 | 1.00 | 19.38 |
| ATOM | 1724 | CB | VAL A | 254 | 55.595 | 35.473 | 21.753 | 1.00 | 19.88 |
| ATOM | 1725 | CG1 | VAL A | 254 | 56.036 | 34.380 | 22.708 | 1.00 | 20.19 |
| ATOM | 1726 | CG2 | VAL A | 254 | 55.326 | 34.893 | 20.377 | 1.00 | 19.39 |
| ATOM | 1727 | C | VAL A | 254 | 54.592 | 36.723 | 23.686 | 1.00 | 17.52 |
| ATOM | 1728 | O | VAL A | 254 | 55.307 | 37.706 | 23.835 | 1.00 | 16.58 |
| ATOM | 1729 | N | LYS A | 255 | 54.001 | 36.104 | 24.700 | 1.00 | 18.56 |
| ATOM | 1730 | CA | LYS A | 255 | 54.204 | 36.539 | 26.078 | 1.00 | 17.98 |
| ATOM | 1731 | CB | LYS A | 255 | 52.890 | 36.476 | 26.861 | 1.00 | 16.57 |
| ATOM | 1732 | CG | LYS A | 255 | 52.994 | 37.018 | 28.277 | 1.00 | 17.78 |
| ATOM | 1733 | CD | LYS A | 255 | 51.616 | 37.306 | 28.861 | 1.00 | 18.41 |
| ATOM | 1734 | CE | LYS A | 255 | 51.713 | 37.881 | 30.270 | 1.00 | 18.09 |
| ATOM | 1735 | NZ | LYS A | 255 | 50.374 | 38.287 | 30.777 | 1.00 | 17.48 |
| ATOM | 1736 | C | LYS A | 255 | 55.250 | 35.630 | 26.716 | 1.00 | 18.74 |
| ATOM | 1737 | O | LYS A | 255 | 55.067 | 34.412 | 26.799 | 1.00 | 18.62 |
| ATOM | 1738 | N | ILE A | 256 | 56.339 | 36.239 | 27.176 | 1.00 | 17.14 |
| ATOM | 1739 | CA | ILE A | 256 | 57.446 | 35.504 | 27.765 | 1.00 | 16.56 |

TABLE 31-continued

| | | | | | | | | | |
|---|---|---|---|---|---|---|---|---|---|
| ATOM | 1740 | CB | ILE A | 256 | 58.769 | 35.898 | 27.080 | 1.00 | 16.85 |
| ATOM | 1741 | CG2 | ILE A | 256 | 58.633 | 35.744 | 25.573 | 1.00 | 16.06 |
| ATOM | 1742 | CG1 | ILE A | 256 | 59.122 | 37.348 | 27.422 | 1.00 | 15.70 |
| ATOM | 1743 | CD1 | ILE A | 256 | 60.404 | 37.844 | 26.774 | 1.00 | 14.24 |
| ATOM | 1744 | C | ILE A | 256 | 57.629 | 35.668 | 29.268 | 1.00 | 17.29 |
| ATOM | 1745 | O | ILE A | 256 | 57.076 | 36.579 | 29.895 | 1.00 | 15.74 |
| ATOM | 1746 | N | ALA A | 257 | 58.433 | 34.778 | 29.835 | 1.00 | 16.30 |
| ATOM | 1747 | CA | ALA A | 257 | 58.715 | 34.795 | 31.263 | 1.00 | 18.80 |
| ATOM | 1748 | CB | ALA A | 257 | 59.079 | 33.381 | 31.740 | 1.00 | 17.75 |
| ATOM | 1749 | C | ALA A | 257 | 59.846 | 35.765 | 31.605 | 1.00 | 18.13 |
| ATOM | 1750 | O | ALA A | 257 | 60.594 | 36.211 | 30.733 | 1.00 | 17.13 |
| ATOM | 1751 | N | PRO A | 258 | 59.963 | 36.122 | 32.890 | 1.00 | 17.72 |
| ATOM | 1752 | CD | PRO A | 258 | 58.899 | 35.989 | 33.904 | 1.00 | 16.97 |
| ATOM | 1753 | CA | PRO A | 258 | 61.006 | 37.036 | 33.354 | 1.00 | 16.91 |
| ATOM | 1754 | CB | PRO A | 258 | 60.299 | 37.815 | 34.446 | 1.00 | 16.77 |
| ATOM | 1755 | CG | PRO A | 258 | 59.484 | 36.739 | 35.100 | 1.00 | 15.59 |
| ATOM | 1756 | C | PRO A | 258 | 62.171 | 36.218 | 33.907 | 1.00 | 18.80 |
| ATOM | 1757 | O | PRO A | 258 | 63.165 | 36.768 | 34.377 | 1.00 | 18.56 |
| ATOM | 1758 | N | ASP A | 259 | 62.041 | 34.897 | 33.840 | 1.00 | 18.60 |
| ATOM | 1759 | CA | ASP A | 259 | 63.068 | 34.003 | 34.362 | 1.00 | 20.43 |
| ATOM | 1760 | CB | ASP A | 259 | 62.405 | 32.914 | 35.217 | 1.00 | 18.43 |
| ATOM | 1761 | CG | ASP A | 259 | 61.400 | 33.482 | 36.218 | 1.00 | 20.36 |
| ATOM | 1762 | OD1 | ASP A | 259 | 61.745 | 34.445 | 36.937 | 1.00 | 18.40 |
| ATOM | 1763 | OD2 | ASP A | 259 | 60.263 | 32.963 | 36.288 | 1.00 | 19.98 |
| ATOM | 1764 | C | ASP A | 259 | 63.921 | 33.356 | 33.269 | 1.00 | 21.61 |
| ATOM | 1765 | O | ASP A | 259 | 64.562 | 32.335 | 33.497 | 1.00 | 24.74 |
| ATOM | 1766 | N | LEU A | 260 | 63.933 | 33.954 | 32.086 | 1.00 | 21.80 |
| ATOM | 1767 | CA | LEU A | 260 | 64.705 | 33.419 | 30.969 | 1.00 | 21.12 |
| ATOM | 1768 | CB | LEU A | 260 | 64.196 | 34.018 | 29.652 | 1.00 | 20.21 |
| ATOM | 1769 | CG | LEU A | 260 | 62.714 | 33.826 | 29.301 | 1.00 | 20.54 |
| ATOM | 1770 | CD1 | LEU A | 260 | 62.370 | 34.651 | 28.068 | 1.00 | 20.36 |
| ATOM | 1771 | CD2 | LEU A | 260 | 62.421 | 32.355 | 29.064 | 1.00 | 17.51 |
| ATOM | 1772 | C | LEU A | 260 | 66.203 | 33.699 | 31.096 | 1.00 | 21.45 |
| ATOM | 1773 | O | LEU A | 260 | 66.612 | 34.727 | 31.638 | 1.00 | 22.50 |
| ATOM | 1774 | N | THR A | 261 | 67.018 | 32.780 | 30.589 | 1.00 | 21.53 |
| ATOM | 1775 | CA | THR A | 261 | 68.470 | 32.947 | 30.606 | 1.00 | 21.15 |
| ATOM | 1776 | CB | THR A | 261 | 69.198 | 31.616 | 30.348 | 1.00 | 20.05 |
| ATOM | 1777 | OG1 | THR A | 261 | 68.858 | 31.140 | 29.040 | 1.00 | 20.20 |
| ATOM | 1778 | CG2 | THR A | 261 | 68.802 | 30.569 | 31.384 | 1.00 | 16.57 |
| ATOM | 1779 | C | THR A | 261 | 68.816 | 33.882 | 29.452 | 1.00 | 22.22 |
| ATOM | 1780 | O | THR A | 261 | 67.957 | 34.197 | 28.629 | 1.00 | 21.75 |
| ATOM | 1781 | N | SER A | 262 | 70.068 | 34.321 | 29.383 | 1.00 | 22.31 |
| ATOM | 1782 | CA | SER A | 262 | 70.486 | 35.202 | 28.300 | 1.00 | 24.10 |
| ATOM | 1783 | CB | SER A | 262 | 71.940 | 35.639 | 28.488 | 1.00 | 25.21 |
| ATOM | 1784 | OG | SER A | 262 | 72.070 | 36.517 | 29.589 | 1.00 | 30.65 |
| ATOM | 1785 | C | SER A | 262 | 70.346 | 34.475 | 26.967 | 1.00 | 23.76 |
| ATOM | 1786 | O | SER A | 262 | 70.027 | 35.087 | 25.944 | 1.00 | 23.73 |
| ATOM | 1787 | N | GLN A | 263 | 70.586 | 33.167 | 26.992 | 1.00 | 22.66 |
| ATOM | 1788 | CA | GLN A | 263 | 70.488 | 32.338 | 25.799 | 1.00 | 22.80 |
| ATOM | 1789 | CB | GLN A | 263 | 70.984 | 30.919 | 26.099 | 1.00 | 23.32 |
| ATOM | 1790 | CG | GLN A | 263 | 70.906 | 29.971 | 24.911 | 1.00 | 28.22 |
| ATOM | 1791 | CD | GLN A | 263 | 71.986 | 30.228 | 23.870 | 1.00 | 30.88 |
| ATOM | 1792 | OE1 | GLN A | 263 | 73.154 | 29.893 | 24.077 | 1.00 | 31.95 |
| ATOM | 1793 | NE2 | GLN A | 263 | 71.599 | 30.829 | 22.749 | 1.00 | 30.56 |
| ATOM | 1794 | C | GLN A | 263 | 69.043 | 32.293 | 25.308 | 1.00 | 21.39 |
| ATOM | 1795 | O | GLN A | 263 | 68.781 | 32.465 | 24.113 | 1.00 | 20.07 |
| ATOM | 1796 | N | ASP A | 264 | 68.108 | 32.064 | 26.231 | 1.00 | 21.04 |
| ATOM | 1797 | CA | ASP A | 264 | 66.689 | 32.010 | 25.882 | 1.00 | 20.35 |
| ATOM | 1798 | CB | ASP A | 264 | 65.806 | 31.813 | 27.125 | 1.00 | 23.87 |
| ATOM | 1799 | CG | ASP A | 264 | 66.025 | 30.473 | 27.813 | 1.00 | 25.55 |
| ATOM | 1800 | OD1 | ASP A | 264 | 66.306 | 29.475 | 27.122 | 1.00 | 24.81 |
| ATOM | 1801 | OD2 | ASP A | 264 | 65.890 | 30.423 | 29.057 | 1.00 | 28.84 |
| ATOM | 1802 | C | ASP A | 264 | 66.253 | 33.304 | 25.204 | 1.00 | 19.30 |
| ATOM | 1803 | O | ASP A | 264 | 65.540 | 33.282 | 24.205 | 1.00 | 19.20 |
| ATOM | 1804 | N | LYS A | 265 | 66.681 | 34.435 | 25.753 | 1.00 | 19.99 |
| ATOM | 1805 | CA | LYS A | 265 | 66.305 | 35.728 | 25.198 | 1.00 | 20.75 |
| ATOM | 1806 | CB | LYS A | 265 | 66.742 | 36.851 | 26.139 | 1.00 | 21.01 |
| ATOM | 1807 | CG | LYS A | 265 | 66.049 | 36.790 | 27.489 | 1.00 | 23.04 |
| ATOM | 1808 | CD | LYS A | 265 | 66.718 | 37.703 | 28.504 | 1.00 | 25.84 |
| ATOM | 1809 | CE | LYS A | 265 | 66.395 | 37.261 | 29.924 | 1.00 | 25.41 |
| ATOM | 1810 | NZ | LYS A | 265 | 67.246 | 37.944 | 30.933 | 1.00 | 25.82 |
| ATOM | 1811 | C | LYS A | 265 | 66.867 | 35.944 | 23.802 | 1.00 | 20.04 |
| ATOM | 1812 | O | LYS A | 265 | 66.161 | 36.443 | 22.924 | 1.00 | 21.04 |
| ATOM | 1813 | N | GLU A | 266 | 68.127 | 35.568 | 23.594 | 1.00 | 19.65 |
| ATOM | 1814 | CA | GLU A | 266 | 68.751 | 35.709 | 22.278 | 1.00 | 20.20 |
| ATOM | 1815 | CB | GLU A | 266 | 70.208 | 35.228 | 22.304 | 1.00 | 18.79 |
| ATOM | 1816 | CG | GLU A | 266 | 71.131 | 36.087 | 23.139 | 1.00 | 26.13 |
| ATOM | 1817 | CD | GLU A | 266 | 72.540 | 35.514 | 23.258 | 1.00 | 28.06 |
| ATOM | 1818 | OE1 | GLU A | 266 | 73.312 | 36.035 | 24.090 | 1.00 | 28.12 |

TABLE 31-continued

| | | | | | | | | |
|---|---|---|---|---|---|---|---|---|
| ATOM | 1819 | OE2 | GLU A | 266 | 72.875 | 34.554 | 22.525 | 1.00 | 29.89 |
| ATOM | 1820 | C | GLU A | 266 | 67.977 | 34.881 | 21.255 | 1.00 | 19.59 |
| ATOM | 1821 | O | GLU A | 266 | 67.668 | 35.363 | 20.168 | 1.00 | 19.33 |
| ATOM | 1822 | N | ASP A | 267 | 67.670 | 33.634 | 21.609 | 1.00 | 19.65 |
| ATOM | 1823 | CA | ASP A | 267 | 66.937 | 32.746 | 20.709 | 1.00 | 21.97 |
| ATOM | 1824 | CB | ASP A | 267 | 66.802 | 31.344 | 21.314 | 1.00 | 22.01 |
| ATOM | 1825 | CG | ASP A | 267 | 68.137 | 30.637 | 21.456 | 1.00 | 24.73 |
| ATOM | 1826 | OD1 | ASP A | 267 | 69.129 | 31.106 | 20.851 | 1.00 | 24.83 |
| ATOM | 1827 | OD2 | ASP A | 267 | 68.193 | 29.606 | 22.166 | 1.00 | 23.73 |
| ATOM | 1828 | C | ASP A | 267 | 65.553 | 33.292 | 20.381 | 1.00 | 21.47 |
| ATOM | 1829 | O | ASP A | 267 | 65.145 | 33.313 | 19.216 | 1.00 | 22.04 |
| ATOM | 1830 | N | ILE A | 268 | 64.834 | 33.732 | 21.408 | 1.00 | 19.95 |
| ATOM | 1831 | CA | ILE A | 268 | 63.503 | 34.275 | 21.211 | 1.00 | 19.17 |
| ATOM | 1832 | CB | ILE A | 268 | 62.888 | 34.744 | 22.542 | 1.00 | 18.87 |
| ATOM | 1833 | CG2 | ILE A | 268 | 61.705 | 35.656 | 22.274 | 1.00 | 16.95 |
| ATOM | 1834 | CG1 | ILE A | 268 | 62.485 | 33.528 | 23.375 | 1.00 | 18.97 |
| ATOM | 1835 | CD1 | ILE A | 268 | 61.948 | 33.877 | 24.746 | 1.00 | 23.19 |
| ATOM | 1836 | C | ILE A | 268 | 63.552 | 35.450 | 20.248 | 1.00 | 20.01 |
| ATOM | 1837 | O | ILE A | 268 | 62.743 | 35.538 | 19.320 | 1.00 | 19.24 |
| ATOM | 1838 | N | ALA A | 269 | 64.509 | 36.348 | 20.463 | 1.00 | 20.09 |
| ATOM | 1839 | CA | ALA A | 269 | 64.651 | 37.515 | 19.601 | 1.00 | 21.80 |
| ATOM | 1840 | CB | ALA A | 269 | 65.779 | 38.409 | 20.111 | 1.00 | 21.97 |
| ATOM | 1841 | C | ALA A | 269 | 64.941 | 37.065 | 18.171 | 1.00 | 22.48 |
| ATOM | 1842 | O | ALA A | 269 | 64.396 | 37.613 | 17.212 | 1.00 | 21.58 |
| ATOM | 1843 | N | SER A | 270 | 65.801 | 36.059 | 18.040 | 1.00 | 21.92 |
| ATOM | 1844 | CA | SER A | 270 | 66.168 | 35.531 | 16.733 | 1.00 | 22.88 |
| ATOM | 1845 | CB | SER A | 270 | 67.242 | 34.452 | 16.891 | 1.00 | 22.22 |
| ATOM | 1846 | OG | SER A | 270 | 67.580 | 33.882 | 15.642 | 1.00 | 23.76 |
| ATOM | 1847 | C | SER A | 270 | 64.949 | 34.957 | 16.006 | 1.00 | 23.52 |
| ATOM | 1848 | O | SER A | 270 | 64.714 | 35.262 | 14.837 | 1.00 | 24.62 |
| ATOM | 1849 | N | VAL A | 271 | 64.176 | 34.124 | 16.694 | 1.00 | 22.03 |
| ATOM | 1850 | CA | VAL A | 271 | 62.987 | 33.537 | 16.088 | 1.00 | 23.28 |
| ATOM | 1851 | CB | VAL A | 271 | 62.319 | 32.533 | 17.050 | 1.00 | 22.08 |
| ATOM | 1852 | CG1 | VAL A | 271 | 60.977 | 32.082 | 16.500 | 1.00 | 21.17 |
| ATOM | 1853 | CG2 | VAL A | 271 | 63.232 | 31.339 | 17.252 | 1.00 | 20.02 |
| ATOM | 1854 | C | VAL A | 271 | 61.987 | 34.632 | 15.707 | 1.00 | 24.31 |
| ATOM | 1855 | O | VAL A | 271 | 61.430 | 34.624 | 14.611 | 1.00 | 23.98 |
| ATOM | 1856 | N | VAL A | 272 | 61.781 | 35.583 | 16.612 | 1.00 | 26.58 |
| ATOM | 1857 | CA | VAL A | 272 | 60.859 | 36.689 | 16.379 | 1.00 | 27.45 |
| ATOM | 1858 | CB | VAL A | 272 | 60.911 | 37.701 | 17.551 | 1.00 | 27.39 |
| ATOM | 1859 | CG1 | VAL A | 272 | 60.486 | 39.084 | 17.076 | 1.00 | 25.91 |
| ATOM | 1860 | CG2 | VAL A | 272 | 59.999 | 37.229 | 18.675 | 1.00 | 26.08 |
| ATOM | 1861 | C | VAL A | 272 | 61.150 | 37.423 | 15.070 | 1.00 | 29.27 |
| ATOM | 1862 | O | VAL A | 272 | 60.241 | 37.702 | 14.285 | 1.00 | 28.76 |
| ATOM | 1863 | N | LYS A | 273 | 62.418 | 37.730 | 14.829 | 1.00 | 30.44 |
| ATOM | 1864 | CA | LYS A | 273 | 62.790 | 38.438 | 13.612 | 1.00 | 33.44 |
| ATOM | 1865 | CB | LYS A | 273 | 64.132 | 39.147 | 13.817 | 1.00 | 35.26 |
| ATOM | 1866 | CG | LYS A | 273 | 64.046 | 40.267 | 14.863 | 1.00 | 39.31 |
| ATOM | 1867 | CD | LYS A | 273 | 65.346 | 41.039 | 15.002 | 1.00 | 41.83 |
| ATOM | 1868 | CE | LYS A | 273 | 66.453 | 40.165 | 15.559 | 1.00 | 42.89 |
| ATOM | 1869 | NZ | LYS A | 273 | 67.722 | 40.927 | 15.709 | 1.00 | 43.88 |
| ATOM | 1870 | C | LYS A | 273 | 62.832 | 37.524 | 12.391 | 1.00 | 32.97 |
| ATOM | 1871 | O | LYS A | 273 | 62.728 | 37.986 | 11.258 | 1.00 | 33.61 |
| ATOM | 1872 | N | GLU A | 274 | 62.959 | 36.225 | 12.628 | 1.00 | 32.69 |
| ATOM | 1873 | CA | GLU A | 274 | 63.000 | 35.244 | 11.550 | 1.00 | 32.33 |
| ATOM | 1874 | CB | GLU A | 274 | 63.595 | 33.932 | 12.064 | 1.00 | 34.02 |
| ATOM | 1875 | CG | GLU A | 274 | 63.777 | 32.860 | 11.005 | 1.00 | 38.20 |
| ATOM | 1876 | CD | GLU A | 274 | 63.910 | 31.468 | 11.606 | 1.00 | 41.49 |
| ATOM | 1877 | OE1 | GLU A | 274 | 64.611 | 31.326 | 12.631 | 1.00 | 43.83 |
| ATOM | 1878 | OE2 | GLU A | 274 | 63.321 | 30.513 | 11.051 | 1.00 | 42.59 |
| ATOM | 1879 | C | GLU A | 274 | 61.597 | 34.971 | 10.995 | 1.00 | 32.28 |
| ATOM | 1880 | O | GLU A | 274 | 61.427 | 34.748 | 9.796 | 1.00 | 32.54 |
| ATOM | 1881 | N | LEU A | 275 | 60.594 | 34.991 | 11.871 | 1.00 | 29.68 |
| ATOM | 1882 | CA | LEU A | 275 | 59.218 | 34.715 | 11.463 | 1.00 | 27.61 |
| ATOM | 1883 | CB | LEU A | 275 | 58.547 | 33.794 | 12.482 | 1.00 | 26.94 |
| ATOM | 1884 | CG | LEU A | 275 | 59.253 | 32.467 | 12.760 | 1.00 | 26.89 |
| ATOM | 1885 | CD1 | LEU A | 275 | 58.481 | 31.695 | 13.822 | 1.00 | 26.39 |
| ATOM | 1886 | CD2 | LEU A | 275 | 59.357 | 31.663 | 11.468 | 1.00 | 25.26 |
| ATOM | 1887 | C | LEU A | 275 | 58.353 | 35.952 | 11.272 | 1.00 | 26.91 |
| ATOM | 1888 | O | LEU A | 275 | 57.278 | 35.873 | 10.685 | 1.00 | 27.65 |
| ATOM | 1889 | N | GLY A | 276 | 58.808 | 37.091 | 11.772 | 1.00 | 26.85 |
| ATOM | 1890 | CA | GLY A | 276 | 58.024 | 38.305 | 11.627 | 1.00 | 25.44 |
| ATOM | 1891 | C | GLY A | 276 | 56.956 | 38.486 | 12.697 | 1.00 | 26.13 |
| ATOM | 1892 | O | GLY A | 276 | 55.893 | 39.050 | 12.427 | 1.00 | 26.58 |
| ATOM | 1893 | N | ILE A | 277 | 57.224 | 38.001 | 13.907 | 1.00 | 24.15 |
| ATOM | 1894 | CA | ILE A | 277 | 56.282 | 38.151 | 15.008 | 1.00 | 23.32 |
| ATOM | 1895 | CB | ILE A | 277 | 56.870 | 37.596 | 16.322 | 1.00 | 23.73 |
| ATOM | 1896 | CG2 | ILE A | 277 | 55.978 | 37.967 | 17.500 | 1.00 | 22.70 |
| ATOM | 1897 | CG1 | ILE A | 277 | 57.002 | 36.078 | 16.217 | 1.00 | 22.63 |

TABLE 31-continued

| | | | | | | | | | |
|---|---|---|---|---|---|---|---|---|---|
| ATOM | 1898 | CD1 | ILE A | 277 | 55.695 | 35.400 | 15.862 | 1.00 | 25.70 |
| ATOM | 1899 | C | ILE A | 277 | 55.990 | 39.641 | 15.167 | 1.00 | 23.51 |
| ATOM | 1900 | O | ILE A | 277 | 56.900 | 40.464 | 15.133 | 1.00 | 24.00 |
| ATOM | 1901 | N | ASP A | 278 | 54.721 | 39.984 | 15.347 | 1.00 | 22.59 |
| ATOM | 1902 | CA | ASP A | 278 | 54.313 | 41.378 | 15.468 | 1.00 | 21.70 |
| ATOM | 1903 | CB | ASP A | 278 | 52.800 | 41.478 | 15.291 | 1.00 | 20.81 |
| ATOM | 1904 | CG | ASP A | 278 | 52.337 | 40.895 | 13.973 | 1.00 | 21.70 |
| ATOM | 1905 | OD1 | ASP A | 278 | 52.800 | 41.381 | 12.921 | 1.00 | 23.06 |
| ATOM | 1906 | OD2 | ASP A | 278 | 51.519 | 39.951 | 13.985 | 1.00 | 21.16 |
| ATOM | 1907 | C | ASP A | 278 | 54.725 | 42.090 | 16.753 | 1.00 | 22.21 |
| ATOM | 1908 | O | ASP A | 278 | 54.861 | 43.317 | 16.767 | 1.00 | 22.86 |
| ATOM | 1909 | N | GLY A | 279 | 54.922 | 41.335 | 17.828 | 1.00 | 20.59 |
| ATOM | 1910 | CA | GLY A | 279 | 55.305 | 41.960 | 19.080 | 1.00 | 19.11 |
| ATOM | 1911 | C | GLY A | 279 | 55.495 | 41.006 | 20.241 | 1.00 | 19.37 |
| ATOM | 1912 | O | GLY A | 279 | 55.215 | 39.810 | 20.149 | 1.00 | 20.05 |
| ATOM | 1913 | N | LEU A | 280 | 55.965 | 41.554 | 21.354 | 1.00 | 19.59 |
| ATOM | 1914 | CA | LEU A | 280 | 56.219 | 40.770 | 22.548 | 1.00 | 19.01 |
| ATOM | 1915 | CB | LEU A | 280 | 57.727 | 40.701 | 22.819 | 1.00 | 16.13 |
| ATOM | 1916 | CG | LEU A | 280 | 58.636 | 39.942 | 21.852 | 1.00 | 18.39 |
| ATOM | 1917 | CD1 | LEU A | 280 | 60.090 | 40.186 | 22.215 | 1.00 | 17.15 |
| ATOM | 1918 | CD2 | LEU A | 280 | 58.322 | 38.453 | 21.907 | 1.00 | 17.74 |
| ATOM | 1919 | C | LEU A | 280 | 55.537 | 41.384 | 23.759 | 1.00 | 18.66 |
| ATOM | 1920 | O | LEU A | 280 | 55.483 | 42.607 | 23.899 | 1.00 | 19.48 |
| ATOM | 1921 | N | ILE A | 281 | 54.992 | 40.533 | 24.620 | 1.00 | 16.58 |
| ATOM | 1922 | CA | ILE A | 281 | 54.381 | 41.008 | 25.850 | 1.00 | 16.94 |
| ATOM | 1923 | CB | ILE A | 281 | 53.028 | 40.345 | 26.138 | 1.00 | 13.57 |
| ATOM | 1924 | CG2 | ILE A | 281 | 52.571 | 40.719 | 27.537 | 1.00 | 12.68 |
| ATOM | 1925 | CG1 | ILE A | 281 | 51.998 | 40.805 | 25.094 | 1.00 | 13.42 |
| ATOM | 1926 | CD1 | ILE A | 281 | 50.543 | 40.631 | 25.526 | 1.00 | 9.50 |
| ATOM | 1927 | C | ILE A | 281 | 55.433 | 40.543 | 26.832 | 1.00 | 19.04 |
| ATOM | 1928 | O | ILE A | 281 | 55.630 | 39.339 | 27.039 | 1.00 | 20.47 |
| ATOM | 1929 | N | VAL A | 282 | 56.127 | 41.495 | 27.436 | 1.00 | 20.25 |
| ATOM | 1930 | CA | VAL A | 282 | 57.222 | 41.107 | 28.288 | 1.00 | 20.82 |
| ATOM | 1931 | CB | VAL A | 282 | 58.449 | 41.986 | 27.990 | 1.00 | 20.22 |
| ATOM | 1932 | CG1 | VAL A | 282 | 59.658 | 41.516 | 28.781 | 1.00 | 15.02 |
| ATOM | 1933 | CG2 | VAL A | 282 | 58.750 | 41.897 | 26.493 | 1.00 | 16.68 |
| ATOM | 1934 | C | VAL A | 282 | 57.004 | 40.935 | 29.768 | 1.00 | 24.85 |
| ATOM | 1935 | O | VAL A | 282 | 56.667 | 41.850 | 30.525 | 1.00 | 23.91 |
| ATOM | 1936 | N | THR A | 283 | 57.250 | 39.676 | 30.110 | 1.00 | 27.60 |
| ATOM | 1937 | CA | THR A | 283 | 57.170 | 39.027 | 31.399 | 1.00 | 24.79 |
| ATOM | 1938 | CB | THR A | 283 | 58.151 | 39.615 | 32.454 | 1.00 | 24.20 |
| ATOM | 1939 | OG1 | THR A | 283 | 57.456 | 39.821 | 33.690 | 1.00 | 20.26 |
| ATOM | 1940 | CG2 | THR A | 283 | 58.814 | 40.891 | 31.960 | 1.00 | 27.48 |
| ATOM | 1941 | C | THR A | 283 | 55.823 | 38.783 | 32.033 | 1.00 | 23.31 |
| ATOM | 1942 | O | THR A | 283 | 54.988 | 39.665 | 32.254 | 1.00 | 21.75 |
| ATOM | 1943 | N | ASN A | 284 | 55.652 | 37.496 | 32.279 | 1.00 | 20.32 |
| ATOM | 1944 | CA | ASN A | 284 | 54.513 | 36.914 | 32.923 | 1.00 | 16.76 |
| ATOM | 1945 | CB | ASN A | 284 | 54.398 | 35.463 | 32.467 | 1.00 | 13.23 |
| ATOM | 1946 | CG | ASN A | 284 | 53.008 | 34.918 | 32.624 | 1.00 | 13.70 |
| ATOM | 1947 | OD1 | ASN A | 284 | 52.432 | 34.975 | 33.708 | 1.00 | 12.58 |
| ATOM | 1948 | ND2 | ASN A | 284 | 52.454 | 34.384 | 31.537 | 1.00 | 11.64 |
| ATOM | 1949 | C | ASN A | 284 | 54.967 | 36.982 | 34.383 | 1.00 | 15.03 |
| ATOM | 1950 | O | ASN A | 284 | 55.833 | 37.789 | 34.728 | 1.00 | 14.08 |
| ATOM | 1951 | N | THR A | 285 | 54.405 | 36.143 | 35.239 | 1.00 | 14.23 |
| ATOM | 1952 | CA | THR A | 285 | 54.809 | 36.143 | 36.638 | 1.00 | 14.14 |
| ATOM | 1953 | CB | THR A | 285 | 53.748 | 35.471 | 37.520 | 1.00 | 13.30 |
| ATOM | 1954 | OG1 | THR A | 285 | 53.423 | 34.190 | 36.974 | 1.00 | 15.78 |
| ATOM | 1955 | CG2 | THR A | 285 | 52.490 | 36.323 | 37.587 | 1.00 | 14.21 |
| ATOM | 1956 | C | THR A | 285 | 56.128 | 35.378 | 36.757 | 1.00 | 14.83 |
| ATOM | 1957 | O | THR A | 285 | 56.488 | 34.613 | 35.863 | 1.00 | 13.04 |
| ATOM | 1958 | N | THR A | 286 | 56.845 | 35.585 | 37.858 | 1.00 | 14.34 |
| ATOM | 1959 | CA | THR A | 286 | 58.123 | 34.910 | 38.067 | 1.00 | 13.36 |
| ATOM | 1960 | CB | THR A | 286 | 59.184 | 35.889 | 38.605 | 1.00 | 10.54 |
| ATOM | 1961 | OG1 | THR A | 286 | 60.378 | 35.168 | 38.925 | 1.00 | 14.37 |
| ATOM | 1962 | CG2 | THR A | 286 | 58.689 | 36.580 | 39.868 | 1.00 | 12.42 |
| ATOM | 1963 | C | THR A | 286 | 58.030 | 33.739 | 39.047 | 1.00 | 13.96 |
| ATOM | 1964 | O | THR A | 286 | 57.276 | 33.794 | 40.020 | 1.00 | 14.35 |
| ATOM | 1965 | N | VAL A | 287 | 58.790 | 32.678 | 38.784 | 1.00 | 14.22 |
| ATOM | 1966 | CA | VAL A | 287 | 58.801 | 31.530 | 39.681 | 1.00 | 16.50 |
| ATOM | 1967 | CB | VAL A | 287 | 59.043 | 30.187 | 38.945 | 1.00 | 17.45 |
| ATOM | 1968 | CG1 | VAL A | 287 | 57.928 | 29.930 | 37.950 | 1.00 | 16.54 |
| ATOM | 1969 | CG2 | VAL A | 287 | 60.413 | 30.192 | 38.264 | 1.00 | 17.41 |
| ATOM | 1970 | C | VAL A | 287 | 59.924 | 31.732 | 40.692 | 1.00 | 16.94 |
| ATOM | 1971 | O | VAL A | 287 | 60.149 | 30.892 | 41.557 | 1.00 | 17.91 |
| ATOM | 1972 | N | SER A | 288 | 60.642 | 32.844 | 40.571 | 1.00 | 15.98 |
| ATOM | 1973 | CA | SER A | 288 | 61.713 | 33.128 | 41.517 | 1.00 | 16.76 |
| ATOM | 1974 | CB | SER A | 288 | 62.718 | 34.123 | 40.930 | 1.00 | 16.69 |
| ATOM | 1975 | OG | SER A | 288 | 62.166 | 35.432 | 40.901 | 1.00 | 17.63 |
| ATOM | 1976 | C | SER A | 288 | 61.060 | 33.756 | 42.743 | 1.00 | 17.52 |

TABLE 31-continued

| | | | | | | | | | |
|---|---|---|---|---|---|---|---|---|---|
| ATOM | 1977 | O | SER A | 288 | 59.885 | 34.135 | 42.712 | 1.00 | 16.42 |
| ATOM | 1978 | N | ARG A | 289 | 61.826 | 33.862 | 43.821 | 1.00 | 17.88 |
| ATOM | 1979 | CA | ARG A | 289 | 61.333 | 34.466 | 45.047 | 1.00 | 18.33 |
| ATOM | 1980 | CB | ARG A | 289 | 61.026 | 33.388 | 46.091 | 1.00 | 18.54 |
| ATOM | 1981 | CG | ARG A | 289 | 59.832 | 32.501 | 45.744 | 1.00 | 18.01 |
| ATOM | 1982 | CD | ARG A | 289 | 58.509 | 33.273 | 45.794 | 1.00 | 16.90 |
| ATOM | 1983 | NE | ARG A | 289 | 57.360 | 32.413 | 45.506 | 1.00 | 15.93 |
| ATOM | 1984 | CZ | ARG A | 289 | 56.922 | 32.112 | 44.284 | 1.00 | 17.27 |
| ATOM | 1985 | NH1 | ARG A | 289 | 55.874 | 31.311 | 44.134 | 1.00 | 16.11 |
| ATOM | 1986 | NH2 | ARG A | 289 | 57.515 | 32.620 | 43.209 | 1.00 | 13.70 |
| ATOM | 1987 | C | ARG A | 289 | 62.425 | 35.398 | 45.541 | 1.00 | 18.67 |
| ATOM | 1988 | O | ARG A | 289 | 63.272 | 35.012 | 46.344 | 1.00 | 19.04 |
| ATOM | 1989 | N | PRO A | 290 | 62.425 | 36.642 | 45.044 | 1.00 | 18.96 |
| ATOM | 1990 | CD | PRO A | 290 | 61.414 | 37.188 | 44.118 | 1.00 | 19.15 |
| ATOM | 1991 | CA | PRO A | 290 | 63.403 | 37.668 | 45.407 | 1.00 | 18.97 |
| ATOM | 1992 | CB | PRO A | 290 | 62.753 | 38.952 | 44.897 | 1.00 | 18.09 |
| ATOM | 1993 | CG | PRO A | 290 | 62.050 | 38.488 | 43.665 | 1.00 | 17.63 |
| ATOM | 1994 | C | PRO A | 290 | 63.676 | 37.713 | 46.904 | 1.00 | 20.35 |
| ATOM | 1995 | O | PRO A | 290 | 62.759 | 37.579 | 47.717 | 1.00 | 20.48 |
| ATOM | 1996 | N | ALA A | 291 | 64.942 | 37.886 | 47.267 | 1.00 | 20.76 |
| ATOM | 1997 | CA | ALA A | 291 | 65.306 | 37.975 | 48.676 | 1.00 | 19.97 |
| ATOM | 1998 | CB | ALA A | 291 | 66.820 | 38.117 | 48.825 | 1.00 | 18.35 |
| ATOM | 1999 | C | ALA A | 291 | 64.607 | 39.214 | 49.231 | 1.00 | 18.32 |
| ATOM | 2000 | O | ALA A | 291 | 64.572 | 40.256 | 48.574 | 1.00 | 18.54 |
| ATOM | 2001 | N | GLY A | 292 | 64.036 | 39.100 | 50.423 | 1.00 | 16.06 |
| ATOM | 2002 | CA | GLY A | 292 | 63.367 | 40.247 | 51.011 | 1.00 | 15.84 |
| ATOM | 2003 | C | GLY A | 292 | 61.861 | 40.134 | 51.148 | 1.00 | 15.05 |
| ATOM | 2004 | O | GLY A | 292 | 61.256 | 40.922 | 51.865 | 1.00 | 17.29 |
| ATOM | 2005 | N | LEU A | 293 | 61.244 | 39.177 | 50.461 | 1.00 | 16.21 |
| ATOM | 2006 | CA | LEU A | 293 | 59.794 | 39.002 | 50.567 | 1.00 | 15.09 |
| ATOM | 2007 | CB | LEU A | 293 | 59.333 | 37.772 | 49.784 | 1.00 | 14.95 |
| ATOM | 2008 | CG | LEU A | 293 | 59.498 | 37.772 | 48.261 | 1.00 | 15.03 |
| ATOM | 2009 | CD1 | LEU A | 293 | 58.985 | 36.443 | 47.710 | 1.00 | 15.13 |
| ATOM | 2010 | CD2 | LEU A | 293 | 58.726 | 38.944 | 47.644 | 1.00 | 14.56 |
| ATOM | 2011 | C | LEU A | 293 | 59.457 | 38.813 | 52.034 | 1.00 | 14.63 |
| ATOM | 2012 | O | LEU A | 293 | 60.110 | 38.035 | 52.722 | 1.00 | 13.78 |
| ATOM | 2013 | N | GLN A | 294 | 58.442 | 39.527 | 52.508 | 1.00 | 15.71 |
| ATOM | 2014 | CA | GLN A | 294 | 58.025 | 39.444 | 53.902 | 1.00 | 17.52 |
| ATOM | 2015 | CB | GLN A | 294 | 57.812 | 40.851 | 54.474 | 1.00 | 18.01 |
| ATOM | 2016 | CG | GLN A | 294 | 59.072 | 41.680 | 54.535 | 1.00 | 19.97 |
| ATOM | 2017 | CD | GLN A | 294 | 60.177 | 40.954 | 55.264 | 1.00 | 20.66 |
| ATOM | 2018 | OE1 | GLN A | 294 | 60.000 | 40.540 | 56.404 | 1.00 | 22.11 |
| ATOM | 2019 | NE2 | GLN A | 294 | 61.322 | 40.790 | 54.607 | 1.00 | 18.57 |
| ATOM | 2020 | C | GLN A | 294 | 56.747 | 38.641 | 54.086 | 1.00 | 18.13 |
| ATOM | 2021 | O | GLN A | 294 | 56.514 | 38.075 | 55.158 | 1.00 | 18.69 |
| ATOM | 2022 | N | GLY A | 295 | 55.920 | 38.607 | 53.043 | 1.00 | 17.25 |
| ATOM | 2023 | CA | GLY A | 295 | 54.657 | 37.891 | 53.106 | 1.00 | 15.78 |
| ATOM | 2024 | C | GLY A | 295 | 54.750 | 36.505 | 53.712 | 1.00 | 15.71 |
| ATOM | 2025 | O | GLY A | 295 | 55.653 | 35.738 | 53.394 | 1.00 | 15.57 |
| ATOM | 2026 | N | ALA A | 296 | 53.809 | 36.183 | 54.590 | 1.00 | 15.03 |
| ATOM | 2027 | CA | ALA A | 296 | 53.784 | 34.873 | 55.233 | 1.00 | 17.37 |
| ATOM | 2028 | CB | ALA A | 296 | 52.668 | 34.826 | 56.279 | 1.00 | 13.26 |
| ATOM | 2029 | C | ALA A | 296 | 53.581 | 33.749 | 54.217 | 1.00 | 17.38 |
| ATOM | 2030 | O | ALA A | 296 | 53.942 | 32.599 | 54.472 | 1.00 | 19.30 |
| ATOM | 2031 | N | LEU A | 297 | 53.020 | 34.087 | 53.061 | 1.00 | 16.13 |
| ATOM | 2032 | CA | LEU A | 297 | 52.733 | 33.091 | 52.034 | 1.00 | 16.03 |
| ATOM | 2033 | CB | LEU A | 297 | 51.318 | 33.331 | 51.501 | 1.00 | 14.34 |
| ATOM | 2034 | CG | LEU A | 297 | 50.289 | 33.400 | 52.634 | 1.00 | 15.64 |
| ATOM | 2035 | CD1 | LEU A | 297 | 48.928 | 33.906 | 52.125 | 1.00 | 14.34 |
| ATOM | 2036 | CD2 | LEU A | 297 | 50.173 | 32.014 | 53.261 | 1.00 | 14.99 |
| ATOM | 2037 | C | LEU A | 297 | 53.734 | 33.105 | 50.886 | 1.00 | 15.69 |
| ATOM | 2038 | O | LEU A | 297 | 53.458 | 32.593 | 49.805 | 1.00 | 15.52 |
| ATOM | 2039 | N | ARG A | 298 | 54.903 | 33.682 | 51.140 | 1.00 | 18.00 |
| ATOM | 2040 | CA | ARG A | 298 | 55.955 | 33.799 | 50.134 | 1.00 | 17.07 |
| ATOM | 2041 | CB | ARG A | 298 | 57.142 | 34.567 | 50.715 | 1.00 | 17.89 |
| ATOM | 2042 | CG | ARG A | 298 | 57.956 | 33.765 | 51.710 | 1.00 | 19.96 |
| ATOM | 2043 | CD | ARG A | 298 | 59.024 | 34.625 | 52.374 | 1.00 | 19.70 |
| ATOM | 2044 | NE | ARG A | 298 | 59.866 | 33.837 | 53.271 | 1.00 | 19.62 |
| ATOM | 2045 | CZ | ARG A | 298 | 60.717 | 34.362 | 54.146 | 1.00 | 19.91 |
| ATOM | 2046 | NH1 | ARG A | 298 | 61.445 | 33.570 | 54.925 | 1.00 | 16.38 |
| ATOM | 2047 | NH2 | ARG A | 298 | 60.832 | 35.683 | 54.248 | 1.00 | 19.27 |
| ATOM | 2048 | C | ARG A | 298 | 56.454 | 32.478 | 49.560 | 1.00 | 16.46 |
| ATOM | 2049 | O | ARG A | 298 | 56.963 | 32.447 | 48.441 | 1.00 | 16.84 |
| ATOM | 2050 | N | SER A | 299 | 56.323 | 31.387 | 50.307 | 1.00 | 15.46 |
| ATOM | 2051 | CA | SER A | 299 | 56.795 | 30.104 | 49.799 | 1.00 | 16.47 |
| ATOM | 2052 | CB | SER A | 299 | 57.508 | 29.315 | 50.900 | 1.00 | 16.12 |
| ATOM | 2053 | OG | SER A | 299 | 58.770 | 29.897 | 51.192 | 1.00 | 17.77 |
| ATOM | 2054 | C | SER A | 299 | 55.724 | 29.239 | 49.146 | 1.00 | 15.87 |
| ATOM | 2055 | O | SER A | 299 | 55.937 | 28.047 | 48.927 | 1.00 | 16.82 |

TABLE 31-continued

| | | | | | | | | | |
|---|---|---|---|---|---|---|---|---|---|
| ATOM | 2056 | N | GLU A | 300 | 54.575 | 29.835 | 48.842 | 1.00 | 14.59 |
| ATOM | 2057 | CA | GLU A | 300 | 53.506 | 29.113 | 48.153 | 1.00 | 15.91 |
| ATOM | 2058 | CB | GLU A | 300 | 52.201 | 29.925 | 48.155 | 1.00 | 14.89 |
| ATOM | 2059 | CG | GLU A | 300 | 51.489 | 30.000 | 49.499 | 1.00 | 19.34 |
| ATOM | 2060 | CD | GLU A | 300 | 50.803 | 28.695 | 49.870 | 1.00 | 20.55 |
| ATOM | 2061 | OE1 | GLU A | 300 | 50.331 | 28.570 | 51.018 | 1.00 | 23.41 |
| ATOM | 2062 | OE2 | GLU A | 300 | 50.728 | 27.796 | 49.008 | 1.00 | 22.41 |
| ATOM | 2063 | C | GLU A | 300 | 53.968 | 28.926 | 46.703 | 1.00 | 16.00 |
| ATOM | 2064 | O | GLU A | 300 | 54.659 | 29.780 | 46.142 | 1.00 | 15.73 |
| ATOM | 2065 | N | THR A | 301 | 53.597 | 27.802 | 46.105 | 1.00 | 16.98 |
| ATOM | 2066 | CA | THR A | 301 | 53.949 | 27.518 | 44.724 | 1.00 | 15.65 |
| ATOM | 2067 | CB | THR A | 301 | 53.642 | 26.055 | 44.372 | 1.00 | 18.57 |
| ATOM | 2068 | OG1 | THR A | 301 | 54.617 | 25.200 | 44.985 | 1.00 | 18.86 |
| ATOM | 2069 | CG2 | THR A | 301 | 53.638 | 25.854 | 42.852 | 1.00 | 16.16 |
| ATOM | 2070 | C | THR A | 301 | 53.138 | 28.408 | 43.786 | 1.00 | 15.99 |
| ATOM | 2071 | O | THR A | 301 | 51.956 | 28.672 | 44.030 | 1.00 | 14.76 |
| ATOM | 2072 | N | GLY A | 302 | 53.769 | 28.867 | 42.711 | 1.00 | 14.89 |
| ATOM | 2073 | CA | GLY A | 302 | 53.057 | 29.696 | 41.758 | 1.00 | 14.82 |
| ATOM | 2074 | C | GLY A | 302 | 53.882 | 30.841 | 41.215 | 1.00 | 16.15 |
| ATOM | 2075 | O | GLY A | 302 | 55.076 | 30.950 | 41.490 | 1.00 | 15.43 |
| ATOM | 2076 | N | GLY A | 303 | 53.235 | 31.694 | 40.429 | 1.00 | 16.40 |
| ATOM | 2077 | CA | GLY A | 303 | 53.916 | 32.836 | 39.852 | 1.00 | 14.72 |
| ATOM | 2078 | C | GLY A | 303 | 53.739 | 34.053 | 40.735 | 1.00 | 14.35 |
| ATOM | 2079 | O | GLY A | 303 | 52.634 | 34.327 | 41.212 | 1.00 | 13.54 |
| ATOM | 2080 | N | LEU A | 304 | 54.831 | 34.776 | 40.962 | 1.00 | 13.61 |
| ATOM | 2081 | CA | LEU A | 304 | 54.807 | 35.975 | 41.795 | 1.00 | 14.28 |
| ATOM | 2082 | CB | LEU A | 304 | 56.132 | 36.096 | 42.558 | 1.00 | 15.31 |
| ATOM | 2083 | CG | LEU A | 304 | 56.432 | 37.328 | 43.419 | 1.00 | 16.52 |
| ATOM | 2084 | CD1 | LEU A | 304 | 55.427 | 37.462 | 44.552 | 1.00 | 18.84 |
| ATOM | 2085 | CD2 | LEU A | 304 | 57.832 | 37.182 | 43.991 | 1.00 | 19.39 |
| ATOM | 2086 | C | LEU A | 304 | 54.586 | 37.208 | 40.918 | 1.00 | 14.66 |
| ATOM | 2087 | O | LEU A | 304 | 55.164 | 37.316 | 39.830 | 1.00 | 14.61 |
| ATOM | 2088 | N | SER A | 305 | 53.743 | 38.127 | 41.387 | 1.00 | 12.97 |
| ATOM | 2089 | CA | SER A | 305 | 53.449 | 39.353 | 40.646 | 1.00 | 13.05 |
| ATOM | 2090 | CB | SER A | 305 | 52.061 | 39.272 | 40.001 | 1.00 | 11.51 |
| ATOM | 2091 | OG | SER A | 305 | 51.044 | 39.187 | 40.991 | 1.00 | 11.71 |
| ATOM | 2092 | C | SER A | 305 | 53.503 | 40.559 | 41.579 | 1.00 | 13.60 |
| ATOM | 2093 | O | SER A | 305 | 53.588 | 40.404 | 42.799 | 1.00 | 14.71 |
| ATOM | 2094 | N | GLY A | 306 | 53.458 | 41.762 | 41.013 | 1.00 | 12.19 |
| ATOM | 2095 | CA | GLY A | 306 | 53.493 | 42.946 | 41.853 | 1.00 | 13.31 |
| ATOM | 2096 | C | GLY A | 306 | 54.853 | 43.605 | 41.953 | 1.00 | 14.74 |
| ATOM | 2097 | O | GLY A | 306 | 55.739 | 43.350 | 41.133 | 1.00 | 15.44 |
| ATOM | 2098 | N | LYS A | 307 | 55.034 | 44.432 | 42.979 | 1.00 | 15.30 |
| ATOM | 2099 | CA | LYS A | 307 | 56.285 | 45.172 | 43.147 | 1.00 | 17.60 |
| ATOM | 2100 | CB | LYS A | 307 | 56.244 | 46.009 | 44.439 | 1.00 | 19.20 |
| ATOM | 2101 | CG | LYS A | 307 | 57.248 | 47.177 | 44.435 | 1.00 | 24.22 |
| ATOM | 2102 | CD | LYS A | 307 | 57.307 | 47.949 | 45.766 | 1.00 | 28.95 |
| ATOM | 2103 | CE | LYS A | 307 | 56.028 | 48.754 | 46.030 | 1.00 | 30.49 |
| ATOM | 2104 | NZ | LYS A | 307 | 55.713 | 49.722 | 44.926 | 1.00 | 31.16 |
| ATOM | 2105 | C | LYS A | 307 | 57.590 | 44.368 | 43.088 | 1.00 | 16.74 |
| ATOM | 2106 | O | LYS A | 307 | 58.560 | 44.810 | 42.474 | 1.00 | 17.98 |
| ATOM | 2107 | N | PRO A | 308 | 57.640 | 43.184 | 43.720 | 1.00 | 15.79 |
| ATOM | 2108 | CD | PRO A | 308 | 56.652 | 42.578 | 44.632 | 1.00 | 15.73 |
| ATOM | 2109 | CA | PRO A | 308 | 58.879 | 42.392 | 43.684 | 1.00 | 14.87 |
| ATOM | 2110 | CB | PRO A | 308 | 58.552 | 41.196 | 44.579 | 1.00 | 15.23 |
| ATOM | 2111 | CG | PRO A | 308 | 57.529 | 41.759 | 45.549 | 1.00 | 14.01 |
| ATOM | 2112 | C | PRO A | 308 | 59.310 | 41.953 | 42.279 | 1.00 | 15.73 |
| ATOM | 2113 | O | PRO A | 308 | 60.468 | 41.595 | 42.056 | 1.00 | 16.91 |
| ATOM | 2114 | N | LEU A | 309 | 58.371 | 41.982 | 41.339 | 1.00 | 14.07 |
| ATOM | 2115 | CA | LEU A | 309 | 58.632 | 41.581 | 39.963 | 1.00 | 14.46 |
| ATOM | 2116 | CB | LEU A | 309 | 57.406 | 40.847 | 39.404 | 1.00 | 14.21 |
| ATOM | 2117 | CG | LEU A | 309 | 57.307 | 40.671 | 37.880 | 1.00 | 13.52 |
| ATOM | 2118 | CD1 | LEU A | 309 | 58.420 | 39.763 | 37.397 | 1.00 | 14.58 |
| ATOM | 2119 | CD2 | LEU A | 309 | 55.948 | 40.080 | 37.504 | 1.00 | 12.51 |
| ATOM | 2120 | C | LEU A | 309 | 58.961 | 42.760 | 39.041 | 1.00 | 16.10 |
| ATOM | 2121 | O | LEU A | 309 | 59.589 | 42.579 | 37.994 | 1.00 | 15.89 |
| ATOM | 2122 | N | ARG A | 310 | 58.549 | 43.958 | 39.445 | 1.00 | 14.15 |
| ATOM | 2123 | CA | ARG A | 310 | 58.731 | 45.160 | 38.639 | 1.00 | 15.63 |
| ATOM | 2124 | CB | ARG A | 310 | 58.485 | 46.415 | 39.485 | 1.00 | 14.41 |
| ATOM | 2125 | CG | ARG A | 310 | 58.504 | 47.711 | 38.662 | 1.00 | 17.37 |
| ATOM | 2126 | CD | ARG A | 310 | 58.331 | 48.936 | 39.539 | 1.00 | 16.00 |
| ATOM | 2127 | NE | ARG A | 310 | 59.378 | 48.988 | 40.556 | 1.00 | 16.92 |
| ATOM | 2128 | CZ | ARG A | 310 | 59.328 | 49.752 | 41.641 | 1.00 | 15.82 |
| ATOM | 2129 | NH1 | ARG A | 310 | 60.328 | 49.723 | 42.511 | 1.00 | 12.25 |
| ATOM | 2130 | NH2 | ARG A | 310 | 58.277 | 50.538 | 41.857 | 1.00 | 11.34 |
| ATOM | 2131 | C | ARG A | 310 | 60.039 | 45.340 | 37.868 | 1.00 | 16.73 |
| ATOM | 2132 | O | ARG A | 310 | 60.049 | 45.314 | 36.635 | 1.00 | 16.19 |
| ATOM | 2133 | N | ASP A | 311 | 61.141 | 45.534 | 38.583 | 1.00 | 17.13 |
| ATOM | 2134 | CA | ASP A | 311 | 62.415 | 45.768 | 37.917 | 1.00 | 17.51 |

TABLE 31-continued

| | | | | | | | | | |
|---|---|---|---|---|---|---|---|---|---|
| ATOM | 2135 | CB | ASP A | 311 | 63.413 | 46.309 | 38.941 | 1.00 | 16.83 |
| ATOM | 2136 | CG | ASP A | 311 | 63.066 | 47.741 | 39.368 | 1.00 | 19.40 |
| ATOM | 2137 | OD1 | ASP A | 311 | 61.901 | 48.154 | 39.159 | 1.00 | 17.25 |
| ATOM | 2138 | OD2 | ASP A | 311 | 63.938 | 48.454 | 39.904 | 1.00 | 18.54 |
| ATOM | 2139 | C | ASP A | 311 | 62.954 | 44.576 | 37.130 | 1.00 | 17.90 |
| ATOM | 2140 | O | ASP A | 311 | 63.648 | 44.748 | 36.125 | 1.00 | 17.56 |
| ATOM | 2141 | N | LEU A | 312 | 62.623 | 43.368 | 37.567 | 1.00 | 17.93 |
| ATOM | 2142 | CA | LEU A | 312 | 63.042 | 42.183 | 36.834 | 1.00 | 18.46 |
| ATOM | 2143 | CB | LEU A | 312 | 62.583 | 40.921 | 37.564 | 1.00 | 19.59 |
| ATOM | 2144 | CG | LEU A | 312 | 62.919 | 39.572 | 36.924 | 1.00 | 23.20 |
| ATOM | 2145 | CD1 | LEU A | 312 | 64.430 | 39.435 | 36.725 | 1.00 | 24.90 |
| ATOM | 2146 | CD2 | LEU A | 312 | 62.399 | 38.457 | 37.830 | 1.00 | 23.93 |
| ATOM | 2147 | C | LEU A | 312 | 62.386 | 42.270 | 35.445 | 1.00 | 17.74 |
| ATOM | 2148 | O | LEU A | 312 | 63.006 | 41.930 | 34.432 | 1.00 | 15.60 |
| ATOM | 2149 | N | SER A | 313 | 61.136 | 42.744 | 35.404 | 1.00 | 16.62 |
| ATOM | 2150 | CA | SER A | 313 | 60.408 | 42.898 | 34.136 | 1.00 | 18.24 |
| ATOM | 2151 | CB | SER A | 313 | 58.923 | 43.211 | 34.372 | 1.00 | 19.90 |
| ATOM | 2152 | OG | SER A | 313 | 58.194 | 42.044 | 34.702 | 1.00 | 27.76 |
| ATOM | 2153 | C | SER A | 313 | 61.004 | 44.020 | 33.296 | 1.00 | 16.66 |
| ATOM | 2154 | O | SER A | 313 | 61.262 | 43.846 | 32.105 | 1.00 | 16.80 |
| ATOM | 2155 | N | THR A | 314 | 61.206 | 45.174 | 33.922 | 1.00 | 15.56 |
| ATOM | 2156 | CA | THR A | 314 | 61.770 | 46.322 | 33.231 | 1.00 | 15.84 |
| ATOM | 2157 | CB | THR A | 314 | 62.014 | 47.496 | 34.202 | 1.00 | 15.11 |
| ATOM | 2158 | OG1 | THR A | 314 | 60.768 | 47.899 | 34.784 | 1.00 | 14.85 |
| ATOM | 2159 | CG2 | THR A | 314 | 62.626 | 48.677 | 33.466 | 1.00 | 13.49 |
| ATOM | 2160 | C | THR A | 314 | 63.085 | 45.932 | 32.564 | 1.00 | 16.33 |
| ATOM | 2161 | O | THR A | 314 | 63.317 | 46.264 | 31.399 | 1.00 | 18.25 |
| ATOM | 2162 | N | GLN A | 315 | 63.935 | 45.210 | 33.290 | 1.00 | 15.30 |
| ATOM | 2163 | CA | GLN A | 315 | 65.214 | 44.786 | 32.725 | 1.00 | 14.23 |
| ATOM | 2164 | CB | GLN A | 315 | 66.093 | 44.140 | 33.804 | 1.00 | 12.18 |
| ATOM | 2165 | CG | GLN A | 315 | 66.574 | 45.115 | 34.889 | 1.00 | 15.16 |
| ATOM | 2166 | CD | GLN A | 315 | 67.541 | 46.186 | 34.362 | 1.00 | 18.05 |
| ATOM | 2167 | OE1 | GLN A | 315 | 67.240 | 46.904 | 33.406 | 0.50 | 13.54 |
| ATOM | 2168 | NE2 | GLN A | 315 | 68.699 | 46.297 | 34.999 | 0.50 | 15.47 |
| ATOM | 2169 | C | GLN A | 315 | 65.018 | 43.822 | 31.551 | 1.00 | 14.24 |
| ATOM | 2170 | O | GLN A | 315 | 65.779 | 43.860 | 30.584 | 1.00 | 15.73 |
| ATOM | 2171 | N | THR A | 316 | 64.001 | 42.966 | 31.625 | 1.00 | 14.27 |
| ATOM | 2172 | CA | THR A | 316 | 63.737 | 42.014 | 30.546 | 1.00 | 14.28 |
| ATOM | 2173 | CB | THR A | 316 | 62.649 | 40.967 | 30.937 | 1.00 | 15.87 |
| ATOM | 2174 | OG1 | THR A | 316 | 63.020 | 40.306 | 32.156 | 1.00 | 15.52 |
| ATOM | 2175 | CG2 | THR A | 316 | 62.506 | 39.915 | 29.838 | 1.00 | 13.35 |
| ATOM | 2176 | C | THR A | 316 | 63.260 | 42.782 | 29.315 | 1.00 | 14.86 |
| ATOM | 2177 | O | THR A | 316 | 63.586 | 42.433 | 28.181 | 1.00 | 13.99 |
| ATOM | 2178 | N | ILE A | 317 | 62.484 | 43.833 | 29.546 | 1.00 | 14.52 |
| ATOM | 2179 | CA | ILE A | 317 | 61.987 | 44.654 | 28.451 | 1.00 | 14.79 |
| ATOM | 2180 | CB | ILE A | 317 | 61.030 | 45.741 | 28.965 | 1.00 | 14.10 |
| ATOM | 2181 | CG2 | ILE A | 317 | 60.796 | 46.788 | 27.883 | 1.00 | 13.16 |
| ATOM | 2182 | CG1 | ILE A | 317 | 59.719 | 45.097 | 29.420 | 1.00 | 11.47 |
| ATOM | 2183 | CD1 | ILE A | 317 | 58.834 | 46.020 | 30.221 | 1.00 | 9.53 |
| ATOM | 2184 | C | ILE A | 317 | 63.175 | 45.333 | 27.794 | 1.00 | 16.65 |
| ATOM | 2185 | O | ILE A | 317 | 63.290 | 45.380 | 26.565 | 1.00 | 16.75 |
| ATOM | 2186 | N | ARG A | 318 | 64.062 | 45.850 | 28.640 | 1.00 | 16.88 |
| ATOM | 2187 | CA | ARG A | 318 | 65.257 | 46.548 | 28.197 | 1.00 | 17.27 |
| ATOM | 2188 | CB | ARG A | 318 | 66.049 | 47.026 | 29.422 | 1.00 | 16.80 |
| ATOM | 2189 | CG | ARG A | 318 | 66.993 | 48.183 | 29.157 | 1.00 | 16.19 |
| ATOM | 2190 | CD | ARG A | 318 | 67.763 | 48.572 | 30.420 | 1.00 | 15.62 |
| ATOM | 2191 | NE | ARG A | 318 | 66.912 | 49.093 | 31.491 | 1.00 | 12.95 |
| ATOM | 2192 | CZ | ARG A | 318 | 66.287 | 50.267 | 31.457 | 1.00 | 13.25 |
| ATOM | 2193 | NH1 | ARG A | 318 | 66.406 | 51.058 | 30.402 | 1.00 | 12.39 |
| ATOM | 2194 | NH2 | ARG A | 318 | 65.548 | 50.656 | 32.487 | 1.00 | 11.89 |
| ATOM | 2195 | C | ARG A | 318 | 66.123 | 45.645 | 27.314 | 1.00 | 18.16 |
| ATOM | 2196 | O | ARG A | 318 | 66.580 | 46.063 | 26.248 | 1.00 | 18.08 |
| ATOM | 2197 | N | GLU A | 319 | 66.330 | 44.402 | 27.742 | 1.00 | 18.16 |
| ATOM | 2198 | CA | GLU A | 319 | 67.150 | 43.477 | 26.965 | 1.00 | 19.04 |
| ATOM | 2199 | CB | GLU A | 319 | 67.505 | 42.228 | 27.793 | 1.00 | 21.85 |
| ATOM | 2200 | CG | GLU A | 319 | 68.788 | 41.525 | 27.319 | 1.00 | 30.49 |
| ATOM | 2201 | CD | GLU A | 319 | 69.140 | 40.265 | 28.118 | 1.00 | 36.16 |
| ATOM | 2202 | OE1 | GLU A | 319 | 69.040 | 40.276 | 29.368 | 1.00 | 36.36 |
| ATOM | 2203 | OE2 | GLU A | 319 | 69.538 | 39.261 | 27.487 | 1.00 | 39.86 |
| ATOM | 2204 | C | GLU A | 319 | 66.479 | 43.052 | 25.657 | 1.00 | 18.06 |
| ATOM | 2205 | O | GLU A | 319 | 67.143 | 42.957 | 24.632 | 1.00 | 18.69 |
| ATOM | 2206 | N | MET A | 320 | 65.172 | 42.797 | 25.680 | 1.00 | 18.33 |
| ATOM | 2207 | CA | MET A | 320 | 64.480 | 42.377 | 24.460 | 1.00 | 18.60 |
| ATOM | 2208 | CB | MET A | 320 | 63.066 | 41.881 | 24.781 | 1.00 | 17.12 |
| ATOM | 2209 | CG | MET A | 320 | 63.015 | 40.651 | 25.697 | 1.00 | 16.85 |
| ATOM | 2210 | SD | MET A | 320 | 64.127 | 39.287 | 25.203 | 1.00 | 19.70 |
| ATOM | 2211 | CE | MET A | 320 | 63.525 | 38.893 | 23.541 | 1.00 | 13.82 |
| ATOM | 2212 | C | MET A | 320 | 64.419 | 43.497 | 23.415 | 1.00 | 18.70 |
| ATOM | 2213 | O | MET A | 320 | 64.518 | 43.245 | 22.214 | 1.00 | 18.14 |

TABLE 31-continued

| | | | | | | | | | |
|---|---|---|---|---|---|---|---|---|---|
| ATOM | 2214 | N | TYR | A | 321 | 64.267 | 44.732 | 23.879 | 1.00 | 19.06 |
| ATOM | 2215 | CA | TYR | A | 321 | 64.208 | 45.885 | 22.990 | 1.00 | 19.32 |
| ATOM | 2216 | CB | TYR | A | 321 | 64.026 | 47.167 | 23.804 | 1.00 | 17.79 |
| ATOM | 2217 | CG | TYR | A | 321 | 63.837 | 48.414 | 22.964 | 1.00 | 19.03 |
| ATOM | 2218 | CD1 | TYR | A | 321 | 62.629 | 48.666 | 22.319 | 1.00 | 18.88 |
| ATOM | 2219 | CE1 | TYR | A | 321 | 62.445 | 49.814 | 21.568 | 1.00 | 18.27 |
| ATOM | 2220 | CD2 | TYR | A | 321 | 64.861 | 49.348 | 22.828 | 1.00 | 18.63 |
| ATOM | 2221 | CE2 | TYR | A | 321 | 64.688 | 50.501 | 22.075 | 1.00 | 17.09 |
| ATOM | 2222 | CZ | TYR | A | 321 | 63.479 | 50.729 | 21.450 | 1.00 | 19.28 |
| ATOM | 2223 | OH | TYR | A | 321 | 63.295 | 51.874 | 20.710 | 1.00 | 20.77 |
| ATOM | 2224 | C | TYR | A | 321 | 65.506 | 45.982 | 22.189 | 1.00 | 19.97 |
| ATOM | 2225 | O | TYR | A | 321 | 65.487 | 46.184 | 20.976 | 1.00 | 18.20 |
| ATOM | 2226 | N | ALA | A | 322 | 66.629 | 45.839 | 22.889 | 1.00 | 20.65 |
| ATOM | 2227 | CA | ALA | A | 322 | 67.952 | 45.910 | 22.277 | 1.00 | 20.61 |
| ATOM | 2228 | CB | ALA | A | 322 | 69.024 | 46.001 | 23.370 | 1.00 | 18.34 |
| ATOM | 2229 | C | ALA | A | 322 | 68.226 | 44.710 | 21.365 | 1.00 | 20.54 |
| ATOM | 2230 | O | ALA | A | 322 | 68.820 | 44.853 | 20.303 | 1.00 | 19.72 |
| ATOM | 2231 | N | LEU | A | 323 | 67.794 | 43.528 | 21.782 | 1.00 | 21.03 |
| ATOM | 2232 | CA | LEU | A | 323 | 68.003 | 42.334 | 20.972 | 1.00 | 22.34 |
| ATOM | 2233 | CB | LEU | A | 323 | 67.595 | 41.087 | 21.756 | 1.00 | 22.34 |
| ATOM | 2234 | CG | LEU | A | 323 | 68.535 | 40.722 | 22.908 | 1.00 | 23.73 |
| ATOM | 2235 | CD1 | LEU | A | 323 | 67.953 | 39.568 | 23.727 | 1.00 | 23.66 |
| ATOM | 2236 | CD2 | LEU | A | 323 | 69.893 | 40.342 | 22.332 | 1.00 | 24.68 |
| ATOM | 2237 | C | LEU | A | 323 | 67.218 | 42.410 | 19.664 | 1.00 | 22.79 |
| ATOM | 2238 | O | LEU | A | 323 | 67.639 | 41.860 | 18.649 | 1.00 | 24.20 |
| ATOM | 2239 | N | THR | A | 324 | 66.079 | 43.096 | 19.688 | 1.00 | 22.20 |
| ATOM | 2240 | CA | THR | A | 324 | 65.261 | 43.232 | 18.489 | 1.00 | 20.96 |
| ATOM | 2241 | CB | THR | A | 324 | 63.755 | 43.053 | 18.811 | 1.00 | 19.95 |
| ATOM | 2242 | OG1 | THR | A | 324 | 63.345 | 44.007 | 19.801 | 1.00 | 17.13 |
| ATOM | 2243 | CG2 | THR | A | 324 | 63.495 | 41.646 | 19.326 | 1.00 | 17.79 |
| ATOM | 2244 | C | THR | A | 324 | 65.489 | 44.581 | 17.808 | 1.00 | 21.51 |
| ATOM | 2245 | O | THR | A | 324 | 64.767 | 44.951 | 16.886 | 1.00 | 21.72 |
| ATOM | 2246 | N | GLN | A | 325 | 66.506 | 45.304 | 18.272 | 1.00 | 22.07 |
| ATOM | 2247 | CA | GLN | A | 325 | 66.872 | 46.605 | 17.718 | 1.00 | 22.99 |
| ATOM | 2248 | CB | GLN | A | 325 | 67.391 | 46.454 | 16.278 | 1.00 | 26.13 |
| ATOM | 2249 | CG | GLN | A | 325 | 68.721 | 45.719 | 16.143 | 1.00 | 30.04 |
| ATOM | 2250 | CD | GLN | A | 325 | 68.592 | 44.225 | 16.351 | 1.00 | 35.44 |
| ATOM | 2251 | OE1 | GLN | A | 325 | 67.920 | 43.539 | 15.580 | 1.00 | 40.43 |
| ATOM | 2252 | NE2 | GLN | A | 325 | 69.235 | 43.709 | 17.395 | 1.00 | 37.40 |
| ATOM | 2253 | C | GLN | A | 325 | 65.741 | 47.622 | 17.732 | 1.00 | 22.90 |
| ATOM | 2254 | O | GLN | A | 325 | 65.660 | 48.479 | 16.851 | 1.00 | 23.32 |
| ATOM | 2255 | N | GLY | A | 326 | 64.875 | 47.534 | 18.734 | 1.00 | 22.53 |
| ATOM | 2256 | CA | GLY | A | 326 | 63.768 | 48.465 | 18.832 | 1.00 | 22.38 |
| ATOM | 2257 | C | GLY | A | 326 | 62.810 | 48.420 | 17.654 | 1.00 | 22.83 |
| ATOM | 2258 | O | GLY | A | 326 | 62.076 | 49.378 | 17.419 | 1.00 | 21.73 |
| ATOM | 2259 | N | ARG | A | 327 | 62.804 | 47.310 | 16.919 | 1.00 | 23.29 |
| ATOM | 2260 | CA | ARG | A | 327 | 61.927 | 47.166 | 15.758 | 1.00 | 25.92 |
| ATOM | 2261 | CB | ARG | A | 327 | 62.728 | 46.639 | 14.561 | 1.00 | 28.46 |
| ATOM | 2262 | CG | ARG | A | 327 | 63.821 | 47.598 | 14.096 | 1.00 | 33.87 |
| ATOM | 2263 | CD | ARG | A | 327 | 64.739 | 46.980 | 13.050 | 1.00 | 38.29 |
| ATOM | 2264 | NE | ARG | A | 327 | 65.816 | 47.898 | 12.674 | 1.00 | 43.49 |
| ATOM | 2265 | CZ | ARG | A | 327 | 66.892 | 47.549 | 11.970 | 1.00 | 45.02 |
| ATOM | 2266 | NH1 | ARG | A | 327 | 67.043 | 46.296 | 11.555 | 1.00 | 45.41 |
| ATOM | 2267 | NH2 | ARG | A | 327 | 67.828 | 48.451 | 11.693 | 1.00 | 43.95 |
| ATOM | 2268 | C | ARG | A | 327 | 60.734 | 46.250 | 16.032 | 1.00 | 25.90 |
| ATOM | 2269 | O | ARG | A | 327 | 59.890 | 46.037 | 15.164 | 1.00 | 26.33 |
| ATOM | 2270 | N | VAL | A | 328 | 60.671 | 45.702 | 17.240 | 1.00 | 24.56 |
| ATOM | 2271 | CA | VAL | A | 328 | 59.568 | 44.828 | 17.609 | 1.00 | 22.68 |
| ATOM | 2272 | CB | VAL | A | 328 | 60.068 | 43.433 | 18.031 | 1.00 | 22.99 |
| ATOM | 2273 | CG1 | VAL | A | 328 | 58.908 | 42.603 | 18.552 | 1.00 | 21.00 |
| ATOM | 2274 | CG2 | VAL | A | 328 | 60.723 | 42.737 | 16.842 | 1.00 | 21.97 |
| ATOM | 2275 | C | VAL | A | 328 | 58.809 | 45.454 | 18.767 | 1.00 | 21.90 |
| ATOM | 2276 | O | VAL | A | 328 | 59.358 | 45.640 | 19.851 | 1.00 | 23.29 |
| ATOM | 2277 | N | PRO | A | 329 | 57.537 | 45.805 | 18.543 | 1.00 | 20.29 |
| ATOM | 2278 | CD | PRO | A | 329 | 56.804 | 45.685 | 17.271 | 1.00 | 19.73 |
| ATOM | 2279 | CA | PRO | A | 329 | 56.694 | 46.418 | 19.575 | 1.00 | 18.81 |
| ATOM | 2280 | CB | PRO | A | 329 | 55.329 | 46.509 | 18.895 | 1.00 | 18.78 |
| ATOM | 2281 | CG | PRO | A | 329 | 55.687 | 46.689 | 17.448 | 1.00 | 17.49 |
| ATOM | 2282 | C | PRO | A | 329 | 56.651 | 45.575 | 20.853 | 1.00 | 18.50 |
| ATOM | 2283 | O | PRO | A | 329 | 56.452 | 44.354 | 20.810 | 1.00 | 16.92 |
| ATOM | 2284 | N | ILE | A | 330 | 56.833 | 46.231 | 21.991 | 1.00 | 15.45 |
| ATOM | 2285 | CA | ILE | A | 330 | 56.804 | 45.528 | 23.257 | 1.00 | 15.61 |
| ATOM | 2286 | CB | ILE | A | 330 | 58.176 | 45.604 | 23.968 | 1.00 | 15.68 |
| ATOM | 2287 | CG2 | ILE | A | 330 | 58.062 | 45.057 | 25.379 | 1.00 | 14.36 |
| ATOM | 2288 | CG1 | ILE | A | 330 | 59.224 | 44.823 | 23.178 | 1.00 | 14.42 |
| ATOM | 2289 | CD1 | ILE | A | 330 | 60.631 | 44.968 | 23.735 | 1.00 | 15.43 |
| ATOM | 2290 | C | ILE | A | 330 | 55.754 | 46.078 | 24.212 | 1.00 | 16.03 |
| ATOM | 2291 | O | ILE | A | 330 | 55.612 | 47.298 | 24.375 | 1.00 | 15.26 |
| ATOM | 2292 | N | ILE | A | 331 | 55.004 | 45.170 | 24.828 | 1.00 | 15.71 |

TABLE 31-continued

| ATOM | 2293 | CA | ILE A | 331 | 54.016 | 45.559 | 25.824 | 1.00 | 15.25 |
|---|---|---|---|---|---|---|---|---|---|
| ATOM | 2294 | CB | ILE A | 331 | 52.689 | 44.779 | 25.681 | 1.00 | 15.14 |
| ATOM | 2295 | CG2 | ILE A | 331 | 51.736 | 45.170 | 26.810 | 1.00 | 12.02 |
| ATOM | 2296 | CG1 | ILE A | 331 | 52.044 | 45.082 | 24.324 | 1.00 | 15.56 |
| ATOM | 2297 | CD1 | ILE A | 331 | 50.696 | 44.422 | 24.124 | 1.00 | 13.64 |
| ATOM | 2298 | C | ILE A | 331 | 54.670 | 45.189 | 27.153 | 1.00 | 16.63 |
| ATOM | 2299 | O | ILE A | 331 | 54.932 | 44.006 | 27.417 | 1.00 | 15.95 |
| ATOM | 2300 | N | GLY A | 332 | 54.959 | 46.202 | 27.968 | 1.00 | 15.10 |
| ATOM | 2301 | CA | GLY A | 332 | 55.592 | 45.975 | 29.259 | 1.00 | 14.50 |
| ATOM | 2302 | C | GLY A | 332 | 54.609 | 45.654 | 30.371 | 1.00 | 14.08 |
| ATOM | 2303 | O | GLY A | 332 | 53.618 | 46.357 | 30.560 | 1.00 | 16.41 |
| ATOM | 2304 | N | VAL A | 333 | 54.899 | 44.602 | 31.128 | 1.00 | 14.35 |
| ATOM | 2305 | CA | VAL A | 333 | 54.021 | 44.170 | 32.209 | 1.00 | 13.53 |
| ATOM | 2306 | CB | VAL A | 333 | 53.091 | 43.023 | 31.750 | 1.00 | 14.02 |
| ATOM | 2307 | CG1 | VAL A | 333 | 51.850 | 42.971 | 32.637 | 1.00 | 13.16 |
| ATOM | 2308 | CG2 | VAL A | 333 | 52.739 | 43.188 | 30.296 | 1.00 | 16.07 |
| ATOM | 2309 | C | VAL A | 333 | 54.829 | 43.634 | 33.378 | 1.00 | 12.62 |
| ATOM | 2310 | O | VAL A | 333 | 55.777 | 42.875 | 33.189 | 1.00 | 12.37 |
| ATOM | 2311 | N | GLY A | 334 | 54.435 | 44.010 | 34.589 | 1.00 | 13.68 |
| ATOM | 2312 | CA | GLY A | 334 | 55.139 | 43.536 | 35.765 | 1.00 | 12.74 |
| ATOM | 2313 | C | GLY A | 334 | 55.392 | 44.600 | 36.812 | 1.00 | 12.69 |
| ATOM | 2314 | O | GLY A | 334 | 56.300 | 45.422 | 36.666 | 1.00 | 12.36 |
| ATOM | 2315 | N | GLY A | 335 | 54.576 | 44.591 | 37.864 | 1.00 | 13.87 |
| ATOM | 2316 | CA | GLY A | 335 | 54.735 | 45.542 | 38.953 | 1.00 | 13.62 |
| ATOM | 2317 | C | GLY A | 335 | 54.524 | 47.013 | 38.636 | 1.00 | 14.82 |
| ATOM | 2318 | O | GLY A | 335 | 55.149 | 47.877 | 39.253 | 1.00 | 16.20 |
| ATOM | 2319 | N | VAL A | 336 | 53.667 | 47.317 | 37.673 | 1.00 | 15.48 |
| ATOM | 2320 | CA | VAL A | 336 | 53.401 | 48.714 | 37.354 | 1.00 | 16.86 |
| ATOM | 2321 | CB | VAL A | 336 | 52.932 | 48.892 | 35.899 | 1.00 | 17.58 |
| ATOM | 2322 | CG1 | VAL A | 336 | 52.416 | 50.312 | 35.690 | 1.00 | 17.86 |
| ATOM | 2323 | CG2 | VAL A | 336 | 54.080 | 48.611 | 34.949 | 1.00 | 17.23 |
| ATOM | 2324 | C | VAL A | 336 | 52.299 | 49.189 | 38.292 | 1.00 | 17.67 |
| ATOM | 2325 | O | VAL A | 336 | 51.202 | 48.626 | 38.316 | 1.00 | 18.02 |
| ATOM | 2326 | N | SER A | 337 | 52.589 | 50.225 | 39.066 | 1.00 | 17.73 |
| ATOM | 2327 | CA | SER A | 337 | 51.608 | 50.732 | 40.007 | 1.00 | 19.15 |
| ATOM | 2328 | CB | SER A | 337 | 51.932 | 50.195 | 41.405 | 1.00 | 19.61 |
| ATOM | 2329 | OG | SER A | 337 | 50.979 | 50.643 | 42.353 | 1.00 | 27.71 |
| ATOM | 2330 | C | SER A | 337 | 51.534 | 52.258 | 40.037 | 1.00 | 18.75 |
| ATOM | 2331 | O | SER A | 337 | 50.711 | 52.829 | 40.750 | 1.00 | 19.78 |
| ATOM | 2332 | N | SER A | 338 | 52.383 | 52.913 | 39.253 | 1.00 | 17.88 |
| ATOM | 2333 | CA | SER A | 338 | 52.415 | 54.369 | 39.217 | 1.00 | 15.56 |
| ATOM | 2334 | CB | SER A | 338 | 53.340 | 54.894 | 40.320 | 1.00 | 15.85 |
| ATOM | 2335 | OG | SER A | 338 | 54.696 | 54.624 | 39.992 | 1.00 | 12.85 |
| ATOM | 2336 | C | SER A | 338 | 52.925 | 54.887 | 37.875 | 1.00 | 14.63 |
| ATOM | 2337 | O | SER A | 338 | 53.390 | 54.116 | 37.033 | 1.00 | 15.49 |
| ATOM | 2338 | N | GLY A | 339 | 52.850 | 56.202 | 37.697 | 1.00 | 13.08 |
| ATOM | 2339 | CA | GLY A | 339 | 53.324 | 56.818 | 36.474 | 1.00 | 12.66 |
| ATOM | 2340 | C | GLY A | 339 | 54.793 | 56.514 | 36.241 | 1.00 | 13.17 |
| ATOM | 2341 | O | GLY A | 339 | 55.203 | 56.222 | 35.118 | 1.00 | 12.67 |
| ATOM | 2342 | N | GLN A | 340 | 55.591 | 56.579 | 37.301 | 1.00 | 13.06 |
| ATOM | 2343 | CA | GLN A | 340 | 57.016 | 56.295 | 37.177 | 1.00 | 14.17 |
| ATOM | 2344 | CB | GLN A | 340 | 57.741 | 56.523 | 38.508 | 1.00 | 14.21 |
| ATOM | 2345 | CG | GLN A | 340 | 59.226 | 56.203 | 38.444 | 1.00 | 13.71 |
| ATOM | 2346 | CD | GLN A | 340 | 59.936 | 56.441 | 39.761 | 1.00 | 14.67 |
| ATOM | 2347 | OE1 | GLN A | 340 | 59.940 | 57.557 | 40.280 | 1.00 | 14.48 |
| ATOM | 2348 | NE2 | GLN A | 340 | 60.542 | 55.391 | 40.310 | 1.00 | 11.42 |
| ATOM | 2349 | C | GLN A | 340 | 57.252 | 54.859 | 36.708 | 1.00 | 14.11 |
| ATOM | 2350 | O | GLN A | 340 | 58.096 | 54.622 | 35.836 | 1.00 | 14.42 |
| ATOM | 2351 | N | ASP A | 341 | 56.514 | 53.906 | 37.279 | 1.00 | 11.49 |
| ATOM | 2352 | CA | ASP A | 341 | 56.663 | 52.502 | 36.884 | 1.00 | 12.60 |
| ATOM | 2353 | CB | ASP A | 341 | 55.719 | 51.591 | 37.684 | 1.00 | 12.24 |
| ATOM | 2354 | CG | ASP A | 341 | 55.960 | 51.665 | 39.189 | 1.00 | 16.04 |
| ATOM | 2355 | OD1 | ASP A | 341 | 57.082 | 52.047 | 39.591 | 1.00 | 15.13 |
| ATOM | 2356 | OD2 | ASP A | 341 | 55.031 | 51.327 | 39.965 | 1.00 | 13.13 |
| ATOM | 2357 | C | ASP A | 341 | 56.365 | 52.343 | 35.395 | 1.00 | 13.28 |
| ATOM | 2358 | O | ASP A | 341 | 57.066 | 51.629 | 34.676 | 1.00 | 13.43 |
| ATOM | 2359 | N | ALA A | 342 | 55.316 | 53.014 | 34.937 | 1.00 | 13.11 |
| ATOM | 2360 | CA | ALA A | 342 | 54.934 | 52.953 | 33.537 | 1.00 | 12.86 |
| ATOM | 2361 | CB | ALA A | 342 | 53.596 | 53.667 | 33.333 | 1.00 | 12.58 |
| ATOM | 2362 | C | ALA A | 342 | 56.009 | 53.592 | 32.659 | 1.00 | 14.10 |
| ATOM | 2363 | O | ALA A | 342 | 56.454 | 52.997 | 31.667 | 1.00 | 14.84 |
| ATOM | 2364 | N | LEU A | 343 | 56.432 | 54.796 | 33.031 | 1.00 | 12.15 |
| ATOM | 2365 | CA | LEU A | 343 | 57.439 | 55.510 | 32.258 | 1.00 | 13.26 |
| ATOM | 2366 | CB | LEU A | 343 | 57.654 | 56.922 | 32.816 | 1.00 | 12.73 |
| ATOM | 2367 | CG | LEU A | 343 | 58.567 | 57.798 | 31.949 | 1.00 | 16.01 |
| ATOM | 2368 | CD1 | LEU A | 343 | 58.063 | 57.773 | 30.503 | 1.00 | 12.43 |
| ATOM | 2369 | CD2 | LEU A | 343 | 58.609 | 59.226 | 32.491 | 1.00 | 12.05 |
| ATOM | 2370 | C | LEU A | 343 | 58.772 | 54.774 | 32.191 | 1.00 | 13.16 |
| ATOM | 2371 | O | LEU A | 343 | 59.443 | 54.810 | 31.164 | 1.00 | 15.02 |

TABLE 31-continued

| | | | | | | | | | |
|---|---|---|---|---|---|---|---|---|---|
| ATOM | 2372 | N | GLU | A | 344 | 59.165 | 54.110 | 33.275 | 1.00 | 13.69 |
| ATOM | 2373 | CA | GLU | A | 344 | 60.426 | 53.378 | 33.263 | 1.00 | 13.68 |
| ATOM | 2374 | CB | GLU | A | 344 | 60.756 | 52.814 | 34.650 | 1.00 | 15.25 |
| ATOM | 2375 | CG | GLU | A | 344 | 61.171 | 53.877 | 35.661 | 1.00 | 16.62 |
| ATOM | 2376 | CD | GLU | A | 344 | 61.776 | 53.285 | 36.929 | 1.00 | 18.34 |
| ATOM | 2377 | OE1 | GLU | A | 344 | 61.446 | 52.128 | 37.263 | 1.00 | 20.22 |
| ATOM | 2378 | OE2 | GLU | A | 344 | 62.569 | 53.980 | 37.601 | 1.00 | 16.51 |
| ATOM | 2379 | C | GLU | A | 344 | 60.389 | 52.250 | 32.237 | 1.00 | 14.20 |
| ATOM | 2380 | O | GLU | A | 344 | 61.382 | 51.994 | 31.553 | 1.00 | 14.32 |
| ATOM | 2381 | N | LYS | A | 345 | 59.246 | 51.577 | 32.121 | 1.00 | 13.49 |
| ATOM | 2382 | CA | LYS | A | 345 | 59.122 | 50.498 | 31.146 | 1.00 | 14.71 |
| ATOM | 2383 | CB | LYS | A | 345 | 57.874 | 49.658 | 31.438 | 1.00 | 14.57 |
| ATOM | 2384 | CG | LYS | A | 345 | 58.094 | 48.647 | 32.550 | 1.00 | 14.32 |
| ATOM | 2385 | CD | LYS | A | 345 | 56.844 | 47.839 | 32.832 | 1.00 | 15.62 |
| ATOM | 2386 | CE | LYS | A | 345 | 57.177 | 46.571 | 33.599 | 1.00 | 16.36 |
| ATOM | 2387 | NZ | LYS | A | 345 | 57.899 | 46.844 | 34.871 | 1.00 | 15.43 |
| ATOM | 2388 | C | LYS | A | 345 | 59.076 | 51.074 | 29.732 | 1.00 | 14.36 |
| ATOM | 2389 | O | LYS | A | 345 | 59.661 | 50.518 | 28.802 | 1.00 | 13.74 |
| ATOM | 2390 | N | ILE | A | 346 | 58.386 | 52.195 | 29.571 | 1.00 | 14.93 |
| ATOM | 2391 | CA | ILE | A | 346 | 58.313 | 52.839 | 28.268 | 1.00 | 16.11 |
| ATOM | 2392 | CB | ILE | A | 346 | 57.371 | 54.069 | 28.305 | 1.00 | 16.07 |
| ATOM | 2393 | CG2 | ILE | A | 346 | 57.469 | 54.856 | 26.990 | 1.00 | 14.19 |
| ATOM | 2394 | CG1 | ILE | A | 346 | 55.933 | 53.591 | 28.544 | 1.00 | 15.01 |
| ATOM | 2395 | CD1 | ILE | A | 346 | 54.929 | 54.691 | 28.737 | 1.00 | 15.20 |
| ATOM | 2396 | C | ILE | A | 346 | 59.720 | 53.259 | 27.828 | 1.00 | 16.73 |
| ATOM | 2397 | O | ILE | A | 346 | 60.143 | 52.946 | 26.717 | 1.00 | 16.30 |
| ATOM | 2398 | N | ARG | A | 347 | 60.449 | 53.949 | 28.704 | 1.00 | 16.86 |
| ATOM | 2399 | CA | ARG | A | 347 | 61.809 | 54.382 | 28.378 | 1.00 | 16.55 |
| ATOM | 2400 | CB | ARG | A | 347 | 62.406 | 55.217 | 29.517 | 1.00 | 17.95 |
| ATOM | 2401 | CG | ARG | A | 347 | 61.684 | 56.539 | 29.803 | 1.00 | 20.16 |
| ATOM | 2402 | CD | ARG | A | 347 | 62.472 | 57.388 | 30.800 | 1.00 | 21.27 |
| ATOM | 2403 | NE | ARG | A | 347 | 63.840 | 57.588 | 30.338 | 1.00 | 25.93 |
| ATOM | 2404 | CZ | ARG | A | 347 | 64.480 | 58.754 | 30.349 | 1.00 | 29.53 |
| ATOM | 2405 | NH1 | ARG | A | 347 | 63.877 | 59.846 | 30.810 | 1.00 | 29.00 |
| ATOM | 2406 | NH2 | ARG | A | 347 | 65.719 | 58.832 | 29.874 | 1.00 | 26.21 |
| ATOM | 2407 | C | ARG | A | 347 | 62.713 | 53.177 | 28.118 | 1.00 | 16.64 |
| ATOM | 2408 | O | ARG | A | 347 | 63.668 | 53.257 | 27.343 | 1.00 | 16.63 |
| ATOM | 2409 | N | ALA | A | 348 | 62.411 | 52.062 | 28.775 | 1.00 | 14.46 |
| ATOM | 2410 | CA | ALA | A | 348 | 63.197 | 50.851 | 28.603 | 1.00 | 14.27 |
| ATOM | 2411 | CB | ALA | A | 348 | 62.926 | 49.869 | 29.752 | 1.00 | 11.73 |
| ATOM | 2412 | C | ALA | A | 348 | 62.881 | 50.201 | 27.258 | 1.00 | 14.91 |
| ATOM | 2413 | O | ALA | A | 348 | 63.626 | 49.326 | 26.799 | 1.00 | 16.61 |
| ATOM | 2414 | N | GLY | A | 349 | 61.781 | 50.617 | 26.626 | 1.00 | 12.73 |
| ATOM | 2415 | CA | GLY | A | 349 | 61.445 | 50.054 | 25.328 | 1.00 | 12.91 |
| ATOM | 2416 | C | GLY | A | 349 | 60.010 | 49.614 | 25.091 | 1.00 | 14.02 |
| ATOM | 2417 | O | GLY | A | 349 | 59.671 | 49.197 | 23.988 | 1.00 | 13.81 |
| ATOM | 2418 | N | ALA | A | 350 | 59.163 | 49.702 | 26.109 | 1.00 | 13.85 |
| ATOM | 2419 | CA | ALA | A | 350 | 57.771 | 49.303 | 25.955 | 1.00 | 16.14 |
| ATOM | 2420 | CB | ALA | A | 350 | 57.159 | 49.002 | 27.320 | 1.00 | 15.86 |
| ATOM | 2421 | C | ALA | A | 350 | 56.961 | 50.389 | 25.255 | 1.00 | 17.71 |
| ATOM | 2422 | O | ALA | A | 350 | 57.080 | 51.572 | 25.585 | 1.00 | 16.71 |
| ATOM | 2423 | N | SER | A | 351 | 56.147 | 49.983 | 24.285 | 1.00 | 16.76 |
| ATOM | 2424 | CA | SER | A | 351 | 55.297 | 50.918 | 23.559 | 1.00 | 17.15 |
| ATOM | 2425 | CB | SER | A | 351 | 55.016 | 50.403 | 22.146 | 1.00 | 16.62 |
| ATOM | 2426 | OG | SER | A | 351 | 56.181 | 50.446 | 21.345 | 1.00 | 20.56 |
| ATOM | 2427 | C | SER | A | 351 | 53.980 | 51.058 | 24.323 | 1.00 | 16.46 |
| ATOM | 2428 | O | SER | A | 351 | 53.284 | 52.068 | 24.213 | 1.00 | 16.26 |
| ATOM | 2429 | N | LEU | A | 352 | 53.658 | 50.022 | 25.091 | 1.00 | 15.13 |
| ATOM | 2430 | CA | LEU | A | 352 | 52.446 | 49.970 | 25.904 | 1.00 | 15.38 |
| ATOM | 2431 | CB | LEU | A | 352 | 51.334 | 49.216 | 25.169 | 1.00 | 12.70 |
| ATOM | 2432 | CG | LEU | A | 352 | 50.889 | 49.651 | 23.773 | 1.00 | 15.23 |
| ATOM | 2433 | CD1 | LEU | A | 352 | 50.006 | 48.557 | 23.165 | 1.00 | 11.58 |
| ATOM | 2434 | CD2 | LEU | A | 352 | 50.138 | 50.984 | 23.853 | 1.00 | 13.14 |
| ATOM | 2435 | C | LEU | A | 352 | 52.761 | 49.208 | 27.192 | 1.00 | 13.73 |
| ATOM | 2436 | O | LEU | A | 352 | 53.703 | 48.415 | 27.237 | 1.00 | 12.90 |
| ATOM | 2437 | N | VAL | A | 353 | 51.976 | 49.450 | 28.235 | 1.00 | 13.10 |
| ATOM | 2438 | CA | VAL | A | 353 | 52.166 | 48.739 | 29.490 | 1.00 | 14.60 |
| ATOM | 2439 | CB | VAL | A | 353 | 52.772 | 49.632 | 30.608 | 1.00 | 15.22 |
| ATOM | 2440 | CG1 | VAL | A | 353 | 54.074 | 50.246 | 30.131 | 1.00 | 15.03 |
| ATOM | 2441 | CG2 | VAL | A | 353 | 51.778 | 50.702 | 31.036 | 1.00 | 14.13 |
| ATOM | 2442 | C | VAL | A | 353 | 50.822 | 48.231 | 29.971 | 1.00 | 15.79 |
| ATOM | 2443 | O | VAL | A | 353 | 49.771 | 48.707 | 29.529 | 1.00 | 15.51 |
| ATOM | 2444 | N | GLN | A | 354 | 50.869 | 47.249 | 30.863 | 1.00 | 15.70 |
| ATOM | 2445 | CA | GLN | A | 354 | 49.668 | 46.667 | 31.447 | 1.00 | 15.81 |
| ATOM | 2446 | CB | GLN | A | 354 | 49.376 | 45.274 | 30.875 | 1.00 | 15.87 |
| ATOM | 2447 | CG | GLN | A | 354 | 49.121 | 45.206 | 29.378 | 1.00 | 17.93 |
| ATOM | 2448 | CD | GLN | A | 354 | 48.967 | 43.766 | 28.899 | 1.00 | 18.91 |
| ATOM | 2449 | OE1 | GLN | A | 354 | 49.736 | 42.887 | 29.294 | 1.00 | 18.78 |
| ATOM | 2450 | NE2 | GLN | A | 354 | 47.981 | 43.521 | 28.042 | 1.00 | 17.21 |

TABLE 31-continued

| ATOM | 2451 | C   | GLN A | 354 | 49.927 | 46.517 | 32.934 | 1.00 | 15.00 |
|------|------|-----|-------|-----|--------|--------|--------|------|-------|
| ATOM | 2452 | O   | GLN A | 354 | 51.072 | 46.529 | 33.381 | 1.00 | 15.73 |
| ATOM | 2453 | N   | LEU A | 355 | 48.859 | 46.375 | 33.700 | 1.00 | 14.64 |
| ATOM | 2454 | CA  | LEU A | 355 | 48.997 | 46.176 | 35.130 | 1.00 | 15.27 |
| ATOM | 2455 | CB  | LEU A | 355 | 48.939 | 47.514 | 35.875 | 1.00 | 13.69 |
| ATOM | 2456 | CG  | LEU A | 355 | 47.681 | 48.387 | 35.758 | 1.00 | 13.82 |
| ATOM | 2457 | CD1 | LEU A | 355 | 46.594 | 47.877 | 36.703 | 1.00 | 13.24 |
| ATOM | 2458 | CD2 | LEU A | 355 | 48.044 | 49.828 | 36.101 | 1.00 | 12.06 |
| ATOM | 2459 | C   | LEU A | 355 | 47.867 | 45.270 | 35.575 | 1.00 | 16.12 |
| ATOM | 2460 | O   | LEU A | 355 | 46.827 | 45.184 | 34.913 | 1.00 | 15.56 |
| ATOM | 2461 | N   | TYR A | 356 | 48.084 | 44.566 | 36.677 | 1.00 | 16.25 |
| ATOM | 2462 | CA  | TYR A | 356 | 47.053 | 43.699 | 37.216 | 1.00 | 16.45 |
| ATOM | 2463 | CB  | TYR A | 356 | 47.214 | 42.258 | 36.696 | 1.00 | 14.66 |
| ATOM | 2464 | CG  | TYR A | 356 | 46.143 | 41.280 | 37.173 | 1.00 | 14.33 |
| ATOM | 2465 | CD1 | TYR A | 356 | 46.053 | 40.004 | 36.630 | 1.00 | 13.71 |
| ATOM | 2466 | CE1 | TYR A | 356 | 45.110 | 39.093 | 37.082 | 1.00 | 11.25 |
| ATOM | 2467 | CD2 | TYR A | 356 | 45.248 | 41.618 | 38.188 | 1.00 | 13.31 |
| ATOM | 2468 | CE2 | TYR A | 356 | 44.301 | 40.711 | 38.647 | 1.00 | 12.21 |
| ATOM | 2469 | CZ  | TYR A | 356 | 44.238 | 39.451 | 38.091 | 1.00 | 12.75 |
| ATOM | 2470 | OH  | TYR A | 356 | 43.300 | 38.542 | 38.540 | 1.00 | 11.10 |
| ATOM | 2471 | C   | TYR A | 356 | 47.121 | 43.739 | 38.733 | 1.00 | 16.00 |
| ATOM | 2472 | O   | TYR A | 356 | 46.185 | 44.200 | 39.386 | 1.00 | 17.57 |
| ATOM | 2473 | N   | THR A | 357 | 48.237 | 43.284 | 39.289 | 1.00 | 16.04 |
| ATOM | 2474 | CA  | THR A | 357 | 48.396 | 43.236 | 40.740 | 1.00 | 15.39 |
| ATOM | 2475 | CB  | THR A | 357 | 49.803 | 42.738 | 41.115 | 1.00 | 14.82 |
| ATOM | 2476 | OG1 | THR A | 357 | 50.003 | 41.441 | 40.544 | 1.00 | 11.74 |
| ATOM | 2477 | CG2 | THR A | 357 | 49.953 | 42.641 | 42.630 | 1.00 | 13.55 |
| ATOM | 2478 | C   | THR A | 357 | 48.111 | 44.551 | 41.462 | 1.00 | 15.12 |
| ATOM | 2479 | O   | THR A | 357 | 47.484 | 44.552 | 42.523 | 1.00 | 14.91 |
| ATOM | 2480 | N   | ALA A | 358 | 48.564 | 45.665 | 40.896 | 1.00 | 13.89 |
| ATOM | 2481 | CA  | ALA A | 358 | 48.332 | 46.966 | 41.513 | 1.00 | 13.56 |
| ATOM | 2482 | CB  | ALA A | 358 | 48.952 | 48.062 | 40.674 | 1.00 | 12.26 |
| ATOM | 2483 | C   | ALA A | 358 | 46.838 | 47.218 | 41.677 | 1.00 | 15.00 |
| ATOM | 2484 | O   | ALA A | 358 | 46.410 | 47.833 | 42.654 | 1.00 | 15.57 |
| ATOM | 2485 | N   | LEU A | 359 | 46.045 | 46.745 | 40.718 | 1.00 | 15.00 |
| ATOM | 2486 | CA  | LEU A | 359 | 44.596 | 46.914 | 40.779 | 1.00 | 14.68 |
| ATOM | 2487 | CB  | LEU A | 359 | 43.950 | 46.429 | 39.479 | 1.00 | 16.11 |
| ATOM | 2488 | CG  | LEU A | 359 | 42.418 | 46.354 | 39.441 | 1.00 | 17.58 |
| ATOM | 2489 | CD1 | LEU A | 359 | 41.818 | 47.752 | 39.545 | 1.00 | 15.57 |
| ATOM | 2490 | CD2 | LEU A | 359 | 41.978 | 45.680 | 38.148 | 1.00 | 16.77 |
| ATOM | 2491 | C   | LEU A | 359 | 44.003 | 46.140 | 41.962 | 1.00 | 14.70 |
| ATOM | 2492 | O   | LEU A | 359 | 43.009 | 46.562 | 42.548 | 1.00 | 14.02 |
| ATOM | 2493 | N   | THR A | 360 | 44.618 | 45.013 | 42.313 | 1.00 | 14.46 |
| ATOM | 2494 | CA  | THR A | 360 | 44.125 | 44.195 | 43.423 | 1.00 | 15.22 |
| ATOM | 2495 | CB  | THR A | 360 | 44.750 | 42.781 | 43.416 | 1.00 | 14.92 |
| ATOM | 2496 | OG1 | THR A | 360 | 46.117 | 42.854 | 43.844 | 1.00 | 13.82 |
| ATOM | 2497 | CG2 | THR A | 360 | 44.699 | 42.189 | 42.014 | 1.00 | 15.29 |
| ATOM | 2498 | C   | THR A | 360 | 44.384 | 44.820 | 44.793 | 1.00 | 16.37 |
| ATOM | 2499 | O   | THR A | 360 | 43.793 | 44.400 | 45.785 | 1.00 | 18.61 |
| ATOM | 2500 | N   | PHE A | 361 | 45.267 | 45.812 | 44.855 | 1.00 | 16.42 |
| ATOM | 2501 | CA  | PHE A | 361 | 45.558 | 46.475 | 46.127 | 1.00 | 17.90 |
| ATOM | 2502 | CB  | PHE A | 361 | 47.071 | 46.634 | 46.335 | 1.00 | 17.58 |
| ATOM | 2503 | CG  | PHE A | 361 | 47.786 | 45.347 | 46.637 | 1.00 | 18.37 |
| ATOM | 2504 | CD1 | PHE A | 361 | 48.595 | 44.748 | 45.686 | 1.00 | 14.59 |
| ATOM | 2505 | CD2 | PHE A | 361 | 47.640 | 44.733 | 47.874 | 1.00 | 17.75 |
| ATOM | 2506 | CE1 | PHE A | 361 | 49.246 | 43.566 | 45.959 | 1.00 | 16.05 |
| ATOM | 2507 | CE2 | PHE A | 361 | 48.290 | 43.544 | 48.153 | 1.00 | 16.55 |
| ATOM | 2508 | CZ  | PHE A | 361 | 49.095 | 42.961 | 47.191 | 1.00 | 17.17 |
| ATOM | 2509 | C   | PHE A | 361 | 44.915 | 47.854 | 46.253 | 1.00 | 19.13 |
| ATOM | 2510 | O   | PHE A | 361 | 44.343 | 48.182 | 47.285 | 1.00 | 21.10 |
| ATOM | 2511 | N   | TRP A | 362 | 45.003 | 48.651 | 45.190 | 1.00 | 20.60 |
| ATOM | 2512 | CA  | TRP A | 362 | 44.486 | 50.013 | 45.195 | 1.00 | 21.41 |
| ATOM | 2513 | CB  | TRP A | 362 | 45.496 | 50.920 | 44.490 | 1.00 | 22.91 |
| ATOM | 2514 | CG  | TRP A | 362 | 46.898 | 50.632 | 44.933 | 1.00 | 26.83 |
| ATOM | 2515 | CD2 | TRP A | 362 | 47.349 | 50.422 | 46.281 | 1.00 | 28.83 |
| ATOM | 2516 | CE2 | TRP A | 362 | 48.720 | 50.113 | 46.218 | 1.00 | 29.25 |
| ATOM | 2517 | CE3 | TRP A | 362 | 46.724 | 50.464 | 47.534 | 1.00 | 30.95 |
| ATOM | 2518 | CD1 | TRP A | 362 | 47.985 | 50.452 | 44.136 | 1.00 | 26.57 |
| ATOM | 2519 | NE1 | TRP A | 362 | 49.084 | 50.137 | 44.898 | 1.00 | 28.79 |
| ATOM | 2520 | CZ2 | TRP A | 362 | 49.481 | 49.845 | 47.360 | 1.00 | 31.64 |
| ATOM | 2521 | CZ3 | TRP A | 362 | 47.483 | 50.196 | 48.670 | 1.00 | 31.33 |
| ATOM | 2522 | CH2 | TRP A | 362 | 48.844 | 49.891 | 48.574 | 1.00 | 31.06 |
| ATOM | 2523 | C   | TRP A | 362 | 43.103 | 50.207 | 44.591 | 1.00 | 21.32 |
| ATOM | 2524 | O   | TRP A | 362 | 42.443 | 51.213 | 44.856 | 1.00 | 21.63 |
| ATOM | 2525 | N   | GLY A | 363 | 42.665 | 49.251 | 43.782 | 1.00 | 20.14 |
| ATOM | 2526 | CA  | GLY A | 363 | 41.356 | 49.364 | 43.170 | 1.00 | 19.06 |
| ATOM | 2527 | C   | GLY A | 363 | 41.365 | 50.224 | 41.923 | 1.00 | 19.91 |
| ATOM | 2528 | O   | GLY A | 363 | 42.398 | 50.776 | 41.545 | 1.00 | 20.15 |
| ATOM | 2529 | N   | PRO A | 364 | 40.209 | 50.361 | 41.262 | 1.00 | 19.64 |

TABLE 31-continued

| | | | | | | | | | |
|---|---|---|---|---|---|---|---|---|---|
| ATOM | 2530 | CD | PRO | A | 364 | 38.936 | 49.783 | 41.731 | 1.00 | 19.35 |
| ATOM | 2531 | CA | PRO | A | 364 | 40.006 | 51.145 | 40.040 | 1.00 | 19.08 |
| ATOM | 2532 | CB | PRO | A | 364 | 38.489 | 51.295 | 39.980 | 1.00 | 18.78 |
| ATOM | 2533 | CG | PRO | A | 364 | 38.019 | 49.989 | 40.535 | 1.00 | 19.83 |
| ATOM | 2534 | C | PRO | A | 364 | 40.715 | 52.497 | 39.979 | 1.00 | 18.77 |
| ATOM | 2535 | O | PRO | A | 364 | 41.272 | 52.859 | 38.951 | 1.00 | 21.11 |
| ATOM | 2536 | N | PRO | A | 365 | 40.703 | 53.265 | 41.079 | 1.00 | 20.00 |
| ATOM | 2537 | CD | PRO | A | 365 | 40.089 | 53.024 | 42.398 | 1.00 | 18.27 |
| ATOM | 2538 | CA | PRO | A | 365 | 41.370 | 54.571 | 41.048 | 1.00 | 18.58 |
| ATOM | 2539 | CB | PRO | A | 365 | 41.237 | 55.060 | 42.491 | 1.00 | 19.56 |
| ATOM | 2540 | CG | PRO | A | 365 | 39.955 | 54.429 | 42.946 | 1.00 | 18.79 |
| ATOM | 2541 | C | PRO | A | 365 | 42.828 | 54.538 | 40.588 | 1.00 | 18.76 |
| ATOM | 2542 | O | PRO | A | 365 | 43.366 | 55.557 | 40.149 | 1.00 | 19.39 |
| ATOM | 2543 | N | VAL | A | 366 | 43.472 | 53.378 | 40.680 | 1.00 | 16.81 |
| ATOM | 2544 | CA | VAL | A | 366 | 44.870 | 53.284 | 40.278 | 1.00 | 15.69 |
| ATOM | 2545 | CB | VAL | A | 366 | 45.471 | 51.900 | 40.632 | 1.00 | 17.04 |
| ATOM | 2546 | CG1 | VAL | A | 366 | 45.032 | 50.854 | 39.620 | 1.00 | 14.83 |
| ATOM | 2547 | CG2 | VAL | A | 366 | 46.983 | 51.999 | 40.703 | 1.00 | 15.11 |
| ATOM | 2548 | C | VAL | A | 366 | 45.062 | 53.549 | 38.786 | 1.00 | 15.92 |
| ATOM | 2549 | O | VAL | A | 366 | 46.099 | 54.056 | 38.369 | 1.00 | 15.23 |
| ATOM | 2550 | N | VAL | A | 367 | 44.061 | 53.218 | 37.977 | 1.00 | 17.40 |
| ATOM | 2551 | CA | VAL | A | 367 | 44.173 | 53.437 | 36.539 | 1.00 | 18.65 |
| ATOM | 2552 | CB | VAL | A | 367 | 42.922 | 52.944 | 35.798 | 1.00 | 18.77 |
| ATOM | 2553 | CG1 | VAL | A | 367 | 43.078 | 53.191 | 34.309 | 1.00 | 18.70 |
| ATOM | 2554 | CG2 | VAL | A | 367 | 42.704 | 51.462 | 36.081 | 1.00 | 18.63 |
| ATOM | 2555 | C | VAL | A | 367 | 44.379 | 54.918 | 36.227 | 1.00 | 18.80 |
| ATOM | 2556 | O | VAL | A | 367 | 45.329 | 55.292 | 35.542 | 1.00 | 18.91 |
| ATOM | 2557 | N | GLY | A | 368 | 43.488 | 55.759 | 36.737 | 1.00 | 19.35 |
| ATOM | 2558 | CA | GLY | A | 368 | 43.609 | 57.184 | 36.501 | 1.00 | 19.40 |
| ATOM | 2559 | C | GLY | A | 368 | 44.870 | 57.742 | 37.131 | 1.00 | 20.84 |
| ATOM | 2560 | O | GLY | A | 368 | 45.485 | 58.671 | 36.595 | 1.00 | 18.86 |
| ATOM | 2561 | N | LYS | A | 369 | 45.265 | 57.169 | 38.267 | 1.00 | 21.29 |
| ATOM | 2562 | CA | LYS | A | 369 | 46.463 | 57.626 | 38.966 | 1.00 | 22.15 |
| ATOM | 2563 | CB | LYS | A | 369 | 46.666 | 56.856 | 40.276 | 1.00 | 22.26 |
| ATOM | 2564 | CG | LYS | A | 369 | 47.657 | 57.537 | 41.213 | 1.00 | 24.45 |
| ATOM | 2565 | CD | LYS | A | 369 | 48.206 | 56.605 | 42.288 | 1.00 | 25.07 |
| ATOM | 2566 | CE | LYS | A | 369 | 49.237 | 55.649 | 41.706 | 1.00 | 25.57 |
| ATOM | 2567 | NZ | LYS | A | 369 | 49.956 | 54.891 | 42.763 | 1.00 | 24.73 |
| ATOM | 2568 | C | LYS | A | 369 | 47.688 | 57.436 | 38.085 | 1.00 | 21.35 |
| ATOM | 2569 | O | LYS | A | 369 | 48.510 | 58.344 | 37.937 | 1.00 | 21.02 |
| ATOM | 2570 | N | VAL | A | 370 | 47.806 | 56.249 | 37.499 | 1.00 | 20.37 |
| ATOM | 2571 | CA | VAL | A | 370 | 48.935 | 55.945 | 36.632 | 1.00 | 19.21 |
| ATOM | 2572 | CB | VAL | A | 370 | 48.886 | 54.478 | 36.144 | 1.00 | 18.24 |
| ATOM | 2573 | CD1 | VAL | A | 370 | 49.994 | 54.231 | 35.133 | 1.00 | 15.06 |
| ATOM | 2574 | CG2 | VAL | A | 370 | 49.030 | 53.529 | 37.336 | 1.00 | 15.86 |
| ATOM | 2575 | C | VAL | A | 370 | 48.968 | 56.875 | 35.425 | 1.00 | 20.39 |
| ATOM | 2576 | O | VAL | A | 370 | 50.022 | 57.409 | 35.073 | 1.00 | 20.38 |
| ATOM | 2577 | N | LYS | A | 371 | 47.815 | 57.078 | 34.794 | 1.00 | 19.77 |
| ATOM | 2578 | CA | LYS | A | 371 | 47.754 | 57.951 | 33.625 | 1.00 | 20.81 |
| ATOM | 2579 | CB | LYS | A | 371 | 46.371 | 57.868 | 32.963 | 1.00 | 20.10 |
| ATOM | 2580 | CG | LYS | A | 371 | 46.123 | 56.531 | 32.267 | 1.00 | 20.41 |
| ATOM | 2581 | CD | LYS | A | 371 | 44.848 | 56.533 | 31.451 | 1.00 | 20.06 |
| ATOM | 2582 | CE | LYS | A | 371 | 43.618 | 56.701 | 32.328 | 1.00 | 19.96 |
| ATOM | 2583 | NZ | LYS | A | 371 | 42.374 | 56.688 | 31.510 | 1.00 | 18.17 |
| ATOM | 2584 | C | LYS | A | 371 | 48.098 | 59.404 | 33.944 | 1.00 | 21.10 |
| ATOM | 2585 | O | LYS | A | 371 | 48.805 | 60.055 | 33.176 | 1.00 | 20.91 |
| ATOM | 2586 | N | ARG | A | 372 | 47.603 | 59.910 | 35.071 | 1.00 | 21.53 |
| ATOM | 2587 | CA | ARG | A | 372 | 47.879 | 61.288 | 35.465 | 1.00 | 23.57 |
| ATOM | 2588 | CB | ARG | A | 372 | 47.065 | 61.667 | 36.710 | 1.00 | 25.05 |
| ATOM | 2589 | CG | ARG | A | 372 | 47.244 | 63.119 | 37.135 | 1.00 | 29.47 |
| ATOM | 2590 | CD | ARG | A | 372 | 46.456 | 63.480 | 38.403 | 1.00 | 32.48 |
| ATOM | 2591 | NE | ARG | A | 372 | 46.958 | 62.807 | 39.604 | 1.00 | 37.06 |
| ATOM | 2592 | CZ | ARG | A | 372 | 46.379 | 61.755 | 40.179 | 1.00 | 37.86 |
| ATOM | 2593 | NH1 | ARG | A | 372 | 45.265 | 61.242 | 39.665 | 1.00 | 37.52 |
| ATOM | 2594 | NH2 | ARG | A | 372 | 46.916 | 61.215 | 41.269 | 1.00 | 35.72 |
| ATOM | 2595 | C | ARG | A | 372 | 49.370 | 61.503 | 35.744 | 1.00 | 23.58 |
| ATOM | 2596 | O | ARG | A | 372 | 49.954 | 62.486 | 35.284 | 1.00 | 23.18 |
| ATOM | 2597 | N | GLU | A | 373 | 49.983 | 60.584 | 36.490 | 1.00 | 22.43 |
| ATOM | 2598 | CA | GLU | A | 373 | 51.406 | 60.694 | 36.818 | 1.00 | 22.21 |
| ATOM | 2599 | CB | GLU | A | 373 | 51.798 | 59.655 | 37.879 | 1.00 | 22.58 |
| ATOM | 2600 | CG | GLU | A | 373 | 51.049 | 59.816 | 39.203 | 1.00 | 21.57 |
| ATOM | 2601 | CD | GLU | A | 373 | 51.332 | 58.689 | 40.183 | 1.00 | 25.08 |
| ATOM | 2602 | OE1 | GLU | A | 373 | 51.542 | 57.547 | 39.722 | 1.00 | 25.29 |
| ATOM | 2603 | OE2 | GLU | A | 373 | 51.327 | 58.936 | 41.412 | 1.00 | 23.49 |
| ATOM | 2604 | C | GLU | A | 373 | 52.265 | 60.509 | 35.576 | 1.00 | 21.94 |
| ATOM | 2605 | O | GLU | A | 373 | 53.284 | 61.178 | 35.407 | 1.00 | 23.16 |
| ATOM | 2606 | N | LEU | A | 374 | 51.853 | 59.601 | 34.702 | 1.00 | 20.39 |
| ATOM | 2607 | CA | LEU | A | 374 | 52.601 | 59.363 | 33.481 | 1.00 | 20.47 |
| ATOM | 2608 | CB | LEU | A | 374 | 51.928 | 58.270 | 32.648 | 1.00 | 18.16 |

TABLE 31-continued

| | | | | | | | | | |
|---|---|---|---|---|---|---|---|---|---|
| ATOM | 2609 | CG | LEU A | 374 | 52.562 | 57.989 | 31.285 | 1.00 | 17.79 |
| ATOM | 2610 | CD1 | LEU A | 374 | 54.043 | 57.696 | 31.467 | 1.00 | 15.43 |
| ATOM | 2611 | CD2 | LEU A | 374 | 51.851 | 56.817 | 30.607 | 1.00 | 17.19 |
| ATOM | 2612 | C | LEU A | 374 | 52.648 | 60.661 | 32.685 | 1.00 | 21.91 |
| ATOM | 2613 | O | LEU A | 374 | 53.711 | 61.102 | 32.253 | 1.00 | 21.82 |
| ATOM | 2614 | N | GLU A | 375 | 51.482 | 61.270 | 32.505 | 1.00 | 22.52 |
| ATOM | 2615 | CA | GLU A | 375 | 51.368 | 62.516 | 31.760 | 1.00 | 25.37 |
| ATOM | 2616 | CB | GLU A | 375 | 49.916 | 62.995 | 31.777 | 1.00 | 27.60 |
| ATOM | 2617 | CG | GLU A | 375 | 49.635 | 64.139 | 30.831 | 1.00 | 34.21 |
| ATOM | 2618 | CD | GLU A | 375 | 48.194 | 64.599 | 30.906 | 1.00 | 37.55 |
| ATOM | 2619 | OE1 | GLU A | 375 | 47.291 | 63.739 | 30.809 | 1.00 | 39.84 |
| ATOM | 2620 | OE2 | GLU A | 375 | 47.967 | 65.818 | 31.056 | 1.00 | 39.87 |
| ATOM | 2621 | C | GLU A | 375 | 52.278 | 63.598 | 32.339 | 1.00 | 23.91 |
| ATOM | 2622 | O | GLU A | 375 | 53.038 | 64.232 | 31.609 | 1.00 | 22.96 |
| ATOM | 2623 | N | ALA A | 376 | 52.204 | 63.798 | 33.651 | 1.00 | 22.62 |
| ATOM | 2624 | CA | ALA A | 376 | 53.030 | 64.803 | 34.314 | 1.00 | 22.53 |
| ATOM | 2625 | CB | ALA A | 376 | 52.687 | 64.872 | 35.811 | 1.00 | 17.94 |
| ATOM | 2626 | C | ALA A | 376 | 54.518 | 64.499 | 34.121 | 1.00 | 22.35 |
| ATOM | 2627 | O | ALA A | 376 | 55.301 | 65.400 | 33.820 | 1.00 | 23.58 |
| ATOM | 2628 | N | LEU A | 377 | 54.902 | 63.232 | 34.285 | 1.00 | 21.82 |
| ATOM | 2629 | CA | LEU A | 377 | 56.298 | 62.834 | 34.116 | 1.00 | 21.73 |
| ATOM | 2630 | CB | LEU A | 377 | 56.501 | 61.371 | 34.528 | 1.00 | 19.85 |
| ATOM | 2631 | CG | LEU A | 377 | 56.432 | 61.109 | 36.038 | 1.00 | 22.75 |
| ATOM | 2632 | CD1 | LEU A | 377 | 56.466 | 59.608 | 36.303 | 1.00 | 21.26 |
| ATOM | 2633 | CD2 | LEU A | 377 | 57.593 | 61.816 | 36.741 | 1.00 | 16.51 |
| ATOM | 2634 | C | LEU A | 377 | 56.791 | 63.041 | 32.687 | 1.00 | 22.19 |
| ATOM | 2635 | O | LEU A | 377 | 57.945 | 63.415 | 32.475 | 1.00 | 22.40 |
| ATOM | 2636 | N | LEU A | 378 | 55.934 | 62.793 | 31.702 | 1.00 | 22.32 |
| ATOM | 2637 | CA | LEU A | 378 | 56.343 | 62.999 | 30.315 | 1.00 | 22.98 |
| ATOM | 2638 | CB | LEU A | 378 | 55.248 | 62.525 | 29.355 | 1.00 | 19.93 |
| ATOM | 2639 | CG | LEU A | 378 | 55.048 | 61.011 | 29.213 | 1.00 | 19.44 |
| ATOM | 2640 | CD1 | LEU A | 378 | 53.777 | 60.727 | 28.423 | 1.00 | 17.32 |
| ATOM | 2641 | CD2 | LEU A | 378 | 56.256 | 60.393 | 28.528 | 1.00 | 15.65 |
| ATOM | 2642 | C | LEU A | 378 | 56.637 | 64.490 | 30.090 | 1.00 | 24.90 |
| ATOM | 2643 | O | LEU A | 378 | 57.625 | 64.846 | 29.446 | 1.00 | 24.47 |
| ATOM | 2644 | N | LYS A | 379 | 55.781 | 65.355 | 30.630 | 1.00 | 26.23 |
| ATOM | 2645 | CA | LYS A | 379 | 55.962 | 66.798 | 30.491 | 1.00 | 30.27 |
| ATOM | 2646 | CB | LYS A | 379 | 54.801 | 67.558 | 31.140 | 1.00 | 32.19 |
| ATOM | 2647 | CG | LYS A | 379 | 53.431 | 67.329 | 30.517 | 1.00 | 36.01 |
| ATOM | 2648 | CD | LYS A | 379 | 52.365 | 68.055 | 31.337 | 1.00 | 38.83 |
| ATOM | 2649 | CE | LYS A | 379 | 50.981 | 67.944 | 30.717 | 1.00 | 40.37 |
| ATOM | 2650 | NZ | LYS A | 379 | 50.901 | 68.651 | 29.410 | 1.00 | 42.67 |
| ATOM | 2651 | C | LYS A | 379 | 57.253 | 67.215 | 31.182 | 1.00 | 30.76 |
| ATOM | 2652 | O | LYS A | 379 | 58.109 | 67.876 | 30.600 | 1.00 | 31.75 |
| ATOM | 2653 | N | GLU A | 380 | 57.374 | 66.809 | 32.438 | 1.00 | 31.41 |
| ATOM | 2654 | CA | GLU A | 380 | 58.529 | 67.125 | 33.258 | 1.00 | 32.37 |
| ATOM | 2655 | CB | GLU A | 380 | 58.332 | 66.516 | 34.646 | 1.00 | 33.86 |
| ATOM | 2656 | CG | GLU A | 380 | 59.501 | 66.700 | 35.586 | 1.00 | 40.81 |
| ATOM | 2657 | CD | GLU A | 380 | 59.276 | 66.017 | 36.924 | 1.00 | 44.51 |
| ATOM | 2658 | OE1 | GLU A | 380 | 60.208 | 66.025 | 37.759 | 1.00 | 47.77 |
| ATOM | 2659 | OE2 | GLU A | 380 | 58.167 | 65.476 | 37.139 | 1.00 | 43.32 |
| ATOM | 2660 | C | GLU A | 380 | 59.859 | 66.658 | 32.670 | 1.00 | 32.10 |
| ATOM | 2661 | O | GLU A | 380 | 60.904 | 67.240 | 32.957 | 1.00 | 31.86 |
| ATOM | 2662 | N | GLN A | 381 | 59.830 | 65.617 | 31.844 | 1.00 | 31.04 |
| ATOM | 2663 | CA | GLN A | 381 | 61.068 | 65.109 | 31.265 | 1.00 | 30.66 |
| ATOM | 2664 | CB | GLN A | 381 | 61.147 | 63.588 | 31.448 | 1.00 | 30.50 |
| ATOM | 2665 | CG | GLN A | 381 | 61.526 | 63.191 | 32.880 | 1.00 | 29.05 |
| ATOM | 2666 | CD | GLN A | 381 | 61.349 | 61.711 | 33.165 | 1.00 | 30.02 |
| ATOM | 2667 | OE1 | GLN A | 381 | 61.666 | 60.863 | 32.331 | 1.00 | 30.88 |
| ATOM | 2668 | NE2 | GLN A | 381 | 60.855 | 61.393 | 34.359 | 1.00 | 27.15 |
| ATOM | 2669 | C | GLN A | 381 | 61.299 | 65.494 | 29.810 | 1.00 | 30.65 |
| ATOM | 2670 | O | GLN A | 381 | 62.152 | 64.918 | 29.135 | 1.00 | 30.89 |
| ATOM | 2671 | N | GLY A | 382 | 60.534 | 66.472 | 29.336 | 1.00 | 29.73 |
| ATOM | 2672 | CA | GLY A | 382 | 60.695 | 66.958 | 27.976 | 1.00 | 29.28 |
| ATOM | 2673 | C | GLY A | 382 | 60.160 | 66.145 | 26.812 | 1.00 | 29.75 |
| ATOM | 2674 | O | GLY A | 382 | 60.547 | 66.396 | 25.669 | 1.00 | 29.78 |
| ATOM | 2675 | N | PHE A | 383 | 59.281 | 65.183 | 27.066 | 1.00 | 28.22 |
| ATOM | 2676 | CA | PHE A | 383 | 58.740 | 64.390 | 25.968 | 1.00 | 28.21 |
| ATOM | 2677 | CB | PHE A | 383 | 58.480 | 62.949 | 26.410 | 1.00 | 26.99 |
| ATOM | 2678 | CG | PHE A | 383 | 59.718 | 62.209 | 26.827 | 1.00 | 25.43 |
| ATOM | 2679 | CD1 | PHE A | 383 | 60.001 | 62.005 | 28.167 | 1.00 | 23.15 |
| ATOM | 2680 | CD2 | PHE A | 383 | 60.592 | 61.709 | 25.879 | 1.00 | 21.77 |
| ATOM | 2681 | CE1 | PHE A | 383 | 61.131 | 61.311 | 28.552 | 1.00 | 22.73 |
| ATOM | 2682 | CE2 | PHE A | 383 | 61.722 | 61.019 | 26.258 | 1.00 | 22.44 |
| ATOM | 2683 | CZ | PHE A | 383 | 61.991 | 60.818 | 27.598 | 1.00 | 23.36 |
| ATOM | 2684 | C | PHE A | 383 | 57.450 | 64.988 | 25.427 | 1.00 | 28.57 |
| ATOM | 2685 | O | PHE A | 383 | 56.561 | 65.365 | 26.189 | 1.00 | 29.14 |
| ATOM | 2686 | N | GLY A | 384 | 57.356 | 65.081 | 24.104 | 1.00 | 28.87 |
| ATOM | 2687 | CA | GLY A | 384 | 56.154 | 65.620 | 23.497 | 1.00 | 29.02 |

TABLE 31-continued

| | | | | | | | | | |
|---|---|---|---|---|---|---|---|---|---|
| ATOM | 2688 | C | GLY A | 384 | 54.977 | 64.714 | 23.799 | 1.00 | 29.17 |
| ATOM | 2689 | O | GLY A | 384 | 53.846 | 65.173 | 23.949 | 1.00 | 30.43 |
| ATOM | 2690 | N | GLY A | 385 | 55.255 | 63.418 | 23.895 | 1.00 | 28.68 |
| ATOM | 2691 | CA | GLY A | 385 | 54.220 | 62.444 | 24.189 | 1.00 | 27.39 |
| ATOM | 2692 | C | GLY A | 385 | 54.822 | 61.072 | 24.428 | 1.00 | 27.16 |
| ATOM | 2693 | O | GLY A | 385 | 56.034 | 60.891 | 24.312 | 1.00 | 27.57 |
| ATOM | 2694 | N | VAL A | 386 | 53.975 | 60.104 | 24.757 | 1.00 | 25.93 |
| ATOM | 2695 | CA | VAL A | 386 | 54.416 | 58.738 | 25.018 | 1.00 | 25.76 |
| ATOM | 2696 | CB | VAL A | 386 | 53.208 | 57.784 | 25.135 | 1.00 | 26.31 |
| ATOM | 2697 | CG1 | VAL A | 386 | 53.683 | 56.337 | 25.139 | 1.00 | 26.62 |
| ATOM | 2698 | CG2 | VAL A | 386 | 52.426 | 58.093 | 26.396 | 1.00 | 26.19 |
| ATOM | 2699 | C | VAL A | 386 | 55.338 | 58.198 | 23.930 | 1.00 | 25.24 |
| ATOM | 2700 | O | VAL A | 386 | 56.382 | 57.612 | 24.216 | 1.00 | 24.74 |
| ATOM | 2701 | N | THR A | 387 | 54.938 | 58.403 | 22.680 | 1.00 | 25.11 |
| ATOM | 2702 | CA | THR A | 387 | 55.698 | 57.930 | 21.530 | 1.00 | 24.97 |
| ATOM | 2703 | CB | THR A | 387 | 55.054 | 58.417 | 20.211 | 1.00 | 26.77 |
| ATOM | 2704 | OG1 | THR A | 387 | 53.687 | 57.988 | 20.162 | 1.00 | 27.82 |
| ATOM | 2705 | CG2 | THR A | 387 | 55.800 | 57.856 | 19.006 | 1.00 | 23.16 |
| ATOM | 2706 | C | THR A | 387 | 57.166 | 58.348 | 21.542 | 1.00 | 24.24 |
| ATOM | 2707 | O | THR A | 387 | 58.040 | 57.566 | 21.171 | 1.00 | 24.21 |
| ATOM | 2708 | N | ASP A | 388 | 57.446 | 59.573 | 21.970 | 1.00 | 24.13 |
| ATOM | 2709 | CA | ASP A | 388 | 58.828 | 60.049 | 21.989 | 1.00 | 24.01 |
| ATOM | 2710 | CB | ASP A | 388 | 58.872 | 61.572 | 22.140 | 1.00 | 28.08 |
| ATOM | 2711 | CG | ASP A | 388 | 57.979 | 62.282 | 21.152 | 1.00 | 31.47 |
| ATOM | 2712 | OD1 | ASP A | 388 | 56.834 | 62.614 | 21.531 | 1.00 | 35.57 |
| ATOM | 2713 | OD2 | ASP A | 388 | 58.416 | 62.498 | 19.999 | 1.00 | 32.91 |
| ATOM | 2714 | C | ASP A | 388 | 59.671 | 59.428 | 23.096 | 1.00 | 21.44 |
| ATOM | 2715 | O | ASP A | 388 | 60.894 | 59.431 | 23.018 | 1.00 | 20.73 |
| ATOM | 2716 | N | ALA A | 389 | 59.020 | 58.904 | 24.128 | 1.00 | 19.41 |
| ATOM | 2717 | CA | ALA A | 389 | 59.735 | 58.305 | 25.249 | 1.00 | 18.82 |
| ATOM | 2718 | CB | ALA A | 389 | 58.946 | 58.528 | 26.548 | 1.00 | 17.68 |
| ATOM | 2719 | C | ALA A | 389 | 60.024 | 56.816 | 25.059 | 1.00 | 17.88 |
| ATOM | 2720 | O | ALA A | 389 | 60.871 | 56.253 | 25.749 | 1.00 | 18.18 |
| ATOM | 2721 | N | ILE A | 390 | 59.320 | 56.179 | 24.130 | 1.00 | 17.83 |
| ATOM | 2722 | CA | ILE A | 390 | 59.516 | 54.753 | 23.875 | 1.00 | 16.78 |
| ATOM | 2723 | CB | ILE A | 390 | 58.612 | 54.264 | 22.716 | 1.00 | 16.58 |
| ATOM | 2724 | CG2 | ILE A | 390 | 58.915 | 52.808 | 22.398 | 1.00 | 13.38 |
| ATOM | 2725 | CG1 | ILE A | 390 | 57.134 | 54.435 | 23.097 | 1.00 | 16.11 |
| ATOM | 2726 | CD1 | ILE A | 390 | 56.171 | 54.247 | 21.933 | 1.00 | 14.39 |
| ATOM | 2727 | C | ILE A | 390 | 60.968 | 54.425 | 23.533 | 1.00 | 16.91 |
| ATOM | 2728 | O | ILE A | 390 | 61.451 | 54.751 | 22.452 | 1.00 | 18.16 |
| ATOM | 2729 | N | GLY A | 391 | 61.661 | 53.785 | 24.467 | 1.00 | 17.39 |
| ATOM | 2730 | CA | GLY A | 391 | 63.048 | 53.409 | 24.242 | 1.00 | 16.81 |
| ATOM | 2731 | C | GLY A | 391 | 64.078 | 54.510 | 24.445 | 1.00 | 16.75 |
| ATOM | 2732 | O | GLY A | 391 | 65.248 | 54.322 | 24.118 | 1.00 | 16.88 |
| ATOM | 2733 | N | ALA A | 392 | 63.663 | 55.641 | 25.007 | 1.00 | 16.78 |
| ATOM | 2734 | CA | ALA A | 392 | 64.573 | 56.766 | 25.222 | 1.00 | 19.33 |
| ATOM | 2735 | CB | ALA A | 392 | 63.842 | 57.901 | 25.930 | 1.00 | 17.91 |
| ATOM | 2736 | C | ALA A | 392 | 65.862 | 56.421 | 25.977 | 1.00 | 19.71 |
| ATOM | 2737 | O | ALA A | 392 | 66.906 | 57.011 | 25.713 | 1.00 | 20.84 |
| ATOM | 2738 | N | ASP A | 393 | 65.795 | 55.475 | 26.911 | 1.00 | 20.21 |
| ATOM | 2739 | CA | ASP A | 393 | 66.982 | 55.083 | 27.679 | 1.00 | 19.61 |
| ATOM | 2740 | CB | ASP A | 393 | 66.640 | 53.993 | 28.700 | 1.00 | 18.27 |
| ATOM | 2741 | CG | ASP A | 393 | 65.886 | 54.521 | 29.904 | 1.00 | 20.38 |
| ATOM | 2742 | OD1 | ASP A | 393 | 65.702 | 55.753 | 30.020 | 1.00 | 21.42 |
| ATOM | 2743 | OD2 | ASP A | 393 | 65.483 | 53.690 | 30.744 | 1.00 | 20.13 |
| ATOM | 2744 | C | ASP A | 393 | 68.096 | 54.551 | 26.776 | 1.00 | 21.69 |
| ATOM | 2745 | O | ASP A | 393 | 69.277 | 54.689 | 27.091 | 1.00 | 20.91 |
| ATOM | 2746 | N | HIS A | 394 | 67.712 | 53.939 | 25.659 | 1.00 | 22.48 |
| ATOM | 2747 | CA | HIS A | 394 | 68.676 | 53.360 | 24.730 | 1.00 | 24.97 |
| ATOM | 2748 | CB | HIS A | 394 | 67.991 | 52.297 | 23.864 | 1.00 | 21.33 |
| ATOM | 2749 | CG | HIS A | 394 | 67.382 | 51.177 | 24.650 | 1.00 | 20.93 |
| ATOM | 2750 | CD2 | HIS A | 394 | 66.226 | 51.107 | 25.354 | 1.00 | 19.80 |
| ATOM | 2751 | ND1 | HIS A | 394 | 67.985 | 49.945 | 24.782 | 1.00 | 18.59 |
| ATOM | 2752 | CE1 | HIS A | 394 | 67.226 | 49.164 | 25.531 | 1.00 | 18.75 |
| ATOM | 2753 | NE2 | HIS A | 394 | 66.153 | 49.845 | 25.891 | 1.00 | 18.96 |
| ATOM | 2754 | C | HIS A | 394 | 69.339 | 54.391 | 23.825 | 1.00 | 27.88 |
| ATOM | 2755 | O | HIS A | 394 | 70.392 | 54.130 | 23.253 | 1.00 | 28.20 |
| ATOM | 2756 | N | ARG A | 395 | 68.725 | 55.560 | 23.699 | 1.00 | 32.23 |
| ATOM | 2757 | CA | ARG A | 395 | 69.262 | 56.599 | 22.832 | 1.00 | 37.69 |
| ATOM | 2758 | CB | ARG A | 395 | 68.110 | 57.372 | 22.176 | 1.00 | 36.52 |
| ATOM | 2759 | CG | ARG A | 395 | 67.250 | 56.510 | 21.253 | 1.00 | 37.79 |
| ATOM | 2760 | CD | ARG A | 395 | 66.316 | 57.351 | 20.384 | 1.00 | 38.73 |
| ATOM | 2761 | NE | ARG A | 395 | 65.140 | 57.850 | 21.097 | 1.00 | 39.62 |
| ATOM | 2762 | CZ | ARG A | 395 | 64.091 | 57.101 | 21.430 | 1.00 | 40.14 |
| ATOM | 2763 | NH1 | ARG A | 395 | 63.064 | 57.643 | 22.077 | 1.00 | 38.94 |
| ATOM | 2764 | NH2 | ARG A | 395 | 64.064 | 55.810 | 21.114 | 1.00 | 38.68 |
| ATOM | 2765 | C | ARG A | 395 | 70.222 | 57.566 | 23.521 | 1.00 | 41.10 |
| ATOM | 2766 | O | ARG A | 395 | 71.015 | 58.231 | 22.861 | 1.00 | 42.39 |

TABLE 31-continued

| ATOM | 2767 | N | ARG A | 396 | 70.163 | 57.644 | 24.844 | 1.00 | 46.02 |
|------|------|---|-------|-----|--------|--------|--------|------|-------|
| ATOM | 2768 | CA | ARG A | 396 | 71.053 | 58.543 | 25.568 | 1.00 | 50.86 |
| ATOM | 2769 | CB | ARG A | 396 | 70.511 | 58.820 | 26.975 | 1.00 | 53.12 |
| ATOM | 2770 | CG | ARG A | 396 | 70.485 | 57.618 | 27.900 | 1.00 | 54.92 |
| ATOM | 2771 | CD | ARG A | 396 | 70.063 | 58.038 | 29.297 | 1.00 | 58.19 |
| ATOM | 2772 | NE | ARG A | 396 | 70.847 | 59.180 | 29.757 | 1.00 | 60.28 |
| ATOM | 2773 | CZ | ARG A | 396 | 70.773 | 59.698 | 30.978 | 1.00 | 61.40 |
| ATOM | 2774 | NH1 | ARG A | 396 | 71.525 | 60.742 | 31.302 | 1.00 | 61.39 |
| ATOM | 2775 | NH2 | ARG A | 396 | 69.954 | 59.167 | 31.876 | 1.00 | 62.88 |
| ATOM | 2776 | C | ARG A | 396 | 72.467 | 57.968 | 25.661 | 1.00 | 52.71 |
| ATOM | 2777 | O | ARG A | 396 | 73.403 | 58.630 | 25.164 | 1.00 | 54.67 |
| ATOM | 2778 | OXT | ARG A | 396 | 72.626 | 56.864 | 26.225 | 1.00 | 54.59 |
| TER | 1 | | ARG A | 396 | | | | | |
| END | | | | | | | | | |

What is claimed is:

1. A compound of formula (III)

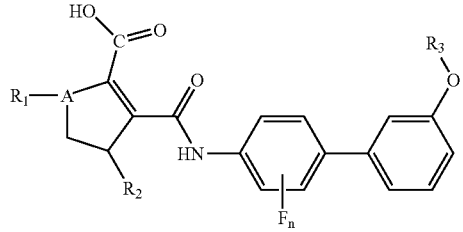

wherein

A is C or S $R_1$ is H or OH, except when A is S $R_1$ is H $R_2$ is H or OH $R_3$ is $CH_3$ or $CF_3$, and n is an integer value between $CH_1$ and $CH_4$ inclusive.

2. A compound of claim 1 is:

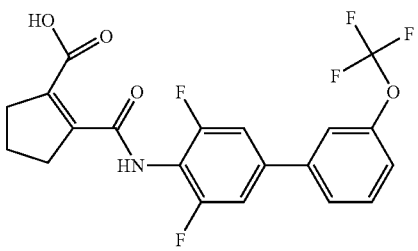

Compound 2

3. A compound of claim 1 is:

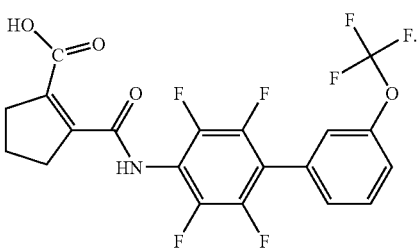

4. A compound of claim 1 is:
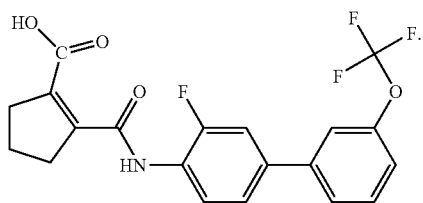
5. A compound of claim 1 is:
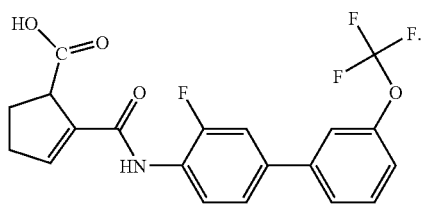
6. A compound of claim 1 is:
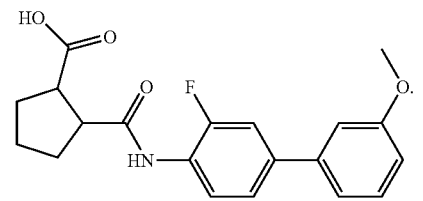
7. A compound of claim 1 is:
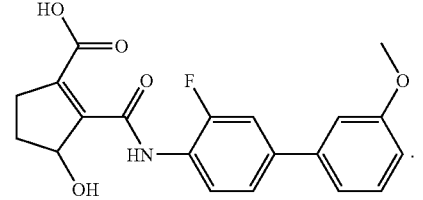
8. A compound of claim 1 is:
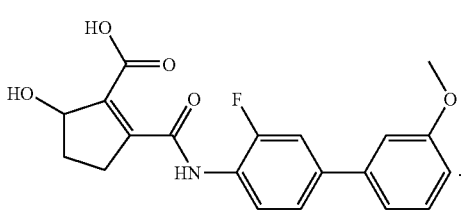
9. A compound of claim 1 is:
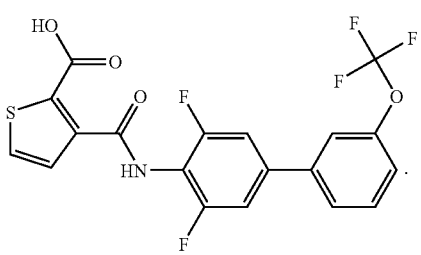
10. A compound of claim 1 is:
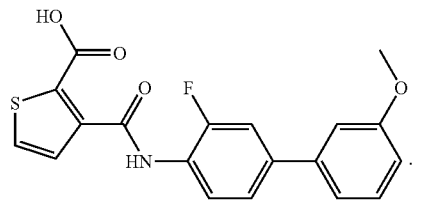
* * * * *

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Synthetic DNA

<400> SEQUENCE: 1
ggaattccat atggccacgg gagatgagcg                          30

<210> SEQ ID NO 2
<211> LENGTH: 28
<212> TYPE: DNA
<213> ORGANISM: Artificial Sequence
<220> FEATURE:
<223> OTHER INFORMATION: Synthetic DNA

<400> SEQUENCE: 2
gcgcggatcc tcacctccga tgatctgc                            28